(12) United States Patent
Pons et al.

(10) Patent No.: US 12,404,340 B2
(45) Date of Patent: Sep. 2, 2025

(54) ANTIBODIES AGAINST SIGNAL-REGULATORY PROTEIN ALPHA AND METHODS OF USE

(71) Applicant: ALX Oncology Inc., South San Francisco, CA (US)

(72) Inventors: Jaume Pons, San Francisco, CA (US); Bang Janet Sim, South San Francisco, CA (US); Hong Wan, Foster City, CA (US); Tracy Chia-Chien Kuo, San Carlos, CA (US); Steven Elliot Kauder, San Mateo, CA (US); William Don Harriman, Alameda, CA (US); Shelley Izquierdo, Berkeley, CA (US)

(73) Assignee: ALX Oncology Inc., South San Francisco, CA (US)

( * ) Notice: Subject to any disclaimer, the term of this patent is extended or adjusted under 35 U.S.C. 154(b) by 956 days.

(21) Appl. No.: 17/337,180

(22) Filed: Jun. 2, 2021

(65) Prior Publication Data

US 2023/0018821 A1    Jan. 19, 2023

Related U.S. Application Data

(62) Division of application No. 15/710,798, filed on Sep. 20, 2017, now Pat. No. 11,401,338.

(60) Provisional application No. 62/515,480, filed on Jun. 5, 2017, provisional application No. 62/397,752, filed on Sep. 21, 2016.

(51) Int. Cl.
    C07K 16/28     (2006.01)
    A61K 39/00     (2006.01)
    G01N 33/68     (2006.01)

(52) U.S. Cl.
    CPC ...... *C07K 16/2896* (2013.01); *C07K 16/2803* (2013.01); *C07K 16/2818* (2013.01); *G01N 33/6854* (2013.01); *A61K 2039/505* (2013.01); *A61K 2039/507* (2013.01); *C07K 16/2827* (2013.01); *C07K 2317/23* (2013.01); *C07K 2317/24* (2013.01); *C07K 2317/30* (2013.01); *C07K 2317/31* (2013.01); *C07K 2317/34* (2013.01); *C07K 2317/52* (2013.01); *C07K 2317/56* (2013.01); *C07K 2317/565* (2013.01); *C07K 2317/622* (2013.01); *C07K 2317/76* (2013.01); *C07K 2317/92* (2013.01); *G01N 2333/70503* (2013.01); *G01N 2333/70596* (2013.01); *G01N 2500/02* (2013.01)

(58) Field of Classification Search
    CPC .......... A61K 2039/505; C07K 16/2896; C07K 16/2803; G01N 33/6854
    See application file for complete search history.

(56) References Cited

U.S. PATENT DOCUMENTS

| RE30,985 E | 6/1982 | Cartaya |
|---|---|---|
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,731,168 A | 3/1998 | Carter et al. |
| 5,869,046 A | 2/1999 | Presta et al. |

(Continued)

FOREIGN PATENT DOCUMENTS

| EP | 2242512 B1 | 4/2016 |
|---|---|---|
| EP | 3482772 A1 | 6/2017 |

(Continued)

OTHER PUBLICATIONS

Sim et al. (MAbs. Aug./Sep. 2019; 11 (6): 1036-1052).*

(Continued)

*Primary Examiner* — Janet L Epps-Smith
*Assistant Examiner* — Nada Ahmed Mahmou Elmansy
(74) *Attorney, Agent, or Firm* — MORRISON & FOERSTER LLP

(57) ABSTRACT

Provided herein, inter alia, are isolated antibodies that bind an extracellular domain of a human SIRP-α v1 polypeptide (e.g., the D1 domain), an extracellular domain of a human SIRP-α v2 polypeptide, or both. In some embodiments, the antibodies also bind an extracellular domain of a monkey SIRP-α polypeptide, an extracellular domain of a mouse SIRP-α polypeptide, an extracellular domain of a human SIRP-β polypeptide, and/or an extracellular domain of a human SIRP-γ polypeptide. In some embodiments, the antibodies block or do not binding between an extracellular domain of a human SIRP-α polypeptide and an IgSF domain of a human CD47 polypeptide, while in some embodiments, the antibodies reduce the affinity of a human SIRP-α polypeptide for binding an IgSF domain of a human CD47 polypeptide. Further provided herein are methods, polynucleotides, vectors, and host cells related thereto.

37 Claims, 85 Drawing Sheets

Specification includes a Sequence Listing.

(56) References Cited

U.S. PATENT DOCUMENTS

| | | |
|---|---|---|
| 6,075,181 A | 6/2000 | Kucherlapati et al. |
| 6,143,559 A | 11/2000 | Michael et al. |
| 6,150,584 A | 11/2000 | Kucherlapati et al. |
| 6,180,370 B1 | 1/2001 | Queen et al. |
| 6,248,516 B1 | 6/2001 | Winter et al. |
| 7,575,893 B2 | 8/2009 | Simmons |
| 8,088,896 B2 | 1/2012 | Tesar et al. |
| 8,475,792 B2 | 7/2013 | Dall'Acqua et al. |
| 8,592,644 B2 | 11/2013 | Harriman et al. |
| 9,151,760 B2 | 10/2015 | Weissman et al. |
| 9,352,037 B2 | 5/2016 | van den Berg |
| 9,380,769 B2 | 7/2016 | Leighton et al. |
| 9,399,682 B2 | 7/2016 | Jaiswal et al. |
| 9,493,575 B2 | 11/2016 | Jaiswal et al. |
| 9,605,076 B2 | 3/2017 | Jaiswal et al. |
| 9,611,329 B2 | 4/2017 | Jaiswal et al. |
| 9,623,079 B2 | 4/2017 | Willingham et al. |
| 9,624,305 B2 | 4/2017 | Jaiswal et al. |
| 9,765,143 B2 | 9/2017 | Jaiswal et al. |
| 9,771,428 B2 | 9/2017 | Weiskopf et al. |
| 9,790,275 B2 | 10/2017 | van den Berg |
| 9,920,122 B2 | 3/2018 | van den Berg |
| 10,064,925 B2 | 9/2018 | Tseng et al. |
| 10,081,680 B2 | 9/2018 | Weiskopf et al. |
| 10,184,004 B2 | 1/2019 | Weiskopf et al. |
| 10,301,387 B2 | 5/2019 | Willingham et al. |
| 10,329,354 B2 | 6/2019 | Leeper et al. |
| 10,344,094 B2 | 7/2019 | Weissman et al. |
| 10,611,842 B2 | 4/2020 | Liu et al. |
| 10,618,976 B2 | 4/2020 | Weissman et al. |
| 10,723,803 B2 | 7/2020 | Weiskopf et al. |
| 10,780,117 B2 | 9/2020 | Weissman et al. |
| 10,781,256 B2 | 9/2020 | Weiskopf et al. |
| 10,851,164 B2 | 12/2020 | Van Eenennaam et al. |
| 11,242,404 B2 | 2/2022 | Pons et al. |
| 11,292,850 B2 | 4/2022 | Pons et al. |
| 11,401,338 B2 | 8/2022 | Pons et al. |
| 11,939,393 B2 | 3/2024 | Pons et al. |
| 2002/0114807 A1 | 8/2002 | Berg et al. |
| 2003/0026803 A1 | 2/2003 | Barclay |
| 2003/0054415 A1 | 3/2003 | Buhring et al. |
| 2004/0147731 A1 | 7/2004 | Parkos |
| 2004/0213792 A1 | 10/2004 | Clemmons et al. |
| 2006/0263356 A1 | 11/2006 | Endl et al. |
| 2008/0160013 A1 | 7/2008 | Clemmons et al. |
| 2010/0215640 A1 | 8/2010 | Clemmons et al. |
| 2010/0239578 A1 | 9/2010 | Danska et al. |
| 2013/0189253 A1 | 7/2013 | Danska et al. |
| 2014/0065169 A1 | 3/2014 | Jaiswal et al. |
| 2014/0161825 A1 | 6/2014 | Jaiswal et al. |
| 2014/0242095 A1 | 8/2014 | Wang et al. |
| 2016/0186150 A1 | 6/2016 | Deming et al. |
| 2016/0333093 A1 | 11/2016 | Weiskopf et al. |
| 2017/0114134 A1 | 4/2017 | Clemmons et al. |
| 2017/0151282 A1 | 6/2017 | Discher et al. |
| 2017/0247464 A1 | 8/2017 | Poirier et al. |
| 2018/0105600 A1 | 4/2018 | Pons et al. |
| 2018/0155424 A1 | 6/2018 | van den Berg |
| 2018/0214524 A1 | 8/2018 | Weissman et al. |
| 2018/0244748 A1 | 8/2018 | Gill et al. |
| 2018/0312587 A1 | 11/2018 | Van Eenennaam et al. |
| 2018/0312600 A1 | 11/2018 | Poirier et al. |
| 2019/0119396 A1 | 4/2019 | Liu et al. |
| 2019/0127477 A1 | 5/2019 | Poirier et al. |
| 2019/0134089 A1 | 5/2019 | Liu et al. |
| 2019/0153095 A1 | 5/2019 | Matozaki et al. |
| 2019/0233515 A1 | 8/2019 | Jaiswal et al. |
| 2019/0275150 A1 | 9/2019 | Pincetic et al. |
| 2019/0322986 A1 | 10/2019 | Keller et al. |
| 2019/0352419 A1 | 11/2019 | Pons et al. |
| 2019/0359707 A1 | 11/2019 | Pincetic et al. |
| 2020/0102387 A1 | 4/2020 | Abbasian et al. |
| 2020/0129557 A1 | 4/2020 | Shizuru et al. |
| 2020/0223923 A1 | 7/2020 | Schnorr et al. |
| 2020/0262918 A1 | 8/2020 | Liu et al. |
| 2020/0297842 A1 | 9/2020 | Puro et al. |
| 2020/0354469 A1 | 11/2020 | Weiskopf et al. |
| 2022/0002434 A1 | 1/2022 | Pons et al. |
| 2022/0324996 A1 | 10/2022 | Pons et al. |

FOREIGN PATENT DOCUMENTS

| | | |
|---|---|---|
| EP | 3308641 B1 | 7/2019 |
| EP | 2931752 B1 | 8/2019 |
| EP | 3180363 B1 | 9/2019 |
| EP | 3186395 B1 | 9/2019 |
| EP | 3421601 B1 | 12/2019 |
| EP | 3043181 B1 | 4/2020 |
| EP | 3209691 B1 | 7/2020 |
| EP | 3209769 B1 | 8/2020 |
| WO | WO-1987/000195 A1 | 1/1987 |
| WO | WO-1990/003430 A1 | 4/1990 |
| WO | WO-1991/010741 A1 | 7/1991 |
| WO | WO-1993/016185 A2 | 8/1993 |
| WO | WO-1994/004690 A1 | 3/1994 |
| WO | WO-1996/033735 A1 | 10/1996 |
| WO | WO-1996/034096 A1 | 10/1996 |
| WO | WO-1997/048723 A2 | 12/1997 |
| WO | WO-1998/024893 A2 | 6/1998 |
| WO | WO-1999/040940 A1 | 8/1999 |
| WO | WO-2005/014653 A2 | 2/2005 |
| WO | WO-2009/111014 A2 | 9/2009 |
| WO | WO-2011/019844 A1 | 2/2011 |
| WO | WO-2012/162422 A2 | 11/2012 |
| WO | WO-2013/056352 A1 | 4/2013 |
| WO | WO-2013/059159 A1 | 4/2013 |
| WO | WO-2015/138600 A2 | 9/2015 |
| WO | WO-2016/063233 A1 | 4/2016 |
| WO | WO-2017/178653 A2 | 10/2017 |
| WO | WO-2018/057669 A1 | 3/2018 |
| WO | WO-2018190719 A2 | 10/2018 |
| WO | WO-2018/210793 A2 | 11/2018 |
| WO | WO-2018210795 A1 | 11/2018 |
| WO | WO-2020013170 A1 | 1/2020 |
| WO | WO-2020099653 A1 | 5/2020 |

OTHER PUBLICATIONS

Araghi et al. (J. Feline Med. Surg. Apr. 2014; 16 (4): 265-74).*
Lee et al. (J. Immunol. Dec. 1, 2007; 179 (11): 7741-50).*
Liu et al. (J. Mol. Biol. Jan. 19, 2007; 365 (3): 680-93).*
Barclay et al. (Annu. Rev. Immunol. 2014; 32: 25-50).*
Winkler et al. (J. Immunol 2000; 165: 4505-14).*
"Functional Elements on SIRPalpha IgV Domain Mediate Cell Surface Binding to CD47," Liu et al,J.Mol.Biology, 365, 680-693 (Year: 2007)*
Almagro and Fransson (2008). "Humanization of antibodies," Front. Biosci. 13:1619-1633.
Araghi et al., (2014). "Flow cytometric immunophenotyping of feline bone marrow cells and haematopoietic progenitor cells using anti-human antibodies," J. Feline Med. Surg. 16(4):265-74.
Baca et al. (1997). "Antibody humanization using monovalent phage display," J. Biol. Chem., 272(16):10678-10684.
Barclay et al., (2014). "The interaction between signal regulatory protein alpha (SIRPa) and CD47: structure, function, and therapeutic target," Annu. Rev. Immunol., 32:25-50.
Barclay, A.N. and Brown, M.H. (2006). "The SIRP family of receptors and immune regulation," Nat. Rev. Immunol., 6(6):457-464.
Barnes et al. (1980). "Methods for growth of cultured cells in serum-free medium," Anal. Biochem. 102:255-70.
BioLegend. (2016). "Purified anti-human CD172a/b (SIRPa/b) Antibody," https://www.biolegend.com/en-gb/global-elements/pdf-popup/purified-anti-human-cd172a-b-sirpalpha-beta-antibody-4028?filename=Purified%20anti-human%20CD172ab%20SIRPalphabeta%20Antibody.pdf&pdfgen=true, Retrieved: Dec. 15, 2017.
Boerner et al. (1991). "Production of antigen-specific human monoclonal antibodies from in vitro-primed human splenocytes," J. Immunol., 147(1):86-95.

(56) References Cited

OTHER PUBLICATIONS

Bravman, T. et al. (2006). "Exploring "one-shot" kinetics and small molecule analysis using the ProteOn XPR36 array biosensor," Anal. Biochem., 358(2):281-288.
Brennan et al. (1985). "Preparation of bispecific antibodies by chemical recombination of monoclonal immunoglobulin G1 fragments," Science, 229(4708):81-3.
Bruggemann et al. (1993). "Designer mice: the production of human antibody repertoires in transgenic animals," Year in Immunol., 7:33-40.
Carter et al. (1992). "High level *Escherichia coli* expression and production of a bivalent humanized antibody fragment," Biotechnology, 10(2):163-167.
Carter et al. (1992). "Humanization of an anti-p185HER2 antibody for human cancer therapy," Proc. Natl. Acad. Sci. USA, 89(10):4285-9.
Champe et al. (1995). "Monoclonal antibodies that block the activity of leukocyte function-associated antigen 1 recognize three discrete epitopes in the inserted domain of CD11a," J. Biol. Chem., 270(3):1388-1394.
Chin et al., (2008). "Immune intervention with monoclonal antibodies targeting CD152 (CTLA-4) for autoimmune and malignant diseases," Chang Gung Med J., 31(1):1-15.
Chothia and Lesk, (1987). "Canonical structures for the hypervariable regions of immunoglobulins," J. Mal. Biol., 196(4):901-917.
Clackson et al. (1991). "Making antibody fragments using phage display libraries," Nature, 352: 624-628.
Fellouse (2004). "Synthetic antibodies from a four-amino-acid code: a dominant role for tyrosine in antigen recognition," Proc. Natl. Acad. Sci. USA, 101(34):12467-12472.
Fishwild et al. (1996). "High-avidity human IgG kappa monoclonal antibodies from a novel strain of minilocus transgenic mice," Nature Biotechnol., 14(7):845-851.
George et al. (1998). "Differential effects of anti-beta2-glycoprotein I antibodies on endothelial cells and on the manifestations of experimental antiphospholipid syndrome," Circulation, 97:900-906.
Glanville, J. et al. (2009). "Precise determination of the diversity of a combinatorial antibody library gives insight into the human immunoglobulin repertoire," Proc. Natl. Acad. Sci., 106(48):20216-20221.
Graham et al. (1977). "Characteristics of a human cell line transformed by DNA from human adenovirus type 5," J. Gen Viral., 36(1):59-74.
Griffiths et al. (1993). "Human anti-self antibodies with high specificity from phage display libraries," EMBO J, 12(2):725-734.
Gruber et al. (1994). "Efficient tumor cell lysis mediated by a bispecific single chain antibody expressed in *Escherichia coli*," J. Immunol, 152(11):5368-74.
Ham et al. (1979). "Media and growth requirements," Meth. Enz., 58:44-93.
Hamers-Casterman et al. (1993). "Naturally occurring antibodies devoid of light chains," Nature, 363(6428):446-448.
Hatherley, D. et al. (2007). "The structure of the macrophage signal regulatory protein alpha (SIRPalpha) inhibitory receptor reveals a binding face reminiscent of that used by T cell receptors," J. Biol. Chem., 282(19):14567-75.
Hatherley, D. et al. (2008). "Paired receptor specificity explained by structures of signal regulatory proteins alone and complexed with CD47," Mal. Cell, 31(2):266-77.
Hatherley, D. et al. (2009). "Structure of signal-regulatory protein alpha: a link to antigen receptor evolution," J. Biol. Chem., 284(39):26613-9.
Hollinger et al. (1993). "'Diabodies': small bivalent and bispecific antibody fragments," Proc. Natl. Acad. Sci. USA, 90(14):6444-6448.
Hongo et al. (1995). "Development and characterization of murine monoclonal antibodies to the latency-associated peptide of transforming growth factor beta 1," Hybridoma, 14(3):253-260.

Hoogenboom and Winter (1992). "By-passing ignalingon. Human antibodies from synthetic repertoires of germline VH gene segments rearranged in vitro," J. Mol. Biol., 227(2):381-388.
Hoogenboom, H.R. (2002). "Overview of antibody phage-display technology and its applications," Methods in Molecular Biology, 178:1-37.
Hudson et al. (2003). "Engineered antibodies," Nat. Med., 9(1):129-134.
International Search Report and Written Opinion directed to PCT Application No. PCT/US2017/052592, dated Dec. 20, 2017, 22 pages.
International Search Report and Written Opinion directed to PCT Application No. PCT/US2019/023238, dated May 20, 2019, 6 pages.
Jakobovits et al. (1993). "Analysis of homozygous mutant chimeric mice: deletion of the immunoglobulin heavy-chain joining region blocks B-cell development and antibody production," Proc. Natl. Acad. Sci. USA, 90(36):2551-5.
Jakobovits et al. (1993). "Germ-line transmission and expression of a human-derived yeast artificial chromosome," Nature, 362(6417):255-258.
Jayaram, N. et al. (2012). "Germline VH/VL pairing in antibodies," Protein Eng. Des. Sel., 25(10):523-529.
Jiang et al., (2005). "A Novel Peptide Isolated from a Phage Display Peptide Library with Trastuzumab Can Mimic Antigen Epitope of HER-2," J. Biol. Chem., 280(6):4656-4662.
Jones et al. (1986). "Replacing the complementarity-determining regions in a human antibody with those from a mouse," Nature, 321(6069):522-525.
Kharitonenkov, A. et al. (1997). "A family of proteins that inhibit ignaling through tyrosine kinase receptors," Nature, 386(6621):181-6.
Kim, E.J. et al. (2013). "SHPS-1 and a synthetic peptide representing its ITIM inhibit the MyD88, but not TRIF, pathway of TLR signaling through activation of SHP and PI3K in THP-1 cells," Inflammation Research, 62(4):377-86.
Kohler and Milstein, (1975). "Continuous cultures of fused cells secreting antibody of predefined specificity," Nature, 256(5517):495-97.
Kostelny et al. (1992). "Formation of a bispecific antibody by the use of leucine zippers." J. Immunol., 148(5):1547-1553.
Krieg et al. (2005). "Functional analysis of B and T lymphocyte attenuator engagement on CD4+ and CD8+ T cells," Journal of Immunology (Baltimore, MD. : 1950), vol. 175, No. 10, pp. 6420-6427, ISSN: 0022-1767.
Lee et al. (2004). "Bivalent antibody phage display mimics natural immunoglobulin," J. Immunol. Methods, 284(1-2):119-132.
Lee et al. (2004). "High-affinity human antibodies from phage-displayed synthetic Fab libraries with a single framework scaffold," J. Mol. Biol., 340(5):1073-1093.
Lee, W. Y. et al. (2010). "The role of cis dimerization of signal regulatory protein alpha (SIRPalpha) in binding to CD47," J. Biol. Chem., 285(49):37953-63.
Lee, W.Y. et al. (2007). "Novel structural determinants on SIRP alpha that mediate binding to CD47," J. Immunol., 179(11):7741-50.
Li et al. (2006). "Optimization of humanized IgGs in glycoengineered Pichia pastoris," Nat. Biotech., 24(2):210-215.
Liu et al., (2007). "Functional elements on SIRPalpha IgV domain mediate cell surface binding to CD47," J. Mol. Biol., 365(3):680-93.
Lloyd, C. et al. (2009). "Modelling the human immune response: performance of a 1011 human antibody repertoire against a broad panel of therapeutically relevant antigens," Protein Eng. Des. Sel., 22(3):159-168.
Lonberg (2008). "Fully human antibodies from transgenic mouse and phage display platforms," Curr. Opin. Immunol., 20(4):450-459.
Lonberg and Huszar (1995) "Human antibodies from transgenic mice," Intern. Rev. Immunol., 13(1):65-93.
Lonberg et al. (1994). "Antigen-specific human antibodies from mice comprising four distinct genetic modifications," Nature, 368(6474):856-859.

(56) References Cited

OTHER PUBLICATIONS

Ludwig et al. (2017). "Mechanisms of Autoantibody-Induced Pathology," Front Immunol, 8: 603.
Majeti, R. et al. (2009). "CD47 is an adverse prognostic factor and therapeutic antibody target on human acute myeloid leukemia stem cells," Cell, 138(2):286-99.
Marks et al. (1992). "By-passing immunization. Human antibodies from V-gene libraries displayed on phage," J. Mol. Biol., 222(3): 581-597.
Marks et al. (1992). "By-passing immunization: building high affinity human antibodies by chain shuffling," Biotechnology, 10(7):779-783.
Mather (1980). "Establishment and characterization of two distinct mouse testicular epithelial cell lines," Biol. Reprod., 23(1):243-252.
Mather et al. (1982). "Culture of testicular cells in hormone-supplemented serum-free medium," Annals N.Y. Acad. Sci., 383:44-68.
Mettler Izquierdo, S. et al. (2016). "High-efficiency antibody discovery achieved with multiplexed microscopy," Microscopy (Oxf), 341-52.
Morimoto et al. (1992). "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, 24(1-2):107-117.
Morrison (1994). "Immunology. Success in specification," Nature, 368(6474):812-813.
Morrison et al. (1984). "Chimeric human antibody molecules: mouse antigen-binding domains with human constant region domains," Proc. Natl. Acad. Sci. USA, 81(21):6851-6855.
Murata, Y. et al. (2014). The CD47-SIRPα signaling system: its physiological roles and therapeutic application, The Journal of Biochemistry, 155(6):335-344.
Nakaishi, A. et al. (2008). "Structural insight into the specific interaction between murine SHPS-1/SIRP alpha and its ligand CD47," J. Mal. Biol. 375:650-60.
Nettleship, J. et al. (2013). "Crystal structure of signal regulatory protein gamma (SIRPg) in complex with an antibody Fab fragment", BMC Structural Biology, 13(13):1-8.
Neuberger (1996). "Generating high-avidity human Mabs in mice," Nature Biotechnol., 14(7):826.
Ochi, F. et al. (1997). "Epidermal growth factor stimulates the tyrosine phosphorylation of SHPS-1 and association of SHPS-1 with SHP-2, a SH2 domain-containing protein tyrosine phosphatase," Biochem. Biophys. Res. Commun., 239(2):483-7.
Presta (1992). "Antibody engineering," Curr. Op. Struct. Biol. 2:593-596.
Presta et al. (1993). "Humanization of an antibody directed against IgE," J. Immunol., 151(5):2623-32.
Riechmann et al. (1988). "Reshaping human antibodies for therapy," Nature, 332(6162):323-327.
Riemer et al., (2005). "Matching of trastuzumab (Herceptin) epitope mimics onto the surface of Her-2/neu—a new method of epitope definition," Mol. Immunol., 42:1121-1124.
Rudikoff et al. (1982). "Single amino acid substitution altering antigen-binding specificity," Proc. Nat. Acad. Sci., vol. 79, pp. 1979-1983, Immunology.
Seiffert, M. et al. (1999). "Human Signal-Regulatory Protein Is Expressed on Normal, But Not on Subsets of Leukemic Myeloid Cells and Mediates Cellular Adhesion Involving Its Counterreceptor CD47," Blood, 94(11):3633-3643.
Seiffert, M. et al. (2001). "Signal-regulatory protein a (SIRPa) but not SIRPb is involved in T-cell activation, binds to CD47 with high affinity, and is expressed on immature CD34+CD38-hematopoietic cells," Blood, 97(9):2741-2749.
Sheriff et al. (1996). "Redefining the minimal antigen-binding fragment," Nature Struct. Biol., 3(9):733-736.
Sidhu et al. (2004). "Phage-displayed antibody libraries of synthetic heavy chain complementarity determining regions," J. Mol. Biol., 338(2): 299-310.
Sim et al. (2019). "Discovery of high affinity, pan-allelic, and pan-mammalian reactive antibodies against the myeloid checkpoint receptor SIRPα," MAbs. 11(6):1036-1052.
Sims et al. (1993). "A humanized CD18 antibody can block function without cell destruction," J. Immunol., 151(4):2296-308.
Spiess, C. et al. (2015). "Alternative molecular formats and therapeutic applications for bispecific antibodies," Mal. Immunol., 67(2 Pt A):95-106.
Takenaka, K. et al. (2007). "Polymorphism in Sirpa modulates engraftment of human hematopoietic stem cells," Nat. Immunol., 8(12):1313-23.
Treffers et al., (2018). "Genetic variation of human neutrophil Fcγ receptors and SIRPα in antibody-dependent cellular cytotoxicity towards cancer cells," European Journal of Immunology 48(2):344-354.
Urlaub et al. (1980). "Isolation of Chinese hamster cell mutants deficient in dihydrofolate reductase activity," Proc. Natl. Acad. Sci. USA, 77(7):4216-20.
Van Der Heijden, J. (Jul. 1, 2014). "Genetic Variation in Human Fc Gamma Receptors: Functional Consequences of Polymorphisms and Copy Number Variation," located at <https://dare.uva.nl/search?identifier=54e3332e-a8c8-4fec-a49d-833b35617f2f> last visited on Sep. 7, 2017, pp. 115-135, 22 pages.
Vollmers and Brandlein, (2005). "Death by stress: natural IgM-induced apoptosis," Methods and Findings in Experimental and Clinical Pharmacology, 27(3):185-91.
Vollmers and Brandlein, (2005). "The 'early birds': natural IgM antibodies and immune surveillance," Histology and Histopathology, 20(3):927-937.
Weiskopf, K. et al. (2013). "Engineered SIRPα variants as immunotherapeutic adjuvants to anticancer antibodies," Science, 341(6141):88-91.
Willingham, S.B. et al. (2012). "The CD47-signal regulatory protein alpha (SIRPa) interaction is a therapeutic target for human solid tumors," 109(17):6662-7.
Winkler et al. (2000). "Changing the antigen binding specificity by single point mutations of an anti-p24 (HIV-1) antibody," J Immunol. 165(8):4505-14.
Winter et al. (1994). "Making antibodies by phage display technology," Ann. Rev. Immunol., 12:433-455.
Yanagita, T. et al. (2017). "Anti-SIRPα antibodies as a potential new tool for cancer immunotherapy," JCI Insight, 2(1):e89140.
Yi et al (2015). "Splenic dendritic cells survey red blood cells for missing self-CD47 to trigger adaptive immune responses," Immunity, 433(4):764-775.
Zhang et al. (2020). "CD47 decline in pancreatic islet cells promotes macrophage-mediated phagocytosis in type I diabetes," World J Diabetes, 11(6): 239-251.
Zhao, X.W. et al. (2011). "CD47-signal regulatory protein-α (SIRPα) interactions form a barrier for antibody-mediated tumor cell destruction," Proc. Natl. Acad. Sci., 108(45):18342-7.
U.S. Appl. No. 17/337,348, filed Jun. 2, 2021, titled "Antibodies Against Signal-Regulatory Protein Alpha and Methods of Use," inventor Pons et al., Applicant ALX Oncology Inc. (Copy not submitted herewith pursuant to the waiver of 37 C.F.R. § 1.98(a)(2)(iii)).
U.S. Appl. No. 17/337,176, filed Jun. 2, 2021, titled "Antibodies Against Signal-Regulatory Protein Alpha and Methods of Use," inventor Pons et al., Applicant ALX Oncology Inc. (Copy not submitted herewith pursuant to the waiver of 37 C.F.R. § 1.98(a)(2)(iii)).
Hlavacek et al. (1999). "Steric Effects on Multivalent Ligand-Receptor Binding: Exclusion of Ligand Sites by Bound Cell Surface Receptors," Biophysical Journal, vol. 76, Issue 6, pp. 3031-3043.
Plückthun et al. (1997). "New protein engineering approaches to multivalent and bispecific antibody fragments," Immunotechnology, 3(2):83-105.
Bostrom et al. (2009). "Improving antibody binding affinity and specificity for therapeutic development," Methods Mol Biol, 525:353-376.
Gonzales et al. (2005). "Minimizing the immunogenicity of antibodies for clinical application," Tumour Biol, 26(1): 31-43.
Janeway et al. (2001). "Immunobiology: the immune system in health and disease." 5th Editions, New York, Garland Science, 5 pages.

(56) References Cited

OTHER PUBLICATIONS

Kipriyanov et al. (2004). "Generation and production of engineered antibodies." Molecular biotechnology, 26(1):39-60.
Kunik et al. (2012). "Structural consensus among antibodies defines the antigen binding site," 8(2):e1002388, 12 pages.
NCBI (2015). Genbank Accession No. EAX10606.1, protein tyrosine phosphatase, non-receptor type substrate 1, isoform CRA_a, 1 page.
Padlan (1994). "Anatomy of the antibody molecule," Mol. Immunol., 31: 169-217.
Ratnikova et al. (2017). "CD47 receptor as a primary target for cancer therapy. Molecular Biology," 51(2):251-261 (translation of abstract only, in p. 261).
Silva et al. (2015.) "The S228P Mutation Prevents in Vivo and in Vitro IgG4 Fab-arm Exchange as Demonstrated using a Combination of Novel Quantitative Immunoassays and Physiological Matrix Preparation." The Journal of Biological Chemistry, 290(9): 5462-5469.
Wark et al. (2006). "Latest technologies for the enhancement of antibody affinity," Adv Drug Deliv Rev, 58(5-6): 657-670.

* cited by examiner

```
v1   (1)   EEELQVIQPDKSVLVAAGETATLRCTATSLIPVGPIQWFRGAGPGRELIY         50
v2   (1)   EEELQVIQPDKSVLVAAGETATLRCTATSLIPVGPIQWFRGAGPGRELIY
v3   (1)   EEELQVIQPDKSVSVAAGESAILHCTVTSLIPVGPIQWFRGAGPAREELIY
v4   (1)   EEELQVIQPDKSVSVAAGESAILLCTVTSLIPVGPIQWFRGAGPAREELIY
v5   (1)   EEELQVIQPDKSVSVAAGESAILLCTVTSLIPVGPIQWFRGAGPAREELIY
v6   (1)   EEGLQVIQPDKFVLVAAGETATLRCTATSLIPVGPIQWFRGAGPGRELIY
v7   (1)   EEELQVIQPDKSVLVAAGETATLRCTATSLIPVGPIQWFRGAGPGRELIY
v8   (1)   EEELQVIQPDKSVSVAAGESAILHCTVTSLIPVGPIQWFRGAGPAREELIY
v9   (1)   EEELQVIQPDKSVSVAAGESAILHCTVTSLIPVGPIQWFRGAGPGRELIY
v10  (1)   EEELQVIQPDKSVSVAAGESAILHCTVTSLIPVGPIQWFRGAGPAREELIY
                *                         *

51                                                      100
v1   (51)  MQKEGHFPRVTTVSDLTKRNNMDFSIRIGNITPADAGTYYCVKFRKGSPD
v2   (51)  MQKEGHFPRVTTVSESTKRENMDFSISISNITPADAGTYYCVKFRKGS-P
v3   (51)  MQKEGHFPRVTTVSESTKRENMDFSISISNITPADAGTYYCVKFRKGS-P
v4   (51)  MQKEGHFPRVTTVSESTKRENMDFSISISNITPADAGTYYCVKFRKGS-P
v5   (51)  MQKEGHFPRVTTVSDLTKRNNMDFSIRIGNITPADAGTYYCVKFRKGSPD
v6   (51)  MQKEGHFPRVTTVSDLTKRNNMDFPIRIGNITPADAGTYYCVKFRKGSPD
v7   (51)  MQKEGHFPRVTTVSESTKRENMDFSISISNITPADAGTYYCVKFRKGS-P
v8   (51)  MQKEGHFPRVTTVSESTKREMDFSISISNITPADAGTYYCVKFRKGS-P
v9   (51)  MQKEGHFPRVTTVSDLTKRNNMDFSIRIGNITPADAGTYYCVKFRKGSPD
v10  (51)  MQKEGHFPRVTTVSESTKRENMDFSISISNITPADAGTYYCVKFRKGS-P
                *         *                     *         **

101                 119
v1   (101) DVEFKSGAGTELSVRAKPS
v2   (100) DTEFKSGAGTELSVRAKPS
v3   (100) DTEFKSGAGTELSVRAKPS
v4   (101) DVEFKSGAGTELSVRAKPS
v5   (101) DVEFKSGAGTELSVRAKPS
v6   (101) DVEFKSGAGTELSVRAKPS
v7   (100) DTEFKSGAGTELSVRGKPS
v8   (100) DTEFKSGAGTELSVRAKPS
v9   (101) DVEFKSGAGTELSVRAKPS
v10  (100) DTEFKSGAGTELSVRAKPS
                *
```

FIG. 1A

```
              1                                                      50
Human_v1   (1) EEELQVIQPDKSVLVAAGETATLRCTATSLIPVGPIQWFRGAGPGRELIY
Human_v2   (1) EEELQVIQPDKSVSVSVAAGESAILHCTVTSLIPVGPIQWFRGAGPARELIY
   Cyno   (1) EEELQPEKSVSVSVAAGESATLNCTATSLIPVGPIQWFRGVGPGRELIY
129mouse   (1) -KELKVTQPEKSVSVAAGDSTVLNCTLTSLLPVGPIKWYRGVGQSRLLIY
               ** ** ***** **    ** *  *  ** ***  * **  *   *   * **

51                                                    100
Human_v1  (51) NQKEGHFPRVTTVSDLTKRNNMDFSIRIGNITPADAGTYYCVKFRKGSP-
Human_v2  (51) NQKEGHFPRVTTVSESTKRENMDFSISISNITPADAGTYYCVKFRKGS--
   Cyno  (51) HQKEGHFPRVTPVSDPTKRNNMDFSIRISNITPADAGTYYCVKFRKGS--
129mouse  (50) SFTGEHFPRVTNVSDATKRNNMDFSIRISNVTPEDAGTYYCVKFQKGPSE
                  *****  **   ** ****** *  *  ** *********** **

101           120
Human_v1 (100) DDVEFKSGAGTELSVRAKPS
Human_v2  (99) PDTEFKSGAGTELSVRAKPS
   Cyno  (99) PDVELKSGAGTELSVRAKPS
129mouse (100) PDTEIQSGGGTEVYVLAKPS
                *      * ***   * ***
```

FIG. 1B

```
                                        R1
                    1                                                                        50
Human_v1   (1)   EEELQVIQPDKSVLVAAGETATLRCTATSLLIPVGPIQWFRGAGPGRELIY
Human_v2   (1)   EEELQVIQPDKSVLVAAGESAILHCTVTSLLIPVGPIQWFRGAGPARELIY
129mouse   (1)   -KELKVTQPEKSVSVSVAAGESAILHCTVTSLLPVGPIQWFRGAGPARELIY
NOD        (1)   -TEVKVIQPEKSVSVSVAAGDSTVLNCTLTSLLPVGPIKWYRGVGQSRQLIY
BL6        (1)   -KELKVTQPEKSVSVSVAAGDSTVLNCTLTSLLPVGPIRWYRGVGQSRLLIY
BALBC      (1)   -TEVKVTQPEKSVSVSVAAGDSTILNCTVTSLLPVGPIRWYRGVGQSRLLIY
                  *   ** ***** * *  * * ** **** *** ** ** *  *  * **

R2                                           R3             100
Human_v1  (51)   NQKEGHFPRVTTVSDLTKRNNMDFSIRIGNITPADAGTYYCVKFRKGSP-
Human_v2  (51)   NQKEGHFPRVTTVSESTKRENMDFSISNITPADAGTYYCVKFRKGS--
129mouse  (50)   SFTGEHFPRVTNVSDATKRNNMDFSIRISNVTPEDAGTYYCVKFQGPSE
NOD       (50)   SFTTEHFPRVTNVSDATKRSNLDFSIRISNVTPEDAGTYYCVKFQRGS--
BL6       (50)   SFAGEYVPRIRNVSDTTKRNNMDFSIRISNVTPADAGIYYCVKFQKGSSE
BALBC     (50)   SFTGEHFPRIRNVSDTTKRNNMDFSIRISNVTPEDAGTYYCVKFQRGSSE
                  *    ****  **  ** * * ****  * *** ** * ****   *

101                     120
Human_v1 (100)   DDVEFKSGAGTELSVRAKPS
Human_v2  (99)   PDTEFKSGAGTELSVRAKPS
129mouse (100)   PDTEIQSGGGTEVYVLAKPS
NOD       (98)   PDTEIQSGGGTEVYVLAK--
BL6      (100)   PDTEIQSGGGTEVYVLAK--
BALBC    (100)   PDTEIQSGGGTEVYVLAK--
                  ** *  *  *** * ***
```

FIG.1C

```
                    1                                                    50
Human_v1    (1)    EEELQVIQPDKSVLVAAGETATLRCTATSLIPVGPIQWFRGAGPGRELIY
Human_v2    (1)    EEELQVIQPDKSVLVAAGESAILHCTVTSLIPVGPIQWFRGAGPARELIY
Cyno        (1)    EEELQVIQPEKSVSVAAGESAILHCTATSLIPVGPIQWFRGVGPGRELIY
129mouse    (1)    -KELKVTQPEKSVTVLNCTLTSLLPVGPIKWYRGVGQSRLLIY
chicken     (1)    --DEKLQQPQSSVVVIKGDTLTLNCTASGSGPIGAVKWVKGWGSDNQTVY
                        *  *   *      *   *  **  *  * *    *

51                                                   100
Human_v1   (51)    NQKEGHFPRVTTVSDLTKRNNMDFSIRIGNITPADAGTYYCVKFRKGS-P
Human_v2   (51)    NQKEGHFPRVTTVSESTKRENMDFSISISNITPADAGTYYCVKFRKGS--
Cyno       (51)    HQKEGHFPRVTPVSDPTKRNNMDFSIRIGNITPADAGTYYCVKFRKGS--
129mouse   (50)    SFTGEHFPRVTNVSDATKRNNMDFSIRISNVTPEDAGTYYCVKFQKGPSE
chicken    (49)    EHKGSFPRVMRAVPDPTN----DFTIRISNVSLEDAGTYYCVKLRKGIV-
                       * ****      *      ** *      ** ********  **

101                120
Human_v1  (100)    DDVEFKSGAGTELSVRAKPS
Human_v2   (99)    PDTEFKSGAGTELSVRAKPS
Cyno       (99)    PDVELKSGAGTELSVRAKPS
129mouse  (100)    PDTEIQSGGGTEVYVLAKPS
chicken    (94)    DDVVFTRGGGTEVSVHA---
                    *    * ***  *
```

FIG. 2

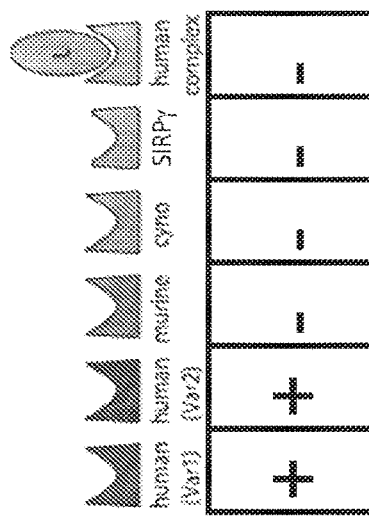
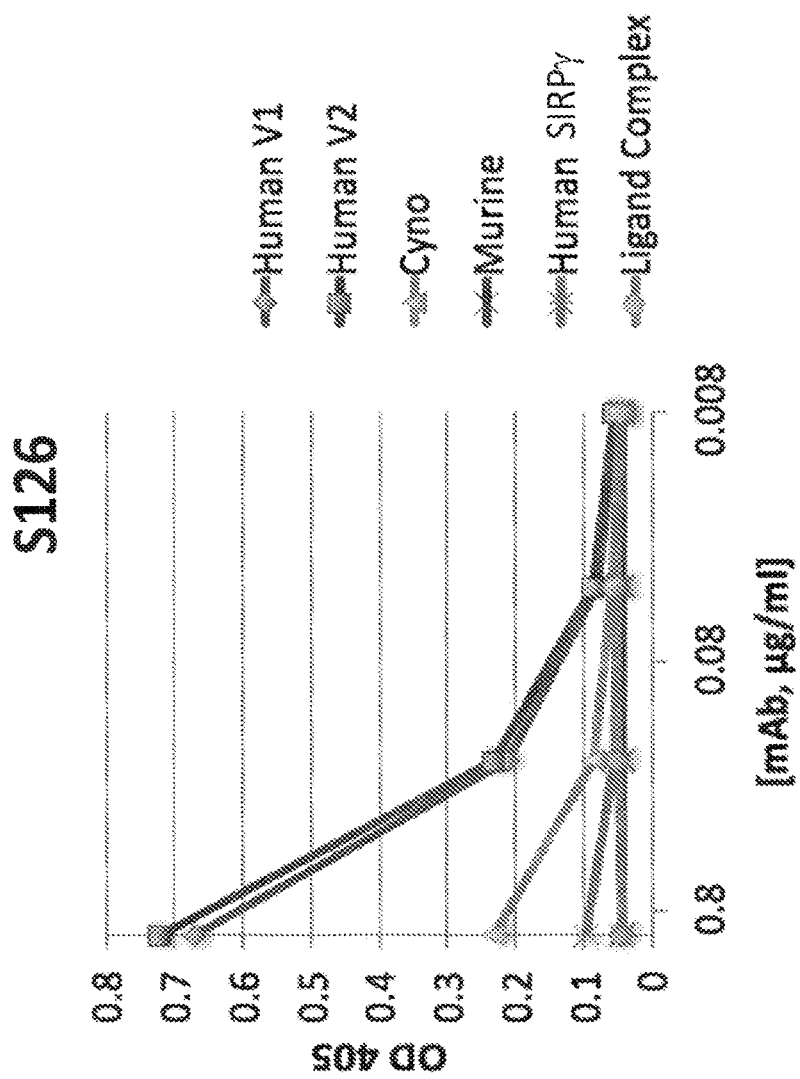
FIG. 8B
FIG. 8A

```
                    1                                                      50
S1   (1)   ALTQPASVSANPGETVEITCSGG-GSNNAYGWFQQKSPGSAPLTVIYDNG
S2   (1)   AVTQPASVSANPGETVRITCSG--DSSSYYSWHQQKSPGSAPVSVIYSNT
S8   (1)   AVTQPSSVSANPGETVEITCSG--SST-YGWYQQKSPGSAPVTVIYND-
S9   (1)   ALTQPSSVSANPGETVKITCSGDNSAHYYYGWYQQKSPGSAPVTVIYND-
S11  (1)   AVTQPASVSANPGETVKITCSG--SSSGSYGWYQQKSPGSAPVTLIYETN
S12  (1)   AVTQPASVSANPGETVKITCSG--DSS-YYGWYQQKSPGSAPVTVIYDDN
S13  (1)   AVTQPASVSANLGETVKITCSG--SSS-YYGWYRQKSPGSAPVTLIYDND
S14  (1)   AVTQPASVSANPGETVKITCSG--DSS-YYGWYQQKAPGSAPVTLIYDND
                *    *     *      *    *               *    **
                                L1

51                                                     100
S1   (50)  KRPSDIPSRFSGSKSDSTGTLTLITRVQAEDEAVYCGSADN-SGAGVFGA
S2   (49)  DRPSDIPSRFSGSASGSTATLTITGVQAEDEAVYFCGAYDSSSDSDIFGA
S8   (48)  KRPSDIPSRFSGSASGSTATLIITGVQVEDEAVYFCGNEDNN-YVAIFGA
S9   (51)  KRPSGIPSRFSGSSTHTLIITGVQVEDEAVYFCGSADSS-NPAIFGA
S11  (49)  KRPSNIPSRFSGSKSGSTATLIITGVQAEDEAVYFCGSEDSSTYLSIFGA
S12  (48)  KRPSDIPSRFSGSKSGSTGLTLITGVQADDEAVYFCGNEDNS-YVGIFGA
S13  (48)  KRPSGIPSRFSGSKSGSTNTLLIITGVQADDEAVYFCGNEDNS-YVGIFGA
S14  (48)  KRPSNIPSRFSGSKSGSTATLTITGVQADDEAVYYCGNEDMN-YVGIFGA
              *         *     *     *          *           ****
                L2                              L3
```

FIG. 10A

```
                          101                               linker                                150
S1   (99)   GTTLTVLGQSSRSSGGGGSSGGGGSMAAVTLDESGGGLQTPGGALSLVCK
S2   (99)   GTTLTVLGQSSRSSGGGGSSGGGGSMAAVTLDESGGGLQTPGGALSLVCK
S8   (97)   GTTLTVLGQSSRSSGGGGSSGGGGSMAAVTLDESGGGLQTPGGALSLVCK
S9   (100)  GTTLTVLGQSSRSSGGGGSSGGGGSMAAVTLDESGGGLQTPGRALSLVCK
S11  (99)   GTTLTVLGQSSRSSGGGGSSGGGGSMAAVTLDESGGGLQTPGGALSLVCR
S12  (97)   GTTLTVLGQSSRSSGGGGSSGGGGSMAAVTLDESGGGLQTPGGALSLVCK
S13  (97)   GTTLTVLGQSSRSSGGGGSSGGGGSMAAVTLDESGGGLQTPGGALSLVCK
S14  (97)   GTTLTVLGQSSRSSGGGGSSGGGGSMAAVTLDESGGGLQTPGGALSLVCK
                                                      **         *

151       H1                                H2               200
S1   (149)  GSGFTFSSHAMNWVRQAPGKGLEWVAGISS----DGRFTYYGAAVQGRAT
S2   (149)  ASGFDFSNFNMAWVRQGPGKGLEYVAEISD----TGSTPYYGSAVQGRAT
S8   (147)  ASGFTFSSYNMGWVRQAPGKGLEFVAGIYASGSSTDTDTTYGPAVAGRAT
S9   (150)  GSGFSISSYNMGWVRQAPGKGLEFIASIGS----DGSSTHYAPAVKGRAT
S11  (149)  ASGFTFSSFNMGWVRQAPGKGLEFVAAIYS-----GNSAEYGAAVQGRAT
S12  (97)   ASGFTFSSYNMGWVRQAPGKGLEFVAGIYI--ASGDLGTTYGAAVQGRAT
S13  (97)   ASGFTFSSYNMGWVRQAPDKGLEFVAGIYTG-SDAGLSTTYGAAVQGRAT
S14  (97)   ASGFTFNSYNMGWVRQAPGKGLEFVAGIYS--AGGDTSTTYGAAVNGRAT
                *   *   *     *   *    *       *                **
```

FIG. 10B

```
                            H3
       201                                                            250
S1  (195) ISRDNGQSTVRLQLNNLRAEDTATYYCTKNGG----CGSGGDLDCIDAW
S2  (195) ISRDNGQSTVRLQLNNLRAEDTGTYFCTRN-------FGSSVSSIDAW
S8  (197) ISRDNGQSTVRLQLNNLRAEDTGTYYCAKAAGGCSTHTCTAYIADSIDAW
S9  (196) ITRDVGQSTVRLQLNNLRAEDTGTYYCAKDAYQCS-YATCNDYLDTIDAW
S11 (194) ISRDNGQSTVRLQLNNLRAEDTGIYFCAKDTGTYFCAKDAG-SGCYSGVCAGTSSIDAW
S12 (195) ISRDDGQSTVRLQLNNLRAEDTGTYFCAKSAGGCSAHSCDTYIADSIDAW
S13 (196) ISRDNGQSTVRLQLNNLGAEDTGIYFCTKSAGGCSDYNCDAYIADSIDAW
S14 (195) ISRDNGQSTVRLQLNNLRAEDTGIYFCAKAAGGCTAHNCDAYIADSIDAW
               *              *      *   * ****************

251    261
S1  (240) GHGTEVIVSSS
S2  (236) GHGTEVIVSSS
S8  (247) GHGTEVIVSSS
S9  (245) GHGTEVIVSSS
S11 (243) GHGTEVIVSSS
S12 (245) GHGTEVIVSSS
S13 (246) GHGTEVIVSSS
S14 (245) GHGTEVIVSSS
```

FIG. 10C

```
                                                    L1
              1                                                         50
S115  (1)   ETVLTQSPATLSVSPGERATLSCRASQTVG-SKLAWHQQKPGQAPRLLIY
S116  (1)   ETVLTQSPATLSVSPGERATLSCRASQTVG-SKLAWHQQKPGQAPRLLIY
S117  (1)   ETVLTQSPATLSVSPGERATLSCRASQTVG-SKLAWHQQKPGQAPRLLIY
S118  (1)   ETVLTQSPATLSVSPGERATFSCRASQTVG-SKLAWHQQKPGQAPRLLIY
S119  (1)   ETVLTQSPATLSVSPGERATFSCRASQNVK-NDLAWYQQRPGQAPRLLIY
S120  (1)   ETVLTQSPATLSVSPGERATFSCRASQNVK-NDLAWYQQRPGQAPRLLIY
S122  (1)   ETVLTQSPATLSVSPGERATFSCRASQNVK-NDLAWYQQRPGQAPRLLIY
S123  (1)   EIVLTQSPGTLSVSPGERVTLTCRASQGIAG-KIAWYQQKPGQAPRLLIY
S126  (1)   EIVLTQSPGTLSVSPGERATLSCRASQSIGSSYLAWYQQKPGQAPRLLIY
S128  (1)   ETVLTQSPATLSVSPGERATLSCRASQNVR-SDLAWYQQKPGQAPRLLIY
S130  (1)   EIVLTQSPGTLTLSPGERVTFSCRASQNVR-SDIAWYQQKPGQAPRLLIY
S135  (1)   ETVLTQSPGTLTLSPGERATLTCRASQSVY-TYLAWYQEKPGQAPRLLIY
S137  (1)   EIVLTQSPGERVLLTCRASQSVDTYNLAWYQQKPGQAPRLLIY
S138  (1)   
              *  ****   **  ****   *******      ****  ******

51          L2                               L3    100
S115  (50)  DATNRATGISDRFSGSGSGTDFTLTISSLQTEDSAVYYCQQYYWPPYRF
S116  (50)  DATNRATGISDRFSGSGSGTDFTLTISSLQTEDSAVYYCQQYYWPPYRF
S117  (50)  DATNRATGIPDRFSGSGSRSGTDFTLTISSLQTEDSAVYYCQQYYWPPYRF
S118  (50)  DASRRATGIPDRFSGSGSGTDFTLTISSLQTEDSAVYYCQQYYWPPYRF
S119  (50)  AARIRETGIPERFSGSGSGTEFTLTITSLQSEDFAVYYCQQYYDWPFTF
S120  (50)  AARIRETGIPERFSGSGSGTEFTLTITSLQSEDFAVYYCQQYYDWPFTF
S122  (50)  AARIRETGIPERFSGSGSGTEFTLTITSLQSEDFAVYYCQQYYDWPFTF
S123  (50)  DASSRATGIPGRFSGSGSGTEFTLTITSLQSEDFAVYYCQQHYDWSPLTF
S126  (50)  DATNRATGIPDRFSGSGSGTEFTLTITSLQSEDFAVYYCQQYYWPPYRF
S128  (51)  DASNRATGIPDRFSGSGSGTEFTLTITSLQSEDFAVYYCQQYYDWPPVTF
S130  (50)  DANTRATDIPDRFSGSGSGTEFTLTITSLQSEDFAVYYCQHYDWPFTF
S135  (50)  AASSRDTGIPDRFSGSGSGTEFTLTITSLQSEDEGVYYCQQYYDWPFTF
S137  (50)  GASSRATGIPDRFSGSGSGTVFTLTITSLQSEDFAVYYCQQYDRPLTF
S138  (51)  DLSTRATGIPDRFSGSGSGTEFTLTINSLEPEDFAVYYCHQYYDWPYTF
              *      *  ****** **  ***  *  *    *  *  **
```

```
                    201                                                       250
S115 (200) NSENTLYLQMNSLRAEDTAVYYCAKQY----DWNSFFDYWGLGALVTIVSSS
S116 (200) NSENTLYLQMNSLRAEDTAVYYCAKQY----DWNSFFDYWGLGALVTIVSSS
S117 (200) NSENTLYLQMNSLRAEDTAVYYCAKQY----DWNGFFDYWGLGALVTIVSSS
S118 (200) NSKNTLYLQMNSLRAEDTAVYYCAKQY----DWNGFFDYWGLGALVTIVSSS
S119 (198) NSKNTLYLQMNSLRAEDTAVYYCAKDSTVSWSGDFFDYWGLGTLVTIVSSS
S120 (198) NSKNTLYLQMNSLRAEDTAVYYCAKDSTVSWSGDEFFDYWGLGTRVTIVSSS
S122 (198) NSKNTLYLQMNSLRAEDTAVYYCAKDSTVSWSGDFFDYWGLGTLVTIVSSS
S123 (199) NSKNTLYLQMNSLRAEDTAIYYCAKVT----WNN-FFDYWGLGTLVTIVSSS
S126 (201) NSKNTLYLQMNSLRAEDTAVYYCAKMN----RWW--FDYWGLGTLVTIVSSS
S128 (200) NSKNTLYLQMNSLRAEDTAVYYCAKQY----DWNSFFDYWGLGAPVTIVSSS
S130 (200) NSKNTLYLQMNSLRAEDTAVYYCAKDGAAHYYDIFFDYWGLGTPVTIVSSS
S135 (198) NSKNTLYLQMNSLRAEDTAVYYCAKDSTVGWSGDFFDYWGLGTLVTIVSSS
S137 (200) NSKNTLYLQMNSLRAEDTAVYYCAKEN----NRYRFFDDWGLGTLVTIVSSS
S138 (201) NSKNTLYLQMNSLRAEDTAIYYCAKGT----WNYGSFDYWGLGTLVTIVSSS
                *              *             ********   **   **
                                         H3
```

```
                    61  H2                                                          H3                              119
S16    (60) VDSVKGRFTISRDNS-KNTLYLQVNSLTAEDTAIYYCARETWNHLFDYWGLGTLVTVSS
S27    (60) VDSVKGRFTISRDNS-KNTLYLQVNSLTAEDTAIYYCARETWNHLFDYWGLGTLVTVSS
S55    (60) VDSVKGRFTISRDNS-KNTLYLQVNSLTAEDTAIYYCARETWNHLFDYWGLGTLVTVSS
S59    (60) VDSVKGRFTISRDNS-KNTLYLQVNSLTAEDTAVYYCARETWNHLFDYWGLGTLVTVSS
S29    (60) VDSVKGRFTISRDNS-KNTLYLQVNSLTAEDTAVYYCARETWNHLFDYWGLGTMVTVSS
S201   (61) ADSVKGRSTISRDNS-KNTLYLRMSSLTAEDTAVYYCARETWNHLFDYWGLGTLVTVSS
S206   (61) ADSVKGRSTISRDNS-KNTLYLRMSSLTAEDTAVYYCARETWNHLFDYWGLGTLVTLSS
S26    (61) GDSVKGRFTMSRDNS-KNTLYLQMNSLTAEDTAVYYCARETWNHLFDYWGLGTLVTVSS
S25    (60) GDSVKGRLTISRDNS-KNILYLQMNSLTAEDTAVYYCARETWNHLFDYWGLGTLVTVSS
S73    (60) GDSVKGRLTISRDNS-KNILYLQMNSLTAEDTAVYYCARETWNHLFDYWGLGTLVTVSS
S30    (60) GGSVKGRFTISRDNS-KNTLYLQMNSLTAEDTAVYYCARETWNHLFDYWGLGTLVTVSS
S28    (60) SGSMKGRFTISRDNS-KNTLYLQMNSLTAEDTAVYYCARETWNHLFDYWGLGTLVTVSS
S21    (61) PASVKGRFTISRDNP-KNTLYLQMNTLTAEDTAVYYCARETWNHLFDYWGLGTLVTVSS
S24    (61) PASVKGRFTISRDNP-KNTLYLQMNTLTAEDTAVYYCARETWNHLFDYWGLGTLVTVSS
S74    (61) PASVKGRFTISRDNP-KNTLYLQMNTLTAEDTAVYYCARETWNHLFDYWGLGTLVTVSS
S23    (61) IDSVKGRFTISRDNS-KSSLYLRMNSLTAEDTAVYYCARETWNHLFDYWGLGTLVTVSS
S17    (61) IDSVKGRFTISRRDNS-ENSLYLQMNSLTAEDTAVYYCARETWNHLFDYWGLGTLVTVSS
S22    (61) IDSVKGRFTISRRQFQEQSLSPNEPALTAEDTAVYYCARETWNHLFDYWGLGTLVTVSS
S66    (61) IDSVKGRFTISRDNP-KNSLYLQMNSLTAEDTAVYYCARETWNHLFDYWGLGTLVTVSS
S56    (61) IDSVKGRFTISRDNS-KNSLYLQMNSLTAEDTAVYYCARETWNHLFDYWGLGTLVTVSS
S70    (61) IDSVKGRFTISRDNS-KNSLYLQMNSLTAEDTAVYYCARETWNHLFDYWGLGTLVTVSS
S202   (61) IDSVKGRFTISRDNS-KNSLYLQMNSLTAEDTAVYYCARETWNHLFDYWGLGTLVTVSS
S60    (61) IDSVKGRFTISRDNS-KNSLYLQMNSLTAEDTAVYYCARETWNHLFDYWGLGTLVTVSS
S65    (61) IDSVKGRFTISRDNS-KNSLYLQMNSLTAEDTAVYYCARETWNHLFDYWGLGTLVTVSS
S69    (61) IDSVKGRFTISRDNS-KNSLYLQMNSLTAEDTAVYYCARETWNHLFDYWGLGTLVTVSS
S71    (61) IDSVKGRFTISRDNS-KNSLYLQMNSLTAEDTAVYYCARETWNHLFDYWGLGTLVTVSS
S76    (61) IDSVKGRFTISRDNS-KNSLYLQMNSLTAEDTAVYYCARETWNHLFDYWGLGTLVTVSS
              **   * *    *          *    *       *   *****************  *
```

FIG. 11C

```
                           L1                                    L2
         1                                                            54
S16  (1) ALTQPASVSANLGETVKITCSGGDSSSHYYGWYQQKSPGSAPVTTVIYSDDERPS
S59  (1) ALTQPASVSANLGETVKITCSGGDSSSHYYGWYQQKSPGSAPVTTVIYSDDERPS
S27  (1) ALTQPASVSADLGETVKITCSGGDSSSHYYGWYQQKSPGSAPVTTVIYSDDERPS
S55  (1) ALTQPASVSANLGETVEITCSGGDSSSHYYGWYQQKSPGSAPVTTVIYSDDERPS
S29  (1) ALTQPASVSANLGETVKITCSGGDSSSHYYGWFQQKSPGSAPVTTVIYSDDERPS
S26  (1) ALTQPASVSANLGGTVEITCSGGSSS--YYGWYQQKSPGSAPVTTVIYSDNQRPS
S21  (1) ALTQPASVSANPGETVKITCSGGDYYSYYYGWYQQKAPGSALVTTVIYSDDKRPS
S24  (1) ALTQPASVSANPGETVKIACSGGSYYSYYYGWYQQKSPGSALVTTVIYSDDKRPS
S74  (1) ALTQPASVSANPGETVKIACSGGSYYSYYYGWYQQKSPGSAPVTLIYSDDKRPS
S25  (1) ALTQPASVSANPGETVEITCSGGSYYSYYYAWYQQKSPGSAPVTLIYSDDKRPS
S73  (1) ALTQPASVSANPGETVEITCSGGSYYSYYYGWYQQKSPGSAPVTTVIYSDNKRPS
S30  (1) ALTQPASVSANPGETVKITCSGGIYYSYYYGWYQQKSPGSAPVTTVIYSDDQRPP
S28  (1) ALTQPASVSASPGETVKITCSGG-SDSYYYGWHQQKSPGSAPVTVIYSDDQRPP
S201 (1) ALTQPASVSANPGETVKITCSGG-GTSSYYGWYQQKSPGSAPVTTVIHSDDKRPS
S206 (1) ALTQPASVSANPGETVKITCSGG-GTSSYYGWYQQKSPGSAPVTILIHSDDKRPS
S22  (1) ALTQPASVSANPGETVKITCSGGDYYSTYYGWYQQKSPGSAPVTTVIHSDDKRPS
S60  (1) ALTQPASVSANPGETVKITCSGGDYYSTYYGWYQQKSPGSAPVTTVIHSDDKRPS
S65  (1) ALTQPASVSANPGETVKITCSGGDYYSTYYGWYQQKSPGSAPVTTVIHSDDKRPS
S69  (1) ALTQPASVSANPGETVKITCSGGDYYSTYYGWYQQKSPGSAPVTTVIHSDDKRPS
S23  (1) ALTQPASVSANPGETVKITCSGGDYYSTYYAWYQQKSPGSAPVTTVIHSDDERPS
S66  (1) ALTQPASVSANPGETVKITCSGGDWYSTYYGWYQQKSPGSAPVTTVIHSDDKRPS
S17  (1) ALTQPASVSANPGETVKITCSGGDWYSTYYGWYQQKSPGSAPVTTVIHSDDKRPS
S70  (1) ALTQPASVSANPGETVKITCSGGGYYSTYYGWYQQRSPGSAPVTTVIHSDDKRPS
S76  (1) ALTQPASVSANPGETVKITCSGGGYYSTYYGWYQQKSPGSAPVTTVIHSDDKRPS
S202 (1) ALTQPASVSANPGETVKITCSGGGYYSTYYGWYQQKSPGSAPVTTVIHSDDKRPS
S56  (1) ALTQPASVSANPGETVKITCSGGGYYSTYYGWYQQKSPGSAPVTTVIHSDDKRPS
S71  (1) ALTQPASVSANPGETVKITCSGGGYYSTYYGWYQQKSPGSAPVTTVIHSDDKRPS
         *  *   *   *    *         **    **  *   *    *     *
```

FIG. 11D

```
                                                          L3
       55                                                                             107
S16 (55) DIPSRFSGSASGSTATLTITGVRVEDEAIYYCGAYDGSTYANTFGAGTTLTVL
S59 (55) DIPSRFSGSASGSTATLTITGVRVEDEAIYYCGAYDGSTYANTFGAGTTLTVL
S27 (55) DIPSRFSGSASGSTATLTITGVRVEDEAIYYCGAYDGSTYANTFGAGTTLTVL
S55 (55) DIPSRFSGSASGSTATLTITGVRVEDEAIYYCGAYDGSTYANTFGAGTTLTVL
S29 (53) DIPSRFSGSASDSTATLTITGVRVEDEAIYYCGAYDGSTYANTFGAGTTLTVL
S26 (55) DIPSRFSGSASGSTATLTITGVQVEDEAIYYCGGYDSSTYANTFGAGTTLTVL
S21 (55) DIPSRFSGSASGSTATLTITGVRAEDEAVYYCGGYDYSSTYANAFGAGTTLTVL
S24 (55) GIPSRFSGSASGSTATLTITGVRAEDEAVYYCGGYDYSSTYNDFGAGTTLTVL
S74 (55) GIPSRFSGSASGSTATLTITGVRAEDEAVYFCGGYDQSSYTNPFGAGTTLTVL
S25 (55) NIPSRFSGSASGSTATLTITGVRVEDEAVYYCGGYDYSTYTNPFGAGTTLTVL
S73 (55) NIPSRFSGSASGSTATLTITGVRVEDEAVYYCGGYDYSTYTNPFGAGTTLTVL
S30 (54) DIPSRFSGSASGSTATLTITGVQVEDEAVYYCGGYDYTTYVNTFGAGTTLTVL
S28 (54) DIPSRFSGSASGSTATLTITGVRVEDEAVYYCGGYDYTTYVNTFGAGTTLTVL
S201 (55) DIPSRFSGSASGSAATLTITGVRVEDEAVYFCGAYDGRTYINTFGAGTTLTVL
S206 (55) DIPSRFSGSASGSAATLTIAGVRVEDEAVYFCGAYDGRTYINTFGAGTTLTVL
S22 (55) DIPSRFSGSASGSAATLTITGVRVEDEAVYFCGAYDGRTYINTFGAGTTLTVL
S60 (55) DIPSRFSGSASGSAATLTITGVRVEDEAVYFCGGYDGRTYINTFGAGTTLTVL
S65 (55) DIPSRFSGSASGSAATLTITGVRVEDEAVYYCGGYDGRTYINTFGAGTTLTVL
S69 (55) DIPSRFSGSASGSAATLTITGVRVEDEAVYYCGGYDGRTYINTFGAGTTLTVL
S23 (55) DIPSRFSGSASGSAATLTITGVRVEDEAVYYCGGYDGRTYINTFGAGTTLTVL
S66 (55) DIPSRFSGSASGSAATLTITGVRVEDEAVYYCGGYDGRTYINTFGAGTTLTVL
S17 (55) DIPSRFSGSASGSAATLTITGVRVEDEAVYYCAGYDGRTYINTFGAGTTLTVL
S70 (55) DIPSRFSGSASGSAATLTITGVRVEDEAVYYCAGYDGRTYINTFGAGTTLTVL
S76 (55) DIPSRFSGSASGSAATLTITGVRVEDEAVYYCAGYDGRTYLNTFGAGTTLTVL
S202 (55) DIPSRFSGSASGSAATLTITGVRVEDEAVYYCAGYDGRTYINTFCAGTTLTVL
S56 (55) DIPSRFSGSASGSAATLTITGVRVEDEAVYYCAGYDARTYINTFGAGTTLTVL
S71 (55) *            *     *       *   **  *         *
```

FIG. 11E

|  | | H1 | H2 | 60 |
|---|---|---|---|---|
| 136 | (1) | DVQLVESGGGVVRPGESLRLSCAASGFTFSSYDMNWVRQAPGEGLEWVSLISGSGEIYY |
| 137 | (1) | DVQLVESGGGVVRPGESLRLSCAASGFTFSSYDMNWVRQAPGEGLEWVSLISGSGEIYY |
| S185 | (1) | DVQLVESGGGVVRPGESLRLSCAASGFTFSTSYDMNWVRQAPGEGLEWVSLISGSGEIYY |
| S175 | (1) | DVQLVESGGGVVRPGESLRLSCAASGFTFSTSYDMNWVRQAPGEGLEWVSLISGSGEIYY |
| S189 | (1) | DVQLVESGGGVVRPGESLRLSCAASGFTFSSSYDMNWVRQAPGEGLEWVSLISGSGEIYY |
| S193 | (1) | DVQLVESGGGVVRPGESLRLSCAASGFTFSSYDMNWVRQAPGEGLEWVSLISGSGEIYY |
| S180 | (1) | DVQLVESGGGVVRPGESLRLSCAASGFTFSSYDMNWVRQAPGEGLEWVSLISGSGEIYY |
| S177 | (1) | DVQLVESGGGVVRPGESLRLSCAASGFTFSSYDMNWVRQAPGEGLEWVSLISGSGEIYY |
| S178 | (1) | DVQLVESGGGVVRPGESLRLSCAASGFTFSSYDMNWVRQAPGEGLEWVSLISGSGEIYY |
| S184 | (1) | DVQLVESGGGVVRPGESLRLSCAASGFTFSSYDMNWVRQAPGEGLEWVSLISGSGEIYY |
| S190 | (1) | DVQLVESGGGVVRPGESLRLSCAASGFTFSSYDMNWVRQAPGEGLEWVSLISGSGEIYY |
|  |  |  | * |  |

|  | 61 | H2 | H3 | 119 |
|---|---|---|---|---|
| 136 | (61) | ADSVKGRFTISRDNSKNTLYLQMNSLRAEDTAVYYCAKENNRYRFFDYWGLGTLVTVSS |
| 137 | (61) | ADSVKGRFTISRDNSKNTLYLQMNSLRAEDTAVYYCAKENNRYRFFDDWGLGTLVTVSS |
| S185 | (61) | ADSVKGRFTISRDNSKNTLYLQMNSLRAEDTAVYYCAKENNRYRFFDDWGLGTLVTVSS |
| S175 | (61) | ADSVKGRFTISRDNSKNTLYLQMNSLRAEDTAVYYCAKENDRYRFFDYWGLGTLVTVSS |
| S189 | (61) | ADSVKGRFTISRDNSKNTLYLQMNSLRAEDTAVYYCAKENDRYRFFDYWGLGTLVTVSS |
| S193 | (61) | ADSVKGRFTISRDNSKNTLYLQMNSLRAEDTAIYYCAKENDRYRFFDYWGLGTLVTVSS |
| S180 | (61) | ADSVKGRFTISRDNSKNTLYLQMNSLRAEDTAVYYCAKENNMYRFFDYWGLGTLVTVSS |
| S177 | (61) | ADSVKGRFTISRDNSKNTLYLQMNSLRAEDTAVYYCAKENNRYRFFDYWGLGTLVTVSS |
| S178 | (61) | ADSVKGRFTISRDNSKNTLYLQMNSLRAEDTAVYYCAKENNRYRFFDYWGLGTLVTVSS |
| S184 | (61) | ADSVKGRFTISRDNSKNTLYLQMNSLRAEDTAVYYCAKENNRYRFFDYWGLGTLVTVSS |
| S190 | (61) | ADSVKGRFTISRDNSKNTLYLQMNSLRAEDTAVYYCAKEDNRYRFFDYWGLGALVTVSS |
|  |  | * | *** | * |

FIG. 11F

```
                                                              L1                                 L2   54
S136   (1) ETVLTQSPGTLTLSPGERATLTCRASQSVTYLAWYQEKPGQAPRLLIYGASSR
S137   (1) ETVLTQSPGTLTLSPGERATLTCRASQSVTYLAWYQEKPGQAPRLLIYGASSR
S175   (1) ETVLTQSPGTILSLSPGERATLTCRASQSVTYLAWYQERPGQAPRLLIYGASSR
S177   (1) KTVLTQSPGTLSLSPGERATLTCRADQSVTYLAWYQERPGQAPRLLIYGASSR
S184   (1) ETVLTQSPGTLSLSPGERATINCRASQSVTYLAWYQERPGQAPRLLIYDASSR
S185   (1) ETVLTQSPGTLSLSPGERATINCRASQSVYSYLAWYQERPGQAPRLLIYGASTR
S189   (1) ETVLTQSPGTLSLSPGERATLSCRASQSVTYLAWYQKPGQPPRLLIHAARNR
S193   (1) ETVLTQSPGTLSLSPGERATLSCRASQSVTYLAWYQEKPGQAPRLLIYAASTR
S178   (1) ETVLTQSPGTLTLSPGERATLTCRASQSVTYLAWYQEKPGQAPRLLIYGASSR
S180   (1) ETVLTQSPGTLTLSPGERTTLTCRASQSVTYLAWYQEKPGQAPRLLIYGASSR
S190   (1) ETVLTQSPGTLTLSPGERATLTCRASQSVTYLAWYQEKPGQAPRLLIYGASSR
           *      *    *      *    *     * *    *      *

L3                              108
S136  (55) ATGIPDRFSGSGSGTEFTLTISSLQSEDFAVYYCQQYYDRPPLTFGGGTKVEIK
S137  (55) ATGIPDRFSGSGSGTEFTLTISSLQSEDFAVYYCQQYYDRPPLTFGGGTKVEIK
S175  (55) AAGIPDRFSGSGSGTEFTLTISSLQSEDFAVYYCQQYYDRPPLTFGGGTKVEIK
S177  (55) ATGIPDRFSGSGSGTVFTLTISSLQSEDFAVYYCQQYYDRPPLTFGGGTKVEIK
S184  (55) ATGIPDRFSGSGSGTEFTLTISSLQSEDFAVYYCQQYYDRPPLTFGGGTKVEIK
S185  (55) ATGIPDRFSGSGSGTEFTLTISSLESDFAVYYCQQYYDRPPLTFGGGTKVEIK
S189  (55) AAGIPDRFSGSGSGTEFTLTISSLQSEDFAVYYCQQYYDRPPLTFGGGTKVEIK
S193  (55) ATGIPDRFSGSGSGTEFTLTISSLQSEDFAVYYCQQYYDRPPLTFGGGTKVEIK
S178  (55) ATGVPDRFSGSGSGTEFTLTISSLQSEDFAVYYCQQYYDRPPLTFGGGTKVEIK
S180  (55) ATGIPDRFSGSGSGTEFTLTISSLQSEDFAVYYCQQYYDRPPLTFGGGTKVEIK
S190  (55) ATGIPDRFSGSGSGTEFTLTISSLQSEDFAVYYCQQYYDRPPLTFGGGTKVEIK
              *               *      *    *
```

FIG. 11G

|  |  | 1 |  |  |  | H1 |  |  | H2 | 60 |
|---|---|---|---|---|---|---|---|---|---|---|
| S115 | (1) | DVQLVESGGGVVRPGESLRLSCAASGFSFSSYAMNWVRQAPGEGLEWVSRINSGGGGTDY |
| S116 | (1) | DVQLVESGGGVVRPGESLRLSCAASGFSFSSYAMNWVRQAPGEGLEWVSRINSGGGGTDY |
| S117 | (1) | DVQLVESGGGVVRPGESLRLSCAASGFSFSSYAMNWVRQAPGEGLEWVSRINSGGGGTDY |
| S118 | (1) | DVQLVESGGGVVRPGESLRLSCAASGFSFSSYAMNWVRQAPGEGLEWVSRINSGGGGTDY |
| S132 | (1) | DVQLVESGGGVVRPGESLRLSCAASGFSFRSYAMNWVRQAPGEGLEWVSRINSGGGGTDY |
| S191 | (1) | DVQLVESGGGVVRPGESLRLSCAASGFESSYAMNWVRQAPGEGLEWVSRINSGGGGTDY |
| S198 | (1) | DVQLVESGGGVVRPGESLRLSCAASGFSFSSHAMNWVRQAPGEGLEWVSRINSGGGGTDY |
|  |  |  |  |  |  | * |  |  |  |  |

|  |  | 61 |  |  |  |  |  | H3 |  | 119 |
|---|---|---|---|---|---|---|---|---|---|---|
| S115 | (61) | AESVKGRFTISRDNSENTLYLQMNSLRAEDTAVYYCAKQYDWNSFFDYWGLGALVTVSS |
| S116 | (61) | AESVKGRFTISRDNSENTLYLQMNSLRAEDTAVYYCAKQYDWNSFFDYWGLGALVTVSS |
| S117 | (60) | AESVKGRFTISRDNSENTLYLQMNSLRAEDTAVYYCAKQYDWNGFFDYWGLGALVTVSS |
| S118 | (61) | AESVKGRFTISRDNSKNTLYLQMNSLRAEDTAVYYCAKQYDWNGFFDYWGLGALVTVSS |
| S132 | (61) | ADSVKGRFTISRDNSENTLYLQMNSLRAEDTAVYYCAKQYDWNGFFDYWGLGALVTVSS |
| S191 | (61) | AESVKGRFTISRDNSENTLYLQMNSLRAEDTAVYYCAKQYDWNGFFDYWGLGALVTVSS |
| S198 | (61) | AESVKGRFTISRDNSENTLYLQMNSLRAEDTAVYYCAKQYDWNGFFDYWGLGALVTVSS |
|  |  | * |  |  |  | * |  |  | * |  |

FIG. 11H

```
                1  ETVLTQSPATLSVSPGERATLSCRASQTVGSKLAWHQQKPGQAPRLLIYDATNR
                        L1                                    L2   54
S115  (1)  ETVLTQSPATLSVSPGERATLSCRASQTVGSKLAWHQQKPGQAPRLLIYDATNR
S116  (1)  ETVLTQSPATLSVSPGERATLSCRASQTVGSKLAWHQQKPGQAPRLLIYDATNR
S117  (1)  ETVLTQSPATLSVSPGERATLSCRASQTVGSKLAWHQQKPGQAPRLLIYDATNR
S118  (1)  ETVLTQSPATLSVSPGERATLSCRASQTVGSKLAWHQQKPGQAPRLLIYDASRR
S132  (1)  ETVLTQSPATLSVSPGERATLSCRASQTVGSKLAWHQQKPGQAPRLLIYDASNR
S191  (1)  ETVLTQSPATLSVSPGERATLSCRASQTVGSKLAWHQQKPGQAPRLLIYDATNR
S198  (1)  ETVLTQSPATLSVSPGERATLSCRASQTVGSKLAWHQQKPGQAPRLLIYDATNR
                                                            **

55  ATGIPDRFSGSGSGTDFTLTISSLQTEDSAVYYCQQYYWPPYRFGGGTKVEIK
                                                   L3                108
S115 (55)  ATGISDRFSGSGSGTDFTLTISSLQTEDSAVYYCQQYYWPPYRFGGGTKVEIK
S116 (55)  ATGISDRFSGSGSGTDFTLTISSLQTEDSAVYYCQQYYWPPYRFGGGTKVEIK
S117 (55)  ATGISDRFSGSGSRSGTDFTLTISSLQTEDSAVYYCQQYYWPPYRFGGGTKVEIK
S118 (55)  ATGIPDRFSGSGSGTDFTLTISSLQTEDSAVYYCQQYYWPPYRFGGGTKVEIK
S132 (55)  ATGIPDRFSGSGSGTDFTLTISSPQTEDSAVYYCQQYYWPPYRFGGGTKVEIK
S191 (55)  ATGIPDRFSGSGSGTDFTLTISGLQTEDSAVYYCQQYYWPPYRFGGGTKVEIK
S198 (55)  ATGIPDRFSGSGSGTDFTLTISSLQTEDSAVYYCQQYYWPPYRFGGGTKVEIK
               *                     **
```

FIG. 11I

```
                                                                    H1                                H2    60
S173  (1)  DVQLVESGGGGVRPGESLRLSCAASGFAFSDHDMSWVRQGPGEGLEWVAGISLRGGVTWY
S174  (1)  DVQLVESGGGGVRPGESLRLSCAASGFTFSDHDMSWVRQGPGEGLEWVAGISLRGGVTWY

118
S173 (61)  ADSVKGRFTISRDNSKNTLYLRLFSLRTEDTAIYCARESWNTFFDYWGLGTLVTVSS
S174 (61)  ADSVKGRFTISRDNSKNTLYLRLFSLRTEDTAIYCARESWNTFFDYWGLGTLVTVSS
                                    *                            H3

L1                                    L2    55
S173  (1)  EIVLTQSPGTLSLSPGETATLSCRASQNVRSNLAWYQQKPGQAPRLLIYDASSRA
S174  (1)  EIVLTQSPGTLSLSPGETATLSCRASQNVRSNLAWYQQKPGQAPRLLIYDASSRA

L3          108
S173 (56)  TGIPDRFSGSGSGTDFTLTISSLQSEDFAVYYCQQYGNGPPLTFGGGTKVEIK
S174 (56)  TGIPDRFSGSGSGTDFTLTISSLQSEDFAVYYCQQYGNGPPLTFGGGTKVEIK
```

FIG. 11J

```
                                                                              H1                                H2      60
S213   (1)  DVQLVESGGGVVRPGESLRLSCEASGFTERNYYMTWVRQAPGEGLEWVSTISDTGDTAYY
S214   (1)  DVQLVESGGGVVRPGESLRLSCEASGFTERNSYMTWVRQAPGEGLEWVSTISDTGDTAYY
                                     *
                                                                H3                             119
S213  (61)  ADSVKGRFTISRDNSKNSLYLQMNSLRADDTAIYYCAKSWIWTFFDYWGLGTLVTVSS
S214  (61)  ADSVKGRFTISRDNSKNSLYLQMNSLRAEDTAIYYCAKSWIWTFFDYWGLGTLVTVSS
                                              *

L1                                         L2         55
S213   (1)  ALTQPASVSANLGGTVEITCSGGNSNHYGWYQQKSPGSAPVTLIYADTNRPSNIP
S214   (1)  ALTQPASVSANLGGTVEITCSGGNSNHYGWYQQKSPGSAPVTLIYADTNRPSNIP

L3                     103
S213  (56)  SRFSGSTSGSTTTLTITGVQAEDEAVYYCGGSSTGDGIFGAGTTLTVL
S214  (56)  SRFSGSTSGSTTTLTITGVQAEDEAVYYCGGSSTGDGIFGAGTTLTVL
                                     *
```

FIG. 11K

>209_VH
DVQLVESGGAVVRPGESLRLSCKASGFTFTNFAMSWVRQAPGEGLEWVSGISGSDDTTYYA
DSVKGRFTISRDNSESTLYLQMNSLRAEDTAVYYCVKDSTVSWNTFFDYWGLGTLVTVSS

>209_VL
ALTQPASVSANLGGTVKITCSGGYGSDDGSSSYYGWYQQKSPGSAPVILIYWDDKRPSDIP
SRFSGSTSGSTTTLTITGVQAEDEAVYFCGTYDTSSGAIFGAGTTLTVL

FIG. 11L

```
                                                                                            H1                                          H2   59
S123  (1)   DVQLVESGGGLVQPGGSLRLSCTASGFTFRNYGMSWVRQAPGEGLEWVSASSGSGSTYY
S194  (1)   DVQLVESGGGVVRPGESLRLSCAASGFTFRNYGMSWVRQAPGEGLEWVSASSGSGSTYY
                         *              *

H3                              117
S123  (60)  TDSVKGRFTISRDNSKNTLYLQMNSLRAEDTAIYYCAKVTWNNFFDYWGLGTLVTVSS
S194  (60)  ADSVKGRFTISRDNSKNTLYLQMNSLRAEDTAIYYCAKVTWNNFFDYWGLGTLVTVSS
            *

L1                           L2
S123  (1)   EIVLTQSPGTLSVSPGERVTLTCRASQGIAGKIAWYQQKPGQAPRLLIYDASSRATGIP
S194  (1)   EIVLAQSPDTLSVSPGERATLTCRASQDVAGKLAWYQQKPGQAPRLLIHATSSRADGIP
                *   *           *       *   * *                  * ***

L3                          108
S123  (60)  GRFSGSGSGTEFTLTITSLQSEDFAVYYCQQHYDWSPLTFGGGTKVEIK
S194  (60)  ARFSGSGSGTEFTLTITGLQSEDFAVYYCQQHYDWSPLTFGGGTKVEIK
            *                *
```

FIG. 11M

```
                              H1                                          H2      59
S161  (1)  DVQLVESGGGVVRPGESLRLSCAASGFTFSNFAMTWVRQAPGKGPEWVSLVSVTATTYY
S162  (1)  DVQLVESGGGLVRPGESLRLSCAASGFTFTNYAVTWVRQAPGEGLEWVSLISVTGTTYY
S163  (1)  DVQLVESGGGLVRPGESLRLSCAASGFTFTNYAVTWVRQAPGEGLEWVSLISVTGTTYY
S164  (1)  DVQLVESGGGLVRPGESLRLSCAASGFTFTNYAVTWVRQAPGEGLEWVSLISVTGTTYY
                                              *              *     *
                       1                                    H3              117
S161  (60) ADSVKGRFTISRDNSKSTLYLQMNSLRAEDTAVYYCAKITWNNLFDYWGLGTLVTVSS
S162  (60) ADSVKGRFTISRDNSKSTLYLQMNSLRAEDTAVYYCAKVTWKNVFDYWGLGTLVTVSS
S163  (60) ADSVKGRFTISRDNSKSTLYLQMNGLRAEDTAVYYCAKVTWKNVFDYWGLGTLVTVSS
S164  (60) ADSVKGRFTISRDNSKSTLYLQMNGLRAEDTAVYYCAKVTWKNVFDYWGLGTLVTVSS
                                  *                *    *

L1                                    L2      59
S161  (1)  EIVLTQSPGTLSLSPGERATLSCRASQTVGSKLAWYQQKPGQAPRLLIYDSSRASGIP
S162  (1)  EIVLTQSPGTLSVSPGERATESCRASQTVGSKLAWYQQKPGQAPRLLIYDANTRATGIP
S163  (1)  EIVLTQSPGTLSVSPGERATESCRASQTVGSKLAWYQQKPGQAPRLLIYDANTRATGIP
S164  (1)  EIVLTQSPGTLSVSPGERATESCRASQTVGSKLAWYQQKPGQAPRLLIYDANTRATGIP
                      *          *                              ***
                                              L3              108
S161  (60) DRFSGSGSGTDFTLTISSLQSEDSAVYYCQQHNDWPPYTFGGGTKVEIK
S162  (60) ARFSGSGSGTEFTLTISSLQSEDFAVYYCQQHTDWPPYTFGGGTKVEIK
S163  (60) ARFSGSGSGTEFTLTISSLQSEDFAVYYCQQHTDWPPYTFGGGTKVEIK
S164  (60) ARFSGSRSGTEFTLTISSLQSEDFAVYYCQQHTDWPPYTFGGGTKVEIK
            *                  *      *
```

FIG. 11N

>S149_VH
DVQLVESGGGVVRPGESLRLSCAASGFTFSNFAMNWVRQAPGEGLEWVSLISVTATTYYA
DSVKGRFTISRDNSKNTLYLQMNSLRAEDTAVYYCAKVTWNNLFDYWGLGTLVTVSS

>S149_VL
EIVLTQSPGTLSLSPGERATLSCRASQPIDSYLAWYQQKPGQAPRLLIYNTVTRATGIPD
RFSGSGSGTDFTLTINRLEPEDFAVYYCQHQYDWPPYIFGGGTKVEIK

>S218_VH
DVQLVESGGGVVRPGESLTLSCTASGFTFTSSTMNWVRQAPGEGLDWVSSISTSGVITYY
ADSVKGRATISRDNSKNTLYLRLFSLRADDTAIYYCATDTFDHWGPGTLVTVSS

>S218_VL
ALTQPASVSANPGETVKITCFGSSGNYGWFQQKSPGSAPVTVIHYNNKRPSDIPSRFSGS
KSGSTGTLTITGVRAEDEAVYFCGAWETGSATFGAGTTLTVL

FIG. 110

```
                            H1
        1                                                              H2    61
119 (1) DVQLLESGGGVVQPGGSLRLSCAASGFSNFAMTWVRQAPGEGLEWVSTIGSGDTYYADS
120 (1) DVQLVESGGGVVQPGGSLRLSCAASGFSNFAMTWVRQAPGEGLEWVSTIGSGDTYYADS
121 (1) DVQLVESGGGVVQPGGSLRLSCAASGFSNFAMTWVRQAPGEGLEWVSTIGSGDTYYADS
122 (1) DVQLVESGGGVVRPGESLRLSCAASGFRFSNFAMTWVRQAPGEGLEWVSTIGSGDTYYADS
            *          *           *
                                                       H3
        62                                                              120
119 (61) VKGRFTISRDNSKNTLYLQMNSLRAEDTAVYYCAKDSTVSWSGDFFDYWGLGTLVTVSS
120 (61) VKGRFTISRDNSKNTLYLQMNSLRAEDTAVYYCAKDSTVSWSGDFFDYWGLGTRVTVSS
121 (61) VKGRFTISRDNSKNTLYLQMNSLRAEDTAVYYCAKDSTVSWSGDFFDYWGLGTILVTVSS
122 (61) VKGRFTISRDNSKNTLYLQMNSLRAEDTAVYYCAKDSTVSWSGDFFDYWGLGTILVTVSS
                                                                        *
```

FIG. 11P

```
              1                                                        L1                                    L2   54
119   (1)    EIVLTQSPATLSVSPGERATFSCRASQNVKNDLAWYQQRPGQAPRLLIYAARIR
120   (1)    EIVLTQSPATLSVSPGERATFSCRASQNVKNDLAWYQQRPGQAPRLLIYAARIR
121   (1)    EIVLTQSPATLSVSPGERATFSCRASQNVKNDLAWYQQRPGQAPRLLIYAARIR
122   (1)    EIVLTQSPATLSVSPGERATFSCRASQNVKNDLAWYQQRPGQAPRLLIYAARIR

55                                                       L3                                    108
119   (55)   ETGIPERFSGSGSGTEFTLTITSLQSEDFAVYYCQQYYDWPPFTFGGGTKVEIK
120   (55)   ETGIPERFSGSGSGTEFTLTITSLQSEDFAVYYCQQYYDWPPFTFGGGTKVEIK
121   (55)   ETGIPERFSGSGSGTEFTLTITSLQSEDFAVYYCQQYYDWPPFTFGGGTKVEIK
122   (55)   ETGIPERFSGSGSGTEFTLTITSLQSEDFAVYYCQQYYDWPPFTFGGGTKVEIK
```

FIG. 20E

| | | | Buried Surface Area (square angstrom) | | | |
|---|---|---|---|---|---|---|
| Residue name | Residue number | CD47 | Complex 1 (119) | Complex 2 (136) | Complex 3 (3) | Complex 4 (115) |
| TYR | 90 | | | -48.8 | -4.7 | |
| LYS | 93 | -5.2 | | | | |
| ARG | 95 | | -44.5 | | | |
| LYS | 96 | 96.8 | 88.2 | | | |
| GLY | 97 | -22.7 | -2.9 | | | |
| SER | 98 | 56.1 | -14.2 | | | |
| PRO | 99 | -19.7 | | | | |
| ASP | 100 | | | | | -12.4 |
| ASP | 101 | -9.9 | | | | |
| GLU | 103 | | | -20.1 | | |
| PHE | 104 | | | -6.9 | | |
| LYS | 105 | | | -13.1 | | |
| SER | 106 | | | -49.9 | | |
| GLY | 107 | | | -6.9 | | |
| ALA | 108 | | | 83.6 | 14.9 | |
| GLY | 109 | | | -12.5 | -8.5 | |
| GLU | 111 | | | 96.8 | 77 | |
| LEU | 112 | | | -3 | | |
| SER | 113 | | | -41.5 | -3.7 | |
| ARG | 115 | | | -4.9 | -4.6 | |
| ALA | 116 | | | -23.8 | | |

```
                                                        H1           40
119_VH_Wt          (1) DVQLLESGGGVVQPGGSLRLSCAASGFSFSNFAMTWVRQA
119_VH_MutAll      (1) EVQLLESGGGVVQPGGSLRLSCAASGFSFSNFAMTWVRQA
119_VH_MutAll_V34M (1) EVQLLESGGGVVQPGGSLRLSCAASGFSFSNFAMTWVRQA
119_VH_MutAll_V34L (1) EVQLLESGGGVVQPGGSLRLSCAASGFSFSNFALTWVRQA
                                                              *

H2                             80
119_VH_Wt         (41) PGEGLEWVSTIGSGDTYYADSVKGRFTISRDNSKNTLYLQ
119_VH_MutAll     (41) PGKGLEWVSTIGSGDTYYADSVKGRFTISRDNSKNTLYLQ
119_VH_MutAll_V34M(41) PGKGLEWVSTIGSGDTYYADSVKGRFTISRDNSKNTLYLQ
119_VH_MutAll_V34L(41) PGKGLEWVSTIGSGDTYYADSVKGRFTISRDNSKNTLYLQ
                         *

H3                            120
119_VH_Wt         (81) MNSLRAEDTAVYYCAKDSTVSWSGDEFDYWGLGTLVTVSS
119_VH_MutAll     (81) MNSLRAEDTAVYYCAKDSTVSWSGDEFDYWGQGTLVTVSS
119_VH_MutAll_V34M(81) MNSLRAEDTAVYYCAKDSTVSWSGDEFDYWGQGTLVTVSS
119_VH_MutAll_V34L(81) MNSLRAEDTAVYYCAKDSTVSWSGDEFDYWGQGTLVTVSS
                                                   *
```

FIG. 24A

```
                              L1
              1   EIVLTQSPATLSVSPGERATFSCRASQNVKNDLAWYQQRPGQAPRLLIYAARIRET
119_VL_wt   (1)   EIVLTQSPATLSVSPGERATFSCRASQNVKNDLAWYQQRPGQAPRLLIYAARIRET
119_VL_mutAll (1) EIVLTQSPATLSVSPGERATLSCRASQNVKNDLAWYQQKPGQAPRLLIYAARIRET
                                      *                *                    L2  56

57  GIPERFSGSGSGTEFTLTITSLQSEDFAVYYCQQYYDWPPFTEGGGTKVEIK
119_VL_wt   (57)  GIPERFSGSGSGTEFTLTITSLQSEDFAVYYCQQYYDWPPFTEGGGTKVEIK
119_VL_mutAll (57) GIPARFSGSGSGTEFTLTISSLQSEDFAVYYCQQYYDWPPFTEGGGTKVEIK
                      *                  *                               108
                                                        L3
```

FIG. 24B

```
                                            L1                                              L2
                                _____                        _____
     135_VL_wt     (1) EIVLTQSPATLSVSPGERVTFSCRASQNVRSDIAWYQQKPGQAPRLLIYAASSRDT
135_VL_mutAll     (1) EIVLTQSPATLSVSPGERVTFSCRASQNVRSDIAWYQQKPGQAPRLLIYAASSRDT
                                                *
                                                                              108
     135_VL_wt    (57) GIPDRFSGSGSGTDFTLTISSLQSEDFGVYYCQQYDWPPFTFGGGTKVEIK
135_VL_mutAll    (57) GIPARFSGSGSGTDFTLTISSLQSEDFGVYYCQQYDWPPFTFGGGTKVEIK
                              *                                        _____
                                                                             L3
```

FIG. 25A

```
                                                           H1                    40
           1    DVQLVESGGGGVVRPGESLRLSCAASGFSFSTYAMSWVRQA
135_VH_wt  (1)  EVQLVESGGGVVQPGGSLRLSCAASGFSFSTYAMSWVRQA
135_VH_MutAll (1) EVQLVESGGGVVQPGGSLRLSCAASGFSFSTYAVSWVRQA
135_VH_MutAll_V34M (1) EVQLVESGGGVVQPGGSLRLSCAASGFSFSTYAMSWVRQA
135_VH_MutAll_V34L (1) EVQLVESGGGVVQPGGSLRLSCAASGFSFSTYALSWVRQA
                                              *
                            H2                              80
           41   PGEGLEWVSTIGADDTYYADSVKGRFTISRDNSKNTLYLQ
135_VH_wt  (41) PGKGLEWVSTIGADDTYYADSVKGRFTISRDNSKNTLYLQ
135_VH_MutAll (41) PGKGLEWVSTIGADDTYYADSVKGRFTISRDNSKNTLYLQ
135_VH_MutAll_V34M (41) PGKGLEWVSTIGADDTYYADSVKGRFTISRDNSKNTLYLQ
135_VH_MutAll_V34L (41) PGKGLEWVSTIGADDTYYADSVKGRFTISRDNSKNTLYLQ

H3                    120
           81   MNSLRAEDTAVYYCAKDSTVGWSGDFEDYWGLGTLVTVSS
135_VH_wt  (81) MNSLRAEDTAVYYCAKDSTVGWSGDFEDYWGQGTLVTVSS
135_VH_MutAll (81) MNSLRAEDTAVYYCAKDSTVGWSGDFEDYWGQGTLVTVSS
135_VH_MutAll_V34M (81) MNSLRAEDTAVYYCAKDSTVGWSGDFEDYWGQGTLVTVSS
135_VH_MutAll_V34L (81) MNSLRAEDTAVYYCAKDSTVGWSGDFEDYWGQGTLVTVSS
                                              *
```

FIG. 25B

```
                          L1                                            L2    56
136_VL_wt        (1)  ETVLTQSPGTLTLSPGERATLTCRASQSVTTYLAWYQEKPGQAPRLLIYGASSRAT
136_VL_mutall    (1)  EIVLTQSPGTLSLSPGERATLSCRASQSVTTYLAWYQQKPGQAPRLLIYGASSRAT
136_VL_Mutall_I2T (1) ETVLTQSPGTLSLSPGERATLSCRASQSVTTYLAWYQQKPGQAPRLLIYGASSRAT
                                   *              *      *

108
136_VL_wt        (57) GIPDRFSGSGSGTEFTLTISSLQSEDFAVYYCQQYYDRPPLTFGGGTKVEIK
136_VL_mutall    (57) GIPDRFSGSGSGTEFTLTISSLQSEDFAVYYCQQYYDRPPLTFGGGTKVEIK
136_VL_Mutall_I2T (57) GIPDRFSGSGSGTEFTLTISSLQSEDFAVYYCQQYYDRPPLTFGGGTKVEIK
                                                        L3
```

FIG. 26A

```
                            1                                              H1              40
136_VH_wt            (1)    DVQLVESGGGVVRPGESLRLSCAASGFTFSSYDMNWVRQA
136_VH_mutall        (1)    EVQLVESGGGVVQPGRSLRLSCAASGFTFSSYDMNWVRQA
136_VH_Mutall_V34M   (1)    EVQLVESGGGVVQPGRSLRLSCAASGFTFSSYDMMWVRQA
136_VH_Mutall_V34L   (1)    EVQLVESGGGVVQPGRSLRLSCAASGFTFSSYDLNWVRQA
                                   *                               *

41              H2                             80
136_VH_wt           (41)    PGEGLEWVSLISGSGEIIYYADSVKGRFTISRDNSKNTLY
136_VH_mutall       (41)    PGKGLEWVSLISGSGEIIYYADSVKGRFTISRDNSKNTLY
136_VH_Mutall_V34M  (41)    PGKGLEWVSLISGSGEIIYYADSVKGRFTISRDNSKNTLY
136_VH_Mutall_V34L  (41)    PGKGLEWVSLISGSGEIIYYADSVKGRFTISRDNSKNTLY
                              *

81                                H3           119
136_VH_wt           (81)    LQMNSLRAEDTAVYYCAKENNRYRFFDDWGLGTLVTVSS
136_VH_mutall       (81)    LQMNSLRAEDTAVYYCAKENNRYRFFDDWGQGTLVTVSS
136_VH_Mutall_V34M  (81)    LQMNSLRAEDTAVYYCAKENNRYRFFDDWGQGTLVTVSS
136_VH_Mutall_V34L  (81)    LQMNSLRAEDTAVYYCAKENNRYRFFDDWGQGTLVTVSS
                                                              *
```

FIG. 26B

```
                                                            L2   54
                  1                                         ___  __
Hum1  (1)  SYELTQPPSVSVSPGQTARITCSGGSYSSYYYAWYQQKPGQAPVTLLIYSDDKRP
Hum8  (1)  SYELTQPPSVSVSPGQTARITCSGGAYSSYYYAWYQQKPGQAPVLVIYSDSKRP
hum9  (1)  SYELTQPPSVSVSPGQTARITCSGGAYSSYYYAWYQQKPGQAPVLVIYSDDKRP
                                              *           **

L3                      108
           55                         __                      ___
Hum1  (55) SNIPERFSGSSSGTTVTLTITISGVQAEDEADYYCGGYDQSSYTNPFGGGTKLTVL
Hum8  (55) SGIPERFSGSSSGTTVTLTITISGVQAEDEADYYCGGYDQSSYTNPFGGGTKLTVL
hum9  (55) SGIPERFSGSSSGTTVTLTITISGVQAEDEADYYCGGYDQSSYTNPFGGGTKLTVL
            *

FIG. 29
```

```
                                              H1                    40
AB21_HC_MutAll       (1) EVQLVESGGGVVQPGGSLRLSCAASGFTFSSNAMSWVRQA
AB21_HC_MutAll_M34V  (1) EVQLVESGGGVVQPGGSLRLSCAASGFTFSSNAVSWVRQA
AB21_HC_MutAll_M34L  (1) EVQLVESGGGVVQPGGSLRLSCAASGFTFSSNALSWVRQA
AB27_HC_MutAll       (1) EVQLVESGGGVVQPGGSLRLSCAASGFTFSSYAMSWVRQA
AB27_HC_MutAll_M34V  (1) EVQLVESGGGVVQPGGSLRLSCAASGERFSSYAVSWVRQA
AB27_HC_MutAll_M34L  (1) EVQLVESGGGVVQPGGSLRLSCAASGFRFSSYALSWVRQA
AB25_HC_MutAll       (1) EVQLVESGGGVVQPGGSLRLSCAASGFTFSSNAMSWVRQA
AB25_HC_MutAll_M34V  (1) EVQLVESGGGVVQPGGSLRLSCAASGFTFSSNAVSWVRQA
AB25_HC_MutAll_M34L  (1) EVQLVESGGGVVQPGGSLRLSCAASGFTFSSNALSWVRQA
                                              *

H2                    80
AB21_HC_MutAll      (41) PGKGLEWVAGISAGGSDTYYPASVKGRFTISRDNSKNTLY
AB21_HC_MutAll_M34V (41) PGKGLEWVAGISAGGSDTYYPASVKGRFTISRDNSKNTLY
AB21_HC_MutAll_M34L (41) PGKGLEWVAGISAGGSDTYYPASVKGRFTISRDNSKNTLY
AB27_HC_MutAll      (41) PGKGLEWVSGISSG-GDTYYVDSVKGRFTISRDNSKNTLY
AB27_HC_MutAll_M34V (41) PGKGLEWVSGISSG-GDTYYVDSVKGRFTISRDNSKNTLY
AB27_HC_MutAll_M34L (41) PGKGLEWVSGISSG-GDTYYVDSVKGRFTISRDNSKNTLY
AB25_HC_MutAll      (41) PGKGLEWVAGISSG-SDTYYGDSVKGRFTISRDNSKNTLY
AB25_HC_MutAll_M34V (41) PGKGLEWVAGISSG-SDTYYGDSVKGRFTISRDNSKNTLY
AB25_HC_MutAll_M34L (41) PGKGLEWVAGISSG-SDTYYGDSVKGRFTISRDNSKNTLY
                                *            *        **

H3                   118
AB21_HC_MutAll      (81) LQMNSLRAEDTAVYYCARETWNHLFDYWGQGTLVTVSS
AB21_HC_MutAll_M34V (81) LQMNSLRAEDTAVYYCARETWNHLFDYWGQGTLVTVSS
AB21_HC_MutAll_M34L (81) LQMNSLRAEDTAVYYCARETWNHLFDYWGQGTLVTVSS
AB27_HC_MutAll      (81) LQMNSLRAEDTAVYYCARETWNHLFDYWGQGTLVTVSS
AB27_HC_MutAll_M34V (81) LQMNSLRAEDTAVYYCARETWNHLFDYWGQGTLVTVSS
AB27_HC_MutAll_M34L (81) LQMNSLRAEDTAVYYCARETWNHLFDYWGQGTLVTVSS
AB25_HC_MutAll      (80) LQMNSLRAEDTAVYYCARETWNHLFDYWGQGTLVTVSS
AB25_HC_MutAll_M34V (80) LQMNSLRAEDTAVYYCARETWNHLFDYWGQGTLVTVSS
AB25_HC_MutAll_M34L (80) LQMNSLTAEDTAVYYCARETWNHLFDYWGQGTLVTVSS
                                *
```

FIG. 30

SEQUENCE LISTING

<160> NUMBER OF SEQ ID NOS: 426

<210> SEQ ID NO 1
<211> LENGTH: 348
<212> TYPE: PRT
<213> ORGANISM: Artificial Sequence
<220> FEATURE:
<223> OTHER INFORMATION: Synthetic Construct

<400> SEQUENCE: 1

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
            195                 200                 205

Val Leu His Gln Asp Trp Leu Asn Gly Lys Glu Tyr Lys Cys Lys Val
    210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 2
<211> LENGTH: 347
<212> TYPE: PRT
<213> ORGANISM: Artificial Sequence
<220> FEATURE:
<223> OTHER INFORMATION: Synthetic Construct

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

```
Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
                260                 265                 270

Tyr Pro Ser Asp Ile Ala Val Glu Trp Glu Ser Asn Gly Gln Pro Glu
            275                 280                 285

Asn Asn Tyr Lys Thr Thr Pro Pro Val Leu Asp Ser Asp Gly Ser Phe
290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
                340                 345

<210> SEQ ID NO 3
<211> LENGTH: 346
<212> TYPE: PRT
<213> ORGANISM: Artificial Sequence
<220> FEATURE:
<223> OTHER INFORMATION: Synthetic Construct

<400> SEQUENCE: 3

Lys Glu Leu Lys Val Thr Gln Pro Glu Lys Ser Val Ser Val Ala Ala
1               5                   10                  15

Gly Asp Ser Thr Val Leu Asn Cys Thr Leu Thr Ser Leu Leu Pro Val
                20                  25                  30

Gly Pro Ile Lys Trp Tyr Arg Gly Val Gly Gln Ser Arg Leu Leu Ile
                35                  40                  45

Tyr Ser Phe Thr Gly Glu His Phe Pro Arg Val Thr Asn Val Ser Asp
        50                  55                  60

Ala Thr Lys Arg Asn Asn Met Asp Phe Ser Ile Arg Ile Ser Asn Val
65                  70                  75                  80

Thr Pro Glu Asp Ala Gly Thr Tyr Tyr Cys Val Lys Phe Gln Lys Gly
                85                  90                  95

Pro Ser Glu Pro Asp Thr Glu Ile Gln Ser Gly Gly Gly Thr Glu Val
                100                 105                 110

Tyr Val Leu Ala Lys Pro Ser Asp Lys Thr His Thr Cys Pro Pro Cys
            115                 120                 125

Pro Ala Pro Glu Ala Ala Gly Ala Pro Ser Val Phe Leu Phe Pro Pro
        130                 135                 140

Lys Pro Lys Asp Thr Leu Met Ile Ser Arg Thr Pro Glu Val Thr Cys
145                 150                 155                 160

Val Val Val Asp Val Ser His Glu Asp Pro Glu Val Lys Phe Asn Trp
                165                 170                 175

Tyr Val Asp Gly Val Glu Val His Asn Ala Lys Thr Lys Pro Arg Glu
                180                 185                 190

Glu Gln Tyr Ala Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
        210                 215                 220
```

Lys Ala Leu Pro Ala Pro Ile Glu Lys Thr Ile Ser Lys Ala Lys Gly
225                 230                 235                 240

Gln Pro Arg Glu Pro Gln Val Tyr Thr Leu Pro Pro Ser Arg Glu Glu
            245                 250                 255

Met Thr Lys Asn Gln Val Ser Leu Thr Cys Leu Val Lys Gly Phe Tyr
        260                 265                 270

Pro Ser Asp Ile Ala Val Glu Trp Glu Ser Asn Gly Gln Pro Glu Asn
    275                 280                 285

Asn Tyr Lys Thr Thr Pro Pro Val Leu Asp Ser Asp Gly Ser Phe Phe
290                 295                 300

Leu Tyr Ser Lys Leu Thr Val Asp Lys Ser Arg Trp Gln Gln Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 4
<211> LENGTH: 342
<212> TYPE: PRT
<213> ORGANISM: Artificial Sequence
<220> FEATURE:
<223> OTHER INFORMATION: Synthetic Construct

<400> SEQUENCE: 4

Thr Glu Val Lys Val Ile Gln Pro Glu Lys Ser Val Ser Val Ala Ala
1               5                   10                  15

Gly Asp Ser Thr Val Leu Asn Cys Thr Leu Thr Ser Leu Leu Pro Val
            20                  25                  30

Gly Pro Ile Arg Trp Tyr Arg Gly Val Gly Gln Ser Arg Gln Leu Ile
        35                  40                  45

Tyr Ser Phe Thr Thr Glu His Phe Pro Arg Val Thr Asn Val Ser Asp
50                  55                  60

Ala Thr Lys Arg Ser Asn Leu Asp Phe Ser Ile Arg Ile Ser Asn Val
65                  70                  75                  80

Thr Pro Glu Asp Ala Gly Thr Tyr Tyr Cys Val Lys Phe Gln Arg Gly
                85                  90                  95

Ser Pro Asp Thr Glu Ile Gln Ser Gly Gly Gly Thr Glu Val Tyr Val
            100                 105                 110

Leu Ala Lys Asp Lys Thr His Thr Cys Pro Pro Cys Pro Ala Pro Glu
        115                 120                 125

Ala Ala Gly Ala Pro Ser Val Phe Leu Phe Pro Pro Lys Pro Lys Asp
    130                 135                 140

Thr Leu Met Ile Ser Arg Thr Pro Glu Val Thr Cys Val Val Val Asp
145                 150                 155                 160

Val Ser His Glu Asp Pro Glu Val Lys Phe Asn Trp Tyr Val Asp Gly
                165                 170                 175

Val Glu Val His Asn Ala Lys Thr Lys Pro Arg Glu Glu Gln Tyr Ala
            180                 185                 190

Ser Thr Tyr Arg Val Val Ser Val Leu Thr Val Leu His Gln Asp Trp
        195                 200                 205

Leu Asn Gly Lys Glu Tyr Lys Cys Lys Val Ser Asn Lys Ala Leu Pro
    210                 215                 220

Ala Pro Ile Glu Lys Thr Ile Ser Lys Ala Lys Gly Gln Pro Arg Glu
225                 230                 235                 240

-continued

Pro Gln Val Tyr Thr Leu Pro Pro Ser Arg Glu Glu Met Thr Lys Asn
                    245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 5
<211> LENGTH: 119
<212> TYPE: PRT
<213> ORGANISM: Homo sapiens

<400> SEQUENCE: 5

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 6
<211> LENGTH: 118
<212> TYPE: PRT
<213> ORGANISM: Homo sapiens

<400> SEQUENCE: 6

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

```
Gly Ser Pro Asp Thr Glu Phe Lys Ser Ala Gly Thr Glu Leu Ser
                100                 105                 110
Val Arg Ala Lys Pro Ser
            115

<210> SEQ ID NO 7
<211> LENGTH: 119
<212> TYPE: PRT
<213> ORGANISM: Mus musculus

<400> SEQUENCE: 7

Lys Glu Leu Lys Val Thr Gln Pro Glu Lys Ser Val Ser Val Ala Ala
1               5                   10                  15
Gly Asp Ser Thr Val Leu Asn Cys Thr Leu Thr Ser Leu Leu Pro Val
                20                  25                  30
Gly Pro Ile Lys Trp Tyr Arg Gly Val Gly Gln Ser Arg Leu Leu Ile
            35                  40                  45
Tyr Ser Phe Thr Gly Glu His Phe Pro Arg Val Thr Asn Val Ser Asp
        50                  55                  60
Ala Thr Lys Arg Asn Asn Met Asp Phe Ser Ile Arg Ile Ser Asn Val
65                  70                  75                  80
Thr Pro Glu Asp Ala Gly Thr Tyr Tyr Cys Val Lys Phe Gln Lys Gly
                85                  90                  95
Pro Ser Glu Pro Asp Thr Glu Ile Gln Ser Gly Gly Thr Glu Val
                100                 105                 110
Tyr Val Leu Ala Lys Pro Ser
            115

<210> SEQ ID NO 8
<211> LENGTH: 115
<212> TYPE: PRT
<213> ORGANISM: Mus musculus

<400> SEQUENCE: 8

Thr Glu Val Lys Val Ile Gln Pro Glu Lys Ser Val Ser Val Ala Ala
1               5                   10                  15
Gly Asp Ser Thr Val Leu Asn Cys Thr Leu Thr Ser Leu Leu Pro Val
                20                  25                  30
Gly Pro Ile Arg Trp Tyr Arg Gly Val Gly Gln Ser Arg Gln Leu Ile
            35                  40                  45
Tyr Ser Phe Thr Thr Glu His Phe Pro Arg Val Thr Asn Val Ser Asp
        50                  55                  60
Ala Thr Lys Arg Ser Asn Leu Asp Phe Ser Ile Arg Ile Ser Asn Val
65                  70                  75                  80
Thr Pro Glu Asp Ala Gly Thr Tyr Tyr Cys Val Lys Phe Gln Arg Gly
                85                  90                  95
Ser Pro Asp Thr Glu Ile Gln Ser Gly Gly Gly Thr Glu Val Tyr Val
                100                 105                 110
Leu Ala Lys
        115

<210> SEQ ID NO 9
<211> LENGTH: 117
<212> TYPE: PRT
<213> ORGANISM: Mus musculus

<400> SEQUENCE: 9

Lys Glu Leu Lys Val Thr Gln Pro Glu Lys Ser Val Ser Val Ala Ala
```

```
              1               5                  10                 15
Gly Asp Ser Thr Val Leu Asn Cys Thr Leu Thr Ser Leu Leu Pro Val
             20                  25                 30

Gly Pro Ile Arg Trp Tyr Arg Gly Val Gly Pro Ser Arg Leu Leu Ile
             35                  40                 45

Tyr Ser Phe Ala Gly Glu Tyr Val Pro Arg Ile Arg Asn Val Ser Asp
             50                  55                 60

Thr Thr Lys Arg Asn Asn Met Asp Phe Ser Ile Arg Ile Ser Asn Val
65                70                  75                       80

Thr Pro Ala Asp Ala Gly Ile Tyr Tyr Cys Val Lys Phe Gln Lys Gly
                 85                  90                 95

Ser Ser Glu Pro Asp Thr Glu Ile Gln Ser Gly Gly Gly Thr Glu Val
             100                 105                110

Tyr Val Leu Ala Lys
             115

<210> SEQ ID NO 10
<211> LENGTH: 117
<212> TYPE: PRT
<213> ORGANISM: Mus musculus

<400> SEQUENCE: 10

Thr Glu Val Lys Val Thr Gln Pro Glu Lys Ser Val Ser Val Ala Ala
1               5                   10                  15

Gly Asp Ser Thr Ile Leu Asn Cys Thr Val Thr Ser Leu Leu Pro Val
             20                  25                 30

Gly Pro Ile Arg Trp Tyr Arg Gly Val Gly Gln Ser Arg Leu Leu Ile
             35                  40                 45

Tyr Ser Phe Thr Gly Glu His Phe Pro Arg Ile Arg Asn Val Ser Asp
             50                  55                 60

Thr Thr Lys Arg Asn Asn Met Asp Phe Ser Ile Arg Ile Ser Asn Val
65                70                  75                       80

Thr Pro Glu Asp Ala Gly Thr Tyr Tyr Cys Val Lys Phe Gln Arg Gly
                 85                  90                 95

Ser Ser Glu Pro Asp Thr Glu Ile Gln Ser Gly Gly Gly Thr Glu Val
             100                 105                110

Tyr Val Leu Ala Lys
             115

<210> SEQ ID NO 11
<211> LENGTH: 118
<212> TYPE: PRT
<213> ORGANISM: Macaca fascicularis

<400> SEQUENCE: 11

Glu Glu Glu Leu Gln Val Ile Gln Pro Glu Lys Ser Val Ser Val Ala
1               5                   10                  15

Ala Gly Glu Ser Ala Thr Leu Asn Cys Thr Ala Thr Ser Leu Ile Pro
             20                  25                 30

Val Gly Pro Ile Gln Trp Phe Arg Gly Val Gly Pro Gly Arg Glu Leu
             35                  40                 45

Ile Tyr His Gln Lys Glu Gly His Phe Pro Arg Val Thr Pro Val Ser
             50                  55                 60

Asp Pro Thr Lys Arg Asn Asn Met Asp Phe Ser Ile Arg Ile Ser Asn
65                70                  75                       80

Ile Thr Pro Ala Asp Ala Gly Thr Tyr Tyr Cys Val Lys Phe Arg Lys
```

-continued

```
                85                  90                  95

Gly Ser Pro Asp Val Glu Leu Lys Ser Gly Ala Gly Thr Glu Leu Ser
            100                 105                 110

Val Arg Ala Lys Pro Ser
        115

<210> SEQ ID NO 12
<211> LENGTH: 118
<212> TYPE: PRT
<213> ORGANISM: Macaca fascicularis

<400> SEQUENCE: 12

Glu Glu Glu Leu Gln Val Ile Gln Pro Glu Lys Ser Val Ser Val Ala
1               5                   10                  15

Ala Gly Asp Ser Ala Thr Leu Asn Cys Thr Val Ser Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Leu Lys Glu Gly His Phe Pro Arg Val Thr Ala Val Ser
    50                  55                  60

Asp Pro Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Val Glu Leu Lys Ser Gly Ala Gly Thr Glu Leu Ser
            100                 105                 110

Val Arg Ala Lys Pro Ser
        115

<210> SEQ ID NO 13
<211> LENGTH: 119
<212> TYPE: PRT
<213> ORGANISM: Homo sapiens

<400> SEQUENCE: 13

Glu Asp Glu Leu Gln Val Ile Gln Pro Glu Lys Ser Val Ser Val Ala
1               5                   10                  15

Ala Gly Glu Ser Ala Thr Leu Arg Cys Ala Met Thr Ser Leu Ile Pro
            20                  25                  30

Val Gly Pro Ile Met Trp Phe Arg Gly Ala Gly Ala Gly Arg Glu Leu
        35                  40                  45

Ile Tyr Asn Gln Lys Glu Gly His Phe Pro Arg Val Thr Thr Val Ser
    50                  55                  60

Glu Leu Thr Lys Arg Asn Asn Leu Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 14
<211> LENGTH: 119
<212> TYPE: PRT
<213> ORGANISM: Homo sapiens

<400> SEQUENCE: 14
```

Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
        50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp His Val Glu Phe Lys Ser Gly Ala Gly Thr Glu Leu
                100                 105                 110

Ser Val Arg Ala Lys Pro Ser
            115

<210> SEQ ID NO 15
<211> LENGTH: 119
<212> TYPE: PRT
<213> ORGANISM: Homo sapiens

<400> SEQUENCE: 15

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
            35                  40                  45

Ile Tyr Asn Gln Lys Glu Gly His Phe Pro Arg Val Thr Thr Val Ser
        50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
                100                 105                 110

Ala Leu Gly Ala Lys Pro Ser
            115

<210> SEQ ID NO 16
<211> LENGTH: 117
<212> TYPE: PRT
<213> ORGANISM: Homo sapiens

<400> SEQUENCE: 16

Gln Leu Leu Phe Asn Lys Thr Lys Ser Val Glu Phe Thr Phe Ser Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
            35                  40                  45

Thr Phe Asp Gly Ala Leu Asn Lys Ser Thr Val Pro Thr Asp Phe Ser
        50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser
        115

<210> SEQ ID NO 17
<211> LENGTH: 119
<212> TYPE: PRT
<213> ORGANISM: Artificial Sequence
<220> FEATURE:
<223> OTHER INFORMATION: Synthetic Construct

<400> SEQUENCE: 17

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 18
<211> LENGTH: 118
<212> TYPE: PRT
<213> ORGANISM: Artificial Sequence
<220> FEATURE:
<223> OTHER INFORMATION: Synthetic Construct

<400> SEQUENCE: 18

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

```
<210> SEQ ID NO 19
<211> LENGTH: 118
<212> TYPE: PRT
<213> ORGANISM: Artificial Sequence
<220> FEATURE:
<223> OTHER INFORMATION: Synthetic Construct

<400> SEQUENCE: 19

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 20
<211> LENGTH: 118
<212> TYPE: PRT
<213> ORGANISM: Artificial Sequence
<220> FEATURE:
<223> OTHER INFORMATION: Synthetic Construct

<400> SEQUENCE: 20

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 21
<211> LENGTH: 118
<212> TYPE: PRT
<213> ORGANISM: Artificial Sequence
<220> FEATURE:
<223> OTHER INFORMATION: Synthetic Construct

<400> SEQUENCE: 21

Glu Glu Glu Leu Gln Ile Ile Gln Pro Asp Lys Ser Val Ser Val Ala
1               5                   10                  15
```

```
Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 22
<211> LENGTH: 118
<212> TYPE: PRT
<213> ORGANISM: Artificial Sequence
<220> FEATURE:
<223> OTHER INFORMATION: Synthetic Construct

<400> SEQUENCE: 22

```
Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

<210> SEQ ID NO 23
<211> LENGTH: 118
<212> TYPE: PRT
<213> ORGANISM: Artificial Sequence
<220> FEATURE:
<223> OTHER INFORMATION: Synthetic Construct

<400> SEQUENCE: 23

```
Glu Glu Glu Leu Gln Ile Ile Gln Pro Asp Lys Ser Val Ser Val Ala
 1               5                  10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
```

```
                65                  70                  75                  80
Ile Thr Pro Ala Asp Ala Gly Thr Tyr Tyr Cys Ile Lys Phe Arg Lys
                    85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 24
<211> LENGTH: 118
<212> TYPE: PRT
<213> ORGANISM: Artificial Sequence
<220> FEATURE:
<223> OTHER INFORMATION: Synthetic Construct

<400> SEQUENCE: 24

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Lys Gln Gly Pro Phe Pro Arg Val Thr Val Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                    85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 25
<211> LENGTH: 118
<212> TYPE: PRT
<213> ORGANISM: Artificial Sequence
<220> FEATURE:
<223> OTHER INFORMATION: Synthetic Construct

<400> SEQUENCE: 25

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Val Leu
            35                  40                  45

Ile Tyr Asn Gln Arg Glu Gly Pro Phe Pro Arg Val Thr Val Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                    85                  90                  95

Gly Ser Pro Asp Thr Glu Phe Lys Ser Gly Ala Gly Thr Glu Leu Ser
                100                 105                 110

Val Arg Ala Lys Pro Ser
            115
```

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 27
<211> LENGTH: 118
<212> TYPE: PRT
<213> ORGANISM: Artificial Sequence
<220> FEATURE:
<223> OTHER INFORMATION: Synthetic Construct

<400> SEQUENCE: 27

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 28
<211> LENGTH: 118
<212> TYPE: PRT
<213> ORGANISM: Artificial Sequence
<220> FEATURE:
<223> OTHER INFORMATION: Synthetic Construct

<400> SEQUENCE: 28

Glu Glu Glu Leu Gln Ile Ile Gln Pro Asp Lys Ser Val Ser Val Ala

```
            1               5                  10                 15
Ala Gly Glu Ser Ala Ile Leu His Cys Thr Ile Thr Ser Leu Phe Pro
            20                 25                 30

Val Gly Pro Ile Gln Trp Phe Arg Gly Ala Gly Pro Ala Arg Val Leu
            35                 40                 45

Ile Tyr Asn Gln Arg Gln Gly Pro Phe Pro Arg Val Thr Thr Val Ser
            50                 55                 60

Glu Thr Thr Lys Arg Glu Asn Met Asp Phe Ser Ile Ser Ile Ser Asn
 65                70                 75                       80

Ile Thr Pro Ala Asp Ala Gly Thr Tyr Tyr Cys Val Lys Phe Arg Lys
                85                 90                 95

Gly Ser Pro Asp Thr Glu Phe Lys Ser Gly Ala Gly Thr Glu Leu Ser
              100                105                110

Val Arg Ala Lys Pro Ser
              115

<210> SEQ ID NO 29
<211> LENGTH: 118
<212> TYPE: PRT
<213> ORGANISM: Artificial Sequence
<220> FEATURE:
<223> OTHER INFORMATION: Synthetic Construct

<400> SEQUENCE: 29

Glu Glu Glu Leu Gln Val Ile Gln Pro Asp Lys Ser Val Ser Val Ala
 1               5                  10                 15

Ala Gly Glu Ser Ala Ile Leu His Cys Thr Val Thr Ser Leu Ile Pro
            20                 25                 30

Val Gly Pro Ile Gln Trp Phe Arg Gly Ala Gly Pro Ala Arg Glu Leu
            35                 40                 45

Ile Tyr Asn Gln Arg Glu Gly Pro Phe Pro Arg Val Thr Thr Val Ser
            50                 55                 60

Glu Ser Thr Lys Arg Glu Asn Met Asp Phe Ser Ile Ser Ile Ser Asn
 65                70                 75                       80

Ile Thr Pro Ala Asp Ala Gly Thr Tyr Tyr Cys Val Lys Phe Arg Lys
                85                 90                 95

Gly Ser Pro Asp Thr Glu Phe Lys Ser Gly Ala Gly Thr Glu Leu Ser
              100                105                110

Val Arg Ala Lys Pro Ser
              115

<210> SEQ ID NO 30
<211> LENGTH: 118
<212> TYPE: PRT
<213> ORGANISM: Artificial Sequence
<220> FEATURE:
<223> OTHER INFORMATION: Synthetic Construct

<400> SEQUENCE: 30

Glu Glu Glu Leu Gln Val Ile Gln Pro Asp Lys Ser Val Ser Val Ala
 1               5                  10                 15

Ala Gly Glu Ser Ala Ile Leu His Cys Thr Val Thr Ser Leu Phe Pro
            20                 25                 30

Val Gly Pro Ile Gln Trp Phe Arg Gly Ala Gly Pro Ala Arg Glu Leu
            35                 40                 45

Ile Tyr Asn Gln Arg Glu Gly Pro Phe Pro Arg Val Thr Thr Val Ser
            50                 55                 60
```

-continued

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 31
<211> LENGTH: 118
<212> TYPE: PRT
<213> ORGANISM: Artificial Sequence
<220> FEATURE:
<223> OTHER INFORMATION: Synthetic Construct

<400> SEQUENCE: 31

Glu Glu Glu Leu Gln Val Ile Gln Pro Asp Lys Ser Val Ser Val Ala
 1               5                  10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
        50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 32
<211> LENGTH: 118
<212> TYPE: PRT
<213> ORGANISM: Artificial Sequence
<220> FEATURE:
<223> OTHER INFORMATION: Synthetic Construct

<400> SEQUENCE: 32

Glu Glu Glu Leu Gln Val Ile Gln Pro Asp Lys Ser Val Ser Val Ala
 1               5                  10                  15

Ala Gly Glu Ser Ala Ile Leu His Cys Thr Ile Thr Ser Leu Phe Pro
                20                  25                  30

Val Gly Pro Ile Gln Trp Phe Arg Gly Ala Gly Pro Ala Arg Glu Leu
            35                  40                  45

Ile Tyr Asn Gln Arg Glu Gly Pro Phe Pro Arg Val Thr Thr Val Ser
        50                  55                  60

Glu Thr Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
        115
```

-continued

```
<210> SEQ ID NO 33
<211> LENGTH: 118
<212> TYPE: PRT
<213> ORGANISM: Artificial Sequence
<220> FEATURE:
<223> OTHER INFORMATION: Synthetic Construct

<400> SEQUENCE: 33

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 34
<211> LENGTH: 118
<212> TYPE: PRT
<213> ORGANISM: Artificial Sequence
<220> FEATURE:
<223> OTHER INFORMATION: Synthetic Construct

<400> SEQUENCE: 34

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 35
<211> LENGTH: 118
<212> TYPE: PRT
<213> ORGANISM: Artificial Sequence
<220> FEATURE:
<223> OTHER INFORMATION: Synthetic Construct

<400> SEQUENCE: 35
```

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly Pro Phe Pro Arg Val Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 36
<211> LENGTH: 119
<212> TYPE: PRT
<213> ORGANISM: Artificial Sequence
<220> FEATURE:
<223> OTHER INFORMATION: Synthetic Construct

<400> SEQUENCE: 36

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
                100                 105                 110

Ser Val Arg Ala Lys Pro Ser
            115

<210> SEQ ID NO 37
<211> LENGTH: 119
<212> TYPE: PRT
<213> ORGANISM: Artificial Sequence
<220> FEATURE:
<223> OTHER INFORMATION: Synthetic Construct

<400> SEQUENCE: 37

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

```
Asp Leu Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
        115
```

<210> SEQ ID NO 38
<211> LENGTH: 119
<212> TYPE: PRT
<213> ORGANISM: Artificial Sequence
<220> FEATURE:
<223> OTHER INFORMATION: Synthetic Construct

<400> SEQUENCE: 38

```
Glu Glu Glu Leu Gln Val Ile Gln Pro Asp Lys Ser Val Leu Val Ala
  1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Thr Val Ser
         50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
        115
```

<210> SEQ ID NO 39
<211> LENGTH: 119
<212> TYPE: PRT
<213> ORGANISM: Artificial Sequence
<220> FEATURE:
<223> OTHER INFORMATION: Synthetic Construct

<400> SEQUENCE: 39

```
Glu Glu Glu Leu Gln Ile Ile Gln Pro Asp Lys Ser Val Leu Val Ala
  1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Thr Val Ser
         50                  55                  60

Asp Thr Thr Lys Arg Asn Asn Met Asp Phe Ser Ile Arg Ile Gly Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
                100                 105                 110

Ser Val Arg Ala Lys Pro Ser
```

<210> SEQ ID NO 40
<211> LENGTH: 119
<212> TYPE: PRT
<213> ORGANISM: Artificial Sequence
<220> FEATURE:
<223> OTHER INFORMATION: Synthetic Construct

<400> SEQUENCE: 40

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 41
<211> LENGTH: 119
<212> TYPE: PRT
<213> ORGANISM: Artificial Sequence
<220> FEATURE:
<223> OTHER INFORMATION: Synthetic Construct

<400> SEQUENCE: 41

```
Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115
```

<210> SEQ ID NO 42
<211> LENGTH: 119
<212> TYPE: PRT
<213> ORGANISM: Artificial Sequence
<220> FEATURE:
<223> OTHER INFORMATION: Synthetic Construct

<400> SEQUENCE: 42

-continued

```
Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 43
<211> LENGTH: 119
<212> TYPE: PRT
<213> ORGANISM: Artificial Sequence
<220> FEATURE:
<223> OTHER INFORMATION: Synthetic Construct

<400> SEQUENCE: 43

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 44
<211> LENGTH: 119
<212> TYPE: PRT
<213> ORGANISM: Artificial Sequence
<220> FEATURE:
<223> OTHER INFORMATION: Synthetic Construct

<400> SEQUENCE: 44

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
```

```
                    50                  55                  60
Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                     85                  90                  95

Gly Ser Pro Asp Asp Val Glu Phe Lys Ser Gly Ala Gly Thr Glu Leu
                    100                 105                 110

Ser Val Arg Ala Lys Pro Ser
            115
```

<210> SEQ ID NO 45
<211> LENGTH: 119
<212> TYPE: PRT
<213> ORGANISM: Artificial Sequence
<220> FEATURE:
<223> OTHER INFORMATION: Synthetic Construct

<400> SEQUENCE: 45

```
Glu Glu Glu Leu Gln Ile Ile Gln Pro Asp Lys Ser Val Leu Val Ala
  1               5                  10                  15

Ala Gly Glu Thr Ala Thr Leu Arg Cys Thr Ile Thr Ser Leu Phe Pro
                 20                  25                  30

Val Gly Pro Ile Gln Trp Phe Arg Gly Ala Gly Pro Gly Arg Val Leu
             35                  40                  45

Ile Tyr Asn Gln Arg Glu Gly Pro Phe Pro Arg Val Thr Thr Val Ser
         50                  55                  60

Asp Thr Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Ile Lys Phe Arg Lys
                     85                  90                  95

Gly Ser Pro Asp Asp Val Glu Phe Lys Ser Gly Ala Gly Thr Glu Leu
                    100                 105                 110

Ser Val Arg Ala Lys Pro Ser
            115
```

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

```
Glu Glu Glu Leu Gln Val Ile Gln Pro Asp Lys Ser Val Leu Val Ala
  1               5                  10                  15

Ala Gly Glu Thr Ala Thr Leu Arg Cys Thr Ala Thr Ser Leu Phe Pro
                 20                  25                  30

Val Gly Pro Ile Gln Trp Phe Arg Gly Ala Gly Pro Gly Arg Glu Leu
             35                  40                  45

Ile Tyr Asn Gln Arg Glu Gly Pro Phe Pro Arg Val Thr Thr Val Ser
         50                  55                  60

Asp Leu Thr Lys Arg Asn Asn Met Asp Phe Ser Ile Arg Ile Gly Ala
 65                  70                  75                  80

Ile Thr Pro Ala Asp Ala Gly Thr Tyr Tyr Cys Val Lys Phe Arg Lys
                     85                  90                  95

Gly Ser Pro Asp Asp Val Glu Phe Lys Ser Gly Ala Gly Thr Glu Leu
                    100                 105                 110
```

Ser Val Arg Ala Lys Pro Ser
        115

<210> SEQ ID NO 47
<211> LENGTH: 119
<212> TYPE: PRT
<213> ORGANISM: Artificial Sequence
<220> FEATURE:
<223> OTHER INFORMATION: Synthetic Construct

<400> SEQUENCE: 47

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 48
<211> LENGTH: 119
<212> TYPE: PRT
<213> ORGANISM: Artificial Sequence
<220> FEATURE:
<223> OTHER INFORMATION: Synthetic Construct

<400> SEQUENCE: 48

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 49
<211> LENGTH: 119
<212> TYPE: PRT
<213> ORGANISM: Artificial Sequence
<220> FEATURE:
<223> OTHER INFORMATION: Synthetic Construct -continued

```
<400> SEQUENCE: 49

Glu Glu Glu Leu Gln Val Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 50
<211> LENGTH: 119
<212> TYPE: PRT
<213> ORGANISM: Homo sapiens

<400> SEQUENCE: 50

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 51
<211> LENGTH: 119
<212> TYPE: PRT
<213> ORGANISM: Artificial Sequence
<220> FEATURE:
<223> OTHER INFORMATION: Synthetic Construct

<400> SEQUENCE: 51

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Glu Gly Pro Phe Pro Arg Val Thr Thr Val Ser
    50                  55                  60
```

Asp Thr Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Phe Pro
            20                  25                  30

Val Gly Pro Ile Gln Trp Phe Arg Gly Ala Gly Pro Gly Arg Glu Leu
        35                  40                  45

Ile Tyr Asn Gln Arg Gln Gly Pro Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Val Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 53
<211> LENGTH: 484
<212> TYPE: PRT
<213> ORGANISM: Artificial Sequence
<220> FEATURE:
<223> OTHER INFORMATION: Synthetic Construct

<400> SEQUENCE: 53

Ala Leu Thr Gln Pro Ala Ser Val Ser Ala Asn Pro Gly Glu Thr Val
1               5                   10                  15

Glu Ile Thr Cys Ser Gly Gly Gly Ser Asn Asn Ala Tyr Gly Trp Phe
            20                  25                  30

Gln Gln Lys Ser Pro Gly Ser Ala Pro Leu Thr Val Ile Tyr Asp Asn
        35                  40                  45

Gly Lys Arg Pro Ser Asp Ile Pro Ser Arg Phe Ser Gly Ser Lys Ser
    50                  55                  60

Asp Ser Thr Gly Thr Leu Thr Ile Thr Arg Val Gln Ala Glu Asp Glu
65                  70                  75                  80

Ala Val Tyr Tyr Cys Gly Ser Ala Asp Asn Ser Gly Ala Gly Val Phe
                85                  90                  95

Gly Ala Gly Thr Thr Leu Thr Val Leu Gly Gln Ser Ser Arg Ser Ser
            100                 105                 110

Gly Gly Gly Gly Ser Ser Gly Gly Gly Gly Ser Met Ala Ala Val Thr

```
            115                 120                 125

Leu Asp Glu Ser Gly Gly Leu Gln Thr Pro Gly Ala Leu Ser
130                 135                 140

Leu Val Cys Lys Gly Ser Gly Phe Thr Phe Ser Ser His Ala Met Asn
145                 150                 155                 160

Trp Val Arg Gln Ala Pro Gly Lys Gly Leu Glu Trp Val Ala Gly Ile
                165                 170                 175

Ser Ser Asp Gly Arg Phe Thr Tyr Tyr Gly Ala Ala Val Gln Gly Arg
            180                 185                 190

Ala Thr Ile Ser Arg Asp Asn Gly Gln Ser Thr Val Arg Leu Gln Leu
        195                 200                 205

Asn Asn Leu Arg Ala Glu Asp Thr Ala Thr Tyr Tyr Cys Thr Lys Asn
210                 215                 220

Gly Gly Cys Gly Ser Gly Gly Asp Leu Asp Cys Ile Asp Ala Trp Gly
225                 230                 235                 240

His Gly Thr Glu Val Ile Val Ser Ser Ser Leu Asp Pro Lys Ser Ser
                245                 250                 255

Asp Lys Thr His Thr Cys Pro Pro Cys Pro Ala Pro Glu Leu Leu Gly
            260                 265                 270

Gly Pro Ser Val Phe Leu Phe Pro Pro Lys Pro Lys Asp Thr Leu Met
        275                 280                 285

Ile Ser Arg Thr Pro Glu Val Thr Cys Val Val Val Asp Val Ser His
290                 295                 300

Glu Asp Pro Glu Val Lys Phe Asn Trp Tyr Val Asp Gly Val Glu Val
305                 310                 315                 320

His Asn Ala Lys Thr Lys Pro Arg Glu Glu Gln Tyr Asn Ser Thr Tyr
                325                 330                 335

Arg Val Val Ser Val Leu Thr Val Leu His Gln Asp Trp Leu Asn Gly
            340                 345                 350

Lys Glu Tyr Lys Cys Lys Val Ser Asn Lys Ala Leu Pro Ala Pro Ile
        355                 360                 365

Glu Lys Thr Ile Ser Lys Ala Lys Gly Gln Pro Arg Glu Pro Gln Val
370                 375                 380

Tyr Thr Leu Pro Pro Ser Arg Asp Glu Leu Thr Lys Asn Gln Val Ser
385                 390                 395                 400

Leu Thr Cys Leu Val Lys Gly Phe Tyr Pro Ser Asp Ile Ala Val Glu
                405                 410                 415

Trp Glu Ser Asn Gly Gln Pro Glu Asn Asn Tyr Lys Thr Thr Pro Pro
            420                 425                 430

Val Leu Asp Ser Asp Gly Ser Phe Phe Leu Tyr Ser Lys Leu Thr Val
        435                 440                 445

Asp Lys Ser Arg Trp Gln Gln Gly Asn Val Phe Ser Cys Ser Val Met
450                 455                 460

His Glu Ala Leu His Asn His Tyr Thr Gln Lys Ser Leu Ser Leu Ser
465                 470                 475                 480

Pro Gly Lys Val

<210> SEQ ID NO 54
<211> LENGTH: 480
<212> TYPE: PRT
<213> ORGANISM: Artificial Sequence
<220> FEATURE:
<223> OTHER INFORMATION: Synthetic Construct

<400> SEQUENCE: 54
```

-continued

```
Ala Val Thr Gln Pro Ala Ser Val Ser Ala Asn Pro Gly Glu Thr Val
1               5                   10                  15

Arg Ile Thr Cys Ser Gly Asp Ser Ser Tyr Tyr Ser Trp His Gln
                20                  25                  30

Gln Lys Ser Pro Gly Ser Ala Pro Val Ser Val Ile Tyr Ser Asn Thr
                35                  40                  45

Asp Arg Pro Ser Asp Ile Pro Ser Arg Phe Ser Gly Ser Ala Ser Gly
            50                  55                  60

Ser Thr Ala Thr Leu Thr Ile Thr Gly Val Gln Ala Glu Asp Glu Ala
65                  70                  75                  80

Val Tyr Phe Cys Gly Ala Tyr Asp Ser Ser Ser Asp Ser Asp Ile Phe
                85                  90                  95

Gly Ala Gly Thr Thr Leu Thr Val Leu Gly Gln Ser Ser Arg Ser Ser
                100                 105                 110

Gly Gly Gly Gly Ser Ser Gly Gly Gly Ser Met Ala Ala Val Thr
                115                 120                 125

Leu Asp Glu Ser Gly Gly Gly Leu Gln Thr Pro Gly Gly Gly Leu Ser
        130                 135                 140

Leu Val Cys Lys Ala Ser Gly Phe Asp Phe Ser Asn Phe Asn Met Ala
145                 150                 155                 160

Trp Val Arg Gln Gly Pro Gly Lys Gly Leu Glu Tyr Val Ala Glu Ile
                165                 170                 175

Ser Asp Thr Gly Ser Thr Pro Tyr Tyr Gly Ser Ala Val Gln Gly Arg
                180                 185                 190

Ala Thr Ile Ser Arg Asp Asn Gly Gln Ser Thr Val Arg Leu Gln Leu
                195                 200                 205

Asn Asn Leu Arg Ala Glu Asp Thr Gly Thr Tyr Phe Cys Thr Arg Asn
210                 215                 220

Phe Gly Ser Ser Val Ser Ser Ile Asp Ala Trp Gly His Gly Thr Glu
225                 230                 235                 240

Val Ile Val Ser Ser Ser Leu Asp Pro Lys Ser Ser Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
                275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
                355                 360                 365

Ser Lys Ala Lys Gly Gln Pro Arg Glu Pro Gln Val Tyr Thr Leu Pro
        370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415
```

```
Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Val
465                 470                 475                 480

<210> SEQ ID NO 55
<211> LENGTH: 491
<212> TYPE: PRT
<213> ORGANISM: Artificial Sequence
<220> FEATURE:
<223> OTHER INFORMATION: Synthetic Construct

<400> SEQUENCE: 55

Ala Val Thr Gln Pro Ser Ser Val Ser Ala Asn Pro Gly Glu Thr Val
1               5                   10                  15

Glu Ile Thr Cys Ser Gly Ser Ser Thr Tyr Tyr Gly Trp Tyr Gln Gln
            20                  25                  30

Lys Ser Pro Gly Ser Ala Pro Val Thr Val Ile Tyr Asp Asn Asp Lys
        35                  40                  45

Arg Pro Ser Asp Ile Pro Ser Arg Phe Ser Gly Ser Lys Ser Gly Ser
    50                  55                  60

Thr His Thr Leu Ile Ile Thr Gly Val Gln Val Asp Glu Ala Val
65                  70                  75                  80

Tyr Phe Cys Gly Asn Glu Asp Asn Asn Tyr Val Ala Ile Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Ser Met Ala Ala Val Thr Leu Asp
        115                 120                 125

Glu Ser Gly Gly Gly Leu Gln Thr Pro Gly Gly Ala Leu Ser Leu Val
130                 135                 140

Cys Lys Ala Ser Gly Phe Thr Phe Ser Ser Tyr Asn Met Gly Trp Val
145                 150                 155                 160

Arg Gln Ala Pro Gly Lys Gly Leu Glu Phe Val Ala Gly Ile Tyr Ala
                165                 170                 175

Ser Gly Ser Ser Thr Asp Thr Asp Thr Thr Tyr Gly Pro Ala Val Ala
            180                 185                 190

Gly Arg Ala Thr Ile Ser Arg Asp Asn Gly Gln Ser Thr Val Arg Leu
        195                 200                 205

Gln Leu Asn Asn Leu Arg Ala Glu Asp Thr Gly Thr Tyr Tyr Cys Ala
    210                 215                 220

Lys Ala Ala Gly Gly Cys Ser His Thr Cys Thr Ala Tyr Ile Ala
225                 230                 235                 240

Asp Ser Ile Asp Ala Trp Gly His Gly Thr Glu Val Ile Val Ser Ser
                245                 250                 255

Ser Leu Asp Pro Lys Ser Ser Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300
```

```
Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
            325                 330                 335

Glu Gln Tyr Asn Ser Thr Tyr Arg Val Val Ser Val Leu Thr Val Leu
        340                 345                 350

His Gln Asp Trp Leu Asn Gly Lys Glu Tyr Lys Cys Lys Val Ser Asn
    355                 360                 365

Lys Ala Leu Pro Ala Pro Ile Glu Lys Thr Ile Ser Lys Ala Lys Gly
370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys Val
                485                 490

<210> SEQ ID NO 56
<211> LENGTH: 489
<212> TYPE: PRT
<213> ORGANISM: Artificial Sequence
<220> FEATURE:
<223> OTHER INFORMATION: Synthetic Construct

<400> SEQUENCE: 56

Ala Leu Thr Gln Pro Ser Ser Val Ser Ala Asn Pro Gly Glu Thr Val
1               5                   10                  15

Lys Ile Thr Cys Ser Gly Asp Asn Ser Ala His Tyr Tyr Tyr Gly Trp
            20                  25                  30

Tyr Gln Gln Lys Ser Pro Gly Ser Ala Pro Val Thr Val Ile Tyr Tyr
        35                  40                  45

Asn Asp Lys Arg Pro Ser Gly Ile Pro Ser Arg Phe Ser Gly Ser Ala
    50                  55                  60

Ser Gly Ser Thr Ala Thr Leu Ile Ile Thr Gly Val Gln Val Glu Asp
65                  70                  75                  80

Glu Ala Val Tyr Phe Cys Gly Ser Ala Asp Ser Ser Asn Pro Ala Ile
                85                  90                  95

Phe Gly Ala Gly Thr Thr Leu Thr Val Leu Gly Gln Ser Ser Arg Ser
            100                 105                 110

Ser Gly Gly Gly Gly Ser Gly Gly Gly Ser Met Ala Ala Val
            115                 120                 125

Thr Leu Asp Glu Ser Gly Gly Gly Leu Gln Thr Pro Gly Arg Ala Leu
130                 135                 140

Ser Leu Val Cys Arg Gly Ser Gly Phe Ser Ile Ser Ser Tyr Asn Met
145                 150                 155                 160

Gly Trp Val Arg Gln Ala Pro Gly Lys Gly Leu Glu Phe Ile Ala Ser
                165                 170                 175
```

Ile Gly Ser Asp Gly Ser Ser Thr His Tyr Ala Pro Ala Val Lys Gly
                180                 185                 190

Arg Ala Thr Ile Thr Arg Asp Val Gly Gln Ser Thr Val Arg Leu Gln
            195                 200                 205

Leu Asn Asn Leu Arg Ala Glu Asp Thr Gly Thr Tyr Phe Cys Ala Lys
        210                 215                 220

Asp Ala Tyr Gln Cys Ser Tyr Ala Thr Cys Asn Asp Tyr Leu Asp Thr
225                 230                 235                 240

Ile Asp Ala Trp Gly His Gly Thr Glu Val Ile Val Ser Ser Ser Leu
                245                 250                 255

Asp Pro Lys Ser Ser Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
            325                 330                 335

Tyr Asn Ser Thr Tyr Arg Val Val Ser Val Leu Thr Val Leu His Gln
        340                 345                 350

Asp Trp Leu Asn Gly Lys Glu Tyr Lys Cys Lys Val Ser Asn Lys Ala
    355                 360                 365

Leu Pro Ala Pro Ile Glu Lys Thr Ile Ser Lys Ala Lys Gly Gln Pro
370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
            405                 410                 415

Asp Ile Ala Val Glu Trp Glu Ser Asn Gly Gln Pro Glu Asn Asn Tyr
        420                 425                 430

Lys Thr Thr Pro Pro Val Leu Asp Ser Asp Gly Ser Phe Phe Leu Tyr
    435                 440                 445

Ser Lys Leu Thr Val Asp Lys Ser Arg Trp Gln Gln Gly Asn Val Phe
450                 455                 460

Ser Cys Ser Val Met His Glu Ala Leu His Asn His Tyr Thr Gln Lys
465                 470                 475                 480

Ser Leu Ser Leu Ser Pro Gly Lys Val
            485

<210> SEQ ID NO 57
<211> LENGTH: 487
<212> TYPE: PRT
<213> ORGANISM: Artificial Sequence
<220> FEATURE:
<223> OTHER INFORMATION: Synthetic Construct

<400> SEQUENCE: 57

Ala Val Thr Gln Pro Ala Ser Val Ser Ala Asn Pro Gly Glu Thr Val
1               5                   10                  15

Lys Ile Thr Cys Ser Gly Ser Ser Gly Ser Tyr Gly Trp Tyr Gln
            20                  25                  30

Gln Lys Ser Pro Gly Ser Ala Pro Val Thr Leu Ile Tyr Glu Thr Asn
        35                  40                  45

```
Lys Arg Pro Ser Asn Ile Pro Ser Arg Phe Ser Gly Ser Lys Ser Gly
 50                  55                  60

Ser Thr Ala Thr Leu Thr Ile Thr Gly Val Gln Ala Asp Asp Glu Ala
 65                  70                  75                  80

Val Tyr Tyr Cys Gly Ser Glu Asp Ser Ser Thr Tyr Leu Ser Ile Phe
                 85                  90                  95

Gly Ala Gly Thr Thr Leu Thr Val Leu Gly Gln Ser Ser Arg Ser Ser
            100                 105                 110

Gly Gly Gly Gly Ser Ser Gly Gly Gly Ser Met Ala Ala Val Thr
            115                 120                 125

Leu Asp Glu Ser Gly Gly Leu Gln Thr Pro Gly Gly Ala Leu Ser
130                 135                 140

Leu Val Cys Lys Ala Ser Gly Phe Thr Phe Ser Ser Phe Asn Met Gly
145                 150                 155                 160

Trp Val Arg Gln Ala Pro Gly Lys Gly Leu Glu Phe Val Ala Ala Ile
                165                 170                 175

Tyr Ser Gly Asn Ser Ala Glu Tyr Gly Ala Ala Val Gln Gly Arg Ala
            180                 185                 190

Thr Ile Ser Arg Asp Asn Gly Gln Ser Thr Val Arg Leu Gln Leu Asn
            195                 200                 205

Asn Leu Arg Ala Glu Asp Thr Gly Ile Tyr Phe Cys Ala Lys Asp Ala
210                 215                 220

Gly Ser Gly Cys Tyr Ser Gly Val Cys Ala Gly Thr Ser Ser Ile Asp
225                 230                 235                 240

Ala Trp Gly His Gly Thr Glu Val Ile Val Ser Ser Ser Leu Asp Pro
                245                 250                 255

Lys Ser Ser Asp Lys Thr His Thr Cys Pro Pro Cys Pro Ala Pro Glu
            260                 265                 270

Leu Leu Gly Gly Pro Ser Val Phe Leu Phe Pro Pro Lys Pro Lys Asp
            275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Glu Glu Tyr Lys Cys Lys Val Ser Asn Lys Ala Leu Pro
            355                 360                 365

Ala Pro Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
            435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
```

```
                465                 470                 475                 480
Ser Leu Ser Pro Gly Lys Val
                    485

<210> SEQ ID NO 58
<211> LENGTH: 489
<212> TYPE: PRT
<213> ORGANISM: Artificial Sequence
<220> FEATURE:
<223> OTHER INFORMATION: Synthetic Construct

<400> SEQUENCE: 58

Ala Val Thr Gln Pro Ala Ser Val Ser Ala Asn Pro Gly Glu Thr Val
1               5                   10                  15

Lys Ile Thr Cys Ser Gly Asp Ser Ser Tyr Tyr Gly Trp Tyr Gln Gln
            20                  25                  30

Lys Ser Pro Gly Ser Ala Pro Val Thr Val Ile Tyr Asp Asp Asn Lys
        35                  40                  45

Arg Pro Ser Asn Ile Pro Ser Arg Phe Ser Gly Ser Lys Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Asn Glu Asp Asn Ser Tyr Val Ala Ile Phe Gly Ala
                85                  90                  95

Gly Thr Thr Leu Thr Val Leu Gly Gln Ser Ser Arg Ser Ser Gly Gly
            100                 105                 110

Gly Gly Ser Ser Gly Gly Gly Ser Met Ala Ala Val Thr Leu Asp
        115                 120                 125

Glu Ser Gly Gly Gly Leu Gln Thr Pro Gly Gly Ala Leu Ser Leu Val
130                 135                 140

Cys Lys Ala Ser Gly Phe Thr Phe Ser Ser Tyr Asn Met Gly Trp Val
145                 150                 155                 160

Arg Gln Ala Pro Gly Lys Gly Leu Glu Phe Val Ala Gly Ile Tyr Ile
                165                 170                 175

Ala Ser Gly Asp Leu Gly Thr Thr Tyr Gly Ala Ala Val Gln Gly Arg
            180                 185                 190

Ala Thr Ile Ser Arg Asp Asp Gly Gln Ser Thr Val Arg Leu Gln Leu
        195                 200                 205

Asn Asn Leu Arg Ala Glu Asp Thr Gly Thr Tyr Phe Cys Ala Lys Ser
    210                 215                 220

Ala Gly Gly Cys Ser Ala His Ser Cys Asp Thr Tyr Ile Ala Asp Ser
225                 230                 235                 240

Ile Asp Ala Trp Gly His Gly Thr Glu Val Ile Val Ser Ser Ser Leu
                245                 250                 255

Asp Pro Lys Ser Ser Asp Lys Thr His Thr Cys Pro Pro Cys Pro Ala
            260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
```

```
                    340                 345                 350
Asp Trp Leu Asn Gly Lys Glu Tyr Lys Cys Lys Val Ser Asn Lys Ala
            355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Val
                485

<210> SEQ ID NO 59
<211> LENGTH: 490
<212> TYPE: PRT
<213> ORGANISM: Artificial Sequence
<220> FEATURE:
<223> OTHER INFORMATION: Synthetic Construct

<400> SEQUENCE: 59

Ala Val Thr Gln Pro Ala Ser Val Ser Ala Asn Pro Gly Glu Thr Val
1               5                   10                  15

Lys Ile Thr Cys Ser Gly Ser Ser Ser Tyr Tyr Gly Trp Tyr Arg Gln
            20                  25                  30

Lys Ser Pro Gly Ser Ala Pro Val Thr Leu Ile Tyr Asp Asn Asp Lys
        35                  40                  45

Arg Pro Ser Gly Ile Pro Ser Arg Phe Ser Gly Ser Lys Ser Gly Ser
    50                  55                  60

Thr Asn Thr Leu Thr Ile Thr Gly Val Gln Ala Asp Asp Glu Ala Val
65                  70                  75                  80

Tyr Tyr Cys Gly Asn Glu Asp Asn Ser Tyr Val Gly Ile Phe Gly Ala
                85                  90                  95

Gly Thr Thr Leu Thr Val Leu Gly Gln Ser Ser Arg Ser Ser Gly Gly
            100                 105                 110

Gly Gly Ser Gly Gly Gly Gly Ser Met Ala Ala Val Thr Leu Asp
        115                 120                 125

Glu Ser Gly Gly Gly Leu Gln Thr Pro Gly Gly Ala Leu Ser Leu Val
    130                 135                 140

Cys Lys Ala Ser Gly Phe Thr Phe Ser Ser Tyr Asn Met Gly Trp Val
145                 150                 155                 160

Arg Gln Ala Pro Asp Lys Gly Leu Glu Phe Val Ala Gly Ile Tyr Thr
                165                 170                 175

Gly Ser Asp Ala Gly Leu Ser Thr Thr Tyr Gly Ala Ala Val Gln Gly
            180                 185                 190

Arg Ala Thr Ile Ser Arg Asp Asn Gly Gln Ser Thr Val Arg Leu Gln
        195                 200                 205

Leu Asn Asn Leu Gly Ala Glu Asp Thr Gly Ile Tyr Phe Cys Thr Lys
```

```
              210                 215                 220
Ser Ala Gly Gly Cys Ser Asp Tyr Asn Cys Asp Ala Tyr Ile Ala Asp
225                 230                 235                 240

Ser Ile Asp Ala Trp Gly His Gly Thr Glu Val Ile Val Ser Ser Ser
                    245                 250                 255

Leu Asp Pro Lys Ser Ser Asp Lys Thr His Thr Cys Pro Pro Cys Pro
                260                 265                 270

Ala Pro Glu Leu Leu Gly Gly Pro Ser Val Phe Leu Phe Pro Pro Lys
            275                 280                 285

Pro Lys Asp Thr Leu Met Ile Ser Arg Thr Pro Glu Val Thr Cys Val
        290                 295                 300

Val Val Asp Val Ser His Glu Asp Pro Glu Val Lys Phe Asn Trp Tyr
305                 310                 315                 320

Val Asp Gly Val Glu Val His Asn Ala Lys Thr Lys Pro Arg Glu Glu
                325                 330                 335

Gln Tyr Asn Ser Thr Tyr Arg Val Val Ser Val Leu Thr Val Leu His
                340                 345                 350

Gln Asp Trp Leu Asn Gly Lys Glu Tyr Lys Cys Lys Val Ser Asn Lys
            355                 360                 365

Ala Leu Pro Ala Pro Ile Glu Lys Thr Ile Ser Lys Ala Lys Gly Gln
        370                 375                 380

Pro Arg Glu Pro Gln Val Tyr Thr Leu Pro Pro Ser Arg Asp Glu Leu
385                 390                 395                 400

Thr Lys Asn Gln Val Ser Leu Thr Cys Leu Val Lys Gly Phe Tyr Pro
                405                 410                 415

Ser Asp Ile Ala Val Glu Trp Glu Ser Asn Gly Gln Pro Glu Asn Asn
                420                 425                 430

Tyr Lys Thr Thr Pro Pro Val Leu Asp Ser Asp Gly Ser Phe Phe Leu
            435                 440                 445

Tyr Ser Lys Leu Thr Val Asp Lys Ser Arg Trp Gln Gln Gly Asn Val
        450                 455                 460

Phe Ser Cys Ser Val Met His Glu Ala Leu His Asn His Tyr Thr Gln
465                 470                 475                 480

Lys Ser Leu Ser Leu Ser Pro Gly Lys Val
                485                 490

<210> SEQ ID NO 60
<211> LENGTH: 489
<212> TYPE: PRT
<213> ORGANISM: Artificial Sequence
<220> FEATURE:
<223> OTHER INFORMATION: Synthetic Construct

<400> SEQUENCE: 60

Ala Val Thr Gln Pro Ala Ser Val Ser Ala Asn Leu Gly Glu Thr Val
1               5                   10                  15

Lys Ile Thr Cys Ser Gly Asp Ser Ser Tyr Tyr Gly Trp Tyr Gln Gln
                20                  25                  30

Lys Ala Pro Gly Ser Ala Pro Val Thr Leu Ile Tyr Asp Asn Asp Lys
            35                  40                  45

Arg Pro Ser Asn Ile Pro Ser Arg Phe Ser Gly Ser Lys Ser Gly Ser
        50                  55                  60

Thr Ala Thr Leu Thr Ile Thr Gly Val Gln Ala Asp Asp Glu Ala Val
65                  70                  75                  80

Tyr Tyr Cys Gly Asn Glu Asp Met Asn Tyr Val Gly Ile Phe Gly Ala
```

```
            85                  90                  95
Gly Thr Thr Leu Thr Val Leu Gly Gln Ser Ser Arg Ser Ser Gly Gly
            100                 105                 110

Gly Gly Ser Ser Gly Gly Gly Ser Met Ala Ala Val Thr Leu Asp
        115                 120                 125

Glu Ser Gly Gly Gly Leu Gln Thr Pro Gly Gly Ala Leu Ser Leu Val
    130                 135                 140

Cys Lys Ala Ser Gly Phe Thr Phe Asn Ser Tyr Asn Met Gly Trp Val
145                 150                 155                 160

Arg Gln Ala Pro Gly Lys Gly Leu Glu Phe Val Ala Gly Ile Tyr Ser
                165                 170                 175

Ala Gly Gly Asp Thr Ser Thr Tyr Gly Ala Ala Val Asn Gly Arg
            180                 185                 190

Ala Thr Ile Ser Arg Asp Asn Gly Gln Ser Thr Val Arg Leu Gln Leu
            195                 200                 205

Asn Asn Leu Arg Ala Glu Asp Thr Gly Ile Tyr Phe Cys Ala Lys Ala
    210                 215                 220

Ala Gly Gly Cys Thr Ala His Asn Cys Asp Ala Tyr Ile Ala Asp Ser
225                 230                 235                 240

Ile Asp Ala Trp Gly His Gly Thr Glu Val Ile Val Ser Ser Ser Leu
                245                 250                 255

Asp Pro Lys Ser Ser Asp Lys Thr His Thr Cys Pro Pro Cys Pro Ala
        260                 265                 270

Pro Glu Leu Leu Gly Gly Pro Ser Val Phe Leu Phe Pro Pro Lys Pro
        275                 280                 285

Lys Asp Thr Leu Met Ile Ser Arg Thr Pro Glu Val Thr Cys Val Val
        290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
        370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
        450                 455                 460

Ser Cys Ser Val Met His Glu Ala Leu His Asn His Tyr Thr Gln Lys
465                 470                 475                 480

Ser Leu Ser Leu Ser Pro Gly Lys Val
                485

<210> SEQ ID NO 61
```

```
<211> LENGTH: 480
<212> TYPE: PRT
<213> ORGANISM: Artificial Sequence
<220> FEATURE:
<223> OTHER INFORMATION: Synthetic Construct

<400> SEQUENCE: 61
```

| | | | | | | | | | | | | | | | |
|---|---|---|---|---|---|---|---|---|---|---|---|---|---|---|---|
| Glu | Thr | Val | Leu | Thr | Gln | Ser | Pro | Ala | Thr | Leu | Ser | Val | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Thr | Val | Gly | Ser | Lys |
| | | | 20 | | | | | 25 | | | | | 30 | | |
| Leu | Ala | Trp | His | Gln | Gln | Lys | Pro | Gly | Gln | Ala | Pro | Arg | Leu | Leu | Ile |
| | | | 35 | | | | | 40 | | | | | 45 | | |
| Tyr | Asp | Ala | Thr | Asn | Arg | Ala | Thr | Gly | Ile | Ser | Asp | Arg | Phe | Ser | Gly |
| | | | 50 | | | | | 55 | | | | | 60 | | |
| Ser | Gly | Ser | Gly | Thr | Asp | Phe | Thr | Leu | Thr | Ile | Ser | Ser | Leu | Gln | Thr |
| 65 | | | | | 70 | | | | | 75 | | | | | 80 |
| Glu | Asp | Ser | Ala | Val | Tyr | Tyr | Cys | Gln | Gln | Tyr | Tyr | Tyr | Trp | Pro | Pro |
| | | | | 85 | | | | | 90 | | | | | 95 | |
| Tyr | Arg | Phe | Gly | Gly | Gly | Thr | Lys | Val | Glu | Ile | Lys | Gly | Gln | Ser | Ser |
| | | | 100 | | | | | 105 | | | | | 110 | | |
| Arg | Ser | Ser | Gly | Gly | Gly | Gly | Ser | Gly | Gly | Gly | Ser | Asp | Val |
| | | | 115 | | | | | 120 | | | | | 125 | |
| Gln | Leu | Val | Glu | Ser | Gly | Gly | Gly | Val | Val | Arg | Pro | Gly | Glu | Ser | Leu |
| | 130 | | | | | 135 | | | | | 140 | | | | |
| Arg | Leu | Ser | Cys | Ala | Ala | Ser | Gly | Phe | Ser | Phe | Ser | Ser | Tyr | Ala | Met |
| 145 | | | | | 150 | | | | | 155 | | | | | 160 |
| Asn | Trp | Val | Arg | Gln | Ala | Pro | Gly | Glu | Gly | Leu | Glu | Trp | Val | Ser | Arg |
| | | | | 165 | | | | | 170 | | | | | 175 | |
| Ile | Asn | Ser | Gly | Gly | Gly | Gly | Thr | Asp | Tyr | Ala | Glu | Ser | Val | Lys | Gly |
| | | | 180 | | | | | 185 | | | | | 190 | | |
| Arg | Phe | Thr | Ile | Ser | Arg | Asp | Asn | Ser | Glu | Asn | Thr | Leu | Tyr | Leu | Gln |
| | | | 195 | | | | | 200 | | | | | 205 | | |
| Met | Asn | Ser | Leu | Arg | Ala | Glu | Asp | Thr | Ala | Val | Tyr | Tyr | Cys | Ala | Lys |
| | 210 | | | | | 215 | | | | | 220 | | | | |
| Gln | Tyr | Asp | Trp | Asn | Ser | Phe | Phe | Asp | Tyr | Trp | Gly | Leu | Gly | Ala | Leu |
| 225 | | | | | 230 | | | | | 235 | | | | | 240 |
| Val | Thr | Val | Ser | Ser | Ser | Leu | Asp | Pro | Lys | Ser | Ser | Asp | Lys | Thr | His |
| | | | | 245 | | | | | 250 | | | | | 255 | |
| Thr | Cys | Pro | Pro | Cys | Pro | Ala | Pro | Glu | Leu | Leu | Gly | Gly | Pro | Ser | Val |
| | | | 260 | | | | | 265 | | | | | 270 | | |
| Phe | Leu | Phe | Pro | Pro | Lys | Pro | Lys | Asp | Thr | Leu | Met | Ile | Ser | Arg | Thr |
| | | | 275 | | | | | 280 | | | | | 285 | | |
| Pro | Glu | Val | Thr | Cys | Val | Val | Val | Asp | Val | Ser | His | Glu | Asp | Pro | Glu |
| | 290 | | | | | 295 | | | | | 300 | | | | |
| Val | Lys | Phe | Asn | Trp | Tyr | Val | Asp | Gly | Val | Glu | Val | His | Asn | Ala | Lys |
| 305 | | | | | 310 | | | | | 315 | | | | | 320 |
| Thr | Lys | Pro | Arg | Glu | Glu | Gln | Tyr | Asn | Ser | Thr | Tyr | Arg | Val | Val | Ser |
| | | | | 325 | | | | | 330 | | | | | 335 | |
| Val | Leu | Thr | Val | Leu | His | Gln | Asp | Trp | Leu | Asn | Gly | Lys | Glu | Tyr | Lys |
| | | | 340 | | | | | 345 | | | | | 350 | | |
| Cys | Lys | Val | Ser | Asn | Lys | Ala | Leu | Pro | Ala | Pro | Ile | Glu | Lys | Thr | Ile |
| | | | 355 | | | | | 360 | | | | | 365 | | |
| Ser | Lys | Ala | Lys | Gly | Gln | Pro | Arg | Glu | Pro | Gln | Val | Tyr | Thr | Leu | Pro |
| | 370 | | | | | 375 | | | | | 380 | | | | |

```
Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
        420                 425                 430

Asp Gly Ser Phe Phe Leu Tyr Ser Lys Leu Thr Val Asp Lys Ser Arg
    435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Val
465                 470                 475                 480

<210> SEQ ID NO 62
<211> LENGTH: 480
<212> TYPE: PRT
<213> ORGANISM: Artificial Sequence
<220> FEATURE:
<223> OTHER INFORMATION: Synthetic Construct

<400> SEQUENCE: 62

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Ser Asp Arg Phe Ser Gly
    50                  55                  60

Ser Arg Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys Gly Gln Ser Ser
            100                 105                 110

Arg Ser Ser Gly Gly Gly Gly Ser Gly Gly Gly Gly Ser Asp Val
        115                 120                 125

Gln Leu Val Glu Ser Gly Gly Gly Val Val Arg Pro Gly Glu Ser Leu
    130                 135                 140

Arg Leu Ser Cys Ala Ala Ser Gly Phe Ser Phe Ser Ser Tyr Ala Met
145                 150                 155                 160

Asn Trp Val Arg Gln Ala Pro Gly Glu Gly Leu Glu Trp Val Ser Arg
                165                 170                 175

Ile Asn Ser Gly Gly Gly Gly Thr Asp Tyr Ala Glu Ser Val Lys Gly
            180                 185                 190

Arg Phe Thr Ile Ser Arg Asp Asn Ser Glu Asn Thr Leu Tyr Leu Gln
        195                 200                 205

Met Asn Ser Leu Arg Ala Glu Asp Thr Ala Val Tyr Tyr Cys Ala Lys
    210                 215                 220

Gln Tyr Asp Trp Asn Ser Phe Phe Asp Tyr Trp Gly Leu Gly Ala Leu
225                 230                 235                 240

Val Thr Val Ser Ser Leu Asp Pro Lys Ser Ser Asp Lys Thr His
                245                 250                 255

Thr Cys Pro Pro Cys Pro Ala Pro Glu Leu Leu Gly Gly Pro Ser Val
            260                 265                 270
```

```
Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
        340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
    370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Val
465                 470                 475                 480

<210> SEQ ID NO 63
<211> LENGTH: 480
<212> TYPE: PRT
<213> ORGANISM: Artificial Sequence
<220> FEATURE:
<223> OTHER INFORMATION: Synthetic Construct

<400> SEQUENCE: 63

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Trp Pro Pro
                85                  90                  95

Tyr Arg Phe Gly Gly Gly Thr Lys Val Glu Ile Lys Gly Gln Ser Ser
                100                 105                 110

Arg Ser Ser Gly Gly Gly Gly Ser Arg Gly Gly Ser Asp Val
            115                 120                 125

Gln Leu Val Glu Ser Gly Gly Gly Val Val Arg Pro Gly Glu Ser Leu
    130                 135                 140

Arg Leu Ser Cys Ala Ala Ser Gly Phe Ser Phe Ser Ser Tyr Ala Met
145                 150                 155                 160
```

Asn Trp Val Arg Gln Ala Pro Gly Glu Gly Leu Glu Trp Val Ser Arg
            165                 170                 175

Ile Asn Ser Gly Gly Gly Thr Asp Tyr Ala Glu Ser Val Lys Gly
        180                 185                 190

Arg Phe Thr Ile Ser Arg Asp Asn Ser Glu Asn Thr Leu Tyr Leu Gln
            195                 200                 205

Met Asn Ser Leu Arg Ala Glu Asp Thr Ala Val Tyr Tyr Cys Ala Lys
    210                 215                 220

Gln Tyr Asp Trp Asn Gly Phe Phe Asp Tyr Trp Gly Leu Gly Ala Leu
225                 230                 235                 240

Val Thr Val Ser Ser Ser Leu Asp Pro Lys Ser Ser Asp Lys Thr His
            245                 250                 255

Thr Cys Pro Pro Cys Pro Val Pro Glu Leu Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser His Glu Asp Pro Glu
    290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
            325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
            405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
450                 455                 460

His Asn His Tyr Thr Gln Lys Ser Leu Ser Leu Ser Pro Gly Lys Val
465                 470                 475                 480

<210> SEQ ID NO 64
<211> LENGTH: 480
<212> TYPE: PRT
<213> ORGANISM: Artificial Sequence
<220> FEATURE:
<223> OTHER INFORMATION: Synthetic Construct

<400> SEQUENCE: 64

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

-continued

```
Tyr Asp Ala Ser Arg Arg Ala Thr Gly Ile Pro Asp Arg Phe Ser Gly
     50                  55                  60

Ser Gly Ser Gly Thr Asp Phe Thr Leu Thr Ile Ser Ser Leu Gln Thr
 65                  70                  75                  80

Glu Asp Ser Ala Val Tyr Tyr Cys Gln Gln Tyr Tyr Tyr Trp Pro Pro
                 85                  90                  95

Tyr Arg Phe Gly Gly Gly Thr Lys Val Glu Ile Lys Gly Gln Ser Ser
                100                 105                 110

Arg Ser Ser Gly Gly Gly Gly Ser Gly Gly Gly Gly Ser Asp Val
             115                 120                 125

Gln Leu Val Glu Ser Gly Gly Val Val Arg Pro Gly Glu Ser Leu
         130                 135                 140

Arg Leu Ser Cys Ala Ala Ser Gly Phe Ser Phe Ser Ser Tyr Ala Met
145                 150                 155                 160

Asn Trp Val Arg Gln Ala Pro Gly Glu Gly Leu Glu Trp Val Ser Arg
                165                 170                 175

Ile Asn Ser Gly Gly Gly Gly Thr Asp Tyr Ala Glu Ser Val Lys Gly
                180                 185                 190

Arg Phe Thr Ile Ser Arg Asp Asn Ser Glu Asn Thr Leu Tyr Leu Gln
             195                 200                 205

Met Asn Ser Leu Arg Ala Glu Asp Thr Ala Val Tyr Tyr Cys Ala Lys
         210                 215                 220

Gln Tyr Asp Trp Asn Gly Phe Phe Asp Tyr Trp Gly Leu Gly Ala Leu
225                 230                 235                 240

Val Thr Val Ser Ser Ser Leu Asp Pro Lys Ser Ser Asp Lys Thr His
                245                 250                 255

Thr Cys Pro Pro Cys Pro Ala Pro Glu Leu Leu Gly Gly Pro Ser Val
             260                 265                 270

Phe Leu Phe Pro Pro Lys Pro Lys Asp Thr Leu Met Ile Ser Arg Thr
         275                 280                 285

Pro Glu Val Thr Cys Val Val Val Asp Val Ser His Glu Asp Pro Glu
         290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
             340                 345                 350

Cys Lys Val Ser Asn Lys Ala Leu Pro Ala Pro Ile Glu Lys Thr Ile
         355                 360                 365

Ser Lys Ala Lys Gly Gln Pro Arg Glu Pro Gln Val Tyr Thr Leu Pro
     370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
             420                 425                 430

Asp Gly Ser Phe Phe Leu Tyr Ser Lys Leu Thr Val Asp Lys Ser Arg
         435                 440                 445

Trp Gln Gln Gly Asn Val Phe Ser Cys Ser Val Met His Glu Ala Leu
     450                 455                 460
```

```
His Asn His Tyr Thr Gln Lys Ser Leu Ser Leu Ser Pro Gly Lys Val
465                 470                 475                 480

<210> SEQ ID NO 65
<211> LENGTH: 481
<212> TYPE: PRT
<213> ORGANISM: Artificial Sequence
<220> FEATURE:
<223> OTHER INFORMATION: Synthetic Construct

<400> SEQUENCE: 65

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys Gly Gln Ser Ser
            100                 105                 110

Arg Ser Ser Gly Gly Gly Gly Ser Gly Gly Gly Ser Asp Val
        115                 120                 125

Gln Leu Leu Glu Ser Gly Gly Val Val Gln Pro Gly Gly Ser Leu
130                 135                 140

Arg Leu Ser Cys Ala Ala Ser Gly Phe Ser Phe Ser Asn Phe Ala Met
145                 150                 155                 160

Thr Trp Val Arg Gln Ala Pro Gly Glu Gly Leu Glu Trp Val Ser Thr
                165                 170                 175

Ile Gly Ser Gly Asp Thr Tyr Tyr Ala Asp Ser Val Lys Gly Arg Phe
            180                 185                 190

Thr Ile Ser Arg Asp Asn Ser Lys Asn Thr Leu Tyr Leu Gln Met Asn
        195                 200                 205

Ser Leu Arg Ala Glu Asp Thr Ala Val Tyr Tyr Cys Ala Lys Asp Ser
210                 215                 220

Thr Val Ser Trp Ser Gly Asp Phe Asp Tyr Trp Gly Leu Gly Thr
225                 230                 235                 240

Leu Val Thr Val Ser Ser Leu Asp Pro Lys Ser Ser Asp Lys Pro
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350
```

```
Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
    370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

Val

<210> SEQ ID NO 66
<211> LENGTH: 481
<212> TYPE: PRT
<213> ORGANISM: Artificial Sequence
<220> FEATURE:
<223> OTHER INFORMATION: Synthetic Construct

<400> SEQUENCE: 66

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys Gly Gln Ser Ser
                100                 105                 110

Arg Ser Ser Gly Gly Gly Gly Ser Ser Gly Gly Gly Ser Asp Val
            115                 120                 125

Gln Leu Val Glu Ser Gly Gly Gly Val Val Gln Pro Gly Gly Ser Leu
    130                 135                 140

Arg Leu Ser Cys Ala Ala Ser Gly Phe Ser Phe Ser Asn Phe Ala Met
145                 150                 155                 160

Thr Trp Val Arg Gln Ala Pro Gly Glu Gly Leu Glu Trp Val Ser Thr
                165                 170                 175

Ile Gly Ser Gly Asp Thr Tyr Tyr Ala Asp Ser Val Lys Gly Arg Phe
                180                 185                 190

Thr Ile Ser Arg Asp Asn Ser Lys Asn Thr Leu Tyr Leu Gln Met Asn
            195                 200                 205

Ser Leu Arg Ala Glu Asp Thr Ala Val Tyr Tyr Cys Ala Lys Asp Ser
    210                 215                 220

Thr Val Ser Trp Ser Gly Asp Phe Phe Asp Tyr Trp Gly Leu Gly Thr
```

```
                225                 230                 235                 240
Arg Val Thr Val Ser Ser Leu Asp Pro Lys Ser Ser Asp Lys Thr
                245                 250                 255

His Thr Cys Pro Pro Cys Pro Ala Pro Glu Leu Leu Gly Gly Pro Ser
                260                 265                 270

Val Phe Leu Phe Pro Pro Lys Pro Lys Asp Thr Leu Met Ile Ser Arg
            275                 280                 285

Thr Pro Glu Val Thr Cys Val Val Val Asp Val Ser His Glu Asp Pro
        290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
        435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

Val

<210> SEQ ID NO 67
<211> LENGTH: 481
<212> TYPE: PRT
<213> ORGANISM: Artificial Sequence
<220> FEATURE:
<223> OTHER INFORMATION: Synthetic Construct

<400> SEQUENCE: 67

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys Gly Gln Ser Ser
            100                 105                 110
```

```
Arg Ser Ser Gly Gly Gly Ser Gly Gly Gly Ser Asp Val
        115                 120             125

Gln Leu Val Glu Ser Gly Gly Val Val Arg Pro Gly Glu Ser Leu
    130                 135             140

Arg Leu Ser Cys Ala Ala Ser Gly Phe Arg Phe Ser Asn Phe Ala Met
145                 150                 155                 160

Thr Trp Val Arg Gln Ala Pro Gly Glu Gly Leu Glu Trp Val Ser Thr
                165                 170                 175

Ile Gly Ser Gly Asp Thr Tyr Tyr Ala Asp Ser Val Lys Gly Arg Phe
                180                 185                 190

Thr Ile Ser Arg Asp Asn Ser Lys Asn Thr Leu Tyr Leu Gln Met Asn
            195                 200                 205

Ser Leu Arg Ala Glu Asp Thr Ala Val Tyr Tyr Cys Ala Lys Asp Ser
        210                 215                 220

Thr Val Ser Trp Ser Gly Asp Phe Phe Asp Tyr Trp Gly Leu Gly Thr
225                 230                 235                 240

Leu Val Thr Val Ser Ser Ser Leu Asp Pro Lys Ser Ser Asp Lys Thr
                245                 250                 255

His Thr Cys Pro Pro Cys Pro Ala Pro Glu Leu Leu Gly Gly Pro Ser
            260                 265                 270

Val Phe Leu Phe Pro Pro Lys Pro Lys Asp Thr Leu Met Ile Ser Arg
        275                 280                 285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
        355                 360                 365

Ile Ser Lys Ala Lys Gly Gln Pro Arg Glu Pro Gln Val Tyr Thr Leu
370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
                420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
    450                 455                 460

Leu His Asn His Tyr Thr Gln Lys Ser Leu Ser Leu Ser Pro Gly Lys
465                 470                 475                 480

Val
```

<210> SEQ ID NO 68
<211> LENGTH: 478
<212> TYPE: PRT
<213> ORGANISM: Artificial Sequence
<220> FEATURE:
<223> OTHER INFORMATION: Synthetic Construct

<400> SEQUENCE: 68

```
Glu Ile Val Leu Thr Gln Ser Pro Gly Thr Leu Ser Val Ser Pro Gly
1               5                   10                  15

Glu Arg Val Thr Leu Thr Cys Arg Ala Ser Gln Gly Ile Ala Gly Lys
            20                  25                  30

Ile Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Gly Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln His Tyr Asp Trp Ser Pro
                85                  90                  95

Leu Thr Phe Gly Gly Gly Thr Lys Val Glu Ile Lys Gly Gln Ser Ser
            100                 105                 110

Arg Ser Ser Gly Gly Gly Ser Ser Gly Gly Gly Ser Asp Val
        115                 120                 125

Gln Leu Val Glu Ser Gly Gly Leu Val Gln Pro Gly Gly Ser Leu
130                 135                 140

Arg Leu Ser Cys Thr Ala Ser Gly Phe Thr Phe Arg Asn Tyr Gly Met
145                 150                 155                 160

Ser Trp Val Arg Gln Ala Pro Gly Glu Gly Leu Glu Trp Val Ser Ala
                165                 170                 175

Ser Ser Gly Ser Gly Ser Thr Tyr Tyr Thr Asp Ser Val Lys Gly Arg
            180                 185                 190

Phe Thr Ile Ser Arg Asp Asn Ser Lys Asn Thr Leu Tyr Leu Gln Met
        195                 200                 205

Asn Ser Leu Arg Ala Glu Asp Thr Ala Ile Tyr Tyr Cys Ala Lys Val
    210                 215                 220

Thr Trp Asn Asn Phe Phe Asp Tyr Trp Gly Leu Gly Thr Leu Val Thr
225                 230                 235                 240

Val Ser Ser Ser Leu Asp Pro Lys Ser Ser Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
    290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
            340                 345                 350

Val Ser Asn Lys Ala Leu Pro Ala Pro Ile Glu Lys Thr Ile Ser Lys
        355                 360                 365

Ala Lys Gly Gln Pro Arg Glu Pro Gln Val Tyr Thr Leu Pro Pro Ser
    370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
```

```
                         405                 410                 415
Pro Glu Asn Asn Tyr Lys Thr Thr Pro Pro Val Leu Asp Ser Asp Gly
                420                 425                 430

Ser Phe Phe Leu Tyr Ser Lys Leu Thr Val Asp Lys Ser Arg Trp Gln
            435                 440                 445

Gln Gly Asn Val Phe Ser Cys Ser Val Met His Glu Ala Leu His Asn
        450                 455                 460

His Tyr Thr Gln Lys Ser Leu Ser Leu Ser Pro Gly Lys Val
465                 470                 475

<210> SEQ ID NO 69
<211> LENGTH: 478
<212> TYPE: PRT
<213> ORGANISM: Artificial Sequence
<220> FEATURE:
<223> OTHER INFORMATION: Synthetic Construct

<400> SEQUENCE: 69

Glu Ile Val Leu Thr Gln Ser Pro Gly Thr Leu Thr Leu Ser Pro Gly
1               5                   10                  15

Glu Arg Ala Thr Leu Ser Cys Arg Ala Ser Gln Ser Ile Gly Ser Ser
            20                  25                  30

Tyr Leu Ala Trp Tyr Gln Gln Lys Pro Gly Gln Ala Pro Arg Leu Leu
        35                  40                  45

Ile Tyr Asp Ala Thr Asn Arg Ala Thr Gly Ile Pro Asp Arg Phe Ser
    50                  55                  60

Gly Ser Gly Ser Gly Thr Asp Phe Thr Leu Thr Ile Ser Ser Leu Gln
65                  70                  75                  80

Thr Glu Asp Ser Ala Val Tyr Tyr Cys Gln Gln Tyr Tyr Tyr Trp Pro
                85                  90                  95

Pro Tyr Arg Phe Gly Gly Gly Thr Lys Val Glu Ile Lys Gly Gln Ser
            100                 105                 110

Ser Arg Ser Ser Gly Gly Gly Ser Ser Gly Gly Gly Ser Asp
        115                 120                 125

Val Gln Leu Val Glu Ser Gly Gly Val Val Arg Pro Gly Glu Ser
    130                 135                 140

Leu Arg Leu Ser Cys Ala Ala Ser Gly Phe Thr Phe Ser Asn Tyr Asp
145                 150                 155                 160

Met Thr Trp Val Arg Gln Ala Pro Gly Glu Gly Leu Glu Trp Val Ser
                165                 170                 175

Gly Ile Ser Gly Asn Gly Gly Ser Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Val Tyr Tyr Cys Ala
    210                 215                 220

Met Asn Arg Trp Trp Phe Asp Tyr Trp Gly Leu Gly Thr Leu Val Thr
225                 230                 235                 240

Val Ser Ser Ser Leu Asp Pro Lys Ser Asp Lys Thr His Thr Cys
                245                 250                 255

Pro Pro Cys Pro Ala Pro Glu Leu Leu Gly Gly Pro Ser Val Phe Leu
            260                 265                 270

Phe Pro Pro Lys Pro Lys Asp Thr Leu Met Ile Ser Arg Thr Pro Glu
        275                 280                 285

Val Thr Cys Val Val Val Asp Val Ser His Glu Asp Pro Glu Val Lys
```

```
                290             295             300
Phe Asn Trp Tyr Val Asp Gly Val Glu Val His Asn Ala Lys Thr Lys
305                 310             315                 320

Pro Arg Glu Glu Gln Tyr Asn Ser Thr Tyr Arg Val Val Ser Val Leu
                325             330             335

Thr Val Leu His Gln Asp Trp Leu Asn Gly Lys Glu Tyr Lys Cys Lys
            340             345             350

Val Ser Asn Lys Ala Leu Pro Ala Pro Ile Glu Lys Thr Ile Ser Lys
        355             360             365

Ala Lys Gly Gln Pro Arg Glu Pro Gln Val Tyr Thr Leu Pro Pro Ser
    370             375             380

Arg Asp Glu Leu Thr Lys Asn Gln Val Ser Leu Thr Cys Leu Val Lys
385             390             395             400

Gly Phe Tyr Pro Ser Asp Ile Ala Val Glu Trp Glu Ser Asn Gly Gln
                405             410             415

Pro Glu Asn Asn Tyr Lys Thr Thr Pro Pro Val Leu Asp Ser Asp Gly
                420             425             430

Ser Phe Phe Leu Tyr Ser Lys Leu Thr Val Asp Lys Ser Arg Trp Gln
            435             440             445

Gln Gly Asn Val Phe Ser Cys Ser Val Met His Glu Ala Leu His Asn
        450             455             460

His Tyr Thr Gln Lys Ser Leu Ser Leu Ser Pro Gly Lys Val
465             470             475

<210> SEQ ID NO 70
<211> LENGTH: 480
<212> TYPE: PRT
<213> ORGANISM: Artificial Sequence
<220> FEATURE:
<223> OTHER INFORMATION: Synthetic Construct

<400> SEQUENCE: 70

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Trp Pro Pro
                85                  90                  95

Tyr Arg Phe Gly Gly Gly Thr Lys Val Glu Ile Lys Gly Gln Ser Ser
                100             105             110

Arg Ser Ser Gly Gly Gly Ser Ser Gly Gly Gly Ser Asp Val
            115             120             125

Gln Leu Val Glu Ser Gly Gly Val Val Arg Pro Gly Glu Ser Leu
    130             135             140

Arg Leu Ser Cys Ala Ala Ser Gly Phe Ser Phe Arg Ser Tyr Ala Met
145             150             155             160

Asn Trp Val Arg Gln Ala Pro Gly Glu Gly Leu Glu Trp Val Ser Arg
                165             170             175

Ile Asp Ser Gly Gly Gly Gly Thr Asp Tyr Ala Asp Ser Val Lys Gly
```

```
            180                 185                 190
Arg Phe Thr Ile Ser Arg Asp Asn Ser Lys Asn Thr Leu Tyr Leu Gln
                195                 200                 205

Met Asn Ser Leu Arg Ala Glu Asp Thr Ala Val Tyr Tyr Cys Ala Lys
    210                 215                 220

Gln Tyr Asp Trp Asn Ser Phe Phe Asp Tyr Trp Gly Leu Gly Ala Pro
225                 230                 235                 240

Val Thr Val Ser Ser Ser Leu Asp Pro Lys Ser Ser Asp Lys Thr His
                245                 250                 255

Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
            290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
                340                 345                 350

Cys Lys Val Ser Asn Lys Ala Leu Pro Ala Pro Ile Glu Lys Thr Ile
            355                 360                 365

Ser Lys Ala Lys Gly Gln Pro Arg Glu Pro Gln Val Tyr Thr Leu Pro
        370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Val
465                 470                 475                 480

<210> SEQ ID NO 71
<211> LENGTH: 483
<212> TYPE: PRT
<213> ORGANISM: Artificial Sequence
<220> FEATURE:
<223> OTHER INFORMATION: Synthetic Construct

<400> SEQUENCE: 71

Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Asn Val Arg Ser Asp
            20                  25                  30

Leu Ala Trp Tyr Gln Gln Lys Leu Gly Gln Ala Pro Arg Leu Leu Ile
        35                  40                  45

Tyr Asp Ala Asn Thr Arg Ala Thr Asp Ile Pro Asp Arg Phe Ser Gly
    50                  55                  60

Ser Gly Ser Gly Thr Glu Phe Thr Leu Thr Ile Ser Ser Leu Gln Ser
```

-continued

```
                65                  70                  75                  80
        Glu Asp Phe Ala Val Tyr Tyr Cys Gln His Tyr Tyr Asp Trp Pro Pro
                            85                  90                  95
        Val Thr Phe Gly Gly Gly Thr Lys Val Glu Ile Lys Gly Gln Ser Ser
                        100                 105                 110
        Arg Ser Ser Gly Gly Gly Gly Ser Gly Gly Gly Gly Ser Asp Val
                        115                 120                 125
        Gln Leu Val Glu Ser Gly Gly Val Val Arg Pro Gly Glu Ser Leu
                    130                 135                 140
        Arg Leu Ser Cys Ala Ala Ser Gly Phe Thr Phe Ser Asn Tyr Ala Met
                    145                 150                 155                 160
        Ser Trp Val Arg Gln Ala Pro Gly Glu Gly Leu Glu Trp Val Ser Leu
                            165                 170                 175
        Ile Thr Thr Asn Gly Asp Gly Ala Tyr Tyr Ala Asp Ser Val Lys Gly
                        180                 185                 190
        Arg Phe Thr Ile Ser Arg Asp Asn Ser Lys Asn Thr Leu Tyr Leu Gln
                        195                 200                 205
        Met Asn Ser Leu Arg Ala Glu Asp Thr Ala Ile Tyr Tyr Cys Ala Lys
                    210                 215                 220
        Asp Gly Ala Ala His Tyr Tyr Asp Ile Phe Phe Asp Tyr Trp Gly Leu
        225                 230                 235                 240
        Gly Thr Pro Val Thr Val Ser Ser Ser Leu Asp Pro Lys Ser Ser Asp
                        245                 250                 255
        Lys Thr His Thr Cys Pro Pro Cys Pro Ala Pro Glu Leu Leu Gly Gly
                        260                 265                 270
        Pro Ser Val Phe Leu Phe Pro Pro Lys Pro Lys Asp Thr Leu Met Ile
                        275                 280                 285
        Ser Arg Thr Pro Glu Val Thr Cys Val Val Val Asp Val Ser His Glu
                    290                 295                 300
        Asp Pro Glu Val Lys Phe Asn Trp Tyr Val Asp Gly Val Glu Val His
        305                 310                 315                 320
        Asn Ala Lys Thr Lys Pro Arg Glu Glu Gln Tyr Asn Ser Thr Tyr Arg
                        325                 330                 335
        Val Val Ser Val Leu Thr Val Leu His Gln Asp Trp Leu Asn Gly Lys
                        340                 345                 350
        Glu Tyr Lys Cys Lys Val Ser Asn Lys Ala Leu Pro Ala Pro Ile Glu
                    355                 360                 365
        Lys Thr Ile Ser Lys Ala Lys Gly Gln Pro Arg Glu Pro Gln Val Tyr
                    370                 375                 380
        Thr Leu Pro Pro Ser Arg Asp Glu Leu Thr Lys Asn Gln Val Ser Leu
        385                 390                 395                 400
        Thr Cys Leu Val Lys Gly Phe Tyr Pro Ser Asp Ile Ala Val Glu Trp
                        405                 410                 415
        Glu Ser Asn Gly Gln Pro Glu Asn Asn Tyr Lys Thr Thr Pro Pro Val
                        420                 425                 430
        Leu Asp Ser Asp Gly Ser Phe Phe Leu Tyr Ser Lys Leu Thr Val Asp
                        435                 440                 445
        Lys Ser Arg Trp Gln Gln Gly Asn Val Phe Ser Cys Ser Val Met His
                    450                 455                 460
        Glu Ala Leu His Asn His Tyr Thr Gln Lys Ser Leu Ser Leu Ser Pro
        465                 470                 475                 480
        Gly Lys Val
```

-continued

```
<210> SEQ ID NO 72
<211> LENGTH: 481
<212> TYPE: PRT
<213> ORGANISM: Artificial Sequence
<220> FEATURE:
<223> OTHER INFORMATION: Synthetic Construct

<400> SEQUENCE: 72
```

| | | | | | | | | | | | | | | |
|---|---|---|---|---|---|---|---|---|---|---|---|---|---|---|
| Glu | Ile | Val | Leu | Thr | Gln | Ser | Pro | Ala | Thr | Leu | Ser | Val | Ser | Pro | Gly |
| 1 | | | | 5 | | | | | 10 | | | | | 15 | |

Glu Arg Val Thr Phe Ser Cys Arg Ala Ser Gln Asn Val Arg Ser Asp
            20                 25                   30

Ile Ala Trp Tyr Gln Gln Lys Pro Gly Gln Ala Pro Arg Leu Leu Ile
            35                 40                   45

Tyr Ala Ala Ser Ser Arg Asp Thr Gly Ile Pro Asp Arg Phe Ser Gly
    50                 55                   60

Ser Gly Ser Gly Thr Asp Phe Thr Leu Thr Ile Ser Ser Leu Gln Ser
65                 70                 75               80

Glu Asp Phe Gly Val Tyr Tyr Cys Gln Gln Tyr Tyr Asp Trp Pro Pro
            85               90                  95

Phe Thr Phe Gly Gly Gly Thr Lys Val Glu Ile Lys Gly Gln Ser Ser
          100               105              110

Arg Ser Ser Gly Gly Gly Gly Ser Gly Gly Gly Gly Ser Asp Val
       115              120              125

Gln Leu Val Glu Ser Gly Gly Val Val Arg Pro Gly Glu Ser Leu
130               135                 140

Arg Leu Ser Cys Ala Ala Ser Gly Phe Ser Phe Ser Ile Tyr Ala Met
145                 150                 155              160

Ser Trp Val Arg Gln Ala Pro Gly Glu Gly Leu Glu Trp Val Ser Thr
            165               170              175

Ile Gly Ala Asp Asp Thr Tyr Tyr Ala Asp Ser Val Lys Gly Arg Phe
            180               185              190

Thr Ile Ser Arg Asp Asn Ser Lys Asn Thr Leu Tyr Leu Gln Met Asn
         195              200               205

Ser Leu Arg Ala Glu Asp Thr Ala Val Tyr Tyr Cys Ala Lys Asp Ser
    210                 215                 220

Thr Val Gly Trp Ser Gly Asp Phe Phe Asp Tyr Trp Gly Leu Gly Thr
225                 230                 235              240

Leu Val Thr Val Ser Ser Ser Leu Asp Pro Lys Ser Ser Asp Lys Thr
            245               250              255

His Thr Cys Pro Pro Cys Pro Ala Pro Glu Leu Leu Gly Gly Pro Ser
         260              265               270

Val Phe Leu Phe Pro Pro Lys Pro Lys Asp Thr Leu Met Ile Ser Arg
        275               280               285

Thr Pro Glu Val Thr Cys Val Val Val Asp Val Ser His Glu Asp Pro
    290                 295                 300

Glu Val Lys Phe Asn Trp Tyr Val Asp Gly Val Glu Val His Asn Ala
305                 310                 315              320

Lys Thr Lys Pro Arg Glu Glu Gln Tyr Asn Ser Thr Tyr Arg Val Val
            325               330              335

Ser Val Leu Thr Val Leu His Gln Asp Trp Leu Asn Gly Lys Glu Tyr
         340              345               350

Lys Cys Lys Val Ser Asn Lys Ala Leu Pro Ala Pro Ile Glu Lys Thr
       355              360              365

```
Ile Ser Lys Ala Lys Gly Gln Pro Arg Glu Pro Gln Val Tyr Thr Leu
370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
            405                 410                 415

Asn Gly Gln Pro Glu Asn Asn Tyr Lys Thr Thr Pro Pro Val Leu Asp
                420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
450                 455                 460

Leu His Asn His Tyr Thr Gln Lys Ser Leu Ser Leu Ser Pro Gly Lys
465                 470                 475                 480

Val
```

<210> SEQ ID NO 73
<211> LENGTH: 480
<212> TYPE: PRT
<213> ORGANISM: Artificial Sequence
<220> FEATURE:
<223> OTHER INFORMATION: Synthetic Construct

<400> SEQUENCE: 73

```
Glu Thr Val Leu Thr Gln Ser Pro Gly Thr Leu Thr Leu Ser Pro Gly
1               5                   10                  15

Glu Arg Ala Thr Leu Thr Cys Arg Ala Ser Gln Ser Val Tyr Thr Tyr
            20                  25                  30

Leu Ala Trp Tyr Gln Glu Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

Ser Gly Ser Gly Thr Val Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
            85                  90                  95

Leu Thr Phe Gly Gly Gly Thr Lys Val Glu Ile Lys Gly Gln Ser Ser
            100                 105                 110

Arg Ser Ser Gly Gly Gly Gly Ser Gly Gly Gly Ser Asp Val
        115                 120                 125

Gln Leu Val Glu Ser Gly Gly Gly Val Val Arg Pro Gly Glu Ser Leu
    130                 135                 140

Arg Leu Ser Cys Ala Ala Ser Gly Phe Thr Phe Ser Ser Tyr Asp Met
145                 150                 155                 160

Asn Trp Val Arg Gln Ala Pro Gly Glu Gly Leu Glu Trp Val Ser Leu
                165                 170                 175

Ile Ser Gly Ser Gly Glu Ile Ile Tyr Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Ala Lys
    210                 215                 220

Glu Asn Asn Arg Tyr Arg Phe Phe Asp Asp Trp Gly Leu Gly Thr Leu
225                 230                 235                 240

Val Thr Val Ser Ser Ser Leu Asp Pro Lys Ser Ser Asp Lys Thr His
```

```
                    245                 250                 255
Thr Cys Pro Pro Cys Pro Ala Pro Glu Leu Leu Gly Gly Pro Ser Val
                260                 265                 270

Phe Leu Phe Pro Pro Lys Pro Lys Asp Thr Leu Met Ile Ser Arg Thr
            275                 280                 285

Pro Glu Val Thr Cys Val Val Val Asp Val Ser His Glu Asp Pro Glu
        290                 295                 300

Val Lys Phe Asn Trp Tyr Val Asp Gly Val Glu Val His Asn Ala Lys
305                 310                 315                 320

Thr Lys Pro Arg Glu Glu Gln Tyr Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Ala Leu Pro Ala Pro Ile Glu Lys Thr Ile
        355                 360                 365

Ser Lys Ala Lys Gly Gln Pro Arg Glu Pro Gln Val Tyr Thr Leu Pro
370                 375                 380

Pro Ser Arg Asp Glu Leu Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Lys Leu Thr Val Asp Lys Ser Arg
        435                 440                 445

Trp Gln Gln Gly Asn Val Phe Ser Cys Ser Val Met His Glu Ala Leu
    450                 455                 460

His Asn His Tyr Thr Gln Lys Ser Leu Ser Leu Ser Pro Gly Lys Val
465                 470                 475                 480

<210> SEQ ID NO 74
<211> LENGTH: 315
<212> TYPE: PRT
<213> ORGANISM: Artificial Sequence
<220> FEATURE:
<223> OTHER INFORMATION: Synthetic Construct

<400> SEQUENCE: 74

Glu Ile Val Leu Thr Gln Ser Pro Gly Thr Leu Ser Val Ser Pro Gly
1               5                   10                  15

Glu Arg Val Ile Leu Thr Cys Arg Ala Ser Gln Ser Val Asp Thr Tyr
            20                  25                  30

Asn Leu Ala Trp Tyr Gln Gln Lys Pro Gly Gln Ala Pro Arg Leu Leu
        35                  40                  45

Ile Tyr Asp Leu Ser Thr Arg Ala Thr Gly Ile Pro Asp Arg Phe Ser
    50                  55                  60

Gly Ser Gly Ser Gly Thr Glu Phe Thr Leu Thr Ile Asn Ser Leu Glu
65                  70                  75                  80

Pro Glu Asp Phe Ala Val Tyr Tyr Cys His Gln Tyr Tyr Asp Trp Pro
                85                  90                  95

Pro Tyr Thr Phe Gly Gly Gly Thr Lys Val Glu Ile Lys Gly Gln Ser
            100                 105                 110

Ser Arg Ser Ser Gly Gly Gly Ser Gly Gly Gly Ser Asp
        115                 120                 125

Val Gln Leu Val Glu Ser Gly Gly Gly Val Val Arg Pro Gly Glu Ser
```

```
            130                 135                 140
Leu Arg Leu Ser Cys Ala Ala Ser Gly Phe Thr Phe Ser Asn Tyr Ala
145                 150                 155                 160

Met Asn Trp Val Arg Gln Ala Pro Gly Glu Gly Leu Glu Trp Val Ser
                165                 170                 175

Gly Ile Ser Gly Arg Gly Gly Asp Thr Tyr Tyr Ala Asp Ser Val Lys
            180                 185                 190

Gly Arg Phe Thr Ile Ser Arg Asp Asn Ser Lys Asn Thr Leu Tyr Leu
        195                 200                 205

Gln Met Asn Ser Leu Arg Ala Glu Asp Thr Ala Ile Tyr Tyr Cys Ala
    210                 215                 220

Lys Gly Thr Trp Asn Tyr Gly Ser Phe Asp Tyr Trp Gly Leu Gly Thr
225                 230                 235                 240

Leu Val Thr Val Ser Ser Leu Asp Pro Lys Ser Ser Asp Lys Thr
                245                 250                 255

Asp Thr Cys Pro Pro Cys Pro Ala Pro Glu Leu Leu Gly Gly Pro Ser
                260                 265                 270

Val Phe Leu Phe Pro Pro Lys Pro Lys Asp Thr Leu Met Ile Ser Arg
            275                 280                 285

Thr Pro Glu Val Thr Cys Val Val Asp Val Ser His Glu Asp Pro
        290                 295                 300

Glu Val Lys Phe Asn Trp Tyr Val Asp Gly Val
305                 310                 315
```

<210> SEQ ID NO 75
<211> LENGTH: 481
<212> TYPE: PRT
<213> ORGANISM: Artificial Sequence
<220> FEATURE:
<223> OTHER INFORMATION: Synthetic Construct

<400> SEQUENCE: 75

```
Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys Gly Gln Ser Ser
            100                 105                 110

Arg Ser Ser Gly Gly Gly Gly Ser Ser Gly Gly Gly Ser Asp Val
        115                 120                 125

Gln Leu Val Glu Ser Gly Gly Val Val Gln Pro Gly Gly Ser Leu
    130                 135                 140

Arg Leu Ser Cys Ala Ala Ser Gly Phe Ser Phe Ser Asn Phe Ala Met
145                 150                 155                 160

Thr Trp Val Arg Gln Ala Pro Gly Glu Gly Leu Glu Trp Val Ser Thr
                165                 170                 175

Ile Gly Ser Gly Asp Thr Tyr Tyr Ala Asp Ser Val Lys Gly Arg Phe
```

```
            180                 185                 190
Thr Ile Ser Arg Asp Asn Ser Lys Asn Thr Leu Tyr Leu Gln Met Asn
            195                 200                 205
Ser Leu Arg Ala Glu Asp Thr Ala Val Tyr Tyr Cys Ala Lys Asp Ser
        210                 215                 220
Thr Val Ser Trp Ser Gly Asp Phe Phe Asp Tyr Trp Gly Leu Gly Thr
225                 230                 235                 240
Leu Val Thr Val Ser Ser Leu Asp Pro Lys Ser Ser Asp Lys Thr
                245                 250                 255
His Thr Cys Pro Pro Cys Pro Ala Pro Glu Leu Leu Gly Gly Pro Ser
            260                 265                 270
Val Phe Leu Phe Pro Pro Lys Pro Lys Asp Thr Leu Met Ile Ser Arg
        275                 280                 285
Thr Pro Glu Val Thr Cys Val Val Val Asp Val Ser His Glu Asp Pro
    290                 295                 300
Glu Val Lys Phe Asn Trp Tyr Val Asp Gly Val Glu Val His Asn Ala
305                 310                 315                 320
Lys Thr Lys Pro Arg Glu Glu Gln Tyr Asn Ser Thr Tyr Arg Val Val
                325                 330                 335
Ser Val Leu Thr Val Leu His Gln Asp Trp Leu Asn Gly Lys Glu Tyr
            340                 345                 350
Lys Cys Lys Val Ser Asn Lys Ala Leu Pro Ala Pro Ile Glu Lys Thr
        355                 360                 365
Ile Ser Lys Ala Lys Gly Gln Pro Arg Glu Pro Gln Val Tyr Thr Leu
    370                 375                 380
Pro Pro Ser Arg Asp Glu Leu Thr Lys Asn Gln Val Ser Leu Thr Cys
385                 390                 395                 400
Leu Val Lys Gly Phe Tyr Pro Ser Asp Ile Ala Val Glu Trp Glu Ser
                405                 410                 415
Asn Gly Gln Pro Glu Asn Asn Tyr Lys Thr Thr Pro Pro Val Leu Asp
            420                 425                 430
Ser Asp Gly Ser Phe Phe Leu Tyr Ser Lys Leu Thr Val Asp Lys Ser
        435                 440                 445
Arg Trp Gln Gln Gly Asn Val Phe Ser Cys Ser Val Met His Glu Ala
    450                 455                 460
Leu His Asn His Tyr Thr Gln Lys Ser Leu Ser Leu Ser Pro Gly Lys
465                 470                 475                 480
Val

<210> SEQ ID NO 76
<211> LENGTH: 118
<212> TYPE: PRT
<213> ORGANISM: Homo sapiens

<400> SEQUENCE: 76

Glu Glu Glu Leu Gln Val Ile Gln Pro Asp Lys Ser Val Ser Val Ala
1               5                   10                  15
Ala Gly Glu Ser Ala Ile Leu Leu Cys Thr Val Thr Ser Leu Ile Pro
            20                  25                  30
Val Gly Pro Ile Gln Trp Phe Arg Gly Ala Gly Pro Ala Arg Glu Leu
        35                  40                  45
Ile Tyr Asn Gln Lys Glu Gly His Phe Pro Arg Val Thr Thr Val Ser
    50                  55                  60
Glu Ser Thr Lys Arg Glu Asn Met Asp Phe Ser Ile Ser Ile Ser Asn
```

```
                65                  70                  75                  80
Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 77
<211> LENGTH: 119
<212> TYPE: PRT
<213> ORGANISM: Homo sapiens

<400> SEQUENCE: 77

Glu Glu Gly Leu Gln Val Ile Gln Pro Asp Lys Ser Val Ser Val Ala
1               5                   10                  15

Ala Gly Glu Ser Ala Ile Leu His Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 78
<211> LENGTH: 119
<212> TYPE: PRT
<213> ORGANISM: Homo sapiens

<400> SEQUENCE: 78

Glu Glu Glu Leu Gln Val Ile Gln Pro Asp Lys Phe Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 79
<211> LENGTH: 119
<212> TYPE: PRT
```

-continued

<213> ORGANISM: Homo sapiens

<400> SEQUENCE: 79

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Pro Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 80
<211> LENGTH: 118
<212> TYPE: PRT
<213> ORGANISM: Homo sapiens

<400> SEQUENCE: 80

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Gly Lys Pro Ser
        115

<210> SEQ ID NO 81
<211> LENGTH: 118
<212> TYPE: PRT
<213> ORGANISM: Homo sapiens

<400> SEQUENCE: 81

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

```
Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 82
<211> LENGTH: 119
<212> TYPE: PRT
<213> ORGANISM: Homo sapiens

<400> SEQUENCE: 82

Glu Glu Glu Leu Gln Val Ile Gln Pro Asp Lys Ser Val Leu Val Ala
 1               5                  10                  15

Ala Gly Glu Thr Ala Thr Leu Arg Cys Thr Ala Thr Ser Leu Ile Pro
                20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
     50                  55                  60

Asp Leu Thr Lys Arg Asn Asn Met Asp Phe Ser Ile Arg Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
            115

<210> SEQ ID NO 83
<211> LENGTH: 118
<212> TYPE: PRT
<213> ORGANISM: Homo sapiens

<400> SEQUENCE: 83

Glu Glu Glu Leu Gln Val Ile Gln Pro Asp Lys Ser Val Ser Val Ala
 1               5                  10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
     50                  55                  60

Glu Ser Thr Lys Arg Glu Asn Met Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 84
```

<211> LENGTH: 110
<212> TYPE: PRT
<213> ORGANISM: Gallus gallus

<400> SEQUENCE: 84

Asp Phe Lys Leu Gln Gln Pro Gln Ser Ser Val Val Ile Lys Gly
1               5                   10                  15

Asp Thr Leu Thr Leu Asn Cys Thr Ala Ser Gly Ser Gly Pro Ile Gly
            20                  25                  30

Ala Val Lys Trp Val Lys Gly Trp Gly Ser Asp Asn Gln Thr Val Tyr
        35                  40                  45

Glu His Lys Gly Ser Phe Pro Arg Val Met Arg Ala Val Pro Asp Pro
    50                  55                  60

Thr Asn Asp Phe Thr Ile Arg Ile Ser Asn Val Ser Leu Glu Asp Ala
65                  70                  75                  80

Gly Thr Tyr Tyr Cys Val Lys Leu Arg Lys Gly Ile Val Asp Asp Val
                85                  90                  95

Val Phe Thr Arg Gly Gly Gly Thr Glu Val Ser Val His Ala
            100                 105                 110

<210> SEQ ID NO 85
<211> LENGTH: 105
<212> TYPE: PRT
<213> ORGANISM: Artificial Sequence
<220> FEATURE:
<223> OTHER INFORMATION: Synthetic Construct

<400> SEQUENCE: 85

Ala Leu Thr Gln Pro Ala Ser Val Ser Ala Asn Pro Gly Glu Thr Val
1               5                   10                  15

Glu Ile Thr Cys Ser Gly Gly Gly Ser Asn Asn Ala Tyr Gly Trp Phe
            20                  25                  30

Gln Gln Lys Ser Pro Gly Ser Ala Pro Leu Thr Val Ile Tyr Asp Asn
        35                  40                  45

Gly Lys Arg Pro Ser Asp Ile Pro Ser Arg Phe Ser Gly Ser Lys Ser
    50                  55                  60

Asp Ser Thr Gly Thr Leu Thr Ile Thr Arg Val Gln Ala Glu Asp Glu
65                  70                  75                  80

Ala Val Tyr Tyr Cys Gly Ser Ala Asp Asn Ser Gly Ala Gly Val Phe
                85                  90                  95

Gly Ala Gly Thr Thr Leu Thr Val Leu
            100                 105

<210> SEQ ID NO 86
<211> LENGTH: 105
<212> TYPE: PRT
<213> ORGANISM: Artificial Sequence
<220> FEATURE:
<223> OTHER INFORMATION: Synthetic Construct

<400> SEQUENCE: 86

Ala Val Thr Gln Pro Ala Ser Val Ser Ala Asn Pro Gly Glu Thr Val
1               5                   10                  15

Arg Ile Thr Cys Ser Gly Asp Ser Ser Ser Tyr Tyr Ser Trp His Gln
            20                  25                  30

Gln Lys Ser Pro Gly Ser Ala Pro Val Ser Val Ile Tyr Ser Asn Thr
        35                  40                  45

Asp Arg Pro Ser Asp Ile Pro Ser Arg Phe Ser Gly Ser Ala Ser Gly
    50                  55                  60

```
Ser Thr Ala Thr Leu Thr Ile Thr Gly Val Gln Ala Glu Asp Glu Ala
 65                  70                  75                  80

Val Tyr Phe Cys Gly Ala Tyr Asp Ser Ser Asp Ser Asp Ile Phe
                 85                  90                  95

Gly Ala Gly Thr Thr Leu Thr Val Leu
            100                 105

<210> SEQ ID NO 87
<211> LENGTH: 103
<212> TYPE: PRT
<213> ORGANISM: Artificial Sequence
<220> FEATURE:
<223> OTHER INFORMATION: Synthetic Construct

<400> SEQUENCE: 87

Ala Val Thr Gln Pro Ser Ser Val Ser Ala Asn Pro Gly Glu Thr Val
 1               5                  10                  15

Glu Ile Thr Cys Ser Gly Ser Ser Thr Tyr Tyr Gly Trp Tyr Gln Gln
                20                  25                  30

Lys Ser Pro Gly Ser Ala Pro Val Thr Val Ile Tyr Asp Asn Asp Lys
             35                  40                  45

Arg Pro Ser Asp Ile Pro Ser Arg Phe Ser Gly Ser Lys Ser Gly Ser
 50                  55                  60

Thr His Thr Leu Ile Ile Thr Gly Val Gln Val Glu Asp Glu Ala Val
 65                  70                  75                  80

Tyr Phe Cys Gly Asn Glu Asp Asn Asn Tyr Val Ala Ile Phe Gly Ala
                 85                  90                  95

Gly Thr Thr Leu Thr Val Leu
            100

<210> SEQ ID NO 88
<211> LENGTH: 106
<212> TYPE: PRT
<213> ORGANISM: Artificial Sequence
<220> FEATURE:
<223> OTHER INFORMATION: Synthetic Construct

<400> SEQUENCE: 88

Ala Leu Thr Gln Pro Ser Ser Val Ser Ala Asn Pro Gly Glu Thr Val
 1               5                  10                  15

Lys Ile Thr Cys Ser Gly Asp Asn Ser Ala His Tyr Tyr Tyr Gly Trp
                20                  25                  30

Tyr Gln Gln Lys Ser Pro Gly Ser Ala Pro Val Thr Val Ile Tyr Tyr
             35                  40                  45

Asn Asp Lys Arg Pro Ser Gly Ile Pro Ser Arg Phe Ser Gly Ser Ala
 50                  55                  60

Ser Gly Ser Thr Ala Thr Leu Ile Ile Thr Gly Val Gln Val Glu Asp
 65                  70                  75                  80

Glu Ala Val Tyr Phe Cys Gly Ser Ala Asp Ser Ser Asn Pro Ala Ile
                 85                  90                  95

Phe Gly Ala Gly Thr Thr Leu Thr Val Leu
            100                 105

<210> SEQ ID NO 89
<211> LENGTH: 105
<212> TYPE: PRT
<213> ORGANISM: Artificial Sequence
<220> FEATURE:
<223> OTHER INFORMATION: Synthetic Construct
```

<400> SEQUENCE: 89

Ala Val Thr Gln Pro Ala Ser Val Ser Ala Asn Pro Gly Glu Thr Val
1               5                   10                  15

Lys Ile Thr Cys Ser Gly Ser Ser Gly Ser Tyr Gly Trp Tyr Gln
            20                  25                  30

Gln Lys Ser Pro Gly Ser Ala Pro Val Thr Leu Ile Tyr Glu Thr Asn
        35                  40                  45

Lys Arg Pro Ser Asn Ile Pro Ser Arg Phe Ser Gly Ser Lys Ser Gly
50                  55                  60

Ser Thr Ala Thr Leu Thr Ile Thr Gly Val Gln Ala Asp Asp Glu Ala
65                  70                  75                  80

Val Tyr Tyr Cys Gly Ser Glu Asp Ser Ser Thr Tyr Leu Ser Ile Phe
                85                  90                  95

Gly Ala Gly Thr Thr Leu Thr Val Leu
                100                 105

<210> SEQ ID NO 90
<211> LENGTH: 103
<212> TYPE: PRT
<213> ORGANISM: Artificial Sequence
<220> FEATURE:
<223> OTHER INFORMATION: Synthetic Construct

<400> SEQUENCE: 90

Ala Val Thr Gln Pro Ala Ser Val Ser Ala Asn Pro Gly Glu Thr Val
1               5                   10                  15

Lys Ile Thr Cys Ser Gly Asp Ser Ser Tyr Tyr Gly Trp Tyr Gln Gln
            20                  25                  30

Lys Ser Pro Gly Ser Ala Pro Val Thr Val Ile Tyr Asp Asp Asn Lys
        35                  40                  45

Arg Pro Ser Asn Ile Pro Ser Arg Phe Ser Gly Ser Lys Ser Gly Ser
    50                  55                  60

Thr Gly Thr Leu Thr Ile Thr Gly Val Gln Ala Asp Asp Glu Ala Val
65                  70                  75                  80

Tyr Phe Cys Gly Asn Glu Asp Asn Ser Tyr Val Ala Ile Phe Gly Ala
                85                  90                  95

Gly Thr Thr Leu Thr Val Leu
                100

<210> SEQ ID NO 91
<211> LENGTH: 103
<212> TYPE: PRT
<213> ORGANISM: Artificial Sequence
<220> FEATURE:
<223> OTHER INFORMATION: Synthetic Construct

<400> SEQUENCE: 91

Ala Val Thr Gln Pro Ala Ser Val Ser Ala Asn Pro Gly Glu Thr Val
1               5                   10                  15

Lys Ile Thr Cys Ser Gly Ser Ser Tyr Tyr Gly Trp Tyr Arg Gln
            20                  25                  30

Lys Ser Pro Gly Ser Ala Pro Val Thr Leu Ile Tyr Asp Asn Asp Lys
        35                  40                  45

Arg Pro Ser Gly Ile Pro Ser Arg Phe Ser Gly Ser Lys Ser Gly Ser
    50                  55                  60

Thr Asn Thr Leu Thr Ile Thr Gly Val Gln Ala Asp Asp Glu Ala Val
65                  70                  75                  80

-continued

Tyr Tyr Cys Gly Asn Glu Asp Asn Ser Tyr Val Gly Ile Phe Gly Ala
                85                  90                  95

Gly Thr Thr Leu Thr Val Leu
            100

<210> SEQ ID NO 92
<211> LENGTH: 103
<212> TYPE: PRT
<213> ORGANISM: Artificial Sequence
<220> FEATURE:
<223> OTHER INFORMATION: Synthetic Construct

<400> SEQUENCE: 92

Ala Val Thr Gln Pro Ala Ser Val Ser Ala Asn Leu Gly Glu Thr Val
1               5                   10                  15

Lys Ile Thr Cys Ser Gly Asp Ser Ser Tyr Tyr Gly Trp Tyr Gln Gln
            20                  25                  30

Lys Ala Pro Gly Ser Ala Pro Val Thr Leu Ile Tyr Asp Asn Asp Lys
        35                  40                  45

Arg Pro Ser Asn Ile Pro Ser Arg Phe Ser Gly Ser Lys Ser Gly Ser
    50                  55                  60

Thr Ala Thr Leu Thr Ile Thr Gly Val Gln Ala Asp Asp Glu Ala Val
65                  70                  75                  80

Tyr Tyr Cys Gly Asn Glu Asp Met Asn Tyr Val Gly Ile Phe Gly Ala
                85                  90                  95

Gly Thr Thr Leu Thr Val Leu
            100

<210> SEQ ID NO 93
<211> LENGTH: 108
<212> TYPE: PRT
<213> ORGANISM: Artificial Sequence
<220> FEATURE:
<223> OTHER INFORMATION: Synthetic Construct

<400> SEQUENCE: 93

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Ser Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys
            100                 105

<210> SEQ ID NO 94
<211> LENGTH: 108
<212> TYPE: PRT
<213> ORGANISM: Artificial Sequence
<220> FEATURE:
<223> OTHER INFORMATION: Synthetic Construct

<400> SEQUENCE: 94

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Ser Asp Arg Phe Ser Gly
    50                  55                  60

Ser Arg Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys
            100                 105

<210> SEQ ID NO 95
<211> LENGTH: 108
<212> TYPE: PRT
<213> ORGANISM: Artificial Sequence
<220> FEATURE:
<223> OTHER INFORMATION: Synthetic Construct

<400> SEQUENCE: 95

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys
            100                 105

<210> SEQ ID NO 96
<211> LENGTH: 108
<212> TYPE: PRT
<213> ORGANISM: Artificial Sequence
<220> FEATURE:
<223> OTHER INFORMATION: Synthetic Construct

<400> SEQUENCE: 96

Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Ser Arg Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

```
Tyr Arg Phe Gly Gly Gly Thr Lys Val Glu Ile Lys
            100                 105

<210> SEQ ID NO 97
<211> LENGTH: 108
<212> TYPE: PRT
<213> ORGANISM: Artificial Sequence
<220> FEATURE:
<223> OTHER INFORMATION: Synthetic Construct

<400> SEQUENCE: 97

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105

<210> SEQ ID NO 98
<211> LENGTH: 108
<212> TYPE: PRT
<213> ORGANISM: Artificial Sequence
<220> FEATURE:
<223> OTHER INFORMATION: Synthetic Construct

<400> SEQUENCE: 98

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
    50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105

<210> SEQ ID NO 99
<211> LENGTH: 108
<212> TYPE: PRT
<213> ORGANISM: Artificial Sequence
<220> FEATURE:
<223> OTHER INFORMATION: Synthetic Construct

<400> SEQUENCE: 99

Glu Ile Val Leu Thr Gln Ser Pro Ala Thr Leu Ser Val Ser Pro Gly
1               5                   10                  15
```

```
Glu Arg Ala Thr Phe Ser Cys Arg Ala Ser Gln Asn Val Lys Asn Asp
                20                  25                  30

Leu Ala Trp Tyr Gln Gln Arg Pro Gly Gln Ala Pro Arg Leu Leu Ile
            35                  40                  45

Tyr Ala Ala Arg Ile Arg Glu Thr Gly Ile Pro Glu Arg Phe Ser Gly
 50                  55                  60

Ser Gly Ser Gly Thr Glu Phe Thr Leu Thr Ile Thr Ser Leu Gln Ser
 65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105
```

```
<210> SEQ ID NO 100
<211> LENGTH: 108
<212> TYPE: PRT
<213> ORGANISM: Artificial Sequence
<220> FEATURE:
<223> OTHER INFORMATION: Synthetic Construct

<400> SEQUENCE: 100

Glu Ile Val Leu Thr Gln Ser Pro Gly Thr Leu Ser Val Ser Pro Gly
 1               5                  10                  15

Glu Arg Val Thr Leu Thr Cys Arg Ala Ser Gln Gly Ile Ala Gly Lys
                20                  25                  30

Ile Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Gly Arg Phe Ser Gly
 50                  55                  60

Ser Gly Ser Gly Thr Glu Phe Thr Leu Thr Ile Thr Ser Leu Gln Ser
 65                  70                  75                  80

Glu Asp Phe Ala Val Tyr Tyr Cys Gln Gln His Tyr Asp Trp Ser Pro
                85                  90                  95

Leu Thr Phe Gly Gly Gly Thr Lys Val Glu Ile Lys
            100                 105
```

```
<210> SEQ ID NO 101
<211> LENGTH: 109
<212> TYPE: PRT
<213> ORGANISM: Artificial Sequence
<220> FEATURE:
<223> OTHER INFORMATION: Synthetic Construct

<400> SEQUENCE: 101

Glu Ile Val Leu Thr Gln Ser Pro Gly Thr Leu Thr Leu Ser Pro Gly
 1               5                  10                  15

Glu Arg Ala Thr Leu Ser Cys Arg Ala Ser Gln Ser Ile Gly Ser Ser
                20                  25                  30

Tyr Leu Ala Trp Tyr Gln Gln Lys Pro Gly Gln Ala Pro Arg Leu Leu
            35                  40                  45

Ile Tyr Asp Ala Thr Asn Arg Ala Thr Gly Ile Pro Asp Arg Phe Ser
 50                  55                  60

Gly Ser Gly Ser Gly Thr Asp Phe Thr Leu Thr Ile Ser Ser Leu Gln
 65                  70                  75                  80

Thr Glu Asp Ser Ala Val Tyr Tyr Cys Gln Gln Tyr Tyr Tyr Trp Pro
                85                  90                  95

Pro Tyr Arg Phe Gly Gly Gly Thr Lys Val Glu Ile Lys
            100                 105
```

<210> SEQ ID NO 102
<211> LENGTH: 108
<212> TYPE: PRT
<213> ORGANISM: Artificial Sequence
<220> FEATURE:
<223> OTHER INFORMATION: Synthetic Construct

<400> SEQUENCE: 102

```
Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys
            100                 105
```

<210> SEQ ID NO 103
<211> LENGTH: 108
<212> TYPE: PRT
<213> ORGANISM: Artificial Sequence
<220> FEATURE:
<223> OTHER INFORMATION: Synthetic Construct

<400> SEQUENCE: 103

```
Glu Ile Val Leu Thr Gln Ser Pro Gly Thr Leu Ser Val Ser Pro Gly
1               5                   10                  15

Glu Arg Ala Thr Leu Ser Cys Arg Ala Ser Gln Asn Val Arg Ser Asp
            20                  25                  30

Leu Ala Trp Tyr Gln Gln Lys Leu Gly Gln Ala Pro Arg Leu Leu Ile
        35                  40                  45

Tyr Asp Ala Asn Thr Arg Ala Thr Asp Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Tyr Asp Trp Pro Pro
                85                  90                  95

Val Thr Phe Gly Gly Gly Thr Lys Val Glu Ile Lys
            100                 105
```

<210> SEQ ID NO 104
<211> LENGTH: 108
<212> TYPE: PRT
<213> ORGANISM: Artificial Sequence
<220> FEATURE:
<223> OTHER INFORMATION: Synthetic Construct

<400> SEQUENCE: 104

```
Glu Ile Val Leu Thr Gln Ser Pro Ala Thr Leu Ser Val Ser Pro Gly
1               5                   10                  15

Glu Arg Val Thr Phe Ser Cys Arg Ala Ser Gln Asn Val Arg Ser Asp
            20                  25                  30
```

```
Ile Ala Trp Tyr Gln Gln Lys Pro Gly Gln Ala Pro Arg Leu Leu Ile
            35                  40                  45

Tyr Ala Ala Ser Ser Arg Asp Thr Gly Ile Pro Asp Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Gly Val Tyr Tyr Cys Gln Gln Tyr Tyr Asp Trp Pro Pro
                 85                  90                  95

Phe Thr Phe Gly Gly Gly Thr Lys Val Glu Ile Lys
                100                 105
```

<210> SEQ ID NO 105
<211> LENGTH: 108
<212> TYPE: PRT
<213> ORGANISM: Artificial Sequence
<220> FEATURE:
<223> OTHER INFORMATION: Synthetic Construct

<400> SEQUENCE: 105

```
Glu Thr Val Leu Thr Gln Ser Pro Gly Thr Leu Thr Leu Ser Pro Gly
 1               5                  10                  15

Glu Arg Ala Thr Leu Thr Cys Arg Ala Ser Gln Ser Val Tyr Thr Tyr
                20                  25                  30

Leu Ala Trp Tyr Gln Glu Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
 50                  55                  60

Ser Gly Ser Gly Thr Val Phe Thr Leu Thr Ile Ser Ser Leu Gln Ser
 65                  70                  75                  80

Glu Asp Phe Ala Val Tyr Tyr Cys Gln Gln Tyr Tyr Asp Arg Pro Pro
                 85                  90                  95

Leu Thr Phe Gly Gly Gly Thr Lys Val Glu Ile Lys
                100                 105
```

<210> SEQ ID NO 106
<211> LENGTH: 109
<212> TYPE: PRT
<213> ORGANISM: Artificial Sequence
<220> FEATURE:
<223> OTHER INFORMATION: Synthetic Construct

<400> SEQUENCE: 106

```
Glu Ile Val Leu Thr Gln Ser Pro Gly Thr Leu Ser Val Ser Pro Gly
 1               5                  10                  15

Glu Arg Val Ile Leu Thr Cys Arg Ala Ser Gln Ser Val Asp Thr Tyr
                20                  25                  30

Asn Leu Ala Trp Tyr Gln Gln Lys Pro Gly Gln Ala Pro Arg Leu Leu
            35                  40                  45

Ile Tyr Asp Leu Ser Thr Arg Ala Thr Gly Ile Pro Asp Arg Phe Ser
 50                  55                  60

Gly Ser Gly Ser Gly Thr Glu Phe Thr Leu Thr Ile Asn Ser Leu Glu
 65                  70                  75                  80

Pro Glu Asp Phe Ala Val Tyr Tyr Cys His Gln Tyr Tyr Asp Trp Pro
                 85                  90                  95

Pro Tyr Thr Phe Gly Gly Gly Thr Lys Val Glu Ile Lys
                100                 105
```

<210> SEQ ID NO 107

```
<211> LENGTH: 108
<212> TYPE: PRT
<213> ORGANISM: Artificial Sequence
<220> FEATURE:
<223> OTHER INFORMATION: Synthetic Construct

<400> SEQUENCE: 107

Glu Ile Val Leu Thr Gln Ser Pro Ala Thr Leu Ser Val Ser Pro Gly
1               5                   10                  15

Glu Arg Ala Thr Phe Ser Cys Arg Ala Ser Gln Asn Val Lys Asn Asp
            20                  25                  30

Leu Ala Trp Tyr Gln Gln Arg Pro Gly Gln Ala Pro Arg Leu Leu Ile
        35                  40                  45

Tyr Ala Ala Arg Ile Arg Glu Thr Gly Ile Pro Glu Arg Phe Ser Gly
50                  55                  60

Ser Gly Ser Gly Thr Glu Phe Thr Leu Thr Ile Thr Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105

<210> SEQ ID NO 108
<211> LENGTH: 124
<212> TYPE: PRT
<213> ORGANISM: Artificial Sequence
<220> FEATURE:
<223> OTHER INFORMATION: Synthetic Construct

<400> SEQUENCE: 108

Ala Val Thr Leu Asp Glu Ser Gly Gly Leu Gln Thr Pro Gly Gly
1               5                   10                  15

Ala Leu Ser Leu Val Cys Lys Gly Ser Gly Phe Thr Phe Ser Ser His
            20                  25                  30

Ala Met Asn Trp Val Arg Gln Ala Pro Gly Lys Gly Leu Glu Trp Val
        35                  40                  45

Ala Gly Ile Ser Ser Asp Gly Arg Phe Thr Tyr Tyr Gly Ala Ala Val
50                  55                  60

Gln Gly Arg Ala Thr Ile Ser Arg Asp Asn Gly Gln Ser Thr Val Arg
65                  70                  75                  80

Leu Gln Leu Asn Asn Leu Arg Ala Glu Asp Thr Ala Thr Tyr Tyr Cys
                85                  90                  95

Thr Lys Asn Gly Gly Cys Gly Ser Gly Gly Asp Leu Asp Cys Ile Asp
            100                 105                 110

Ala Trp Gly His Gly Thr Glu Val Ile Val Ser Ser
        115                 120

<210> SEQ ID NO 109
<211> LENGTH: 120
<212> TYPE: PRT
<213> ORGANISM: Artificial Sequence
<220> FEATURE:
<223> OTHER INFORMATION: Synthetic Construct

<400> SEQUENCE: 109

Ala Val Thr Leu Asp Glu Ser Gly Gly Leu Gln Thr Pro Gly Gly
1               5                   10                  15

Gly Leu Ser Leu Val Cys Lys Ala Ser Gly Phe Asp Phe Ser Asn Phe
            20                  25                  30
```

```
Asn Met Ala Trp Val Arg Gln Gly Pro Gly Lys Gly Leu Glu Tyr Val
            35                  40                  45

Ala Glu Ile Ser Asp Thr Gly Ser Thr Pro Tyr Tyr Gly Ser Ala Val
 50                  55                  60

Gln Gly Arg Ala Thr Ile Ser Arg Asp Asn Gly Gln Ser Thr Val Arg
 65                  70                  75                  80

Leu Gln Leu Asn Asn Leu Arg Ala Glu Asp Thr Gly Thr Tyr Phe Cys
                85                  90                  95

Thr Arg Asn Phe Gly Ser Ser Val Ser Ser Ile Asp Ala Trp Gly His
            100                 105                 110

Gly Thr Glu Val Ile Val Ser Ser
        115                 120

<210> SEQ ID NO 110
<211> LENGTH: 133
<212> TYPE: PRT
<213> ORGANISM: Artificial Sequence
<220> FEATURE:
<223> OTHER INFORMATION: Synthetic Construct

<400> SEQUENCE: 110

Ala Val Thr Leu Asp Glu Ser Gly Gly Gly Leu Gln Thr Pro Gly Gly
 1               5                  10                  15

Ala Leu Ser Leu Val Cys Lys Ala Ser Gly Phe Thr Phe Ser Ser Tyr
                20                  25                  30

Asn Met Gly Trp Val Arg Gln Ala Pro Gly Lys Gly Leu Glu Phe Val
            35                  40                  45

Ala Gly Ile Tyr Ala Ser Gly Ser Ser Thr Asp Thr Asp Thr Thr Tyr
 50                  55                  60

Gly Pro Ala Val Ala Gly Arg Ala Thr Ile Ser Arg Asp Asn Gly Gln
 65                  70                  75                  80

Ser Thr Val Arg Leu Gln Leu Asn Asn Leu Arg Ala Glu Asp Thr Gly
                85                  90                  95

Thr Tyr Tyr Cys Ala Lys Ala Ala Gly Gly Cys Ser Thr His Thr Cys
            100                 105                 110

Thr Ala Tyr Ile Ala Asp Ser Ile Asp Ala Trp Gly His Gly Thr Glu
        115                 120                 125

Val Ile Val Ser Ser
    130

<210> SEQ ID NO 111
<211> LENGTH: 128
<212> TYPE: PRT
<213> ORGANISM: Artificial Sequence
<220> FEATURE:
<223> OTHER INFORMATION: Synthetic Construct

<400> SEQUENCE: 111

Ala Val Thr Leu Asp Glu Ser Gly Gly Gly Leu Gln Thr Pro Gly Arg
 1               5                  10                  15

Ala Leu Ser Leu Val Cys Arg Gly Ser Gly Phe Ser Ile Ser Ser Tyr
                20                  25                  30

Asn Met Gly Trp Val Arg Gln Ala Pro Gly Lys Gly Leu Glu Phe Ile
            35                  40                  45

Ala Ser Ile Gly Ser Asp Gly Ser Ser Thr His Tyr Ala Pro Ala Val
 50                  55                  60

Lys Gly Arg Ala Thr Ile Thr Arg Asp Val Gly Gln Ser Thr Val Arg
 65                  70                  75                  80
```

-continued

```
Leu Gln Leu Asn Asn Leu Arg Ala Glu Asp Thr Gly Thr Tyr Phe Cys
                85                  90                  95

Ala Lys Asp Ala Tyr Gln Cys Ser Tyr Ala Thr Cys Asn Asp Tyr Leu
            100                 105                 110

Asp Thr Ile Asp Ala Trp Gly His Gly Thr Glu Val Ile Val Ser Ser
        115                 120                 125

<210> SEQ ID NO 112
<211> LENGTH: 127
<212> TYPE: PRT
<213> ORGANISM: Artificial Sequence
<220> FEATURE:
<223> OTHER INFORMATION: Synthetic Construct

<400> SEQUENCE: 112

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Phe
            20                  25                  30

Asn Met Gly Trp Val Arg Gln Ala Pro Gly Lys Gly Leu Glu Phe Val
        35                  40                  45

Ala Ala Ile Tyr Ser Gly Asn Ser Ala Glu Tyr Gly Ala Ala Val Gln
    50                  55                  60

Gly Arg Ala Thr Ile Ser Arg Asp Asn Gly Gln Ser Thr Val Arg Leu
65                  70                  75                  80

Gln Leu Asn Asn Leu Arg Ala Glu Asp Thr Gly Ile Tyr Phe Cys Ala
                85                  90                  95

Lys Asp Ala Gly Ser Gly Cys Tyr Ser Gly Val Cys Ala Gly Thr Ser
            100                 105                 110

Ser Ile Asp Ala Trp Gly His Gly Thr Glu Val Ile Val Ser Ser
        115                 120                 125

<210> SEQ ID NO 113
<211> LENGTH: 131
<212> TYPE: PRT
<213> ORGANISM: Artificial Sequence
<220> FEATURE:
<223> OTHER INFORMATION: Synthetic Construct

<400> SEQUENCE: 113

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asn Met Gly Trp Val Arg Gln Ala Pro Gly Lys Gly Leu Glu Phe Val
        35                  40                  45

Ala Gly Ile Tyr Ile Ala Ser Gly Asp Leu Gly Thr Thr Tyr Gly Ala
    50                  55                  60

Ala Val Gln Gly Arg Ala Thr Ile Ser Arg Asp Asp Gly Gln Ser Thr
65                  70                  75                  80

Val Arg Leu Gln Leu Asn Asn Leu Arg Ala Glu Asp Thr Gly Thr Tyr
                85                  90                  95

Phe Cys Ala Lys Ser Ala Gly Gly Cys Ser Ala His Ser Cys Asp Thr
            100                 105                 110

Tyr Ile Ala Asp Ser Ile Asp Ala Trp Gly His Gly Thr Glu Val Ile
        115                 120                 125

Val Ser Ser
```

<210> SEQ ID NO 114
<211> LENGTH: 132
<212> TYPE: PRT
<213> ORGANISM: Artificial Sequence
<220> FEATURE:
<223> OTHER INFORMATION: Synthetic Construct

<400> SEQUENCE: 114

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
            20                  25                  30

Asn Met Gly Trp Val Arg Gln Ala Pro Asp Lys Gly Leu Glu Phe Val
        35                  40                  45

Ala Gly Ile Tyr Thr Gly Ser Asp Ala Gly Leu Ser Thr Thr Tyr Gly
    50                  55                  60

Ala Ala Val Gln Gly Arg Ala Thr Ile Ser Arg Asp Asn Gly Gln Ser
65                  70                  75                  80

Thr Val Arg Leu Gln Leu Asn Asn Leu Gly Ala Glu Asp Thr Gly Ile
                85                  90                  95

Tyr Phe Cys Thr Lys Ser Ala Gly Gly Cys Ser Asp Tyr Asn Cys Asp
            100                 105                 110

Ala Tyr Ile Ala Asp Ser Ile Asp Ala Trp Gly His Gly Thr Glu Val
        115                 120                 125

Ile Val Ser Ser
    130

<210> SEQ ID NO 115
<211> LENGTH: 131
<212> TYPE: PRT
<213> ORGANISM: Artificial Sequence
<220> FEATURE:
<223> OTHER INFORMATION: Synthetic Construct

<400> SEQUENCE: 115

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Asn Ser Tyr
            20                  25                  30

Asn Met Gly Trp Val Arg Gln Ala Pro Gly Lys Gly Leu Glu Phe Val
        35                  40                  45

Ala Gly Ile Tyr Ser Ala Gly Gly Asp Thr Ser Thr Thr Tyr Gly Ala
    50                  55                  60

Ala Val Asn Gly Arg Ala Thr Ile Ser Arg Asp Asn Gly Gln Ser Thr
65                  70                  75                  80

Val Arg Leu Gln Leu Asn Asn Leu Arg Ala Glu Asp Thr Gly Ile Tyr
                85                  90                  95

Phe Cys Ala Lys Ala Ala Gly Gly Cys Thr Ala His Asn Cys Asp Ala
            100                 105                 110

Tyr Ile Ala Asp Ser Ile Asp Ala Trp Gly His Gly Thr Glu Val Ile
        115                 120                 125

Val Ser Ser
    130

<210> SEQ ID NO 116
<211> LENGTH: 118

```
<212> TYPE: PRT
<213> ORGANISM: Artificial Sequence
<220> FEATURE:
<223> OTHER INFORMATION: Synthetic Construct

<400> SEQUENCE: 116

Val Gln Leu Val Glu Ser Gly Gly Val Val Arg Pro Gly Glu Ser
1               5                   10                  15

Leu Arg Leu Ser Cys Ala Ala Ser Gly Phe Ser Phe Ser Ser Tyr Ala
                20                  25                  30

Met Asn Trp Val Arg Gln Ala Pro Gly Glu Gly Leu Glu Trp Val Ser
            35                  40                  45

Arg Ile Asn Ser Gly Gly Gly Thr Asp Tyr Ala Glu Ser Val Lys
    50                  55                  60

Gly Arg Phe Thr Ile Ser Arg Asp Asn Ser Glu Asn Thr Leu Tyr Leu
65              70                  75                  80

Gln Met Asn Ser Leu Arg Ala Glu Asp Thr Ala Val Tyr Tyr Cys Ala
                85                  90                  95

Lys Gln Tyr Asp Trp Asn Ser Phe Phe Asp Tyr Trp Gly Leu Gly Ala
            100                 105                 110

Leu Val Thr Val Ser Ser
            115

<210> SEQ ID NO 117
<211> LENGTH: 118
<212> TYPE: PRT
<213> ORGANISM: Artificial Sequence
<220> FEATURE:
<223> OTHER INFORMATION: Synthetic Construct

<400> SEQUENCE: 117

Val Gln Leu Val Glu Ser Gly Gly Val Val Arg Pro Gly Glu Ser
1               5                   10                  15

Leu Arg Leu Ser Cys Ala Ala Ser Gly Phe Ser Phe Ser Ser Tyr Ala
                20                  25                  30

Met Asn Trp Val Arg Gln Ala Pro Gly Glu Gly Leu Glu Trp Val Ser
            35                  40                  45

Arg Ile Asn Ser Gly Gly Gly Thr Asp Tyr Ala Glu Ser Val Lys
    50                  55                  60

Gly Arg Phe Thr Ile Ser Arg Asp Asn Ser Glu Asn Thr Leu Tyr Leu
65              70                  75                  80

Gln Met Asn Ser Leu Arg Ala Glu Asp Thr Ala Val Tyr Tyr Cys Ala
                85                  90                  95

Lys Gln Tyr Asp Trp Asn Ser Phe Phe Asp Tyr Trp Gly Leu Gly Ala
            100                 105                 110

Leu Val Thr Val Ser Ser
            115

<210> SEQ ID NO 118
<211> LENGTH: 118
<212> TYPE: PRT
<213> ORGANISM: Artificial Sequence
<220> FEATURE:
<223> OTHER INFORMATION: Synthetic Construct

<400> SEQUENCE: 118

Val Gln Leu Val Glu Ser Gly Gly Val Val Arg Pro Gly Glu Ser
1               5                   10                  15

Leu Arg Leu Ser Cys Ala Ala Ser Gly Phe Ser Phe Ser Ser Tyr Ala
```

-continued

```
                20                  25                  30
Met Asn Trp Val Arg Gln Ala Pro Gly Glu Gly Leu Glu Trp Val Ser
            35                  40                  45

Arg Ile Asn Ser Gly Gly Gly Thr Asp Tyr Ala Glu Ser Val Lys
        50                  55                  60

Gly Arg Phe Thr Ile Ser Arg Asp Asn Ser Glu Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gln Tyr Asp Trp Asn Gly Phe Phe Asp Tyr Trp Gly Leu Gly Ala
                100                 105                 110

Leu Val Thr Val Ser Ser
            115

<210> SEQ ID NO 119
<211> LENGTH: 118
<212> TYPE: PRT
<213> ORGANISM: Artificial Sequence
<220> FEATURE:
<223> OTHER INFORMATION: Synthetic Construct

<400> SEQUENCE: 119

Val Gln Leu Val Glu Ser Gly Gly Gly Val Val Arg Pro Gly Glu Ser
1               5                   10                  15

Leu Arg Leu Ser Cys Ala Ala Ser Gly Phe Ser Phe Ser Ser Tyr Ala
                20                  25                  30

Met Asn Trp Val Arg Gln Ala Pro Gly Glu Gly Leu Glu Trp Val Ser
            35                  40                  45

Arg Ile Asn Ser Gly Gly Gly Thr Asp Tyr Ala Glu Ser Val Lys
        50                  55                  60

Gly Arg Phe Thr Ile Ser Arg Asp Asn Ser Glu Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Gln Tyr Asp Trp Asn Gly Phe Phe Asp Tyr Trp Gly Leu Gly Ala
                100                 105                 110

Leu Val Thr Val Ser Ser
            115

<210> SEQ ID NO 120
<211> LENGTH: 119
<212> TYPE: PRT
<213> ORGANISM: Artificial Sequence
<220> FEATURE:
<223> OTHER INFORMATION: Synthetic Construct

<400> SEQUENCE: 120

Val Gln Leu Leu Glu Ser Gly Gly Gly Val Val Gln Pro Gly Gly Ser
1               5                   10                  15

Leu Arg Leu Ser Cys Ala Ala Ser Gly Phe Ser Phe Ser Asn Phe Ala
                20                  25                  30

Met Thr Trp Val Arg Gln Ala Pro Gly Glu Gly Leu Glu Trp Val Ser
            35                  40                  45

Thr Ile Gly Ser Gly Asp Thr Tyr Tyr Ala Asp Ser Val Lys Gly Arg
        50                  55                  60

Phe Thr Ile Ser Arg Asp Asn Ser Lys Asn Thr Leu Tyr Leu Gln Met
65                  70                  75                  80
```

```
Asn Ser Leu Arg Ala Glu Asp Thr Ala Val Tyr Tyr Cys Ala Lys Asp
                85                  90                  95

Ser Thr Val Ser Trp Ser Gly Asp Phe Phe Asp Tyr Trp Gly Leu Gly
            100                 105                 110

Thr Leu Val Thr Val Ser Ser
        115

<210> SEQ ID NO 121
<211> LENGTH: 119
<212> TYPE: PRT
<213> ORGANISM: Artificial Sequence
<220> FEATURE:
<223> OTHER INFORMATION: Synthetic Construct

<400> SEQUENCE: 121

Val Gln Leu Val Glu Ser Gly Gly Gly Val Val Gln Pro Gly Gly Ser
1               5                   10                  15

Leu Arg Leu Ser Cys Ala Ala Ser Gly Phe Ser Phe Ser Asn Phe Ala
            20                  25                  30

Met Thr Trp Val Arg Gln Ala Pro Gly Glu Gly Leu Glu Trp Val Ser
        35                  40                  45

Thr Ile Gly Ser Gly Asp Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Ser Thr Val Ser Trp Ser Gly Asp Phe Phe Asp Tyr Trp Gly Leu Gly
            100                 105                 110

Thr Arg Val Thr Val Ser Ser
        115

<210> SEQ ID NO 122
<211> LENGTH: 119
<212> TYPE: PRT
<213> ORGANISM: Artificial Sequence
<220> FEATURE:
<223> OTHER INFORMATION: Synthetic Construct

<400> SEQUENCE: 122

Val Gln Leu Val Glu Ser Gly Gly Gly Val Val Arg Pro Gly Glu Ser
1               5                   10                  15

Leu Arg Leu Ser Cys Ala Ala Ser Gly Phe Arg Phe Ser Asn Phe Ala
            20                  25                  30

Met Thr Trp Val Arg Gln Ala Pro Gly Glu Gly Leu Glu Trp Val Ser
        35                  40                  45

Thr Ile Gly Ser Gly Asp Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Ser Thr Val Ser Trp Ser Gly Asp Phe Phe Asp Tyr Trp Gly Leu Gly
            100                 105                 110

Thr Leu Val Thr Val Ser Ser
        115

<210> SEQ ID NO 123
```

```
<211> LENGTH: 116
<212> TYPE: PRT
<213> ORGANISM: Artificial Sequence
<220> FEATURE:
<223> OTHER INFORMATION: Synthetic Construct

<400> SEQUENCE: 123

Val Gln Leu Val Glu Ser Gly Gly Gly Leu Val Gln Pro Gly Gly Ser
1               5                   10                  15

Leu Arg Leu Ser Cys Thr Ala Ser Gly Phe Thr Phe Arg Asn Tyr Gly
            20                  25                  30

Met Ser Trp Val Arg Gln Ala Pro Gly Glu Gly Leu Glu Trp Val Ser
        35                  40                  45

Ala Ser Ser Gly Ser Gly Ser Thr Tyr Tyr Thr Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Ile Tyr Tyr Cys Ala Lys
                85                  90                  95

Val Thr Trp Asn Asn Phe Phe Asp Tyr Trp Gly Leu Gly Thr Leu Val
            100                 105                 110

Thr Val Ser Ser
        115

<210> SEQ ID NO 124
<211> LENGTH: 115
<212> TYPE: PRT
<213> ORGANISM: Artificial Sequence
<220> FEATURE:
<223> OTHER INFORMATION: Synthetic Construct

<400> SEQUENCE: 124

Val Gln Leu Val Glu Ser Gly Gly Val Val Arg Pro Gly Glu Ser
1               5                   10                  15

Leu Arg Leu Ser Cys Ala Ala Ser Gly Phe Thr Phe Ser Asn Tyr Asp
            20                  25                  30

Met Thr Trp Val Arg Gln Ala Pro Gly Glu Gly Leu Glu Trp Val Ser
        35                  40                  45

Gly Ile Ser Gly Asn Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Met Asn Arg Trp Trp Phe Asp Tyr Trp Gly Leu Gly Thr Leu Val Thr
            100                 105                 110

Val Ser Ser
        115

<210> SEQ ID NO 125
<211> LENGTH: 118
<212> TYPE: PRT
<213> ORGANISM: Artificial Sequence
<220> FEATURE:
<223> OTHER INFORMATION: Synthetic Construct

<400> SEQUENCE: 125

Val Gln Leu Val Glu Ser Gly Gly Gly Val Val Arg Pro Gly Glu Ser
1               5                   10                  15
```

```
Leu Arg Leu Ser Cys Ala Ala Ser Gly Phe Ser Phe Arg Ser Tyr Ala
            20                  25                  30

Met Asn Trp Val Arg Gln Ala Pro Gly Glu Gly Leu Glu Trp Val Ser
        35                  40                  45

Arg Ile Asp Ser Gly Gly Gly Thr Asp Tyr Ala Asp Ser Val Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Val Tyr Tyr Cys Ala
                85                  90                  95

Lys Gln Tyr Asp Trp Asn Ser Phe Phe Asp Tyr Trp Gly Leu Gly Ala
            100                 105                 110

Pro Val Thr Val Ser Ser
        115

<210> SEQ ID NO 126
<211> LENGTH: 121
<212> TYPE: PRT
<213> ORGANISM: Artificial Sequence
<220> FEATURE:
<223> OTHER INFORMATION: Synthetic Construct

<400> SEQUENCE: 126

Val Gln Leu Val Glu Ser Gly Gly Gly Val Val Arg Pro Gly Glu Ser
1               5                   10                  15

Leu Arg Leu Ser Cys Ala Ala Ser Gly Phe Thr Phe Ser Asn Tyr Ala
            20                  25                  30

Met Ser Trp Val Arg Gln Ala Pro Gly Glu Gly Leu Glu Trp Val Ser
        35                  40                  45

Leu Ile Thr Thr Asn Gly Asp Gly Ala Tyr Tyr Ala Asp Ser Val Lys
    50                  55                  60

Gly Arg Phe Thr Ile Ser Arg Asp Asn Ser Lys Asn Thr Leu Tyr Leu
65              70                  75                  80

Gln Met Asn Ser Leu Arg Ala Glu Asp Thr Ala Ile Tyr Tyr Cys Ala
                85                  90                  95

Lys Asp Gly Ala Ala His Tyr Tyr Asp Ile Phe Phe Asp Tyr Trp Gly
            100                 105                 110

Leu Gly Thr Pro Val Thr Val Ser Ser
        115                 120

<210> SEQ ID NO 127
<211> LENGTH: 119
<212> TYPE: PRT
<213> ORGANISM: Artificial Sequence
<220> FEATURE:
<223> OTHER INFORMATION: Synthetic Construct

<400> SEQUENCE: 127

Val Gln Leu Val Glu Ser Gly Gly Gly Val Val Arg Pro Gly Glu Ser
1               5                   10                  15

Leu Arg Leu Ser Cys Ala Ala Ser Gly Phe Ser Phe Ser Ile Tyr Ala
            20                  25                  30

Met Ser Trp Val Arg Gln Ala Pro Gly Glu Gly Leu Glu Trp Val Ser
        35                  40                  45

Thr Ile Gly Ala Asp Asp Thr Tyr Tyr Ala Asp Ser Val Lys Gly Arg
    50                  55                  60

Phe Thr Ile Ser Arg Asp Asn Ser Lys Asn Thr Leu Tyr Leu Gln Met
65              70                  75                  80
```

Asn Ser Leu Arg Ala Glu Asp Thr Ala Val Tyr Tyr Cys Ala Lys Asp
            85                  90                  95

Ser Thr Val Gly Trp Ser Gly Asp Phe Phe Asp Tyr Trp Gly Leu Gly
            100                 105                 110

Thr Leu Val Thr Val Ser Ser
        115

<210> SEQ ID NO 128
<211> LENGTH: 118
<212> TYPE: PRT
<213> ORGANISM: Artificial Sequence
<220> FEATURE:
<223> OTHER INFORMATION: Synthetic Construct

<400> SEQUENCE: 128

Val Gln Leu Val Glu Ser Gly Gly Gly Val Val Arg Pro Gly Glu Ser
1               5                   10                  15

Leu Arg Leu Ser Cys Ala Ala Ser Gly Phe Thr Phe Ser Ser Tyr Asp
            20                  25                  30

Met Asn Trp Val Arg Gln Ala Pro Gly Glu Gly Leu Glu Trp Val Ser
            35                  40                  45

Leu Ile Ser Gly Ser Gly Glu Ile Ile Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Lys Glu Asn Asn Arg Tyr Arg Phe Phe Asp Asp Trp Gly Leu Gly Thr
            100                 105                 110

Leu Val Thr Val Ser Ser
        115

<210> SEQ ID NO 129
<211> LENGTH: 118
<212> TYPE: PRT
<213> ORGANISM: Artificial Sequence
<220> FEATURE:
<223> OTHER INFORMATION: Synthetic Construct

<400> SEQUENCE: 129

Val Gln Leu Val Glu Ser Gly Gly Gly Val Val Arg Pro Gly Glu Ser
1               5                   10                  15

Leu Arg Leu Ser Cys Ala Ala Ser Gly Phe Thr Phe Ser Asn Tyr Ala
            20                  25                  30

Met Asn Trp Val Arg Gln Ala Pro Gly Glu Gly Leu Glu Trp Val Ser
            35                  40                  45

Gly Ile Ser Gly Arg Gly Gly Asp Thr Tyr Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Ile Tyr Tyr Cys Ala
            85                  90                  95

Lys Gly Thr Trp Asn Tyr Gly Ser Phe Asp Tyr Trp Gly Leu Gly Thr
            100                 105                 110

Leu Val Thr Val Ser Ser
        115

```
<210> SEQ ID NO 130
<211> LENGTH: 119
<212> TYPE: PRT
<213> ORGANISM: Artificial Sequence
<220> FEATURE:
<223> OTHER INFORMATION: Synthetic Construct

<400> SEQUENCE: 130

Val Gln Leu Val Glu Ser Gly Gly Val Val Gln Pro Gly Gly Ser
1               5                   10                  15

Leu Arg Leu Ser Cys Ala Ala Ser Gly Phe Ser Phe Ser Asn Phe Ala
                20                  25                  30

Met Thr Trp Val Arg Gln Ala Pro Gly Glu Gly Leu Glu Trp Val Ser
            35                  40                  45

Thr Ile Gly Ser Gly Asp Thr Tyr Tyr Ala Asp Ser Val Lys Gly Arg
        50                  55                  60

Phe Thr Ile Ser Arg Asp Asn Ser Lys Asn Thr Leu Tyr Leu Gln Met
65                  70                  75                  80

Asn Ser Leu Arg Ala Glu Asp Thr Ala Val Tyr Tyr Cys Ala Lys Asp
                85                  90                  95

Ser Thr Val Ser Trp Ser Gly Asp Phe Phe Asp Tyr Trp Gly Leu Gly
            100                 105                 110

Thr Leu Val Thr Val Ser Ser
        115

<210> SEQ ID NO 131
<211> LENGTH: 102
<212> TYPE: PRT
<213> ORGANISM: Homo sapiens

<400> SEQUENCE: 131

Ala Pro Val Val Ser Gly Pro Ala Ala Arg Ala Thr Pro Gln His Thr
1               5                   10                  15

Val Ser Phe Thr Cys Glu Ser His Gly Phe Ser Pro Arg Asp Ile Thr
                20                  25                  30

Leu Lys Trp Phe Lys Asn Gly Asn Glu Leu Ser Asp Phe Gln Thr Asn
            35                  40                  45

Val Asp Pro Val Gly Glu Ser Val Ser Tyr Ser Ile His Ser Thr Ala
        50                  55                  60

Lys Val Val Leu Thr Arg Glu Asp Val His Ser Gln Val Ile Cys Glu
65                  70                  75                  80

Val Ala His Val Thr Leu Gln Gly Asp Pro Leu Arg Gly Thr Ala Asn
                85                  90                  95

Leu Ser Glu Thr Ile Arg
            100

<210> SEQ ID NO 132
<211> LENGTH: 99
<212> TYPE: PRT
<213> ORGANISM: Homo sapiens

<400> SEQUENCE: 132

Val Pro Pro Thr Leu Glu Val Thr Gln Gln Pro Val Arg Ala Glu Asn
1               5                   10                  15

Gln Val Asn Val Thr Cys Gln Val Arg Lys Phe Tyr Pro Gln Arg Leu
                20                  25                  30

Gln Leu Thr Trp Leu Glu Asn Gly Asn Val Ser Arg Thr Glu Thr Ala
            35                  40                  45
```

```
Ser Thr Val Thr Glu Asn Lys Asp Gly Thr Tyr Asn Trp Met Ser Trp
    50                  55                  60

Leu Leu Val Asn Val Ser Ala His Arg Asp Asp Val Lys Leu Thr Cys
 65                  70                  75                  80

Gln Val Glu His Asp Gly Gln Pro Ala Val Ser Lys Ser His Asp Leu
                 85                  90                  95

Lys Val Ser
```

```
<210> SEQ ID NO 133
<211> LENGTH: 119
<212> TYPE: PRT
<213> ORGANISM: Artificial Sequence
<220> FEATURE:
<223> OTHER INFORMATION: Synthetic Construct

<400> SEQUENCE: 133

Asp Val Gln Leu Val Glu Ser Gly Gly Gly Val Val Arg Pro Gly Glu
  1               5                  10                  15

Ser Leu Arg Leu Ser Cys Ala Ala Ser Gly Phe Thr Phe Ser Ser Tyr
                 20                  25                  30

Asp Met Asn Trp Val Arg Gln Ala Pro Gly Glu Gly Leu Glu Trp Val
             35                  40                  45

Ser Leu Ile Ser Gly Ser Gly Glu Ile Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Asn Asn Arg Tyr Arg Phe Phe Asp Asp Trp Gly Leu Gly
                100                 105                 110

Thr Leu Val Thr Val Ser Ser
        115
```

```
<210> SEQ ID NO 134
<211> LENGTH: 108
<212> TYPE: PRT
<213> ORGANISM: Artificial Sequence
<220> FEATURE:
<223> OTHER INFORMATION: Synthetic Construct

<400> SEQUENCE: 134

Glu Thr Val Leu Thr Gln Ser Pro Gly Thr Leu Thr Leu Ser Pro Gly
  1               5                  10                  15

Glu Arg Ala Thr Leu Thr Cys Arg Ala Ser Gln Ser Val Tyr Thr Tyr
                 20                  25                  30

Leu Ala Trp Tyr Gln Glu Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr Asp Arg Pro Pro
                 85                  90                  95

Leu Thr Phe Gly Gly Gly Thr Lys Val Glu Ile Lys
                100                 105
```

```
<210> SEQ ID NO 135
<211> LENGTH: 118
```

```
<212> TYPE: PRT
<213> ORGANISM: Artificial Sequence
<220> FEATURE:
<223> OTHER INFORMATION: Synthetic Construct

<400> SEQUENCE: 135

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 136
<211> LENGTH: 107
<212> TYPE: PRT
<213> ORGANISM: Artificial Sequence
<220> FEATURE:
<223> OTHER INFORMATION: Synthetic Construct

<400> SEQUENCE: 136

Ala Leu Thr Gln Pro Ala Ser Val Ser Ala Asn Pro Gly Glu Thr Val
1               5                   10                  15

Lys Ile Ala Cys Ser Gly Gly Asp Tyr Tyr Ser Tyr Tyr Tyr Gly Trp
            20                  25                  30

Tyr Gln Gln Lys Ala Pro Gly Ser Ala Leu Val Thr Val Ile Tyr Ser
        35                  40                  45

Asp Asp Lys Arg Pro Ser Asp Ile Pro Ser Arg Phe Ser Gly Ser Ala
    50                  55                  60

Ser Gly Ser Thr Ala Thr Leu Thr Ile Thr Gly Val Arg Ala Glu Asp
65                  70                  75                  80

Glu Ala Val Tyr Tyr Cys Gly Gly Tyr Asp Tyr Ser Thr Tyr Ala Asn
                85                  90                  95

Ala Phe Gly Ala Gly Thr Thr Leu Thr Val Leu
            100                 105

<210> SEQ ID NO 137
<211> LENGTH: 117
<212> TYPE: PRT
<213> ORGANISM: Artificial Sequence
<220> FEATURE:
<223> OTHER INFORMATION: Synthetic Construct

<400> SEQUENCE: 137

Asp Val Gln Leu Val Glu Ser Gly Gly Gly Val Val Arg Pro Gly Glu
1               5                   10                  15

Ser Leu Arg Leu Ser Cys Glu Ala Ser Gly Phe Thr Phe Ser Ser Asn
            20                  25                  30

Ala Met Ser Trp Val Arg Gln Ala Pro Gly Lys Gly Leu Glu Trp Val
```

```
                    35                  40                  45
Ala Gly Ile Ser Ser Gly Ser Asp Thr Tyr Tyr Gly Asp Ser Val Lys
            50                  55                  60

Gly Arg Leu Thr Ile Ser Arg Asp Asn Ser Lys Asn Ile Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
            115

<210> SEQ ID NO 138
<211> LENGTH: 107
<212> TYPE: PRT
<213> ORGANISM: Artificial Sequence
<220> FEATURE:
<223> OTHER INFORMATION: Synthetic Construct

<400> SEQUENCE: 138

Ala Leu Thr Gln Pro Ala Ser Val Ser Ala Asn Pro Gly Glu Thr Val
1               5                   10                  15

Glu Ile Thr Cys Ser Gly Gly Ser Tyr Ser Tyr Tyr Tyr Ala Trp
            20                  25                  30

Tyr Gln Gln Lys Ser Pro Gly Ser Ala Pro Val Thr Leu Ile Tyr Ser
            35                  40                  45

Asp Asp Lys Arg Pro Ser Asn Ile Pro Ser Arg Phe Ser Gly Ser Ala
        50                  55                  60

Ser Gly Ser Thr Ala Thr Leu Thr Ile Thr Gly Val Arg Ala Glu Asp
65                  70                  75                  80

Glu Ala Val Tyr Phe Cys Gly Tyr Asp Gln Ser Ser Tyr Thr Asn
                85                  90                  95

Pro Phe Gly Ala Gly Thr Thr Leu Thr Val Leu
            100                 105

<210> SEQ ID NO 139
<211> LENGTH: 117
<212> TYPE: PRT
<213> ORGANISM: Artificial Sequence
<220> FEATURE:
<223> OTHER INFORMATION: Synthetic Construct

<400> SEQUENCE: 139

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
            20                  25                  30

Ala Met Ser Trp Val Arg Gln Ala Pro Gly Lys Gly Leu Glu Trp Val
            35                  40                  45

Ser Gly Ile Ser Ser Gly Gly Asp Thr Tyr Tyr Val Asp Ser Val Lys
        50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110
```

```
Val Thr Val Ser Ser
        115

<210> SEQ ID NO 140
<211> LENGTH: 107
<212> TYPE: PRT
<213> ORGANISM: Artificial Sequence
<220> FEATURE:
<223> OTHER INFORMATION: Synthetic Construct

<400> SEQUENCE: 140

Ala Leu Thr Gln Pro Ala Ser Val Ser Ala Asp Leu Gly Glu Thr Val
1               5                   10                  15

Lys Ile Thr Cys Ser Gly Gly Asp Ser Ser His Tyr Tyr Gly Trp
            20                  25                  30

Tyr Gln Gln Lys Ser Pro Gly Ser Ala Pro Val Thr Val Ile Tyr Ser
        35                  40                  45

Asp Asp Glu Arg Pro Ser Asp Ile Pro Ser Arg Phe Ser Gly Ser Ala
    50                  55                  60

Ser Gly Ser Thr Ala Thr Leu Thr Ile Thr Gly Val Arg Val Glu Asp
65                  70                  75                  80

Glu Ala Ile Tyr Tyr Cys Gly Ala Tyr Asp Gly Ser Thr Tyr Ala Asn
                85                  90                  95

Thr Phe Gly Ala Gly Thr Thr Leu Thr Val Leu
            100                 105

<210> SEQ ID NO 141
<211> LENGTH: 118
<212> TYPE: PRT
<213> ORGANISM: Artificial Sequence
<220> FEATURE:
<223> OTHER INFORMATION: Synthetic Construct

<400> SEQUENCE: 141

Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Pro Lys Asn Ser Leu Tyr
65                  70                  75                  80

Leu Gln Met Ser Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 142
<211> LENGTH: 107
<212> TYPE: PRT
<213> ORGANISM: Artificial Sequence
<220> FEATURE:
<223> OTHER INFORMATION: Synthetic Construct

<400> SEQUENCE: 142

Ala Leu Thr Gln Pro Ala Ser Val Ser Ala Asn Pro Gly Glu Thr Val
```

```
1               5                   10                  15
Lys Ile Thr Cys Ser Gly Gly Asp Tyr Tyr Ser Thr Tyr Tyr Ala Trp
                20                  25                  30
Tyr Gln Gln Lys Ser Pro Gly Ser Ala Pro Val Thr Val Ile His Ser
                35                  40                  45
Asp Asp Lys Arg Pro Ser Asp Ile Pro Ser Arg Phe Ser Gly Ser Ala
                50                  55                  60
Ser Gly Ser Ala Ala Thr Leu Ile Ile Thr Gly Val Arg Val Glu Asp
65                  70                  75                  80
Glu Ala Val Tyr Tyr Cys Gly Gly Tyr Asp Gly Arg Thr Tyr Ile Asn
                85                  90                  95
Thr Phe Gly Ala Gly Thr Thr Leu Thr Val Leu
                100                 105
```

<210> SEQ ID NO 143
<211> LENGTH: 10
<212> TYPE: PRT
<213> ORGANISM: Artificial Sequence
<220> FEATURE:
<223> OTHER INFORMATION: Synthetic Construct

<400> SEQUENCE: 143

```
Gly Phe Ser Phe Ser Asn Phe Ala Met Thr
1               5                   10
```

<210> SEQ ID NO 144
<211> LENGTH: 15
<212> TYPE: PRT
<213> ORGANISM: Artificial Sequence
<220> FEATURE:
<223> OTHER INFORMATION: Synthetic Construct

<400> SEQUENCE: 144

```
Thr Ile Gly Ser Gly Asp Thr Tyr Tyr Ala Asp Ser Val Lys Gly
1               5                   10                  15
```

<210> SEQ ID NO 145
<211> LENGTH: 13
<212> TYPE: PRT
<213> ORGANISM: Artificial Sequence
<220> FEATURE:
<223> OTHER INFORMATION: Synthetic Construct

<400> SEQUENCE: 145

```
Asp Ser Thr Val Ser Trp Ser Gly Asp Phe Phe Asp Tyr
1               5                   10
```

<210> SEQ ID NO 146
<211> LENGTH: 11
<212> TYPE: PRT
<213> ORGANISM: Artificial Sequence
<220> FEATURE:
<223> OTHER INFORMATION: Synthetic Construct

<400> SEQUENCE: 146

```
Arg Ala Ser Gln Asn Val Lys Asn Asp Leu Ala
1               5                   10
```

<210> SEQ ID NO 147
<211> LENGTH: 7
<212> TYPE: PRT
<213> ORGANISM: Artificial Sequence
<220> FEATURE:
<223> OTHER INFORMATION: Synthetic Construct

<400> SEQUENCE: 147

Ala Ala Arg Ile Arg Glu Thr
1               5

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Gln Gln Tyr Tyr Asp Trp Pro Pro Phe Thr
1               5                   10

<210> SEQ ID NO 149
<211> LENGTH: 10
<212> TYPE: PRT
<213> ORGANISM: Artificial Sequence
<220> FEATURE:
<223> OTHER INFORMATION: Synthetic Construct

<400> SEQUENCE: 149

Gly Phe Ser Phe Ser Ile Tyr Ala Met Ser
1               5                   10

<210> SEQ ID NO 150
<211> LENGTH: 15
<212> TYPE: PRT
<213> ORGANISM: Artificial Sequence
<220> FEATURE:
<223> OTHER INFORMATION: Synthetic Construct

<400> SEQUENCE: 150

Thr Ile Gly Ala Asp Asp Thr Tyr Tyr Ala Asp Ser Val Lys Gly
1               5                   10                  15

<210> SEQ ID NO 151
<211> LENGTH: 13
<212> TYPE: PRT
<213> ORGANISM: Artificial Sequence
<220> FEATURE:
<223> OTHER INFORMATION: Synthetic Construct

<400> SEQUENCE: 151

Asp Ser Thr Val Gly Trp Ser Gly Asp Phe Phe Asp Tyr
1               5                   10

<210> SEQ ID NO 152
<211> LENGTH: 11
<212> TYPE: PRT
<213> ORGANISM: Artificial Sequence
<220> FEATURE:
<223> OTHER INFORMATION: Synthetic Construct

<400> SEQUENCE: 152

Arg Ala Ser Gln Asn Val Arg Ser Asp Ile Ala
1               5                   10

<210> SEQ ID NO 153
<211> LENGTH: 7
<212> TYPE: PRT
<213> ORGANISM: Artificial Sequence
<220> FEATURE:
<223> OTHER INFORMATION: Synthetic Construct

```
<400> SEQUENCE: 153

Ala Ala Ser Ser Arg Asp Thr
1               5

<210> SEQ ID NO 154

<400> SEQUENCE: 154

000

<210> SEQ ID NO 155
<211> LENGTH: 10
<212> TYPE: PRT
<213> ORGANISM: Artificial Sequence
<220> FEATURE:
<223> OTHER INFORMATION: Synthetic Construct

<400> SEQUENCE: 155

Gly Phe Thr Phe Ser Ser Tyr Asp Met Asn
1               5                   10

<210> SEQ ID NO 156
<211> LENGTH: 17
<212> TYPE: PRT
<213> ORGANISM: Artificial Sequence
<220> FEATURE:
<223> OTHER INFORMATION: Synthetic Construct

<400> SEQUENCE: 156

Leu Ile Ser Gly Ser Gly Glu Ile Ile Tyr Tyr Ala Asp Ser Val Lys
1               5                   10                  15

Gly

<210> SEQ ID NO 157
<211> LENGTH: 10
<212> TYPE: PRT
<213> ORGANISM: Artificial Sequence
<220> FEATURE:
<223> OTHER INFORMATION: Synthetic Construct

<400> SEQUENCE: 157

Glu Asn Asn Arg Tyr Arg Phe Phe Asp Asp
1               5                   10

<210> SEQ ID NO 158
<211> LENGTH: 11
<212> TYPE: PRT
<213> ORGANISM: Artificial Sequence
<220> FEATURE:
<223> OTHER INFORMATION: Synthetic Construct

<400> SEQUENCE: 158

Arg Ala Ser Gln Ser Val Tyr Thr Tyr Leu Ala
1               5                   10

<210> SEQ ID NO 159
<211> LENGTH: 7
<212> TYPE: PRT
<213> ORGANISM: Artificial Sequence
<220> FEATURE:
<223> OTHER INFORMATION: Synthetic Construct

<400> SEQUENCE: 159

Gly Ala Ser Ser Arg Ala Thr
1               5
```

<210> SEQ ID NO 160
<211> LENGTH: 10
<212> TYPE: PRT
<213> ORGANISM: Artificial Sequence
<220> FEATURE:
<223> OTHER INFORMATION: Synthetic Construct

<400> SEQUENCE: 160

Gln Gln Tyr Tyr Asp Arg Pro Pro Leu Thr
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Synthetic Construct

<400> SEQUENCE: 161

Gly Phe Thr Phe Ser Ser Asn Ala
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic Construct

<400> SEQUENCE: 162

Ile Ser Ala Gly Gly Ser Asp Thr
1               5

<210> SEQ ID NO 163
<211> LENGTH: 11
<212> TYPE: PRT
<213> ORGANISM: Artificial Sequence
<220> FEATURE:
<223> OTHER INFORMATION: Synthetic Construct

<400> SEQUENCE: 163

Ala Arg Glu Thr Trp Asn His Leu Phe Asp Tyr
1               5                   10

<210> SEQ ID NO 164
<211> LENGTH: 11
<212> TYPE: PRT
<213> ORGANISM: Artificial Sequence
<220> FEATURE:
<223> OTHER INFORMATION: Synthetic Construct

<400> SEQUENCE: 164

Ser Gly Gly Asp Tyr Tyr Ser Tyr Tyr Tyr Gly
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Synthetic Construct

<400> SEQUENCE: 165

Thr Val Ile Tyr Ser Asp Asp Lys Arg Pro Ser Asp
1               5                   10

```
<210> SEQ ID NO 166
<211> LENGTH: 11
<212> TYPE: PRT
<213> ORGANISM: Artificial Sequence
<220> FEATURE:
<223> OTHER INFORMATION: Synthetic Construct

<400> SEQUENCE: 166

Gly Gly Tyr Asp Tyr Ser Thr Tyr Ala Asn Ala
1               5                   10

<210> SEQ ID NO 167

<400> SEQUENCE: 167

000

<210> SEQ ID NO 168
<211> LENGTH: 7
<212> TYPE: PRT
<213> ORGANISM: Artificial Sequence
<220> FEATURE:
<223> OTHER INFORMATION: Synthetic Construct

<400> SEQUENCE: 168

Ile Ser Ser Gly Ser Asp Thr
1               5

<210> SEQ ID NO 169

<400> SEQUENCE: 169

000

<210> SEQ ID NO 170
<211> LENGTH: 11
<212> TYPE: PRT
<213> ORGANISM: Artificial Sequence
<220> FEATURE:
<223> OTHER INFORMATION: Synthetic Construct

<400> SEQUENCE: 170

Ser Gly Gly Ser Tyr Ser Ser Tyr Tyr Tyr Ala
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Synthetic Construct

<400> SEQUENCE: 171

Thr Leu Ile Tyr Ser Asp Asp Lys Arg Pro Ser Asn
1               5                   10

<210> SEQ ID NO 172
<211> LENGTH: 11
<212> TYPE: PRT
<213> ORGANISM: Artificial Sequence
<220> FEATURE:
<223> OTHER INFORMATION: Synthetic Construct

<400> SEQUENCE: 172

Gly Gly Tyr Asp Gln Ser Ser Tyr Thr Asn Pro
1               5                   10
```

```
<210> SEQ ID NO 173
<211> LENGTH: 8
<212> TYPE: PRT
<213> ORGANISM: Artificial Sequence
<220> FEATURE:
<223> OTHER INFORMATION: Synthetic Construct

<400> SEQUENCE: 173

Gly Phe Arg Phe Ser Ser Tyr Ala
1               5

<210> SEQ ID NO 174
<211> LENGTH: 7
<212> TYPE: PRT
<213> ORGANISM: Artificial Sequence
<220> FEATURE:
<223> OTHER INFORMATION: Synthetic Construct

<400> SEQUENCE: 174

Ile Ser Ser Gly Gly Asp Thr
1               5

<210> SEQ ID NO 175
<211> LENGTH: 5
<212> TYPE: PRT
<213> ORGANISM: Artificial Sequence
<220> FEATURE:
<223> OTHER INFORMATION: Synthetic Construct

<400> SEQUENCE: 175

Asn Phe Ala Met Thr
1               5

<210> SEQ ID NO 176
<211> LENGTH: 11
<212> TYPE: PRT
<213> ORGANISM: Artificial Sequence
<220> FEATURE:
<223> OTHER INFORMATION: Synthetic Construct

<400> SEQUENCE: 176

Ser Gly Gly Asp Ser Ser Ser His Tyr Tyr Gly
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Synthetic Construct

<400> SEQUENCE: 177

Thr Val Ile Tyr Ser Asp Asp Glu Arg Pro Ser Asp
1               5                   10

<210> SEQ ID NO 178
<211> LENGTH: 11
<212> TYPE: PRT
<213> ORGANISM: Artificial Sequence
<220> FEATURE:
<223> OTHER INFORMATION: Synthetic Construct

<400> SEQUENCE: 178

Gly Ala Tyr Asp Gly Ser Thr Tyr Ala Asn Thr
1               5                   10

<210> SEQ ID NO 179
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 179

Gly Phe Thr Phe Ser Ser Tyr Ala
1               5

<210> SEQ ID NO 180

<400> SEQUENCE: 180

000

<210> SEQ ID NO 181

<400> SEQUENCE: 181

000

<210> SEQ ID NO 182
<211> LENGTH: 11
<212> TYPE: PRT
<213> ORGANISM: Artificial Sequence
<220> FEATURE:
<223> OTHER INFORMATION: Synthetic Construct

<400> SEQUENCE: 182

Ser Gly Gly Asp Tyr Tyr Ser Thr Tyr Tyr Ala
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthetic Construct

<400> SEQUENCE: 183

Thr Val Ile His Ser Asp Asp Lys Arg Pro Ser Asp
1               5                   10

<210> SEQ ID NO 184
<211> LENGTH: 11
<212> TYPE: PRT
<213> ORGANISM: Artificial Sequence
<220> FEATURE:
<223> OTHER INFORMATION: Synthetic Construct

<400> SEQUENCE: 184

Gly Gly Tyr Asp Gly Arg Thr Tyr Ile Asn Thr
1               5                   10

<210> SEQ ID NO 185
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asn or Ile
<220> FEATURE:
<221> NAME/KEY: VARIANT
<222> LOCATION: 7
<223> OTHER INFORMATION: Xaa = Phe or Tyr
```

```
<220> FEATURE:
<221> NAME/KEY: VARIANT
<222> LOCATION: 10
<223> OTHER INFORMATION: Xaa = Thr or Ser

<400> SEQUENCE: 185

Gly Phe Ser Phe Ser Xaa Xaa Ala Met Xaa
1               5                   10

<210> SEQ ID NO 186
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Ala
<220> FEATURE:
<221> NAME/KEY: VARIANT
<222> LOCATION: 5
<223> OTHER INFORMATION: Xaa = Gly or Asp

<400> SEQUENCE: 186

Thr Ile Gly Xaa Xaa Asp Thr Tyr Tyr Ala Asp Ser Val Lys Gly
1               5                   10                  15

<210> SEQ ID NO 187
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Gly

<400> SEQUENCE: 187

Asp Ser Thr Val Xaa Trp Ser Gly Asp Phe Phe Asp Tyr
1               5                   10

<210> SEQ ID NO 188
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Lys or Arg
<220> FEATURE:
<221> NAME/KEY: VARIANT
<222> LOCATION: 8
<223> OTHER INFORMATION: Xaa = Asn or Ser
<220> FEATURE:
<221> NAME/KEY: VARIANT
<222> LOCATION: 10
<223> OTHER INFORMATION: Xaa = Leu or Ile

<400> SEQUENCE: 188

Arg Ala Ser Gln Asn Val Xaa Xaa Asp Xaa Ala
1               5                   10

<210> SEQ ID NO 189
<211> LENGTH: 7
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: VARIANT
<222> LOCATION: 3
<223> OTHER INFORMATION: Xaa = Arg or Ser
<220> FEATURE:
<221> NAME/KEY: VARIANT
<222> LOCATION: 4
<223> OTHER INFORMATION: Xaa = Ile or Ser
<220> FEATURE:
<221> NAME/KEY: VARIANT
<222> LOCATION: 6
<223> OTHER INFORMATION: Xaa = Glu or Asp

<400> SEQUENCE: 189

Ala Ala Xaa Xaa Arg Xaa Thr
1               5

<210> SEQ ID NO 190
<211> LENGTH: 9
<212> TYPE: PRT
<213> ORGANISM: Artificial Sequence
<220> FEATURE:
<223> OTHER INFORMATION: Synthetic Construct

<400> SEQUENCE: 190

Gly Gly Tyr Asp Tyr Ser Thr Tyr Ala
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Construct

<400> SEQUENCE: 191

Gly Phe Thr Phe Ser Ser Asn
1               5

<210> SEQ ID NO 192
<211> LENGTH: 6
<212> TYPE: PRT
<213> ORGANISM: Artificial Sequence
<220> FEATURE:
<223> OTHER INFORMATION: Synthetic Construct

<400> SEQUENCE: 192

Ser Ala Gly Gly Ser Asp
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic Construct

<400> SEQUENCE: 193

Glu Thr Trp Asn His Leu Phe Asp Tyr
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 194

Ser Asn Ala Met Ser
1               5

<210> SEQ ID NO 195
<211> LENGTH: 17
<212> TYPE: PRT
<213> ORGANISM: Artificial Sequence
<220> FEATURE:
<223> OTHER INFORMATION: Synthetic Construct

<400> SEQUENCE: 195

Gly Ile Ser Ala Gly Gly Ser Asp Thr Tyr Tyr Pro Ala Ser Val Lys
1               5                   10                  15

Gly

<210> SEQ ID NO 196
<211> LENGTH: 5
<212> TYPE: PRT
<213> ORGANISM: Artificial Sequence
<220> FEATURE:
<223> OTHER INFORMATION: Synthetic Construct

<400> SEQUENCE: 196

Ser Ser Gly Ser Asp
1               5

<210> SEQ ID NO 197
<211> LENGTH: 16
<212> TYPE: PRT
<213> ORGANISM: Artificial Sequence
<220> FEATURE:
<223> OTHER INFORMATION: Synthetic Construct

<400> SEQUENCE: 197

Gly Ile Ser Ser Gly Ser Asp Thr Tyr Tyr Gly Asp Ser Val Lys Gly
1               5                   10                  15

<210> SEQ ID NO 198
<211> LENGTH: 7
<212> TYPE: PRT
<213> ORGANISM: Artificial Sequence
<220> FEATURE:
<223> OTHER INFORMATION: Synthetic Construct

<400> SEQUENCE: 198

Gly Phe Arg Phe Ser Ser Tyr
1               5

<210> SEQ ID NO 199
<211> LENGTH: 5
<212> TYPE: PRT
<213> ORGANISM: Artificial Sequence
<220> FEATURE:
<223> OTHER INFORMATION: Synthetic Construct

<400> SEQUENCE: 199

Ser Ser Gly Gly Asp
1               5

<210> SEQ ID NO 200
<211> LENGTH: 5
<212> TYPE: PRT
<213> ORGANISM: Artificial Sequence
<220> FEATURE:
<223> OTHER INFORMATION: Synthetic Construct
```

<400> SEQUENCE: 200

Ser Tyr Ala Met Ser
1               5

<210> SEQ ID NO 201
<211> LENGTH: 16
<212> TYPE: PRT
<213> ORGANISM: Artificial Sequence
<220> FEATURE:
<223> OTHER INFORMATION: Synthetic Construct

<400> SEQUENCE: 201

Gly Ile Ser Ser Gly Gly Asp Thr Tyr Tyr Val Asp Ser Val Lys Gly
1               5                   10                  15

<210> SEQ ID NO 202
<211> LENGTH: 7
<212> TYPE: PRT
<213> ORGANISM: Artificial Sequence
<220> FEATURE:
<223> OTHER INFORMATION: Synthetic Construct

<400> SEQUENCE: 202

Gly Phe Ser Phe Ser Asn Phe
1               5

<210> SEQ ID NO 203
<211> LENGTH: 4
<212> TYPE: PRT
<213> ORGANISM: Artificial Sequence
<220> FEATURE:
<223> OTHER INFORMATION: Synthetic Construct

<400> SEQUENCE: 203

Gly Ser Gly Asp
1

<210> SEQ ID NO 204
<211> LENGTH: 5
<212> TYPE: PRT
<213> ORGANISM: Artificial Sequence
<220> FEATURE:
<223> OTHER INFORMATION: Synthetic Construct

<400> SEQUENCE: 204

Asn Phe Ala Val Thr
1               5

<210> SEQ ID NO 205
<211> LENGTH: 8
<212> TYPE: PRT
<213> ORGANISM: Artificial Sequence
<220> FEATURE:
<223> OTHER INFORMATION: Synthetic Construct

<400> SEQUENCE: 205

Gly Phe Ser Phe Ser Asn Phe Ala
1               5

<210> SEQ ID NO 206
<211> LENGTH: 6
<212> TYPE: PRT
<213> ORGANISM: Artificial Sequence
<220> FEATURE:
<223> OTHER INFORMATION: Synthetic Construct

```
<400> SEQUENCE: 206

Ile Gly Ser Gly Asp Thr
1               5

<210> SEQ ID NO 207
<211> LENGTH: 15
<212> TYPE: PRT
<213> ORGANISM: Artificial Sequence
<220> FEATURE:
<223> OTHER INFORMATION: Synthetic Construct

<400> SEQUENCE: 207

Ala Lys Asp Ser Thr Val Ser Trp Ser Gly Asp Phe Phe Asp Tyr
1               5                  10                  15

<210> SEQ ID NO 208
<211> LENGTH: 6
<212> TYPE: PRT
<213> ORGANISM: Artificial Sequence
<220> FEATURE:
<223> OTHER INFORMATION: Synthetic Construct

<400> SEQUENCE: 208

Gln Asn Val Lys Asn Asp
1               5

<210> SEQ ID NO 209
<211> LENGTH: 3
<212> TYPE: PRT
<213> ORGANISM: Artificial Sequence
<220> FEATURE:
<223> OTHER INFORMATION: Synthetic Construct

<400> SEQUENCE: 209

Ala Ala Arg
1

<210> SEQ ID NO 210
<211> LENGTH: 7
<212> TYPE: PRT
<213> ORGANISM: Artificial Sequence
<220> FEATURE:
<223> OTHER INFORMATION: Synthetic Construct

<400> SEQUENCE: 210

Gln Gln Tyr Tyr Asp Trp Pro
1               5

<210> SEQ ID NO 211
<211> LENGTH: 7
<212> TYPE: PRT
<213> ORGANISM: Artificial Sequence
<220> FEATURE:
<223> OTHER INFORMATION: Synthetic Construct

<400> SEQUENCE: 211

Gly Phe Ser Phe Ser Ile Tyr
1               5

<210> SEQ ID NO 212
<211> LENGTH: 4
<212> TYPE: PRT
<213> ORGANISM: Artificial Sequence
<220> FEATURE:
<223> OTHER INFORMATION: Synthetic Construct

<400> SEQUENCE: 212
```

Gly Ala Asp Asp
1

<210> SEQ ID NO 213
<211> LENGTH: 5
<212> TYPE: PRT
<213> ORGANISM: Artificial Sequence
<220> FEATURE:
<223> OTHER INFORMATION: Synthetic Construct

<400> SEQUENCE: 213

Ile Tyr Ala Val Ser
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic Construct

<400> SEQUENCE: 214

Gly Phe Ser Phe Ser Ile Tyr Ala
1               5

<210> SEQ ID NO 215
<211> LENGTH: 6
<212> TYPE: PRT
<213> ORGANISM: Artificial Sequence
<220> FEATURE:
<223> OTHER INFORMATION: Synthetic Construct

<400> SEQUENCE: 215

Ile Gly Ala Asp Asp Thr
1               5

<210> SEQ ID NO 216
<211> LENGTH: 15
<212> TYPE: PRT
<213> ORGANISM: Artificial Sequence
<220> FEATURE:
<223> OTHER INFORMATION: Synthetic Construct

<400> SEQUENCE: 216

Ala Lys Asp Ser Thr Val Gly Trp Ser Gly Asp Phe Phe Asp Tyr
1               5                   10                  15

<210> SEQ ID NO 217
<211> LENGTH: 6
<212> TYPE: PRT
<213> ORGANISM: Artificial Sequence
<220> FEATURE:
<223> OTHER INFORMATION: Synthetic Construct

<400> SEQUENCE: 217

Gln Asn Val Arg Ser Asp
1               5

<210> SEQ ID NO 218
<211> LENGTH: 3
<212> TYPE: PRT
<213> ORGANISM: Artificial Sequence
<220> FEATURE:
<223> OTHER INFORMATION: Synthetic Construct

<400> SEQUENCE: 218

Ala Ala Ser
1

<210> SEQ ID NO 219
<211> LENGTH: 7
<212> TYPE: PRT
<213> ORGANISM: Artificial Sequence
<220> FEATURE:
<223> OTHER INFORMATION: Synthetic Construct

<400> SEQUENCE: 219

Gly Phe Thr Phe Ser Ser Tyr
1               5

<210> SEQ ID NO 220
<211> LENGTH: 6
<212> TYPE: PRT
<213> ORGANISM: Artificial Sequence
<220> FEATURE:
<223> OTHER INFORMATION: Synthetic Construct

<400> SEQUENCE: 220

Ser Gly Ser Gly Glu Ile
1               5

<210> SEQ ID NO 221
<211> LENGTH: 5
<212> TYPE: PRT
<213> ORGANISM: Artificial Sequence
<220> FEATURE:
<223> OTHER INFORMATION: Synthetic Construct

<400> SEQUENCE: 221

Ser Tyr Asp Val Asn
1               5

<210> SEQ ID NO 222
<211> LENGTH: 8
<212> TYPE: PRT
<213> ORGANISM: Artificial Sequence
<220> FEATURE:
<223> OTHER INFORMATION: Synthetic Construct

<400> SEQUENCE: 222

Gly Phe Thr Phe Ser Ser Tyr Asp
1               5

<210> SEQ ID NO 223
<211> LENGTH: 8
<212> TYPE: PRT
<213> ORGANISM: Artificial Sequence
<220> FEATURE:
<223> OTHER INFORMATION: Synthetic Construct

<400> SEQUENCE: 223

Ile Ser Gly Ser Gly Glu Ile Ile
1               5

<210> SEQ ID NO 224
<211> LENGTH: 12
<212> TYPE: PRT
<213> ORGANISM: Artificial Sequence
<220> FEATURE:
<223> OTHER INFORMATION: Synthetic Construct

<400> SEQUENCE: 224

Ala Lys Glu Asn Asn Arg Tyr Arg Phe Phe Asp Asp

```
1               5              10
```

<210> SEQ ID NO 225
<211> LENGTH: 6
<212> TYPE: PRT
<213> ORGANISM: Artificial Sequence
<220> FEATURE:
<223> OTHER INFORMATION: Synthetic Construct

<400> SEQUENCE: 225

```
Gln Ser Val Tyr Thr Tyr
1               5
```

<210> SEQ ID NO 226
<211> LENGTH: 3
<212> TYPE: PRT
<213> ORGANISM: Artificial Sequence
<220> FEATURE:
<223> OTHER INFORMATION: Synthetic Construct

<400> SEQUENCE: 226

```
Gly Ala Ser
1
```

<210> SEQ ID NO 227
<211> LENGTH: 5
<212> TYPE: PRT
<213> ORGANISM: Artificial Sequence
<220> FEATURE:
<223> OTHER INFORMATION: Synthetic Construct

<400> SEQUENCE: 227

```
Asp Tyr Gly Met Asn
1               5
```

<210> SEQ ID NO 228
<211> LENGTH: 16
<212> TYPE: PRT
<213> ORGANISM: Artificial Sequence
<220> FEATURE:
<223> OTHER INFORMATION: Synthetic Construct

<400> SEQUENCE: 228

```
Gln Ile Thr Ser Gly Ser Arg Thr Tyr Tyr Gly Ala Ala Val Lys Gly
1               5                   10                  15
```

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct

<400> SEQUENCE: 229

```
Asp Phe Gly Ser Gly Val Gly Ser Ile Asp Ala
1               5                   10
```

<210> SEQ ID NO 230
<211> LENGTH: 7
<212> TYPE: PRT
<213> ORGANISM: Artificial Sequence
<220> FEATURE:
<223> OTHER INFORMATION: Synthetic Construct

<400> SEQUENCE: 230

```
Gly Phe Ile Phe Ser Asp Tyr
1               5
```

<210> SEQ ID NO 231
<211> LENGTH: 5
<212> TYPE: PRT
<213> ORGANISM: Artificial Sequence
<220> FEATURE:
<223> OTHER INFORMATION: Synthetic Construct

<400> SEQUENCE: 231

Thr Ser Gly Ser Arg
1               5

<210> SEQ ID NO 232
<211> LENGTH: 8
<212> TYPE: PRT
<213> ORGANISM: Artificial Sequence
<220> FEATURE:
<223> OTHER INFORMATION: Synthetic Construct

<400> SEQUENCE: 232

Ser Gly Ser Arg Gly Arg Tyr Gly
1               5

<210> SEQ ID NO 233
<211> LENGTH: 7
<212> TYPE: PRT
<213> ORGANISM: Artificial Sequence
<220> FEATURE:
<223> OTHER INFORMATION: Synthetic Construct

<400> SEQUENCE: 233

Arg Asp Asn Gln Arg Pro Ser
1               5

<210> SEQ ID NO 234
<211> LENGTH: 9
<212> TYPE: PRT
<213> ORGANISM: Artificial Sequence
<220> FEATURE:
<223> OTHER INFORMATION: Synthetic Construct

<400> SEQUENCE: 234

Gly Ser Tyr Asp Gly Ser Ile Asp Ile
1               5

<210> SEQ ID NO 235
<211> LENGTH: 5
<212> TYPE: PRT
<213> ORGANISM: Artificial Sequence
<220> FEATURE:
<223> OTHER INFORMATION: Synthetic Construct

<400> SEQUENCE: 235

Ser Tyr Ala Met Gly
1               5

<210> SEQ ID NO 236
<211> LENGTH: 17
<212> TYPE: PRT
<213> ORGANISM: Artificial Sequence
<220> FEATURE:
<223> OTHER INFORMATION: Synthetic Construct

<400> SEQUENCE: 236

Gly Ile Asp Asp Asp Gly Ser Thr Ala Asn Tyr Gly Pro Ala Val Lys
1               5                   10                  15

Gly

<210> SEQ ID NO 237
<211> LENGTH: 16
<212> TYPE: PRT
<213> ORGANISM: Artificial Sequence
<220> FEATURE:
<223> OTHER INFORMATION: Synthetic Construct

<400> SEQUENCE: 237

Ala Ser Val Thr Gly Trp Ser Ala His Ile Ser Gly Arg Leu Asp Thr
1               5                   10                  15

<210> SEQ ID NO 238
<211> LENGTH: 5
<212> TYPE: PRT
<213> ORGANISM: Artificial Sequence
<220> FEATURE:
<223> OTHER INFORMATION: Synthetic Construct

<400> SEQUENCE: 238

Asp Asp Gly Ser Thr
1               5

<210> SEQ ID NO 239
<211> LENGTH: 9
<212> TYPE: PRT
<213> ORGANISM: Artificial Sequence
<220> FEATURE:
<223> OTHER INFORMATION: Synthetic Construct

<400> SEQUENCE: 239

Ser Gly Gly Gly Ile Tyr Tyr Tyr Gly
1               5

<210> SEQ ID NO 240
<211> LENGTH: 7
<212> TYPE: PRT
<213> ORGANISM: Artificial Sequence
<220> FEATURE:
<223> OTHER INFORMATION: Synthetic Construct

<400> SEQUENCE: 240

Glu Asn Asp Lys Arg Pro Ser
1               5

<210> SEQ ID NO 241
<211> LENGTH: 11
<212> TYPE: PRT
<213> ORGANISM: Artificial Sequence
<220> FEATURE:
<223> OTHER INFORMATION: Synthetic Construct

<400> SEQUENCE: 241

Gly Gly Tyr Asp Ser Asn Thr Thr Ser Gly Ile
1               5                   10

<210> SEQ ID NO 242
<211> LENGTH: 119
<212> TYPE: PRT
<213> ORGANISM: Artificial Sequence
<220> FEATURE:
<223> OTHER INFORMATION: Synthetic Construct

<400> SEQUENCE: 242

Ala Val Thr Leu Asp Glu Ser Gly Gly Gly Leu Gln Thr Pro Gly Gly
1               5                   10                  15

-continued

Ala Ser Leu Val Cys Lys Ala Ser Gly Phe Ile Phe Ser Asp Tyr
         20                  25                  30

Gly Met Asn Trp Val Arg Gln Ala Pro Gly Lys Gly Leu Glu Phe Val
                 35                  40                  45

Ala Gln Ile Thr Ser Gly Ser Arg Thr Tyr Tyr Gly Ala Ala Val Lys
50                  55                  60

Gly Arg Ala Thr Ile Ser Arg Asp Asn Arg Gln Ser Thr Val Lys Leu
65                  70                  75                  80

Gln Leu Asn Asn Leu Arg Ala Glu Asp Thr Gly Ile Tyr Phe Cys Ala
                 85                  90                  95

Arg Asp Phe Gly Ser Gly Val Gly Ser Ile Asp Ala Trp Gly Asn Gly
            100                 105                 110

Thr Glu Val Ile Val Ser Ser
            115

<210> SEQ ID NO 243
<211> LENGTH: 102
<212> TYPE: PRT
<213> ORGANISM: Artificial Sequence
<220> FEATURE:
<223> OTHER INFORMATION: Synthetic Construct

<400> SEQUENCE: 243

Ala Leu Thr Gln Pro Ala Ser Val Ser Ala Asn Leu Gly Gly Thr Val
1               5                   10                  15

Lys Ile Thr Cys Ser Gly Ser Arg Gly Arg Tyr Gly Trp Tyr Gln Gln
                20                  25                  30

Arg Ser Pro Gly Ser Ala Pro Val Thr Val Ile Tyr Arg Asp Asn Gln
            35                  40                  45

Arg Pro Ser Asn Ile Pro Ser Arg Phe Ser Ser Ser Thr Ser Gly Ser
   50                  55                  60

Thr Ser Thr Leu Thr Ile Thr Gly Val Gln Ala Asp Asp Glu Ser Val
65                  70                  75                  80

Tyr Phe Cys Gly Ser Tyr Asp Gly Ser Ile Asp Ile Phe Gly Ala Gly
                 85                  90                  95

Thr Thr Leu Thr Val Leu
            100

<210> SEQ ID NO 244
<211> LENGTH: 125
<212> TYPE: PRT
<213> ORGANISM: Artificial Sequence
<220> FEATURE:
<223> OTHER INFORMATION: Synthetic Construct

<400> SEQUENCE: 244

Ala Val Thr Leu Asp Glu Ser Gly Gly Gly Leu Gln Thr Pro Gly Gly
1               5                   10                  15

Ala Leu Ser Leu Val Cys Lys Ala Ser Gly Phe Thr Phe Ser Ser Tyr
                20                  25                  30

Ala Met Gly Trp Val Arg Gln Ala Pro Gly Lys Gly Leu Glu Trp Val
            35                  40                  45

Ala Gly Ile Asp Asp Asp Gly Ser Thr Ala Asn Tyr Gly Pro Ala Val
   50                  55                  60

Lys Gly Arg Ala Thr Ile Ser Arg Asp Asn Gly Gln Ser Thr Val Arg
65                  70                  75                  80

Leu Gln Leu Asn Asn Pro Arg Ala Glu Asp Ser Gly Thr Tyr Phe Cys

```
                85                  90                  95
Ala Lys Ala Ser Val Thr Gly Trp Ser Ala His Ile Ser Gly Arg Leu
            100                 105                 110

Asp Thr Trp Gly His Gly Thr Glu Val Ile Val Ser Ser
            115                 120                 125

<210> SEQ ID NO 245
<211> LENGTH: 105
<212> TYPE: PRT
<213> ORGANISM: Artificial Sequence
<220> FEATURE:
<223> OTHER INFORMATION: Synthetic Construct

<400> SEQUENCE: 245

Ala Leu Thr Gln Pro Ala Ser Val Ser Ala Asn Pro Gly Glu Thr Val
1               5                   10                  15

Lys Ile Thr Cys Ser Gly Gly Ile Tyr Tyr Gly Trp Tyr Gln
            20                  25                  30

Gln Lys Ser Pro Gly Ser Ala Pro Val Thr Leu Ile Tyr Glu Asn Asp
            35                  40                  45

Lys Arg Pro Ser Asp Ile Pro Ser Arg Phe Ser Gly Ser Thr Ser Gly
50                  55                  60

Ser Thr Asn Thr Phe Thr Ile Thr Gly Val Gln Ala Glu Asp Glu Ala
65                  70                  75                  80

Val Tyr Tyr Cys Gly Gly Tyr Asp Ser Asn Thr Ser Gly Ile Phe
            85                  90                  95

Gly Ala Gly Thr Thr Leu Thr Val Leu
            100                 105

<210> SEQ ID NO 246
<211> LENGTH: 120
<212> TYPE: PRT
<213> ORGANISM: Artificial Sequence
<220> FEATURE:
<223> OTHER INFORMATION: Synthetic Construct

<400> SEQUENCE: 246

Glu Val Gln Leu Leu Glu Ser Gly Gly Val Val Gln Pro Gly Gly
1               5                   10                  15

Ser Leu Arg Leu Ser Cys Ala Ala Ser Gly Phe Ser Phe Ser Asn Phe
            20                  25                  30

Ala Val Thr Trp Val Arg Gln Ala Pro Gly Lys Gly Leu Glu Trp Val
            35                  40                  45

Ser Thr Ile Gly Ser Gly Asp Thr Tyr Tyr Ala Asp Ser Val Lys Gly
            50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
            85                  90                  95

Asp Ser Thr Val Ser Trp Ser Gly Asp Phe Phe Asp Tyr Trp Gly Gln
            100                 105                 110

Gly Thr Leu Val Thr Val Ser Ser
        115                 120

<210> SEQ ID NO 247
<211> LENGTH: 120
<212> TYPE: PRT
<213> ORGANISM: Artificial Sequence
<220> FEATURE:
```

<223> OTHER INFORMATION: Synthetic Construct

<400> SEQUENCE: 247

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Phe Ser Ile Tyr
            20                  25                  30

Ala Val Ser Trp Val Arg Gln Ala Pro Gly Lys Gly Leu Glu Trp Val
        35                  40                  45

Ser Thr Ile Gly Ala Asp Asp Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Gly Trp Ser Gly Asp Phe Phe Asp Tyr Trp Gly Gln
            100                 105                 110

Gly Thr Leu Val Thr Val Ser Ser
        115                 120

<210> SEQ ID NO 248
<211> LENGTH: 108
<212> TYPE: PRT
<213> ORGANISM: Artificial Sequence
<220> FEATURE:
<223> OTHER INFORMATION: Synthetic Construct

<400> SEQUENCE: 248

Glu Ile Val Leu Thr Gln Ser Pro Ala Thr Leu Ser Val Ser Pro Gly
1               5                   10                  15

Glu Arg Val Thr Leu Ser Cys Arg Ala Ser Gln Asn Val Arg Ser Asp
            20                  25                  30

Ile Ala Trp Tyr Gln Gln Lys Pro Gly Gln Ala Pro Arg Leu Leu Ile
        35                  40                  45

Tyr Ala Ala Ser Ser Arg Asp Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Gly Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105

<210> SEQ ID NO 249
<211> LENGTH: 119
<212> TYPE: PRT
<213> ORGANISM: Artificial Sequence
<220> FEATURE:
<223> OTHER INFORMATION: Synthetic Construct

<400> SEQUENCE: 249

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Val Asn Trp Val Arg Gln Ala Pro Gly Lys Gly Leu Glu Trp Val
        35                  40                  45

Ser Leu Ile Ser Gly Ser Gly Glu Ile Ile Tyr Tyr Ala Asp Ser Val

```
                  50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                     85                  90                  95

Ala Lys Glu Asn Asn Arg Tyr Arg Phe Phe Asp Asp Trp Gly Gln Gly
                100                 105                 110

Thr Leu Val Thr Val Ser Ser
            115

<210> SEQ ID NO 250
<211> LENGTH: 108
<212> TYPE: PRT
<213> ORGANISM: Artificial Sequence
<220> FEATURE:
<223> OTHER INFORMATION: Synthetic Construct

<400> SEQUENCE: 250

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Tyr Thr Tyr
                20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr Asp Arg Pro Pro
                 85                  90                  95

Leu Thr Phe Gly Gly Gly Thr Lys Val Glu Ile Lys
            100                 105

<210> SEQ ID NO 251
<211> LENGTH: 108
<212> TYPE: PRT
<213> ORGANISM: Artificial Sequence
<220> FEATURE:
<223> OTHER INFORMATION: Synthetic Construct

<400> SEQUENCE: 251

Glu Thr Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Tyr Thr Tyr
                20                  25                  30

Leu Ala Trp Tyr Gln Gln Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr Asp Arg Pro Pro
                 85                  90                  95

Leu Thr Phe Gly Gly Gly Thr Lys Val Glu Ile Lys
            100                 105

<210> SEQ ID NO 252
<211> LENGTH: 108
```

```
<212> TYPE: PRT
<213> ORGANISM: Artificial Sequence
<220> FEATURE:
<223> OTHER INFORMATION: Synthetic Construct

<400> SEQUENCE: 252

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu
            100                 105

<210> SEQ ID NO 253
<211> LENGTH: 108
<212> TYPE: PRT
<213> ORGANISM: Artificial Sequence
<220> FEATURE:
<223> OTHER INFORMATION: Synthetic Construct

<400> SEQUENCE: 253

Gln Ser Val Leu Thr Gln Pro Pro Ser Val Ser Ala Ala Pro Gly Gln
1               5                   10                  15

Lys Val Thr Ile Ser Cys Ser Gly Gly Ser Tyr Ser Tyr Tyr Tyr Tyr
            20                  25                  30

Ala Trp Tyr Gln Gln Leu Pro Gly Thr Ala Pro Lys Thr Leu Ile Tyr
        35                  40                  45

Ser Asp Asp Lys Arg Pro Ser Asn Ile Pro Asp Arg Phe Ser Gly Ser
    50                  55                  60

Lys Ser Gly Thr Ser Ala Thr Leu Gly Ile Thr Gly Leu Gln Thr Gly
65                  70                  75                  80

Asp Glu Ala Asp Tyr Tyr Cys Gly Gly Tyr Asp Gln Ser Ser Tyr Thr
                85                  90                  95

Asn Pro Phe Gly Thr Gly Thr Lys Val Thr Val Leu
            100                 105

<210> SEQ ID NO 254
<211> LENGTH: 108
<212> TYPE: PRT
<213> ORGANISM: Artificial Sequence
<220> FEATURE:
<223> OTHER INFORMATION: Synthetic Construct

<400> SEQUENCE: 254

Ser Tyr Glu Leu Thr Gln Pro Pro Ser Val Ser Val Ser Pro Gly Gln
1               5                   10                  15

Thr Ala Arg Ile Thr Cys Ser Gly Gly Asp Tyr Tyr Ser Thr Tyr Tyr
            20                  25                  30

Ala Trp Tyr Gln Gln Lys Pro Gly Gln Ala Pro Val Thr Val Ile His
        35                  40                  45

Ser Asp Asp Lys Arg Pro Ser Asp Ile Pro Glu Arg Phe Ser Gly Ser
```

```
            50                  55                  60
Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gly Arg Thr Tyr Ile
                 85                  90                  95

Asn Thr Phe Gly Gly Gly Thr Lys Leu Thr Val Leu
            100                 105

<210> SEQ ID NO 255
<211> LENGTH: 108
<212> TYPE: PRT
<213> ORGANISM: Artificial Sequence
<220> FEATURE:
<223> OTHER INFORMATION: Synthetic Construct

<400> SEQUENCE: 255

Gln Ser Val Leu Thr Gln Pro Pro Ser Val Ser Ala Ala Pro Gly Gln
 1               5                  10                  15

Lys Val Thr Ile Ser Cys Ser Gly Gly Asp Tyr Tyr Ser Thr Tyr Tyr
             20                  25                  30

Ala Trp Tyr Gln Gln Leu Pro Gly Thr Ala Pro Lys Thr Val Ile His
         35                  40                  45

Ser Asp Asp Lys Arg Pro Ser Asp Ile Pro Asp Arg Phe Ser Gly Ser
 50                  55                  60

Lys Ser Gly Thr Ser Ala Thr Leu Gly Ile Thr Gly Leu Gln Thr Gly
 65                  70                  75                  80

Asp Glu Ala Asp Tyr Tyr Cys Gly Gly Tyr Asp Gly Arg Thr Tyr Ile
                 85                  90                  95

Asn Thr Phe Gly Thr Gly Thr Lys Val Thr Val Leu
            100                 105

<210> SEQ ID NO 256
<211> LENGTH: 113
<212> TYPE: PRT
<213> ORGANISM: Artificial Sequence
<220> FEATURE:
<223> OTHER INFORMATION: Synthetic Construct

<400> SEQUENCE: 256

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Ser Tyr
             20                  25                  30

Ser Ser Tyr Tyr Tyr Ala Trp Tyr Gln Gln His Pro Gly Lys Ala Pro
         35                  40                  45

Lys Thr Leu Ile Tyr Ser Asp Asp Lys Arg Pro Ser Asn Val Ser Asn
 50                  55                  60

Arg Phe Ser Gly Ser Lys Ser Gly Asn Thr Ala Ser Leu Thr Ile Ser
 65                  70                  75                  80

Gly Leu Gln Ala Glu Asp Glu Ala Asp Tyr Tyr Cys Gly Gly Tyr Asp
                 85                  90                  95

Gln Ser Ser Tyr Thr Asn Pro Phe Gly Gly Gly Thr Lys Leu Thr Val
            100                 105                 110

Leu

<210> SEQ ID NO 257
<211> LENGTH: 108
<212> TYPE: PRT
```

```
<213> ORGANISM: Artificial Sequence
<220> FEATURE:
<223> OTHER INFORMATION: Synthetic Construct

<400> SEQUENCE: 257

Gln Ser Val Leu Thr Gln Pro Pro Ser Val Ser Ala Ala Pro Gly Gln
1               5                   10                  15

Lys Val Thr Ile Ser Cys Ser Gly Gly Asp Tyr Tyr Ser Tyr Tyr Tyr
            20                  25                  30

Gly Trp Tyr Gln Gln Leu Pro Gly Thr Ala Pro Lys Thr Val Ile Tyr
        35                  40                  45

Ser Asp Asp Lys Arg Pro Ser Asp Ile Pro Asp Arg Phe Ser Gly Ser
50                  55                  60

Lys Ser Gly Thr Ser Ala Thr Leu Gly Ile Thr Gly Leu Gln Thr Gly
65                  70                  75                  80

Asp Glu Ala Asp Tyr Tyr Cys Gly Gly Tyr Asp Tyr Ser Thr Tyr Ala
                85                  90                  95

Asn Ala Phe Gly Thr Gly Thr Lys Val Thr Val Leu
            100                 105

<210> SEQ ID NO 258
<211> LENGTH: 120
<212> TYPE: PRT
<213> ORGANISM: Artificial Sequence
<220> FEATURE:
<223> OTHER INFORMATION: Synthetic Construct

<400> SEQUENCE: 258

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Ser Phe Ser Asn Phe
            20                  25                  30

Ala Met Thr Trp Val Arg Gln Ala Pro Gly Lys Gly Leu Glu Trp Val
        35                  40                  45

Ser Thr Ile Gly Ser Gly Asp Thr Tyr Tyr Ala Asp Ser Val Lys Gly
50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Ser Trp Ser Gly Asp Phe Phe Asp Tyr Trp Gly Gln
            100                 105                 110

Gly Thr Leu Val Thr Val Ser Ser
        115                 120

<210> SEQ ID NO 259
<211> LENGTH: 120
<212> TYPE: PRT
<213> ORGANISM: Artificial Sequence
<220> FEATURE:
<223> OTHER INFORMATION: Synthetic Construct

<400> SEQUENCE: 259

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Phe Ser Ile Tyr
            20                  25                  30

Ala Met Ser Trp Val Arg Gln Ala Pro Gly Lys Gly Leu Glu Trp Val
        35                  40                  45
```

Ser Thr Ile Gly Ala Asp Asp Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Gly Trp Ser Gly Asp Phe Phe Asp Tyr Trp Gly Gln
            100                 105                 110

Gly Thr Leu Val Thr Val Ser Ser
            115                 120

<210> SEQ ID NO 260
<211> LENGTH: 119
<212> TYPE: PRT
<213> ORGANISM: Artificial Sequence
<220> FEATURE:
<223> OTHER INFORMATION: Synthetic Construct

<400> SEQUENCE: 260

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Lys Gly Leu Glu Trp Val
        35                  40                  45

Ser Leu Ile Ser Gly Ser Gly Glu Ile Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Asp Trp Gly Gln Gly
            100                 105                 110

Thr Leu Val Thr Val Ser Ser
        115

<210> SEQ ID NO 261
<211> LENGTH: 11
<212> TYPE: PRT
<213> ORGANISM: Artificial Sequence
<220> FEATURE:
<223> OTHER INFORMATION: Synthetic Construct

<400> SEQUENCE: 261

Ser Gly Gly Ala Tyr Ser Ser Tyr Tyr Tyr Ala
1               5                   10

<210> SEQ ID NO 262
<211> LENGTH: 108
<212> TYPE: PRT
<213> ORGANISM: Artificial Sequence
<220> FEATURE:
<223> OTHER INFORMATION: Synthetic Construct

<400> SEQUENCE: 262

Ser Tyr Glu Leu Thr Gln Pro Pro Ser Val Ser Val Ser Pro Gly Gln
1               5                   10                  15

Thr Ala Arg Ile Thr Cys Ser Gly Gly Ala Tyr Ser Ser Tyr Tyr Tyr
            20                  25                  30

```
Ala Trp Tyr Gln Gln Lys Pro Gly Gln Ala Pro Val Leu Val Ile Tyr
             35                  40                  45

Ser Asp Asp Lys Arg Pro Ser Gly Ile Pro Glu Arg Phe Ser Gly Ser
 50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                 85                  90                  95

Asn Pro Phe Gly Gly Gly Thr Lys Leu Thr Val Leu
            100                 105

<210> SEQ ID NO 263
<211> LENGTH: 118
<212> TYPE: PRT
<213> ORGANISM: Artificial Sequence
<220> FEATURE:
<223> OTHER INFORMATION: Synthetic Construct

<400> SEQUENCE: 263

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Ser Asn
             20                  25                  30

Ala Met Ser Trp Val Arg Gln Ala Pro Gly Lys Gly Leu Glu Trp Val
         35                  40                  45

Ala Gly Ile Ser Ala Gly Gly Ser Asp Thr Tyr Tyr Pro Ala Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Thr Trp Asn His Leu Phe Asp Tyr Trp Gly Gln Gly Thr
            100                 105                 110

Leu Val Thr Val Ser Ser
        115

<210> SEQ ID NO 264
<211> LENGTH: 118
<212> TYPE: PRT
<213> ORGANISM: Artificial Sequence
<220> FEATURE:
<223> OTHER INFORMATION: Synthetic Construct

<400> SEQUENCE: 264

Glu Val Gln Leu Val Glu Ser Gly Gly Gly Val Val Gln Pro Gly Gly
 1               5                  10                  15

Ser Leu Arg Leu Ser Cys Ala Ala Ser Gly Phe Thr Phe Ser Ser Asn
             20                  25                  30

Ala Val Ser Trp Val Arg Gln Ala Pro Gly Lys Gly Leu Glu Trp Val
         35                  40                  45

Ala Gly Ile Ser Ala Gly Gly Ser Asp Thr Tyr Tyr Pro Ala Ser Val
     50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Thr Trp Asn His Leu Phe Asp Tyr Trp Gly Gln Gly Thr
            100                 105                 110
```

Leu Val Thr Val Ser Ser
        115

<210> SEQ ID NO 265
<211> LENGTH: 117
<212> TYPE: PRT
<213> ORGANISM: Artificial Sequence
<220> FEATURE:
<223> OTHER INFORMATION: Synthetic Construct

<400> SEQUENCE: 265

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

<210> SEQ ID NO 266
<211> LENGTH: 117
<212> TYPE: PRT
<213> ORGANISM: Artificial Sequence
<220> FEATURE:
<223> OTHER INFORMATION: Synthetic Construct

<400> SEQUENCE: 266

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Val Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

<210> SEQ ID NO 267
<211> LENGTH: 117
<212> TYPE: PRT
<213> ORGANISM: Artificial Sequence
<220> FEATURE:
<223> OTHER INFORMATION: Synthetic Construct

<400> SEQUENCE: 267

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Thr Trp Asn His Leu Phe Asp Tyr Trp Gly Gln Gly Thr Leu
        100                 105                 110

Val Thr Val Ser Ser
        115

<210> SEQ ID NO 268
<211> LENGTH: 117
<212> TYPE: PRT
<213> ORGANISM: Artificial Sequence
<220> FEATURE:
<223> OTHER INFORMATION: Synthetic Construct

<400> SEQUENCE: 268

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Val Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Thr Trp Asn His Leu Phe Asp Tyr Trp Gly Gln Gly Thr Leu
        100                 105                 110

Val Thr Val Ser Ser
        115

<210> SEQ ID NO 269
<211> LENGTH: 5
<212> TYPE: PRT
<213> ORGANISM: Artificial Sequence
<220> FEATURE:
<223> OTHER INFORMATION: Synthetic Construct

<400> SEQUENCE: 269

Ile Tyr Ala Met Ser
1               5

<210> SEQ ID NO 270
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 270

Ser Tyr Asp Met Asn
1               5

<210> SEQ ID NO 271
<211> LENGTH: 5
<212> TYPE: PRT
<213> ORGANISM: Artificial Sequence
<220> FEATURE:
<223> OTHER INFORMATION: Synthetic Construct

<400> SEQUENCE: 271

Ser Asn Ala Val Ser
1               5

<210> SEQ ID NO 272
<211> LENGTH: 5
<212> TYPE: PRT
<213> ORGANISM: Artificial Sequence
<220> FEATURE:
<223> OTHER INFORMATION: Synthetic Construct

<400> SEQUENCE: 272

Ser Tyr Ala Val Ser
1               5

<210> SEQ ID NO 273
<211> LENGTH: 119
<212> TYPE: PRT
<213> ORGANISM: Artificial Sequence
<220> FEATURE:
<223> OTHER INFORMATION: Synthetic Construct

<400> SEQUENCE: 273

Asp Val Gln Leu Val Glu Ser Gly Gly Val Val Arg Pro Gly Glu
1               5                   10                  15

Ser Leu Arg Leu Ser Cys Ala Ala Ser Gly Phe Ser Phe Ser Ser Tyr
            20                  25                  30

Ala Met Asn Trp Val Arg Gln Ala Pro Gly Glu Gly Leu Glu Trp Val
        35                  40                  45

Ser Arg Ile Asn Ser Gly Gly Gly Gly Thr Asp Tyr Ala Glu Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Tyr Asp Trp Asn Ser Phe Phe Asp Tyr Trp Gly Leu Gly
            100                 105                 110

Ala Leu Val Thr Val Ser Ser
        115

<210> SEQ ID NO 274
<211> LENGTH: 108
<212> TYPE: PRT
<213> ORGANISM: Artificial Sequence
<220> FEATURE:
<223> OTHER INFORMATION: Synthetic Construct

<400> SEQUENCE: 274

Glu Thr Val Leu Thr Gln Ser Pro Ala Thr Leu Ser Val Ser Pro Gly
```

```
                1               5                   10                  15
            Glu Arg Ala Thr Leu Ser Cys Arg Ala Ser Gln Thr Val Gly Ser Lys
                            20                  25                  30

Leu Ala Trp His Gln Gln Lys Pro Gly Gln Ala Pro Arg Leu Leu Ile
                        35                  40                  45

Tyr Asp Ala Thr Asn Arg Ala Thr Gly Ile Ser Asp Arg Phe Ser Gly
                    50                  55                  60

Ser Gly Ser Gly Thr Asp Phe Thr Leu Thr Ile Ser Ser Leu Gln Thr
            65                  70                  75                  80

Glu Asp Ser Ala Val Tyr Tyr Cys Gln Gln Tyr Tyr Tyr Trp Pro Pro
                            85                  90                  95

Tyr Arg Phe Gly Gly Gly Thr Lys Val Glu Ile Lys
                        100                 105
```

<210> SEQ ID NO 275
<211> LENGTH: 119
<212> TYPE: PRT
<213> ORGANISM: Artificial Sequence
<220> FEATURE:
<223> OTHER INFORMATION: Synthetic Construct

<400> SEQUENCE: 275

```
Asp Val Gln Leu Val Glu Ser Gly Gly Val Val Arg Pro Gly Glu
1               5                   10                  15

Ser Leu Arg Leu Ser Cys Glu Ala Ser Gly Phe Thr Phe Arg Asn Tyr
                20                  25                  30

Tyr Met Thr Trp Val Arg Gln Ala Pro Gly Glu Gly Leu Glu Trp Val
            35                  40                  45

Ser Thr Ile Ser Asp Thr Gly Asp Thr Ala Tyr Tyr Ala Asp Ser Val
        50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Asp Asp Thr Ala Ile Tyr Tyr Cys
                85                  90                  95

Ala Lys Ser Trp Ile Trp Trp Thr Phe Phe Asp Tyr Trp Gly Leu Gly
            100                 105                 110

Thr Leu Val Thr Val Ser Ser
        115
```

<210> SEQ ID NO 276
<211> LENGTH: 103
<212> TYPE: PRT
<213> ORGANISM: Artificial Sequence
<220> FEATURE:
<223> OTHER INFORMATION: Synthetic Construct

<400> SEQUENCE: 276

```
Ala Leu Thr Gln Pro Ala Ser Val Ser Ala Asn Leu Gly Gly Thr Val
1               5                   10                  15

Glu Ile Thr Cys Ser Gly Gly Asn Ser Asn His Tyr Gly Trp Tyr Gln
                20                  25                  30

Gln Lys Ser Pro Gly Ser Ala Pro Val Thr Leu Ile Tyr Ala Asp Thr
            35                  40                  45

Asn Arg Pro Ser Asn Ile Pro Ser Arg Phe Ser Gly Ser Thr Ser Gly
        50                  55                  60

Ser Thr Thr Thr Leu Thr Ile Thr Gly Val Gln Ala Glu Asp Glu Ala
65                  70                  75                  80
```

```
Val Tyr Tyr Cys Gly Gly Ser Ser Thr Gly Asp Gly Ile Phe Gly Ala
                85                  90                  95

Gly Thr Thr Leu Thr Val Leu
            100
```

<210> SEQ ID NO 277

<400> SEQUENCE: 277

000

<210> SEQ ID NO 278
<211> LENGTH: 118
<212> TYPE: PRT
<213> ORGANISM: Artificial Sequence
<220> FEATURE:
<223> OTHER INFORMATION: Synthetic Construct

<400> SEQUENCE: 278

```
Asp Val Gln Leu Val Glu Ser Gly Gly Val Val Arg Pro Gly Glu
1               5                   10                  15

Ser Leu Arg Leu Ser Cys Ala Ala Ser Gly Phe Ala Phe Ser Asp His
                20                  25                  30

Asp Met Ser Trp Val Arg Gln Gly Pro Gly Glu Gly Leu Glu Trp Val
            35                  40                  45

Ala Gly Ile Ser Leu Arg Gly Gly Val Thr Trp Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Arg Leu Phe Ser Leu Arg Thr Glu Asp Thr Ala Ile Tyr Tyr Cys
                85                  90                  95

Ala Arg Glu Ser Trp Asn Thr Phe Phe Asp Tyr Trp Gly Leu Gly Thr
            100                 105                 110

Leu Val Thr Val Ser Ser
        115
```

<210> SEQ ID NO 279
<211> LENGTH: 108
<212> TYPE: PRT
<213> ORGANISM: Artificial Sequence
<220> FEATURE:
<223> OTHER INFORMATION: Synthetic Construct

<400> SEQUENCE: 279

```
Glu Ile Val Leu Thr Gln Ser Pro Gly Thr Leu Ser Leu Ser Pro Gly
1               5                   10                  15

Glu Thr Ala Thr Leu Ser Cys Arg Ala Ser Gln Asn Val Arg Ser Asn
                20                  25                  30

Leu Ala Trp Tyr Gln Gln Lys Pro Gly Gln Ala Pro Arg Leu Leu Ile
            35                  40                  45

Tyr Asp Ala Ser Ser Arg Ala Thr Gly Ile Pro Asp Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Gly Asn Gly Pro Pro
                85                  90                  95

Leu Thr Phe Gly Gly Gly Thr Lys Val Glu Ile Lys
            100                 105
```

-continued

```
<210> SEQ ID NO 280
<211> LENGTH: 121
<212> TYPE: PRT
<213> ORGANISM: Artificial Sequence
<220> FEATURE:
<223> OTHER INFORMATION: Synthetic Construct

<400> SEQUENCE: 280

Asp Val Gln Leu Val Glu Ser Gly Gly Ala Val Val Arg Pro Gly Glu
1               5                   10                  15

Ser Leu Arg Leu Ser Cys Lys Ala Ser Gly Phe Thr Phe Thr Asn Phe
            20                  25                  30

Ala Met Ser Trp Val Arg Gln Ala Pro Gly Glu Gly Leu Glu Trp Val
        35                  40                  45

Ser Gly Ile Ser Gly Ser Asp Asp Thr Thr Tyr Tyr Ala Asp Ser Val
    50                  55                  60

Lys Gly Arg Phe Thr Ile Ser Arg Asp Asn Ser Glu Ser Thr Leu Tyr
65                  70                  75                  80

Leu Gln Met Asn Ser Leu Arg Ala Glu Asp Thr Ala Val Tyr Tyr Cys
                85                  90                  95

Val Lys Asp Ser Thr Val Ser Trp Asn Thr Phe Phe Asp Tyr Trp Gly
            100                 105                 110

Leu Gly Thr Leu Val Thr Val Ser Ser
        115                 120

<210> SEQ ID NO 281
<211> LENGTH: 110
<212> TYPE: PRT
<213> ORGANISM: Artificial Sequence
<220> FEATURE:
<223> OTHER INFORMATION: Synthetic Construct

<400> SEQUENCE: 281

Ala Leu Thr Gln Pro Ala Ser Val Ser Ala Asn Leu Gly Gly Thr Val
1               5                   10                  15

Lys Ile Thr Cys Ser Gly Gly Tyr Gly Ser Asp Asp Gly Ser Ser Ser
            20                  25                  30

Tyr Tyr Gly Trp Tyr Gln Gln Lys Ser Pro Gly Ser Ala Pro Val Ile
        35                  40                  45

Leu Ile Tyr Trp Asp Asp Lys Arg Pro Ser Asp Ile Pro Ser Arg Phe
    50                  55                  60

Ser Gly Ser Thr Ser Gly Ser Thr Thr Thr Leu Thr Ile Thr Gly Val
65                  70                  75                  80

Gln Ala Glu Asp Glu Ala Val Tyr Phe Cys Gly Thr Tyr Asp Thr Ser
                85                  90                  95

Ser Gly Ala Ile Phe Gly Ala Gly Thr Thr Leu Thr Val Leu
            100                 105                 110

<210> SEQ ID NO 282
<211> LENGTH: 119
<212> TYPE: PRT
<213> ORGANISM: Artificial Sequence
<220> FEATURE:
<223> OTHER INFORMATION: Synthetic Construct

<400> SEQUENCE: 282

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Arg Ser Tyr
            20                  25                  30
```

```
Ala Met Asn Trp Val Arg Gln Ala Pro Gly Glu Gly Leu Glu Trp Val
        35                  40                  45

Ser Arg Ile Asn Ser Gly Gly Gly Thr Asp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gln Tyr Asp Trp Asn Ser Phe Phe Asp Tyr Trp Gly Leu Gly
            100                 105                 110

Ala Leu Val Thr Val Ser Ser
            115

<210> SEQ ID NO 283
<211> LENGTH: 108
<212> TYPE: PRT
<213> ORGANISM: Artificial Sequence
<220> FEATURE:
<223> OTHER INFORMATION: Synthetic Construct

<400> SEQUENCE: 283

Glu Thr Val Leu Thr Gln Ser Pro Ala Thr Leu Ser Val Ser Pro Gly
 1               5                  10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
 50                  55                  60

Ser Gly Ser Gly Thr Asp Phe Thr Leu Thr Ile Ser Ser Pro Gln Thr
 65                  70                  75                  80

Glu Asp Ser Ala Val Tyr Tyr Cys Gln Gln Tyr Tyr Tyr Trp Pro Pro
                 85                  90                  95

Tyr Arg Phe Gly Gly Gly Thr Lys Val Glu Ile Lys
            100                 105

<210> SEQ ID NO 284
<211> LENGTH: 114
<212> TYPE: PRT
<213> ORGANISM: Artificial Sequence
<220> FEATURE:
<223> OTHER INFORMATION: Synthetic Construct

<400> SEQUENCE: 284

Asp Val Gln Leu Val Glu Ser Gly Gly Gly Val Val Arg Pro Gly Glu
 1               5                  10                  15

Ser Leu Thr Leu Ser Cys Thr Ala Ser Gly Phe Thr Phe Thr Ser Ser
            20                  25                  30

Thr Met Asn Trp Val Arg Gln Ala Pro Gly Glu Gly Leu Asp Trp Val
        35                  40                  45

Ser Ser Ile Ser Thr Ser Gly Val Ile Thr Tyr Tyr Ala Asp Ser Val
 50                  55                  60

Lys Gly Arg Ala Thr Ile Ser Arg Asp Asn Ser Lys Asn Thr Leu Tyr
 65                  70                  75                  80

Leu Arg Leu Phe Ser Leu Arg Ala Asp Asp Thr Ala Ile Tyr Tyr Cys
                 85                  90                  95

Ala Thr Asp Thr Phe Asp His Trp Gly Pro Gly Thr Leu Val Thr Val
```

Ser Ser

<210> SEQ ID NO 285
<211> LENGTH: 102
<212> TYPE: PRT
<213> ORGANISM: Artificial Sequence
<220> FEATURE:
<223> OTHER INFORMATION: Synthetic Construct

<400> SEQUENCE: 285

Ala Leu Thr Gln Pro Ala Ser Val Ser Ala Asn Pro Gly Glu Thr Val
1               5                   10                  15

Lys Ile Thr Cys Phe Gly Ser Ser Gly Asn Tyr Gly Trp Phe Gln Gln
            20                  25                  30

Lys Ser Pro Gly Ser Ala Pro Val Thr Val Ile His Tyr Asn Asn Lys
        35                  40                  45

Arg Pro Ser Asp Ile Pro Ser Arg Phe Ser Gly Ser Lys Ser Gly Ser
    50                  55                  60

Thr Gly Thr Leu Thr Ile Thr Gly Val Arg Ala Glu Asp Glu Ala Val
65                  70                  75                  80

Tyr Phe Cys Gly Ala Trp Glu Thr Gly Ser Ala Thr Phe Gly Ala Gly
                85                  90                  95

Thr Thr Leu Thr Val Leu
            100

<210> SEQ ID NO 286
<211> LENGTH: 117
<212> TYPE: PRT
<213> ORGANISM: Artificial Sequence
<220> FEATURE:
<223> OTHER INFORMATION: Synthetic Construct

<400> SEQUENCE: 286

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Asn Phe
            20                  25                  30

Ala Met Asn Trp Val Arg Gln Ala Pro Gly Glu Gly Leu Glu Trp Val
        35                  40                  45

Ser Leu Ile Ser Val Thr Ala Thr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Val Thr Trp Asn Asn Leu Phe Asp Tyr Trp Gly Leu Gly Thr Leu
            100                 105                 110

Val Thr Val Ser Ser
        115

<210> SEQ ID NO 287
<211> LENGTH: 108
<212> TYPE: PRT
<213> ORGANISM: Artificial Sequence
<220> FEATURE:
<223> OTHER INFORMATION: Synthetic Construct

<400> SEQUENCE: 287

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Pro Ile Asp Ser Tyr
            20                  25                  30

Leu Ala Trp Tyr Gln Gln Lys Pro Gly Gln Ala Pro Arg Leu Leu Ile
        35                  40                  45

Tyr Asn Thr Val Thr Arg Ala Thr Gly Ile Pro Asp Arg Phe Ser Gly
    50                  55                  60

Ser Gly Ser Gly Thr Asp Phe Thr Leu Thr Ile Asn Arg Leu Glu Pro
65                  70                  75                  80

Glu Asp Phe Ala Val Tyr Tyr Cys Gln His Gln Tyr Asp Trp Pro Pro
                85                  90                  95

Tyr Ile Phe Gly Gly Gly Thr Lys Val Glu Ile Lys
                100                 105
```

<210> SEQ ID NO 288
<211> LENGTH: 117
<212> TYPE: PRT
<213> ORGANISM: Artificial Sequence
<220> FEATURE:
<223> OTHER INFORMATION: Synthetic Construct

<400> SEQUENCE: 288

```
Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Asn Phe
            20                  25                  30

Ala Met Thr Trp Val Arg Gln Ala Pro Gly Lys Gly Pro Glu Trp Val
        35                  40                  45

Ser Leu Val Ser Val Thr Ala Thr Thr Tyr Tyr Ala Asp Ser Val Lys
    50                  55                  60

Gly Arg Phe Thr Ile Ser Arg Asp Asn Ser Lys Ser Thr Leu Tyr Leu
65                  70                  75                  80

Gln Met Asn Ser Leu Arg Ala Glu Asp Thr Ala Val Tyr Tyr Cys Ala
                85                  90                  95

Lys Ile Thr Trp Asn Asn Leu Phe Asp Tyr Trp Gly Leu Gly Thr Leu
                100                 105                 110

Val Thr Val Ser Ser
        115
```

<210> SEQ ID NO 289
<211> LENGTH: 108
<212> TYPE: PRT
<213> ORGANISM: Artificial Sequence
<220> FEATURE:
<223> OTHER INFORMATION: Synthetic Construct

<400> SEQUENCE: 289

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Gly Ser Lys
            20                  25                  30

Leu Ala Trp Tyr Gln Gln Lys Pro Gly Gln Ala Pro Arg Leu Leu Ile
        35                  40                  45

Tyr Asp Ser Ser Arg Ala Ser Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80
```

Glu Asp Ser Ala Val Tyr Tyr Cys Gln Gln His Asn Asp Trp Pro Pro
            85                  90                  95

Tyr Thr Phe Gly Gly Gly Thr Lys Val Glu Ile Lys
            100                 105

<210> SEQ ID NO 290
<211> LENGTH: 117
<212> TYPE: PRT
<213> ORGANISM: Artificial Sequence
<220> FEATURE:
<223> OTHER INFORMATION: Synthetic Construct

<400> SEQUENCE: 290

Asp Val Gln Leu Val Glu Ser Gly Gly Gly Leu Val Arg Pro Gly Glu
1               5                   10                  15

Ser Leu Arg Leu Ser Cys Ala Ala Ser Gly Phe Thr Phe Thr Asn Tyr
            20                  25                  30

Ala Val Thr Trp Val Arg Gln Ala Pro Gly Glu Gly Leu Glu Trp Val
        35                  40                  45

Ser Leu Ile Ser Val Thr Gly Thr Thr Tyr Tyr Ala Asp Ser Val Lys
    50                  55                  60

Gly Arg Phe Thr Ile Ser Arg Asp Asn Ser Lys Ser Thr Leu Tyr Leu
65                  70                  75                  80

Gln Met Asn Ser Leu Arg Ala Glu Asp Thr Ala Val Tyr Tyr Cys Ala
                85                  90                  95

Lys Val Thr Trp Lys Asn Val Phe Asp Tyr Trp Gly Leu Gly Thr Leu
            100                 105                 110

Val Thr Val Ser Ser
        115

<210> SEQ ID NO 291
<211> LENGTH: 108
<212> TYPE: PRT
<213> ORGANISM: Artificial Sequence
<220> FEATURE:
<223> OTHER INFORMATION: Synthetic Construct

<400> SEQUENCE: 291

Glu Ile Val Leu Thr Gln Ser Pro Gly Thr Leu Ser Val Ser Pro Gly
1               5                   10                  15

Glu Arg Ala Thr Phe Ser Cys Arg Ala Ser Gln Thr Val Gly Ser Lys
            20                  25                  30

Leu Ala Trp Tyr Gln Gln Lys Pro Gly Gln Ala Pro Arg Leu Leu Ile
        35                  40                  45

Tyr Asp Ala Asn Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Thr Asp Trp Pro Pro
                85                  90                  95

Tyr Thr Phe Gly Gly Gly Thr Lys Val Glu Ile Lys
            100                 105

<210> SEQ ID NO 292
<211> LENGTH: 117
<212> TYPE: PRT
<213> ORGANISM: Artificial Sequence
<220> FEATURE:
<223> OTHER INFORMATION: Synthetic Construct

<400> SEQUENCE: 292

Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Arg Asn Tyr
            20                  25                  30

Gly Met Ser Trp Val Arg Gln Ala Pro Gly Glu Gly Leu Glu Trp Val
        35                  40                  45

Ser Ala Ser Ser Gly Ser Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Ile Tyr Tyr Cys Ala
                85                  90                  95

Lys Val Thr Trp Asn Asn Phe Phe Asp Tyr Trp Gly Leu Gly Thr Leu
            100                 105                 110

Val Thr Val Ser Ser
            115

<210> SEQ ID NO 293
<211> LENGTH: 108
<212> TYPE: PRT
<213> ORGANISM: Artificial Sequence
<220> FEATURE:
<223> OTHER INFORMATION: Synthetic Construct

<400> SEQUENCE: 293

Glu Ile Val Leu Ala Gln Ser Pro Asp Thr Leu Ser Val Ser Pro Gly
1               5                   10                  15

Glu Arg Ala Thr Leu Thr Cys Arg Ala Ser Gln Asp Val Ala Gly Lys
            20                  25                  30

Leu Ala Trp Tyr Gln Gln Lys Pro Gly Gln Ala Pro Arg Leu Leu Ile
        35                  40                  45

His Ala Thr Ser Ser Arg Ala Asp Gly Ile Pro Ala Arg Phe Ser Gly
    50                  55                  60

Ser Gly Ser Gly Thr Glu Phe Thr Leu Thr Ile Thr Gly Leu Gln Ser
65                  70                  75                  80

Glu Asp Phe Ala Val Tyr Tyr Cys Gln Gln His Tyr Asp Trp Ser Pro
                85                  90                  95

Leu Thr Phe Gly Gly Gly Thr Lys Val Glu Ile Lys
            100                 105

<210> SEQ ID NO 294
<211> LENGTH: 117
<212> TYPE: PRT
<213> ORGANISM: Artificial Sequence
<220> FEATURE:
<223> OTHER INFORMATION: Synthetic Construct

<400> SEQUENCE: 294

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

```
Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
            115

<210> SEQ ID NO 295
<211> LENGTH: 107
<212> TYPE: PRT
<213> ORGANISM: Artificial Sequence
<220> FEATURE:
<223> OTHER INFORMATION: Synthetic Construct

<400> SEQUENCE: 295

Ala Leu Thr Gln Pro Ala Ser Val Ser Ala Asn Leu Gly Glu Thr Val
1               5                   10                  15

Lys Ile Thr Cys Ser Gly Gly Asp Ser Ser His Tyr Tyr Gly Trp
            20                  25                  30

Tyr Gln Gln Lys Ser Pro Gly Ser Ala Pro Val Thr Val Ile Tyr Ser
            35                  40                  45

Asp Asp Glu Arg Pro Ser Asp Ile Pro Ser Arg Phe Ser Gly Ser Ala
50                  55                  60

Ser Gly Ser Thr Ala Thr Leu Thr Ile Thr Gly Val Arg Val Glu Asp
65                  70                  75                  80

Glu Ala Ile Tyr Tyr Cys Gly Ala Tyr Asp Gly Ser Thr Tyr Ala Asn
                85                  90                  95

Thr Phe Gly Ala Gly Thr Thr Leu Thr Val Leu
            100                 105

<210> SEQ ID NO 296
<211> LENGTH: 127
<212> TYPE: PRT
<213> ORGANISM: Artificial Sequence
<220> FEATURE:
<223> OTHER INFORMATION: Synthetic Construct

<400> SEQUENCE: 296

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
            35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Ala
65                  70                  75                  80

Ile Thr Pro Ala Asp Ala Gly Thr Tyr Tyr Cys Val Lys Phe Arg Lys
            85                  90                  95

Gly Ser Pro Asp Asp Val Glu Phe Lys Ser Gly Ala Gly Thr Glu Leu
            100                 105                 110

Ser Val Arg Ala Lys Pro Ser Thr Arg His His His His His His
            115                 120                 125
```

```
<210> SEQ ID NO 297
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser or Thr
<220> FEATURE:
<221> NAME/KEY: VARIANT
<222> LOCATION: 2
<223> OTHER INFORMATION: Xaa = Asn or Tyr or His or Asp
<220> FEATURE:
<221> NAME/KEY: VARIANT
<222> LOCATION: 4
<223> OTHER INFORMATION: Xaa = Met or Leu or Val

<400> SEQUENCE: 297

Xaa Xaa Ala Xaa Ser
1               5

<210> SEQ ID NO 298
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ala or Ser
<220> FEATURE:
<221> NAME/KEY: VARIANT
<222> LOCATION: 5
<223> OTHER INFORMATION: Xaa = Gly or Ser or absent
<220> FEATURE:
<221> NAME/KEY: VARIANT
<222> LOCATION: 6
<223> OTHER INFORMATION: Xaa = Ser or Asp or Gly
<220> FEATURE:
<221> NAME/KEY: VARIANT
<222> LOCATION: 7
<223> OTHER INFORMATION: Xaa = Gly or Ser
<220> FEATURE:
<221> NAME/KEY: VARIANT
<222> LOCATION: 8
<223> OTHER INFORMATION: Xaa = Asp or Ser or Gly
<220> FEATURE:
<221> NAME/KEY: VARIANT
<222> LOCATION: 9
<223> OTHER INFORMATION: Xaa = Thr or Ala
<220> FEATURE:
<221> NAME/KEY: VARIANT
<222> LOCATION: 12
<223> OTHER INFORMATION: Xaa = Pro or Gly or Val or Ile or Ala or Ser
<220> FEATURE:
<221> NAME/KEY: VARIANT
<222> LOCATION: 13
<223> OTHER INFORMATION: Xaa = Ala or Asp or Gly
<220> FEATURE:
<221> NAME/KEY: VARIANT
<222> LOCATION: 15
<223> OTHER INFORMATION: Xaa = Val or Met

<400> SEQUENCE: 298

Gly Ile Ser Xaa Xaa Xaa Xaa Xaa Xaa Tyr Tyr Xaa Xaa Ser Xaa Lys
1               5                   10                  15

Gly

<210> SEQ ID NO 299
<211> LENGTH: 11
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Asp or Gly or Ser or Ile or absent
<220> FEATURE:
<221> NAME/KEY: VARIANT
<222> LOCATION: 5
<223> OTHER INFORMATION: Xaa = Ser or Trp or Gly or Tyr or Asp
<220> FEATURE:
<221> NAME/KEY: VARIANT
<222> LOCATION: 6
<223> OTHER INFORMATION: Xaa = Ser or Tyr or Thr or Asp
<220> FEATURE:
<221> NAME/KEY: VARIANT
<222> LOCATION: 8
<223> OTHER INFORMATION: Xaa = His or Thr or Ser or Tyr
<220> FEATURE:
<221> NAME/KEY: VARIANT
<222> LOCATION: 11
<223> OTHER INFORMATION: Xaa = Gly or Ala

<400> SEQUENCE: 299

Ser Gly Gly Xaa Xaa Xaa Ser Xaa Tyr Tyr Xaa
1               5                   10

<210> SEQ ID NO 300
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Asp or Asn
<220> FEATURE:
<221> NAME/KEY: VARIANT
<222> LOCATION: 4
<223> OTHER INFORMATION: Xaa = Glu or Lys or Gln
<220> FEATURE:
<221> NAME/KEY: VARIANT
<222> LOCATION: 7
<223> OTHER INFORMATION: Xaa = Ser or Pro

<400> SEQUENCE: 300

Ser Asp Xaa Xaa Arg Pro Xaa
1               5

<210> SEQ ID NO 301
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Ala
<220> FEATURE:
<221> NAME/KEY: VARIANT
<222> LOCATION: 2
<223> OTHER INFORMATION: Xaa = Gly or Ala
<220> FEATURE:
<221> NAME/KEY: VARIANT
<222> LOCATION: 5
<223> OTHER INFORMATION: Xaa = Gly or Tyr or Gln or Ser or Ala
<220> FEATURE:
<221> NAME/KEY: VARIANT
<222> LOCATION: 6
<223> OTHER INFORMATION: Xaa = Ser or Arg or Thr
<220> FEATURE:
<221> NAME/KEY: VARIANT
```

```
<222> LOCATION: 7
<223> OTHER INFORMATION: Xaa = Thr or Ser
<220> FEATURE:
<221> NAME/KEY: VARIANT
<222> LOCATION: 9
<223> OTHER INFORMATION: Xaa = Ala or Ile or Val or Leu or Thr
<220> FEATURE:
<221> NAME/KEY: VARIANT
<222> LOCATION: 11
<223> OTHER INFORMATION: Xaa = Thr or Ala or Asp or Pro

<400> SEQUENCE: 301

Xaa Xaa Tyr Asp Xaa Xaa Xaa Tyr Xaa Asn Xaa
1               5                   10

<210> SEQ ID NO 302
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Asn or Tyr
<220> FEATURE:
<221> NAME/KEY: VARIANT
<222> LOCATION: 4
<223> OTHER INFORMATION: Xaa = Met or Leu or Val

<400> SEQUENCE: 302

Ser Xaa Ala Xaa Ser
1               5

<210> SEQ ID NO 303
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ala or Ser
<220> FEATURE:
<221> NAME/KEY: VARIANT
<222> LOCATION: 6
<223> OTHER INFORMATION: Xaa = Gly or absent
<220> FEATURE:
<221> NAME/KEY: VARIANT
<222> LOCATION: 7
<223> OTHER INFORMATION: Xaa = Ser or Gly
<220> FEATURE:
<221> NAME/KEY: VARIANT
<222> LOCATION: 12
<223> OTHER INFORMATION: Xaa = Pro or Gly or Val
<220> FEATURE:
<221> NAME/KEY: VARIANT
<222> LOCATION: 13
<223> OTHER INFORMATION: Xaa = Ala or Asp

<400> SEQUENCE: 303

Gly Ile Ser Xaa Gly Xaa Xaa Asp Thr Tyr Tyr Xaa Xaa Ser Val Lys
1               5                   10                  15

Gly

<210> SEQ ID NO 304
<211> LENGTH: 11
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: VARIANT
<222> LOCATION: 4
<223> OTHER INFORMATION: Xaa = Ser or Ala

<400> SEQUENCE: 304

Ser Gly Gly Xaa Tyr Ser Ser Tyr Tyr Tyr Ala
1               5                   10

<210> SEQ ID NO 305
<211> LENGTH: 5
<212> TYPE: PRT
<213> ORGANISM: Artificial Sequence
<220> FEATURE:
<223> OTHER INFORMATION: Synthetic Construct

<400> SEQUENCE: 305

Asn Phe Ala Leu Thr
1               5

<210> SEQ ID NO 306
<211> LENGTH: 5
<212> TYPE: PRT
<213> ORGANISM: Artificial Sequence
<220> FEATURE:
<223> OTHER INFORMATION: Synthetic Construct

<400> SEQUENCE: 306

Ile Tyr Ala Leu Ser
1               5

<210> SEQ ID NO 307
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser or Thr
<220> FEATURE:
<221> NAME/KEY: VARIANT
<222> LOCATION: 2
<223> OTHER INFORMATION: Xaa = Tyr or Ser
<220> FEATURE:
<221> NAME/KEY: VARIANT
<222> LOCATION: 4
<223> OTHER INFORMATION: Xaa = Met or Leu or Val

<400> SEQUENCE: 307

Xaa Xaa Asp Xaa Asn
1               5

<210> SEQ ID NO 308
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9
<223> OTHER INFORMATION: Xaa = Ile or Thr

<400> SEQUENCE: 308

Leu Ile Ser Gly Ser Gly Glu Ile Xaa Tyr Tyr Ala Asp Ser Val Lys
1               5                   10                  15

Gly
```

```
<210> SEQ ID NO 309
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Asn or Asp
<220> FEATURE:
<221> NAME/KEY: VARIANT
<222> LOCATION: 3
<223> OTHER INFORMATION: Xaa = Asn or Asp
<220> FEATURE:
<221> NAME/KEY: VARIANT
<222> LOCATION: 4
<223> OTHER INFORMATION: Xaa = Arg or Met
<220> FEATURE:
<221> NAME/KEY: VARIANT
<222> LOCATION: 10
<223> OTHER INFORMATION: Xaa = Asp or Tyr

<400> SEQUENCE: 309

Glu Xaa Xaa Xaa Tyr Arg Phe Phe Asp Xaa
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Ser or Asp
<220> FEATURE:
<221> NAME/KEY: VARIANT
<222> LOCATION: 8
<223> OTHER INFORMATION: Xaa = Thr or Ser

<400> SEQUENCE: 310

Arg Ala Xaa Gln Ser Val Tyr Xaa Tyr Leu Ala
1               5                   10

<210> SEQ ID NO 311
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Ala or Asp
<220> FEATURE:
<221> NAME/KEY: VARIANT
<222> LOCATION: 3
<223> OTHER INFORMATION: Xaa = Ser or Arg
<220> FEATURE:
<221> NAME/KEY: VARIANT
<222> LOCATION: 4
<223> OTHER INFORMATION: Xaa = Ser or Asn or Thr
<220> FEATURE:
<221> NAME/KEY: VARIANT
<222> LOCATION: 7
<223> OTHER INFORMATION: Xaa = Thr or Ala

<400> SEQUENCE: 311

Xaa Ala Xaa Xaa Arg Ala Xaa
1               5
```

<210> SEQ ID NO 312
<211> LENGTH: 108
<212> TYPE: PRT
<213> ORGANISM: Artificial Sequence
<220> FEATURE:
<223> OTHER INFORMATION: Synthetic Construct

<400> SEQUENCE: 312

Glu Ile Val Leu Thr Gln Ser Pro Ala Thr Leu Ser Val Ser Pro Gly
1               5                   10                  15

Glu Arg Ala Thr Leu Ser Cys Arg Ala Ser Gln Asn Val Lys Asn Asp
            20                  25                  30

Leu Ala Trp Tyr Gln Gln Lys Pro Gly Gln Ala Pro Arg Leu Leu Ile
        35                  40                  45

Tyr Ala Ala Arg Ile Arg Glu Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Trp Pro Pro
                85                  90                  95

Phe Thr Phe Gly Gly Gly Thr Lys Val Glu Ile Lys
            100                 105

<210> SEQ ID NO 313
<211> LENGTH: 5
<212> TYPE: PRT
<213> ORGANISM: Artificial Sequence
<220> FEATURE:
<223> OTHER INFORMATION: Synthetic Construct

<400> SEQUENCE: 313

Ser Tyr Asp Leu Asn
1               5

<210> SEQ ID NO 314
<211> LENGTH: 22
<212> TYPE: PRT
<213> ORGANISM: Homo sapiens

<400> SEQUENCE: 314

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 315
<211> LENGTH: 15
<212> TYPE: PRT
<213> ORGANISM: Homo sapiens

<400> SEQUENCE: 315

Trp Tyr Gln Gln Lys Pro Gly Gln Ala Pro Val Thr Leu Ile Tyr
1               5                   10                  15

<210> SEQ ID NO 316
<211> LENGTH: 32
<212> TYPE: PRT
<213> ORGANISM: Homo sapiens

<400> SEQUENCE: 316

Asn Ile Pro Glu Arg Phe Ser Gly Ser Ser Ser Gly Thr Thr Val Thr

-continued

```
                1               5                  10                  15

Leu Thr Ile Ser Gly Val Gln Ala Glu Asp Glu Ala Asp Tyr Tyr Cys
            20                  25                  30

<210> SEQ ID NO 317
<211> LENGTH: 10
<212> TYPE: PRT
<213> ORGANISM: Homo sapiens

<400> SEQUENCE: 317

Phe Gly Gly Gly Thr Lys Leu Thr Val Leu
1               5                   10

<210> SEQ ID NO 318
<211> LENGTH: 5
<212> TYPE: PRT
<213> ORGANISM: Artificial Sequence
<220> FEATURE:
<223> OTHER INFORMATION: Synthetic Construct

<400> SEQUENCE: 318

Ser Asn Ala Leu Ser
1               5

<210> SEQ ID NO 319
<211> LENGTH: 5
<212> TYPE: PRT
<213> ORGANISM: Artificial Sequence
<220> FEATURE:
<223> OTHER INFORMATION: Synthetic Construct

<400> SEQUENCE: 319

Ser Tyr Ala Leu Ser
1               5

<210> SEQ ID NO 320
<211> LENGTH: 330
<212> TYPE: PRT
<213> ORGANISM: Homo sapiens

<400> SEQUENCE: 320

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 321
<211> LENGTH: 330
<212> TYPE: PRT
<213> ORGANISM: Artificial Sequence
<220> FEATURE:
<223> OTHER INFORMATION: Synthetic Construct

<400> SEQUENCE: 321

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190
```

-continued

His Gln Asp Trp Leu Asn Gly Lys Glu Tyr Lys Cys Lys Val Ser Asn
              195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 322
<211> LENGTH: 326
<212> TYPE: PRT
<213> ORGANISM: Homo sapiens

<400> SEQUENCE: 322

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn

```
                    225                 230                 235                 240
Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 323
<211> LENGTH: 326
<212> TYPE: PRT
<213> ORGANISM: Artificial Sequence
<220> FEATURE:
<223> OTHER INFORMATION: Synthetic Construct

<400> SEQUENCE: 323

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
```

```
                260                 265                 270
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 324
<211> LENGTH: 327
<212> TYPE: PRT
<213> ORGANISM: Artificial Sequence
<220> FEATURE:
<223> OTHER INFORMATION: Synthetic Construct

<400> SEQUENCE: 324

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
                        290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 325
<211> LENGTH: 107
<212> TYPE: PRT
<213> ORGANISM: Homo sapiens

<400> SEQUENCE: 325

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 326
<211> LENGTH: 106
<212> TYPE: PRT
<213> ORGANISM: Homo sapiens

<400> SEQUENCE: 326

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 327
<211> LENGTH: 120
<212> TYPE: PRT
<213> ORGANISM: Artificial Sequence
<220> FEATURE:
<223> OTHER INFORMATION: Synthetic Construct

<400> SEQUENCE: 327

```
Glu Val Gln Leu Leu Glu Ser Gly Gly Gly Val Val Gln Pro Gly Gly
1               5                   10                  15
```

-continued

Ser Leu Arg Leu Ser Cys Ala Ala Ser Gly Phe Ser Phe Ser Asn Phe
            20                  25                  30

Ala Leu Thr Trp Val Arg Gln Ala Pro Gly Lys Gly Leu Glu Trp Val
            35                  40                  45

Ser Thr Ile Gly Ser Gly Asp Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Ser Trp Ser Gly Asp Phe Phe Asp Tyr Trp Gly Gln
            100                 105                 110

Gly Thr Leu Val Thr Val Ser Ser
        115                 120

<210> SEQ ID NO 328
<211> LENGTH: 120
<212> TYPE: PRT
<213> ORGANISM: Artificial Sequence
<220> FEATURE:
<223> OTHER INFORMATION: Synthetic Construct

<400> SEQUENCE: 328

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Ser Phe Ser Ile Tyr
            20                  25                  30

Ala Leu Ser Trp Val Arg Gln Ala Pro Gly Lys Gly Leu Glu Trp Val
            35                  40                  45

Ser Thr Ile Gly Ala Asp Asp Thr Tyr Tyr Ala Asp Ser Val Lys Gly
        50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Gly Trp Ser Gly Asp Phe Phe Asp Tyr Trp Gly Gln
            100                 105                 110

Gly Thr Leu Val Thr Val Ser Ser
        115                 120

<210> SEQ ID NO 329
<211> LENGTH: 119
<212> TYPE: PRT
<213> ORGANISM: Artificial Sequence
<220> FEATURE:
<223> OTHER INFORMATION: Synthetic Construct

<400> SEQUENCE: 329

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Leu Asn Trp Val Arg Gln Ala Pro Gly Lys Gly Leu Glu Trp Val
            35                  40                  45

Ser Leu Ile Ser Gly Ser Gly Glu Ile Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Asp Trp Gly Gln Gly
            100                 105                 110

Thr Leu Val Thr Val Ser Ser
        115

<210> SEQ ID NO 330
<211> LENGTH: 118
<212> TYPE: PRT
<213> ORGANISM: Artificial Sequence
<220> FEATURE:
<223> OTHER INFORMATION: Synthetic Construct

<400> SEQUENCE: 330

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Leu Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser
        115

<210> SEQ ID NO 331
<211> LENGTH: 117
<212> TYPE: PRT
<213> ORGANISM: Artificial Sequence
<220> FEATURE:
<223> OTHER INFORMATION: Synthetic Construct

<400> SEQUENCE: 331

Glu Val Gln Leu Val Glu Ser Gly Gly Gly Val Val Gln Pro Gly Gly
1               5                   10                  15

Ser Leu Arg Leu Ser Cys Ala Ser Gly Phe Thr Phe Ser Ser Asn
            20                  25                  30

Ala Leu Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115
```

<210> SEQ ID NO 332
<211> LENGTH: 117
<212> TYPE: PRT
<213> ORGANISM: Artificial Sequence
<220> FEATURE:
<223> OTHER INFORMATION: Synthetic Construct

<400> SEQUENCE: 332

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Leu Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

<210> SEQ ID NO 333
<211> LENGTH: 106
<212> TYPE: PRT
<213> ORGANISM: Artificial Sequence
<220> FEATURE:
<223> OTHER INFORMATION: Synthetic Construct

<400> SEQUENCE: 333

Gln Ser Ala Leu Thr Gln Pro Ala Ser Val Ser Gly Ser Pro Gly Gln
1               5                   10                  15

Ser Ile Thr Ile Ser Cys Phe Gly Ser Ser Gly Asn Tyr Gly Leu Val
            20                  25                  30

Ser Trp Tyr Gln Gln His Pro Gly Lys Ala Pro Lys Leu Met Ile Tyr
        35                  40                  45

Tyr Asn Asn Lys Arg Pro Ser Gly Val Ser Asn Arg Phe Ser Gly Ser
50                  55                  60

Lys Ser Gly Asn Thr Ala Ser Leu Thr Ile Ser Gly Leu Gln Ala Glu
65                  70                  75                  80

Asp Glu Ala Asp Tyr Tyr Cys Gly Ala Trp Glu Thr Gly Ser Ala Thr
                85                  90                  95

Phe Gly Gly Gly Thr Lys Leu Thr Val Leu
            100                 105

<210> SEQ ID NO 334
<211> LENGTH: 103
<212> TYPE: PRT
<213> ORGANISM: Artificial Sequence
<220> FEATURE:
<223> OTHER INFORMATION: Synthetic Construct

<400> SEQUENCE: 334

Ser Tyr Glu Leu Thr Gln Pro Pro Ser Val Ser Val Ser Pro Gly Gln
1               5                   10                  15

Thr Ala Ser Ile Thr Cys Phe Gly Ser Ser Gly Asn Tyr Gly Trp Tyr
            20                  25                  30

```
Gln Gln Lys Pro Gly Gln Ser Pro Val Leu Val Ile Tyr Tyr Asn Asn
            35                  40                  45

Lys Arg Pro Ser Gly Ile Pro Glu Arg Phe Ser Gly Ser Asn Ser Gly
 50                  55                  60

Asn Thr Ala Thr Leu Thr Ile Ser Gly Thr Gln Ala Met Asp Glu Ala
 65                  70                  75                  80

Asp Tyr Tyr Cys Gly Ala Trp Glu Thr Gly Ser Ala Thr Phe Gly Gly
                 85                  90                  95

Gly Thr Lys Leu Thr Val Leu
            100
```

<210> SEQ ID NO 335
<211> LENGTH: 120
<212> TYPE: PRT
<213> ORGANISM: Artificial Sequence
<220> FEATURE:
<223> OTHER INFORMATION: Synthetic Construct

<400> SEQUENCE: 335

```
Asp Val Gln Leu Leu Glu Ser Gly Gly Gly Val Val Gln Pro Gly Gly
 1               5                  10                  15

Ser Leu Arg Leu Ser Cys Ala Ala Ser Gly Phe Ser Phe Ser Asn Phe
            20                  25                  30

Ala Met Thr Trp Val Arg Gln Ala Pro Gly Glu Gly Leu Glu Trp Val
            35                  40                  45

Ser Thr Ile Gly Ser Gly Asp Thr Tyr Tyr Ala Asp Ser Val Lys Gly
 50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Asp Ser Thr Val Ser Trp Ser Gly Asp Phe Phe Asp Tyr Trp Gly Leu
            100                 105                 110

Gly Thr Leu Val Thr Val Ser Ser
            115                 120
```

<210> SEQ ID NO 336
<211> LENGTH: 7
<212> TYPE: PRT
<213> ORGANISM: Artificial Sequence
<220> FEATURE:
<223> OTHER INFORMATION: Synthetic Construct

<400> SEQUENCE: 336

```
Ser Asp Asp Lys Arg Pro Ser
 1               5
```

<210> SEQ ID NO 337
<211> LENGTH: 5
<212> TYPE: PRT
<213> ORGANISM: Artificial Sequence
<220> FEATURE:
<223> OTHER INFORMATION: Synthetic Construct

<400> SEQUENCE: 337

```
Gly Ser Tyr Ser Ser
 1               5
```

<210> SEQ ID NO 338
<211> LENGTH: 3

```
<212> TYPE: PRT
<213> ORGANISM: Artificial Sequence
<220> FEATURE:
<223> OTHER INFORMATION: Synthetic Construct

<400> SEQUENCE: 338

Ile Tyr Ser
1

<210> SEQ ID NO 339
<211> LENGTH: 9
<212> TYPE: PRT
<213> ORGANISM: Artificial Sequence
<220> FEATURE:
<223> OTHER INFORMATION: Synthetic Construct

<400> SEQUENCE: 339

Gly Gly Tyr Asp Gln Ser Ser Tyr Thr
1               5

<210> SEQ ID NO 340
<211> LENGTH: 5
<212> TYPE: PRT
<213> ORGANISM: Artificial Sequence
<220> FEATURE:
<223> OTHER INFORMATION: Synthetic Construct

<400> SEQUENCE: 340

Gly Asp Tyr Tyr Ser
1               5

<210> SEQ ID NO 341
<211> LENGTH: 120
<212> TYPE: PRT
<213> ORGANISM: Artificial Sequence
<220> FEATURE:
<223> OTHER INFORMATION: Synthetic Construct

<400> SEQUENCE: 341

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Ser Ile Tyr
            20                  25                  30

Ala Met Ser Trp Val Arg Gln Ala Pro Gly Glu Gly Leu Glu Trp Val
        35                  40                  45

Ser Thr Ile Gly Ala Asp Asp Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Gly Trp Ser Gly Asp Phe Phe Asp Tyr Trp Gly Leu
            100                 105                 110

Gly Thr Leu Val Thr Val Ser Ser
        115                 120

<210> SEQ ID NO 342
<211> LENGTH: 118
<212> TYPE: PRT
<213> ORGANISM: Artificial Sequence
<220> FEATURE:
<223> OTHER INFORMATION: Synthetic Construct

<400> SEQUENCE: 342
```

```
Asp Val Gln Leu Val Glu Ser Gly Gly Ala Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Glu Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
            115
```

<210> SEQ ID NO 343
<211> LENGTH: 107
<212> TYPE: PRT
<213> ORGANISM: Artificial Sequence
<220> FEATURE:
<223> OTHER INFORMATION: Synthetic Construct

<400> SEQUENCE: 343

```
Ala Leu Thr Gln Pro Ala Ser Val Ser Ala Asn Pro Gly Glu Thr Val
1               5                   10                  15

Lys Ile Thr Cys Ser Gly Gly Asp Trp Tyr Ser Thr Tyr Tyr Gly Trp
            20                  25                  30

Tyr Gln Gln Lys Ser Pro Gly Ser Ala Pro Val Thr Val Ile His Ser
        35                  40                  45

Asp Asp Lys Arg Pro Ser Asp Ile Pro Ser Arg Phe Ser Gly Ser Ala
    50                  55                  60

Ser Gly Ser Ala Ala Thr Leu Thr Ile Thr Gly Val Arg Val Glu Asp
65                  70                  75                  80

Glu Ala Val Tyr Tyr Cys Ala Gly Tyr Asp Gly Arg Thr Tyr Ile Asn
                85                  90                  95

Thr Phe Gly Ala Gly Thr Thr Leu Thr Val Leu
            100                 105
```

<210> SEQ ID NO 344
<211> LENGTH: 119
<212> TYPE: PRT
<213> ORGANISM: Artificial Sequence
<220> FEATURE:
<223> OTHER INFORMATION: Synthetic Construct

<400> SEQUENCE: 344

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Arg Gln Phe Gln Glu Gln Ser Leu
```

```
65              70              75              80
Ser Pro Asn Glu Pro Ala Leu Thr Ala Glu Asp Thr Ala Val Tyr Tyr
                85                  90                  95

Cys Ala Arg Glu Thr Trp Asn His Leu Phe Asp Tyr Trp Gly Leu Gly
            100                 105                 110

Thr Leu Val Thr Val Ser Ser
        115

<210> SEQ ID NO 345
<211> LENGTH: 107
<212> TYPE: PRT
<213> ORGANISM: Artificial Sequence
<220> FEATURE:
<223> OTHER INFORMATION: Synthetic Construct

<400> SEQUENCE: 345

Ala Leu Thr Gln Pro Ala Ser Val Ser Ala Asn Pro Gly Glu Thr Val
1               5                   10                  15

Lys Ile Thr Cys Ser Gly Gly Asp Tyr Tyr Ser Thr Tyr Tyr Gly Trp
            20                  25                  30

Tyr Gln Gln Lys Ser Pro Gly Ser Ala Pro Val Thr Val Ile His Ser
            35                  40                  45

Asp Asp Lys Arg Pro Ser Asp Ile Pro Ser Arg Phe Ser Gly Ser Ala
50                  55                  60

Ser Gly Ser Ala Ala Thr Leu Thr Ile Ala Gly Val Arg Val Glu Asp
65                  70                  75                  80

Glu Ala Val Tyr Phe Cys Gly Ala Tyr Asp Gly Arg Thr Tyr Ile Asn
                85                  90                  95

Thr Phe Gly Ala Gly Thr Thr Leu Thr Val Leu
            100                 105

<210> SEQ ID NO 346
<211> LENGTH: 118
<212> TYPE: PRT
<213> ORGANISM: Artificial Sequence
<220> FEATURE:
<223> OTHER INFORMATION: Synthetic Construct

<400> SEQUENCE: 346

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser His
            20                  25                  30

Ala Met Ser Trp Val Arg Gln Ala Pro Gly Lys Gly Leu Glu Trp Leu
            35                  40                  45

Ala Gly Ile Ser Ala Gly Gly Ser Asp Thr Tyr Tyr Ile Asp Ser Val
50                  55                  60

Lys Gly Arg Phe Thr Ile Ser Arg Asp Asn Ser Lys Ser Ser Leu Tyr
65                  70                  75                  80

Leu Arg Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 347
<211> LENGTH: 107
```

```
<212> TYPE: PRT
<213> ORGANISM: Artificial Sequence
<220> FEATURE:
<223> OTHER INFORMATION: Synthetic Construct

<400> SEQUENCE: 347

Ala Leu Thr Gln Pro Ala Ser Val Ser Ala Asn Pro Gly Glu Thr Val
1               5                   10                  15

Lys Ile Thr Cys Ser Gly Gly Asp Tyr Tyr Ser Thr Tyr Tyr Ala Trp
            20                  25                  30

Tyr Gln Gln Lys Ser Pro Gly Ser Ala Pro Val Thr Val Ile His Ser
        35                  40                  45

Asp Asp Glu Arg Pro Ser Asp Ile Pro Ser Arg Phe Ser Gly Ser Ala
50                  55                  60

Ser Gly Ser Ala Ala Thr Leu Ile Ile Thr Gly Val Arg Val Glu Asp
65                  70                  75                  80

Glu Ala Val Tyr Phe Cys Gly Tyr Asp Gly Arg Thr Tyr Ile Asn
                85                  90                  95

Thr Phe Gly Ala Gly Thr Thr Leu Thr Val Leu
            100                 105

<210> SEQ ID NO 348
<211> LENGTH: 118
<212> TYPE: PRT
<213> ORGANISM: Artificial Sequence
<220> FEATURE:
<223> OTHER INFORMATION: Synthetic Construct

<400> SEQUENCE: 348

Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Pro Ala Ser Val
50                  55                  60

Lys Gly Arg Phe Thr Ile Ser Arg Asp Asn Pro Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 349
<211> LENGTH: 107
<212> TYPE: PRT
<213> ORGANISM: Artificial Sequence
<220> FEATURE:
<223> OTHER INFORMATION: Synthetic Construct

<400> SEQUENCE: 349

Ala Leu Thr Gln Pro Ala Ser Val Ser Ala Asn Pro Gly Glu Thr Val
1               5                   10                  15

Lys Ile Ala Cys Ser Gly Gly Ser Tyr Tyr Ser Tyr Tyr Tyr Gly Trp
            20                  25                  30

Tyr Gln Gln Lys Ser Pro Gly Ser Ala Leu Val Thr Val Ile Tyr Ser
```

35                  40                  45
Asp Asp Lys Arg Pro Ser Gly Ile Pro Ser Arg Phe Ser Gly Ser Ala
            50                  55                  60
Ser Gly Ser Thr Ala Thr Leu Thr Ile Thr Gly Val Arg Ala Glu Asp
65                  70                  75                  80
Glu Ala Val Tyr Tyr Cys Gly Gly Tyr Asp Tyr Ser Ser Tyr Thr Asn
                85                  90                  95
Asp Phe Gly Ala Gly Thr Thr Leu Thr Val Leu
            100                 105

<210> SEQ ID NO 350
<211> LENGTH: 118
<212> TYPE: PRT
<213> ORGANISM: Artificial Sequence
<220> FEATURE:
<223> OTHER INFORMATION: Synthetic Construct

<400> SEQUENCE: 350

Asp Val Gln Leu Val Glu Ser Gly Gly Gly Val Val Arg Pro Gly Glu
1               5                   10                  15
Ser Leu Arg Leu Ser Cys Ala Ala Ser Gly Phe Thr Phe Ser Thr Tyr
            20                  25                  30
Ala Met Ser Trp Val Arg Gln Ala Pro Gly Lys Gly Leu Glu Trp Val
        35                  40                  45
Ser Gly Ile Ser Ala Ser Gly Ser Thr Tyr Tyr Gly Asp Ser Val
    50                  55                  60
Lys Gly Arg Phe Thr Met Ser Arg Asp Asn Ser Lys Asn Thr Leu Tyr
65                  70                  75                  80
Leu Gln Met Asn Ser Leu Thr Ala Glu Asp Thr Ala Val Tyr Tyr Cys
                85                  90                  95
Ala Arg Glu Thr Trp Asn His Leu Phe Asp Tyr Trp Gly Leu Gly Thr
            100                 105                 110
Leu Val Thr Val Ser Ser
        115

<210> SEQ ID NO 351
<211> LENGTH: 105
<212> TYPE: PRT
<213> ORGANISM: Artificial Sequence
<220> FEATURE:
<223> OTHER INFORMATION: Synthetic Construct

<400> SEQUENCE: 351

Ala Leu Thr Gln Pro Ala Ser Val Ser Ala Asn Leu Gly Gly Thr Val
1               5                   10                  15
Glu Ile Thr Cys Ser Gly Gly Ser Ser Tyr Tyr Gly Trp Tyr Gln
            20                  25                  30
Gln Lys Ser Pro Gly Ser Ala Pro Val Thr Val Ile Tyr Ser Asp Asn
        35                  40                  45
Gln Arg Pro Ser Asp Ile Pro Ser Arg Phe Ser Gly Ser Ala Ser Asp
            50                  55                  60
Ser Thr Ala Thr Leu Thr Ile Thr Gly Val Gln Val Glu Asp Glu Ala
65                  70                  75                  80
Ile Tyr Tyr Cys Gly Gly Tyr Asp Ser Ser Thr Tyr Ala Asn Thr Phe
                85                  90                  95
Gly Ala Gly Thr Thr Leu Thr Val Leu
            100                 105

```
<210> SEQ ID NO 352
<211> LENGTH: 117
<212> TYPE: PRT
<213> ORGANISM: Artificial Sequence
<220> FEATURE:
<223> OTHER INFORMATION: Synthetic Construct

<400> SEQUENCE: 352

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Ser Ser Asn
                20                  25                  30

Ala Met Ser Trp Val Arg Gln Ala Pro Gly Lys Gly Leu Glu Trp Val
            35                  40                  45

Ala Gly Ile Ser Ala Ser Gly Asp Thr Tyr Tyr Ser Gly Ser Met Lys
        50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 353
<211> LENGTH: 106
<212> TYPE: PRT
<213> ORGANISM: Artificial Sequence
<220> FEATURE:
<223> OTHER INFORMATION: Synthetic Construct

<400> SEQUENCE: 353

Ala Leu Thr Gln Pro Ala Ser Val Ser Ala Asn Pro Gly Glu Thr Val
1               5                   10                  15

Lys Ile Thr Cys Ser Gly Gly Ser Asp Ser Tyr Tyr Tyr Gly Trp His
                20                  25                  30

Gln Gln Lys Ser Pro Gly Ser Ala Pro Val Thr Val Ile Tyr Ser Asp
            35                  40                  45

Asp Gln Arg Pro Pro Asp Ile Pro Ser Arg Phe Ser Gly Ser Ala Ser
        50                  55                  60

Gly Ser Thr Thr Thr Leu Thr Ile Thr Gly Val Arg Ala Glu Asp Glu
65                  70                  75                  80

Ala Val Tyr Tyr Cys Gly Gly Tyr Asp Tyr Ser Thr Tyr Thr Asn Thr
                85                  90                  95

Phe Gly Ala Gly Thr Thr Leu Thr Val Leu
            100                 105

<210> SEQ ID NO 354
<211> LENGTH: 117
<212> TYPE: PRT
<213> ORGANISM: Artificial Sequence
<220> FEATURE:
<223> OTHER INFORMATION: Synthetic Construct

<400> SEQUENCE: 354

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
```

```
                    20                  25                  30

Ala Met Ser Trp Val Arg Gln Ala Pro Gly Lys Gly Leu Glu Trp Val
            35                  40                  45

Ser Gly Ile Ser Ser Asp Ser Asp Ala Tyr Tyr Val Asp Ser Val Lys
        50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Met
            100                 105                 110

Val Thr Val Ser Ser
            115

<210> SEQ ID NO 355
<211> LENGTH: 107
<212> TYPE: PRT
<213> ORGANISM: Artificial Sequence
<220> FEATURE:
<223> OTHER INFORMATION: Synthetic Construct

<400> SEQUENCE: 355

Ala Leu Thr Gln Pro Ala Ser Val Ser Ala Asn Leu Gly Glu Thr Val
1               5                   10                  15

Lys Ile Thr Cys Ser Gly Asp Ser Ser His Tyr Tyr Gly Trp
            20                  25                  30

Phe Gln Gln Lys Ser Pro Gly Ser Ala Pro Val Thr Leu Ile Tyr Ser
            35                  40                  45

Asp Asp Glu Arg Pro Ser Asp Ile Pro Ser Arg Phe Ser Gly Ser Ala
        50                  55                  60

Ser Gly Ser Thr Ala Thr Leu Thr Ile Thr Gly Val Arg Val Glu Asp
65                  70                  75                  80

Glu Ala Ile Tyr Phe Cys Gly Ala Tyr Asp Gly Ser Thr Tyr Thr Asn
                85                  90                  95

Thr Phe Gly Ala Gly Thr Thr Leu Thr Val Leu
            100                 105

<210> SEQ ID NO 356
<211> LENGTH: 117
<212> TYPE: PRT
<213> ORGANISM: Artificial Sequence
<220> FEATURE:
<223> OTHER INFORMATION: Synthetic Construct

<400> SEQUENCE: 356

Asp Val Gln Leu Val Glu Ser Gly Gly Val Val Arg Pro Gly Glu
1               5                   10                  15

Ser Leu Arg Leu Ser Cys Glu Ala Ser Gly Phe Thr Phe Ser Ser Asp
            20                  25                  30

Ala Met Ser Trp Val Arg Gln Ala Pro Gly Lys Gly Leu Glu Trp Val
            35                  40                  45

Ser Gly Ile Ser Ser Gly Ser Ser Thr Tyr Tyr Gly Gly Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95
```

```
Arg Glu Thr Trp Asn His Leu Phe Asp Tyr Trp Gly Leu Gly Thr Leu
            100                 105                 110

Val Thr Val Ser Ser
        115

<210> SEQ ID NO 357
<211> LENGTH: 107
<212> TYPE: PRT
<213> ORGANISM: Artificial Sequence
<220> FEATURE:
<223> OTHER INFORMATION: Synthetic Construct

<400> SEQUENCE: 357

Ala Leu Thr Gln Pro Ala Ser Val Ser Ala Ser Pro Gly Glu Thr Val
1               5                   10                  15

Glu Ile Thr Cys Ser Gly Gly Ser Asp Ser Ser Tyr Tyr Tyr Gly Trp
            20                  25                  30

Tyr Gln Gln Lys Ser Pro Gly Ser Ala Pro Val Thr Val Ile Tyr Ser
        35                  40                  45

Asp Asn Lys Arg Pro Ser Asn Ile Pro Ser Arg Phe Ser Gly Ser Ala
    50                  55                  60

Ser Gly Ser Thr Ala Thr Leu Thr Ile Thr Gly Val Arg Val Glu Asp
65                  70                  75                  80

Glu Ala Val Tyr Tyr Cys Gly Gly Tyr Asp Tyr Ser Thr Tyr Thr Asn
                85                  90                  95

Pro Phe Gly Ala Gly Thr Thr Leu Thr Val Leu
            100                 105

<210> SEQ ID NO 358
<211> LENGTH: 117
<212> TYPE: PRT
<213> ORGANISM: Artificial Sequence
<220> FEATURE:
<223> OTHER INFORMATION: Synthetic Construct

<400> SEQUENCE: 358

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 359
<211> LENGTH: 107
<212> TYPE: PRT
<213> ORGANISM: Artificial Sequence
<220> FEATURE:
<223> OTHER INFORMATION: Synthetic Construct
```

<400> SEQUENCE: 359

Ala Leu Thr Gln Pro Ala Ser Val Ser Ala Asn Leu Gly Glu Thr Val
1               5                   10                  15

Glu Ile Thr Cys Ser Gly Gly Asp Ser Ser His Tyr Tyr Gly Trp
            20                  25                  30

Tyr Gln Gln Lys Ser Pro Gly Ser Ala Pro Val Thr Val Ile Tyr Ser
                35                  40                  45

Asp Asp Glu Arg Pro Ser Asp Ile Pro Ser Arg Phe Ser Gly Ser Ala
        50                  55                  60

Ser Gly Ser Thr Ala Thr Leu Thr Ile Thr Gly Val Arg Val Glu Asp
65                  70                  75                  80

Glu Ala Ile Tyr Tyr Cys Gly Ala Tyr Asp Gly Ser Thr Tyr Ala Asn
                85                  90                  95

Thr Phe Gly Ala Gly Thr Thr Leu Thr Val Leu
            100                 105

<210> SEQ ID NO 360
<211> LENGTH: 118
<212> TYPE: PRT
<213> ORGANISM: Artificial Sequence
<220> FEATURE:
<223> OTHER INFORMATION: Synthetic Construct

<400> SEQUENCE: 360

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
65                  70                  75                  80

Leu Gln Val Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 361
<211> LENGTH: 107
<212> TYPE: PRT
<213> ORGANISM: Artificial Sequence
<220> FEATURE:
<223> OTHER INFORMATION: Synthetic Construct

<400> SEQUENCE: 361

Ala Leu Thr Gln Pro Ala Ser Val Ser Ala Asn Pro Gly Glu Thr Val
1               5                   10                  15

Lys Ile Thr Cys Ser Gly Gly Gly Tyr Tyr Ser Thr Tyr Tyr Gly Trp
            20                  25                  30

Tyr Gln Gln Lys Ser Pro Gly Ser Ala Pro Val Thr Val Ile His Ser
                35                  40                  45

Asp Asp Lys Arg Pro Ser Asp Ile Pro Ser Arg Phe Ser Gly Ser Ala
        50                  55                  60

Ser Gly Ser Ala Ala Thr Leu Thr Ile Thr Gly Val Arg Val Glu Asp
65                  70                  75                  80

Glu Ala Val Tyr Tyr Cys Ala Gly Tyr Asp Gly Arg Thr Tyr Ile Asn
                85                  90                  95

Thr Phe Gly Ala Gly Thr Thr Leu Thr Val Leu
            100                 105

<210> SEQ ID NO 362
<211> LENGTH: 117
<212> TYPE: PRT
<213> ORGANISM: Artificial Sequence
<220> FEATURE:
<223> OTHER INFORMATION: Synthetic Construct

<400> SEQUENCE: 362

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser His
                20                  25                  30

Ala Met Ser Trp Val Arg Gln Ala Pro Gly Lys Gly Leu Glu Trp Val
            35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
            115

<210> SEQ ID NO 363
<211> LENGTH: 107
<212> TYPE: PRT
<213> ORGANISM: Artificial Sequence
<220> FEATURE:
<223> OTHER INFORMATION: Synthetic Construct

<400> SEQUENCE: 363

Ala Leu Thr Gln Pro Ala Ser Val Ser Ala Asn Leu Gly Glu Thr Val
1               5                   10                  15

Lys Ile Thr Cys Ser Gly Gly Asp Ser Ser His Tyr Tyr Gly Trp
                20                  25                  30

Tyr Gln Gln Lys Ser Pro Gly Ser Ala Pro Val Thr Val Ile Tyr Ser
            35                  40                  45

Asp Asp Glu Arg Pro Ser Asp Ile Pro Ser Arg Phe Ser Gly Ser Ala
    50                  55                  60

Ser Gly Ser Thr Ala Thr Leu Thr Ile Thr Gly Val Arg Val Glu Asp
65                  70                  75                  80

Glu Ala Ile Tyr Tyr Cys Gly Ala Tyr Asp Gly Ser Thr Tyr Ala Asn
                85                  90                  95

Thr Phe Gly Ala Gly Thr Thr Leu Thr Val Leu
            100                 105

<210> SEQ ID NO 364
<211> LENGTH: 118
<212> TYPE: PRT
<213> ORGANISM: Artificial Sequence

```
<220> FEATURE:
<223> OTHER INFORMATION: Synthetic Construct

<400> SEQUENCE: 364

Asp Val Gln Leu Val Asp Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 365
<211> LENGTH: 107
<212> TYPE: PRT
<213> ORGANISM: Artificial Sequence
<220> FEATURE:
<223> OTHER INFORMATION: Synthetic Construct

<400> SEQUENCE: 365

Ala Leu Thr Gln Pro Ala Ser Val Ser Ala Asn Pro Gly Glu Thr Val
1               5                   10                  15

Lys Ile Thr Cys Ser Gly Gly Asp Tyr Tyr Ser Thr Tyr Tyr Gly Trp
            20                  25                  30

Tyr Gln Gln Lys Ser Pro Gly Ser Ala Pro Val Thr Val Ile His Ser
        35                  40                  45

Asp Asp Lys Arg Pro Ser Asp Ile Pro Ser Arg Phe Ser Gly Ser Ala
    50                  55                  60

Ser Gly Ser Ala Ala Thr Leu Thr Ile Thr Gly Val Arg Val Glu Asp
65                  70                  75                  80

Glu Ala Val Tyr Phe Cys Gly Ala Tyr Asp Gly Arg Thr Tyr Ile Asn
                85                  90                  95

Thr Phe Gly Ala Gly Thr Thr Leu Thr Val Leu
            100                 105

<210> SEQ ID NO 366
<211> LENGTH: 118
<212> TYPE: PRT
<213> ORGANISM: Artificial Sequence
<220> FEATURE:
<223> OTHER INFORMATION: Synthetic Construct

<400> SEQUENCE: 366

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45
```

Ala Gly Ile Ser Ala Gly Gly Ser Asp Thr Tyr Tyr Ile Asp Ser Val
            50                  55                  60

Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
                100                 105                 110

Leu Val Thr Val Ser Ser
            115

<210> SEQ ID NO 367
<211> LENGTH: 107
<212> TYPE: PRT
<213> ORGANISM: Artificial Sequence
<220> FEATURE:
<223> OTHER INFORMATION: Synthetic Construct

<400> SEQUENCE: 367

Ala Leu Thr Gln Pro Ala Ser Val Ser Ala Asn Pro Gly Glu Thr Val
  1               5                  10                  15

Lys Ile Thr Cys Ser Gly Gly Asp Tyr Tyr Ser Thr Tyr Tyr Gly Trp
             20                  25                  30

Tyr Gln Gln Lys Ser Pro Gly Ser Ala Pro Val Thr Val Ile His Ser
         35                  40                  45

Asp Asp Lys Arg Pro Ser Asp Ile Pro Ser Arg Phe Ser Gly Ser Ala
 50                  55                  60

Ser Gly Ser Ala Ala Thr Leu Thr Ile Thr Gly Val Arg Val Glu Asp
 65                  70                  75                  80

Glu Ala Val Tyr Phe Cys Gly Ala Tyr Asp Gly Arg Thr Tyr Ile Asn
                 85                  90                  95

Thr Phe Gly Ala Gly Thr Thr Leu Thr Val Leu
                100                 105

<210> SEQ ID NO 368
<211> LENGTH: 118
<212> TYPE: PRT
<213> ORGANISM: Artificial Sequence
<220> FEATURE:
<223> OTHER INFORMATION: Synthetic Construct

<400> SEQUENCE: 368

Asp Leu Gln Leu Val Glu Ser Gly Gly Val Val Arg Pro Gly Glu
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Leu
         35                  40                  45

Ala Gly Ile Ser Ala Gly Gly Ser Asp Thr Tyr Tyr Ile Asp Ser Val
 50                  55                  60

Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
                100                 105                 110

Leu Val Thr Val Ser Ser
            115

<210> SEQ ID NO 369
<211> LENGTH: 107
<212> TYPE: PRT
<213> ORGANISM: Artificial Sequence
<220> FEATURE:
<223> OTHER INFORMATION: Synthetic Construct

<400> SEQUENCE: 369

Ala Leu Thr Gln Pro Ala Ser Val Ser Ala Asn Pro Gly Glu Thr Val
1               5                   10                  15

Lys Ile Ile Cys Ser Gly Gly Asp Tyr Tyr Ser Thr Tyr Tyr Gly Trp
                20                  25                  30

Tyr Gln Gln Lys Ser Pro Gly Ser Ala Pro Val Thr Val Ile His Ser
            35                  40                  45

Asp Asp Lys Arg Pro Ser Asp Ile Pro Ser Arg Phe Ser Gly Ser Ala
    50                  55                  60

Ser Gly Ser Ala Ala Thr Leu Thr Ile Thr Gly Val Arg Val Glu Asp
65                  70                  75                  80

Glu Ala Val Tyr Phe Cys Gly Ala Tyr Asp Gly Arg Thr Tyr Ile Asn
                85                  90                  95

Thr Phe Gly Ala Gly Thr Thr Leu Thr Val Leu
            100                 105

<210> SEQ ID NO 370
<211> LENGTH: 118
<212> TYPE: PRT
<213> ORGANISM: Artificial Sequence
<220> FEATURE:
<223> OTHER INFORMATION: Synthetic Construct

<400> SEQUENCE: 370

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Leu
            35                  40                  45

Ala Gly Ile Ser Ala Gly Gly Ser Asp Ala Tyr Tyr Ile Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 371
<211> LENGTH: 107
<212> TYPE: PRT
<213> ORGANISM: Artificial Sequence
<220> FEATURE:
<223> OTHER INFORMATION: Synthetic Construct

<400> SEQUENCE: 371

Ala Leu Thr Gln Pro Ala Ser Val Ser Ala Asn Pro Gly Glu Thr Val
1               5                   10                  15

```
Lys Ile Thr Cys Ser Gly Gly Asp Trp Tyr Ser Thr Tyr Tyr Gly Trp
            20                  25                  30

Tyr Gln Gln Lys Ser Pro Gly Ser Ala Pro Val Thr Val Ile His Ser
        35                  40                  45

Asp Asp Lys Arg Pro Ser Asp Ile Pro Ser Arg Phe Ser Gly Ser Ala
    50                  55                  60

Ser Gly Ser Ala Ala Thr Leu Thr Ile Thr Gly Val Arg Val Glu Asp
65                  70                  75                  80

Glu Ala Val Tyr Tyr Cys Ala Gly Tyr Asp Gly Arg Thr Tyr Ile Asn
                85                  90                  95

Thr Phe Gly Ala Gly Thr Thr Leu Thr Val Leu
            100                 105

<210> SEQ ID NO 372
<211> LENGTH: 118
<212> TYPE: PRT
<213> ORGANISM: Artificial Sequence
<220> FEATURE:
<223> OTHER INFORMATION: Synthetic Construct

<400> SEQUENCE: 372

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 373
<211> LENGTH: 107
<212> TYPE: PRT
<213> ORGANISM: Artificial Sequence
<220> FEATURE:
<223> OTHER INFORMATION: Synthetic Construct

<400> SEQUENCE: 373

Ala Leu Thr Gln Pro Ala Ser Val Ser Ala Asn Pro Gly Glu Thr Val
1               5                   10                  15

Lys Ile Thr Cys Ser Gly Gly Gly Tyr Tyr Ser Thr Tyr Tyr Gly Trp
            20                  25                  30

Tyr Gln Gln Lys Ser Pro Gly Ser Ala Pro Val Thr Val Ile His Ser
        35                  40                  45

Asp Asp Lys Arg Pro Ser Asp Ile Pro Ser Arg Phe Ser Gly Ser Ala
    50                  55                  60

Ser Gly Ser Ala Ala Thr Leu Thr Ile Thr Gly Val Arg Val Glu Asp
65                  70                  75                  80

Glu Ala Val Tyr Tyr Cys Ala Gly Tyr Asp Ala Arg Thr Tyr Ile Asn
                85                  90                  95
```

Thr Phe Gly Ala Gly Thr Thr Leu Thr Val Leu
            100                 105

<210> SEQ ID NO 374
<211> LENGTH: 117
<212> TYPE: PRT
<213> ORGANISM: Artificial Sequence
<220> FEATURE:
<223> OTHER INFORMATION: Synthetic Construct

<400> SEQUENCE: 374

Asp Val Gln Leu Val Glu Ser Gly Gly Val Val Arg Pro Gly Glu
1               5                   10                  15

Ser Leu Arg Leu Ser Cys Glu Ala Ser Gly Phe Thr Phe Ser Ser Asn
                20                  25                  30

Ala Met Ser Trp Ala Arg Gln Ala Pro Gly Lys Gly Leu Glu Trp Val
            35                  40                  45

Ala Gly Ile Ser Ser Gly Ser Asp Thr Tyr Tyr Gly Asp Ser Val Lys
        50                  55                  60

Gly Arg Leu Thr Ile Ser Arg Asp Asn Ser Lys Asn Ile Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 375
<211> LENGTH: 107
<212> TYPE: PRT
<213> ORGANISM: Artificial Sequence
<220> FEATURE:
<223> OTHER INFORMATION: Synthetic Construct

<400> SEQUENCE: 375

Ala Leu Thr Gln Pro Ala Ser Val Ser Ala Asn Pro Gly Glu Thr Val
1               5                   10                  15

Lys Ile Thr Cys Ser Gly Gly Ile Tyr Ser Ser Tyr Tyr Ala Trp
                20                  25                  30

Tyr Gln Gln Lys Ser Pro Gly Ser Ala Pro Val Thr Leu Ile Tyr Ser
            35                  40                  45

Asp Asp Lys Arg Pro Ser Asn Ile Pro Ser Arg Phe Ser Gly Ser Ala
        50                  55                  60

Ser Gly Ser Thr Ala Thr Leu Thr Ile Thr Gly Val Arg Ala Glu Asp
65                  70                  75                  80

Glu Ala Val Tyr Phe Cys Gly Gly Tyr Asp Gln Ser Ser Tyr Thr Asn
                85                  90                  95

Pro Phe Gly Ala Gly Thr Thr Leu Thr Val Leu
            100                 105

<210> SEQ ID NO 376
<211> LENGTH: 118
<212> TYPE: PRT
<213> ORGANISM: Artificial Sequence
<220> FEATURE:
<223> OTHER INFORMATION: Synthetic Construct

<400> SEQUENCE: 376

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45

Ala Gly Ile Ser Ala Gly Asp Ser Asp Thr Tyr Tyr Pro Ala Ser Val
    50                  55                  60

Lys Gly Arg Phe Thr Ile Ser Arg Asp Asn Pro Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
            115

<210> SEQ ID NO 377
<211> LENGTH: 107
<212> TYPE: PRT
<213> ORGANISM: Artificial Sequence
<220> FEATURE:
<223> OTHER INFORMATION: Synthetic Construct

<400> SEQUENCE: 377

Ala Leu Thr Gln Pro Ala Ser Val Ser Ala Asn Pro Gly Glu Thr Val
1               5                   10                  15

Lys Ile Ala Cys Ser Gly Gly Ser Tyr Tyr Ser Tyr Tyr Tyr Gly Trp
            20                  25                  30

Tyr Gln Gln Lys Ser Pro Gly Ser Ala Leu Val Thr Val Ile Tyr Ser
        35                  40                  45

Asp Asp Lys Arg Pro Ser Gly Ile Pro Ser Arg Phe Ser Gly Ser Ala
    50                  55                  60

Ser Gly Ser Thr Ala Thr Leu Thr Ile Thr Gly Val Arg Ala Glu Asp
65                  70                  75                  80

Glu Ala Val Tyr Tyr Cys Gly Gly Tyr Asp Tyr Ser Ser Tyr Thr Asn
                85                  90                  95

Asp Phe Gly Ala Gly Thr Thr Leu Thr Val Leu
            100                 105

<210> SEQ ID NO 378
<211> LENGTH: 118
<212> TYPE: PRT
<213> ORGANISM: Artificial Sequence
<220> FEATURE:
<223> OTHER INFORMATION: Synthetic Construct

<400> SEQUENCE: 378

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
65                  70                  75                  80
```

-continued

```
Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 379
<211> LENGTH: 107
<212> TYPE: PRT
<213> ORGANISM: Artificial Sequence
<220> FEATURE:
<223> OTHER INFORMATION: Synthetic Construct

<400> SEQUENCE: 379

Ala Leu Thr Gln Pro Ala Ser Val Ser Ala Asn Pro Gly Glu Thr Val
1               5                   10                  15

Lys Ile Thr Cys Ser Gly Gly Asp Trp Tyr Ser Thr Tyr Tyr Gly Trp
            20                  25                  30

Tyr Gln Gln Lys Ser Pro Gly Ser Ala Pro Val Thr Val Ile His Ser
        35                  40                  45

Asp Asp Lys Arg Pro Ser Asp Ile Pro Ser Arg Phe Ser Gly Ser Ala
50                  55                  60

Ser Gly Ser Ala Ala Thr Leu Thr Ile Thr Gly Val Arg Val Glu Asp
65                  70                  75                  80

Glu Ala Val Tyr Tyr Cys Ala Gly Tyr Asp Gly Arg Thr Tyr Ile Asn
                85                  90                  95

Thr Phe Gly Ala Gly Thr Thr Leu Thr Val Leu
            100                 105

<210> SEQ ID NO 380
<211> LENGTH: 118
<212> TYPE: PRT
<213> ORGANISM: Artificial Sequence
<220> FEATURE:
<223> OTHER INFORMATION: Synthetic Construct

<400> SEQUENCE: 380

Asp Val Gln Leu Val Glu Ser Gly Gly Ala Val Val Arg Pro Gly Glu
1               5                   10                  15

Thr Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ser Gly Ser Asp Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Arg Met Ser Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 381
<211> LENGTH: 106
<212> TYPE: PRT
```

```
<213> ORGANISM: Artificial Sequence
<220> FEATURE:
<223> OTHER INFORMATION: Synthetic Construct

<400> SEQUENCE: 381

Ala Leu Thr Gln Pro Ala Ser Val Ser Ala Asn Pro Gly Glu Thr Val
1               5                   10                  15

Lys Ile Thr Cys Ser Gly Gly Thr Ser Ser Tyr Tyr Gly Trp Tyr
            20                  25                  30

Gln Gln Lys Ser Pro Gly Ser Ala Pro Val Thr Leu Ile His Ser Asp
        35                  40                  45

Asp Lys Arg Pro Ser Asp Ile Pro Ser Arg Phe Ser Gly Ser Ala Ser
    50                  55                  60

Gly Ser Thr Ala Thr Leu Thr Ile Thr Gly Val Gln Val Glu Asp Glu
65                  70                  75                  80

Ala Val Tyr Tyr Cys Gly Gly Tyr Asp Tyr Thr Thr Tyr Val Asn Thr
                85                  90                  95

Phe Gly Ala Gly Thr Thr Leu Thr Val Leu
            100                 105

<210> SEQ ID NO 382
<211> LENGTH: 118
<212> TYPE: PRT
<213> ORGANISM: Artificial Sequence
<220> FEATURE:
<223> OTHER INFORMATION: Synthetic Construct

<400> SEQUENCE: 382

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 383
<211> LENGTH: 107
<212> TYPE: PRT
<213> ORGANISM: Artificial Sequence
<220> FEATURE:
<223> OTHER INFORMATION: Synthetic Construct

<400> SEQUENCE: 383

Ala Leu Thr Gln Pro Ala Ser Val Ser Ala Asn Pro Gly Glu Thr Val
1               5                   10                  15

Lys Ile Thr Cys Ser Gly Gly Gly Tyr Tyr Ser Thr Tyr Tyr Gly Trp
            20                  25                  30

Tyr Gln Gln Arg Ser Pro Gly Ser Ala Pro Val Thr Val Ile His Ser
        35                  40                  45
```

```
Asp Asp Lys Arg Pro Ser Asp Ile Pro Ser Arg Phe Ser Gly Ser Ala
        50                  55                  60

Ser Gly Ser Ala Ala Thr Leu Thr Ile Thr Gly Val Arg Val Glu Asp
 65                  70                  75                  80

Glu Ala Val Tyr Tyr Cys Ala Gly Tyr Asp Gly Arg Thr Tyr Leu Asn
                 85                  90                  95

Thr Phe Gly Ala Gly Thr Thr Leu Thr Val Leu
            100                 105

<210> SEQ ID NO 384
<211> LENGTH: 118
<212> TYPE: PRT
<213> ORGANISM: Artificial Sequence
<220> FEATURE:
<223> OTHER INFORMATION: Synthetic Construct

<400> SEQUENCE: 384

Asp Val Gln Leu Val Glu Ser Gly Gly Ala Val Val Arg Pro Gly Glu
  1               5                  10                  15

Thr Leu Arg Leu Ser Cys Thr Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Gly Ile Ser Ala Ser Gly Ser Asp Thr Tyr Tyr Ala Asp Ser Val
 50                  55                  60

Lys Gly Arg Ser Thr Ile Ser Arg Asp Asn Ser Lys Asn Thr Leu Tyr
 65                  70                  75                  80

Leu Arg Met Ser Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
            100                 105                 110

Leu Val Thr Leu Ser Ser
            115

<210> SEQ ID NO 385
<211> LENGTH: 106
<212> TYPE: PRT
<213> ORGANISM: Artificial Sequence
<220> FEATURE:
<223> OTHER INFORMATION: Synthetic Construct

<400> SEQUENCE: 385

Ala Leu Thr Gln Pro Ala Ser Val Ser Ala Asn Pro Gly Glu Thr Val
  1               5                  10                  15

Lys Ile Thr Cys Ser Gly Gly Gly Thr Ser Ser Tyr Tyr Gly Trp Tyr
             20                  25                  30

Gln Gln Lys Ser Pro Gly Ser Ala Pro Val Thr Leu Ile His Ser Asp
         35                  40                  45

Asp Lys Arg Pro Ser Asp Ile Pro Ser Arg Phe Ser Gly Ser Ala Ser
        50                  55                  60

Gly Ser Thr Ala Thr Leu Thr Ile Thr Gly Val Gln Ala Glu Asp Glu
 65                  70                  75                  80

Ala Val Tyr Tyr Cys Gly Gly Tyr Asp Tyr Thr Thr Tyr Val Asn Thr
                 85                  90                  95

Phe Gly Ala Gly Thr Thr Leu Thr Val Leu
            100                 105
```

```
<210> SEQ ID NO 386
<211> LENGTH: 119
<212> TYPE: PRT
<213> ORGANISM: Artificial Sequence
<220> FEATURE:
<223> OTHER INFORMATION: Synthetic Construct

<400> SEQUENCE: 386
```

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Thr Ser
            20                  25                  30

Asp Met Asn Trp Val Arg Gln Ala Pro Gly Glu Gly Leu Glu Trp Val
        35                  40                  45

Ser Leu Ile Ser Gly Ser Gly Glu Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asp Arg Tyr Arg Phe Phe Asp Tyr Trp Gly Leu Gly
            100                 105                 110

Thr Leu Val Thr Val Ser Ser
        115

```
<210> SEQ ID NO 387
<211> LENGTH: 108
<212> TYPE: PRT
<213> ORGANISM: Artificial Sequence
<220> FEATURE:
<223> OTHER INFORMATION: Synthetic Construct

<400> SEQUENCE: 387
```

Glu Thr Val Leu Thr Gln Ser Pro Gly Ile Leu Ser Leu Ser Pro Gly
1               5                   10                  15

Glu Arg Ala Thr Leu Thr Cys Arg Ala Ser Gln Ser Val Tyr Thr Tyr
            20                  25                  30

Leu Ala Trp Tyr Gln Lys Pro Gly Gln Ala Pro Arg Leu Leu Ile
        35                  40                  45

Tyr Gly Ala Ser Ser Arg Ala Ala Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

```
<210> SEQ ID NO 388
<211> LENGTH: 119
<212> TYPE: PRT
<213> ORGANISM: Artificial Sequence
<220> FEATURE:
<223> OTHER INFORMATION: Synthetic Construct

<400> SEQUENCE: 388
```

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Glu Gly Leu Glu Trp Val
        35                  40                  45

Ser Leu Ile Ser Gly Ser Gly Glu Ile Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Tyr Trp Gly Leu Gly
                100                 105                 110

Thr Leu Val Thr Val Ser Ser
        115

<210> SEQ ID NO 389
<211> LENGTH: 108
<212> TYPE: PRT
<213> ORGANISM: Artificial Sequence
<220> FEATURE:
<223> OTHER INFORMATION: Synthetic Construct

<400> SEQUENCE: 389

Lys Thr Val Leu Thr Gln Ser Pro Gly Thr Leu Ser Leu Ser Pro Gly
1               5                   10                  15

Glu Arg Ala Thr Leu Thr Cys Arg Ala Asp Gln Ser Val Tyr Thr Tyr
            20                  25                  30

Leu Ala Trp Tyr Gln Glu Arg Pro Gly Gln Ala Pro Arg Leu Leu Ile
        35                  40                  45

Tyr Asp Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
                100                 105

<210> SEQ ID NO 390
<211> LENGTH: 119
<212> TYPE: PRT
<213> ORGANISM: Artificial Sequence
<220> FEATURE:
<223> OTHER INFORMATION: Synthetic Construct

<400> SEQUENCE: 390

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Glu Gly Leu Glu Trp Val
        35                  40                  45

Ser Leu Ile Ser Gly Ser Gly Glu Ile Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Tyr Trp Gly Leu Gly

<210> SEQ ID NO 391
<211> LENGTH: 108
<212> TYPE: PRT
<213> ORGANISM: Artificial Sequence
<220> FEATURE:
<223> OTHER INFORMATION: Synthetic Construct

<400> SEQUENCE: 391

Glu Thr Val Leu Thr Gln Ser Pro Gly Thr Leu Thr Leu Ser Pro Gly
1               5                   10                  15
Glu Arg Ala Thr Leu Ser Cys Arg Ala Ser Gln Ser Val Tyr Thr Tyr
            20                  25                  30
Leu Ala Trp Tyr Gln Glu Lys Pro Gly Gln Ala Pro Arg Leu Leu Ile
        35                  40                  45
Tyr Gly Ala Ser Ser Arg Ala Thr Gly Val Pro Asp Arg Phe Ser Gly
    50                  55                  60
Ser Gly Ser Gly Thr Glu Phe Thr Leu Thr Ile Ser Ser Leu Gln Ser
65                  70                  75                  80
Glu Asp Phe Ala Val Tyr Tyr Cys Gln Gln Tyr Tyr Asp Arg Pro Pro
                85                  90                  95
Leu Thr Phe Gly Gly Gly Thr Lys Val Glu Ile Lys
            100                 105

<210> SEQ ID NO 392
<211> LENGTH: 119
<212> TYPE: PRT
<213> ORGANISM: Artificial Sequence
<220> FEATURE:
<223> OTHER INFORMATION: Synthetic Construct

<400> SEQUENCE: 392

Asp Val Gln Leu Val Glu Ser Gly Gly Gly Val Val Arg Pro Gly Glu
1               5                   10                  15
Ser Leu Arg Leu Ser Cys Ala Ala Ser Gly Phe Thr Phe Ser Ser Tyr
            20                  25                  30
Asp Met Asn Trp Val Arg Gln Ala Pro Gly Glu Gly Leu Glu Trp Val
        35                  40                  45
Ser Leu Ile Ser Gly Ser Gly Glu Ile Ile Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Glu Asn Asp Arg Tyr Arg Phe Phe Asp Tyr Trp Gly Leu Gly
            100                 105                 110
Thr Leu Val Thr Val Ser Ser
        115

<210> SEQ ID NO 393
<211> LENGTH: 108
<212> TYPE: PRT
<213> ORGANISM: Artificial Sequence
<220> FEATURE:
<223> OTHER INFORMATION: Synthetic Construct

<400> SEQUENCE: 393

```
Glu Thr Val Leu Thr Gln Ser Pro Gly Thr Leu Ser Leu Ser Pro Gly
1               5                   10                  15

Glu Arg Ala Thr Leu Thr Cys Arg Ala Ser Gln Ser Val Tyr Thr Tyr
                20                  25                  30

Leu Ala Trp Tyr Gln Glu Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 394
<211> LENGTH: 119
<212> TYPE: PRT
<213> ORGANISM: Artificial Sequence
<220> FEATURE:
<223> OTHER INFORMATION: Synthetic Construct

<400> SEQUENCE: 394

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
                20                  25                  30

Asp Met Asn Trp Val Arg Gln Ala Pro Gly Glu Gly Leu Glu Trp Val
            35                  40                  45

Ser Leu Ile Ser Gly Ser Gly Glu Ile Ile Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Tyr Trp Gly Leu Gly
            100                 105                 110

Thr Leu Val Thr Val Ser Ser
        115

<210> SEQ ID NO 395
<211> LENGTH: 108
<212> TYPE: PRT
<213> ORGANISM: Artificial Sequence
<220> FEATURE:
<223> OTHER INFORMATION: Synthetic Construct

<400> SEQUENCE: 395

Glu Thr Val Leu Thr Gln Ser Pro Gly Thr Leu Ser Leu Ser Pro Gly
1               5                   10                  15

Glu Arg Ala Thr Leu Asn Cys Arg Ala Ser Gln Ser Val Tyr Thr Tyr
                20                  25                  30

Leu Ala Trp Tyr Gln Glu Lys Pro Gly Gln Ala Pro Arg Leu Leu Ile
            35                  40                  45

Tyr Asp Ala Ser Ser Arg Ala Thr Gly Ile Pro Asp Arg Phe Ser Gly
        50                  55                  60

Ser Gly Ser Gly Thr Glu Phe Thr Leu Thr Ile Ser Ser Leu Glu Ser
```

```
                65                  70                  75                  80
Glu Asp Phe Ala Val Tyr Tyr Cys Gln Gln Tyr Tyr Asp Arg Pro Pro
                    85                  90                  95

Leu Thr Phe Gly Gly Gly Thr Lys Val Glu Ile Lys
            100                 105

<210> SEQ ID NO 396
<211> LENGTH: 119
<212> TYPE: PRT
<213> ORGANISM: Artificial Sequence
<220> FEATURE:
<223> OTHER INFORMATION: Synthetic Construct

<400> SEQUENCE: 396

Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Tyr
                20                  25                  30

Asp Met Asn Trp Val Arg Gln Ala Pro Gly Glu Gly Leu Glu Trp Val
            35                  40                  45

Ser Leu Ile Ser Gly Ser Gly Glu Ile Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Asp Trp Gly Leu Gly
            100                 105                 110

Thr Leu Val Thr Val Ser Ser
        115

<210> SEQ ID NO 397
<211> LENGTH: 108
<212> TYPE: PRT
<213> ORGANISM: Artificial Sequence
<220> FEATURE:
<223> OTHER INFORMATION: Synthetic Construct

<400> SEQUENCE: 397

Glu Thr Val Leu Thr Gln Ser Pro Gly Thr Leu Ser Leu Ser Pro Gly
1               5                   10                  15

Glu Arg Ala Thr Leu Asn Cys Arg Ala Ser Gln Ser Val Tyr Ser Tyr
                20                  25                  30

Leu Ala Trp Tyr Gln Glu Arg Pro Gly Gln Ala Pro Arg Leu Leu Ile
            35                  40                  45

Tyr Gly Ala Ser Thr Arg Ala Thr Gly Ile Pro Asp Arg Phe Ser Gly
    50                  55                  60

Ser Gly Ser Gly Thr Glu Phe Thr Leu Thr Ile Ser Ser Leu Glu Ser
65                  70                  75                  80

Asp Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 398
<211> LENGTH: 119
<212> TYPE: PRT
<213> ORGANISM: Artificial Sequence
<220> FEATURE:
```

<223> OTHER INFORMATION: Synthetic Construct

<400> SEQUENCE: 398

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Ser
            20                  25                  30

Asp Met Asn Trp Val Arg Gln Ala Pro Gly Glu Gly Leu Glu Trp Val
        35                  40                  45

Ser Leu Ile Ser Gly Ser Gly Glu Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Lys Glu Asn Asn Met Tyr Arg Phe Phe Asp Tyr Trp Gly Leu Gly
            100                 105                 110

Thr Leu Val Thr Val Ser Ser
        115

<210> SEQ ID NO 399
<211> LENGTH: 108
<212> TYPE: PRT
<213> ORGANISM: Artificial Sequence
<220> FEATURE:
<223> OTHER INFORMATION: Synthetic Construct

<400> SEQUENCE: 399

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Thr Tyr
            20                  25                  30

Leu Ala Trp Tyr Gln Gln Lys Pro Gly Gln Pro Pro Arg Leu Leu Ile
        35                  40                  45

His Ala Ala Arg Asn Arg Ala Ala Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 400
<211> LENGTH: 119
<212> TYPE: PRT
<213> ORGANISM: Artificial Sequence
<220> FEATURE:
<223> OTHER INFORMATION: Synthetic Construct

<400> SEQUENCE: 400

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Asp Met Asn Trp Val Arg Gln Ala Pro Gly Glu Gly Leu Glu Trp Val
        35                  40                  45

Ser Leu Ile Ser Gly Ser Gly Glu Ile Ile Tyr Tyr Ala Asp Ser Val

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Asp Asn Arg Tyr Arg Phe Phe Asp Tyr Trp Gly Leu Gly
                100                 105                 110

Ala Leu Val Thr Val Ser Ser
            115

<210> SEQ ID NO 401
<211> LENGTH: 108
<212> TYPE: PRT
<213> ORGANISM: Artificial Sequence
<220> FEATURE:
<223> OTHER INFORMATION: Synthetic Construct

<400> SEQUENCE: 401

Glu Thr Val Leu Thr Gln Ser Pro Gly Thr Leu Thr Leu Ser Pro Gly
 1               5                  10                  15

Glu Arg Thr Thr Leu Thr Cys Arg Ala Ser Gln Ser Val Tyr Thr Tyr
                 20                  25                  30

Leu Ala Trp Tyr Gln Glu Lys Pro Gly Gln Ala Pro Arg Leu Leu Ile
             35                  40                  45

Tyr Gly Ala Ser Ser Arg Ala Thr Gly Ile Pro Asp Arg Phe Ser Gly
         50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr Asp Arg Pro Pro
                 85                  90                  95

Leu Thr Phe Gly Gly Gly Thr Lys Val Glu Ile Lys
                100                 105

<210> SEQ ID NO 402
<211> LENGTH: 119
<212> TYPE: PRT
<213> ORGANISM: Artificial Sequence
<220> FEATURE:
<223> OTHER INFORMATION: Synthetic Construct

<400> SEQUENCE: 402

Asp Val Gln Leu Val Glu Ser Gly Gly Gly Val Val Arg Pro Gly Glu
 1               5                  10                  15

Ser Leu Arg Leu Ser Cys Ala Ala Ser Gly Phe Thr Phe Ser Ser Tyr
                 20                  25                  30

Asp Met Asn Trp Val Arg Gln Ala Pro Gly Glu Gly Leu Glu Trp Val
             35                  40                  45

Ser Leu Ile Ser Gly Ser Gly Glu Ile Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Asn Asn Arg Tyr Arg Phe Phe Asp Tyr Trp Gly Leu Gly
                100                 105                 110

Thr Leu Val Thr Val Ser Ser
            115
```

<210> SEQ ID NO 403
<211> LENGTH: 108
<212> TYPE: PRT
<213> ORGANISM: Artificial Sequence
<220> FEATURE:
<223> OTHER INFORMATION: Synthetic Construct

<400> SEQUENCE: 403

```
Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Thr Tyr
            20                  25                  30

Leu Ala Trp Tyr Gln Glu Lys Pro Gly Gln Ala Pro Arg Leu Leu Ile
        35                  40                  45

Tyr Ala Ala Ser Thr Arg Ala Thr Gly Ile Pro Asp Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105
```

<210> SEQ ID NO 404
<211> LENGTH: 119
<212> TYPE: PRT
<213> ORGANISM: Artificial Sequence
<220> FEATURE:
<223> OTHER INFORMATION: Synthetic Construct

<400> SEQUENCE: 404

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Ser Ser Tyr
            20                  25                  30

Ala Met Asn Trp Val Arg Gln Ala Pro Gly Glu Gly Leu Glu Trp Val
        35                  40                  45

Ser Arg Ile Asn Ser Gly Gly Gly Thr Asp Tyr Ala Glu Ser Val
50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Tyr Asp Trp Asn Gly Phe Phe Asp Tyr Trp Gly Leu Gly
            100                 105                 110

Ala Leu Val Thr Val Ser Ser
        115
```

<210> SEQ ID NO 405
<211> LENGTH: 108
<212> TYPE: PRT
<213> ORGANISM: Artificial Sequence
<220> FEATURE:
<223> OTHER INFORMATION: Synthetic Construct

<400> SEQUENCE: 405

```
Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
```

```
                    20                  25                  30
Leu Ala Trp His Gln Gln Lys Pro Gly Gln Ala Pro Arg Leu Leu Ile
            35                  40                  45

Tyr Asp Ala Thr Asn Arg Ala Thr Gly Ile Pro Asp Arg Phe Ser Gly
        50                  55                  60

Ser Gly Ser Gly Thr Asp Phe Thr Leu Thr Ile Ser Gly Leu Gln Thr
65                  70                  75                  80

Glu Asp Ser Ala Val Tyr Tyr Cys Gln Gln Tyr Tyr Tyr Trp Pro Pro
                85                  90                  95

Tyr Arg Phe Gly Gly Gly Thr Lys Val Glu Ile Lys
            100                 105
```

<210> SEQ ID NO 406
<211> LENGTH: 119
<212> TYPE: PRT
<213> ORGANISM: Artificial Sequence
<220> FEATURE:
<223> OTHER INFORMATION: Synthetic Construct

<400> SEQUENCE: 406

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Ser Ser His
            20                  25                  30

Ala Met Asn Trp Val Arg Gln Ala Pro Gly Glu Gly Leu Glu Trp Val
        35                  40                  45

Ser Arg Ile Asn Ser Gly Gly Gly Thr Asp Tyr Ala Glu Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Tyr Asp Trp Asn Gly Phe Phe Asp Tyr Trp Gly Leu Gly
            100                 105                 110

Ala Leu Val Thr Val Ser Ser
        115
```

<210> SEQ ID NO 407
<211> LENGTH: 108
<212> TYPE: PRT
<213> ORGANISM: Artificial Sequence
<220> FEATURE:
<223> OTHER INFORMATION: Synthetic Construct

<400> SEQUENCE: 407

```
Glu Thr Val Leu Thr Gln Ser Pro Ala Thr Leu Ser Val Ser Pro Gly
1               5                   10                  15

Glu Arg Ala Thr Leu Ser Cys Arg Ala Ser Gln Thr Val Gly Ser Lys
            20                  25                  30

Leu Ala Trp His Gln Gln Lys Pro Gly Gln Ala Pro Arg Leu Leu Ile
        35                  40                  45

Tyr Asp Ala Thr Asn Arg Ala Thr Gly Ile Pro Asp Arg Phe Ser Gly
    50                  55                  60

Ser Gly Ser Gly Thr Asp Phe Thr Leu Thr Ile Ser Ser Leu Gln Thr
65                  70                  75                  80

Glu Asp Ser Ala Val Tyr Tyr Cys Gln Gln Tyr Tyr Tyr Trp Pro Pro
                85                  90                  95
```

```
Tyr Arg Phe Gly Gly Gly Thr Lys Val Glu Ile Lys
            100                 105
```

<210> SEQ ID NO 408
<211> LENGTH: 117
<212> TYPE: PRT
<213> ORGANISM: Artificial Sequence
<220> FEATURE:
<223> OTHER INFORMATION: Synthetic Construct

<400> SEQUENCE: 408

```
Asp Val Gln Leu Val Glu Ser Gly Gly Gly Leu Val Arg Pro Gly Glu
1               5                   10                  15

Ser Leu Arg Leu Ser Cys Ala Ala Ser Gly Phe Thr Phe Thr Asn Tyr
            20                  25                  30

Ala Val Thr Trp Val Arg Gln Ala Pro Gly Glu Gly Leu Glu Trp Val
        35                  40                  45

Ser Leu Ile Ser Val Thr Gly Thr Thr Tyr Tyr Ala Asp Ser Val Lys
    50                  55                  60

Gly Arg Phe Thr Ile Ser Arg Asp Asn Ser Lys Ser Thr Leu Tyr Leu
65                  70                  75                  80

Gln Met Asn Gly Leu Arg Ala Glu Asp Thr Ala Val Tyr Tyr Cys Ala
                85                  90                  95

Lys Val Thr Trp Lys Asn Val Phe Asp Tyr Trp Gly Leu Gly Thr Leu
            100                 105                 110

Val Thr Val Ser Ser
        115
```

<210> SEQ ID NO 409
<211> LENGTH: 108
<212> TYPE: PRT
<213> ORGANISM: Artificial Sequence
<220> FEATURE:
<223> OTHER INFORMATION: Synthetic Construct

<400> SEQUENCE: 409

```
Glu Ile Val Leu Thr Gln Ser Pro Gly Thr Leu Ser Val Ser Pro Gly
1               5                   10                  15

Glu Arg Ala Thr Phe Ser Cys Arg Ala Ser Gln Thr Val Gly Ser Lys
            20                  25                  30

Leu Ala Trp Tyr Gln Lys Pro Gly Gln Ala Pro Arg Leu Leu Ile
        35                  40                  45

Tyr Asp Ala Asn Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His Thr Asp Trp Pro Pro
                85                  90                  95

Tyr Thr Phe Gly Gly Gly Thr Lys Val Glu Ile Lys
            100                 105
```

<210> SEQ ID NO 410
<211> LENGTH: 117
<212> TYPE: PRT
<213> ORGANISM: Artificial Sequence
<220> FEATURE:
<223> OTHER INFORMATION: Synthetic Construct

<400> SEQUENCE: 410

```
Asp Val Gln Leu Val Glu Ser Gly Gly Gly Leu Val Arg Pro Gly Glu
```

-continued

```
1               5                   10                  15
Ser Leu Arg Leu Ser Cys Ala Ala Ser Gly Phe Thr Phe Thr Asn Tyr
            20                  25                  30

Ala Val Thr Trp Val Arg Gln Ala Pro Gly Glu Gly Leu Glu Trp Val
            35                  40                  45

Ser Leu Ile Ser Val Thr Gly Thr Thr Tyr Tyr Ala Asp Ser Val Lys
        50                  55                  60

Gly Arg Phe Thr Ile Ser Arg Asp Asn Ser Lys Ser Thr Leu Tyr Leu
65                  70                  75                  80

Gln Met Asn Gly Leu Arg Ala Glu Asp Thr Ala Val Tyr Tyr Cys Ala
            85                  90                  95

Lys Val Thr Trp Lys Asn Val Phe Asp Tyr Trp Gly Leu Gly Thr Leu
            100                 105                 110

Val Thr Val Ser Ser
            115
```

<210> SEQ ID NO 411
<211> LENGTH: 108
<212> TYPE: PRT
<213> ORGANISM: Artificial Sequence
<220> FEATURE:
<223> OTHER INFORMATION: Synthetic Construct

<400> SEQUENCE: 411

```
Glu Ile Val Leu Thr Gln Ser Pro Gly Thr Leu Ser Val Ser Pro Gly
1               5                   10                  15

Glu Arg Ala Thr Phe Ser Cys Arg Ala Ser Gln Thr Val Gly Ser Lys
            20                  25                  30

Leu Ala Trp Tyr Gln Gln Lys Pro Gly Gln Ala Pro Arg Leu Leu Ile
            35                  40                  45

Tyr Asp Ala Asn Thr Arg Ala Thr Gly Ile Pro Ala Arg Phe Ser Gly
        50                  55                  60

Ser Arg Ser Gly Thr Glu Phe Thr Leu Thr Ile Ser Ser Leu Gln Ser
65                  70                  75                  80

Glu Asp Phe Ala Val Tyr Tyr Cys Gln Gln His Thr Asp Trp Pro Pro
            85                  90                  95

Tyr Thr Phe Gly Gly Gly Thr Lys Val Glu Ile Lys
            100                 105
```

<210> SEQ ID NO 412
<211> LENGTH: 118
<212> TYPE: PRT
<213> ORGANISM: Artificial Sequence
<220> FEATURE:
<223> OTHER INFORMATION: Synthetic Construct

<400> SEQUENCE: 412

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Asp His
            20                  25                  30

Asp Met Ser Trp Val Arg Gln Gly Pro Gly Glu Gly Leu Glu Trp Val
            35                  40                  45

Ala Gly Ile Ser Leu Arg Gly Gly Val Thr Trp Tyr Ala Asp Ser Val
        50                  55                  60

Lys Gly Arg Phe Thr Ile Ser Arg Asp Asn Ser Lys Asn Thr Leu Tyr
65                  70                  75                  80
```

-continued

Leu Arg Leu Phe Ser Leu Arg Thr Glu Asp Thr Ala Ile Tyr Tyr Cys
                85                  90                  95

Ala Arg Glu Ser Trp Asn Thr Phe Phe Asp Tyr Trp Gly Leu Gly Thr
            100                 105                 110

Leu Val Thr Val Ser Ser
        115

<210> SEQ ID NO 413
<211> LENGTH: 108
<212> TYPE: PRT
<213> ORGANISM: Artificial Sequence
<220> FEATURE:
<223> OTHER INFORMATION: Synthetic Construct

<400> SEQUENCE: 413

Glu Ile Val Leu Thr Gln Ser Pro Gly Thr Leu Ser Leu Ser Pro Gly
1               5                   10                  15

Glu Thr Ala Thr Leu Ser Cys Arg Ala Ser Gln Asn Val Arg Ser Asn
            20                  25                  30

Leu Ala Trp Tyr Gln Gln Lys Pro Gly Gln Ala Pro Arg Leu Leu Ile
        35                  40                  45

Tyr Asp Ala Ser Ser Arg Ala Thr Gly Ile Pro Asp Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Gly Asn Gly Pro Pro
                85                  90                  95

Leu Thr Phe Gly Gly Gly Thr Lys Val Glu Ile Lys
            100                 105

<210> SEQ ID NO 414
<211> LENGTH: 119
<212> TYPE: PRT
<213> ORGANISM: Artificial Sequence
<220> FEATURE:
<223> OTHER INFORMATION: Synthetic Construct

<400> SEQUENCE: 414

Asp Val Gln Leu Val Glu Ser Gly Gly Val Val Arg Pro Gly Glu
1               5                   10                  15

Ser Leu Arg Leu Ser Cys Glu Ala Ser Gly Phe Thr Phe Arg Asn Ser
            20                  25                  30

Tyr Met Thr Trp Val Arg Gln Ala Pro Gly Glu Gly Leu Glu Trp Val
        35                  40                  45

Ser Thr Ile Ser Asp Thr Gly Asp Thr Ala Tyr Tyr Ala Asp Ser Val
    50                  55                  60

Lys Gly Arg Phe Thr Ile Ser Arg Asp Asn Lys Asn Ser Leu Tyr
65                  70                  75                  80

Leu Gln Met Asn Ser Leu Arg Ala Glu Asp Thr Ala Ile Tyr Tyr Cys
                85                  90                  95

Ala Lys Ser Trp Ile Trp Trp Thr Phe Phe Asp Tyr Trp Gly Leu Gly
            100                 105                 110

Thr Leu Val Thr Val Ser Ser
        115

<210> SEQ ID NO 415
<211> LENGTH: 103
<212> TYPE: PRT
<213> ORGANISM: Artificial Sequence
<220> FEATURE:
<223> OTHER INFORMATION: Synthetic Construct

<400> SEQUENCE: 415

Ala Leu Thr Gln Pro Ala Ser Val Ser Ala Asn Leu Gly Gly Thr Val
1               5                   10                  15

Glu Ile Thr Cys Ser Gly Gly Asn Ser Asn His Tyr Gly Trp Tyr Gln
            20                  25                  30

Gln Lys Ser Pro Gly Ser Ala Pro Val Thr Leu Ile Tyr Ala Asp Thr
        35                  40                  45

Asn Arg Pro Ser Asn Ile Pro Ser Arg Phe Ser Gly Ser Thr Ser Gly
    50                  55                  60

Ser Thr Ser Thr Leu Thr Ile Thr Gly Val Gln Ala Glu Asp Glu Ala
65                  70                  75                  80

Val Tyr Tyr Cys Gly Ser Ser Thr Gly Asp Gly Ile Phe Gly Ala
                85                  90                  95

Gly Thr Thr Leu Thr Val Leu
            100

<210> SEQ ID NO 416
<211> LENGTH: 108
<212> TYPE: PRT
<213> ORGANISM: Artificial Sequence
<220> FEATURE:
<223> OTHER INFORMATION: Synthetic Construct

<400> SEQUENCE: 416

Ser Tyr Glu Leu Thr Gln Pro Pro Ser Val Ser Val Ser Pro Gly Gln
1               5                   10                  15

Thr Ala Arg Ile Thr Cys Ser Gly Gly Ala Tyr Ser Ser Tyr Tyr Tyr
            20                  25                  30

Ala Trp Tyr Gln Gln Lys Pro Gly Gln Ala Pro Val Leu Val Ile Tyr
        35                  40                  45

Ser Asp Ser Lys Arg Pro Ser Gly Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu
            100                 105

<210> SEQ ID NO 417
<211> LENGTH: 108
<212> TYPE: PRT
<213> ORGANISM: Artificial Sequence
<220> FEATURE:
<223> OTHER INFORMATION: Synthetic Construct

<400> SEQUENCE: 417

Glu Ile Val Leu Thr Gln Ser Pro Gly Thr Leu Thr Leu Ser Pro Gly
1               5                   10                  15

Glu Arg Ala Thr Leu Ser Cys Arg Ala Ser Gln Ser Val Tyr Thr Tyr
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
    50                  55                  60

-continued

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 418
<211> LENGTH: 108
<212> TYPE: PRT
<213> ORGANISM: Artificial Sequence
<220> FEATURE:
<223> OTHER INFORMATION: Synthetic Construct

<400> SEQUENCE: 418

Glu Ile Val Leu Thr Gln Ser Pro Gly Thr Leu Ser Leu Ser Pro Gly
1               5                   10                  15

Glu Arg Ala Thr Leu Thr Cys Arg Ala Ser Gln Ser Val Tyr Thr Tyr
                20                  25                  30

Leu Ala Trp Tyr Gln Gln Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 419
<211> LENGTH: 108
<212> TYPE: PRT
<213> ORGANISM: Artificial Sequence
<220> FEATURE:
<223> OTHER INFORMATION: Synthetic Construct

<400> SEQUENCE: 419

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Tyr Thr Tyr
                20                  25                  30

Leu Ala Trp Tyr Gln Glu Lys Pro Gly Gln Ala Pro Arg Leu Leu Ile
            35                  40                  45

Tyr Gly Ala Ser Ser Arg Ala Thr Gly Ile Pro Asp Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asp Arg Pro Pro
                85                  90                  95

Leu Thr Phe Gly Gly Gly Thr Lys Val Glu Ile Lys
            100                 105

<210> SEQ ID NO 420
<211> LENGTH: 120
<212> TYPE: PRT
<213> ORGANISM: Artificial Sequence
<220> FEATURE:
<223> OTHER INFORMATION: Synthetic Construct -continued

<400> SEQUENCE: 420

Asp Val Gln Leu Leu Glu Ser Gly Gly Gly Val Val Gln Pro Gly Gly
1               5                   10                  15

Ser Leu Arg Leu Ser Cys Ala Ala Ser Gly Phe Ser Phe Ser Asn Phe
            20                  25                  30

Ala Leu Thr Trp Val Arg Gln Ala Pro Gly Glu Gly Leu Glu Trp Val
        35                  40                  45

Ser Thr Ile Gly Ser Gly Asp Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Ser Trp Ser Gly Asp Phe Phe Asp Tyr Trp Gly Leu
            100                 105                 110

Gly Thr Leu Val Thr Val Ser Ser
        115                 120

<210> SEQ ID NO 421
<211> LENGTH: 120
<212> TYPE: PRT
<213> ORGANISM: Artificial Sequence
<220> FEATURE:
<223> OTHER INFORMATION: Synthetic Construct

<400> SEQUENCE: 421

Asp Val Gln Leu Leu Glu Ser Gly Gly Gly Val Val Gln Pro Gly Gly
1               5                   10                  15

Ser Leu Arg Leu Ser Cys Ala Ala Ser Gly Phe Ser Phe Ser Asn Phe
            20                  25                  30

Ala Val Thr Trp Val Arg Gln Ala Pro Gly Glu Gly Leu Glu Trp Val
        35                  40                  45

Ser Thr Ile Gly Ser Gly Asp Thr Tyr Tyr Ala Asp Ser Val Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Lys
                85                  90                  95

Asp Ser Thr Val Ser Trp Ser Gly Asp Phe Phe Asp Tyr Trp Gly Leu
            100                 105                 110

Gly Thr Leu Val Thr Val Ser Ser
        115                 120

<210> SEQ ID NO 422
<211> LENGTH: 120
<212> TYPE: PRT
<213> ORGANISM: Artificial Sequence
<220> FEATURE:
<223> OTHER INFORMATION: Synthetic Construct

<400> SEQUENCE: 422

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Ser Phe Ser Ile Tyr
            20                  25                  30

Ala Leu Ser Trp Val Arg Gln Ala Pro Gly Glu Gly Leu Glu Trp Val
        35                  40                  45

```
Ser Thr Ile Gly Ala Asp Asp Thr Tyr Tyr Ala Asp Ser Val Lys Gly
        50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Asp Ser Thr Val Gly Trp Ser Gly Asp Phe Phe Asp Tyr Trp Gly Leu
                100                 105                 110

Gly Thr Leu Val Thr Val Ser Ser
            115                 120

<210> SEQ ID NO 423
<211> LENGTH: 120
<212> TYPE: PRT
<213> ORGANISM: Artificial Sequence
<220> FEATURE:
<223> OTHER INFORMATION: Synthetic Construct

<400> SEQUENCE: 423

Asp Val Gln Leu Val Glu Ser Gly Gly Gly Val Val Arg Pro Gly Glu
  1               5                  10                  15

Ser Leu Arg Leu Ser Cys Ala Ala Ser Gly Phe Ser Phe Ser Ile Tyr
                 20                  25                  30

Ala Val Ser Trp Val Arg Gln Ala Pro Gly Glu Gly Leu Glu Trp Val
             35                  40                  45

Ser Thr Ile Gly Ala Asp Asp Thr Tyr Tyr Ala Asp Ser Val Lys Gly
        50                  55                  60

Arg Phe Thr Ile Ser Arg Asp Asn Ser Lys Asn Thr Leu Tyr Leu Gln
 65                  70                  75                  80

Met Asn Ser Leu Arg Ala Glu Asp Thr Ala Val Tyr Tyr Cys Ala Lys
                 85                  90                  95

Asp Ser Thr Val Gly Trp Ser Gly Asp Phe Phe Asp Tyr Trp Gly Leu
                100                 105                 110

Gly Thr Leu Val Thr Val Ser Ser
            115                 120

<210> SEQ ID NO 424
<211> LENGTH: 119
<212> TYPE: PRT
<213> ORGANISM: Artificial Sequence
<220> FEATURE:
<223> OTHER INFORMATION: Synthetic Construct

<400> SEQUENCE: 424

Asp Val Gln Leu Val Glu Ser Gly Gly Gly Val Val Arg Pro Gly Glu
  1               5                  10                  15

Ser Leu Arg Leu Ser Cys Ala Ala Ser Gly Phe Thr Phe Ser Ser Tyr
                 20                  25                  30

Asp Leu Asn Trp Val Arg Gln Ala Pro Gly Glu Gly Leu Glu Trp Val
             35                  40                  45

Ser Leu Ile Ser Gly Ser Gly Glu Ile Ile Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Asn Asn Arg Tyr Arg Phe Phe Asp Asp Trp Gly Leu Gly
                100                 105                 110
```

Thr Leu Val Thr Val Ser Ser
        115

<210> SEQ ID NO 425
<211> LENGTH: 119
<212> TYPE: PRT
<213> ORGANISM: Artificial Sequence
<220> FEATURE:
<223> OTHER INFORMATION: Synthetic Construct

<400> SEQUENCE: 425

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Asp Val Asn Trp Val Arg Gln Ala Pro Gly Glu Gly Leu Glu Trp Val
        35                  40                  45

Ser Leu Ile Ser Gly Ser Gly Glu Ile Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Asn Arg Tyr Arg Phe Phe Asp Asp Trp Gly Leu Gly
            100                 105                 110

Thr Leu Val Thr Val Ser Ser
        115

<210> SEQ ID NO 426
<211> LENGTH: 106
<212> TYPE: PRT
<213> ORGANISM: Artificial Sequence
<220> FEATURE:
<223> OTHER INFORMATION: Synthetic Construct

<400> SEQUENCE: 426

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

ANTIBODIES AGAINST SIGNAL-REGULATORY PROTEIN ALPHA AND METHODS OF USE

CROSS REFERENCE TO RELATED APPLICATIONS

This application is a divisional of U.S. patent application Ser. No. 15/710,798, filed Sep. 20, 2017, which claims the priority benefit of U.S. Provisional Application No. 62/397,752, filed Sep. 21, 2016, and U.S. Provisional Application No. 62/515,480, filed Jun. 5, 2017, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 757972000110SEQLIST.txt, date recorded: Jun. 1, 2021, size: 411 KB).

FIELD

The present disclosure relates to isolated antibodies that bind an extracellular domain (e.g., the D1 domain) of a human SIRP-α v1 polypeptide, an extracellular domain (e.g., the D1 domain) of a human SIRP-α v2 polypeptide, or both, as well as polynucleotides, vectors, host cells, and methods related thereto.

BACKGROUND

Signal-regulatory protein alpha (SIRP-α) is part of a family of cell-surface receptors that plays critical roles in the regulation of the immune system (see, e.g., Barclay, A. N. and Brown, M. H. (2006) Nat. Rev. Immunol. 6:457-64). SIRP-α is expressed on the surface of various cells, including leukocytes such as dendritic cells, eosinophils, neutrophils, and macrophages. SIRP-α includes an extracellular domain that interacts with external stimuli such as ligands and an intracellular domain that mediates a variety of intracellular signals.

One of the major roles of SIRP-α is its regulation of the immune response through interactions with CD47. CD47 is expressed on the surface of a variety of cell types. When the IgSF domain of CD47 binds the extracellular domain (e.g., the D1 domain) of SIRP-α expressed on an immune cell (e.g., a macrophage), this transduces a SIRP-α-mediated signal in the immune cell that prevents phagocytosis of the CD47-expressing cell. Thus, CD47 serves to convey what has been termed a "don't eat me" signal to the immune system that prevents phagocytosis of healthy cells (see, e.g., WO2015/138600 and Weiskopf, K. et al. (2013) Science 341:88-91). However, CD47 has also been shown to be highly expressed by a variety of cancers, and its interaction with SIRP-α in this context is thought to allow tumors to mimic the healthy "don't eat me" signal in order to evade immune surveillance and phagocytosis by macrophages (see, e.g., Majeti, R. et al. (2009) Cell 138:286-99; Zhao, X. W. et al. (2011) Proc. Natl. Acad. Sci. 108:18342-7). As such, antibodies that block this interaction are highly desirable.

SIRP-α is known to be a highly polymorphic protein in humans, monkeys, and mice. For example, 20 amino acid differences have been identified between SIRP-α proteins in the NOD and C57BL/6 mouse strains, and these polymorphisms lead to functional consequences related to CD47 binding and engraftment of human hematopoietic stem cells in these mouse strains. In humans, at least 10 distinct alleles of the SIRPA gene have been identified (Takenaka, K. et al. (2007) Nat. Immunol. 8:1313-23, Zhao, X. et al. (2011), PNAS. 108:18342-47; van der Heijden, J. (2014). Genetic variation in human Fc gamma receptors: Functional consequences of polymorphisms and copy number variation (Doctoral dissertation)).

Due to the importance of the SIRP-α-CD47 interaction in normal immune function and tumorigenesis, as well as the polymorphic nature of SIRP-α and the existence of other SIRP family receptors, the identification of antibodies having different binding specificities with intra- and/or interspecies cross-reactivity is of great interest for development of clinical candidates that are effective across human populations and the characterization of these candidates in various animal models. Thus, a need exists for both research tools and potential clinical candidates that modulate SIRP-α function, e.g., its binding interaction with CD47. A need also exists for methods of isolating antibodies with a variety of SIRP-α binding specificities and effects on CD47-SIRP-α binding in order to understand and effectively target this critical interaction.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

SUMMARY

To meet these and other needs, provided herein, inter alia, are isolated antibodies that bind an extracellular domain (e.g., the D1 domain) of a human SIRP-α polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both. In some embodiments, the antibody binds an extracellular domain of a human SIRP-α v1 polypeptide comprising the amino acid sequence of EEELQVIQPDKSVLVAAGETATLRCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS (SEQ ID NO:5). In some embodiments, the antibody binds an extracellular domain of a human SIRP-α v2 polypeptide comprising the amino acid sequence of EEELQVIQPDKSVSVAAGESAILHCTVTSLIPVGPIQWFRGAGPARELIYNQKEGHFPRV TTVSESTKRENMDFSISISNITPADAGTYYCVKFRKGSPDTEFKSGAGTELSVRAKPS (SEQ ID NO:6). In some embodiments, the antibody binds an extracellular domain of a human SIRP-α v1 polypeptide comprising the amino acid sequence of EEELQVIQPDKSVLVAAGETATLRCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS (SEQ ID NO:5) and binds an extracellular domain of a human SIRP-α v2 polypeptide comprising the amino acid sequence of EEELQVIQPDKSVSVAAGESAILHCTVTSLIPVGPIQWFRGAGPARELIYNQKEGHFPRV TTVSESTKRENMDFSISISNITPADAGTYYCVKFRKGSPDTEFKSGAGTELSVRAKPS (SEQ ID NO:6). In some embodiments, the antibody binds the extracellular domains (e.g., the D1 domains) of three, four, five, six, seven, eight, nine or ten different human SIRP-α variant polypeptides. In some embodiments, each of the three, four, five, six, seven, eight, nine or ten different human SIRP-α variant polypeptides comprises an extracellular domain comprising an amino acid sequence selected from the group consisting of SEQ ID NOs: 5, 6, and 76-83. In some embodiments, the antibody binds an extracellular domain (e.g., the D1 domain) of a monkey SIRP-α polypeptide. In some embodiments, the monkey SIRP-α polypeptide is a cynomolgus SIRP-α polypeptide. In some embodiments, the antibody binds the extracellular domains (e.g., the D1 domains) of at least two different monkey SIRP-α variant polypeptides. In some embodiments, the antibody binds an extracellular domain of a cynomolgus SIRP-α polypeptide comprising the amino acid sequence of SEQ ID NO:11, an extracellular domain of a cynomolgus SIRP-α polypeptide comprising the amino acid sequence of SEQ ID NO:12, or both. In some embodiments, the antibody binds an extracellular domain (e.g., the D1 domain) of a murine SIRP-α polypeptide. In some embodiments, the antibody binds the extracellular domains (e.g., the D1 domains) of two or more different murine SIRP-α variant polypeptides. In some embodiments, the antibody binds an extracellular domain of one or more murine SIRP-α polypeptides, and wherein the one or more murine SIRP-α polypeptides each comprise an amino acid sequence selected from the group consisting of SEQ ID NOs: 7-10. In some embodiments, the antibody binds an extracellular domain (e.g., the D1 domain) of a human SIRP-β polypeptide. In some embodiments, the antibody binds an extracellular domain (e.g., the D1 domain) of a human SIRP-γ polypeptide. In some embodiments, the antibody does not bind an extracellular domain (e.g., the D1 domain) of a human SIRP-β polypeptide. In some embodiments, the antibody does not bind an extracellular domain (e.g., the D1 domain) of a human SIRP-γ polypeptide. In some embodiments, the antibody binds the extracellular domain of a human SIRP-β polypeptide comprising the amino acid sequence of SEQ ID NO:13, the extracellular domain of a human SIRP-β polypeptide comprising the amino acid sequence of SEQ ID NO:14, or both. In some embodiments, the antibody binds the extracellular domain of a human SIRP-γ polypeptide comprising the amino acid sequence of SEQ ID NO:15. In some embodiments, the antibody modulates SIRP-α signaling in a cell expressing a human SIRP-α polypeptide. In some embodiments, the cell is a leukocyte selected from the group consisting of a macrophage, a dendritic cell, a neutrophil, an eosinophil, and a myeloid-derived suppressor cell (MDSC). In some embodiments, the antibody inhibits SIRP-α signaling in a macrophage expressing a human SIRP-α polypeptide. In some embodiments, the antibody enhances phagocytosis by a macrophage expressing a human SIRP-α polypeptide. In some embodiments, the antibody blocks binding between an extracellular domain (e.g., the D1 domain) of a human SIRP-α polypeptide and an IgSF domain of a human CD47 polypeptide. In some embodiments, the antibody blocks binding between an extracellular domain (e.g., the D1 domain) of a human SIRP-α polypeptide expressed on the surface of a first cell and an IgSF domain of a human CD47 polypeptide expressed on the surface of a second cell. In some embodiments, the antibody does not bind a complex comprising a SIRP-α D1 variant bound to an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47. In some embodiments, the antibody does not block binding between an extracellular domain (e.g., the D1 domain) of a human SIRP-α polypeptide and an IgSF domain of a human CD47 polypeptide. In some embodiments, the antibody does not block binding between an extracellular domain (e.g., the D1 domain) of a human SIRP-α polypeptide expressed on the surface of a first cell and an IgSF domain of a human CD47 polypeptide expressed on the surface of a second cell. In some embodiments, the antibody binds a complex comprising a SIRP-α D1 variant bound to an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47. In some embodiments, binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, binding of the antibody to an extracellular domain (e.g., the D1 domain) of a human SIRP-α polypeptide expressed on the surface of a first cell reduces affinity of the human SIRP-α polypeptide for binding an IgSF domain of a human CD47 polypeptide expressed on the surface of a second cell. In some embodiments, binding of the antibody to an extracellular domain (e.g., the D1 domain) of a human SIRP-α polypeptide increases $k_{off}$ of the human SIRP-α polypeptide for binding an IgSF domain of a human CD47 polypeptide. In some embodiments, binding of the antibody to an extracellular domain (e.g., the D1 domain) of a human SIRP-α polypeptide expressed on the surface of a first cell increases $k_{off}$ of the human SIRP-α polypeptide for binding an IgSF domain of a human CD47 polypeptide expressed on the surface of a second cell. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; and wherein the antibody does not block binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; and wherein the antibody blocks binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; and wherein binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; wherein the antibody binds the extracellular domain (e.g., the D1 domain) of a murine SIRP-α polypeptide; and wherein the antibody does not block binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; wherein the antibody binds the extracellular domain (e.g., the D1 domain) of a murine SIRP-α polypeptide; and wherein the antibody blocks binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a monkey SIRP-α polypeptide; wherein the antibody binds the extracellular domain (e.g., the D1 domain) of a murine SIRP-α polypeptide; and wherein binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a murine SIRP-α polypeptide; and wherein the antibody does not block binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a murine SIRP-α polypeptide; and wherein the antibody blocks binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both; wherein the antibody binds the extracellular domain (e.g., the D1 domain) of a murine SIRP-α polypeptide; and wherein binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, the antibody binds the extracellular domains (e.g., the D1 domain) of two or more different human SIRP-α variant polypeptides, a murine SIRP-α polypeptide, and a monkey SIRP-α polypeptide; wherein the antibody does not bind at least one of an extracellular domain (e.g., the D1 domain) of a human SIRP-β polypeptide and an extracellular domain (e.g., the D1 domain) of a human SIRP-γ polypeptide; and wherein the antibody blocks binding between the extracellular domain (e.g., the D1 domain) of the human SIRP-α polypeptide and an IgSF domain of a human CD47 polypeptide. In some embodiments, the antibody comprises one, two, three, four, five, or six CDR sequences; a heavy chain variable domain sequence; and/or a light chain variable domain sequence from antibody S130. In some embodiments, the antibody binds the extracellular domains (e.g., the D1 domains) of two or more different human SIRP-α variant polypeptides, a murine SIRP-α polypeptide, a monkey SIRP-α polypeptide, and at least one of an extracellular domain (e.g., the D1 domain) of a human SIRP-β polypeptide and an extracellular domain (e.g., the D1 domain) of a human SIRP-γ polypeptide; and wherein the antibody blocks binding between the extracellular domain (e.g., the D1 domain) of the human SIRP-α polypeptide and an IgSF domain of a human CD47 polypeptide. In some embodiments, the antibody comprises one, two, three, four, five, or six CDR sequences; a heavy chain variable domain sequence; and/or a light chain variable domain sequence from an antibody selected from the group consisting of S8, S13, S14, and S121. In some embodiments, the antibody binds the extracellular domains (e.g., the D1 domains) of two or more different human SIRP-α variant polypeptides, a murine SIRP-α polypeptide, and a monkey SIRP-α polypeptide; wherein the antibody does not bind, or binds with reduced affinity to, at least one of an extracellular domain (e.g., the D1 domain) of a human SIRP-β polypeptide and an extracellular domain (e.g., the D1 domain) of a human SIRP-γ polypeptide; and wherein the antibody does not block binding between the extracellular domain (e.g., the D1 domain) of the human SIRP-α polypeptide and an IgSF domain of a human CD47 polypeptide. In some embodiments, the antibody comprises one, two, three, four, five, or six CDR sequences; a heavy chain variable domain sequence; and/or a light chain variable domain sequence from antibody S137. In some embodiments, the antibody binds the extracellular domains (e.g., the D1 domains) of two or more different human SIRP-α variant polypeptides and a monkey SIRP-α polypeptide; wherein the antibody does not bind a murine SIRP-α polypeptide; wherein the antibody does not bind at least one of an extracellular domain (e.g., the D1 domain) of a human SIRP-β polypeptide and an extracellular domain (e.g., the D1 domain) of a human SIRP-γ polypeptide; and wherein the antibody blocks binding between the extracellular domain (e.g., the D1 domain) of the human SIRP-α polypeptide and an IgSF domain of a human CD47 polypeptide. In some embodiments, the antibody comprises one, two, three, four, five, or six CDR sequences; a heavy chain variable domain sequence; and/or a light chain variable domain sequence from an antibody selected from the group consisting of S128. In some embodiments, the antibody binds the extracellular domains (e.g., the D1 domains) of two or more different human SIRP-α variant polypeptides, a monkey SIRP-α polypeptide, and at least one of an extracellular domain (e.g., the D1 domain) of a human SIRP-β polypeptide and an extracellular domain (e.g., the D1 domain) of a human SIRP-γ polypeptide; wherein the antibody does not bind a murine SIRP-α polypeptide; and wherein the antibody blocks binding between the extracellular domain (e.g., the D1 domain) of the human SIRP-α polypeptide and an IgSF domain of a human CD47 polypeptide. In some embodiments, the antibody comprises one, two, three, four, five, or six CDR sequences; a heavy chain variable domain sequence; and/or a light chain variable domain sequence from an antibody selected from the group consisting of S9, S11, S119, S120, S122, and S135. In some embodiments, the antibody binds the extracellular domains (e.g., the D1 domains) of two or more different human SIRP-α variant polypeptides and the extracellular domains (e.g., the D1 domains) of two or more different monkey SIRP-α variant polypeptides, and wherein binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, the antibody comprises one, two, three, four, five, or six CDR sequences; a heavy chain variable domain sequence; and/or a light chain variable domain sequence from an antibody selected from the group consisting of S115, S116, S117 and S118. In some embodiments, the antibody comprises a VH domain comprising the amino acid sequence of SEQ ID NO:120 and/or a VL domain comprising the amino acid sequence of SEQ ID NO:97. In some embodiments, the antibody comprises a VH domain comprising the amino acid sequence of SEQ ID NO:127 and/or a VL domain comprising the amino acid sequence of SEQ ID NO:104. In some embodiments, the antibody comprises a VH domain comprising the amino acid sequence of SEQ ID NO:133 and/or a VL domain comprising the amino acid sequence of SEQ ID NO:134. In some embodiments, the antibody comprises a VH domain comprising the amino acid sequence of SEQ ID NO:135 and/or a VL domain comprising the amino acid sequence of SEQ ID NO:136. In some embodiments, the antibody comprises a VH domain comprising the amino acid sequence of SEQ ID NO:137 and/or a VL domain comprising the amino acid sequence of SEQ ID NO:138. In some embodiments, the antibody comprises a VH domain comprising the amino acid sequence of SEQ ID NO:139 and/or a VL domain comprising the amino acid sequence of SEQ ID NO:140. In some embodiments, the antibody comprises a VH domain comprising the amino acid sequence of SEQ ID NO:141 and/or a VL domain comprising the amino acid sequence of SEQ ID NO:142.

In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 115 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 115 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 116 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 116 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 117 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 117 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 118 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 118 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 119 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 119 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 120 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 120 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 121 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 121 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 122 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 122 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 123 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 123 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 126 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 126 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 128 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 128 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 130 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 130 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 135 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 135 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 137 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 137 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 138 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 138 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 1 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 1 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 2 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 2 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 8 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 8 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 9 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 9 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 11 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 11 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 12 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 12 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 13 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 13 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 14 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 14 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to the VH domain of antibody 21, 25, 27, or 66 (e.g., as listed in Table 2) and/or a VL domain comprising an amino acid sequence that is 85%, 86%, 87%, 88%, 89%, 90%, 91%, 92%, 93%, 94%, 95%, 96%, 97%, 98%, 99%, or 100% identical to the VL domain of antibody 21, 25, 27, or 66 (e.g., as listed in Table 2). In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:116 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:93. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:117 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:94. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:118 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:95. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:119 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:96. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:335 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:97. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:121 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:98. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:122 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:99. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:123 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:100. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:124 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:101. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:125 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:102. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:126 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:103. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:127 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:104. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:128 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:105. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:129 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:106. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:130 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:107. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:108 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:85. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:109 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:86. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:110 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:87. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:111 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:88. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:112 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:89. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:113 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:90. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:114 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:91. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:115 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:92. In some embodiments, the antibody comprises a VH domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:135, 137, 139, or 141 and/or a VL domain comprising an amino acid sequence that is 85%, 86%, 87%, 88%, 89%, 90%, 91%, 92%, 93%, 94%, 95%, 96%, 97%, 98%, 99%, or 100% identical to SEQ ID NO:136, 138, 140, or 142.

In some embodiments, the antibody comprises (a) a VH domain comprising an HVR-H1 comprising the amino acid sequence of SEQ ID NO:227 or 230, an HVR-H2 comprising the amino acid sequence of SEQ ID NO:228 or 231, and an HVR-H3 comprising the amino acid sequence of SEQ ID NO:229; and/or (b) a VL domain comprising an HVR-L1 comprising the amino acid sequence of SEQ ID NO:232, an HVR-L2 comprising the amino acid sequence of SEQ ID NO:233, and an HVR-L3 comprising the amino acid sequence of SEQ ID NO:234. In some embodiments, the antibody comprises (a) a VH domain comprising an HVR-H1 comprising the amino acid sequence of SEQ ID NO:219 or 235, an HVR-H2 comprising the amino acid sequence of SEQ ID NO:236 or 238, and an HVR-H3 comprising the amino acid sequence of SEQ ID NO:237; and/or (b) a VL domain comprising an HVR-L1 comprising the amino acid sequence of SEQ ID NO:239, an HVR-L2 comprising the amino acid sequence of SEQ ID NO:240, and an HVR-L3 comprising the amino acid sequence of SEQ ID NO:241. In some embodiments, the antibody comprises (a) an HVR-H1 sequence comprising the amino acid sequence of GFSFSX$_1$X$_2$AMX$_3$, wherein X$_1$ is N or I; X$_2$ is F or Y; and X$_3$ is T or S (SEQ ID NO:185); (b) an HVR-H2 sequence comprising the amino acid sequence of TIGX$_4$X$_5$DTYYADSVKG, wherein X$_4$ is S or A and X$_5$ is G or D (SEQ ID NO:186); (c) an HVR-H3 sequence comprising the amino acid sequence of DSTVX$_6$WSGDFFDY, wherein X$_6$ is S or G (SEQ ID NO:187); (d) an HVR-L1 sequence comprising the amino acid sequence of RASQNVX$_7$X$_8$DX$_9$A, wherein X$_7$ is K or R; X$_8$ is N or S; and X$_9$ is L or I (SEQ ID NO:188); (e) an HVR-L2 sequence comprising the amino acid sequence of AAX$_{10}$X$_{11}$RX$_{12}$T, wherein X$_{10}$ is R or S; X$_{11}$ is I or S; and X$_{12}$ is E or D (SEQ ID NO:189); and (f) an HVR-L3 sequence comprising the amino acid sequence of QQYYDWPPFT (SEQ ID NO:148). In some embodiments, the antibody comprises one, two, three, four, five, or six HVR sequences from antibody 119 (e.g., as listed in Table 2). In some embodiments, the antibody comprises one, two, three, four, five, or six HVR sequences from the variable domain sequences of SEQ ID NOs:335 and 97 (e.g., one, two, or three heavy chain HVR sequences from the heavy chain variable domain sequence of SEQ ID NO:335 and/or one, two, or three light chain HVR sequences from the light chain variable domain sequence of SEQ ID NO:97). In some embodiments, the antibody comprises one, two, three, four, five, or six HVR sequences from antibody 135 (e.g., as listed in Table 2). In some embodiments, the antibody comprises one, two, three, four, five, or six HVR sequences from the variable domain sequences of SEQ ID NOs:127 and 104 (e.g., one, two, or three heavy chain HVR sequences from the heavy chain variable domain sequence of SEQ ID NO:127 and/or one, two, or three light chain HVR sequences from the light chain variable domain sequence of SEQ ID NO:104). In some embodiments, the antibody comprises one, two, three, four, five, or six HVR sequences from the variable domain sequences of SEQ ID NOs:97, 104, 120, 335, and 127 (e.g., one, two, or three heavy chain HVR sequences from the heavy chain variable domain sequence of SEQ ID NOs:335 and 127 and/or one, two, or three light chain HVR sequences from the light chain variable domain sequence of SEQ ID NOs:97 and 104). In some embodiments, the antibody comprises one, two, three, four, five, or six HVR sequences having an amino acid sequence selected from SEQ ID NOs:143-148 (e.g., one, two, or three heavy chain HVR sequences selected from SEQ ID NOs:143-145 and/or one, two, or three light chain HVR sequences selected from SEQ ID NOs:146-148). In some embodiments, the antibody comprises one, two, three, four, five, or six HVR sequences having an amino acid sequence selected from SEQ ID NOs:148-153 (e.g., one, two, or three heavy chain HVR sequences selected from SEQ ID NOs:149-151 and/or one, two, or three light chain HVR sequences selected from SEQ ID NOs:152, 153, and 148). In some embodiments, the antibody comprises one, two, three, four, five, or six HVR sequences from antibody 136 (e.g., as listed in Table 2). In some embodiments, the antibody comprises one, two, three, four, five, or six HVR sequences having an amino acid sequence selected from SEQ ID NOs:155-160 (e.g., one, two, or three heavy chain HVR sequences selected from SEQ ID NOs:155-157 and/or one, two, or three light chain HVR sequences selected from SEQ ID NOs:158-160). In some embodiments, the antibody comprises one, two, three, four, five, or six HVR sequences from antibody 21 (e.g., as listed in Table 2). In some embodiments, the antibody comprises one, two, three, four, five, or six HVR sequences having an amino acid sequence selected from SEQ ID NOs:161-166 (e.g., one, two, or three heavy chain HVR sequences selected from SEQ ID NOs: 161-163 and/or one, two, or three light chain HVR sequences selected from SEQ ID NOs:164-166). In some embodiments, the antibody comprises one, two, three, four, five, or six HVR sequences from antibody 25 (e.g., as listed in Table 2). In some embodiments, the antibody comprises one, two, three, four, five, or six HVR sequences having an amino acid sequence selected from SEQ ID NOs: 161, 163, 168, and 170-172 (e.g., one, two, or three heavy chain HVR sequences selected from SEQ ID NOs: 161, 168, and 163 and/or one, two, or three light chain HVR sequences selected from SEQ ID NOs:170-172). In some embodiments, the antibody comprises one, two, three, four, five, or six HVR sequences from antibody 27 (e.g., as listed in Table 2). In some embodiments, the antibody comprises one, two, three, four, five, or six HVR sequences having an amino acid sequence selected from SEQ ID NOs: 163, 173, 174, and 176-178 (e.g., one, two, or three heavy chain HVR sequences selected from SEQ ID NOs:163, 173, and 174 and/or one, two, or three light chain HVR sequences selected from SEQ ID NOs:176-178). In some embodiments, the antibody comprises one, two, three, four, five, or six HVR sequences from antibody 66 (e.g., as listed in Table 2). In some embodiments, the antibody comprises one, two, three, four, five, or six HVR sequences having an amino acid sequence selected from SEQ ID NOs:162, 163, 179, and 182-184 (e.g., one, two, or three heavy chain HVR sequences selected from SEQ ID NOs: 162, 163, and 179 and/or one, two, or three light chain HVR sequences selected from SEQ ID NOs:182-184). In some embodiments, the antibody comprises (a) a VH domain comprising an HVR-H1 comprising the amino acid sequence of SEQ ID NO:143, 202, 204, or 205, an HVR-H2 comprising the amino acid sequence of SEQ ID NO:144, 203, or 206, and an HVR-H3 comprising the amino acid sequence of SEQ ID NO:145 or 207; and/or (b) a VL domain comprising an HVR-L1 comprising the amino acid sequence of SEQ ID NO:146 or 208, an HVR-L2 comprising the amino acid sequence of SEQ ID NO:147 or 209, and an HVR-L3 comprising the amino acid sequence of SEQ ID NO:148 or 210. In some embodiments, the antibody comprises (a) a VH domain comprising an HVR-H1 comprising the amino acid sequence of SEQ ID NO:149, 211, 213, or 214, an HVR-H2 comprising the amino acid sequence of SEQ ID NO:150, 212, or 215, and an HVR-H3 comprising the amino acid sequence of SEQ ID NO:151 or 216; and/or (b) a VL domain comprising an HVR-L1 comprising the amino acid sequence of SEQ ID NO:152 or 217, an HVR-L2 comprising the amino acid sequence of SEQ ID NO:153 or 218, and an HVR-L3 comprising the amino acid sequence of SEQ ID NO:148. In some embodiments, the antibody comprises (a) a VH domain comprising an HVR-H1 comprising the amino acid sequence of SEQ ID NO:155, 219, 221, or 222, an HVR-H2 comprising the amino acid sequence of SEQ ID NO:156, 220, or 223, and an HVR-H3 comprising the amino acid sequence of SEQ ID NO:157 or 224; and/or (b) a VL domain comprising an HVR-L1 comprising the amino acid sequence of SEQ ID NO:158 or 225, an HVR-L2 comprising the amino acid sequence of SEQ ID NO:159 or 226, and an HVR-L3 comprising the amino acid sequence of SEQ ID NO:160. In some embodiments, the antibody comprises (a) a VH domain comprising an HVR-H1 comprising the amino acid sequence of SEQ ID NO:161, 191, or 194, an HVR-H2 comprising the amino acid sequence of SEQ ID NO:162, 192, or 195, and an HVR-H3 comprising the amino acid sequence of SEQ ID NO:163 or 193; and/or (b) a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO:166. In some embodiments, the antibody comprises (a) a VH domain comprising an HVR-H1 comprising the amino acid sequence of SEQ ID NO:161, 191, or 194, an HVR-H2 comprising the amino acid sequence of SEQ ID NO:168, 196, or 197, and an HVR-H3 comprising the amino acid sequence of SEQ ID NO:163 or 193; and/or (b) a VL domain comprising an HVR-L1 comprising the amino acid sequence of SEQ ID NO:170, an HVR-L2 comprising the amino acid sequence of SEQ ID NO:171, and an HVR-L3 comprising the amino acid sequence of SEQ ID NO:172. In some embodiments, the antibody comprises (a) a VH domain comprising an HVR-H1 comprising the amino acid sequence of SEQ ID NO:173, 198, or 200, an HVR-H2 comprising the amino acid sequence of SEQ ID NO:174, 199, or 201, and an HVR-H3 comprising the amino acid sequence of SEQ ID NO:163 or 193; and/or (b) a VL domain comprising an HVR-L1 comprising the amino acid sequence of SEQ ID NO:176, an HVR-L2 comprising the amino acid sequence of SEQ ID NO:177, and an HVR-L3 comprising the amino acid sequence of SEQ ID NO:178. In some embodiments, the antibody comprises (a) a VH domain comprising an HVR-H1 comprising the amino acid sequence of SEQ ID NO:179, an HVR-H2 comprising the amino acid sequence of SEQ ID NO:162, and an HVR-H3 comprising the amino acid sequence of SEQ ID NO:163; and/or (b) a VL domain comprising an HVR-L1 comprising the amino acid sequence of SEQ ID NO:182, an HVR-L2 comprising the amino acid sequence of SEQ ID NO:183, and an HVR-L3 comprising the amino acid sequence of SEQ ID NO:184. In some embodiments, the antibody comprises a VH domain comprising the amino acid sequence of SEQ ID NO:135 and/or a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO:166. In some embodiments, the antibody comprises a VH domain comprising the amino acid sequence of SEQ ID NO:137 and/or a VL domain comprising an HVR-L1 comprising the amino acid sequence of SEQ ID NO:170, an HVR-L2 comprising the amino acid sequence of SEQ ID NO:171, and an HVR-L3 comprising the amino acid sequence of SEQ ID NO:172. In some embodiments, the antibody comprises a VH domain comprising the amino acid sequence of SEQ ID NO:139 and/or a VL domain comprising an HVR-L1 comprising the amino acid sequence of SEQ ID NO:176, an HVR-L2 comprising the amino acid sequence of SEQ ID NO:177, and an HVR-L3 comprising the amino acid sequence of SEQ ID NO:178. In some embodiments, the antibody comprises a VH domain comprising the amino acid sequence of SEQ ID NO:141 and/or a VL domain comprising an HVR-L1 comprising the amino acid sequence of SEQ ID NO:182, an HVR-L2 comprising the amino acid sequence of SEQ ID NO:183, and an HVR-L3 comprising the amino acid sequence of SEQ ID NO:184. In some embodiments, the antibody comprises one, two, three, four, five, or six HVR sequences from antibody 3 (e.g., as listed in Table 2). In some embodiments, the antibody comprises (a) a VH domain comprising one, two, or three HVR sequences from SEQ ID NO:242; and/or (b) a VL domain comprising one, two, or three HVR sequences from SEQ ID NO:243. In some embodiments, the antibody comprises one, two, three, four, five, or six HVR sequences from antibody 45 (e.g., as listed in Table 2). In some embodiments, the antibody comprises (a) a VH domain comprising one, two, or three HVR sequences from SEQ ID NO:244; and/or (b) a VL domain comprising one, two, or three HVR sequences from SEQ ID NO:245. In some embodiments, the antibody comprises a VH domain comprising the amino acid sequence of SEQ ID NO:135 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, the antibody comprises a VH domain comprising the amino acid sequence of SEQ ID NO:137 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, the antibody comprises a VH domain comprising the amino acid sequence of SEQ ID NO:139 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, the antibody comprises a VH domain comprising the amino acid sequence of SEQ ID NO:141 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, one, two, three, four, five, or six of the HVR sequences are defined by Kabat. In some embodiments, one, two, three, four, five, or six of the HVR sequences are defined by Chothia. In some embodiments, one, two, three, four, five, or six of the HVR sequences are defined by IMGT. In some embodiments, the antibody comprises HVR sequences as defined by two or more of Kabat, Chothia, and IMGT (e.g., the antibody comprises one or more HVR sequences as defined by one delineation and one or more HVR sequences as defined by a different delineation).

In other aspects, provided herein is an isolated antibody that binds an extracellular domain of a human SIRP-α polypeptide (e.g., the D1 domain), wherein the antibody comprises: (a) a heavy chain variable (VH) domain comprising (i) an HVR-H1 sequence comprising the amino acid sequence of NFAMT (SEQ ID NO: 175), NFAVT (SEQ ID NO:204), or NFALT (SEQ ID NO:305), (ii) an HVR-H2 sequence comprising the amino acid sequence of TIGSGDTYYADSVKG (SEQ ID NO:144), and (iii) an HVR-H3 sequence comprising the amino acid sequence of DSTVSWSGDFFDY (SEQ ID NO:145); and/or (b) a light chain variable (VL) domain comprising (i) an HVR-L1 sequence comprising the amino acid sequence of RASQNVKNDLA (SEQ ID NO:146), (ii) an HVR-L2 sequence comprising the amino acid sequence of AARIRET (SEQ ID NO:147), and (iii) an HVR-L3 sequence comprising the amino acid sequence of QQYYDWPPFT (SEQ ID NO:148). In some embodiments, the VH domain comprises an amino acid sequence that is at least 90% identical to the amino acid sequence of SEQ ID NO:120, 335, 246, 258, or 327; and/or the VL domain comprises an amino acid sequence that is at least 90% identical to the amino acid sequence of SEQ ID NO:97 or 312. In some embodiments, the VH domain comprises the amino acid sequence of SEQ ID NO:246, and the VL domain comprises the amino acid sequence of SEQ ID NO:97; the VH domain comprises the amino acid sequence of SEQ ID NO:258, and the VL domain comprises the amino acid sequence of SEQ ID NO:97; the VH domain comprises the amino acid sequence of SEQ ID NO:335, and the VL domain comprises the amino acid sequence of SEQ ID NO:97; the VH domain comprises the amino acid sequence of SEQ ID NO:327, and the VL domain comprises the amino acid sequence of SEQ ID NO:97; the VH domain comprises the amino acid sequence of SEQ ID NO:246, and the VL domain comprises the amino acid sequence of SEQ ID NO:312; the VH domain comprises the amino acid sequence of SEQ ID NO:258, and the VL domain comprises the amino acid sequence of SEQ ID NO:312; the VH domain comprises the amino acid sequence of SEQ ID NO:335, and the VL domain comprises the amino acid sequence of SEQ ID NO:312; or the VH domain comprises the amino acid sequence of SEQ ID NO:327, and the VL domain comprises the amino acid sequence of SEQ ID NO:312.

In other aspects, provided herein is an isolated antibody that binds an extracellular domain of a human SIRP-α polypeptide (e.g., the D1 domain), wherein the antibody comprises: (a) a heavy chain variable (VH) domain comprising (i) an HVR-H1 sequence comprising the amino acid sequence of IYAMS (SEQ ID NO:269), IYAVS (SEQ ID NO:213), or IYALS (SEQ ID NO:306), (ii) an HVR-H2 sequence comprising the amino acid sequence of TIGADDTYYADSVKG (SEQ ID NO:150), and (iii) an HVR-H3 sequence comprising the amino acid sequence of DSTVGWSGDFFDY (SEQ ID NO:151); and/or (b) a light chain variable (VL) domain comprising (i) an HVR-L1 sequence comprising the amino acid sequence of RASQNVRSDIA (SEQ ID NO:152), (ii) an HVR-L2 sequence comprising the amino acid sequence of AASSRDT (SEQ ID NO:153), and (iii) an HVR-L3 sequence comprising the amino acid sequence of QQYYDWPPFT (SEQ ID NO:148). In some embodiments, the VH domain comprises an amino acid sequence that is at least 90% identical to the amino acid sequence of SEQ ID NO:341, 247, 259, or 328; and/or the VL domain comprises an amino acid sequence that is at least 90% identical to the amino acid sequence of SEQ ID NO:104 or 248. In some embodiments, the VH domain comprises the amino acid sequence of SEQ ID NO:127, and the VL domain comprises the amino acid sequence of SEQ ID NO:104; the VH domain comprises the amino acid sequence of SEQ ID NO:247, and the VL domain comprises the amino acid sequence of SEQ ID NO:104; the VH domain comprises the amino acid sequence of SEQ ID NO:259, and the VL domain comprises the amino acid sequence of SEQ ID NO:104; the VH domain comprises the amino acid sequence of SEQ ID NO:328, and the VL domain comprises the amino acid sequence of SEQ ID NO:104; the VH domain comprises the amino acid sequence of SEQ ID NO:127, and the VL domain comprises the amino acid sequence of SEQ ID NO:248; the VH domain comprises the amino acid sequence of SEQ ID NO:247, and the VL domain comprises the amino acid sequence of SEQ ID NO:248; the VH domain comprises the amino acid sequence of SEQ ID NO:259, and the VL domain comprises the amino acid sequence of SEQ ID NO:248; or the VH domain comprises the amino acid sequence of SEQ ID NO:328, and the VL domain comprises the amino acid sequence of SEQ ID NO:248.

In other aspects, provided herein is an isolated antibody that binds an extracellular domain of a human SIRP-α polypeptide (e.g., the D1 domain), wherein the antibody comprises: (a) a heavy chain variable (VH) domain comprising: (i) an HVR-H1 sequence comprising the amino acid sequence of $X_1X_2DX_3N$, wherein $X_1$ is S or T; $X_2$ is Y or S; and $X_3$ is M, L, or V (SEQ ID NO:307); (ii) an HVR-H2 sequence comprising the amino acid sequence of LISGSGEIX$_1$YYADSVKG, wherein $X_1$ is I or T (SEQ ID NO:308); and (iii) an HVR-H3 sequence comprising the amino acid sequence of EX$_1$X$_2$X$_3$YRFFDX$_4$, wherein $X_1$ is N or D; $X_2$ is N or D; $X_3$ is R or M; and $X_4$ is D or Y (SEQ ID NO:309); and/or (b) a light chain variable (VL) domain comprising: (i) an HVR-L1 sequence comprising the amino acid sequence of RAX$_1$QSVYX$_2$YLA, wherein $X_1$ is S or D; and $X_2$ is T or S (SEQ ID NO:310); (ii) an HVR-L2 sequence comprising the amino acid sequence of $X_1AX_2X_3RAX_4$, wherein $X_1$ is G, A, or D; $X_2$ is S or R; $X_3$ is S, N, or T; and $X_4$ is T or A (SEQ ID NO:311); and (iii) an HVR-L3 sequence comprising the amino acid sequence of QQYYDRPPLT (SEQ ID NO:160). In some embodiments, the antibody comprises (a) a heavy chain variable (VH) domain comprising (i) an HVR-H1 sequence comprising the amino acid sequence of SYDMN (SEQ ID NO:270), SYDVN (SEQ ID NO:221), or SYDLN (SEQ ID NO:313), (ii) an HVR-H2 sequence comprising the amino acid sequence of LISGSGEIIYYADSVKG (SEQ ID NO:156), and (iii) an HVR-H3 sequence comprising the amino acid sequence of ENNRYRFFDD (SEQ ID NO:157); and/or (b) a light chain variable (VL) domain comprising (i) an HVR-L1 sequence comprising the amino acid sequence of RASQSVYTYLA (SEQ ID NO:158), (ii) an HVR-L2 sequence comprising the amino acid sequence of GASSRAT (SEQ ID NO:159), and (iii) an HVR-L3 sequence comprising the amino acid sequence of QQYYDRPPLT (SEQ ID NO:160). In some embodiments, the VH domain comprises an amino acid sequence that is at least 90% identical to the amino acid sequence of SEQ ID NO: 249, 133, 260, or 329; and/or the VL domain comprises an amino acid sequence that is at least 90% identical to the amino acid sequence of SEQ ID NO:134, 250, or 251. In some embodiments, the VH domain comprises the amino acid sequence of SEQ ID NO:133, and the VL domain comprises the amino acid sequence of SEQ ID NO:134; the VH domain comprises the amino acid sequence of SEQ ID NO:260, and the VL domain comprises the amino acid sequence of SEQ ID NO:134; the VH domain comprises the amino acid sequence of SEQ ID NO:329, and the VL domain comprises the amino acid sequence of SEQ ID NO:134; the VH domain comprises the amino acid sequence of SEQ ID NO:133, and the VL domain comprises the amino acid sequence of SEQ ID NO:250; the VH domain comprises the amino acid sequence of SEQ ID NO:260, and the VL domain comprises the amino acid sequence of SEQ ID NO:250; the VH domain comprises the amino acid sequence of SEQ ID NO:329, and the VL domain comprises the amino acid sequence of SEQ ID NO:250; the VH domain comprises the amino acid sequence of SEQ ID NO:133, and the VL domain comprises the amino acid sequence of SEQ ID NO:251; the VH domain comprises the amino acid sequence of SEQ ID NO:260, and the VL domain comprises the amino acid sequence of SEQ ID NO:251; the VH domain comprises the amino acid sequence of SEQ ID NO:329, and the VL domain comprises the amino acid sequence of SEQ ID NO:251; the VH domain comprises the amino acid sequence of SEQ ID NO:249, and the VL domain comprises the amino acid sequence of SEQ ID NO:134; the VH domain comprises the amino acid sequence of SEQ ID NO:249, and the VL domain comprises the amino acid sequence of SEQ ID NO:250; or the VH domain comprises the amino acid sequence of SEQ ID NO:249, and the VL domain comprises the amino acid sequence of SEQ ID NO:251.

In other aspects, provided herein is an isolated antibody that binds an extracellular domain of a human SIRP-α polypeptide (e.g., the D1 domain), wherein the antibody comprises: a heavy chain variable (VH) domain comprising: an HVR-H1 sequence comprising the amino acid sequence of $X_1X_2AX_3S$, wherein $X_1$ is S or T; $X_2$ is N, Y, H, or D; and $X_3$ is M, L, or V (SEQ ID NO:297); an HVR-H2 sequence comprising the amino acid sequence of $GISX_1X_2X_3X_4X_5X_6YYX_7X_8SX_9KG$, wherein $X_1$ is A or S; $X_2$ is G, S, or absent; $X_3$ is S, D or G; $X_4$ is G or S; $X_5$ is D, S, or G; $X_6$ is T or A; $X_7$ is P, G, V, I, A, or S; $X_8$ is A, D, or G; and $X_9$ is V or M (SEQ ID NO:298); and an HVR-H3 sequence comprising the amino acid sequence of ETWNHLFDY (SEQ ID NO:193); and/or a light chain variable (VL) domain comprising: an HVR-L1 sequence comprising the amino acid sequence of $SGGX_1X_2X_3SX_4YYX_5$, wherein $X_1$ is D, G, S, I, or absent; $X_2$ is S, W, G, Y, D, or absent; $X_3$ is S, Y, T, or D; $X_4$ is H, T, S, or Y; and $X_5$ is G or A (SEQ ID NO:299); an HVR-L2 sequence comprising the amino acid sequence of $SDX_1X_2RPX_3$, wherein $X_1$ is D or N; $X_2$ is E, K, or Q; and $X_3$ is S or P (SEQ ID NO:300); and an HVR-L3 sequence comprising the amino acid sequence of $X_1X_2YDX_3X_4X_5YX_6NX_7$, wherein $X_1$ is G or A; $X_2$ is G or A; $X_3$ is G, Y, Q, S, or A; $X_4$ is S, R, or T; $X_5$ is T or S; $X_6$ is A, I, V, L, or T; and $X_7$ is T, A, D, or P (SEQ ID NO:301). In other aspects, provided herein is an isolated antibody that binds an extracellular domain of a human SIRP-α polypeptide (e.g., the D1 domain), wherein the antibody comprises: a heavy chain variable (VH) domain comprising: a heavy chain variable (VH) domain comprising: an HVR-H1 sequence comprising the amino acid sequence of $SX_1AX_2S$, wherein $X_1$ is N or Y; and wherein $X_2$ is M, L, or V (SEQ ID NO:302); an HVR-H2 sequence comprising the amino acid sequence of $GISX_1GX_2X_3DTYYX_4X_5SVKG$, wherein $X_1$ is A or S; $X_2$ is G or absent; $X_3$ is S or G; $X_4$ is P, G, or V; and $X_5$ is A or D (SEQ ID NO:303); and an HVR-H3 sequence comprising the amino acid sequence of ETWNHLFDY (SEQ ID NO:193); and/or a light chain variable (VL) domain comprising: an HVR-L1 sequence comprising the amino acid sequence of $SGGX_1YSSYYYA$, wherein $X_1$ is S or A (SEQ ID NO:304); an HVR-L2 sequence comprising the amino acid sequence of SDDKRPS (SEQ ID NO:336); and an HVR-L3 sequence comprising the amino acid sequence of GGYDQSSYTNP (SEQ ID NO:172). In some embodiments, the VH domain comprises (i) an HVR-H1 sequence comprising the amino acid sequence of SNAMS (SEQ ID NO:194), SNAVS (SEQ ID NO:271), or SNALS (SEQ ID NO:318), (ii) an HVR-H2 sequence comprising the amino acid sequence of GISAGGSDTYYPASVKG (SEQ ID NO:195), and (iii) an HVR-H3 sequence comprising the amino acid sequence of ETWNHLFDY (SEQ ID NO:193). In some embodiments, the VH domain comprises an amino acid sequence that is at least 90% identical to the amino acid sequence of SEQ ID NO:135, 263, 264, or 330. In some embodiments, the VH domain comprises (i) an HVR-H1 sequence comprising the amino acid sequence of SNAMS (SEQ ID NO:194), SNAVS (SEQ ID NO:271), or SNALS (SEQ ID NO:318), (ii) an HVR-H2 sequence comprising the amino acid sequence of GISSGSDTYYGDSVKG (SEQ ID NO:197), and (iii) an HVR-H3 sequence comprising the amino acid sequence of ETWNHLFDY (SEQ ID NO:193). In some embodiments, the VH domain comprises an amino acid sequence that is at least 90% identical to the amino acid sequence of SEQ ID NO:137, 265, 266, or 331. In some embodiments, the VH domain comprises (i) an HVR-H1 sequence comprising the amino acid sequence of SYAMS (SEQ ID NO:200), SYAVS (SEQ ID NO:272), or SYALS (SEQ ID NO:319), (ii) an HVR-H2 sequence comprising the amino acid sequence of GISSGGDTYYVDSVKG (SEQ ID NO:201), and (iii) an HVR-H3 sequence comprising the amino acid sequence of ETWNHLFDY (SEQ ID NO:193). In some embodiments, the VH domain comprises an amino acid sequence that is at least 90% identical to the amino acid sequence of SEQ ID NO:139, 267, 268, or 332. In some embodiments, the VL domain comprises the sequence FW1-HVR-L1-FW2-HVR-L2-FW3-HVR-L3-FW4 (N-terminus to C-terminus), wherein FW1 comprises the amino acid sequence SYELTQPPSVSVSPGQTARITC (SEQ ID NO:314), FW2 comprises the amino acid sequence WYQQKPGQAPVTLIY (SEQ ID NO:315), FW3 comprises the amino acid sequence NIPERFSGSSSGTTVTLTISGVQAEDEADYYC (SEQ ID NO:316), and FW4 comprises the amino acid sequence FGGGTKLTVL (SEQ ID NO:317). In some embodiments, the VL domain comprises (i) an HVR-L1 sequence comprising the amino acid sequence of SGGSYSSYYYA (SEQ ID NO:170), (ii) an HVR-L2 sequence comprising the amino acid sequence of SDDKRPS (SEQ ID NO:336), and (iii) an HVR-L3 sequence comprising the amino acid sequence of GGYDQSSYTNP (SEQ ID NO:172). In some embodiments, the VL domain comprises an amino acid sequence that is at least 90% identical to the amino acid sequence of SEQ ID NO:252. In some embodiments, the VL domain comprises (i) an HVR-L1 sequence comprising the amino acid sequence of SGGAYSSYYYA (SEQ ID NO:261), (ii) an HVR-L2 sequence comprising the amino acid sequence of SDDKRPS (SEQ ID NO:336), and (iii) an HVR-L3 sequence comprising the amino acid sequence of GGYDQSSYTNP (SEQ ID NO:172). In some embodiments, the VL domain comprises an amino acid sequence that is at least 90% identical to the amino acid sequence of SEQ ID NO:262. In some embodiments, the VH domain comprises the amino acid sequence of SEQ ID NO:263, and the VL domain comprises the amino acid sequence of SEQ ID NO:252; the VH domain comprises the amino acid sequence of SEQ ID NO:264, and the VL domain comprises the amino acid sequence of SEQ ID NO:252; the VH domain comprises the amino acid sequence of SEQ ID NO:330, and the VL domain comprises the amino acid sequence of SEQ ID NO:252; the VH domain comprises the amino acid sequence of SEQ ID NO:135, and the VL domain comprises the amino acid sequence of SEQ ID NO:252; the VH domain comprises the amino acid sequence of SEQ ID NO:137, and the VL domain comprises the amino acid sequence of SEQ ID NO:252; the VH domain comprises the amino acid sequence of SEQ ID NO:139, and the VL domain comprises the amino acid sequence of SEQ ID NO:252; the VH domain comprises the amino acid sequence of SEQ ID NO:265, and the VL domain comprises the amino acid sequence of SEQ ID NO:252; the VH domain comprises the amino acid sequence of SEQ ID NO:266, and the VL domain comprises the amino acid sequence of SEQ ID NO:252; the VH domain comprises the amino acid sequence of SEQ ID NO:331, and the VL domain comprises the amino acid sequence of SEQ ID NO:252; the VH domain comprises the amino acid sequence of SEQ ID NO:267, and the VL domain comprises the amino acid sequence of SEQ ID NO:252; the VH domain comprises the amino acid sequence of SEQ ID NO:268, and the VL domain comprises the amino acid sequence of SEQ ID NO:252; the VH domain comprises the amino acid sequence of SEQ ID NO:332, and the VL domain comprises the amino acid sequence of SEQ ID NO:252; the VH domain comprises the amino acid sequence of SEQ ID NO:263, and the VL domain comprises the amino acid sequence of SEQ ID NO:262; the VH domain comprises the amino acid sequence of SEQ ID NO:264, and the VL domain comprises the amino acid sequence of SEQ ID NO:262; the VH domain comprises the amino acid sequence of SEQ ID NO:330, and the VL domain comprises the amino acid sequence of SEQ ID NO:262; the VH domain comprises the amino acid sequence of SEQ ID NO:265, and the VL domain comprises the amino acid sequence of SEQ ID NO:262; the VH domain comprises the amino acid sequence of SEQ ID NO:266, and the VL domain comprises the amino acid sequence of SEQ ID NO:262; the VH domain comprises the amino acid sequence of SEQ ID NO:331, and the VL domain comprises the amino acid sequence of SEQ ID NO:262; the VH domain comprises the amino acid sequence of SEQ ID NO:267, and the VL domain comprises the amino acid sequence of SEQ ID NO:262; the VH domain comprises the amino acid sequence of SEQ ID NO:268, and the VL domain comprises the amino acid sequence of SEQ ID NO:262; the VH domain comprises the amino acid sequence of SEQ ID NO:332, and the VL domain comprises the amino acid sequence of SEQ ID NO:262; the VH domain comprises the amino acid sequence of SEQ ID NO:135, and the VL domain comprises the amino acid sequence of SEQ ID NO:262; the VH domain comprises the amino acid sequence of SEQ ID NO:137, and the VL domain comprises the amino acid sequence of SEQ ID NO:262; or the VH domain comprises the amino acid sequence of SEQ ID NO:139, and the VL domain comprises the amino acid sequence of SEQ ID NO:262.

In other aspects, provided herein is an isolated antibody that binds an extracellular domain of a human SIRP-α polypeptide (e.g., the D1 domain), wherein the antibody binds to a human SIRP-α v1 polypeptide at one or more amino acid positions selected from the group consisting of I31, V33, Q52, K53, T67, R69, N70, and K96, according to SEQ ID NO:296. In some embodiments, the antibody binds to the human SIRP-α v1 polypeptide at I31, V33, Q52, K53, T67, R69, N70, and K96, according to SEQ ID NO:296. In some embodiments, the antibody further binds to the human SIRP-α v1 polypeptide at one or more amino acid positions selected from the group consisting of L30, P32, E54, T62, N71, M72, F74, and R95, according to SEQ ID NO:296. In some embodiments, the antibody further binds to the human SIRP-α v1 polypeptide at L30, P32, E54, T62, N71, M72, F74, and R95, according to SEQ ID NO:296.

In other aspects, provided herein is an isolated antibody that binds an extracellular domain of a human SIRP-α polypeptide (e.g., the D1 domain), wherein the antibody binds to a human SIRP-α v1 polypeptide at one or more amino acid positions selected from the group consisting of I7, P9, D10, K11, S12, A42, A108, and E111, according to SEQ ID NO:296. In some embodiments, the antibody binds to the human SIRP-α v1 polypeptide at K11, A42, A108, and E111, according to SEQ ID NO:296. In some embodiments, the antibody binds to the human SIRP-α v1 polypeptide at I7, P9, D10, K11, S12, A108, and E111, according to SEQ ID NO:296. In some embodiments, the antibody further binds to the human SIRP-α v1 polypeptide at one or more amino acid positions selected from the group consisting of L14, T26, T28, T88, Y90, S106, S113, and A116, according to SEQ ID NO:296. In some embodiments, the antibody further binds to the human SIRP-α v1 polypeptide at L14, T88, Y90, S106, S113, and A116 of human SIRP-α v1, according to SEQ ID NO:296. In some embodiments, the antibody further binds to the human SIRP-α v1 polypeptide at L14, T26, and T28, according to SEQ ID NO:296.

In other aspects, provided herein is an isolated antibody that binds an extracellular domain of a human SIRP-α polypeptide (e.g., the D1 domain), wherein the antibody binds to a human SIRP-α v1 polypeptide at one or more amino acid positions selected from the group consisting of E47, L48, P58, R59, T82, and A84, according to SEQ ID NO:296. In some embodiments, the antibody binds to the human SIRP-α v1 polypeptide at E47, L48, P58, R59, T82, and A84, according to SEQ ID NO:296. In some embodiments, the antibody further binds to the human SIRP-α v1 polypeptide at one or more amino acid positions selected from the group consisting of A17, P44, G45, I49, E54, G55, H56, F57, and P83, according to SEQ ID NO:296. In some embodiments, the antibody further binds to the human SIRP-α v1 polypeptide at A17, P44, G45, I49, E54, G55, H56, F57, and P83 of human SIRP-α v1, according to SEQ ID NO:296.

In other aspects, provided herein is an isolated antibody that binds an extracellular domain of a human SIRP-α polypeptide (e.g., the D1 domain), wherein the antibody binds the extracellular domain of a human SIRP-α v1 polypeptide with a dissociation constant ($K_D$) of less than 100 nM, and wherein the antibody blocks binding between an extracellular domain of a human SIRP-α polypeptide and an IgSF domain of a human CD47 polypeptide. In some embodiments, the antibody binds the extracellular domain of a human SIRP-α v2 polypeptide with a dissociation constant ($K_D$) of less than 100 nM. In some embodiments, the antibody binds the D1 domain of a human SIRP-α v1 polypeptide and the D1 domain of a human SIRP-α v2 polypeptide. In some embodiments, the antibody binds an extracellular domain of a cynomolgus SIRP-α polypeptide. In some embodiments, the antibody binds an extracellular domain of a human SIRP-β polypeptide. In some embodiments, the antibody binds an extracellular domain of a human SIRP-γ polypeptide. In some embodiments, the antibody binds an extracellular domain of a murine SIRP-α polypeptide.

In other aspects, provided herein is an isolated antibody that binds an extracellular domain of a human SIRP-α polypeptide (e.g., the D1 domain), wherein the antibody binds the D1 domain of a human SIRP-α polypeptide, and wherein the antibody does not block binding between an extracellular domain of a human SIRP-α polypeptide and an IgSF domain of a human CD47 polypeptide. In some embodiments, the antibody binds the D1 domain of a human SIRP-α with a dissociation constant ($K_D$) of less than 100 nM. In some embodiments, the antibody binds the D1 domain of a human SIRP-α v1 polypeptide with a dissociation constant ($K_D$) of less than 100 nM and/or binds the D1 domain of a human SIRP-α v2 polypeptide with a dissociation constant ($K_D$) of less than 100 nM. In some embodiments, the antibody binds the D1 domain of a human SIRP-α v1 polypeptide and the D1 domain of a human SIRP-α v2 polypeptide. In some embodiments, the antibody binds an extracellular domain of a cynomolgus SIRP-α polypeptide. In some embodiments, the antibody binds an extracellular domain of a human SIRP-β polypeptide. In some embodiments, the antibody binds an extracellular domain of a murine SIRP-α polypeptide.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of an antibody selected from the group consisting of antibodies 119, 120, 121, 122, 21, 25, 27, 66, and 135. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising: (a) a heavy chain variable (VH) domain comprising the amino acid sequence of SEQ ID NO:120 and a light chain variable (VL) domain comprising the amino acid sequence of SEQ ID NO:97; (b) a heavy chain variable (VH) domain comprising the amino acid sequence of SEQ ID NO:121 and a light chain variable (VL) domain comprising the amino acid sequence of SEQ ID NO:98; (c) a heavy chain variable (VH) domain comprising the amino acid sequence of SEQ ID NO:130 and a light chain variable (VL) domain comprising the amino acid sequence of SEQ ID NO:107; (d) a heavy chain variable (VH) domain comprising the amino acid sequence of SEQ ID NO:122 and a light chain variable (VL) domain comprising the amino acid sequence of SEQ ID NO:99; (e) a heavy chain variable (VH) domain comprising the amino acid sequence of SEQ ID NO:135 and a light chain variable (VL) domain comprising the amino acid sequence of SEQ ID NO:136; (f) a heavy chain variable (VH) domain comprising the amino acid sequence of SEQ ID NO:137 and a light chain variable (VL) domain comprising the amino acid sequence of SEQ ID NO:138; (g) a heavy chain variable (VH) domain comprising the amino acid sequence of SEQ ID NO:139 and a light chain variable (VL) domain comprising the amino acid sequence of SEQ ID NO:140; (h) a heavy chain variable (VH) domain comprising the amino acid sequence of SEQ ID NO:141 and a light chain variable (VL) domain comprising the amino acid sequence of SEQ ID NO:142; or (i) a heavy chain variable (VH) domain comprising the amino acid sequence of SEQ ID NO:127 and a light chain variable (VL) domain comprising the amino acid sequence of SEQ ID NO:104.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of an antibody selected from the group consisting of antibodies 136 and 137. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising: (a) a heavy chain variable (VH) domain comprising the amino acid sequence of SEQ ID NO:133 and a light chain variable (VL) domain comprising the amino acid sequence of SEQ ID NO:134; or (b) a heavy chain variable (VH) domain comprising the amino acid sequence of SEQ ID NO:128 and a light chain variable (VL) domain comprising the amino acid sequence of SEQ ID NO:105.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of an antibody selected from the group consisting of antibodies 3, 213, 173, and 209. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising: (a) a heavy chain variable (VH) domain comprising the amino acid sequence of SEQ ID NO:242 and a light chain variable (VL) domain comprising the amino acid sequence of SEQ ID NO:243; (b) a heavy chain variable (VH) domain comprising the amino acid sequence of SEQ ID NO:275 and a light chain variable (VL) domain comprising the amino acid sequence of SEQ ID NO:276; (c) a heavy chain variable (VH) domain comprising the amino acid sequence of SEQ ID NO:278 and a light chain variable (VL) domain comprising the amino acid sequence of SEQ ID NO:279; or (d) a heavy chain variable (VH) domain comprising the amino acid sequence of SEQ ID NO:280 and a light chain variable (VL) domain comprising the amino acid sequence of SEQ ID NO:281.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of an antibody selected from the group consisting of antibodies 115, 116, 117, 118, and 132. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising: (a) a heavy chain variable (VH) domain comprising the amino acid sequence of SEQ ID NO:116 and a light chain variable (VL) domain comprising the amino acid sequence of SEQ ID NO:93; (b) a heavy chain variable (VH) domain comprising the amino acid sequence of SEQ ID NO:117 and a light chain variable (VL) domain comprising the amino acid sequence of SEQ ID NO:94; (c) a heavy chain variable (VH) domain comprising the amino acid sequence of SEQ ID NO:118 and a light chain variable (VL) domain comprising the amino acid sequence of SEQ ID NO:95; (d) a heavy chain variable (VH) domain comprising the amino acid sequence of SEQ ID NO:119 and a light chain variable (VL) domain comprising the amino acid sequence of SEQ ID NO:96; or (e) a heavy chain variable (VH) domain comprising the amino acid sequence of SEQ ID NO:282 and a light chain variable (VL) domain comprising the amino acid sequence of SEQ ID NO:283.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of an antibody selected from the group consisting of antibodies 218, 123, 149, 161, 162, and 194. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising: (a) a heavy chain variable (VH) domain comprising the amino acid sequence of SEQ ID NO:284 and a light chain variable (VL) domain comprising the amino acid sequence of SEQ ID NO:285; (b) a heavy chain variable (VH) domain comprising the amino acid sequence of SEQ ID NO:123 and a light chain variable (VL) domain comprising the amino acid sequence of SEQ ID NO:100; (c) a heavy chain variable (VH) domain comprising the amino acid sequence of SEQ ID NO:286 and a light chain variable (VL) domain comprising the amino acid sequence of SEQ ID NO:287; (d) a heavy chain variable (VH) domain comprising the amino acid sequence of SEQ ID NO:288 and a light chain variable (VL) domain comprising the amino acid sequence of SEQ ID NO:289; (e) a heavy chain variable (VH) domain comprising the amino acid sequence of SEQ ID NO:290 and a light chain variable (VL) domain comprising the amino acid sequence of SEQ ID NO:291; or (f) a heavy chain variable (VH) domain comprising the amino acid sequence of SEQ ID NO:292 and a light chain variable (VL) domain comprising the amino acid sequence of SEQ ID NO:293.

In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain and a light chain variable (VL) domain of antibody 45. In other aspects, provided herein is an isolated antibody that binds an extracellular domain of a human SIRP-α polypeptide (e.g., the D1 domain), wherein the antibody competes for binding the extracellular domain of the human SIRP-α polypeptide with a reference anti-SIRP-α antibody comprising a heavy chain variable (VH) domain comprising the amino acid sequence of SEQ ID NO:244 and a light chain variable (VL) domain comprising the amino acid sequence of SEQ ID NO:245.

In some embodiments of any of the above embodiments, the antibody enhances phagocytosis by a macrophage expressing a human SIRP-α polypeptide. In some embodiments, the antibody enhances activation of a dendritic cell expressing a human SIRP-α polypeptide. In some embodiments, the antibody inhibits in vivo growth of a tumor that expresses CD47. In some embodiments, the antibody does not prevent interactions between a CD47-expressing cell and a T cell.

In some embodiments of any of the above embodiments, the antibody is a monoclonal antibody. In some embodiments, the antibody is a scFv-Fc, single domain antibody, single heavy chain antibody, or single light chain antibody. In some embodiments, the antibody comprises a light chain constant region comprising the amino acid sequence of SEQ ID NO:325, 326, or 426. In some embodiments, the antibody comprises an amino acid sequence selected from the group consisting of SEQ ID NOs:320-324. In some embodiments, the antibody comprises an Fc region. In some embodiments, the Fc region is a human Fc region selected from the group consisting of an IgG1 Fc region, an IgG2 Fc region, and an IgG4 Fc region. In some embodiments, the Fc region comprises a human IgG1 Fc region comprising one or more mutations selected from the group consisting of L234A, L235A, L235E, G237A, and N297A, according to EU numbering. In some embodiments, the Fc region comprises a human IgG2 Fc region comprising one or more mutations selected from the group consisting of A330S, P331S and N297A, according to EU numbering. In some embodiments, the Fc region comprises a human IgG4 Fc region comprising one or more mutations selected from the group consisting of S228P, E233P, F234V, L235A, L235E, delG236, and N297A, according to EU numbering. In some embodiments, the antibody is an antibody fragment selected from the group consisting of a Fab, F(ab')2, Fab'-SH, Fv, and scFv fragment. In some embodiments, the antibody is conjugated to a cytotoxic agent or label.

In some embodiments, the antibody is a bispecific antibody. In some embodiments, the antibody comprises a first antigen binding domain that binds an extracellular domain (e.g., the D1 domain) of a human SIRP-α polypeptide and a second antigen binding domain that binds an antigen expressed by a cancer cell. In some embodiments, the antigen expressed by the cancer cell is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PD-L1, PTK7, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. In some embodiments, the antibody is a chicken, humanized, chimeric, or human antibody. In some embodiments, the antibody is generated by or derived from a chicken.

Further provided herein are polynucleotides comprising the antibody according to any one of the above embodiments. Further provided herein are vectors comprising the polynucleotide according to any one of the above embodiments. Further provided herein are host cells comprising the polynucleotide or vector according to any one of the above embodiments. Further provided herein are methods of producing an antibody, comprising culturing the host cell according to any one of the above embodiments such that the antibody is produced. In some embodiments, the methods further include recovering the antibody from the host cell.

Further provided herein are methods of treating or delaying progression of cancer in an individual, the methods comprising administering to the individual an effective amount of the antibody according to any one of the above embodiments. In some embodiments, the methods further comprise administering to the individual an effective amount of a second antibody. In some embodiments, the second antibody binds an antigen expressed by a cancer cell. In some embodiments, the antigen expressed by the cancer cell is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. In some embodiments, the methods further comprise administering to the individual an effective amount of an immunotherapeutic agent. In some embodiments, the immunotherapeutic agent comprises a second antibody. In some embodiments, the second antibody binds to an antigen selected from the group consisting of PD-1, PD-L1, OX40, CTLA-4, CD137/4-1BB, TNFR2, B7-H3, FZD7, CD27, CCR4, CSF1R, CSF, TIM-3, LAG-3, VISTA, ICOS, CCR2, IDO, A2R, CD39, CD73, TIGIT, CD80, CD47, arginase, TDO, and PVRIG. In some embodiments, the first antibody binds the extracellular domain of a human SIRP-α v1 polypeptide, the extracellular domain of a human SIRP-α v2 polypeptide, or the extracellular domains of both a human SIRP-α v1 polypeptide and a human SIRP-α v2 polypeptide with a dissociation constant ($K_D$) of less than 100 nM, wherein the first antibody blocks binding between an extracellular domain of a human SIRP-α polypeptide and an IgSF domain of a human CD47 polypeptide, and wherein the second antibody binds to PD-1. In some embodiments, the first antibody binds the D1 domain of a human SIRP-α polypeptide, wherein the first antibody does not block binding between an extracellular domain of a human SIRP-α polypeptide and an IgSF domain of a human CD47 polypeptide, and wherein the second antibody binds to PD-1. In some embodiments, the first antibody binds the extracellular domain of a human SIRP-α v1 polypeptide with a dissociation constant ($K_D$) of less than 100 nM, wherein the first antibody blocks binding between an extracellular domain of a human SIRP-α polypeptide and an IgSF domain of a human CD47 polypeptide, and wherein the second antibody binds to PD-L1. In some embodiments, the first antibody binds the D1 domain of a human SIRP-α polypeptide, wherein the first antibody does not block binding between an extracellular domain of a human SIRP-α polypeptide and an IgSF domain of a human CD47 polypeptide, and wherein the second antibody binds to PD-L1. In some embodiments, the individual is a human.

Further provided herein are methods of treating or delaying progression of an autoimmune disease or an inflammatory disease in an individual, the methods comprising administering to the individual an effective amount of the antibody according to any one of the above embodiments. In some embodiments, the autoimmune disease or inflammatory disease is selected from the group consisting of multiple sclerosis, rheumatoid arthritis, a spondyloarthropathy, systemic lupus erythematosus, an antibody-mediated inflammatory or autoimmune disease, graft versus host disease, sepsis, diabetes, psoriasis, psoriatic arthritis, atherosclerosis, Sjogren's syndrome, progressive systemic sclerosis, scleroderma, acute coronary syndrome, ischemic reperfusion, Crohn's Disease, ulcerative colitis, endometriosis, glomerulonephritis, IgA nephropathy, polycystic kidney disease, myasthenia gravis, idiopathic pulmonary fibrosis, asthma, atopic dermatitis, acute respiratory distress syndrome (ARDS), vasculitis, and inflammatory autoimmune myositis. In some embodiments, the individual is a human.

Further provided herein are methods of identifying an antigen binding domain that binds an extracellular domain (e.g., the D1 domain) of a human SIRP-α polypeptide and does not block binding between human CD47 and the human SIRP-α polypeptide, the methods comprising (a) providing an antigen binding domain that binds the extracellular domain (e.g., the D1 domain) of a human SIRP-α polypeptide; (b) assembling a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; (c) contacting the antigen binding domain with the assembled complex; and (d) detecting binding of the antigen binding domain to the complex, wherein binding of the antigen binding domain to the complex indicates that the antigen binding domain does not block binding between human CD47 and the human SIRP-α polypeptide. Further provided herein are methods of identifying an antibody or antigen binding domain that binds an extracellular domain (e.g., the D1 domain) of a human SIRP-α polypeptide and does not block binding between human CD47 and the human SIRP-α polypeptide, the methods comprising contacting an antibody or antigen binding domain that binds the extracellular domain (e.g., the D1 domain) of a human SIRP-α polypeptide with a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; and detecting binding of the antigen binding domain to the complex, wherein binding of the antigen binding domain to the complex indicates that the antigen binding domain does not block binding between human CD47 and the human SIRP-α polypeptide. Further provided herein are methods of identifying an antigen binding domain that binds an extracellular domain (e.g., the D1 domain) of a human SIRP-α polypeptide and blocks binding between human CD47 and the human SIRP-α polypeptide, the methods comprising (a) providing an antigen binding domain that binds the extracellular domain (e.g., the D1 domain) of a human SIRP-α polypeptide; (b) assembling a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; (c) contacting the antigen binding domain with the assembled complex; and (d) detecting binding of the antigen binding domain to the complex, wherein a lack of binding of the antigen binding domain to the complex indicates that the antigen binding domain blocks binding between human CD47 and the human SIRP-α polypeptide. Further provided herein are methods of identifying an antibody or antigen binding domain that binds an extracellular domain (e.g., the D1 domain) of a human SIRP-α polypeptide and blocks binding between human CD47 and the human SIRP-α polypeptide, the methods comprising contacting an antibody or antigen binding domain that binds the extracellular domain (e.g., the D1 domain) of a human SIRP-α polypeptide with a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; and (d) detecting binding of the antigen binding domain to the complex, wherein a lack of binding of the antigen binding domain to the complex indicates that the antigen binding domain blocks binding between human CD47 and the human SIRP-α polypeptide. In some embodiments, the SIRP-α D1 variant comprises an amino acid sequence selected from the group consisting of SEQ ID NOs:17-52. In some embodiments, the IgSF domain of CD47 comprises the amino acid sequence of SEQ ID NO:16. In some embodiments, the polypeptide comprising the IgSF domain of CD47 comprises a human CD47 extracellular domain. In some embodiments, the polypeptide comprising the IgSF domain of CD47 further comprises an antibody Fc region.

Further provided herein are methods of producing an anti-SIRP-α antibody that binds the extracellular domain (e.g., the D1 domain) of a human SIRP-α polypeptide, the methods comprising: (a) immunizing a chicken with a peptide comprising at least a portion of a human SIRP-α extracellular domain (e.g., the D1 domain); (b) obtaining an antibody from an antibody-producing cell from the immunized chicken; and (c) detecting binding between the antibody obtained from the cell and the extracellular domains (e.g., the D1 domains) of a human SIRP-α polypeptide, wherein binding between the antibody and the extracellular domain (e.g., the D1 domain) of the human SIRP-α polypeptide indicates that the antibody is an anti-SIRP-α antibody that binds the extracellular domain (e.g., the D1 domain) of a human SIRP-α variant polypeptide. In some embodiments, the antibody is a chicken, humanized, chimeric, or human antibody. In some embodiments, the antibody binds the extracellular domain (e.g., the D1 domain) of a human SIRP-α v1 polypeptide, the extracellular domain (e.g., the D1 domain) of a human SIRP-α v2 polypeptide, or both. In some embodiments, the antibody binds an extracellular domain (e.g., the D1 domain) of a human SIRP-α v1 polypeptide comprising the amino acid sequence of EEELQVIQPDKSVLVAAGETATLRCTATSLIPVG-PIQWFRGAGPGRELIYNQKEGHFPR VTTVSDLTKRNNMDFSIRIGNIT-PADAGTYYCVKFRKGSPDDVEFKSGAGTELSVRAK PS (SEQ ID NO:5). In some embodiments, the antibody binds an extracellular domain (e.g., the D1 domain) of a human SIRP-α v2 polypeptide comprising the amino acid sequence of EEELQVIQPDKSVSVAAGESAILHCTVT-SLIPVGPIQWFRGAGPARELIYNQKEGHFPRV TTVS-ESTKRENMDFSISISNIT-PADAGTYYCVKFRKGSPDTEFKSGAGTELSVRAKPS (SEQ ID NO:6). In some embodiments, the antibody binds an extracellular domain (e.g., the D1 domain) of a human SIRP-α v1 polypeptide comprising the amino acid sequence of EEELQVIQPDKSVLVAAGETATLRCTATSLIPVG-PIQWFRGAGPGRELIYNQKEGHFPR VTTVSDLTKRNNMDFSIRIGNIT-PADAGTYYCVKFRKGSPDDVEFKSGAGTELSVRAK PS (SEQ ID NO:5) and binds an extracellular domain (e.g., the D1 domain) of a human SIRP-α v2 polypeptide comprising the amino acid sequence of EEELQVIQPDKSVSVAAGESAILHCTVTSLIPVG-PIQWFRGAGPARELIYNQKEGHFPRV TTVSES-TKRENMDFSISISNIT-PADAGTYYCVKFRKGSPDTEFKSGAGTELSVRAKPS (SEQ ID NO:6). In some embodiments, the antibody binds the extracellular domains (e.g., the D1 domains) of three, four, five, six, seven, eight, nine or ten different human SIRP-α variant polypeptides. In some embodiments, each of the three, four, five, six, seven, eight, nine or ten different human SIRP-α variant polypeptides comprises an extracellular domain (e.g., the D1 domain) comprising an amino acid sequence selected from the group consisting of SEQ ID NOs: 5, 6, and 76-83. In some embodiments, the methods further comprise detecting binding between the antibody obtained from the cell and an extracellular domain (e.g., the D1 domain) of one or more SIRP-α polypeptides selected from the group consisting of a monkey SIRP-α polypeptide, a murine SIRP-α polypeptide, a human SIRP-β polypeptide, and a human SIRP-γ polypeptide. In some embodiments, the antibody binds an extracellular domain (e.g., the D1 domain) of a monkey SIRP-α polypeptide. In some embodiments, the monkey SIRP-α polypeptide is a cynomolgus SIRP-α polypeptide. In some embodiments, the antibody binds the extracellular domains (e.g., the D1 domains) of at least two different monkey SIRP-α variant polypeptides. In some embodiments, the antibody binds an extracellular domain (e.g., the D1 domain) of a cynomolgus SIRP-α polypeptide comprising the amino acid sequence of SEQ ID NO:11, an extracellular domain (e.g., the D1 domain) of a cynomolgus SIRP-α polypeptide comprising the amino acid sequence of SEQ ID NO:12, or both. In some embodiments, the antibody binds an extracellular domain (e.g., the D1 domain) of a murine SIRP-α polypeptide. In some embodiments, the antibody binds the extracellular domains (e.g., the D1 domains) of two or more different murine SIRP-α variant polypeptides. In some embodiments, the antibody binds an extracellular domain (e.g., the D1 domain) of one or more murine SIRP-α polypeptides, and wherein the one or more murine SIRP-α polypeptides each comprise an amino acid sequence selected from the group consisting of SEQ ID NOs: 7-10. In some embodiments, the antibody binds an extracellular domain (e.g., the D1 domain) of a human SIRP-β polypeptide. In some embodiments, the antibody binds an extracellular domain (e.g., the D1 domain) of a human SIRP-γ polypeptide. In some embodiments, the antibody does not bind an extracellular domain (e.g., the D1 domain) of a human SIRP-0 polypeptide. In some embodiments, the antibody does not bind an extracellular domain (e.g., the D1 domain) of a human SIRP-γ polypeptide. In some embodiments, the antibody binds the extracellular domain (e.g., the D1 domain) of a human SIRP-0 polypeptide comprising the amino acid sequence of SEQ ID NO:13, the extracellular domain (e.g., the D1 domain) of a human SIRP-β polypeptide comprising the amino acid sequence of SEQ ID NO:14, or both. In some embodiments, the antibody binds the extracellular domain (e.g., the D1 domain) of a human SIRP-γ polypeptide comprising the amino acid sequence of SEQ ID NO:15. In some embodiments, the methods further comprise detecting binding or a lack of binding between the antibody obtained from the cell and a complex comprising a SIRP-α D1 variant bound to an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47. In some embodiments, the antibody binds a complex comprising a SIRP-α D1 variant bound to an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47. In some embodiments, the antibody does not block binding between an extracellular domain (e.g., the D1 domain) of a human SIRP-α polypeptide and an IgSF domain of a human CD47 polypeptide. In some embodiments, the antibody does not block binding between an extracellular domain (e.g., the D1 domain) of a human SIRP-α polypeptide expressed on the surface of a first cell and an IgSF domain of a human CD47 polypeptide expressed on the surface of a second cell. In some embodiments, the antibody does not bind a complex comprising a SIRP-α D1 variant bound to an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47. In some embodiments, the antibody blocks binding between an extracellular domain (e.g., the D1 domain) of a human SIRP-α polypeptide and an IgSF domain of a human CD47 polypeptide. In some embodiments, the antibody blocks binding between an extracellular domain (e.g., the D1 domain) of a human SIRP-α polypeptide expressed on the surface of a first cell and an IgSF domain of a human CD47 polypeptide expressed on the surface of a second cell. In some embodiments, binding of the antibody to an extracellular domain (e.g., the D1 domain) of a human SIRP-α polypeptide reduces affinity of the human SIRP-α polypeptide for binding an IgSF domain of a human CD47 polypeptide. In some embodiments, binding of the antibody to an extracellular domain (e.g., the D1 domain) of a human SIRP-α polypeptide expressed on the surface of a first cell reduces affinity of the human SIRP-α polypeptide for binding an IgSF domain of a human CD47 polypeptide expressed on the surface of a second cell. In some embodiments, binding of the antibody to an extracellular domain (e.g., the D1 domain) of a human SIRP-α polypeptide increases $k_{off}$ of the human SIRP-α polypeptide for binding an IgSF domain of a human CD47 polypeptide. In some embodiments, binding of the antibody to an extracellular domain (e.g., the D1 domain) of a human SIRP-α polypeptide expressed on the surface of a first cell increases $k_{off}$ of the human SIRP-α polypeptide for binding an IgSF domain of a human CD47 polypeptide expressed on the surface of a second cell. In some embodiments, the antibody modulates SIRP-α signaling in a cell expressing a human SIRP-α polypeptide. In some embodiments, the cell is a leukocyte selected from the group consisting of a macrophage, a dendritic cell, a neutrophil, an eosinophil, and a myeloid-derived suppressor cell (MDSC). In some embodiments, the antibody inhibits SIRP-α signaling in a macrophage expressing a human SIRP-α polypeptide. In some embodiments, the antibody enhances phagocytosis by a macrophage expressing a human SIRP-α polypeptide.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A shows an alignment among the D1 domains of 10 different human SIRP-α variant polypeptides. Sequences shown correspond to SEQ ID NOs: 5, 6, and 76-83 (from top to bottom). Amino acid differences are indicated by asterisks.

FIG. 1B shows an alignment between human v1, human v2, cynomolgus monkey, and 129 mouse SIRP-α D1 domains. Sequences shown correspond to SEQ ID NOs: 5, 6, 11, and 7 (from top to bottom). Amino acid differences are indicated by asterisks.

FIG. 1C shows alignments between various human and mouse SIRP-α D1 domains, with R1, R2 and R3 loops indicated. Shown is an alignment between human v1, human v2, 129 mouse, NOD mouse, C57BL/6 mouse, and BALB/c mouse SIRP-α D1 domains. Sequences shown correspond to SEQ ID NOs: 5-10 (from top to bottom). Amino acid differences are indicated by asterisks.

FIG. 2 shows an alignment between human v1, human v2, cynomolgus monkey, 129 mouse, and chicken SIRP-α D1 domains. Sequences shown correspond to SEQ ID NOs: 5, 6, 11, 7, and 84 (from top to bottom). Amino acid differences are indicated by asterisks.

FIGS. 3A & 3B show binding specificity of antibody clone S130 for a variety of SIRP peptides. FIG. 3A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants bound to the IgSF domain of CD47 (SEQ ID NO:16). The pre-formed complex was generated by mixing two high affinity human SIRP-α v1 and v2 polypeptides (SEQ ID NOs: 17 and 19) in a 1:1 ratio and combining the mixture with CD47 to generate the SIRP-α:CD47 complex. The pre-formed complex SIRP-α:CD47 complex for FIGS. 4A-9B are also prepared similarly. FIG. 3B summarizes the binding specificity of the clone against each of these targets ("+" indicates binding; "–" indicates non-binding).

FIGS. 4A & 4B show binding specificity of antibody clone S121 for a variety of SIRP peptides. FIG. 4A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 4B summarizes the binding specificity of the clone against each of these targets ("+" indicates binding; "–" indicates non-binding).

FIGS. 5A & 5B show binding specificity of antibody clone S137 for a variety of SIRP peptides. FIG. 5A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 5B summarizes the binding specificity of the clone against each of these targets ("+" indicates binding; "−" indicates non-binding).

FIGS. 6A & 6B show binding specificity of antibody clone S128 for a variety of SIRP peptides. FIG. 6A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 6B summarizes the binding specificity of the clone against each of these targets ("+" indicates binding; "−" indicates non-binding).

FIGS. 7A & 7B show binding specificity of antibody clone S135 for a variety of SIRP peptides. FIG. 7A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 7B summarizes the binding specificity of the clone against each of these targets ("+" indicates binding; "−" indicates non-binding).

FIGS. 8A & 8B show binding specificity of antibody clone S126 for a variety of SIRP peptides. FIG. 8A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 8B summarizes the binding specificity of the clone against each of these targets ("+" indicates binding; "−" indicates non-binding).

FIGS. 9A & 9B show binding specificity of antibody clone S138 for a variety of SIRP peptides. FIG. 9A shows the ELISA binding curves for the antibody against the human v1, human v2, murine, and cynomolgus SIRPα D1 domains, as well as human SIRPγ (SEQ ID NO:15) and a pre-formed complex of high-affinity SIRP-α variants (SEQ ID NO:17 and 19) bound to the IgSF domain of CD47 (SEQ ID NO:16). FIG. 9B summarizes the binding specificity of the clone against each of these targets ("+" indicates binding; "−" indicates non-binding).

FIGS. 10A-10C show an alignment of VH and VL domains of the scFv-Fc clones obtained from a wild-type chicken. SEQ ID NOs:53-60 are shown (in order from top to bottom in the alignment). CDR and linker sequences are indicated by lines. Amino acid differences are indicated by asterisks.

FIGS. 10D-10F show an alignment of VH and VL domains of the scFv-Fc clones obtained from a chicken that produces human antibodies. SEQ ID NOs:61-74 are shown (in order from top to bottom in the alignment). CDR and linker sequences are indicated by lines. Amino acid differences are indicated by asterisks.

FIGS. 11A-11D show an alignment of VH and VL domains of Family 2 clones. The amino acid sequences of the VH domains are SEQ ID NOs: 294, 139, 358, 362, 354, 380, 384, 350, 137, 374, 356, 352, 135, 348, 376, 346, 342, 344, 141, 360, 370, 382, 364, 366, 368, 372, and 378 (in order from top to bottom in the alignment). The amino acid sequences of the VL domains are SEQ ID NOs 295, 363, 140, 359, 355, 351, 136, 349, 377, 138, 375, 357, 353, 381, 385, 345, 365, 367, 369, 347, 142, 343, 371, 379, 383, 361, and 373 (in order from top to bottom in the alignment). HVR sequences are indicated by lines. The HVRs are according to Kabat. Amino acid differences are indicated by asterisks.

FIGS. 11E-11F show an alignment of VH and VL domains of Family 3 clones. The amino acid sequences of the VH domains are SEQ ID NOs: 133, 128, 396, 386, 398, 402, 392, 388, 390, 394, and 400 (in order from top to bottom in the alignment). The amino acid sequences of the VL domains are SEQ ID NOs 134, 105, 387, 389, 395, 397, 399, 403, 391, 393, and 401 (in order from top to bottom in the alignment). HVR sequences are indicated by lines. The HVRs are according to Kabat. Amino acid differences are indicated by asterisks.

FIGS. 11G & 11H show an alignment of VH and VL domains of Family 4 clones. The amino acid sequences of the VH domains are SEQ ID NOs:116, 117, 118, 119, 282, 404, and 406 (in order from top to bottom in the alignment). The amino acid sequences of the VL domains are SEQ ID NOs 93, 94, 95, 96, 283, 405, and 407 (in order from top to bottom in the alignment). HVR sequences are indicated by lines. The HVRs are according to Kabat. Amino acid differences are indicated by asterisks.

FIG. 11I shows an alignment of VH and VL domains of Family 5, Bin 4 clones. The amino acid sequences of the VH domains are SEQ ID NOs: 278 and 412 (in order from top to bottom in the alignment). The amino acid sequences of the VL domains are SEQ ID NOs 279 and 413 (in order from top to bottom in the alignment). HVR sequences are indicated by lines. The HVRs are according to Kabat. Amino acid differences are indicated by asterisks.

FIG. 11J shows an alignment of VH and VL domains of additional Family 5, Bin 4 clones. The amino acid sequences of the VH domains are SEQ ID NOs: 275 and 414 (in order from top to bottom in the alignment). The amino acid sequences of the VL domains are SEQ ID NOs: 276 and 415 (in order from top to bottom in the alignment). HVR and linker sequences are indicated by lines. The HVRs are according to Kabat. Amino acid differences are indicated by asterisks.

FIG. 11K shows the sequences of VH and VL domains (SEQ ID NOs 280 and 281, respectively of Family 5, Bin 4 clone S209. The HVR sequences are underlined.

FIG. 11L shows an alignment of VH and VL domains of Family 5, Bin 5 clones. The amino acid sequences of the VH domains are SEQ ID NOs: 123 and 292 (in order from top to bottom in the alignment). The amino acid sequences of the VL domains are SEQ ID NOs 100 and 293 (in order from top to bottom in the alignment). HVR sequences are indicated by lines. The HVRs are according to Kabat. Amino acid differences are indicated by asterisks.

FIG. 11M shows an alignment of VH and VL domains of additional Family 5, Bin 5 clones. The amino acid sequences of the VH domains are SEQ ID NOs: 288, 290, 408, and 410 (in order from top to bottom in the alignment). The amino acid sequences of the VL domains are SEQ ID NOs: 289, 291, 409, and 411 (in order from top to bottom in the alignment). HVR sequences are indicated by lines. The HVRs are according to Kabat. Amino acid differences are indicated by asterisks.

FIG. 11N shows the sequences of VH and VL domains of clone 149 (SEQ ID NOs 286 and 287, respectively) and clone 218 (SEQ ID NOs 284 and 285, respectively. HVR sequences are underlined.

FIGS. 11O & 11P show an alignment of VH and VL domains of Family 1 clones. The amino acid sequences of the VH domains are SEQ ID NOs: 120, 121, 130, and 122

(in order from top to bottom in the alignment). The amino acid sequences of the VL domains are SEQ ID NOs: 97, 98, 107, and 99 (in order from top to bottom in the alignment). HVR sequences are indicated by lines. The HVRs are according to Kabat. Amino acid differences are indicated by asterisks.

FIGS. 12A-12C show surface plasmon resonance (SPR) binding profiles of representative antibody clones binding a pre-formed complex of a high affinity SIRP-α variant (SEQ ID NO:18) mixed with increasing concentrations of the IgSF domain of CD47 (SEQ ID NO:16). FIG. 12A shows the binding curve of an antibody clone (S123) that does not block CD47 binding to SIRP-α (e.g., a non-blocking antibody). FIG. 12B shows the binding curve of an antibody clone (S119) that blocks CD47 binding to SIRP-α (e.g., a blocking antibody). FIG. 12C shows the binding curve of an antibody clone (S118) that binds to SIRP-α and reduces its affinity for binding CD47 (e.g., a "kick off" antibody).

FIGS. 13A-13G show the results of in vitro tumor cell phagocytosis assays using macrophages treated with anti-SIRP-α antibody (at indicated series of concentrations), cetuximab or trastuzumab, anti-SIRP-α antibody plus cetuximab or trastuzumab, or control antibody (IgG1, κ), as indicated. Macrophages that had phagocytosed tumor cells were identified as cells positive for CD33, CD206, and CFSE by flow cytometry. Tumor cells assayed were DLD-1 (FIGS. 13A-13D & 13G) or OE19 cells (FIGS. 13E & 13F). Anti-SIRP-α antibodies tested were AB3a (FIGS. 13A & 13B), AB45a (FIGS. 13C & 13D), AB119a (FIG. 13E), AB135a (FIG. 13F), and AB136c (FIG. 13G).

FIG. 14 shows the results of in vivo dendritic cell activation assays on dendritic cells isolated from the spleens of Balb/c mice treated with anti-SIRP-α antibody AB136b, control rat anti-mouse anti-SIRP-α antagonistic antibody (clone p84), rat IgG control, or mouse IgG control, as indicated. Mice were intravenously injected with the indicated antibody at 10 mg/kg, and spleens were harvested five hours after injection. Activation marker CD86 on dendritic cells was measured by flow cytometry.

FIG. 15 shows the results of an in vivo syngeneic mouse colon carcinoma model to assess single agent activity. MC38 cells were implanted subcutaneously in C57BL/6 mice and randomized into groups (8 mice/group). Mice were treated with vehicle (PBS), CD47 blocking anti-SIRP-α antibody AB25b, CD47 blocking anti-SIRP-α antibody AB25c, CD47 blocking anti-SIRP-α antibody AB27b, CD47 non-blocking anti-SIRP-α antibody AB3b, or CD47 non-blocking anti-SIRP-α antibody 136b. Treatment was initiated when tumors were an average of 60 mm$^3$, day 7 post implant. Mice were dosed intraperitoneally (IP) at 10 mg/kg twice a week for three weeks with anti-SIRPα antibodies. Animals were sacrificed when tumors reached a volume of ~2000 mm$^3$.

FIG. 16 shows the results of an in vivo syngeneic mouse colon carcinoma model to assess single agent activity. CT26 cells were implanted subcutaneously in BALB/c mice (8-9 mice were used per group) that were treated with AB136b or vehicle (PBS), as indicated. Treatment was initiated when tumors were an average of 80 mm$^3$, day 7 post implant. Mice were dosed intraperitoneally (IP) at 3 mg/kg or 10 mg/kg twice a week for three weeks with anti-SIRPα antibodies. Animals were sacrificed when tumors reached a volume of ~2000 mm$^3$.

FIG. 17A shows a comparison of CD47 and anti-SIRP-α antibody clone 119 Fab binding to SIRP-α, as determined by X-ray crystallography.

FIG. 17B shows the interaction site between anti-SIRP-α antibody clone 119 Fab and SIRP-α, as determined by buried surface area analyses. SIRP-α residues included in the antibody 119 Fab binding epitope are shaded according to buried surface area changes. Key antibody residues in the SIRP-α paratope are indicated: (H)=heavy chain residue; (L)=light chain residue.

FIG. 18A shows a comparison of CD47 and anti-SIRP-α antibody clone 136 Fab binding to SIRP-α, as determined by X-ray crystallography.

FIG. 18B shows the interaction site between anti-SIRP-α antibody clone 136 Fab and SIRP-α, as determined by buried surface area analyses. SIRP-α residues included in the antibody 136 Fab binding epitope are shaded according to buried surface area changes. Key antibody residues in the SIRP-α paratope are indicated: (H)=heavy chain residue; (L)=light chain residue.

FIG. 19A shows a comparison of CD47 and anti-SIRP-α antibody clone 3 Fab binding to SIRP-α, as determined by X-ray crystallography.

FIG. 19B shows the interaction site between anti-SIRP-α antibody clone 3 Fab and SIRP-α, as determined by buried surface area analyses. SIRP-α residues included in the antibody 3 Fab binding epitope are shaded according to buried surface area changes. Key antibody residues in the SIRP-α paratope are indicated: (H)=heavy chain residue; (L)=light chain residue.

FIG. 19C shows a comparison of CD47 and anti-SIRP-α antibody clone 115 Fab binding to SIRP-α, as determined by X-ray crystallography.

FIG. 19D shows the interaction site between anti-SIRP-α antibody clone 115 Fab and SIRP-α, as determined by buried surface area analyses. SIRP-α residues included in the antibody 115 Fab binding epitope are shaded according to buried surface area changes. Key antibody residues in the SIRP-α paratope are indicated: (H)=heavy chain residue; (L)=light chain residue.

FIG. 20A shows a comparison of CD47, anti-SIRP-α antibody clone 119 Fab, anti-SIRP-α antibody clone 136 Fab, anti-SIRP-α antibody clone 3 Fab, anti-SIRP-α antibody clone 115 Fab binding to SIRP-α, as determined by X-ray crystallography.

FIGS. 20B-20E show the epitopes for CD47, anti-SIRP-α antibody clone 119 Fab, anti-SIRP-α antibody clone 136 Fab, anti-SIRP-α antibody clone 3 Fab, and anti-SIRP-α antibody clone 115 Fab binding to SIRP-α, as determined by X-ray crystallography. Values indicate difference between surface accessible area of each residue atom in the Fab/CD47 when analyzed alone vs. when analyzed in complex with SIRP-α, expressed as buried surface area (Å$^2$). Residue numbering according to SEQ ID NO: 296.

Figure 22A:
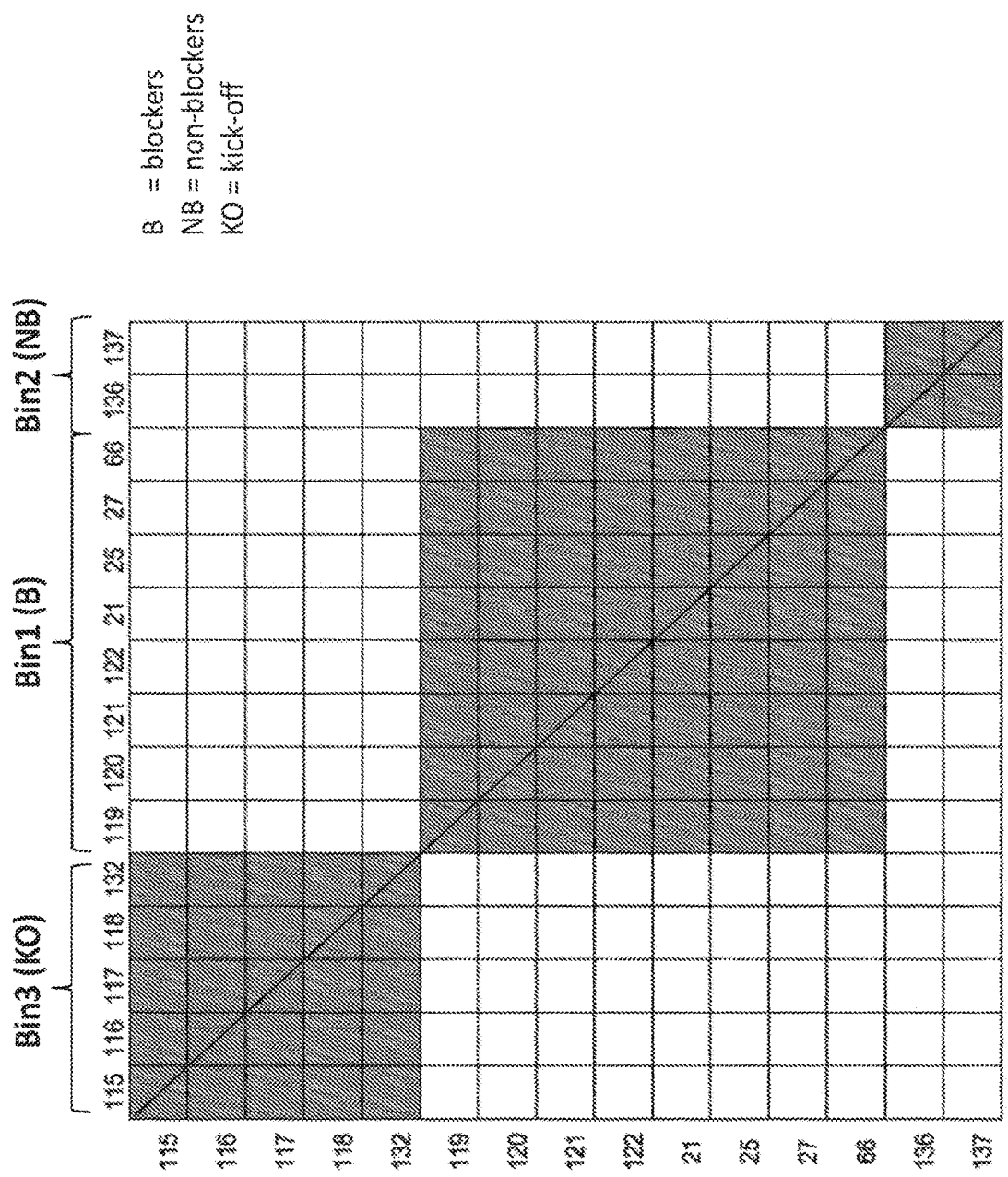
Figure 22B:
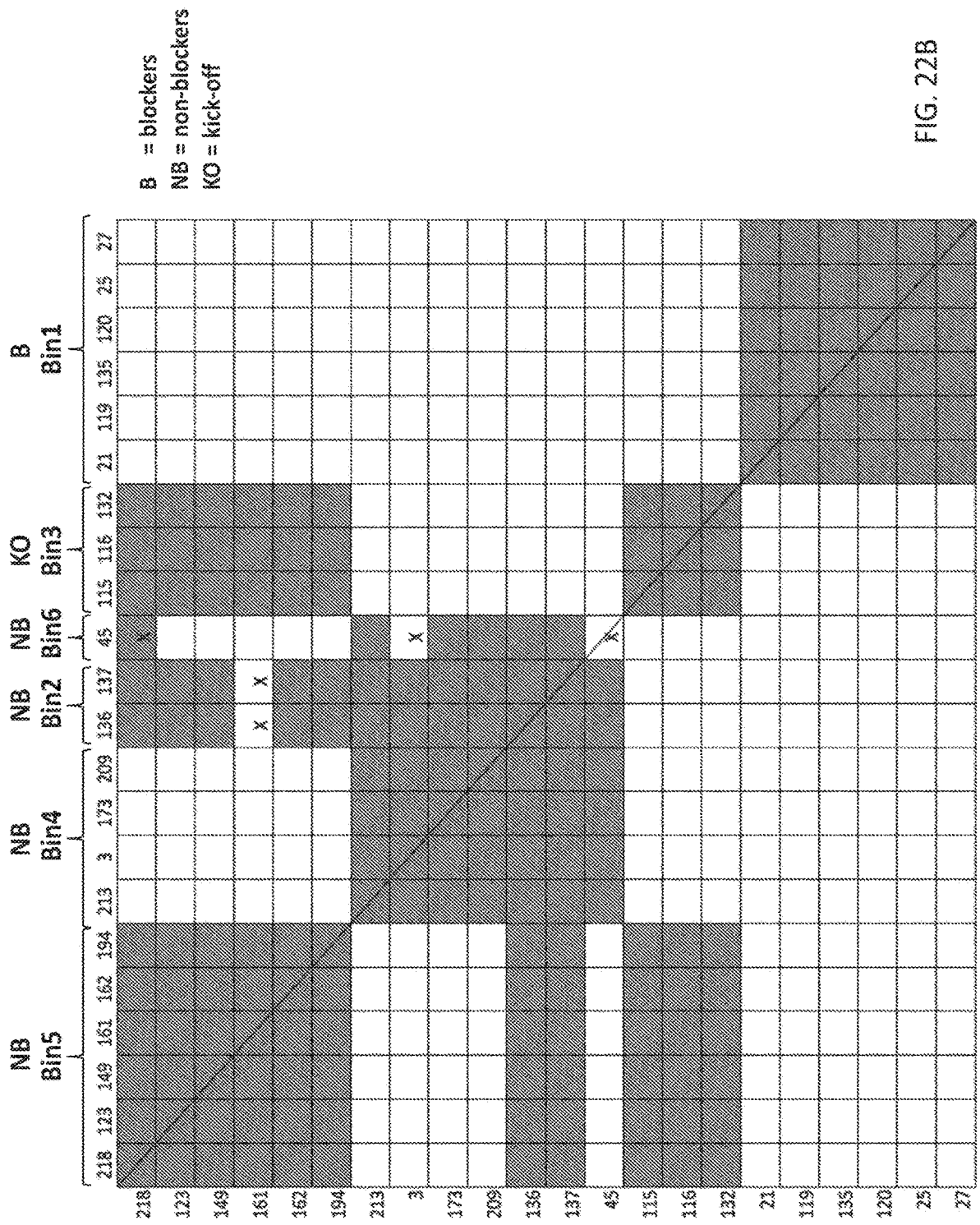

FIGS. 22A & 22B show the results of epitope binning of the indicated anti-SIRP-α antibodies. The clone number for the ligand (anti-SIRPα) bound to the chip is indicated as rows, and the clone number for the analytes (anti-SIRPα) injected over the chip is indicated as columns. White boxes indicate antibodies that form sandwiches (and are considered to bind different epitopes). Gray boxes indicate antibodies that did not form sandwiches (and are considered to bind the same epitope). "X" indicates scenarios where the data from one orientation disagrees with the other.

Figure 23:
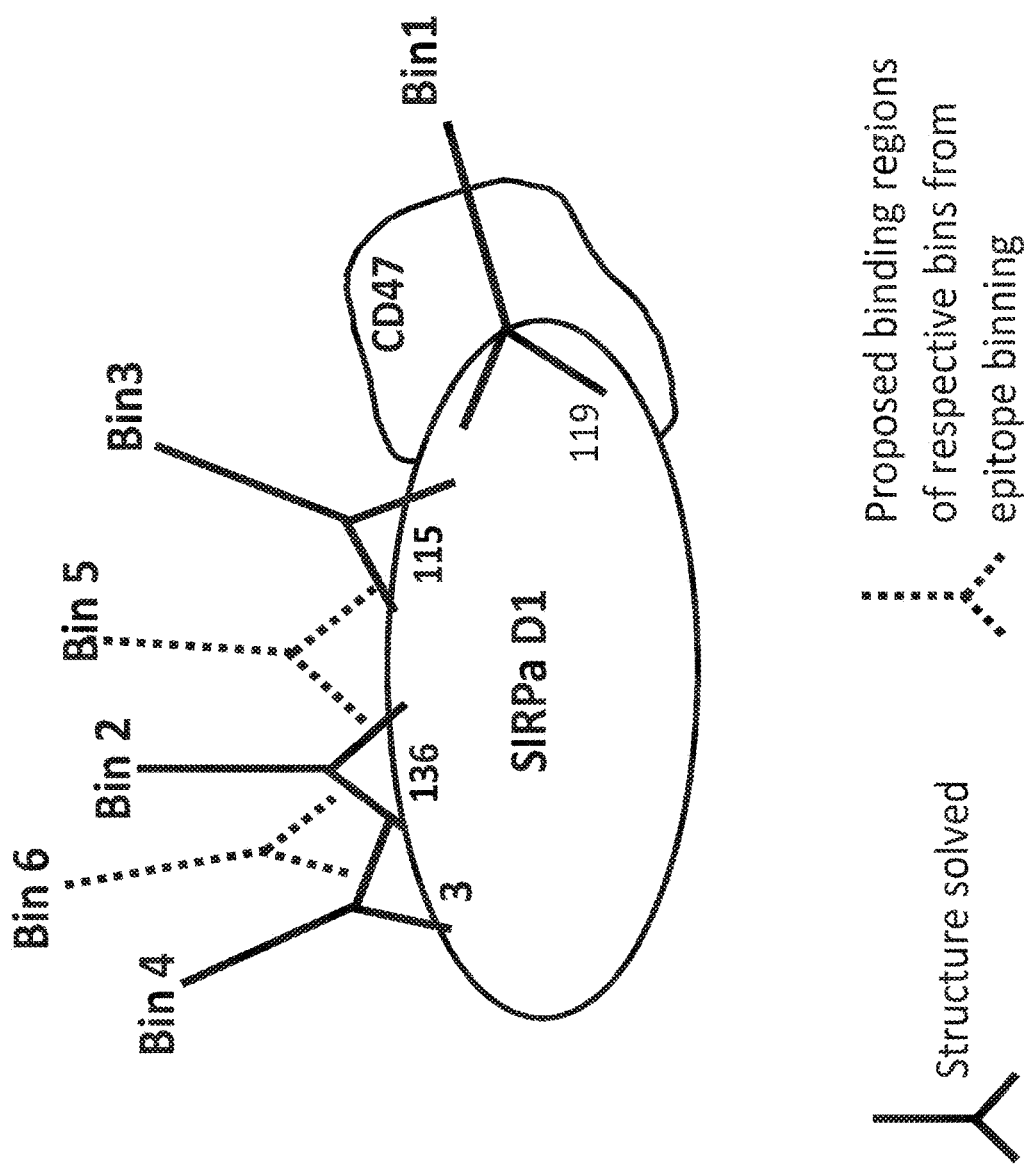

FIG. 23 provides a model for anti-SIRP-α antibody and CD47 binding to the SIRP-α D1 domain based on epitope binning. Representative antibody clones for each bin are provided (and labeled by number).

FIG. 24A shows alignments between the parental 119 heavy chain ("119_VH_Wt"), the 119 variant heavy chain with 4 mutations (3 back-mutations to germline sequence in framework and one mutation in CDR-H1 removing a potential oxidation hot spot; "VH_MutALL"), the 119 variant heavy chain with 3 mutations (3 back-mutations to germline sequence in framework only; "VH_MutAll_V34M"), and the 119 variant heavy chain with 3 mutations and an M34L mutation (3 back-mutations to germline sequence in framework; "VH_MutAll_V34L"). Sequences depicted are: SEQ ID NO:335 for 119_VH_Wt, SEQ ID NO:246 for VH_MutALL, SEQ ID NO:258 for VH_MutAll_V34M, and SEQ ID NO:327 for VH_MutAll_V34L. CDR sequences are indicated with lines; amino acid differences are indicated by asterisks.

FIG. 24B shows alignments between the parental 119 light chain ("119_VL_Wt"), and the 119 variant light chain with 4 mutations (4 back-mutations to germline sequence in framework; "VL_mutAll"). Sequences depicted are: SEQ ID NO:97 for 119_VL_Wt and SEQ ID NO:312 for VL_mutAll. CDR sequences are indicated with lines; amino acid differences are indicated by asterisks.

FIG. 25A shows alignments between the parental 135 light chain ("VL_wt") and the 135 variant light chain with 2 mutations (2 back-mutations to germline sequence in framework; "VL_mutALL"). Sequences depicted are: SEQ ID NO:104 for 135 VL_wt and SEQ ID NO:248 for 135 VL_MutALL. HVR sequences are indicated with lines; amino acid differences are indicated by asterisks.

FIG. 25B shows alignments between the parental 135 heavy chain ("VH_wt") the 135 variant heavy chain with 6 mutations (5 back-mutations to germline sequence in framework and one mutation in CDR-H1 removing a potential oxidation hot spot; "VH_MutAll"), the 135 variant heavy chain with 5 back-mutations to germline sequence in framework ("VH_MutAll_V34M"), and the 135 variant heavy chain with 5 back-mutations to germline sequence in framework and M34L mutation ("VH_MutAll_V34L"). Sequences depicted are: SEQ ID NO:341 for VH_wt, SEQ ID NO:247 for VH_MutAll, and SEQ ID NO:259 for VH_MutAll_V34M, and SEQ ID NO:328 for VH_MutAll_V34L. HVR sequences are indicated with lines; amino acid differences are indicated by asterisks.

FIG. 26A shows alignments between the parental 136 light chain ("VL_wt"), the 136 variant light chain with 4 mutations (4 back-mutations to germline sequence in framework; "VL_mutaLL"), the 136 variant light chain with a single I2T back-mutation reverted to wild-type sequence in an otherwise "all mut" background ("VL_Mutall_I2T"). Sequences depicted are: SEQ ID NO: 134 for VL_wt, SEQ ID NO:250 for VL_mutaLL, and SEQ ID NO:251 for VL_Mutall_I2T. HVR sequences are indicated with lines; amino acid differences are indicated by asterisks.

FIG. 26B shows alignments between the parental 136 heavy chain ("VH_wt"), the 136 variant heavy chain with 6 mutations (5 back-mutations to germline sequence in framework and one mutation in CDR-H1 removing a potential oxidation hot spot; "VH_mutall"), the 136 variant heavy chain with 5 back-mutations to germline sequence in framework ("VH_Mutall_V34M"), and the 136 variant heavy chain with 5 back-mutations to germline sequence in framework and M34L mutation ("VH_Mutall_V34L"). Sequences depicted are: SEQ ID NO:133 for VH_wt, SEQ ID NO:249 for VH_mutall, SEQ ID NO:260 for VH_MutAll_V34M, and SEQ ID NO:329 for VH_Mutall_V34L. HVR sequences are indicated with lines; amino acid differences are indicated by asterisks.

Figure 27A:
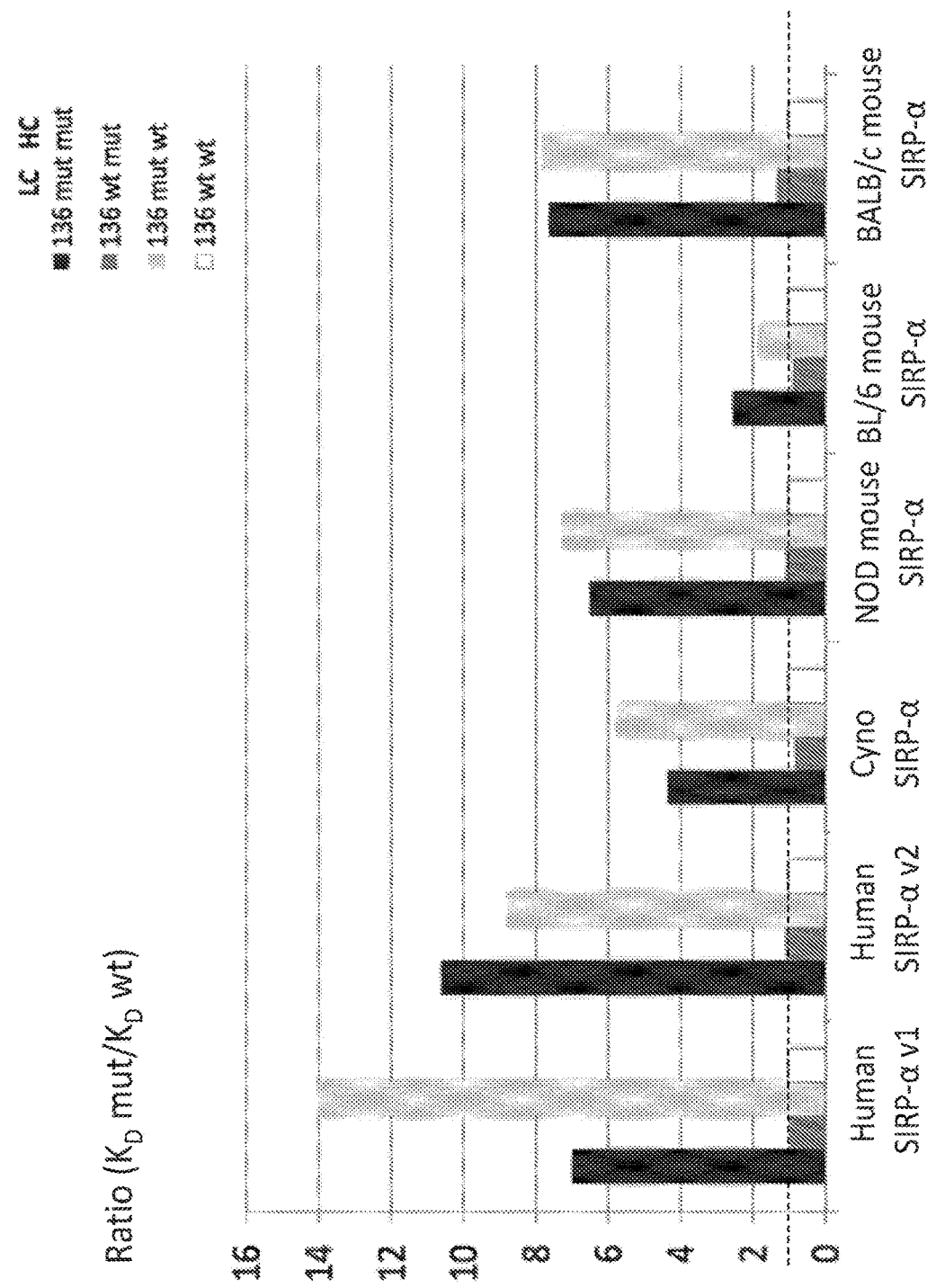

FIG. 27A shows binding affinities of antibody 136 variants to six SIRP-α proteins: human SIRP-α v1 (SEQ ID NO:5), human SIRP-α v2 (SEQ ID NO:6), cynomolgus SIRP-α (SEQ ID NO:11), NOD mouse SIRP-α (SEQ ID NO:8), BL/6 mouse SIRP-α (SEQ ID NO:9), and BALB/c mouse SIRP-α (SEQ ID NO:10). Antibody variants had mutant ("mut") or parental ("wt") light chains and mutant or parental heavy chains, as indicated in the order light chain/heavy chain. On the graph, y-axis indicates the ratio of $K_D$ mut/$K_D$ wt. A ratio of 1 means antibody had equivalent $K_D$ to wt/wt antibody (indicated by dotted line); ratio of >1 indicates lower affinity than wt/wt; and ratio of <1 indicates higher affinity than wt/wt.

Figure 27B:
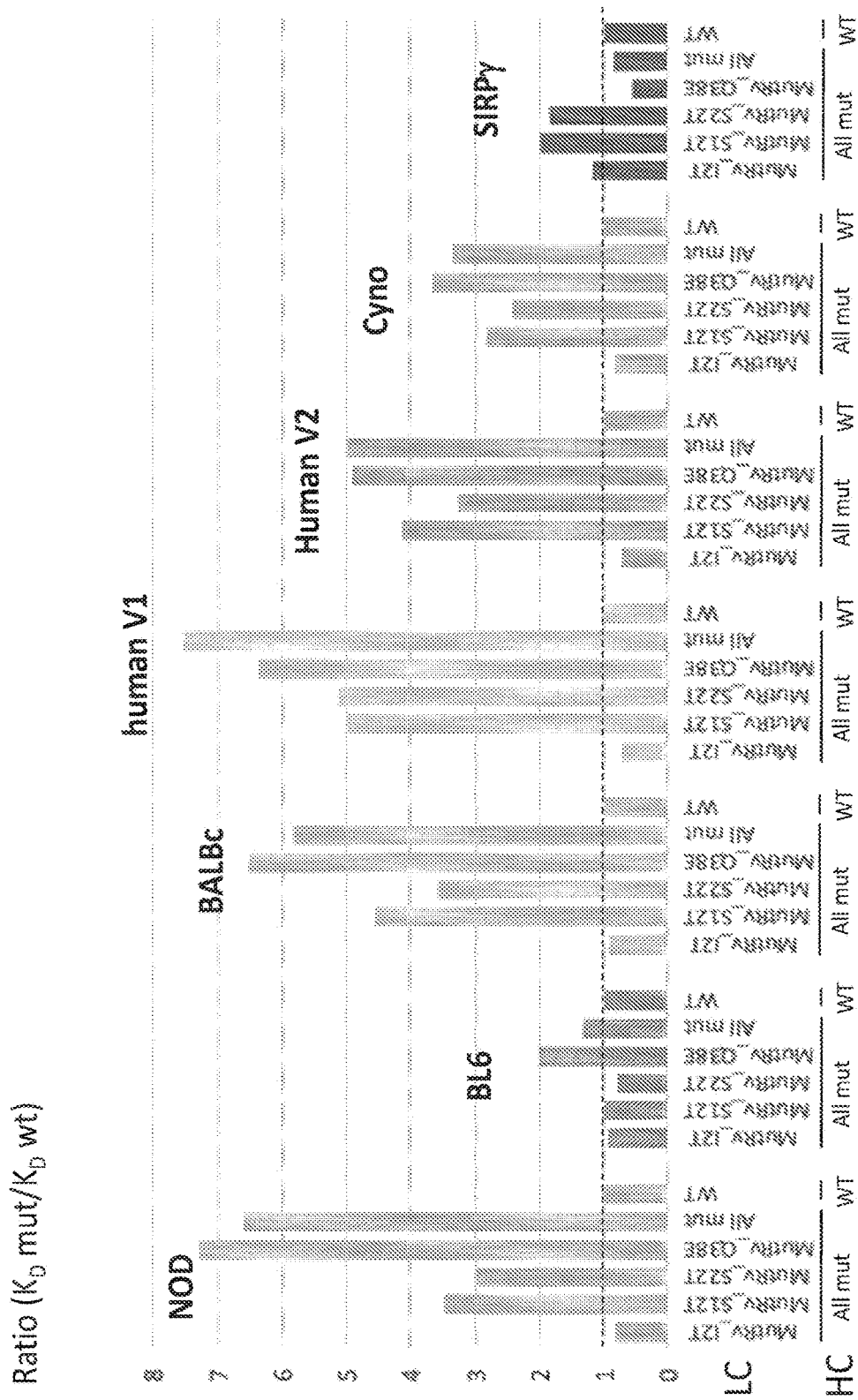

FIG. 27B shows binding affinities of antibody 136 variants to seven SIRP-α proteins: BL/6 mouse SIRP-α (SEQ ID NO:9), NOD mouse SIRP-α (SEQ ID NO:8), BALB/c mouse SIRP-α (SEQ ID NO:10), human SIRP-α v1 (SEQ ID NO:5), human SIRP-α v2 (SEQ ID NO:6), cynomolgus SIRP-α (SEQ ID NO:11), and human SIRP-γ v1 (SEQ ID NO:15). In addition to testing the wt 136 and all mutant 136, variants were constructed eliminating each individual mutation in an all mutant light chain background. On the graph, y-axis indicates the ratio of $K_D$ mut/$K_D$ wt. A ratio of 1 means antibody had equivalent $K_D$ to wt/wt antibody (indicated by dotted line); ratio of >1 indicates lower affinity than wt/wt; and ratio of <1 indicates higher affinity than wt/wt.

Figure 28:
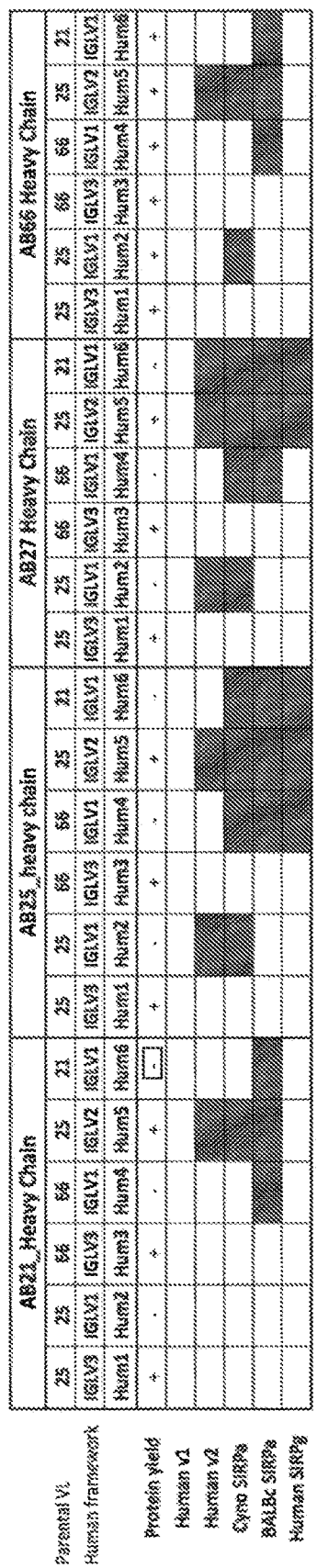

FIG. 28 compares expression yield and binding affinity of antibodies having indicated human heavy chains and humanized light chains in FreeStyle™ 293-FS cells (Thermo Fisher).

FIG. 29 shows an alignment between Hum1, Hum 8, and Hum9 VL domains. Hum8 was generated based on Hum1 but with 5 amino acid substitutions near or in HVR-L1 and -L2 that increase humanness. Hum9 was generated based on Hum1 but with 4 amino acid substitutions near or in HVR-L1 and -L2 that increase humanness. SEQ ID NOs: 252 (Hum1), 416 (Hum 8), and 262 (Hum9) are depicted. HVR sequences are indicated with lines; amino acid differences are indicated by asterisks.

FIG. 30 shows alignments between the antibody 21 variant with germline back-mutations ("HC_MutAll"), the antibody 21 variant with germline back-mutations and mutation in CDR-H1 removing a potential oxidation hot spot M34V ("HC_MutAll_M34V"), the antibody 21 variant with germline back-mutations and M34L mutation ("HC_MutAll_M34L"), the antibody 25 variant with germline back-mutations ("HC_MutAll"), the antibody 25 variant with germline back-mutations and mutation in CDR-H1 removing a potential oxidation hot spot M34V ("HC_MutAll_M34V"), the antibody 25 variant with germline back-mutations and M34L mutation ("HC_MutAll_M34L"), the antibody 27 variant with germline back-mutations ("HC_MutAll"), the antibody 27 variant with germline back-mutations and mutation in CDR-H1 removing a potential oxidation hot spot M34V ("HC_MutAll_M34V"), and the antibody 27 variant with germline back-mutations and M34L mutation ("HC_MutAll_M34L"). Sequences depicted are SEQ ID NOs:263, 264, 330, 267, 268, 332, 265, 266, and 331 (top to bottom). HVR sequences are indicated with lines; amino acid differences are indicated by asterisks.

Figure 31:
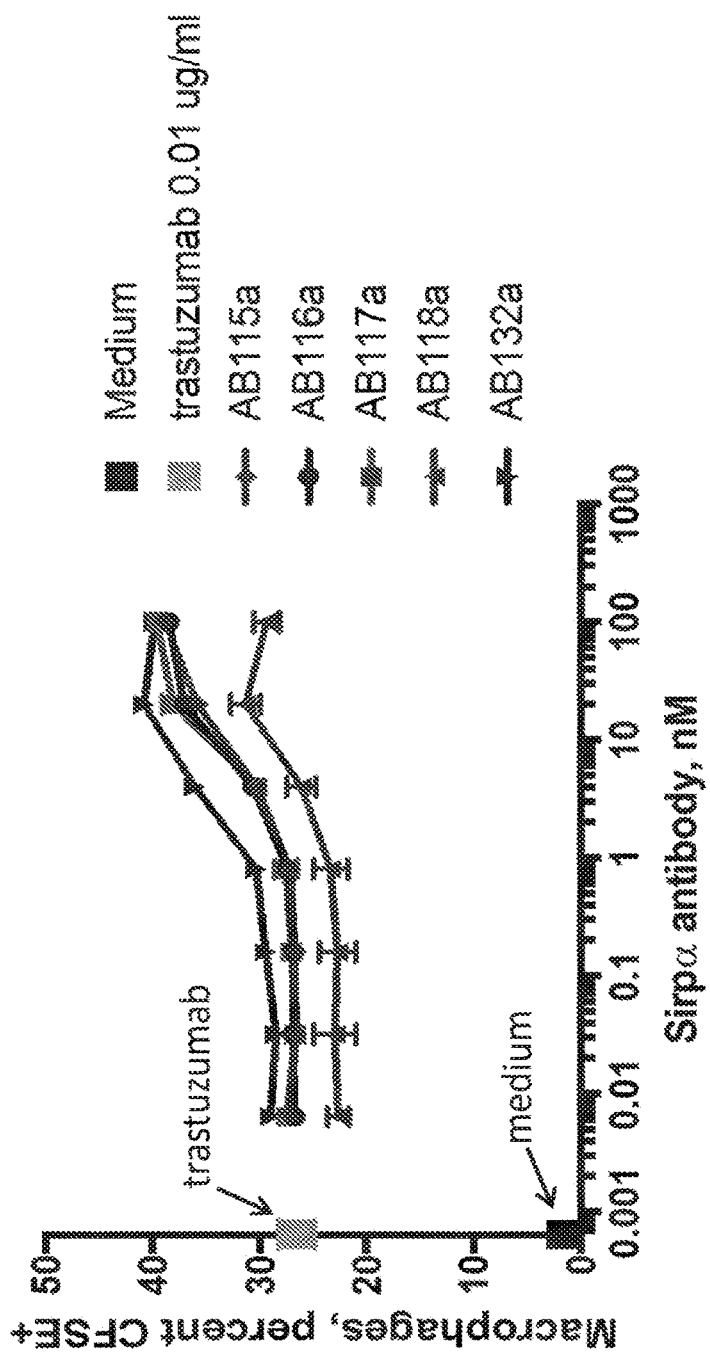

FIG. 31 shows the results of in vitro phagocytosis assays using HER2(+) OE19 cells as the target and M2 macrophages as the phagocytosing cell. "Kick off" anti-SIRP-α antibodies were tested at the indicated concentrations in combination with the anti-HER2 antibody trastuzumab. Phagocytosis was measured by percentage of CFSE+ cells.

Figure 32:
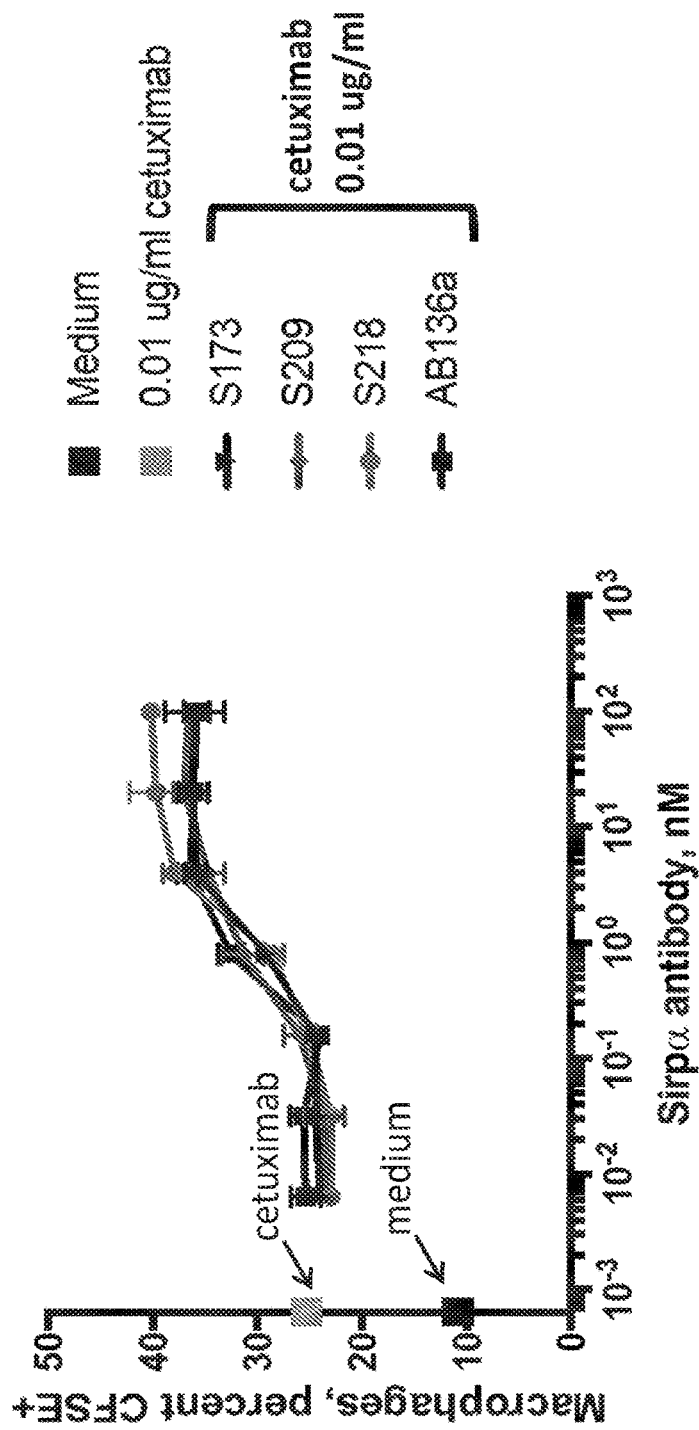

FIG. 32 shows the results of in vitro phagocytosis assays using EGFR(+) DLD-1 cells as the target and M2 macrophages as the phagocytosing cell. Non-blocking anti-SIRP-α antibodies were tested at the indicated concentrations in combination with the anti-EGFR antibody cetuximab. Phagocytosis was measured by percentage of CFSE+ cells.

Figure 33A:
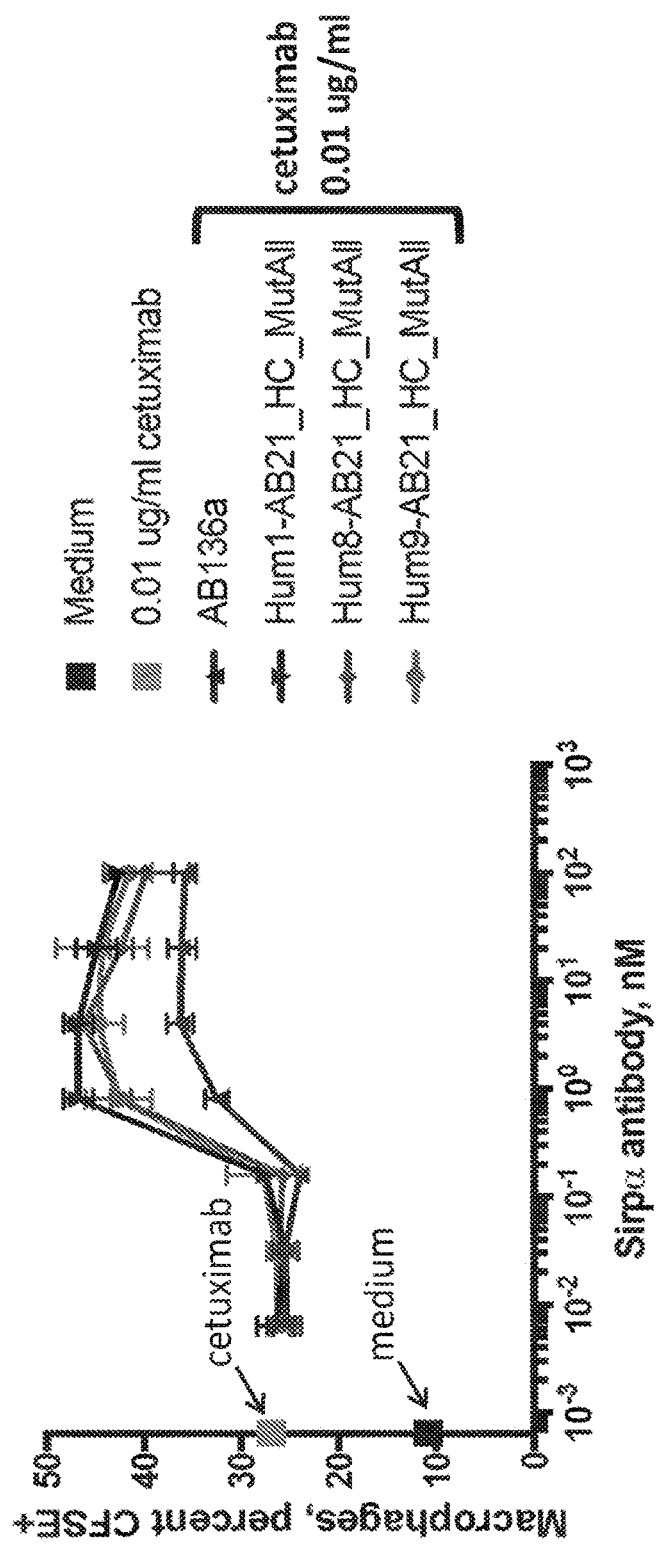
Figure 33B:
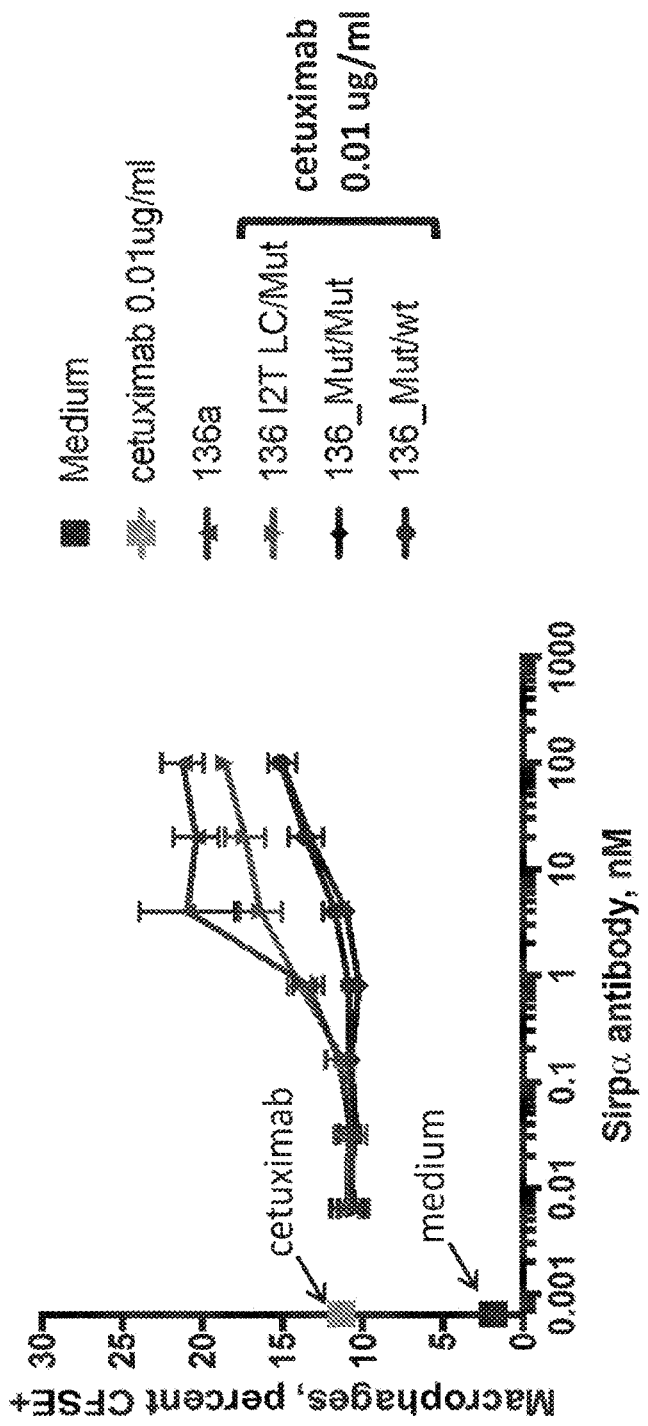
Figure 33C:
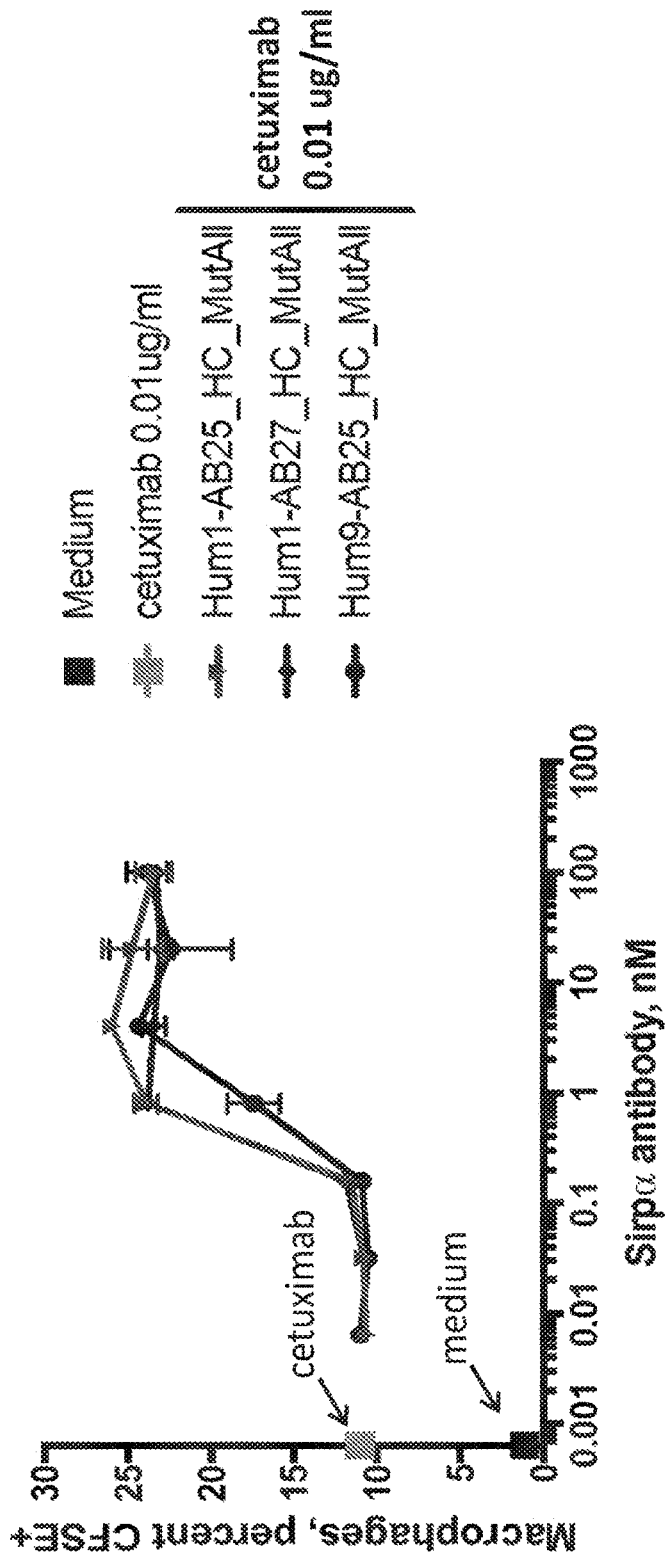

FIGS. 33A-33C show the results of in vitro phagocytosis assays using EGFR(+) DLD-1 cells as the target and M2 macrophages as the phagocytosing cell. Anti-SIRP-α antibodies were tested at the indicated concentrations in combination with the anti-EGFR antibody cetuximab. Phagocytosis was measured by percentage of CFSE+ cells.

Figure 34:
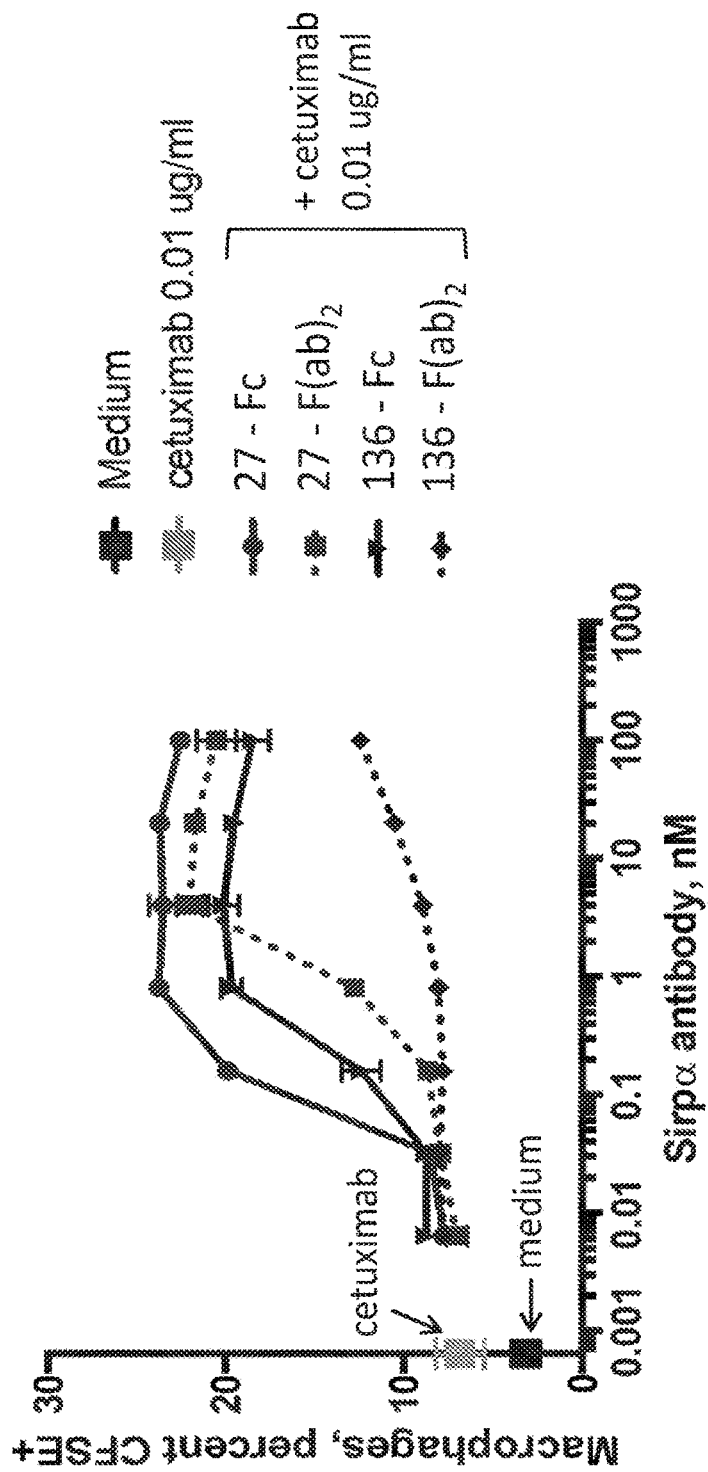

FIG. 34 shows the results of in vitro phagocytosis assays using EGFR(+) DLD-1 cells as the target and M2 macrophages as the phagocytosing cell. Non-blocking anti-SIRP-α antibodies 27 and 136 were each tested as a full-length antibody (with Fc region) or F(ab)$_2$ fragment at the indicated concentrations in combination with the anti-EGFR antibody cetuximab. Phagocytosis was measured by percentage of CFSE+ cells.

Figure 35:
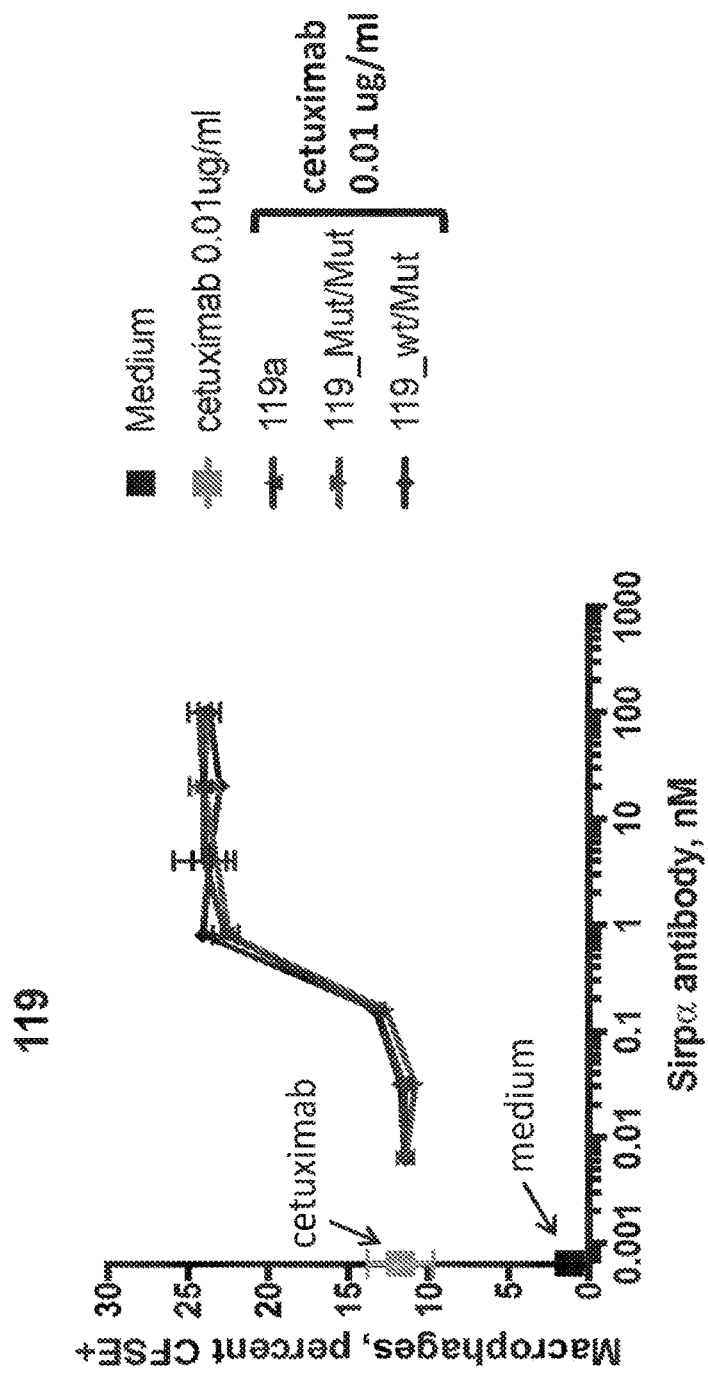

FIG. 35 shows the results of in vitro phagocytosis assays using EGFR(+) DLD-1 cells as the target and M2 macrophages as the phagocytosing cell. Blocking anti-SIRP-α antibody 119 variants were tested at the indicated concentrations in combination with the anti-EGFR antibody cetuximab. Phagocytosis was measured by percentage of CFSE+ cells.

Figure 36:
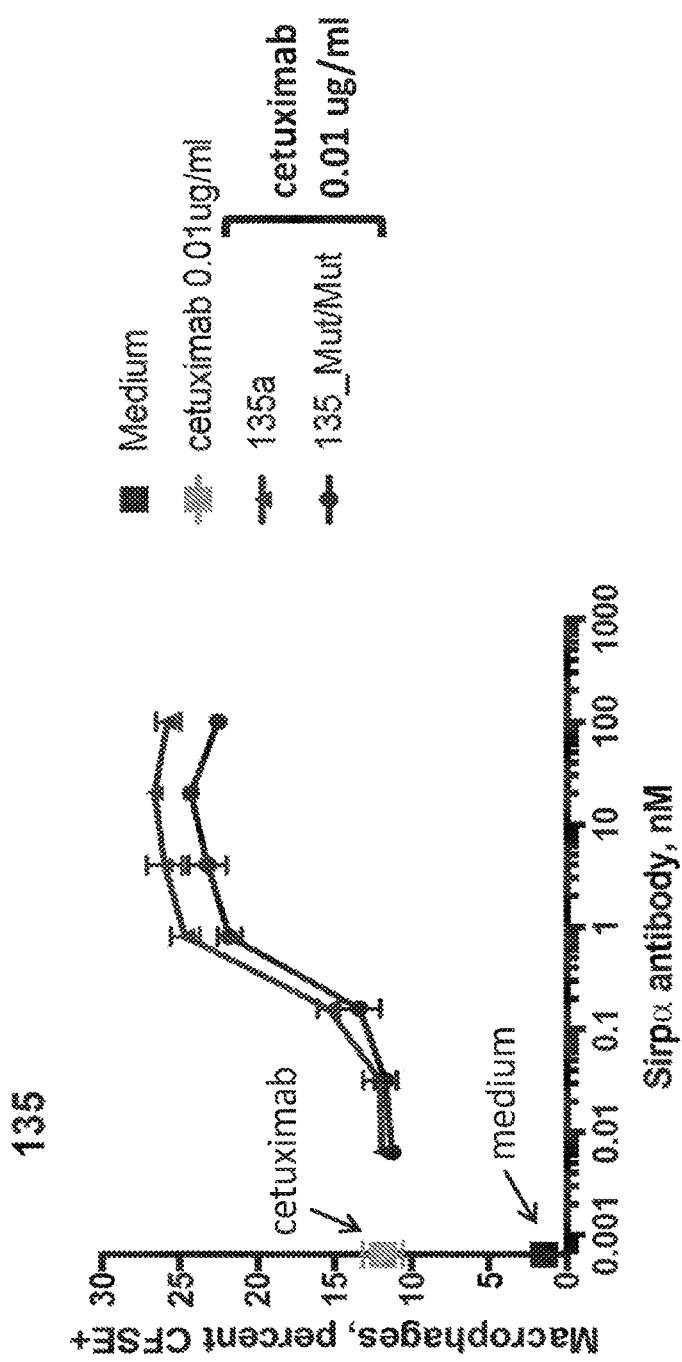

FIG. 36 shows the results of in vitro phagocytosis assays using EGFR(+) DLD-1 cells as the target and M2 macrophages as the phagocytosing cell. Blocking anti-SIRP-α antibody 135 variants were tested at the indicated concentrations in combination with the anti-EGFR antibody cetuximab. Phagocytosis was measured by percentage of CFSE+ cells.

Figure 37:
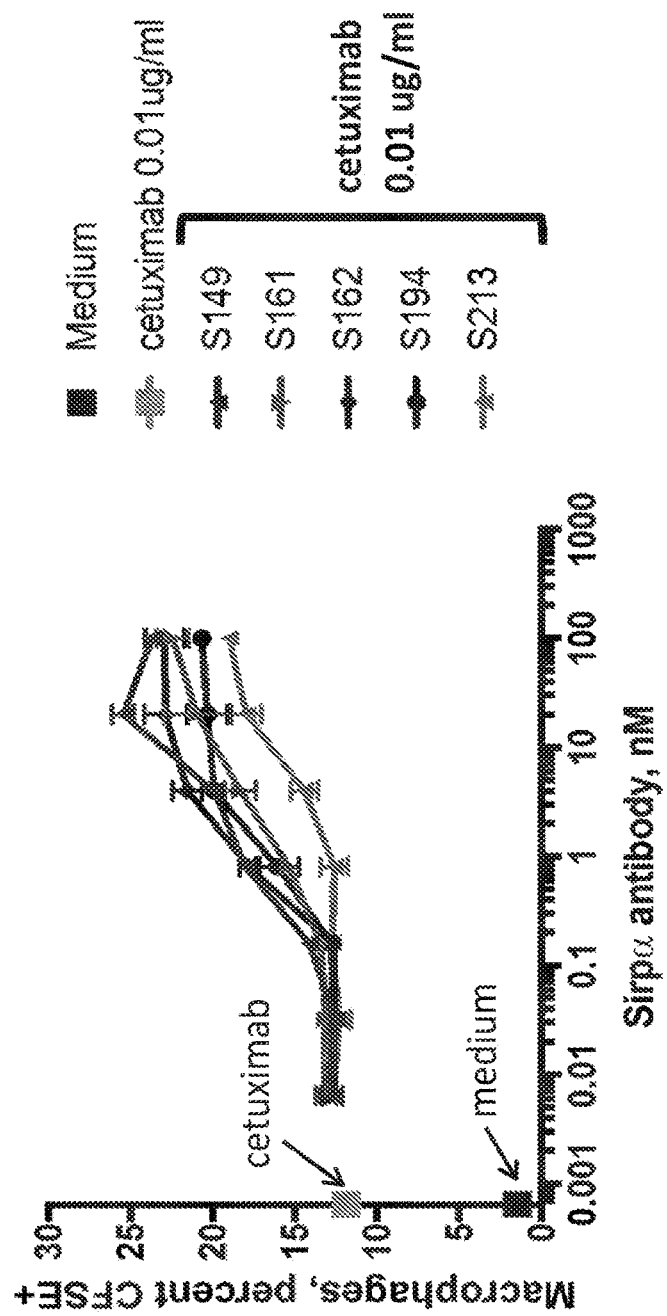

FIG. 37 shows the results of in vitro phagocytosis assays using EGFR(+) DLD-1 cells as the target and M2 macrophages as the phagocytosing cell. Non-blocking anti-SIRP-α antibodies were tested at the indicated concentrations in combination with the anti-EGFR antibody cetuximab. Phagocytosis was measured by percentage of CFSE+ cells.

Figure 38B:
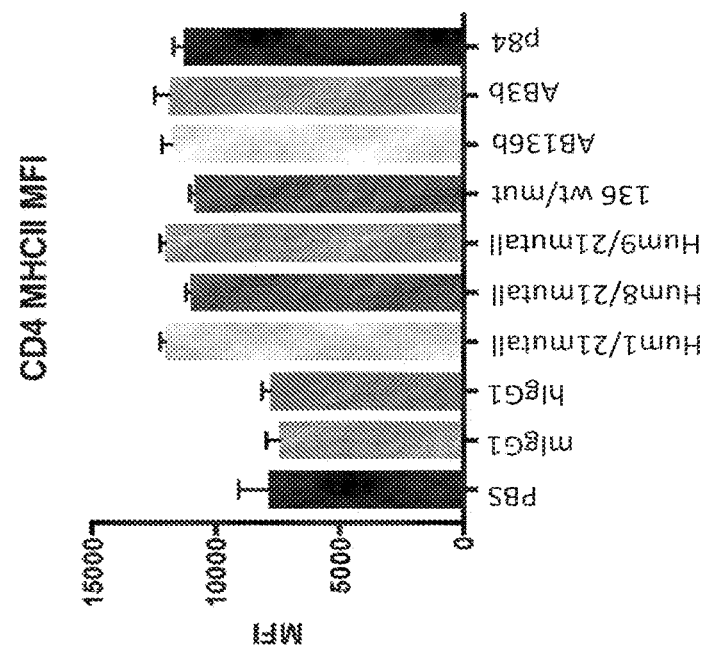
Figure 38A:
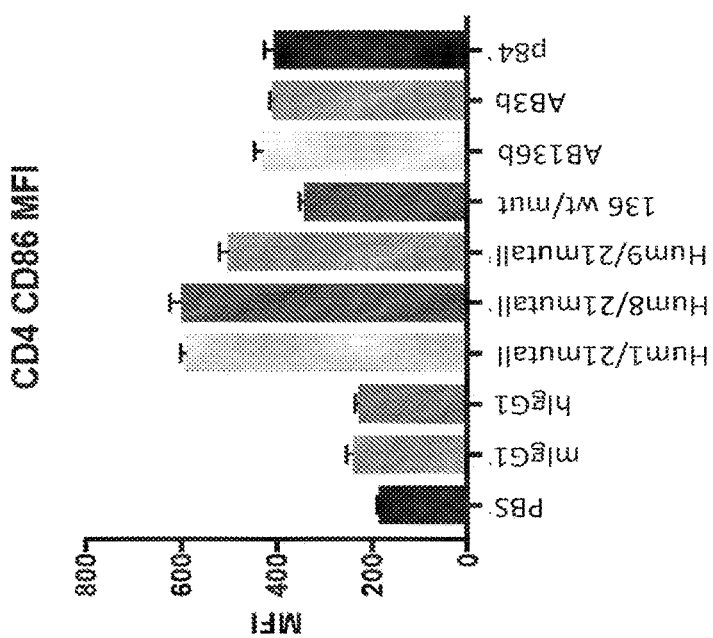

FIGS. 38A-38B show the results of in vivo dendritic cell activation assays with the indicated anti-SIRP-α antibodies. Mice were intravenously injected with the indicated antibody at 10 mg/kg, and spleens were harvested five hours after injection. Activation markers CD86, MHCII and CCR7 on CD4+ dendritic cells were measured by flow cytometry.

Figure 39A:
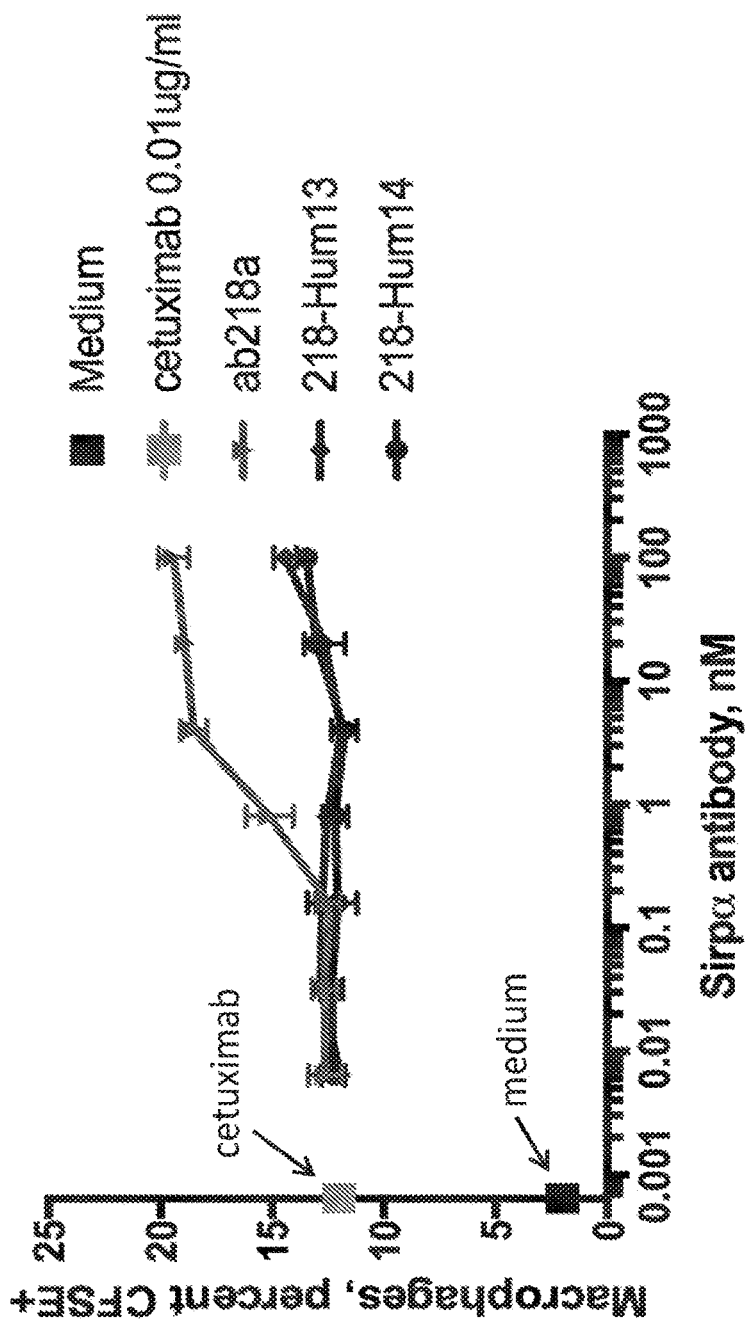

FIG. 39A shows the results of in vitro phagocytosis assays using EGFR(+) DLD-1 cells as the target and M2 macrophages as the phagocytosing cell. 218a and 218 variant anti-SIRP-α antibodies were tested at the indicated concentrations in combination with the anti-EGFR antibody cetuximab. Phagocytosis was measured by percentage of CFSE+ cells.

Figure 39B:
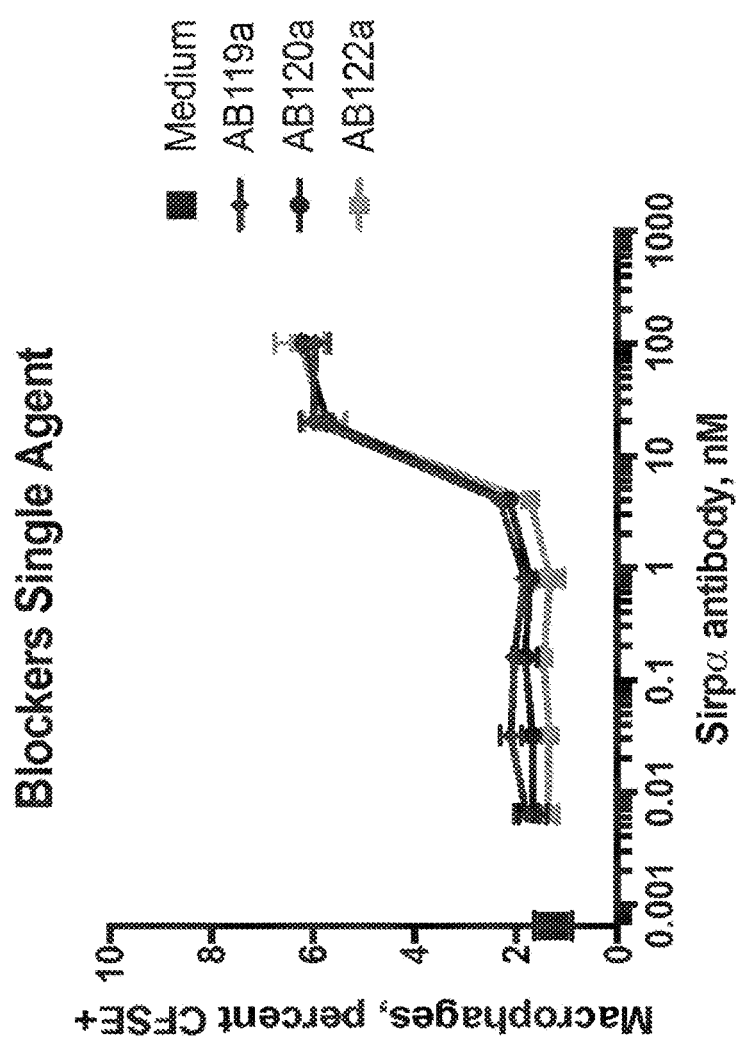

FIG. 39B shows the results of in vitro phagocytosis assays using EGFR(+) DLD-1 cells as the target and M2 macrophages as the phagocytosing cell. Exemplary blocking anti-SIRP-α antibodies 119a, 120a, and 122a were tested at the indicated concentrations. Phagocytosis was measured by percentage of CFSE+ cells.

Figure 39C:
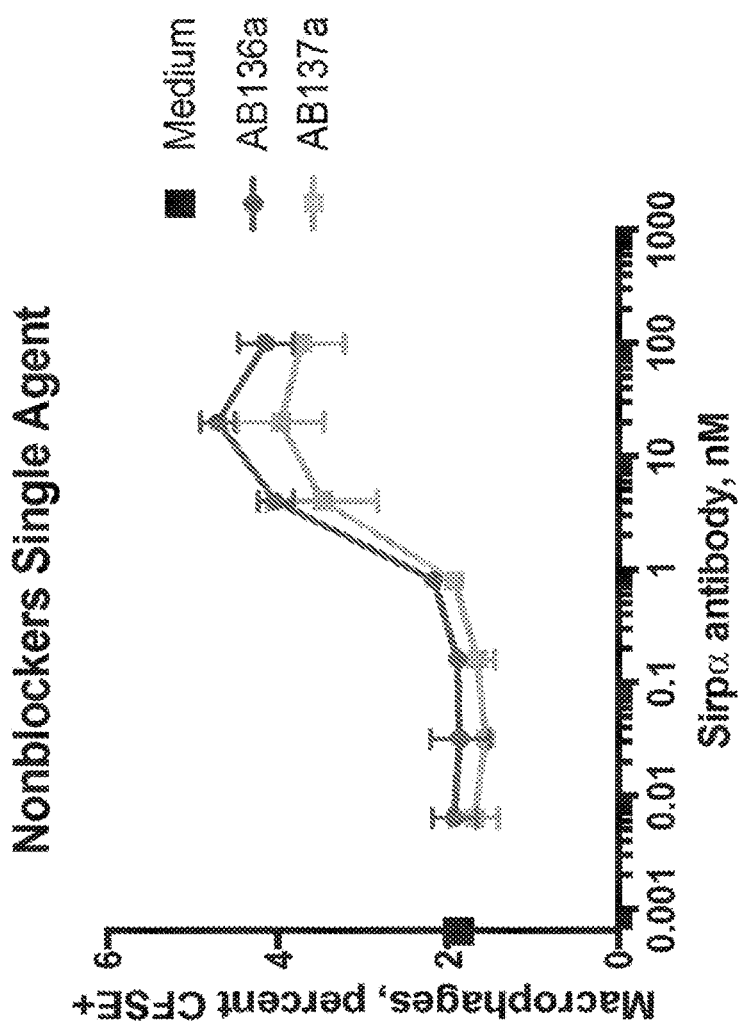

FIG. 39C shows the results of in vitro phagocytosis assays using EGFR(+) DLD-1 cells as the target and M2 macrophages as the phagocytosing cell. Exemplary non-blocking anti-SIRP-α antibodies 136a and 137a were tested at the indicated concentrations. Phagocytosis was measured by percentage of CFSE+ cells.

Figure 39D:
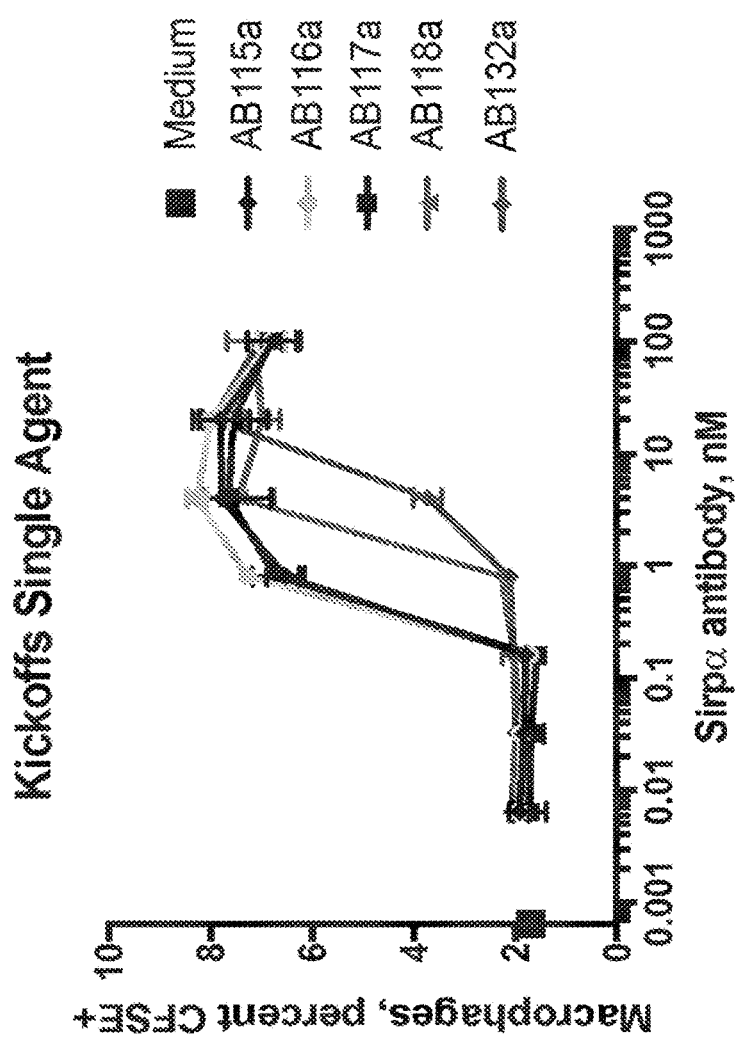

FIG. 39D shows the results of in vitro phagocytosis assays using EGFR(+) DLD-1 cells as the target and M2 macrophages as the phagocytosing cell. Exemplary kick off anti-SIRP-α antibodies 115a, 116a, 117a, 118a, and 132a were tested at the indicated concentrations. Phagocytosis was measured by percentage of CFSE+ cells.

Figure 40:
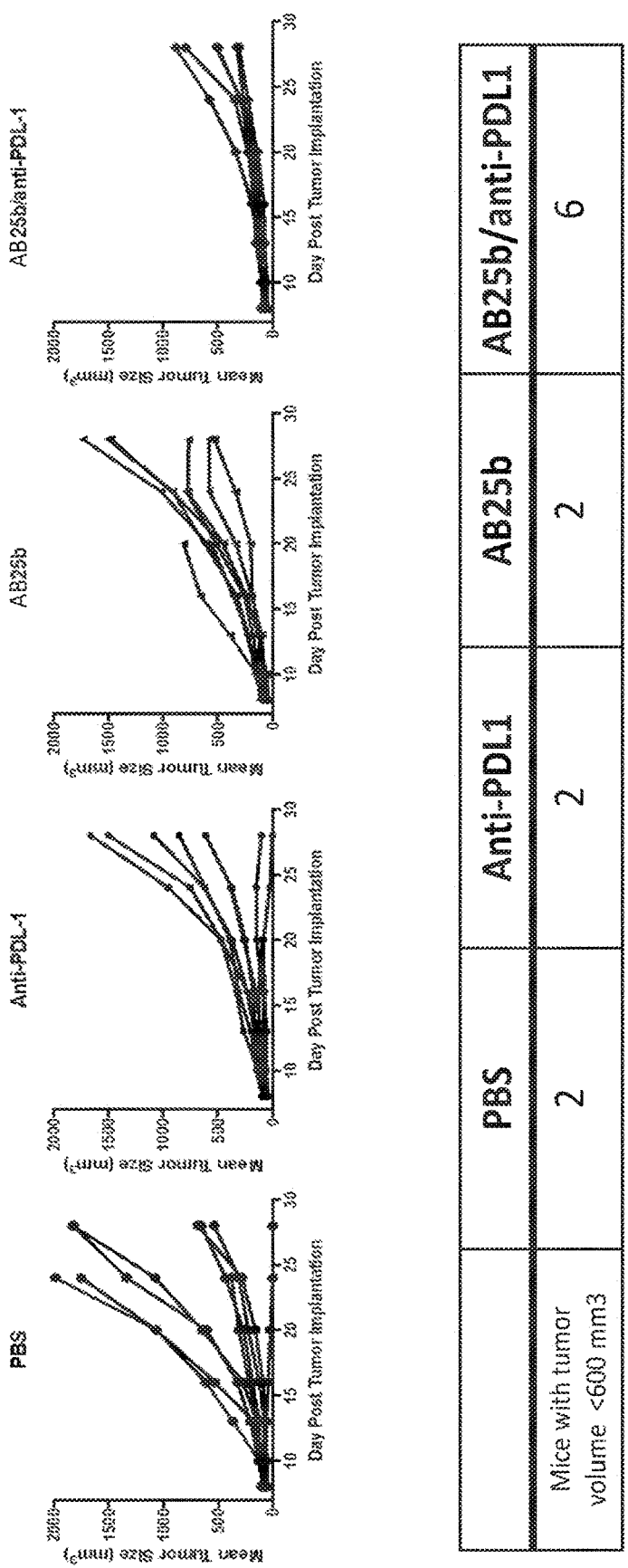

FIG. 40 shows the results of an in vivo syngeneic mouse colon carcinoma model to assess activity of combining anti-SIRP-α treatment with PD-L1/PD-1 pathway inhibition. CT26 cells were implanted subcutaneously in C57BL/6 mice and randomized into groups (8 mice/group). Mice were treated with vehicle (PBS), anti-PD-L1 antibody, CD47 blocking anti-SIRP-α antibody AB25b, or AB25b and PD-L1. Treatment was initiated when tumors were an average of 60 mm$^3$, day 7 post implant. Mice were dosed intraperitoneally (IP) at 10 mg/kg twice a week for three weeks and sacrificed when tumors reach a volume of ~2000 mm$^3$.

Figure 41:
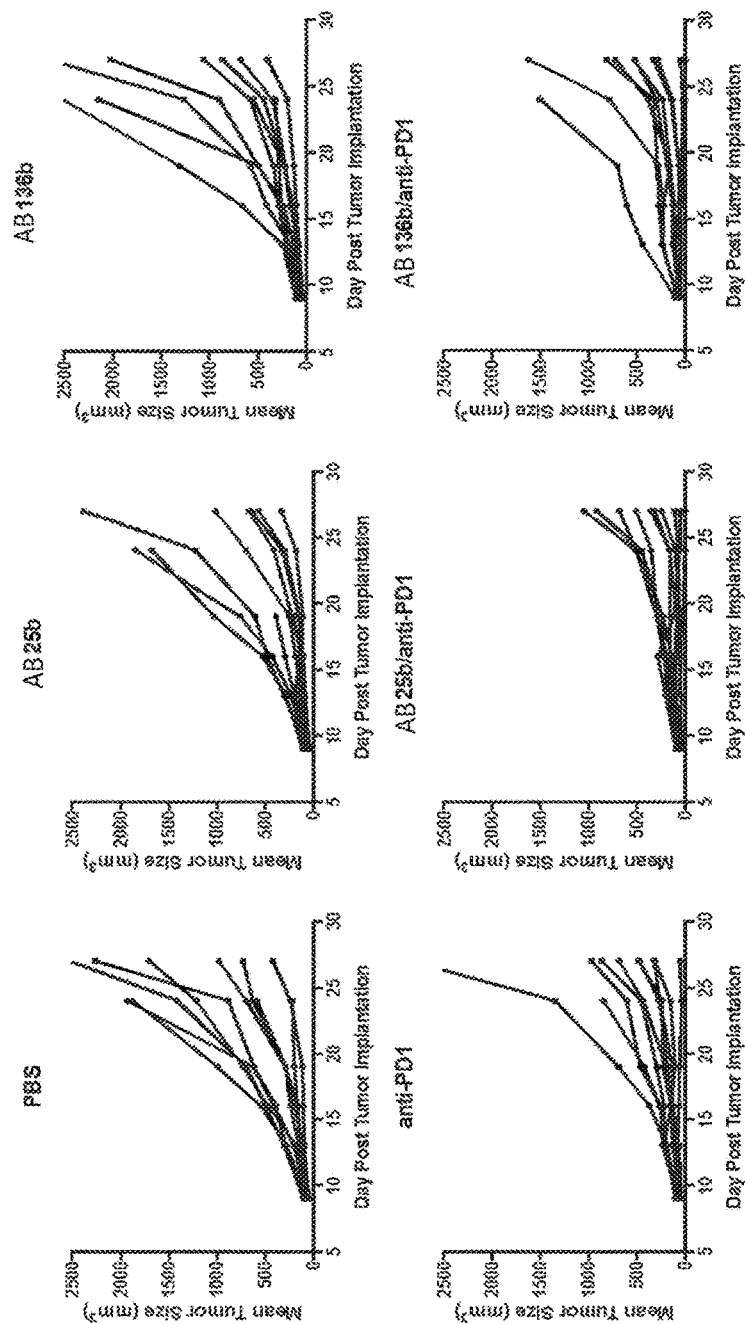

FIG. 41 shows the results of an in vivo syngeneic mouse colon carcinoma model to assess activity of combining anti-SIRP-α treatment with PD-L1/PD-1 pathway inhibition. MC38 cells were implanted subcutaneously in C57BL/6 mice and randomized into groups (8 mice/group). Mice were treated with vehicle (PBS), anti-PD-1 antibody, CD47 blocking anti-SIRP-α antibody AB25b, AB25b and anti-PD-1, CD47 non-blocking anti-SIRP-α antibody AB136b, or AB136b and anti-PD-1. Treatment was initiated when tumors were an average of 60 mm$^3$, day 7 post implant. Mice were dosed intraperitoneally (IP) at 10 mg/kg twice a week for three weeks and sacrificed when tumors reach a volume of ~2000 mm$^3$.

DETAILED DESCRIPTION

The present disclosure describes antibodies that bind the extracellular domains (e.g., the D1 domains) of one or more human SIRP-α polypeptides and have a variety of SIRP-α binding profiles of potential interest. These unique SIRP-α binding profiles include one or more of the following binding capabilities, which are combined in a multifactorial manner to yield a multitude of unique specificities. For instance, the antibody can bind the extracellular domains (e.g., the D1 domains) of human SIRP-α v1, human SIRP-α v2, or both; the antibody can bind the extracellular domains (e.g., the D1 domains) of one or more monkey SIRP-α polypeptides, or it can lack binding thereto; the antibody can bind the extracellular domains (e.g., the D1 domains) of one or more murine SIRP-α polypeptides, or it can lack binding thereto; the antibody can bind the extracellular domain (e.g., the D1 domain) of a human SIRPβ polypeptide, or it can lacking binding thereto; and/or the antibody can bind the extracellular domain (e.g., the D1 domain) of a human SIRPγ polypeptide, or it can lacking binding thereto. In addition, the present disclosure describes antibodies that block binding of CD47 to SIRP-α, antibodies that do not block binding of CD47 to SIRP-α, and antibodies that do not block binding of CD47 to SIRP-α but decrease SIRP-α's affinity for CD47, leading to more rapid dissociation of the CD47/SIRP-α complex. In addition, the present disclosure describes anti-SIRP-α antibodies with one or more in vitro and/or in vivo biological properties of interest, such as the ability to enhance macrophage phagocytosis, enhance dendritic cell activation, inhibit in vivo growth of a tumor that expresses CD47, and/or the ability to accomplish one or more of these activities without preventing interactions between a CD47-expressing cell and a T cell.

The methods described herein may be used to identify antibodies with unique combinations of the above binding specificities. Without wishing to be bound to theory, it is thought that the ability to identify unique anti-SIRP-α antibodies with different binding profiles as described above allows for the identification of antibodies (e.g., those described herein) with desirable clinical properties and advantages for pre-clinical research.

In one aspect, provided herein are isolated antibodies that bind the extracellular domain (e.g., the D1 domain) of a human SIRP-α v1 polypeptide, the extracellular domain (e.g., the D1 domain) of a human SIRP-α v2 polypeptide, or both. Further provided herein are polynucleotides and vectors encoding the antibodies of the present disclosure, as well as methods of antibody production related thereto.

In another aspect, provided herein are methods for treating or delaying progression of cancer in an individual, comprising administering to the individual an effective amount of an antibody of the present disclosure.

In another aspect, provided herein are methods for treating or delaying progression of an autoimmune or inflammatory disease in an individual, comprising administering to the individual an effective amount of an antibody of the present disclosure.

In another aspect, provided herein are methods for identifying an antigen binding domain that binds an extracellular domain (e.g., the D1 domain) of a human SIRP-α polypeptide and does not block binding between human CD47 and the human SIRP-α polypeptide. In some embodiments, the methods include (a) providing an antigen binding domain that binds the extracellular domain (e.g., the D1 domain) of a human SIRP-α polypeptide; (b) assembling a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; (c) contacting the antigen binding domain with the assembled complex; and (d) detecting binding of the antigen binding domain to the complex, wherein binding of the antigen binding domain to the complex indicates that the antigen binding domain does not block binding between human CD47 and the human SIRP-α polypeptide. In another aspect, provided herein are methods for identifying an antigen binding domain that binds an extracellular domain (e.g., the D1 domain) of a human SIRP-α polypeptide and does not block binding between human CD47 and the human SIRP-α polypeptide. In some embodiments, the methods include contacting an antigen binding domain or antibody that binds the extracellular domain (e.g., the D1 domain) of a human SIRP-α polypeptide with a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; and detecting binding of the antigen binding domain to the complex, wherein binding of the antigen binding domain to the complex indicates that the antigen binding domain does not block binding between human CD47 and the human SIRP-α polypeptide.

In another aspect, provided herein are methods for identifying an antigen binding domain that binds an extracellular domain (e.g., the D1 domain) of a human SIRP-α polypeptide and blocks binding between human CD47 and the human SIRP-α polypeptide. In some embodiments, the method includes (a) providing an antigen binding domain that binds the extracellular domain (e.g., the D1 domain) of a human SIRP-α polypeptide; (b) assembling a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; (c) contacting the antigen binding domain with the assembled complex; and (d) detecting binding of the antigen binding domain to the complex, wherein a lack of binding of the antigen binding domain to the complex indicates that the antigen binding domain blocks binding between human CD47 and the human SIRP-α polypeptide. In another aspect, provided herein are methods for identifying an antigen binding domain that binds an extracellular domain (e.g., the D1 domain) of a human SIRP-α polypeptide and blocks binding between human CD47 and the human SIRP-α polypeptide. In some embodiments, the method includes contacting an antigen binding domain or antibody that binds the extracellular domain (e.g., the D1 domain) of a human SIRP-α polypeptide with a complex comprising a SIRP-α D1 variant bound to a polypeptide comprising an IgSF domain of CD47, wherein the SIRP-α D1 variant is a non-naturally occurring high affinity SIRP-α D1 domain, and wherein the SIRP-α D1 variant binds to human CD47 with an affinity that is at least 10-fold greater than the affinity of a naturally occurring SIRP-α D1 domain binding to human CD47; and detecting binding of the antigen binding domain to the complex, wherein a lack of binding of the antigen binding domain to the complex indicates that the antigen binding domain blocks binding between human CD47 and the human SIRP-α polypeptide.

In another aspect, provided herein are methods for producing an anti-SIRP-α antibody that binds the extracellular domains (e.g., the D1 domains) of two or more different human SIRP-α variant polypeptides. In some embodiments, the method includes (a) immunizing a chicken with a peptide comprising at least a portion of a human SIRP-α extracellular domain (e.g., the D1 domain); (b) obtaining an antibody from an antibody-producing cell from the immunized chicken; and (c) detecting binding between the antibody obtained from the cell and the extracellular domains (e.g., the D1 domains) of two or more different human SIRP-α variant polypeptides, wherein binding between the antibody and the extracellular domains (e.g., the D1 domains) of the two or more different human SIRP-α variant polypeptides indicates that the antibody is an anti-SIRP-α antibody that binds the extracellular domains (e.g., the D1 domains) of two or more different human SIRP-α variant polypeptides.

Definitions

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising," "consisting," and "consisting essentially of" aspects and embodiments.

A "SIRP-α polypeptide" as used herein may refer to any endogenous or naturally occurring SIRP-α polypeptide encoded by a genome from any vertebrate, including mammals such as humans, monkeys, rodents (e.g., mouse or rat), and birds, such as chickens. The term also includes naturally occurring variants, e.g., alternatively spliced variants, allelic variants, or polymorphisms (e.g., those described herein). The term may further refer to full-length, unprocessed SIRP-α polypeptides as well as SIRP-α polypeptides that result from cellular processing, e.g., removal of a signal sequence, etc. Exemplary SIRP-α polypeptide sequences are described herein. In some embodiments, a human SIRP-α polypeptide is one encoded by a human SIRPA gene, e.g., as described by NCBI Gene ID No. 140885. As described herein, SIRP-α polypeptides are highly polymorphic within and among species. For example, at least 10 human variants with amino acid polymorphisms in the extracellular domain have been identified.

SIRP-α polypeptides include an extracellular domain that binds ligands/partners, e.g., CD47. SIRP-α polypeptides comprise 3 highly homologous immunoglobulin (Ig)-like extracellular domains—D1, D2, and D3. The SIRP-α D1 domain ("D1 domain") refers to the membrane distal, extracellular domain of SIRP-α and mediates binding of SIRP-α to CD47 (see, e.g., Hatherley, D. et al. (2008) *Mol. Cell* 31:266-77; Hatherley, D. et al. (2007) *J. Biol. Chem.* 282: 14567-75; Hatherley, D. et al. (2009) *J. Biol. Chem.* 284: 26613-9; and Lee, W. Y. et al. (2010) *J. Biol. Chem.* 285:37953-63). The extracellular domain generally refers to the entire extracellular portion of SIRP-α, e.g., as expressed on a cell surface, and may include distinct SIRP-α domains, such as the D1 domain. The D1 domain contains residues shown to be critical for mediating CD47 binding (see, e.g., Lee, W. Y. et al. (2007) *J. Immunol.* 179:7741-50). In some embodiments, an antibody that binds an extracellular domain of a SIRP-α polypeptide binds one or more residues of the D1 domain. Exemplary human SIRP-α D1 domain sequences are described throughout the present disclosure and include without limitation SEQ ID NOs:5, 6, and 76-83. Human SIRP-α D2 and D3 domain sequences are also known and include, without limitation, APVVSGPAARATPQHTVSFT-CESHGFSPRDITLKWFKNGNELSDFQTNVDPVGESV-SYSI HSTAKVVLTREDVHSQVICE-VAHVTLQGDPLRGTANLSETIR (SEQ ID NO:131) for the D2 domain and VPPTLEVTQQPVRAE-NQVNVTCQVRKFYPQRLQLTWLENGNVSRTE-TASTVTENKDGT YNWMSWLLVNVSAH-RDDVKLTCQVEHDGQPAVSKSHDLKVS (SEQ ID NO:132) for the D3 domain.

As used herein, "CD47" (also known as integrin associated protein (IAP), MER6, and OA3) refers to a polypeptide that, among other roles, serves as a binding partner for SIRP-α polypeptides. In some embodiments, CD47 refers to a human CD47 polypeptide, e.g., a polypeptide encoded by a human CD47 gene, such as that described by NCBI Ref Seq ID No. 961. Exemplary human CD47 amino acid sequences are known (see, e.g., NCBI Reference Sequence Accession No. NP_001768). In particular, the IgSF domain of CD47 refers to the N-terminal extracellular domain of CD47 that is known to be critical for SIRP-α binding (see, e.g., Barclay, A. N. and Brown, M. H. (2006) *Nat. Rev. Immunol.* 6:457-64 and Hatherley, D. et al. (2009) *J. Biol. Chem.* 284:26613-9). In some embodiments, an IgSF domain of CD47 comprises the amino acid sequence of QLLFNKTKSVEFTFSNDTVVIPCFVTNMEAQNTTE-VYVKWKFKGRDIYTFDGALNKSTV PTDFSSAKI-EVSQLLKGDASLKMDKSDAVSHTGNYTCEVTEL-TREGETIIELKYRVVS (SEQ ID NO:16). The term "CD47" may also include modified CD47 polypeptides that are able to bind SIRP-α, e.g., a polypeptide comprising an IgSF domain of CD47 conjugated to another polypeptide or other moiety, e.g., an Ig Fc region.

As used herein, a "SIRP-α epitope" may refer to the amino acids of a SIRP-α polypeptide that form the binding site for an anti-SIRP-α antibody of the present disclosure and/or a SIRP-α binding partner, including without limitation CD47. Binding of an antibody or other polypeptide to an epitope can be characterized and/or mapped using a variety of assays known in the art, including without limitation a cross-blocking assay (see *Antibodies, A Laboratory Manual*, Cold Spring Harbor Laboratory, Ed Harlow and David Lane (1988)), epitope mapping (see Champe et al., *J. Biol. Chem.* 270:1388-1394 (1995)), X-ray co-crystallography, epitope binning, site-directed mutagenesis, oligo-peptide scanning, high-throughput mutagenesis mapping, hydrogen/deuterium exchange, limited proteolysis, and so forth.

As used herein "modulating SIRP-α signaling" may refer to antagonizing, agonizing, or otherwise interfering with one or more aspects of SIRP-α signaling in a cell expressing a SIRP-α polypeptide. SIRP-α signaling may refer to one or more intracellular signaling events mediated by activation of a SIRP-α polypeptide, including without limitation tyrosine phosphorylation of the intracellular region of SIRP-α, phosphatase (e.g., SHIP1) binding, adaptor protein binding (e.g., SCAP2, FYB, and/or GRB2), cytokine production (e.g. IL-10, IL-1β, IFN or TNF), and nitric oxide production; and/or one or more intercellular phenotypes, including without limitation macrophage phagocytosis and other activating or suppressive phenotypes of macrophages, eosinophils, neutrophils, dendritic cells, and myeloid-derived suppressor cells (MDSCs).

As used herein, the term "antibody" may refer to intact antibodies; antibody fragments (including without limitation Fab, F(ab')2, Fab'-SH, Fv, diabodies, scFv, scFv-Fc, single domain antibodies, single heavy chain antibodies, and single light chain antibodies), provided that they exhibit the desired biological activity (e.g. epitope binding); monoclonal antibodies; polyclonal antibodies; monospecific antibodies; multi-specific antibodies (e.g., bispecific antibodies); and antibody-like proteins.

As used herein, the term "bispecific" when used in reference to an antibody or antibody fragment includes an antibody or antibody fragment that possesses two different binding specificities. For example, each binding specificity may recognize a different antigen, or each binding specificity may recognize the same antigen with different affinity and/or precise epitope. In some embodiments, each different binding specificity comprises one or more different antibody antigen binding domains (e.g., variable domains), such that the bispecific antibody or antibody fragment comprises at least a first antigen binding domain with a first binding specificity and a second antigen binding domain with a second binding specificity. A variety of exemplary bispecific antibody formats are described herein and known in the art.

An "isolated" antibody may refer to an antibody that has been separated and/or recovered from a component of its natural environment, e.g., a host cell or organism. In some embodiments, an antibody is purified to a desired purity by weight (e.g., at least 95%); and/or homogeneity by SDS-PAGE using, for example, staining by silver, Coomassie, etc. In some embodiments, an isolated antibody is obtained following one or more purification steps.

As is known in the art, "native" antibodies refer to typically heterotetrameric complexes including two identical light (L) chains and two identical heavy (H) chains. Variable numbers of disulfide bonds connect the two heavy chains, and one connects each light chain to a heavy chain, in addition to intrachain disulfide bridges. The heavy chains include a variable domain (VH) followed (N-terminus to C-terminus) by three or four constant domains. The light chains include a variable domain (VL) followed by a constant domain (CL). Typically, mammalian light chains fall into one of two categories based on amino acid sequence: kappa and lambda.

A "constant domain" may refer to the more conserved portion of the antibody or fragment, e.g., outside the variable domains. The term may include the CL domain as well as heavy chain constant domains CH1, CH2, CH3 and optionally CH4.

Constant domains of the heavy chain can be assigned to one of 5 major types: IgA, IgD, IgE, IgG, and IgM. Several subtypes exist for many of these major types. The subunit structures and three-dimensional configurations of different classes of immunoglobulins are well known and described generally in, for example, Abbas et al. *Cellular and Mol. Immunology*, 4th ed. (W.B. Saunders, Co., 2000).

As used herein, the term "antibody variable domain" refers to the portions of the light and heavy chains of an antibody that include the complementary determining regions (CDRs, e.g., CDR L1, CDR L2, CDR L3, CDR H1, CDR H2, and CDR H3) and framework regions (FRs).

The term "variable" refers to the fact that subsequences of the variable domains differ substantially in sequence between antibodies and are critical to the binding specificity of a particular antibody for its antigen. Variability is concentrated in three hypervariable regions (HVRs) in both VH and VL domains. The more conserved portions of variable domains are called the framework regions (FR) in which the HVRs are interspersed. The variable domains of native heavy and light chains each comprise four FR regions connected by three HVRs that form loops (see Kabat et al., *Sequences of Proteins of Immunological Interest*, Fifth Edition, National Institute of Health, Bethesda, Md. (1991)).

The term "hypervariable region (HVR)" may refer to the subregions of the VH and VL domains characterized by enhanced sequence variability and/or formation of defined loops. These include three HVRs in the VH domain (H1, H2, and H3) and three HVRs in the VL domain (L1, L2, and L3). H3 is believed to be critical in imparting fine binding specificity, with L3 and H3 showing the highest level of diversity. See Johnson and Wu, in *Methods in Molecular Biology* 248:1-25 (Lo, ed., Human Press, Totowa, N.J., 2003).

A number of HVR delineations are known. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below. "Framework" or "FR" residues are those variable domain residues other than the HVR residues.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

"Extended" HVRs are also known: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH (Kabat numbering).

"Numbering according to Kabat" may refer to the numbering system used for heavy chain variable domains or light chain variable domains of the compilation of antibodies in Kabat et al., supra. The actual linear amino acid sequence may contain fewer or additional amino acids corresponding to a shortening of, or insertion into, a FR or HVR of the variable domain. The Kabat numbering of residues may be determined for a given antibody by alignment at regions of homology of the sequence of the antibody with a "standard" Kabat numbered sequence. Typically, the Kabat numbering is used when referring to a residue in the variable domains (approximately residues 1-107 of the light chain and residues 1-113 of the heavy chain), whereas the EU numbering system or index (e.g., the EU index as in Kabat, numbering according to EU IgG1) is generally used when referring to a residue in the heavy chain constant region.

"Full length" or "intact" antibodies typically include heavy chains with an Fc region, e.g., as opposed to an antibody fragment. Antigen-binding "Fab" fragments with a single antigen binding site may be released from the residual Fc fragment by papain digestion. F(ab')2 fragments include two antigen-binding sites produced by pepsin treatment of an antibody. Antibody fragments will, however, include one or more antibody variable regions.

An "Fv" fragment contains a complete antigen-binding site. A single chain Fv (scFv) can include a VH and a VL domain linked by a peptide linker such that the VH and VL domains associate, e.g., as in an antibody or Fab fragment, such that the HVRs form an antigen binding site. See Pluckthün, in *The Pharmacology of Monoclonal Antibodies*, vol. 113, Rosenburg and Moore eds., (Springer-Verlag, New York, 1994), pp. 269-315. In some embodiments, the scFv is fused to an antibody Fc domain (e.g., scFv-Fc). While six HVRs typically comprise an antigen binding site, a single variable domain with three HVRs is still capable of binding an antigen, albeit at a lower affinity. See Hamers-Casterman et al., *Nature* 363:446-448 (1993); Sheriff et al., *Nature Struct. Biol.* 3:733-736 (1996). Single domain antibodies (e.g., camelid antibodies) typically include a single, monomeric variable domain for antigen binding. Single heavy chain (VHH) and single light chain antibodies are also known. A Fab' fragment typically includes a few more residues at the C-terminal end than a Fab fragment. A Fab'-SH includes cysteine residues with a free thiol. Various chemical couplings of antibody fragments are known in the art.

A "diabody" includes antibody fragments with two antigen-binding sites. These include a VH and VL domain connected by a linker, which is typically too short to facilitate pairing of domains in the same chain. Diabodies may be bivalent or bispecific. Tribodies and tetrabodies, or other numbers of VH/VL domains are known. See Hudson et al., *Nat. Med.* 9:129-134 (2003).

As used herein, a "monoclonal" antibody refers to an antibody obtained from a population of substantially homogeneous antibodies, e.g., substantially identical but allowing for minor levels of background mutations and/or modifications. "Monoclonal" denotes the substantially homogeneous character of antibodies, and does not require production of the antibody by any particular method. In some embodiments, a monoclonal antibody is selected by its HVR, VH, and/or VL sequences and/or binding properties, e.g., selected from a pool of clones (e.g., recombinant, hybridoma, or phage-derived). A monoclonal antibody may be engineered to include one or more mutations, e.g., to affect binding affinity or other properties of the antibody, create a humanized or chimeric antibody, improve antibody production and/or homogeneity, engineer a multispecific antibody, resultant antibodies of which are still considered to be monoclonal in nature. A population of monoclonal antibodies may be distinguished from polyclonal antibodies as the individual monoclonal antibodies of the population recognize the same antigenic site. A variety of techniques for production of monoclonal antibodies are known; see, e.g., the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

"Chimeric" antibodies may refer to an antibody with one portion of the heavy and/or light chain from a particular isotype, class, or organism and another portion from another isotype, class, or organism. In some embodiments, the variable region will be from one source or organism, and the constant region will be from another.

"Humanized antibodies" may refer to antibodies with predominantly human sequence and a minimal amount of non-human (e.g., mouse or chicken) sequence. In some embodiments, a humanized antibody has one or more HVR sequences (bearing a binding specificity of interest) from an antibody derived from a non-human (e.g., mouse or chicken) organism grafted onto a human recipient antibody framework (FR). In some embodiments, non-human residues are further grafted onto the human framework (not present in either source or recipient antibodies), e.g., to improve antibody properties. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See Jones et al., *Nature* 321:522-525 (1986); Riechmann et al., *Nature* 332:323-329 (1988); and Presta, *Curr. Op. Struct. Biol.* 2:593-596 (1992).

A "human" antibody may refer to an antibody having an amino acid sequence which corresponds to that of an antibody produced by a human and/or has been made using any of the techniques for making human antibodies as disclosed herein. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991); preparation of human monoclonal antibodies as described in Cole et al., *Monoclonal Antibodies and Cancer Therapy*, Alan R. Liss, p. 77 (1985); Boerner et al., *J. Immunol.*, 147(1):86-95 (1991); and by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENO-MOUSE™ technology) or chickens with human immunoglobulin sequence(s) (see, e.g., WO2012162422, WO2011019844, and WO2013059159).

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

The term "cytotoxic agent" as used herein may refer to any agent that inhibits cellular proliferation or induces cell death. Cytotoxic agents include, but are not limited to, chemotherapeutic agents; radioactive isotopes; growth inhibitory agents; and toxins such as small molecule toxins or enzymatically active toxins, including fragments and/or variants thereof. Exemplary cytotoxic agents include without limitation metabolic inhibitors, anti-microtubule agents, platinum containing compounds, alkylating agents, proteasome inhibitors, topoisomerase II inhibitors, antimetabolites, topoisomerase I inhibitors, signal transduction pathway inhibitors, non-receptor tyrosine kinase angiogenesis inhibitors, hormones and hormonal analogues, proapoptotic agents, inhibitors of LDH-A, cell cycle inhibitors, HDAC inhibitors, and antibiotic agents.

As used herein, a "label" may include any moiety that serves as a detection agent, e.g., of binding between a labeled antibody of the present disclosure and a macromolecule or cell. Exemplary labels include without limitation fluorescent (e.g., compounds or proteins), radioactive, or enzymatic moieties, as well as affinity purification tags.

As used herein, an antibody may be said to "bind" an antigen with an affinity sufficient to render the antibody useful for in vitro and/or in vivo manipulation of the antigen. In some embodiments, an antibody that "binds" an antigen has a dissociation constant ($K_D$) for the antigen that is less than or equal to 1 µM at 25° C.

As used herein, the term "affinity" or "binding affinity" refers to the strength of the binding interaction between two molecules. Generally, binding affinity refers to the strength of the sum total of non-covalent interactions between a molecule and its binding partner, such as a high affinity SIRP-α D1 variant and CD47. Unless indicated otherwise, binding affinity refers to intrinsic binding affinity, which reflects a 1:1 interaction between members of a binding pair. The binding affinity between two molecules is commonly described by the dissociation constant ($K_D$) or the association constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. In some embodiments, the $K_D$ of two interacting molecules is determined using known methods and techniques, e.g., surface plasmon resonance (SPR). $K_D$ can be calculated as the ratio of $k_{off}/k_{on}$.

As used herein, the term "$K_D$ less than" refers to a numerically smaller $K_D$ value and an increasing binding affinity relative to the recited $K_D$ value. As used herein, the term "$K_D$ greater than" refers to a numerically larger $K_D$ value and a decreasing binding affinity relative to the recited $K_D$ value.

As used herein, "treatment" may refer to therapeutic administration of a molecule, compound, formulation, composition, etc. so as to alter one or more pathological symptoms in an individual or cell being treated. Desirable effects of treatment can include without limitation decelerating disease progression, ameliorating or palliating a pathological symptom or disease state, improving prognosis, and/or achieving disease remission. For example, an individual's cancer is successfully "treated" if one or more symptoms associated with cancer are mitigated or abolished, such as, without limitation, reducing the proliferation of cancer cells, eliminating cancer cells or tumor burden, decreasing symptoms resulting from the cancer, increasing the quality of life of the individual, lessening the dose of other medication(s), and/or prolonging survival of the individual. As another example, an autoimmune or inflammatory disease may be successfully "treated" if one or more symptoms associated with the autoimmune or inflammatory disease are mitigated or abolished, such as, without limitation, reducing autoreactive immune cells and/or inflammatory immune cells or cytokines, decreasing immune activation and/or inflammation, slowing or mitigating organ damage resulting from the disease, decreasing symptoms resulting from the disease, increasing the quality of life of the individual, lessening the dose of other medication(s), and/or prolonging survival of the individual.

As used herein, "delaying progression" of a disease may refer to slowing, retarding, deferring, postponing development of, stabilizing, or otherwise hindering the pathological course of the disease. In some embodiments, the term may refer to a delay sufficient to effectively encompass prevention, e.g., in preventing the individual from developing the disease. In some embodiments, e.g., an advanced cancer, delaying progression may include delaying metastasis. One of skill in the art will appreciate that the precise length of delay may depend, e.g., upon the specific disease, condition of the individual, and the like.

The terms "cancer" and "cancerous" may describe dysregulated or unregulated cell growth/proliferation by a cell or cells in a mammal. Any cancer type known in the art may be included, such as but not limited to carcinoma, sarcoma, lymphoma, leukemia, lymphoma, and blastoma. More particular examples of such cancers include, but are not limited to, lung cancer, squamous cell cancer, brain tumors, glioblastoma, head and neck cancer, hepatocellular cancer, colorectal cancer (e.g., colon or rectal cancers), liver cancer, bladder cancer, gastric or stomach cancer, pancreatic cancer, cervical cancer, ovarian cancer, cancer of the urinary tract, breast cancer, peritoneal cancer, uterine cancer, salivary gland cancer, kidney or renal cancer, prostate cancer, vulval cancer, thyroid cancer, anal carcinoma, penile carcinoma, melanoma, multiple myeloma and B-cell lymphoma (including non-Hodgkin's lymphomas (NHL)); acute lymphoblastic leukemia (ALL); chronic lymphocytic leukemia (CLL); acute myeloid leukemia (AML); Merkel cell carcinoma; hairy cell leukemia; chronic myeloblastic leukemia (CML); and associated metastases.

As used herein, the term "effective amount" may refer to an amount of an antibody of the present disclosure or a pharmaceutical composition containing an antibody of the present disclosure that is sufficient and effective in achieving a desired therapeutic effect in treating or delaying progression of a patient having a disease, such as a cancer, e.g., solid tumor or hematological cancer. In some embodiments, a therapeutically effective amount will avoid adverse side effects, and/or such side effects will be outweighed by beneficial effects. An effective amount may depend upon the individual being treated, e.g., age, weight, sex, disease state, as well as the ability of the agent to produce a desired response. An effective amount can be administered in one or more administrations. As in the clinical context, an effective amount of a drug, compound, or pharmaceutical composition may or may not be achieved in conjunction with another drug, compound, or pharmaceutical composition, such as another therapeutic agent. Thus, an "effective amount" may also be considered in the context of administering one or more additional therapeutic agents, and a single agent may be considered to be given in an effective amount if, in conjunction with one or more other agents, a desirable result may be or is achieved.

As used herein, the term "pharmaceutical composition" may refer to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with one or more antibodies of the present disclosure. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets.

As used herein, "in conjunction with" or "in combination with" may refer to administration of one therapeutic in addition to (e.g., before, during, and/or after) another therapeutic.

Antibodies

Certain aspects of the present disclosure relate to antibodies that bind the extracellular domain (e.g., the D1 domain) of a human SIRP-α v1 polypeptide, the extracellular domain of a human SIRP-α v2 polypeptide, or both. As demonstrated herein, antibodies have been characterized that specifically bind to v1 or v2, as well as antibodies that bind to both proteins. In humans, at least 10 distinct alleles of SIRPA have been identified (see FIG. 1A; see also Takenaka, K. et al. (2007) *Nat. Immunol.* 8:1313-23). Antibodies that bind one or more human SIRP-α polypeptides and possess one or more of the other binding specificities described herein are an advantageous discovery of the present disclosure. Further, the present disclosure demonstrates methods for producing and identifying antibodies representing a surprising diversity of novel SIRP-α binding specificity profiles.

In some embodiments, an antibody of the present disclosure binds an extracellular domain (e.g., the D1 domain) of a human SIRP-α v1 polypeptide comprising the amino acid sequence of EEELQVIQPDKSVLVAAGETATLRCTATSLIPVGPIQWFRGAGPGRELIYNQKEGHFPRVTTVSDLTKRNNMDFSIRIGNITPADAGTYYCVKFRKGSPDDVEFKSGAGTELSVRAKPS (SEQ ID NO:5). In some embodiments, an antibody of the present disclosure binds an extracellular domain (e.g., the D1 domain) of a human SIRP-α v2 polypeptide comprising the amino acid sequence of EEELQVIQPDKSVSVAAGESAILHCTVTSLIPVGPIQWFRGAGPARELIYNQKEGHFPRVT TVSESTKRENMDFSISISNIT-PADAGTYYCVKFRKGSPDTEFKSGAGTELSVRAKPS (SEQ ID NO:6). In some embodiments, an antibody of the present disclosure binds an extracellular domain (e.g., the D1 domain) of a human SIRP-α v1 polypeptide comprising the amino acid sequence of EEELQVIQPDKSVLVAAGETAWTLRCTATSLIPVGPIQWFRGAGPGRELIYNQKEGHFPRV TTVSDLTKRNNMDFSIRIGNITPADAGTYYCVKFRKGSPDDVEFKSGAGTELSVRAKPS (SEQ ID NO:5) and an extracellular domain (e.g., the D1 domain) of a human SIRP-α v2 polypeptide comprising the amino acid sequence of (SEQ ID NO: 6)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS.

In some embodiments, an antibody of the present disclosure binds the extracellular domains (e.g., the D1 domains) of 1, 2, 3, 4, 5, 6, 7, 8, 9, or 10 different human SIRP-α variant polypeptides. As used herein, a "human SIRP-α variant polypeptide" may refer to a naturally occurring human SIRP-α variant polypeptide or polymorphism found expressed in a human, e.g., as opposed to a variant bearing one or more engineered mutations. For example, in some embodiments, an antibody of the present disclosure binds the extracellular domain (e.g., the D1 domain) of one or more human SIRP-α variant polypeptides comprising a sequence shown in the Table 1. In some embodiments, an antibody of the present disclosure binds to an extracellular domain (e.g., the D1 domain) of a human SIRP-α v1 polypeptide and/or an extracellular domain (e.g., the D1 domain) of a human SIRP-α v2 polypeptide, and binds to an extracellular domain (e.g., the D1 domain) of one or more human SIRP-α polypeptides selected from v3, v4, v5, v6, v7, v8, v9, and v10.

TABLE 1

Human SIRP-α variant polypeptide sequences corresponding to the D1 domain.

| Variant | SEQ ID NO | Sequence |
|---|---|---|
| v1 | 5 | EEELQVIQPDKSVLVAAGETATLRCTATSLIPVGPIQWFRG AGPGRELIYNQKEGHFPRVTTVSDLTKRNNMDFSIRIGNIT PADAGTYYCVKFRKGSPDDVEFKSGAGTELSVRAKPS |
| v2 | 6 | EEELQVIQPDKSVSVAAGESAILHCTVTSLIPVGPIQWFRG AGPARELIYNQKEGHFPRVTTVSESTKRENMDFSISISNITP ADAGTYYCVKFRKGSPDTEFKSGAGTELSVRAKPS |
| v3 | 76 | EEELQVIQPDKSVSVAAGESAILLCTVTSLIPVGPIQWFRGAG PARELIYNQKEGHFPRVTTVSESTKRENMDFSISISNITPADA GTYYCVKFRKGSPDTEFKSGAGTELSVRAKPS |
| v4 | 77 | EEGLQVIQPDKSVSVAAGESAILHCTATSLIPVGPIQWFRG AGPGRELIYNQKEGHFPRVTTVSDLTKRNNMDFSIRIGNIT PADAGTYYCVKFRKGSPDDVEFKSGAGTELSVRAKPS |
| v5 | 78 | EEELQVIQPDKFVLVAAGETATLRCTATSLIPVGPIQWFRG AGPGRELIYNQKEGHFPRVTTVSDLTKRNNMDFSIRIGNIT PADAGTYYCVKFRKGSPDDVEFKSGAGTELSVRAKPS |
| v6 | 79 | EEELQVIQPDKSVLVAAGETATLRCTATSLIPVGPIQWFRG AGPGRELIYNQKEGHFPRVTTVSDLTKRNNMDFPIRIGNIT PADAGTYYCVKFRKGSPDDVEFKSGAGTELSVRAKPS |
| v7 | 80 | EEELQVIQPDKSVSVAAGESAILHCTVTSLIPVGPIQWFRG AGPARELIYNQKEGHFPRVTTVSESTKRENMDFSISISNITP ADAGTYYCVKFRKGSPDTEFKSGAGTELSVRGKPS |

TABLE 1-continued

Human SIRP-α variant polypeptide sequences corresponding to the D1 domain.

| Variant | SEQ ID NO | Sequence |
|---|---|---|
| v8 | 81 | EEELQVIQPDKSVLVAAGETATLRCTATSLIPVGPIQWFRG AGPARELIYNQKEGHFPRVTTVSESTKRENMDFSISISNITP ADAGTYYCVKFRKGSPDTEFKSGAGTELSVRAKPS |
| v9 | 82 | EEELQVIQPDKSVLVAAGETATLRCTATSLIPVGPIQWFRG AGPGRELIYNQKEGHFPRVTTVSDLTKRNNMDFSIRISNIT PADAGTYYCVKFRKGSPDDVEFKSGAGTELSVRAKPS |
| v10 | 83 | EEELQVIQPDKSVSVAAGESAILHCTVTSLIPVGPIQWFRG AGPARELIYNQKEGHFPRVTTVSESTKRENMDFSISISNITP ADAGTYYCVKFRKGSPDTEFKSGAGTELSVRAKPS |

In some embodiments, an antibody of the present disclosure binds an extracellular domain (e.g., the D1 domain) of a monkey SIRP-α polypeptide (e.g., the D1 domain of a monkey SIRP-α polypeptide). In some embodiments, an antibody of the present disclosure binds an extracellular domain (e.g., the D1 domain) of a cynomolgus SIRP-α polypeptide (e.g., found in the organism *Macaca fascicularis*). In some embodiments, the antibody binds the extracellular domains (e.g., the D1 domains) of at least two different monkey SIRP-α variant polypeptides. In some embodiments, the antibody binds the extracellular domains (e.g., the D1 domains) of at least two different cynomolgus SIRP-α variant polypeptides. For example, in some embodiments, the antibody binds an extracellular domain (e.g., the D1 domain) of a cynomolgus SIRP-α polypeptide comprising the amino acid sequence of EEELQVIQPEKSVSVAAGESATLNCTATSLIPVG-PIQWFRGVGPGRELIYHQKEGHFPRV TPVSDPTKRNNMDFSIRISNIT-PADAGTYYCVKFRKGSPDVELKSGAGTELSVRAKPS (SEQ ID NO:11), an extracellular domain (e.g., the D1 domain) of a cynomolgus SIRP-α polypeptide comprising the amino acid sequence of EEELQVIQPEKSVSVAAGD-SATLNCTVSSLIPVGPIQWFRGAGPGRELIYNLKEG-HFPRVT AVSDPTKRNNMDFSIRISNIT-PADAGTYYCVKFRKGSPDVELKSGAGTELSVRAKPS (SEQ ID NO:12), or both.

In some embodiments, an antibody of the present disclosure binds an extracellular domain of a murine or mouse SIRP-α polypeptide (e.g., found in the organism *Mus musculus*; e.g., the D1 domain of a murine or mouse SIRP-α polypeptide). In some embodiments, the antibody binds the extracellular domains (e.g., the D1 domains) of two or more different murine SIRP-α variant polypeptides. A variety of murine SIRP-α variant polypeptides from different mouse strains are known. In some embodiments, the murine SIRP-α variant polypeptide comprises an amino acid sequence selected from (SEQ ID NO: 7; from 129 mouse strain)
KELKVTQPEKSVSVAAGDSTVLNCTLTSLLPVGPIKWYRGVGQSRLLIYS

FTGEHFPRVTNVSDATKRNNMDFSIRISNVTPEDAGTYYCVKFQKGPSEP

DTEIQSGGGTEVYVLAKPS, (SEQ ID NO: 8; from NOD mouse strain)
TEVKVIQPEKSVSVAAGDSTVLNCTLTSLLPVGPIRWYRGVGQSRQLIYS -continued
FTTEHFPRVTNVSDATKRSNLDFSIRISNVTPEDAGTYYCVKFQRGSPDT

EIQSGGGTEVYVLAK, (SEQ ID NO: 9; from C57BL/6 mouse strain)
KELKVTQPEKSVSVAAGDSTVLNCTLTSLLPVGPIRWYRGVGPSRLLIYS

FAGEYVPRIRNVSDTTKRNNMDFSIRISNVTPADAGIYYCVKFQKGSSEP

DTEIQSGGGTEVYVLAK,
and (SEQ ID NO: 10; from BALB/c mouse strain)
TEVKVTQPEKSVSVAAGDSTILNCTVTSLLPVGPIRWYRGVGQSRLLIYS

FTGEHFPRIRNVSDTTKRNNMDFSIRISNVTPEDAGTYYCVKFQRGSSEP

DTEIQSGGGTEVYVLAK.

In some embodiments, an antibody of the present disclosure binds an extracellular domain (e.g., the D1 domain) of a human SIRP family protein. In some embodiments, an antibody of the present disclosure binds an extracellular domain (e.g., the D1 domain) of a human SIRP-β polypeptide. In some embodiments, a human SIRP-β polypeptide refers to a polypeptide encoded by a human SIRPB1 gene, e.g., as described by NCBI Ref Seq ID No. 10326. In some embodiments, the extracellular domain (e.g., the D1 domain) of the human SIRP-β polypeptide comprises the amino acid sequence of (SEQ ID NO: 13)
EDELQVIQPEKSVSVAAGESATLRCAMTSLIPVGPIMWFRGAGAGRELIY

NQKEGHFPRVTTVSELTKRNNLDFSISISNITPADAGTYYCVKFRKGSPD

DVEFKSGAGTELSVRAKPS
or
(SEQ ID NO: 14)
EEELQVIQPDKSISVAAGESATLHCTVTSLIPVGPIQWFRGAGPGRELIY

NQKEGHFPRVTTVSDLTKRNNMDFSIRISNITPADAGTYYCVKFRKGSPD

HVEFKSGAGTELSVRAKPS.

In some embodiments, an antibody of the present disclosure binds an extracellular domain (e.g., the D1 domain) of a human SIRP-γ polypeptide. In some embodiments, a human SIRP-γ polypeptide refers to a polypeptide encoded by a human SIRPG gene, e.g., as described by NCBI Ref Seq ID No. 55423. In some embodiments, the extracellular domain (e.g., the D1 domain) of the human SIRP-γ polypeptide comprises the amino acid sequence of (SEQ ID NO: 15)
EEELQMIQPEKLLLVTVGKTATLHCTVTSLLPVGPVLWFRGVGPGRELIY

NQKEGHFPRVTTVSDLTKRNNMDFSIRISSITPADVGTYYCVKFRKGSPE

NVEFKSGPGTEMALGAKPS.

In addition to antibodies that bind one or more of the polypeptides described above, the present disclosure contemplates antibodies that do not bind one or more of the polypeptides described above. Stated another way, the binding profile of an antibody of the present disclosure may be characterized by positively or negatively reciting any of the binding specificities and/or properties described herein.

In some embodiments, an antibody of the present disclosure modulates SIRP-α signaling in a cell expressing a human SIRP-α polypeptide. In some embodiments, an antibody of the present disclosure antagonizes SIRP-α signaling in a cell expressing a human SIRP-α polypeptide. In some embodiments, an antibody of the present disclosure interferes with SIRP-α signaling in a cell expressing a human SIRP-α polypeptide. In some embodiments, an antibody of the present disclosure agonizes SIRP-α signaling in a cell expressing a human SIRP-α polypeptide. In some embodiments, SIRP-α signaling includes one or more intracellular signaling events mediated by activation of a SIRP-α polypeptide, including without limitation tyrosine phosphorylation of the intracellular region of SIRP-α, phosphatase (e.g., SHIP1) binding, adaptor protein binding (e.g., SCAP2, FYB, and/or GRB2), and nitric oxide production. Various assays for measuring SIRP-α signaling in a cell include without limitation SIRP-α phosphorylation, SHP1 and SHP2 co-immunoprecipitation, PI3-kinase signaling, cytokine production (both inflammatory IL-12, IL-23, TNFα, IFN and suppressive cytokines IL-10, IL-4, IL-13, cell surface markers levels for M1 and M2 macrophage markers) or dendritic cell activation and function; Kharitonenkov, A. et al. (1997) Nature 386: 181-6; Ochi, F. et al. (1997) Biochem. Biophys. Res. Commun. 239:483-7; Kim, E. J. et al. (2013) Inflammation Research 62:377-86; Yi, T. et al. (2015) Immunity 43:764-75.

In some embodiments, the cell expressing a human SIRP-α polypeptide is a leukocyte. In some embodiments, the cell is a macrophage, dendritic cell, neutrophil, eosinophil, or myeloid-derived suppressor cell (MDSC). In some embodiments, an antibody of the present disclosure decreases or antagonizes SIRP-α signaling in a cell expressing a human SIRP-α polypeptide by at least 20%, at least 30%, at least 40%, at least 50%, at least 60%, at least 70%, at least 80%, or at least 90%, e.g., using one or more of the SIRP-α signaling assays described herein or otherwise known in the art. In some embodiments, an antibody of the present disclosure increases or agonizes SIRP-α signaling in a cell expressing a human SIRP-α polypeptide by at least 20%, at least 30%, at least 40%, at least 50%, at least 60%, at least 70%, at least 80%, or at least 90%, e.g., using one or more of the SIRP-α signaling assays described herein or otherwise known in the art.

In some embodiments, an antibody of the present disclosure modulates an intercellular phenotype mediated by SIRP-α. In some embodiments, an antibody of the present disclosure enhances phagocytosis by a macrophage expressing a human SIRP-α polypeptide. For example, phagocytic activity of a macrophage treated or contacted with an antibody of the present disclosure can be compared with phagocytic activity of a macrophage not treated or contacted with the antibody, or phagocytic activity of a macrophage that expresses a human SIRP-α polypeptide and is treated or contacted with an antibody of the present disclosure can be compared with phagocytic activity of a macrophage that does not express a human SIRP-α polypeptide and is treated or contacted with the antibody. Exemplary phagocytosis assays may be found, e.g., in Wieskopf, K. et al (2013) Science 341: 88 and Willingham, S. B. et al. (2012) Proc. Natl. Acad. Sci. 109:6662-7. In some embodiments, an antibody of the present disclosure increases phagocytosis by a macrophage expressing a human SIRP-α polypeptide by at least 20%, at least 30%, at least 40%, at least 50%, at least 60%, at least 70%, at least 80%, or at least 90%, e.g., using one or more of the phagocytosis assays described herein or otherwise known in the art.

In some embodiments, an antibody of the present disclosure enhances activation of dendritic cell(s) expressing a human SIRP-α polypeptide (e.g., an increased level of activation of individual dendritic cells, or an increased proportion of dendritic cells that are activated within a sample population). For example, activation of dendritic cell(s) treated or contacted with an antibody of the present disclosure can be compared with activation of dendritic cell(s) not treated or contacted with the antibody, or activation of dendritic cell(s) that express a human SIRP-α polypeptide and are treated or contacted with an antibody of the present disclosure can be compared with activation of dendritic cell(s) that do not express a human SIRP-α polypeptide and are treated or contacted with the antibody. Exemplary dendritic cell activation assays are described herein. In some embodiments, an antibody of the present disclosure increases dendritic cell (e.g., expressing a human SIRP-α polypeptide) activation by at least 20%, at least 30%, at least 40%, at least 50%, at least 60%, at least 70%, at least 80%, or at least 90%, e.g., using one or more of the dendritic cell activation assays described herein or otherwise known in the art.

In some embodiments, an antibody of the present disclosure inhibits in vivo growth of a tumor that expresses CD47. For example, in vivo growth of a tumor that expresses CD47 and is treated with an antibody of the present disclosure can be compared against in vivo growth of a tumor that expresses CD47 and is not treated with an antibody of the present disclosure. Exemplary in vivo tumor growth assays are described herein. In some embodiments, an antibody of the present disclosure inhibits in vivo growth of a tumor that expresses CD47 by at least 20%, at least 30%, at least 40%, at least 50%, at least 60%, at least 70%, at least 80%, or at least 90%, e.g., using one or more of the in vivo tumor growth assays described herein or otherwise known in the art.

In some embodiments, an antibody of the present disclosure blocks binding between an extracellular domain (e.g., the D1 domain) of a human SIRP-α polypeptide and an IgSF domain of a human CD47 polypeptide (e.g., a "blocking" antibody). For example, the antibody and the CD47 polypeptide may "compete" for the same SIRP-α epitope, and/or antibody binding to SIRP-α may be mutually exclusive with CD47 binding to SIRP-α. The binding interface between SIRP-α and CD47, as well as residues of both proteins that participate in binding, are known; see Hatherley, D. et al. (2007) J. Biol. Chem. 282:14567-75 and Nakaishi, A. et al. (2008) J. Mol. Biol. 375:650-60. Exemplary assays for determining whether an antibody blocks CD47 binding to SIRP-α are described herein. In some embodiments, an antibody of the present disclosure blocks binding between an extracellular domain (e.g., the D1 domain) of a human SIRP-α polypeptide and an IgSF domain of a human CD47 polypeptide in an in vitro assay, e.g., using purified SIRP-α and/or CD47 polypeptides. For example, in vitro ELISA and SPR assays are described herein, although this is not meant to be limiting, as other in vitro binding assays may also be used. In some embodiments, antibody binding to a complex comprising a SIRP-α D1 variant (e.g., a non-naturally occurring high affinity SIRP-α D1 domain binding to CD47 with higher affinity than one or more naturally occurring counterparts as described herein) bound to an IgSF domain of CD47 is used to screen for blocking, non-blocking, and/or kick off antibodies. In some embodiments, "blocking" and/or "non-blocking" antibodies can be tested via surface plasmon resonance (SPR; e.g., as described in Example 1). For example, a complex can be formed between an IgSF domain of CD47 and a SIRP-α D1 variant (e.g., a non-naturally occurring high affinity SIRP-α D1 domain binding to CD47 with higher affinity than one or more naturally occurring counterparts as described herein), then binding of a test antibody to the complex can be measured. For an antibody that blocks binding of SIRP-α to CD47, at increasing concentrations of CD47, one would expect fewer molecules of SIRP-α to be available to bind to the antibody since the antibody competes for the same binding site as CD47 and most/all SIRP-α is complexed with CD47. Therefore, one would expect the resonance (RU) to decrease with increasing concentration of CD47 in the mixture. In some embodiments, a "blocking" anti-SIRP-α antibody of the present disclosure binds to the extracellular domain of a SIRP-α polypeptide (e.g., the D1 domain) at one or more residues of the binding interface between CD47 and SIRP-α, i.e., the blocking antibody and CD47 share partially or completely overlapping epitopes. In some embodiments, a "blocking" anti-SIRP-α antibody of the present disclosure binds to the extracellular domain of a SIRP-α polypeptide (e.g., the D1 domain) at one or more amino acid positions that are also bound by CD47 in the CD47:SIRP-α complex. The binding interfaces between SIRP-α and exemplary anti-SIRP-α antibodies or CD47 are described in Example 4. In some embodiments, an antibody of the present disclosure blocks binding between an extracellular domain (e.g., the D1 domain) of a human SIRP-α polypeptide expressed on the surface of a first cell and an IgSF domain of a human CD47 polypeptide expressed on the surface of a second cell, e.g., an in vivo binding assay between polypeptides expressed on the surface of cells. In some embodiments, the in vivo assay may assess binding between an extracellular domain (e.g., the D1 domain) of a human SIRP-α polypeptide expressed on the surface of a first cell and an IgSF domain of a human CD47 polypeptide expressed on the surface of a second cell by assaying one or more aspects of SIRP-α signaling, e.g., one or more intracellular signaling events mediated by activation of a SIRP-α polypeptide, including without limitation tyrosine phosphorylation of the intracellular region of SIRP-α, phosphatase (e.g., SHIP1) binding, adaptor protein binding (e.g., SCAP2, FYB, and/or GRB2), cytokine production (e.g. IL-10, IL-1β, IFN or TNF), and nitric oxide production; and/or one or more intercellular phenotypes, including without limitation macrophage phagocytosis and other activating or suppressive phenotypes of macrophages, neutrophils, dendritic cells, eosinophils, and myeloid-derived suppressor cells (MDSCs).

In some embodiments, an antibody of the present disclosure does not block binding between an extracellular domain (e.g., the D1 domain) of a human SIRP-α polypeptide and an IgSF domain of a human CD47 polypeptide (e.g., a "non-blocking" antibody). For example, the antibody and the CD47 polypeptide may bind distinct and/or non-overlapping epitopes of SIRP-α. In some embodiments, an antibody of the present disclosure does not block binding between an extracellular domain (e.g., the D1 domain) of a human SIRP-α polypeptide and an IgSF domain of a human CD47 polypeptide in an in vitro assay, e.g., using purified SIRP-α and/or CD47 polypeptides. For example, in vitro ELISA and SPR assays are described herein, although this is not meant to be limiting, as other in vitro binding assays may also be used. In some embodiments, antibody binding to a complex comprising a SIRP-α D1 variant (e.g., a non-naturally occurring high affinity SIRP-α D1 domain binding to CD47 with higher affinity than one or more naturally occurring counterparts as described herein) bound to an IgSF domain of CD47 is used to screen for blocking, non-blocking, and/or kick off antibodies. In some embodiments, "blocking" and/or "non-blocking" antibodies can be tested via surface plasmon resonance (SPR; e.g., as described in Example 1). For example, a complex can be formed between an IgSF domain of CD47 and a SIRP-α D1 variant (e.g., a non-naturally occurring high affinity SIRP-α D1 domain binding to CD47 with higher affinity than one or more naturally occurring counterparts as described herein), then binding of a test antibody to the complex can be measured. For an antibody that does not block binding of SIRP-α to CD47, the antibody would be expected to bind to SIRP-α/CD47 complex and form a sandwich. Therefore, at increasing concentrations of CD47, the resonance would increase accordingly due to increased sandwich formation. In some embodiments, a "non-blocking" anti-SIRP-α antibody of the present disclosure binds to the extracellular domain of a SIRP-α polypeptide (e.g., the D1 domain) at one or more residues that are distinct from the binding interface between CD47 and SIRP-α, i.e., the non-blocking antibody and CD47 share completely non-overlapping epitopes. The binding interfaces between SIRP-α and exemplary anti-SIRP-α antibodies or CD47 are described in Example 4. In some embodiments, an antibody of the present disclosure does not block binding between an extracellular domain (e.g., the D1 domain) of a human SIRP-α polypeptide expressed on the surface of a first cell and an IgSF domain of a human CD47 polypeptide expressed on the surface of a second cell, e.g., an in vivo binding assay between polypeptides expressed on the surface of cells. In some embodiments, the in vivo assay may assess binding between an extracellular domain (e.g., the D1 domain) of a human SIRP-α polypeptide expressed on the surface of a first cell and an IgSF domain of a human CD47 polypeptide expressed on the surface of a second cell by assaying one or more aspects of SIRP-α signaling, e.g., one or more intracellular signaling events mediated by activation of a SIRP-α polypeptide, including without limitation tyrosine phosphorylation of the intracellular region of SIRP-α, phosphatase (e.g., SHIP1) binding, adaptor protein binding (e.g., SCAP2, FYB, and/or GRB2), cytokine production (e.g. IL-10, IL-1β, IFN or TNF), and nitric oxide production; and/or one or more intercellular phenotypes, including without limitation macrophage phagocytosis and other activating or suppressive phenotypes of macrophages, neutrophils, dendritic cells, eosinophils, and myeloid-derived suppressor cells (MDSCs). It is a surprising finding of the present disclosure that antibodies that do not block SIRP-α interaction with CD47 are able to increase phagocytosis and block in vivo tumor growth. Without wishing to be bound to theory, it is thought that non-blocking anti-SIRP-α antibodies can modulate one or more functions of SIRP-α independent of CD47 binding.

In some embodiments, binding of an antibody of the present disclosure to an extracellular domain (e.g., the D1 domain) of a human SIRP-α polypeptide reduces affinity of the human SIRP-α polypeptide for binding an IgSF domain of a human CD47 polypeptide (e.g., a "kick off" antibody). In some embodiments, binding of the antibody to an extracellular domain (e.g., the D1 domain) of a human SIRP-α polypeptide increases $k_{off}$ of the human SIRP-α polypeptide for binding an IgSF domain of a human CD47 polypeptide. In some embodiments binding of the antibody to an extracellular domain (e.g., the D1 domain) of a human high affinity SIRP-α polypeptide (e.g., as described herein) increases the $k_{off}$ of the human high affinity SIRP-α polypeptide (e.g., as described herein) for binding an IgSF domain of a human CD47 polypeptide to greater than about $1 \times 10^{-3}$ 1/s. For example, the antibody and the CD47 polypeptide may have adjacent or partially overlapping SIRP-α epitopes, such that the antibody is able to bind SIRP-α when it is bound to CD47, but the antibody: SIRP-α promotes dissociation of the SIRP-α. CD47 complex. In some embodiments, an antibody of the present disclosure reduces affinity of an extracellular domain (e.g., the D1 domain) of a human SIRP-α polypeptide for binding an IgSF domain of a human CD47 polypeptide in an in vitro assay, e.g., using purified SIRP-α and/or CD47 polypeptides. In some embodiments, binding of the antibody to an extracellular domain (e.g., the D1 domain) of a human SIRP-α polypeptide increases $k_{off}$ of the human SIRP-α polypeptide for binding an IgSF domain of a human CD47 polypeptide in an in vitro assay, e.g., using purified SIRP-α and/or CD47 polypeptides. For example, in vitro ELISA and SPR assays are described herein, although this is not meant to be limiting, as other in vitro binding assays may also be used. In some embodiments, antibody binding to a complex comprising a SIRP-α D1 variant (e.g., a non-naturally occurring high affinity SIRP-α D1 domain binding to CD47 with higher affinity than one or more naturally occurring counterparts as described herein) bound to an IgSF domain of CD47 is used to screen for blocking, non-blocking, and/or kick off antibodies. In some embodiments, an antibody of the present disclosure reduces affinity of an extracellular domain (e.g., the D1 domain) of a human SIRP-α polypeptide expressed on the surface of a first cell for binding an IgSF domain of a human CD47 polypeptide expressed on the surface of a second cell, e.g., an in vivo binding assay between polypeptides expressed on the surface of cells. In some embodiments, a "kick off" anti-SIRP-α antibody of the present disclosure binds to the extracellular domain (e.g., the D1 domain) of a SIRP-α polypeptide at one or more residues of the binding interface between CD47 and SIRP-α, i.e., the kick off antibody and CD47 share partially overlapping epitopes. In some embodiments, a "kick off" anti-SIRP-α antibody of the present disclosure binds to the extracellular domain (e.g., the D1 domain) of a SIRP-α polypeptide at 1 or more residues that are also bound by CD47 in the CD47:SIRP-α complex. For example, a "kick off" anti-SIRP-α antibody can bind to the extracellular domain (e.g., the D1 domain) of a SIRP-α polypeptide at 2 or more residues that are also bound by CD47 in the CD47:SIRP-α complex and are at the periphery of the CD47 binding epitope of SIRP-α. The binding interfaces between SIRP-α and exemplary anti-SIRP-α antibodies or CD47 are described in Example 4. In some embodiments, binding of an antibody of the present disclosure to an extracellular domain (e.g., the D1 domain) of a human SIRP-α polypeptide expressed on the surface of a first cell increases $k_{off}$ of the human SIRP-α polypeptide for binding an IgSF domain of a human CD47 polypeptide expressed on the surface of a second cell, e.g., an in vivo binding assay between polypeptides expressed on the surface of cells. In some embodiments, the in vivo assay may assess binding between an extracellular domain (e.g., the D1 domain) of a human SIRP-α polypeptide expressed on the surface of a first cell and an IgSF domain of a human CD47 polypeptide expressed on the surface of a second cell by assaying one or more aspects of SIRP-α signaling, e.g., one or more intracellular signaling events mediated by activation of a SIRP-α polypeptide, including without limitation tyrosine phosphorylation of the intracellular region of SIRP-α, phosphatase (e.g., SHIP1) binding, adaptor protein binding (e.g., SCAP2, FYB, and/or GRB2), cytokine production (e.g. IL-10, IL-1β, IFN or TNF), and nitric oxide production; and/or one or more intercellular phenotypes, including without limitation macrophage phagocytosis and other activating or suppressive phenotypes of macrophages, neutrophils, dendritic cells, eosinophils, and myeloid-derived suppressor cells (MDSCs).

In some embodiments, an antibody of the present disclosure modulates one or more immune cell functions by binding to two or more (or all three) of SIRP-α, SIRPβ, and SIRPγ.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey SIRP-α polypeptide; and the antibody does not block binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey SIRP-α polypeptide; and the antibody blocks binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey SIRP-α polypeptide; and binding of the antibody to an extracellular domain (e.g., the D1 domain) of a human SIRP-α polypeptide reduces affinity of the human SIRP-α polypeptide for binding an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a murine SIRP-α polypeptide; and the antibody does not block binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a murine SIRP-α polypeptide; and the antibody blocks binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a murine SIRP-α polypeptide; and binding of the antibody to an extracellular domain (e.g., the D1 domain) of a human SIRP-α polypeptide reduces affinity of the human SIRP-α polypeptide for binding an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey (e.g., cynomolgus) SIRP-α polypeptide; binds the extracellular domain (e.g., the D1 domain) of a murine SIRP-α polypeptide; and the antibody does not block binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey (e.g., cynomolgus) SIRP-α polypeptide; binds the extracellular domain (e.g., the D1 domain) of a murine SIRP-α polypeptide; and the antibody blocks binding between an extracellular domain (e.g., the D1 domain) of a human SIRP-α polypeptide and an IgSF domain of a human CD47 polypeptide.

In some embodiments, an antibody of the present disclosure binds the extracellular domain (e.g., the D1 domain) of a human SIRP-α v1 polypeptide, the extracellular domain (e.g., the D1 domain) of a human SIRP-α v2 polypeptide, or both; binds the extracellular domain (e.g., the D1 domain) of a monkey (e.g., cynomolgus) SIRP-α polypeptide; binds the extracellular domain (e.g., the D1 domain) of a murine SIRP-α polypeptide; and binding of the antibody to an extracellular domain (e.g., the D1 domain) of a human SIRP-α polypeptide reduces affinity of the human SIRP-α polypeptide for binding an IgSF domain of a human CD47 polypeptide.

Figures 3A, 3B:
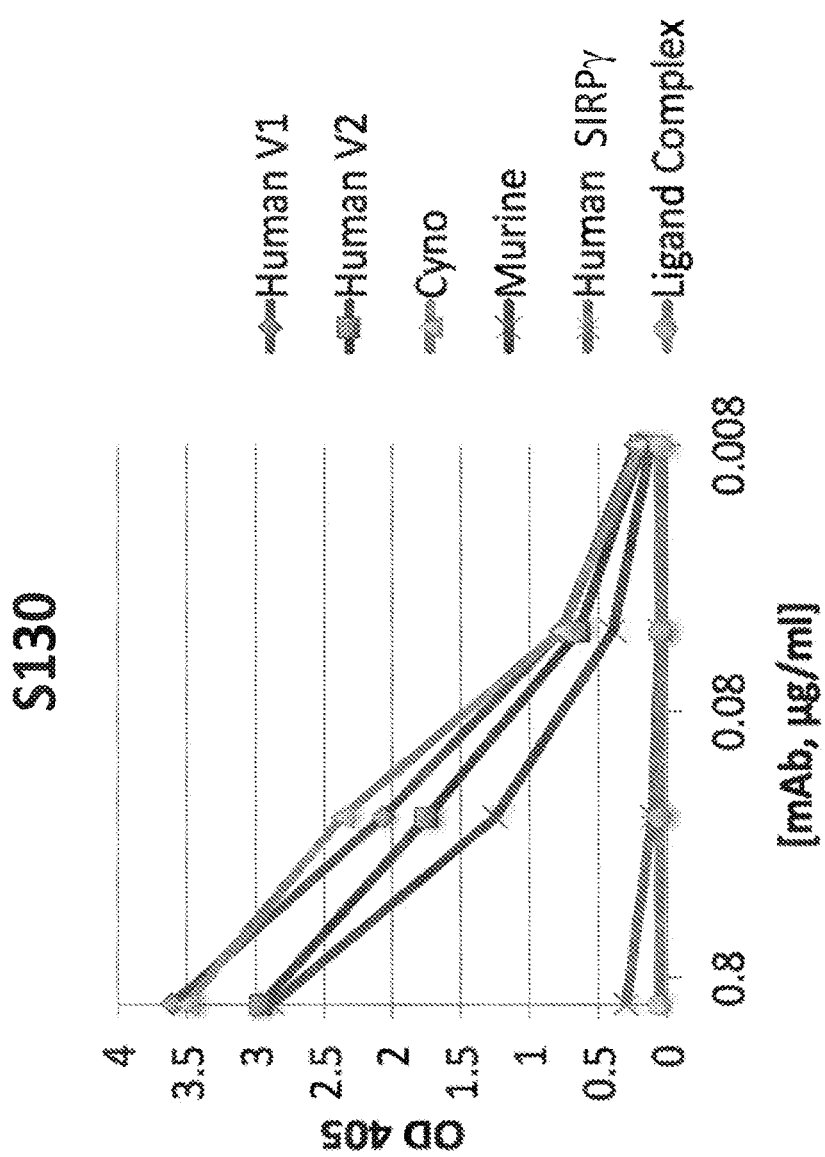

In some embodiments, an antibody of the present disclosure binds the extracellular domains (e.g., the D1 domains) of two or more different human SIRP-α variant polypeptides, a murine SIRP-α polypeptide, and a monkey SIRP-α polypeptide; the antibody does not bind at least one of an extracellular domain (e.g., the D1 domain) of a human SIRP-β polypeptide and an extracellular domain (e.g., the D1 domain) of a human SIRP-γ polypeptide; and the antibody blocks binding between the extracellular domain (e.g., the D1 domain) of the human SIRP-α polypeptide and an IgSF domain of a human CD47 polypeptide (see, e.g., FIGS. 3A & 3B).

Figure 4A:
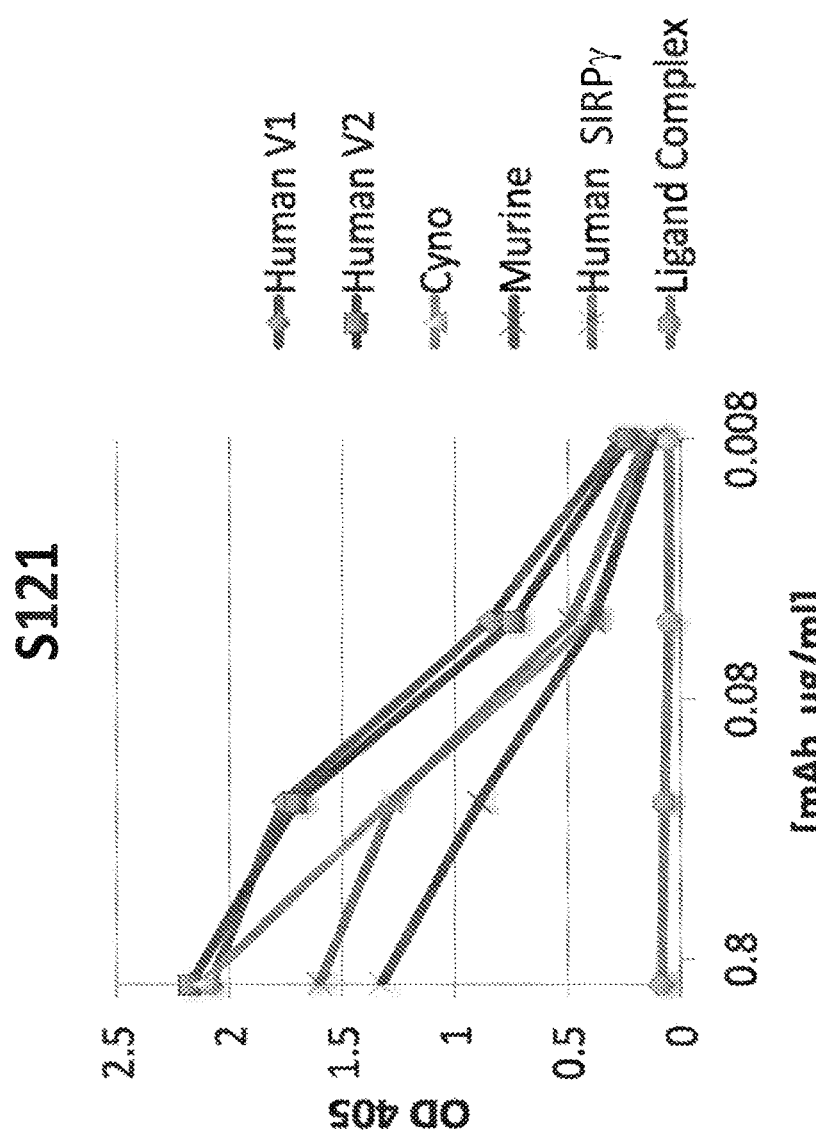
Figure 4B:
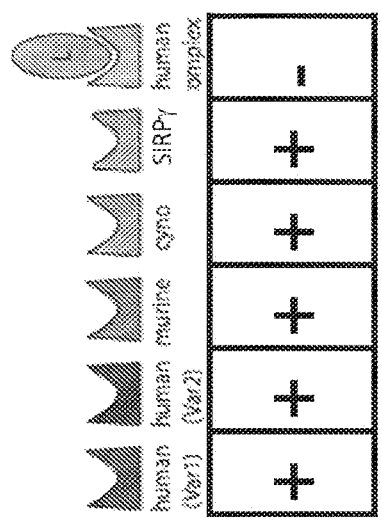

In some embodiments, an antibody of the present disclosure binds the extracellular domains (e.g., the D1 domains) of two or more different human SIRP-α variant polypeptides, a murine SIRP-α polypeptide, a monkey SIRP-α polypeptide, and at least one of an extracellular domain (e.g., the D1 domain) of a human SIRP-β polypeptide and an extracellular domain (e.g., the D1 domain) of a human SIRP-γ polypeptide; and the antibody blocks binding between the extracellular domain (e.g., the D1 domain) of the human SIRP-α polypeptide and an IgSF domain of a human CD47 polypeptide (see, e.g., FIGS. 4A & 4B).

Figures 5A, 5B:
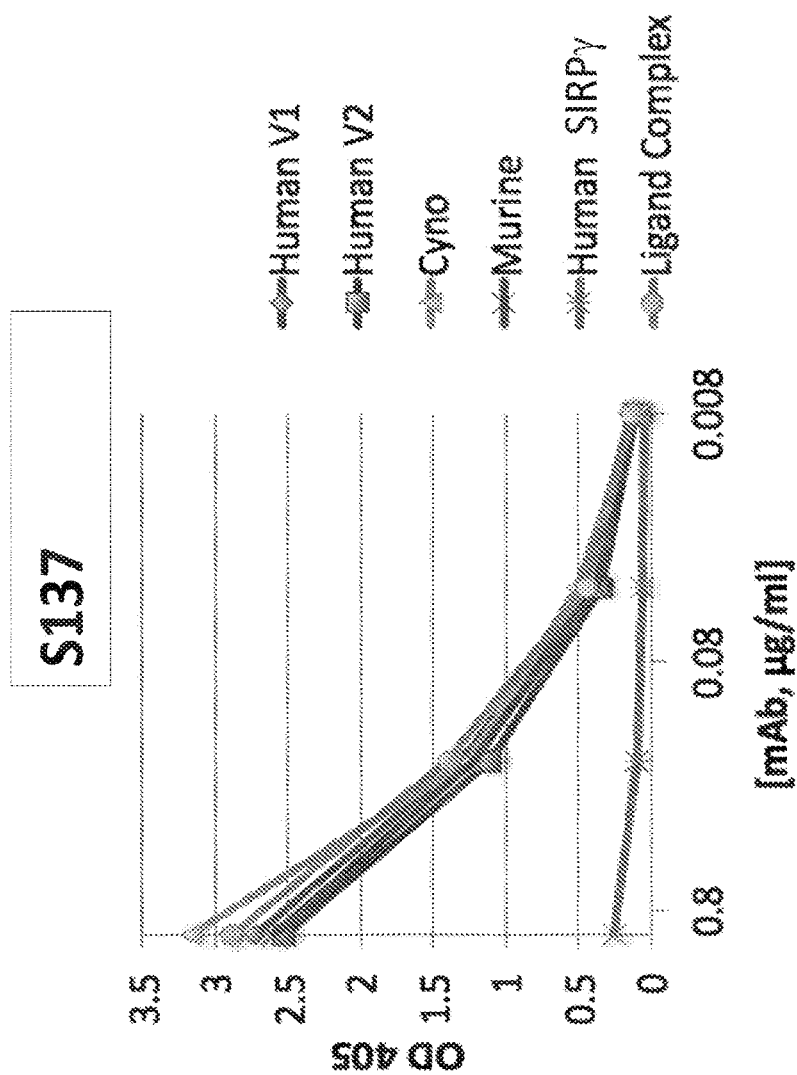

In some embodiments, an antibody of the present disclosure binds the extracellular domains (e.g., the D1 domains) of two or more different human SIRP-α variant polypeptides, a murine SIRP-α polypeptide, and a monkey SIRP-α polypeptide; the antibody does not bind at least one of an extracellular domain (e.g., the D1 domain) of a human SIRP-β polypeptide and an extracellular domain (e.g., the D1 domain) of a human SIRP-γ polypeptide; and the antibody does not block binding between the extracellular domain (e.g., the D1 domain) of the human SIRP-α polypeptide and an IgSF domain of a human CD47 polypeptide (see, e.g., FIGS. 5A & 5B).

Figures 6A, 6B:
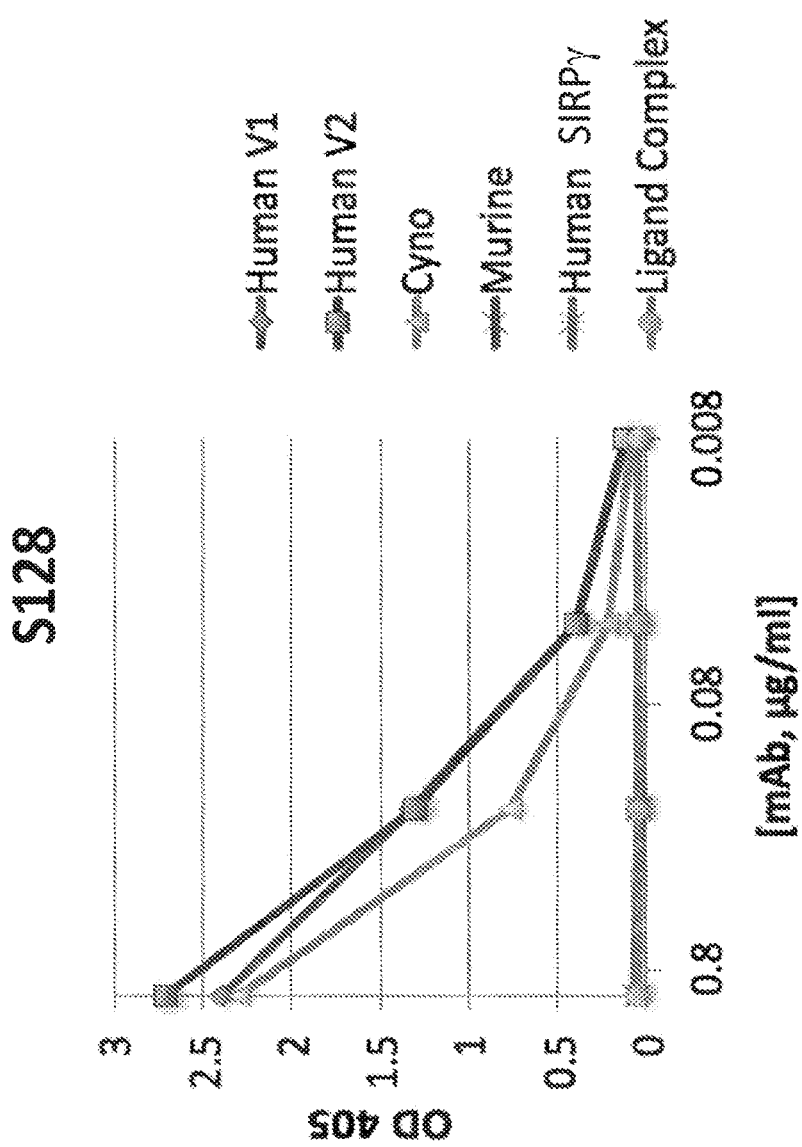

In some embodiments, an antibody of the present disclosure binds the extracellular domains (e.g., the D1 domains) of two or more different human SIRP-α variant polypeptides and a monkey SIRP-α polypeptide; the antibody does not bind a murine SIRP-α polypeptide; the antibody does not bind at least one of an extracellular domain (e.g., the D1 domain) of a human SIRP-β polypeptide and an extracellular domain (e.g., the D1 domain) of a human SIRP-γ polypeptide; and the antibody blocks binding between the extracellular domain (e.g., the D1 domain) of the human SIRP-α polypeptide and an IgSF domain of a human CD47 polypeptide (see, e.g., FIGS. 6A & 6B).

Figure 7B:
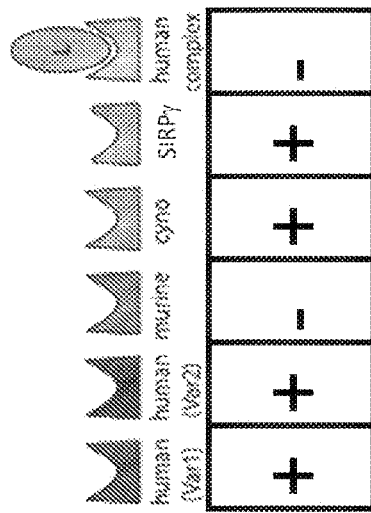
Figure 7A:
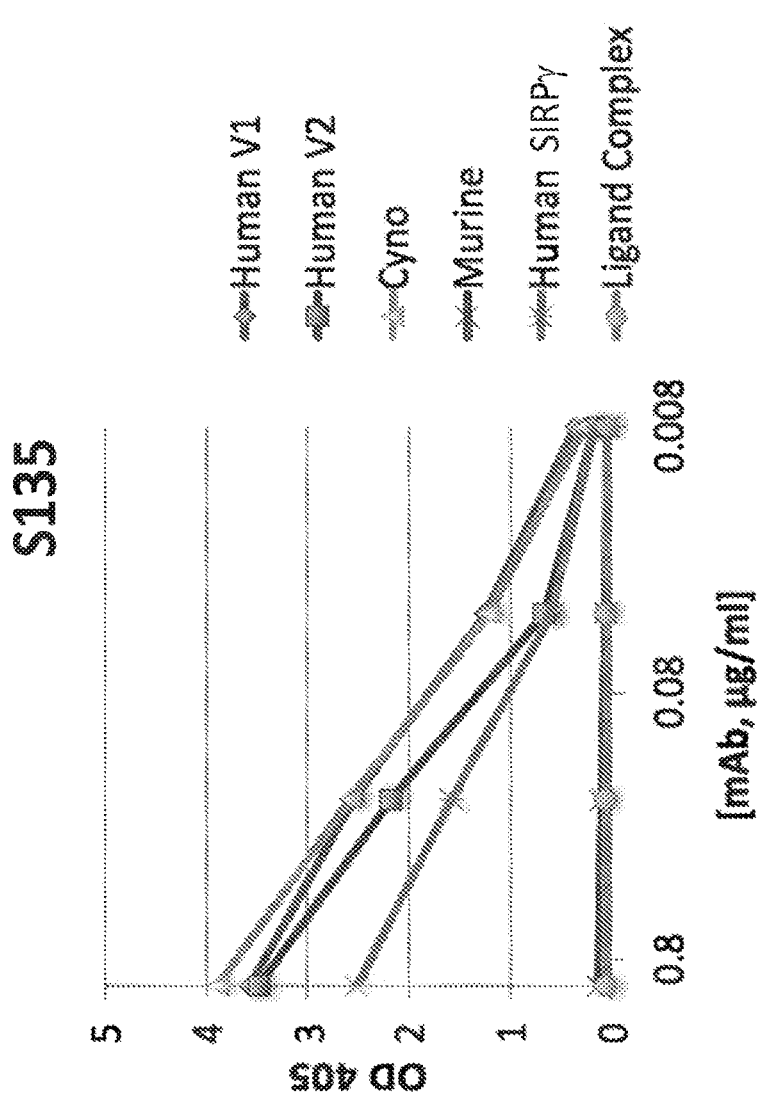

In some embodiments, an antibody of the present disclosure binds the extracellular domains (e.g., the D1 domains) of two or more different human SIRP-α variant polypeptides, a monkey SIRP-α polypeptide, and at least one of an extracellular domain (e.g., the D1 domain) of a human SIRP-β polypeptide and an extracellular domain (e.g., the D1 domain) of a human SIRP-γ polypeptide; the antibody does not bind a murine SIRP-α polypeptide; and the antibody blocks binding between the extracellular domain (e.g., the D1 domain) of the human SIRP-α polypeptide and an IgSF domain of a human CD47 polypeptide (see, e.g., FIGS. 7A & 7B).

In some embodiments, an antibody of the present disclosure comprises three CDRs from a VH domain comprising a sequence set forth in Table 2 and/or three CDRs from a VL domain comprising a sequence set forth in Table 2 (VH and VL sequences with CDRs highlighted are provided in FIGS. 10A-10F & 11A-11P). For example, in some embodiments, an antibody of the present disclosure comprises three CDRs from a VH domain comprising a sequence selected from SEQ ID NOs: 294, 139, 358, 362, 354, 380, 384, 350, 137, 374, 356, 352, 135, 348, 376, 346, 342, 344, 141, 360, 370, 382, 364, 366, 368, 372, 378, 133, 128, 396, 386, 398, 402, 392, 388, 390, 394, 400, 116, 117, 118, 119, 282, 404, 406, 278, 412, 275, 414, 280, 123, 292, 288, 290, 408, 410, 286, 284, 120, 121, 130, and 122 and/or three CDRs from a VL domain comprising a sequence selected from SEQ ID NOs: 295, 363, 140, 359, 355, 351, 136, 349, 377, 138, 375, 357, 353, 381, 385, 345, 365, 367, 369, 347, 142, 343, 371, 379, 383, 361, 373, 134, 105, 387, 389, 395, 397, 399, 403, 391, 393, 401, 93, 94, 95, 96, 283, 405, 407, 279, 413, 276, 415, 281, 100, 293, 289, 291, 409, 411, 287, 285, 97, 98, 107, and 99. In some embodiments, an antibody of the present disclosure comprises a VH domain comprising a sequence set forth in Table 2 and/or a VL domain comprising a sequence set forth in Table 2 (see FIGS. 10A-10F & 11A-11P). For example, in some embodiments, an antibody of the present disclosure comprises a VH domain comprising an amino acid sequence selected from SEQ ID NOs: 294, 139, 358, 362, 354, 380, 384, 350, 137, 374, 356, 352, 135, 348, 376, 346, 342, 344, 141, 360, 370, 382, 364, 366, 368, 372, 378, 133, 128, 396, 386, 398, 402, 392, 388, 390, 394, 400, 116, 117, 118, 119, 282, 404, 406, 278, 412, 275, 414, 280, 123, 292, 288, 290, 408, 410, 286, 284, 120, 121, 130, and 122 and/or a VL domain comprising an amino acid sequence selected from SEQ ID NOs: 295, 363, 140, 359, 355, 351, 136, 349, 377, 138, 375, 357, 353, 381, 385, 345, 365, 367, 369, 347, 142, 343, 371, 379, 383, 361, 373, 134, 105, 387, 389, 395, 397, 399, 403, 391, 393, 401, 93, 94, 95, 96, 283, 405, 407, 279, 413, 276, 415, 281, 100, 293, 289, 291, 409, 411, 287, 285, 97, 98, 107, and 99. In some embodiments, an antibody of the present disclosure comprises six CDR sequences from an antibody described in Table 2 (see FIGS. 10A-10F & 11A-11P). In some embodiments, an antibody of the present disclosure comprises a VL domain comprising the VL domain sequence of VL domains Hum1-Hum9 as described herein. In some embodiments, the antibody is a humanized antibody. In some embodiments, the antibody is a human antibody. In some embodiments, an antibody of the present disclosure comprises a VH domain and/or a VL domain from an antibody described in Table 2. In some embodiments, an antibody of the present disclosure comprises a VH domain comprising a D or E residue followed by (e.g., in the direction of N-terminus to C-terminus) a VH domain sequence selected from SEQ ID NOs:116-130.

TABLE 2

Amino acid sequences of antibody clones described herein.

| Clone/ Antibody | Framework | Domain | SEQ ID NO | Sequence |
|---|---|---|---|---|
| S1 | Chicken | VL | 85 | ALTQPASVSANPGETVEITCSGGGSNNA YGWFQQKSPGSAPLTVIYDNGKRPSDIPS RFSGSKSDSTGTLTITRVQAEDEAVYYC GSADNSGAGVFGAGTTLTVL |
| S2 | Chicken | VL | 86 | AVTQPASVSANPGETVRITCSGDSSSYYS WHQQKSPGSAPVSVIYSNTDRPSDIPSRF SGSASGSTATLTITGVQAEDEAVYFCGA YDSSSDSDIFGAGTTLTVL |
| S8 | Chicken | VL | 87 | AVTQPSSVSANPGETVEITCSGSSTYYGW YQQKSPGSAPVTVIYDNDKRPSDIPSRFS GSKSGSTHTLIITGVQVEDEAVYFCGNED NNYVAIFGAGTTLTVL |
| S9 | Chicken | VL | 88 | ALTQPSSVSANPGETVKITCSGDNSAHY YYGWYQQKSPGSAPVTVIYYNDKRPSGI PSRFSGSASGSTATLIITGVQVEDEAVYF CGSADSSNPAIFGAGTTLTVL |
| S11 | Chicken | VL | 89 | AVTQPASVSANPGETVKITCSGSSSGSYG WYQQKSPGSAPVTLIYETNKRPSNIPSRF SGSKSGSTATLTITGVQADDEAVYYCGS EDSSTYLSIFGAGTTLTVL |
| S12 | Chicken | VL | 90 | AVTQPASVSANPGETVKITCSGDSSYYG WYQQKSPGSAPVTVIYDDNKRPSNIPSRF SGSKSGSTGTLTITGVQADDEAVYFCGN EDNSYVAIFGAGTTLTVL |
| S13 | Chicken | VL | 91 | AVTQPASVSANPGETVKITCSGSSSYYG WYRQKSPGSAPVTLIYDNDKRPSGIPSRF SGSKSGSTNTLTITGVQADDEAVYYCGN EDNSYVGIFGAGTTLTVL |
| S14 | Chicken | VL | 92 | AVTQPASVSANLGETVKITCSGDSSYYG WYQQKAPGSAPVTLIYDNDKRPSNIPSRF SGSKSGSTATLTITGVQADDEAVYYCGN EDMNYVGIFGAGTTLTVL |
| S115 | Human | VL | 93 | ETVLTQSPATLSVSPGERATLSCRASQTV GSKLAWHQQKPGQAPRLLIYDATNRAT GISDRFSGSGSGTDFTLTISSLQTEDSAVY YCQQYYYWPPYRFGGGTKVEIK |
| S116 | Human | VL | 94 | ETVLTQSPATLSVSPGERATLSCRASQTV GSKLAWHQQKPGQAPRLLIYDATNRAT GISDRFSGSRSGTDFTLTISSLQTEDSAVY YCQQYYYWPPYRFGGGTKVEIK |
| S117 | Human | VL | 95 | ETVLTQSPATLSVSPGERATLSCRASQTV GSKLAWHQQKPGQAPRLLIYDATNRAT GIPDRFSGSGSGTDFTLTISSLQTEDSAVY YCQQYYYWPPYRFGGGTKVEIK |
| S118 | Human | VL | 96 | ETVLTQSPATLSVSPGERATLSCRASQTV GSKLAWHQQKPGQAPRLLIYDASRRAT |

TABLE 2-continued

Amino acid sequences of antibody clones described herein.

| Clone/Antibody | Framework | Domain | SEQ ID NO | Sequence |
|---|---|---|---|---|
| | | | | GIPDRFSGSGSGTDFTLTISSLQTEDSAVY YCQQYYYWPPYRFGGGTKVEIK |
| S119 | Human | VL | 97 | EIVLTQSPATLSVSPGERATFSCRASQNV KNDLAWYQQRPGQAPRLLIYAARIRETG IPERFSGSGSGTEFTLTITSLQSEDFAVYY CQQYYDWPPFTFGGGTKVEIK |
| S120 | Human | VL | 98 | EIVLTQSPATLSVSPGERATFSCRASQNV KNDLAWYQQRPGQAPRLLIYAARIRETG IPERFSGSGSGTEFTLTITSLQSEDFAVYY CQQYYDWPPFTFGGGTKVEIK |
| S122 | Human | VL | 99 | EIVLTQSPATLSVSPGERATFSCRASQNV KNDLAWYQQRPGQAPRLLIYAARIRETG IPERFSGSGSGTEFTLTITSLQSEDFAVYY CQQYYDWPPFTFGGGTKVEIK |
| S123 | Human | VL | 100 | EIVLTQSPGTLSVSPGERVTLTCRASQGIA GKIAWYQQKPGQAPRLLIYDASSRATGIP GRFSGSGSGTEFTLTITSLQSEDFAVYYC QQHYDWSPLTFGGGTKVEIK |
| S126 | Human | VL | 101 | EIVLTQSPGTLTLSPGERATLSCRASQSIG SSYLAWYQQKPGQAPRLLIYDATNRATG IPDRFSGSGSGTDFTLTISSLQTEDSAVYY CQQYYYWPPYRFGGGTKVEIK |
| S128 | Human | VL | 102 | ETVLTQSPATLSVSPGERATLSCRASQTV GSKLAWHQQKPGQAPRLLIYDASNRAT GIPDRFSGSGSGTDFTLTISSLQTEDSAVY YCQQYYYWPPYRFGGGTKVEIK |
| S130 | Human | VL | 103 | EIVLTQSPGTLSVSPGERATLSCRASQNV RSDLAWYQQKLGQAPRLLIYDANTRAT DIPDRFSGSGSGTEFTLTISSLQSEDFAVY YCQHYYDWPPVTFGGGTKVEIK |
| S135 | Human | VL | 104 | EIVLTQSPATLSVSPGERVTFSCRASQNV RSDIAWYQQKPGQAPRLLIYAASSRDTGI PDRFSGSGSGTDFTLTISSLQSEDFGVYY CQQYYDWPPFTFGGGTKVEIK |
| S137 | Human | VL | 105 | ETVLTQSPGTLTLSPGERATLTCRASQSV YTYLAWYQEKPGQAPRLLIYGASSRATG IPDRFSGSGSGTVFTLTISSLQSEDFAVYY CQQYYDRPPLTFGGGTKVEIK |
| S138 | Human | VL | 106 | EIVLTQSPGTLSVSPGERVILTCRASQSVD TYNLAWYQQKPGQAPRLLIYDLSTRATG IPDRFSGSGSGTEFTLTINSLEPEDFAVYY CHQYYDWPPYTFGGGTKVEIK |
| S121 | Human | VL | 107 | EIVLTQSPATLSVSPGERATFSCRASQNV KNDLAWYQQRPGQAPRLLIYAARIRETG IPERFSGSGSGTEFTLTITSLQSEDFAVYY CQQYYDWPPFTFGGGTKVEIK |
| S1 | Chicken | VH | 108 | AVTLDESGGGLQTPGGALSLVCKGSGFT FSSHAMNWVRQAPGKGLEWVAGISSDG RFTYYGAAVQGRATISRDNGQSTVRLQL NNLRAEDTATYYCTKNGGCGSGGDLDC IDAWGHGTEVIVSS |
| S2 | Chicken | VH | 109 | AVTLDESGGGLQTPGGGLSLVCKASGFD FSNFNMAWVRQGPGKGLEYVAEISDTGS TPYYGSAVQGRATISRDNGQSTVRLQLN NLRAEDTGTYFCTRNFGSSVSSIDAWGH GTEVIVSS |
| S8 | Chicken | VH | 110 | AVTLDESGGGLQTPGGALSLVCKASGFT FSSYNMGWVRQAPGKGLEFVAGIYASG SSTDTDTTYGPAVAGRATISRDNGQSTV RLQLNNLRAEDTGTYYCAKAAGGCSTH TCTAYIADSIDAWGHGTEVIVSS |

TABLE 2-continued

Amino acid sequences of antibody clones described herein.

| Clone/ Antibody | Framework | Domain | SEQ ID NO | Sequence |
|---|---|---|---|---|
| S9 | Chicken | VH | 111 | AVTLDESGGGLQTPGRALSLVCRGSGFSI SSYNMGWVRQAPGKGLEFIASIGSDGSS THYAPAVKGRATITRDVGQSTVRLQLNN LRAEDTGTYFCAKDAYQCSYATCNDYL DTIDAWGHGTEVIVSS |
| S11 | Chicken | VH | 112 | AVTLDESGGGLQTPGGALSLVCKASGFT FSSFNMGWVRQAPGKGLEFVAAIYSGNS AEYGAAVQGRATISRDNGQSTVRLQLN NLRAEDTGIYFCAKDAGSGCYSGVCAGT SSIDAWGHGTEVIVSS |
| S12 | Chicken | VH | 113 | AVTLDESGGGLQTPGGALSLVCKASGFT FSSYNMGWVRQAPGKGLEFVAGIYIASG DLGTTYGAAVQGRATISRDDGQSTVRLQ LNNLRAEDTGTYFCAKSAGGCSAHSCDT YIADSIDAWGHGTEVIVSS |
| S13 | Chicken | VH | 114 | AVTLDESGGGLQTPGGALSLVCKASGFT FSSYNMGWVRQAPDKGLEFVAGIYTGS DAGLSTTYGAAVQGRATISRDNGQSTVR LQLNNLGAEDTGIYFCTKSAGGCSDYNC DAYIADSIDAWGHGTEVIVSS |
| S14 | Chicken | VH | 115 | AVTLDESGGGLQTPGGALSLVCKASGFT FNSYNMGWVRQAPGKGLEFVAGIYSAG GDTSTTYGAAVNGRATISRDNGQSTVRL QLNNLRAEDTGIYFCAKAAGGCTAHNC DAYIADSIDAWGHGTEVIVSS |
| S115 | Human | VH | 116 | VQLVESGGGVVRPGESLRLSCAASGFSFS SYAMNWVRQAPGEGLEWVSRINSGGGG TDYAESVKGRFTISRDNSENTLYLQMNS LRAEDTAVYYCAKQYDWNSFFDYWGL GALVTVSS |
| S116 | Human | VH | 117 | VQLVESGGGVVRPGESLRLSCAASGFSFS SYAMNWVRQAPGEGLEWVSRINSGGGG TDYAESVKGRFTISRDNSENTLYLQMNS LRAEDTAVYYCAKQYDWNSFFDYWGL GALVTVSS |
| S117 | Human | VH | 118 | VQLVESGGGVVRPGESLRLSCAASGFSFS SYAMNWVRQAPGEGLEWVSRINSGGGG TDYAESVKGRFTISRDNSENTLYLQMNS LRAEDTAVYYCAKQYDWNGFFDYWGL GALVTVSS |
| S118 | Human | VH | 119 | VQLVESGGGVVRPGESLRLSCAASGFSFS SYAMNWVRQAPGEGLEWVSRINSGGGG TDYAESVKGRFTISRDNSENTLYLQMNS LRAEDTAVYYCAKQYDWNGFFDYWGL GALVTVSS |
| S119 | Human | VH | 120 | VQLLESGGGVVQPGGSLRLSCAASGFSF SNFAMTWVRQAPGEGLEWVSTIGSGDT YYADSVKGRFTISRDNSKNTLYLQMNSL RAEDTAVYYCAKDSTVSWSGDFFDYWG LGTLVTVSS |
| S120 | Human | VH | 121 | VQLVESGGGVVQPGGSLRLSCAASGFSF SNFAMTWVRQAPGEGLEWVSTIGSGDT YYADSVKGRFTISRDNSKNTLYLQMNSL RAEDTAVYYCAKDSTVSWSGDFFDYWG LGTRVTVSS |
| S122 | Human | VH | 122 | VQLVESGGGVVRPGESLRLSCAASGFRF SNFAMTWVRQAPGEGLEWVSTIGSGDT YYADSVKGRFTISRDNSKNTLYLQMNSL RAEDTAVYYCAKDSTVSWSGDFFDYWG LGTLVTVSS |
| S123 | Human | VH | 123 | VQLVESGGGLVQPGGSLRLSCTASGFTF RNYGMSWVRQAPGEGLEWVSASSGSGS |

TABLE 2-continued

Amino acid sequences of antibody clones described herein.

| Clone/Antibody | Framework | Domain | SEQ ID NO | Sequence |
|---|---|---|---|---|
| | | | | TYYTDSVKGRFTISRDNSKNTLYLQMNS LRAEDTAIYYCAKVTWNNFFDYWGLGT LVTVSS |
| S126 | Human | VH | 124 | VQLVESGGGVVRPGESLRLSCAASGFTF SNYDMTWVRQAPGEGLEWVSGISGNGG STYYADSVKGRFTISRDNSKNTLYLQMN SLRAEDTAVYYCAMNRWWFDYWGLGT LVTVSS |
| S128 | Human | VH | 125 | VQLVESGGGVVRPGESLRLSCAASGFSF RSYAMNWVRQAPGEGLEWVSRIDSGGG GTDYADSVKGRFTISRDNSKNTLYLQMN SLRAEDTAVYYCAKQYDWNSFFDYWGL GAPVTVSS |
| S130 | Human | VH | 126 | VQLVESGGGVVRPGESLRLSCAASGFTF SNYAMSWVRQAPGEGLEWVSLITTNGD GAYYADSVKGRFTISRDNSKNTLYLQM NSLRAEDTAIYYCAKDGAAHYYDIFFDY WGLGTPVTVSS |
| S135 | Human | VH | 127 | VQLVESGGGVVRPGESLRLSCAASGFSFS IYAMSWVRQAPGEGLEWVSTIGADDTY YADSVKGRFTISRDNSKNTLYLQMNSLR AEDTAVYYCAKDSTVGWSGDFFDYWG LGTLVTVSS |
| S137 | Human | VH | 128 | VQLVESGGGVVRPGESLRLSCAASGFTF SSYDMNWVRQAPGEGLEWVSLISGSGEI IYYADSVKGRFTISRDNSKNTLYLQMNS LRAEDTAVYYCAKENNRYRFFDDWGLG TLVTVSS |
| S138 | Human | VH | 129 | VQLVESGGGVVRPGESLRLSCAASGFTF SNYAMNWVRQAPGEGLEWVSGISGRGG DTYYADSVKGRFTISRDNSKNTLYLQMN SLRAEDTAIYYCAKGTWNYGSFDYWGL GTLVTVSS |
| S121 | Human | VH | 130 | VQLVESGGGVVQPGGSLRLSCAASGFSF SNFAMTWVRQAPGEGLEWVSTIGSGDT YYADSVKGRFTISRDNSKNTLYLQMNSL RAEDTAVYYCAKDSTVSWSGDFFDYWG LGTLVTVSS |
| AB136 | Human | VH | 133 | DVQLVESGGGVVRPGESLRLSCAASGFT FSSYDMNWVRQAPGEGLEWVSLISGSGE IIYYADSVKGRFTISRDNSKNTLYLQMNS LRAEDTAVYYCAKENNRYRFFDDWGLG TLVTVSS |
| AB136 | Human | VL | 134 | ETVLTQSPGTLTLSPGERATLTCRASQSV YTYLAWYQEKPGQAPRLLIYGASSRATG IPDRFSGSGSGTEFTLTISSLQSEDFAVYY CQQYYDRPPLTFGGGTKVEIK |
| AB21 | Human | VH | 135 | DVQLVESGGGVVRPGESLRLSCAASGFT FSSNAMSWVRQAPGKGLEWLAGISAGG SDTYYPASVKGRFTISRDNSKNTLYLQM NTLTAEDTAVYYCARETWNHLFDYWGL GTLVTVSS |
| AB21 | Chicken | VL | 136 | ALTQPASVSANPGETVKIACSGGDYYSY YYGWYQQKAPGSALVTIYSDDKRPSDI PSRFSGSASGSTATLTITGVRAEDEAVYY CGGYDYSTYANAFGAGTTLTVL |
| AB25 | Human | VH | 137 | DVQLVESGGGVVRPGESLRLSCEASGFT FSSNAMSWVRQAPGKGLEWVAGISSGS DTYYGDSVKGRLTISRDNSKNILYLQMN SLTAEDTAVYYCARETWNHLFDYWGLG TLVTVSS |

TABLE 2-continued

Amino acid sequences of antibody clones described herein.

| Clone/Antibody | Framework | Domain | SEQ ID NO | Sequence |
|---|---|---|---|---|
| AB25 | Chicken | VL | 138 | ALTQPASVSANPGETVEITCSGGSYSSYY YAWYQQKSPGSAPVTLIYSDDKRPSNIPS RFSGSASGSTATLTITGVRAEDEAVYFCG GYDQSSYTNPFGAGTTLTVL |
| AB27 | Human | VH | 139 | DVQLVESGGGVVRPGESLRLSCAVSGFR FSSYAMSWVRQAPGKGLEWVSGISSGG DTYYVDSVKGRFTISRDNSKNTLYLQVN SLTAEDTAIYYCARETWNHLFDYWGLG TLVTVSS |
| AB27 | Chicken | VL | 140 | ALTQPASVSADLGETVKITCSGGDSSSHY YGWYQQKSPGSAPVTVIYSDDERPSDIPS RFSGSASGSTATLTITGVRVEDEAIYYCG AYDGSTYANTFGAGTTLTVL |
| AB66 | Human | VH | 141 | DVQLVESGGGVVRPGESLRLSCAASGFT FSSYAMSWVRQAPGKGLEWLAGISAGG SDTYYIDSVKGRFTISRDNPKNSLYLQMS SLTAEDTAVYYCARETWNHLFDYWGLG TLVTVSS |
| AB66 | Chicken | VL | 142 | ALTQPASVSANPGETVKITCSGGDYYST YYAWYQQKSPGSAPVTVIHSDDKRPSDI PSRFSGSASGSAATLIITGVRVEDEAVYY CGGYDGRTYINTFGAGTTLTVL |
| AB119 | Human | HVR-H1 | 143 | GFSFSNFAMT |
| AB119 | Human | HVR-H2 | 144 | TIGSGDTYYADSVKG |
| AB119 | Human | HVR-H3 | 145 | DSTVSWSGDFFDY |
| AB119 | Human | HVR-L1 | 146 | RASQNVKNDLA |
| AB119 | Human | HVR-L2 | 147 | AARIRET |
| AB119 | Human | HVR-L3 | 148 | QQYYDWPPFT |
| AB135 | Human | HVR-H1 | 149 | GFSFSIYAMS |
| AB135 | Human | HVR-H2 | 150 | TIGADDTYYADSVKG |
| AB135 | Human | HVR-H3 | 151 | DSTVGWSGDFFDY |
| AB135 | Human | HVR-L1 | 152 | RASQNVRSDIA |
| AB135 | Human | HVR-L2 | 153 | AASSRDT |
| AB135 | Human | HVR-L3 | 148 | QQYYDWPPFT |
| AB136 | Human | HVR-H1 | 155 | GFTFSSYDMN |
| AB136 | Human | HVR-H2 | 156 | LISGSGEIIYYADSVKG |
| AB136 | Human | HVR-H3 | 157 | ENNRYRFFDD |
| AB136 | Human | HVR-L1 | 158 | RASQSVYTYLA |
| AB136 | Human | HVR-L2 | 159 | GASSRAT |
| AB136 | Human | HVR-L3 | 160 | QQYYDRPPLT |
| AB21 | Human | HVR-H1 | 161 | GFTFSSNA |
| AB21 | Human | HVR-H2 | 162 | ISAGGSDT |
| AB21 | Human | HVR-H3 | 163 | ARETWNHLFDY |
| AB21 | Chicken | HVR-L1 | 164 | SGGDYYSYYYG |
| AB21 | Chicken | HVR-L2 | 165 | TVIYSDDKRPSD |
| AB21 | Chicken | HVR-L3 | 166 | GGYDYSTYANA |

TABLE 2-continued

Amino acid sequences of antibody clones described herein.

| Clone/Antibody | Framework | Domain | SEQ ID NO | Sequence |
|---|---|---|---|---|
| AB25 | Human | HVR-H1 | 161 | GFTFSSNA |
| AB25 | Human | HVR-H2 | 168 | ISSGSDT |
| AB25 | Human | HVR-H3 | 163 | ARETWNHLFDY |
| AB25 | Chicken | HVR-L1 | 170 | SGGSYSSYYYA |
| AB25 | Chicken | HVR-L2 | 171 | TLIYSDDKRPSN |
| AB25 | Chicken | HVR-L3 | 172 | GGYDQSSYTNP |
| AB27 | Human | HVR-H1 | 173 | GFRFSSYA |
| AB27 | Human | HVR-H2 | 174 | ISSGGDT |
| AB27 | Human | HVR-H3 | 163 | ARETWNHLFDY |
| AB27 | Chicken | HVR-L1 | 176 | SGGDSSSHYYG |
| AB27 | Chicken | HVR-L2 | 177 | TVIYSDDERPSD |
| AB27 | Chicken | HVR-L3 | 178 | GAYDGSTYANT |
| AB66 | Human | HVR-H1 | 179 | GFTFSSYA |
| AB66 | Human | HVR-H2 | 162 | ISAGGSDT |
| AB66 | Human | HVR-H3 | 163 | ARETWNHLFDY |
| AB66 | Chicken | HVR-L1 | 182 | SGGDYYSTYYA |
| AB66 | Chicken | HVR-L2 | 183 | TVIHSDDKRPSD |
| AB66 | Chicken | HVR-L3 | 184 | GGYDGRTYINT |
| AB3 | Chicken | VH | 242 | AVTLDESGGGLQTPGGALSLVCKASGFIFSDYGMNWVRQAPGKGLEFVAQITSGSRTYYGAAVKGRATISRDNRQSTVKLQLNNLRAEDTGIYFCARDFGSGVGSIDAWGNGTEVIVSS |
| AB3 | Chicken | VL | 243 | ALTQPASVSANLGGTVKITCSGSRGRYGWYQQRSPGSAPVTVIYRDNQRPSNIPSRFSSSTSGSTSTLTITGVQADDESVYFCGSYDGSIDIFGAGTTLTVL |
| AB45 | Chicken | VH | 244 | AVTLDESGGGLQTPGGALSLVCKASGFTFSSYAMGWVRQAPGKGLEWVAGIDDDGSTANYGPAVKGRATISRDNGQSTVRLQLNNPRAEDSGTYFCAKASVTGWSAHISGRLDTWGHGTEVIVSS |
| AB45 | Chicken | VL | 245 | ALTQPASVSANPGETVKITCSGGGIYYYGWYQQKSPGSAPVTLIYENDKRPSDIPSRFSGSTSGSTNTFTITGVQAEDEAVYYCGGYDSNTTSGIFGAGTTLTVL |
| AB119 mut | Human with D1E, E43K, L112Q, and M34V mutations | VH | 246 | EVQLLESGGGVVQPGGSLRLSCAASGFSFSNFAVTWVRQAPGKGLEWVSTIGSGDTYYADSVKGRFTISRDNSKNTLYLQMNSLRAEDTAVYYCAKDSTVSWSGDFFDYWGQGTLVTVSS |
| AB135 mut | Human with D1E, R13Q, E16G, E43K L112Q, and M34V mutations | VH | 247 | EVQLVESGGGVVQPGGSLRLSCAASGFSFSIYAVSWVRQAPGKGLEWVSTIGADDTYYADSVKGRFTISRDNSKNTLYLQMNSLRAEDTAVYYCAKDSTVGWSGDFFDYWGQGTLVTVSS |
| AB136 mut all | Human with D1E, R13Q, E16R, E43K | VH | 249 | EVQLVESGGGVVQPGRSLRLSCAASGFTFSSYDVNWVRQAPGKGLEWVSLISGSGEIIYYADSVKGRFTISRDNSKNTLYLQMNSLRA |

TABLE 2-continued

Amino acid sequences of antibody clones described herein.

| Clone/Antibody | Framework | Domain | SEQ ID NO | Sequence |
|---|---|---|---|---|
| | L111Q, and M34V mutations | | | EDTAVYYCAKENNRYRFFDDWGQGTLVTVSS |
| AB136 mut all | Human with T2I, T12S, T22S, and E28Q mutations | VL | 250 | EIVLTQSPGTLSLSPGERATLSCRASQSVYTYLAWYQQKPGQAPRLLIYGASSRATGIPDRFSGSGSGTEFTLTISSLQSEDFAVYYCQQYYDRPPLTFGGGTKVEIK |
| AB136 mut all_I2T | Human with T12S, T22S and E38Q mutations | VL | 251 | ETVLTQSPGTLSLSPGERATLSCRASQSVYTYLAWYQQKPGQAPRLLIYGASSRATGIPDRFSGSGSGTEFTLTISSLQSEDFAVYYCQQYYDRPPLTFGGGTKVEIK |
| Hum1 | Humanized | VL | 252 | SYELTQPPSVSVSPGQTARITCSGGSYSSYYYAWYQQKPGQAPVTLIYSDDKRPSNIPERFSGSSSGTTVTLTISGVQAEDEADYYCGGYDQSSYTNP**FGGGTKLTVL |
| Hum2 | Humanized | VL | 253 | QSVLTQPPSVSAAPGQKVTISCSGGSYSSYYYAWYQQLPGTAPKTLIYSDDKRPSNIPDRFSGSKSGTSATLGITGLQTGDEADYYCGGYDQSSYTNPFGTGTKVTVL |
| Hum3 | Humanized | VL | 254 | SYELTQPPSVSVSPGQTARITCSGGDYYSTYYAWYQQKPGQAPVTVIHSDDKRPSDIPERFSGSSSGTTVTLTISGVQAEDEADYYCGGYDGRTYINTFGGGTKLTVL |
| Hum4 | Humanized | VL | 255 | QSVLTQPPSVSAAPGQKVTISCSGGDYYSTYYAWYQQLPGTAPKTVIHSDDKRPSDIPDRFSGSKSGTSATLGITGLQTGDEADYYCGGYDGRTYINTFGTGTKVTVL |
| Hum5 | Humanized | VL | 256 | QSALTQPASVSGSPGQSITISCTGTSSDVGSYSSYYYAWYQQHPGKAPKTLIYSDDKRPSNVSNRFSGSKSGNTASLTISGLQAEDEADYYCGGYDQSSYTNPFGGGTKLTVL |
| Hum6 | Humanized | VL | 257 | QSVLTQPPSVSAAPGQKVTISCSGGDYYSYYYGWYQQLPGTAPKTVIYSDDKRPSDIPDRFSGSKSGTSATLGITGLQTGDEADYYCGGYDYSTYANAFGTGTKVTVL |
| 119 VH MutAll_V34M | Human with D1E, E43K, and L112Q mutations | VH | 258 | EVQLLESGGGVVQPGGSLRLSCAASGFSFSNFAMTWVRQAPGKGLEWVSTIGSGDTYYADSVKGRFTISRDNSKNTLYLQMNSLRAEDTAVYYCAKDSTVSWSGDFFDYWGQGTLVTVSS |
| 135 VH MutAll_V34M | Human with D1E, R13Q, E16G, E43K, and L112Q mutations | VH | 259 | EVQLVESGGGVVQPGGSLRLSCAASGFSFSIYAMSWVRQAPGKGLEWVSTIGADDTYYADSVKGRFTISRDNSKNTLYLQMNSLRAEDTAVYYCAKDSTVGWSGDFFDYWGQGTLVTVSS |
| 136 VH MutAll_V34M | Human with D1E, R13Q, E16R, E43K, and L111Q mutations | VH | 260 | EVQLVESGGGVVQPGRSLRLSCAASGFTFSSYDMNWVRQAPGKGLEWVSLISGSGEIIYYADSVKGRFTISRDNSKNTLYLQMNSLRAEDTAVYYCAKENNRYRFFDDWGQGTLVTVSS |
| Hum 8 | Humanized | VL | 416 | SYELTQPPSVSVSPGQTARITCSGGAYSSYYYAWYQQKPGQAPVLVIYSDKRPSGIPERFSGSSSGTTVTLTISGVQAEDEADYYCGGYDQSSYTNPFGGGTKLTVL |
| Hum9 | Humanized | HVR-L1 | 261 | SGGAYSSYYYA |
| Hum9 | Humanized | VL | 262 | SYELTQPPSVSVSPGQTARITCSGGAYSSYYYAWYQQKPGQAPVLVIYSDDKRPSGIPERFSGSSSGTTVTLTISGVQAEDEADYYCGGYDQSSYTNPFGGGTKLTVL |

TABLE 2-continued

Amino acid sequences of antibody clones described herein.

| Clone/Antibody | Framework | Domain | SEQ ID NO | Sequence |
|---|---|---|---|---|
| AB21 Mut All | Human with germline back-mutations | VH | 263 | EVQLVESGGGVVQPGGSLRLSCAASGFTFSSNAMSWVRQAPGKGLEWVAGISAGGSDTYYPASVKGRFTISRDNSKNTLYLQMNSLRAEDTAVYYCARETWNHLFDYWGQGTLVTVSS |
| AB21 Mut All M34V | Human with germline back-mutations and liability mutation | VH | 264 | EVQLVESGGGVVQPGGSLRLSCAASGFTFSSNAVSWVRQAPGKGLEWVAGISAGGSDTYYPASVKGRFTISRDNSKNTLYLQMNSLRAEDTAVYYCARETWNHLFDYWGQGTLVTVSS |
| AB25 Mut All | Human with germline back-mutations | VH | 265 | EVQLVESGGGVVQPGGSLRLSCAASGFTFSSNAMSWVRQAPGKGLEWVAGISSGSDTYYGDSVKGRFTISRDNSKNTLYLQMNSLTAEDTAVYYCARETWNHLFDYWGQGTLVTVSS |
| AB25 Mut All M34V | Human with germline back-mutations and liability mutation | VH | 266 | EVQLVESGGGVVQPGGSLRLSCAASGFTFSSNAVSWVRQAPGKGLEWVAGISSGSDTYYGDSVKGRFTISRDNSKNTLYLQMNSLTAEDTAVYYCARETWNHLFDYWGQGTLVTVSS |
| AB27 Mut All | Human with germline back-mutations | VH | 267 | EVQLVESGGGVVQPGGSLRLSCAASGFRFSSYAMSWVRQAPGKGLEWVSGISSGGDTYYVDSVKGRFTISRDNSKNTLYLQMNSLRAEDTAVYYCARETWNHLFDYWGQGTLVTVSS |
| AB27 Mut All M34V | Human with germline back-mutations and liability mutation | VH | 268 | EVQLVESGGGVVQPGGSLRLSCAASGFRFSSYAVSWVRQAPGKGLEWVSGISSGGDTYYVDSVKGRFTISRDNSKNTLYLQMNSLRAEDTAVYYCARETWNHLFDYWGQGTLVTVSS |
| 135 V34M | Human with liability mutation | HVR-H1 | 269 | IYAMS |
| 136 V34M | Human with liability mutation | HVR-H1 | 270 | SYDMN |
| 21/25 M34V | Human | HVR-H1 | 271 | SNAVS |
| 27 M34V | Human | HVR-H1 | 272 | SYAVS |
| 115 | Human | VH | 273 | DVQLVESGGGVVRPGESLRLSCAASGFSFSSYAMNWVRQAPGEGLEWVSRINSGGGTDYAESVKGRFTISRDNSENTLYLQMNSLRAEDTAVYYCAKQYDWNSFFDYWGLGALVTVSS |
| 115 | Human | VL | 274 | ETVLTQSPATLSVSPGERATLSCRASQTVGSKLAWHQQKPGQAPRLLIYDATNRATGISDRFSGSGSGTDFTLTISSLQTEDSAVYYCQQYYYWPPYRFGGGTKVEIK |
| 213 | Human | VH | 275 | DVQLVESGGGVVRPGESLRLSCEASGFTFRNYYMTWVRQAPGEGLEWVSTISDTGDTAYYADSVKGRFTISRDNSKNSLYLQMNSLRADDTAIYYCAKSWIWWTFFDYWGLGTLVTVSS |
| 213 | Chicken | VL | 276 | ALTQPASVSANLGGTVEITCSGGNSNHYGWYQQKSPGSAPVTLIYADTNRPSNIPSRFSGSTSGSTTTLTITGVQAEDEAVYYCGGSSTGDGIFGAGTTLTVL |

TABLE 2-continued

Amino acid sequences of antibody clones described herein.

| Clone/Antibody | Framework | Domain | SEQ ID NO | Sequence |
|---|---|---|---|---|
| 173 | Human | VH | 278 | DVQLVESGGGVVRPGESLRLSCAASGFAFSDHDMSWVRQGPGEGLEWVAGISLRGGVTWYADSVKGRFTISRDNSKNTLYLRLFSLRTEDTAIYYCARESWNTFFDYWGLGTLVTVSS |
| 173 | Human | VL | 279 | EIVLTQSPGTLSLSPGETATLSCRASQNVRSNLAWYQQKPGQAPRLLIYDASSRATGIPDRFSGSGSGTDFTLTISSLQSEDFAVYYCQQYGNGPPLTFGGGTKVEIK |
| 209 | Human | VH | 280 | DVQLVESGGAVVRPGESLRLSCKASGFTFTNFAMSWVRQAPGEGLEWVSGISGSDDTTYYADSVKGRFTISRDNSESTLYLQMNSLRAEDTAVYYCVKDSTVSWNTFFDYWGLGTLVTVSS |
| 209 | Chicken | VL | 281 | ALTQPASVSANLGGTVKITCSGGYGSDDGSSSYYGWYQQKSPGSAPVILIYWDDKRPSDIPSRFSGSTSGSTTTLTITGVQAEDEAVYFCGTYDTSSGAIFGAGTTLTVL |
| 132 | Human | VH | 282 | DVQLVESGGGVVRPGESLRLSCAASGFSFRSYAMNWVRQAPGEGLEWVSRINSGGGGTDYADSVK GRFTISRDNSKNTLYLQMNSLRAEDTAVYYCAKQYDWNSFFDYWGLGALVTVSS |
| 132 | Human | VL | 283 | ETVLTQSPATLSVSPGERATLSCRASQTVGSKLAWHQQKPGQAPRLLIYDASNRATGIPDRFSGSGSGTDFTLTISSPQTEDSAVYYCQQYYYWPPYRFGGGTKVEIK |
| 218 | Human | VH | 284 | DVQLVESGGGVVRPGESLTLSCTASGFTFTSSTMNWVRQAPGEGLDWVSSISTSGVITYYADSVKGRATISRDNSKNTLYLRLFSLRADDTAIYYCATDTFDHWGPGTLVTVSS |
| 218 | Chicken | VL | 285 | ALTQPASVSANPGETVKITCFGSSGNYGWFQQKSPGSAPVTVIHYNNKRPSDIPSRFSGSKSGSTGTLTITGVRAEDEAVYFCGAWETGSATFGAGTTLTVL |
| 149 | Human | VH | 286 | DVQLVESGGGVVRPGESLRLSCAASGFTFSNFAMNWVRQAPGEGLEWVSLISVTATTYYADSVKGRFTISRDNSKNTLYLQMNSLRAEDTAVYYCAKVTWNNLFDYWGLGTLVTVSS |
| 149 | Human | VL | 287 | EIVLTQSPGTLSLSPGERATLSCRASQPIDSYLAWYQQKPGQAPRLLIYNTVTRATGIPDRFSGSGSGTDFTLTINRLEPEDFAVYYCHQQYDWPPYIFGGGTKVEIK |
| 161 | Human | VH | 288 | DVQLVESGGGVVRPGESLRLSCAASGFTFSNFAMTWVRQAPGKGPEWVSLVSVTATTYYADSVKGRFTISRDNSKSTLYLQMNSLRAEDTAVYYCAKITWNNLFDYWGLGTLVTVSS |
| 161 | Human | VL | 289 | EIVLTQSPGTLSLSPGERATLSCRASQTVGSKLAWYQQKPGQAPRLLIYDSSSRASGIPDRFSGSGSGTDFTLTISSLQSEDSAVYYCQQHNDWPPYTFGGGTKVEIK |
| 162 | Human | VH | 290 | DVQLVESGGGLVRPGESLRLSCAASGFTFTNYAVTWVRQAPGEGLEWVSLISVTGTTYYADSVKGRFTISRDNSKSTLYLQMNSLRAEDTAVYYCAKVTWKNVFDYWGLGTLVTVSS |
| 162 | Human | VL | 291 | EIVLTQSPGTLSVSPGERATFSCRASQTVGSKLAWYQQKPGQAPRLLIYDANTRATGIPARFSGSGSGTEFTLTISSLQSEDFAVYYCQQHTDWPPYTFGGGTKVEIK |

TABLE 2-continued

Amino acid sequences of antibody clones described herein.

| Clone/ Antibody | Framework | Domain | SEQ ID NO | Sequence |
| --- | --- | --- | --- | --- |
| 194 | Human | VH | 292 | DVQLVESGGGVVRPGESLRLSCAASGFTF RNYGMSWVRQAPGEGLEWVSASSGSGST YYADSVKGRFTISRDNSKNTLYLQMNSLR AEDTAIYYCAKVTWNNFFDYWGLGTLVT VSS |
| 194 | Human | VL | 293 | EIVLAQSPDTLSVSPGERATLTCRASQDVA GKLAWYQQKPGQAPRLLIHATSSRADGIP ARFSGSGSGTEFTLTITGLQSEDFAVYYCQ QHYDWSPLTFGGGTKVEIK |
| 119 M34L | Human with liability mutation | HVR-H1 | 305 | NFALT |
| 135 M34L | Human with liability mutation | HVR-H1 | 306 | IYALS |
| 119 mut all | Human with F21L, R39K, E60A, and T76S mutations | VL | 312 | EIVLTQSPATLSVSPGERATLSCRASQNVK NDLAWYQQKPGQAPRLLIYAA RIRETGIPARFSGSGSGTEFTLTISSLQSEDF AVYYCQQYYDWPPFTFGGGTKVEIK |
| 136 M34L | Human with liability mutation | HVR-H1 | 313 | SYDLN |
| 21/25 M34L | Human with liability mutation | HVR-H1 | 318 | SNALS |
| 27 M34L | Human with liability mutation | HVR-H1 | 319 | SYALS |
| 119_VH_MutAll_V34L | Human with germline back-mutations and liability mutation | VH | 327 | EVQLLESGGGVVQPGGSLRLSCAASGFSFS NFALTWVRQAPGKGLEWVSTI GSGDTYYADSVKGRFTISRDNSKNTLYLQ MNSLRAEDTAVYYCAKDSTVSWSGDFFD YWGQGTLVTVSS |
| 135_VH_MutAll_V34L | Human with germline back-mutations and liability mutation | VH | 328 | EVQLVESGGGVVQPGGSLRLSCAASGFSF SIYALSWVRQAPGKGLEWVSTI GADDTYYADSVKGRFTISRDNSKNTLYLQ MNSLRAEDTAVYYCAKDSTVGWSGDFFD YWGQGTLVTVSS |
| 136_VH_MutAll_V34L | Human with germline back-mutations and liability mutation | VH | 329 | EVQLVESGGGVVQPGRSLRLSCAASGFTF SSYDLNWVRQAPGKGLEWVSLI SGSGEIIYYADSVKGRFTISRDNSKNTLYL QMNSLRAEDTAVYYCAKENNRYRFFDDW GQGTLVTVSS |
| AB21_HC_MutAll_M34L | Human with germline back-mutations and liability mutation | VH | 330 | EVQLVESGGGVVQPGGSLRLSCAASGFTF SSNALSWVRQAPGKGLEWVAGISAGGSD TYYPASVKGRFTISRDNSKNTLYLQMNSL RAEDTAVYYCARETWNHLFDYWGQGTL VTVSS |
| AB25_HC_MutAll_M34L | Human with germline back-mutations and liability mutation | VH | 331 | EVQLVESGGGVVQPGGSLRLSCAASGFTF SSNALSWVRQAPGKGLEWVAGISSGSDTY YGDSVKGRFTISRDNSKNTLYLQMNSLTA EDTAVYYCARETWNHLFDYWGQGTLVT VSS |
| AB27_HC_MutAll_M34L | Human with germline back-mutations and liability mutation | VH | 332 | EVQLVESGGGVVQPGGSLRLSCAASGFRF SSYALSWVRQAPGKGLEWVSGISSGGDTY YVDSVKGRFTISRDNSKNTLYLQMNSLRA EDTAVYYCARETWNHLFDYWGQGTLVT VSS |

TABLE 2-continued

Amino acid sequences of antibody clones described herein.

| Clone/Antibody | Framework | Domain | SEQ ID NO | Sequence |
|---|---|---|---|---|
| 218_Hum13 (218 VL with human IGLV2) | Humanized | VL | 333 | QSALTQPASVSGSPGQSITISCFGSSGNYGL VSWYQQHPGKAPKLMIYYNNKRPSGVSN RFSGSKSGNTASLTISGLQAEDEADYYCG AWETGSATFGGGTKLTVL |
| 218_Hum14 (218 VL with human IGLV3) | Humanized | VL | 334 | SYELTQPPSVSVSPGQTASITCFGSSGNYG WYQQKPGQSPVLVIYYNNKRPSGIPERFSG SNSGNTATLTISGTQAMDEADYYCGAWE TGSATFGGGTKLTVL |
| 119 | Human | VH | 335 | DVQLLESGGGVVQPGGSLRLSCAASGFSF SNFAMTWVRQAPGEGLEWVSTIGSGDTY YADSVKGRFTISRDNSKNTLYLQMNSLRA EDTAVYYCAKDSTVSWSGDFFDYWGLGT LVTVSS |
| 135 | Human | VH | 341 | DVQLVESGGGVVRPGESLRLSCAASGFSFS IYAMSWVRQAPGEGLEWVSTIGADDTYY ADSVKGRFTISRDNSKNTLYLQMNSLRAE DTAVYYCAKDSTVGWSGDFFDYWGLGTL VTVSS |
| 16 | Human | VH | 294 | DVQLVESGGGVVRPGESLRLSCAVSGFRFSSY AMSWVRQAPGKGLEWVSGISSGGDTYYVDSV KGRFTISRDNSKNTLYLQVNSLTAEDTAIYYCA RETWNHLFDYWGLGTLVTVSS |
| 16 | Chicken | VL | 295 | ALTQPASVSANLGETVKITCSGGDSSSHYYGW YQQKSPGSAPVTVIYSDDERPSDIPSRFSGSASG STATLTITGVRVEDEAIYYCGAYDGSTYANTF GAGTTLTVL |
| 17 | Human | VH | 342 | DVQLVESGGAVVRPGESLRLSCAASGFTFSSY AMSWVRQAPGKGLEWLAGISAGGSDTYYIDS VKGRFTISRDNSENSLYLQMNSLTAEDTAVYY CARETWNHLFDYWGLGTLVTVSS |
| 17 | Chicken | VL | 343 | ALTQPASVSANPGETVKITCSGGDWYSTYYG WYQQKSPGSAPVTVIHSDDKRPSDIPSRFSGSA SGSAATLTITGVRVEDEAVYYCAGYDGRTYIN TFGAGTTLTVL |
| 22 | Human | VH | 344 | DVQLVESGGGVVRPGESLRLSCAASGFTFSSY AMSWVRQAPGKGLEWLAGISAGGSDTYYIDS VKGRFTISRRQFQEQSLSPNEPALTAEDTAVYY CARETWNHLFDYWGLGTLVTVSS |
| 22 | Chicken | VL | 345 | ALTQPASVSANPGETVKITCSGGDYYSTYYGW YQQKSPGSAPVTVIHSDDKRPSDIPSRFSGSASG SAATLTIAGVRVEDEAVYFCGAYDGRTYINTF GAGTTLTVL |
| 23 | Human | VH | 346 | DVQLVESGGGVVRPGESLRLSCAASGFTFSSH AMSWVRQAPGKGLEWLAGISAGGSDTYYIDS VKGRFTISRDNSKSSLYLRMNSLTAEDTAVYY CARETWNHLFDYWGLGTLVTVSS |
| 23 | Chicken | VL | 347 | ALTQPASVSANPGETVKITCSGGDYYSTYYAW YQQKSPGSAPVTVIHSDDERPSDIPSRFSGSASG SAATLIITGVRVEDEAVYFCGGYDGRTYINTFG AGTTLTVL |
| 24 | Human | VH | 348 | DVQLVESGGGVVRPGESLRLSCAASGFTFSSN AMSWVRQAPGKGLEWLAGISAGGSDTYYPAS VKGRFTISRDNPKNTLYLQMNTLTAEDTAVYY CARETWNHLFDYWGLGTLVTVSS |
| 24 | Chicken | VL | 349 | ALTQPASVSANPGETVKIACSGGSYYSYYYGW YQQKSPGSALVTVIYSDDKRPSGIPSRFSGSAS GSTATLTITGVRAEDEAVYYCGGYDYSSYTND FGAGTTLTVL |

TABLE 2-continued

Amino acid sequences of antibody clones described herein.

| Clone/Antibody | Framework | Domain | SEQ ID NO | Sequence |
|---|---|---|---|---|
| 26 | Human | VH | 350 | DVQLVESGGGVVRPGESLRLCAASGFTFSTY AMSWVRQAPGKGLEWVSGISASGSGTYYGDS VKGRFTMSRDNSKNTLYLQMNSLTAEDTAVY YCARETWNHLFDYWGLGTLVTVSS |
| 26 | Chicken | VL | 351 | ALTQPASVSANLGGTVEITCSGGSSSYYGWYQ QKSPGSAPVTVIYSDNQRPSDIPSRFSGSASDST ATLTITGVQVEDEAIYYCGGYDSSTYANTFGA GTTLTVL |
| 28 | Human | VH | 352 | DVQLVESGGGVVRPGESLRLCAASGFSFSSN AMSWVRQAPGKGLEWVAGISASGDTYYSGSM KGRFTISRDNSKNTLYLQMNSLTAEDTAVYYC ARETWNHLFDYWGLGTLVTVSS |
| 28 | Chicken | VL | 353 | ALTQPASVSANPGETVKITCSGGSDSYYYGWH QQKSPGSAPVTVIYSDDQRPPDIPSRFSGSASGS TTTLTITGVRAEDEAVYYCGGYDYSTYTNTFG AGTTLTVL |
| 29 | Human | VH | 354 | DVQLVESGGGVVRPGESLRLCAVSGFRFSSY AMSWVRQAPGKGLEWVSGISSDSDAYYVDSV KGRFTISRDNSKNTLYLQVNSLTAEDTAVYYC ARETWNHLFDYWGLGTMVTVSS |
| 29 | Chicken | VL | 355 | ALTQPASVSANLGETVKITCSGGDSSHYYGW FQQKSPGSAPVTLIYSDDERPSDIPSRFSGSASG STATLTITGVRVEDEAIYFCGAYDGSTYTNTFG AGTTLTVL |
| 30 | Human | VH | 356 | DVQLVESGGGVVRPGESLRLCEASGFTFSSDA MSWVRQAPGKGLEWVSGISSGSSTYYGGSVK GRFTISRDNSKNTLYLQMNSLTAEDTAVYYCA RETWNHLFDYWGLGTLVTVSS |
| 30 | Chicken | VL | 357 | ALTQPASVSASPGETVEITCSGGSDSSYYYGW YQQKSPGSAPVTVIYSDNKRPSNIPSRFSGSASG STATLTITGVRVEDEAVYYCGGYDYSTYTNPF GAGTTLTVL |
| 55 | Human | VH | 358 | DVQLVESGGGVVRPGESLRLCAVSGFRFSSY AMSWVRQAPGKGLEWVSGISSGGDTYYVDSV KGRFTISRDNSKNTLYLQVNSLTAEDTAIYYCA RETWNHLFDYWGLGTLVTVSS |
| 55 | Chicken | VL | 359 | ALTQPASVSANLGETVEITCSGGDSSHYYGW YQQKSPGSAPVTVIYSDDERPSDIPSRFSGSASG STATLTITGVRVEDEAIYYCGAYDGSTYANTF GAGTTLTVL |
| 56 | Human | VH | 360 | DVQLVESGGGVVRPGESLRLCAASGFTFSSY AMSWVRQAPGKGLEWLAGISAGGSDTYYIDS VKGRFTISRDNSKNSLYLQVNSLTAEDTAVYY CARETWNHLFDYWGLGTLVTVSS |
| 56 | Chicken | VL | 361 | ALTQPASVSANPGETVKITCSGGGYYSTYYGW YQQKSPGSAPVTVIHSDDKRPSDIPSRFSGSASG SAATLTITGVRVEDEAVYYCAGYDGRTYINTF GAGTTLTVL |
| 59 | Human | VH | 362 | DVQLVESGGGVVRPGESLRLCAVSGFRFSSH AMSWVRQAPGKGLEWVSGISSGGDTYYVDSV KGRFTISRDNSKNTLYLQVNSLTAEDTAIYYCA RETWNHLFDYWGLGTLVTVSS |
| 59 | Chicken | VL | 363 | ALTQPASVSANLGETVKITCSGGDSSHYYGW YQQKSPGSAPVTVIYSDDERPSDIPSRFSGSASG STATLTITGVRVEDEAIYYCGAYDGSTYANTF GAGTTLTVL |
| 60 | Human | VH | 364 | DVQLVDSGGGVVRPGESLRLCAASGFTFSSY AMSWVRQAPGKGLEWLAGISAGGSDTYYIDS VKGRFTISRDNSKNSLYLQMNSLTAEDTAVYY CARETWNHLFDYWGLGTLVTVSS |

TABLE 2-continued

Amino acid sequences of antibody clones described herein.

| Clone/ Antibody | Framework | Domain | SEQ ID NO | Sequence |
|---|---|---|---|---|
| 60 | Chicken | VL | 365 | ALTQPASVSANPGETVKITCSGGDYYSTYYGW YQQKSPGSAPVTVIHSDDKRPSDIPSRFSGSASG SAATLTITGVRVEDEAVYFCGAYDGRTYINTF GAGTTLTVL |
| 65 | Human | VH | 366 | DVQLVESGGGVVRPGESLRLSCAASGFTFSSY AMSWVRQAPGKGLEWLAGISAGGSDTYYIDS VKGRFTISRDNSKNSLYLQMNSLTAEDTAVYY CARETWNHLFDYWGLGTLVTVSS |
| 65 | Chicken | VL | 367 | ALTQPASVSANPGETVKITCSGGDYYSTYYGW YQQKSPGSAPVTVIHSDDKRPSDIPSRFSGSASG SAATLTITGVRVEDEAVYFCGAYDGRTYINTF GAGTTLTVL |
| 69 | Human | VH | 368 | DLQLVESGGGVVRPGESLRLSCAASGFTFSSYA MSWVRQAPGKGLEWLAGISAGGSDTYYIDSV KGRFTISRDNSKNSLYLQMNSLTAEDTAVYYC ARETWNHLFDYWGLGTLVTVSS |
| 69 | Chicken | VL | 369 | ALTQPASVSANPGETVKIICSGGDYYSTYYGW YQQKSPGSAPVTVIHSDDKRPSDIPSRFSGSASG SAATLTITGVRVEDEAVYFCGAYDGRTYINTF GAGTTLTVL |
| 70 | Human | VH | 370 | DVQLVESGGGVVRPGESLRLSCAASGFTFSSY AMSWVRQAPGKGLEWLAGISAGGSDAYYIDS VKGRFTISRDNSKNSLYLQMNSLTAEDTAVYY CARETWNHLFDYWGLGTLVTVSS |
| 70 | Chicken | VL | 371 | ALTQPASVSANPGETVKITCSGGDWYSTYYG WYQQKSPGSAPVTVIHSDDKRPSDIPSRFSGSA SGSAATLTITGVRVEDEAVYYCAGYDGRTYIN TFGAGTTLTVL |
| 71 | Human | VH | 372 | DVQLVESGGGVVRPGESLRLSCAASGFTFSSY AMSWVRQAPGKGLEWLAGISAGGSDTYYIDS VKGRFTISRDNSKNSLYLQMNSLTAEDTAVYY CARETWNHLFDYWGLGTLVTVSS |
| 71 | Chicken | VL | 373 | ALTQPASVSANPGETVKITCSGGGYYSTYYGW YQQKSPGSAPVTVIHSDDKRPSDIPSRFSGSASG SAATLTITGVRVEDEAVYYCAGYDARTYINTF GAGTTLTVL |
| 73 | Human | VH | 374 | DVQLVESGGGVVRPGESLRLSCEASGFTFSSNA MSWARQAPGKGLEWVAGISSGSDTYYGDSVK GRLTISRDNSKNILYLQMNSLTAEDTAVYYCA RETWNHLFDYWGLGTLVTVSS |
| 73 | Chicken | VL | 375 | ALTQPASVSANPGETVKITCSGGIYSSYYYAW YQQKSPGSAPVTLIYSDDKRPSNIPSRFSGSASG STATLTITGVRAEDEAVYFCGGYDQSSYTNPF GAGTTLTVL |
| 74 | Human | VH | 376 | DVQLVESGGGVVRPGESLRLSCAASGFTFSSN AMSWVRQAPGKGLEWLAGISAGDSDTYYPAS VKGRFTISRDNPKNTLYLQMNTLTAEDTAVYY CARETWNHLFDYWGLGTLVTVSS |
| 74 | Chicken | VL | 377 | ALTQPASVSANPGETVKIACSGGSYYSYYYGW YQQKSPGSALVTVIYSDDKRPSGIPSRFSGSAS GSTATLTITGVRAEDEAVYYCGGYDYSSYTND FGAGTTLTVL |
| 76 | Human | VH | 378 | DVQLVESGGGVVRPGESLRLSCAASGFTFSSY AMSWVRQAPGKGLEWLAGISAGGSDTYYIDS VKGRFTISRDNSKNSLYLQMNSLTAEDTAVYY CARETWNHLFDYWGLGTLVTVSS |
| 76 | Chicken | VL | 379 | ALTQPASVSANPGETVKITCSGGDWYSTYYG WYQQKSPGSAPVTVIHSDDKRPSDIPSRFSGSA SGSAATLTITGVRVEDEAVYYCAGYDGRTYIN TFGAGTTLTVL |

TABLE 2-continued

Amino acid sequences of antibody clones described herein.

| Clone/Antibody | Framework | Domain | SEQ ID NO | Sequence |
|---|---|---|---|---|
| 201 | Human | VH | 380 | DVQLVESGGAVVRPGETLRLSCTASGFTFSSY AMSWVRQAPGKGLEWVSGISASGSDTYYADS VKGRSTISRDNSKNTLYLRMSSLTAEDTAVYY CARETWNHLFDYWGLGTLVTVSS |
| 201 | Chicken | VL | 381 | ALTQPASVSANPGETVKITCSGGGTSSYYGWY QQKSPGSAPVTLIHSDDKRPSDIPSRFSGSASGS TATLTITGVQVEDEAVYYCGGYDYTTYVNTFG AGTTLTVL |
| 202 | Human | VH | 382 | DVQLVESGGGVVRPGESLRLSCAASGFTFSSY AMSWVRQAPGKGLEWLAGISAGGSDTYYIDS VKGRFTISRDNSKNSLYLQMNSLTAEDTAVYY CARETWNHLFDYWGLGTLVTVSS |
| 202 | Chicken | VL | 383 | ALTQPASVSANPGETVKITCSGGGYYSTYYGW YQQRSPGSAPVTVIHSDDKRPSDIPSRFSGSASG SAATLTITGVRVEDEAVYYCAGYDGRTYLNTF GAGTTLTVL |
| 206 | Human | VH | 384 | DVQLVESGGAVVRPGETLRLSCTASGFTFSSY AMSWVRQAPGKGLEWVSGISASGSDTYYADS VKGRSTISRDNSKNTLYLRMSSLTAEDTAVYY CARETWNHLFDYWGLGTLVTLSS |
| 206 | Chicken | VL | 385 | ALTQPASVSANPGETVKITCSGGGTSSYYGWY QQKSPGSAPVTLIHSDDKRPSDIPSRFSGSASGS TATLTITGVQAEDEAVYYCGGYDYTTYVNTFG AGTTLTVL |
| 175 | Human | VH | 386 | DVQLVESGGGVVRPGESLRLSCAASGFTFSTSD MNWVRQAPGEGLEWVSLISGSGEITYYADSVK GRFTISRDNSKNTLYLQMNSLRAEDTAVYYCA KENDRYRFFDYWGLGTLVTVSS |
| 175 | Human | VL | 387 | ETVLTQSPGILSLSPGERATLTCRASQSVYTYL AWYQEKPGQAPRLLIYGASSRAAGIPDRFSGS GSGTEFTLTISSLQSEDFAVYYCQQYYDRPPLT FGGGTKVEIK |
| 177 | Human | VH | 388 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKENNRYRFFDYWGLGTLVTVSS |
| 177 | Human | VL | 389 | KTVLTQSPGTLSLSPGERATLTCRADQSVYTYL AWYQERPGQAPRLLIYDASSRATGIPDRFSGSG SGTEFTLTISSLQSEDFAVYYCQQYYDRPPLTF GGGTKVEIK |
| 178 | Human | VH | 390 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKENNRYRFFDYWGLGTLVTVSS |
| 178 | Human | VL | 391 | ETVLTQSPGTLTLSPGERATLSCRASQSVYTYL AWYQEKPGQAPRLLIYGASSRATGVPDRFSGS GSGTEFTLTISSLQSEDFAVYYCQQYYDRPPLT FGGGTKVEIK |
| 180 | Human | VH | 392 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKENDRYRFFDYWGLGTLVTVSS |
| 180 | Human | VL | 393 | ETVLTQSPGTLTLSPGERATLTCRASQSVYTYL AWYQEKPGQAPRLLIYGASSRATGIPDRFSGSG SGTEFTLTISSLQSEDFAVYYCQQYYDRPPLTF GGGTKVEIK |
| 184 | Human | VH | 394 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKENNRYRFFDYWGLGTLVTVSS |

TABLE 2-continued

Amino acid sequences of antibody clones described herein.

| Clone/Antibody | Framework | Domain | SEQ ID NO | Sequence |
|---|---|---|---|---|
| 184 | Human | VL | 395 | ETVLTQSPGTLSLSPGERATLNCRASQSVYTYL AWYQEKPGQAPRLLIYDASSRATGIPDRFSGSG SGTEFTLTISSLESEDFAVYYCQQYYDRPPLTF GGGTKVEIK |
| 185 | Human | VH | 396 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKENNRYRFFDDWGLGTLVTVSS |
| 185 | Human | VL | 397 | ETVLTQSPGTLSLSPGERATLNCRASQSVYSYL AWYQERPGQAPRLLIYGASTRATGIPDRFSGSG SGTEFTLTISSLESDDFAVYYCQQYYDRPPLTF GGGTKVEIK |
| 189 | Human | VH | 398 | DVQLVESGGGVVRPGESLRLSCAASGFTFSSD MNWVRQAPGEGLEWVSLISGSGEITYYADSVK GRFTISRDNSKNTLYLQMNSLRAEDTAIYYCA KENNMYRFFDYWGLGTLVTVSS |
| 189 | Human | VL | 399 | ETVLTQSPGTLSLSPGERATLSCRASQSVYTYL AWYQQKPGQPPRLLIHAARNRAAGIPDRFSGS GSGTEFTLTISSLQSEDFAVYYCQQYYDRPPLT FGGGTKVEIK |
| 190 | Human | VH | 400 | DVQLVESGGGVVRPGESLRLSCAASGFTFSSY DMNWVRQAPGEGLEWVSLISGSGEIIYYADSV KGRFTISRDNSKNTLYLQMNSLRAEDTAVYYC AKEDNRYRFFDYWGLGALVTVSS |
| 190 | Human | VL | 401 | ETVLTQSPGTLTLSPGERTTLTCRASQSVYTYL AWYQEKPGQAPRLLIYGASSRATGIPDRFSGSG SGTEFTLTISSLQSEDFAVYYCQQYYDRPPLTF GGGTKVEIK |
| 193 | Human | VH | 402 | DVQLVESGGGVVRPGESLRLSCAASGFTFSSY DMNWVRQAPGEGLEWVSLISGSGEITYYADSV KGRFTISRDNSKNTLYLQMNSLRAEDTAVYYC AKENNRYRFFDYWGLGTLVTVSS |
| 193 | Human | VL | 403 | ETVLTQSPGTLSLSPGERATLSCRASQSVYTYL AWYQEKPGQAPRLLIYAASTRATGIPDRFSGSG SGTEFTLTISSLQSEDFAVYYCQQYYDRPPLTF GGGTKVEIK |
| 191 | Human | VH | 404 | DVQLVESGGGVVRPGESLRLSCAASGFSFSSY AMNWVRQAPGEGLEWVSRINSGGGTDYAES VKGRFTISRDNSENTLYLQMNSLRAEDTAVYY CAKQYDWNGFFDYWGLGALVTVSS |
| 191 | Human | VL | 405 | ETVLTQSPATLSVSPGERATLSCRASQTVGSKL AWHQQKPGQAPRLLIYD ATNRATGIPDRFSGSGSGTDFTLTISGLQTEDSA VYYCQQYYWPPYRFGGGTKVEIK |
| 198 | Human | VH | 406 | DVQLVESGGGVVRPGESLRLSCAASGFSFSSH AMNWVRQAPGEGLEWVSRINSGGGTDYAES VKGRFTISRDNSENTLYLQMNSLRAEDTAVYY CAKQYDWNGFFDYWGLGALVTVSS |
| 198 | Human | VL | 407 | ETVLTQSPATLSVSPGERATLSCRASQTVGSKL AWHQQKPGQAPRLLIYD ATNRATGIPDRFSGSGSGTDFTLTISSLQTEDSA VYYCQQYYWPPYRFGGGTKVEIK |
| 163 | Human | VH | 408 | DVQLVESGGGLVRPGESLRLSCAASGFTFTNY AVTWVRQAPGEGLEWVSLISVTGTTYYADSV KGRFTISRDNSKSTLYLQMNGLRAEDTAVYYC AKVTWKNVFDYWGLGTLVTVSS |
| 163 | Human | VL | 409 | EIVLTQSPGTLSVSPGERATFSCRASQTVGSKL AWYQQKPGQAPRLLIYDANTRATGIPARFSGS GSGTEFTLTISSLQSEDFAVYYCQQHTDWPPYT FGGGTKVEIK |

TABLE 2-continued

Amino acid sequences of antibody clones described herein.

| Clone/Antibody | Framework | Domain | SEQ ID NO | Sequence |
|---|---|---|---|---|
| 164 | Human | VH | 410 | DVQLVESGGGLVRPGESLRLSCAASGFTFTNY AVTWVRQAPGEGLEWVSLISVTGTTYYADSV KGRFTISRDNSKSTLYLQMNGLRAEDTAVYYC AKVTWKNVFDYWGLGTLVTVSS |
| 164 | Human | VL | 411 | EIVLTQSPGTLSVSPGERATFSCRASQTVGSKL AWYQQKPGQAPRLLIYDANTRATGIPARFSGS RSGTEFTLTISSLQSEDFAVYYCQQHTDWPPYT FGGGTKVEIK |
| 174 | Human | VH | 412 | DVQLVESGGGVVRPGESLRLSCAASGFTFSDH DMSWVRQGPGEGLEWVAGISLRGGVTWYAD SVKGRFTISRDNSKNTLYLRLFSLRTEDTAIYY CARESWNTFFDYWGLGTLVTVSS |
| 174 | Human | VL | 413 | EIVLTQSPGTLSLSPGETATLSCRASQNVRSNL AWYQQKPGQAPRLLIYDASSRATGIPDRFSGS GSGTDFTLTISSLQSEDFAVYYCQQYGNGPPLT FGGGTKVEIK |
| 214 | Human | VH | 414 | DVQLVESEGGVVRPGESLRLSCEASGFTFRNSY MTWVRQAPGEGLEWVSTISDTGDTAYYADSV KGRFTISRDNSKNSLYLQMNSLRAEDTAIYYC AKSWIWWTFFDYWGLGTLVTVSS |
| 214 | Chicken | VL | 415 | ALTQPASVSANLGGTVEITCSGGNSNHYGWYQ QKSPGSAPVTLIYADTNRPSNIPSRFSGSTSGST STLTITGVQAEDEAVYYCGGSSTGDGIFGAGTT LTVL |
| Hum8 | Humanized | VL | 416 | SYELTQPPSVSVSPGQTARITCSGGAYSSYYYA WYQQKPGQAPVLVIYSDSKRPSGIPERFSGSSS GTTVTLTISGVQAEDEADYYCGGYDQSSYTNP FGGGTKLTVL |
| 136_MutAll(Light chain)_S12T | Human with D1E, R13Q, E16R, E43K, and L111Q mutations | VL | 417 | EIVLTQSPGTLTLSPGERATLSCRASQSVYTYL AWYQQKPGQAPRLLIYGA SSRATGIPDRFSGSGSGIEFTLTISSLQSEDFAV YYCQQYYDRPPLTFGGGTKVEIK |
| 136_MutAll(Light chain)_S22T | Human with germline back-mutations | VL | 418 | EIVLTQSPGTLSLSPGERATLTCRASQSVYTYL AWYQQKPGQAPRLLIYGA SSRATGIPDRFSGSGSGIEFTLTISSLQSEDFAV YYCQQYYDRPPLTFGGGTKVEIK |
| 136_MutAll(Light chain)_Q38E | Human with germline back-mutations | VL | 419 | EIVLTQSPGTLSLSPGERATLSCRASQSVYTYL AWYQEKPGQAPRLLIYGA SSRATGIPDRFSGSGSGIEFTLTISSLQSEDFAV YYCQQYYDRPPLTFGGGTKVEIK |
| 119_wt_M34L | Human with liability mutation | VH | 420 | DVQLLESGGGVVQPGGSLRLSCAASGFSFSNF ALTWVRQAPGEGLEWVSTIGSGDTYYADSVK GRFTISR DNSKNTLYLQMNSLRAEDTAVYYCAKDSTVS WSGDFFDYWGLGTLVTVSS |
| 119_wt_M34V | Human with liability mutation | VH | 421 | DVQLLESGGGVVQPGGSLRLSCAASGFSFSNF AVTWVRQAPGEGLEWVSTIGSGDTYYADSVK GRFTISR DNSKNTLYLQMNSLRAEDTAVYYCAKDSTVS WSGDFFDYWGLGTLVTVSS |
| 135_wt_M34L | Human with liability mutation | VH | 422 | DVQLVESGGGVVRPGESLRLSCAASGFSFSIYA LSWVRQAPGEGLEWVSTIGADDTYYADSVKG RFTISR DNSKNTLYLQMNSLRAEDTAVYYCAKDSTVG WSGDFFDYWGLGTLVTVSS |
| 135_wt_M34V | Human with liability mutation | VH | 423 | DVQLVESGGGVVRPGESLRLSCAASGFSFSIYA VSWVRQAPGEGLEWVSTIGADDTYYADSVKG RFTISR DNSKNTLYLQMNSLRAEDTAVYYCAKDSTVG WSGDFFDYWGLGTLVTVSS |

TABLE 2-continued

Amino acid sequences of antibody clones described herein.

| Clone/Antibody | Framework | Domain | SEQ ID NO | Sequence |
|---|---|---|---|---|
| 136_wt_M34L | Human with liability mutation | VH | 424 | DVQLVESGGGVVRPGESLRLSCAASGFTFSSY DLNWVRQAPGEGLEWVSLISGSGEIIYYADSV KGRFTI SRDNSKNTLYLQMNSLRAEDTAVYYCAKENN RYRFFDDWGLGTLVTVSS |
| 136_wt_M34V | Human with liability mutation | VH | 425 | DVQLVESGGGVVRPGESLRLSCAASGFTFSSY DVNWVRQAPGEGLEWVSLISGSGEIIYYADSV KGRFTI SRDNSKNTLYLQMNSLRAEDTAVYYCAKENN RYRFFDDWGLGTLVTVSS |
| 119 HVR-H1 | Human | HVR-H1 | 175 | NFAMT |

In some embodiments, an antibody of the present disclosure binds to a human SIRP-α polypeptide at one or more residues. It is to be understood that residues of a SIRP-α polypeptide that are bound by an antibody of the present disclosure may be described with respect to a reference SIRP-α polypeptide, but this description is not limited to a single SIRP-α polypeptide (i.e., the reference SIRP-α polypeptide). Rather, specific amino acid residues of a reference SIRP-α polypeptide are described to identify corresponding amino acid positions that can be identified on various SIRP-α polypeptides. For example, specific residues that correspond to one or more amino acid positions of SEQ ID NO:296 can be identified for various human SIRP-α polypeptides, such as v1 and/or v2. Since the amino acid sequences of SEQ ID NO:296 and SEQ ID NO:5 differ only at the N80 position (excepting a small number of C-terminal residues of SEQ ID NO:296 useful for protein production and purification), one of skill in the art will appreciate that references herein to amino acid positions with respect to the amino acid sequence of SEQ ID NO:296 will correspond to the same positions in the amino acid sequence of SEQ ID NO:5. Techniques for determining the residues of a SIRP-α polypeptide bound by an antibody are known in the art; exemplary and non-limiting descriptions are provided in Example 4.

SEQ ID NO: 296
EEELQVIQPD KSVLVAAGET ATLRCTATSL IPVGPIQWFR

GAGPGRELIY NQKEGHFPRV TTVSDLTKRN NMDFSIRIGA

ITPADAGTYY CVKFRKGSPD DVEFKSGAGT ELSVRAKPST

RHHHHHH

In some embodiments, an antibody of the present disclosure binds to a human SIRP-α v1 polypeptide at one or more amino acid positions selected from I31, V33, Q52, K53, T67, R69, N70, and K96, according to SEQ ID NO:296. In some embodiments, the antibody further binds to the human SIRP-α v1 polypeptide at one or more amino acid positions selected from L30, P32, E54, T62, N71, M72, F74, and R95, according to SEQ ID NO:296.

In some embodiments, an antibody of the present disclosure binds to a human SIRP-α v1 polypeptide at one or more amino acid positions selected from I7, P9, D10, K11, S12, A42, A108, and E111, according to SEQ ID NO:296. In some embodiments, the antibody binds to the human SIRP-α v1 polypeptide at K11, A42, A108, and E111, according to SEQ ID NO:296. In some embodiments, the antibody binds to the human SIRP-α v1 polypeptide at I7, P9, D10, K11, S12, A108, and E111, according to SEQ ID NO:296. In some embodiments, the antibody further binds to the human SIRP-α v1 polypeptide at one or more amino acid positions selected from L14, T26, T28, T88, Y90, S106, S113, and A116, according to SEQ ID NO:296. In some embodiments, the antibody further binds to the human SIRP-α v1 polypeptide at L14, T88, Y90, S106, S113, and A116 of human SIRP-α v1, according to SEQ ID NO:296. In some embodiments, the antibody further binds to the human SIRP-α v1 polypeptide at L14, T26, and T28, according to SEQ ID NO:296.

In some embodiments, an antibody of the present disclosure binds to a human SIRP-α v1 polypeptide at one or more amino acid positions selected from E47, L48, P58, R59, T82, and A84, according to SEQ ID NO:296. In some embodiments, the antibody further binds to the human SIRP-α v1 polypeptide at one or more amino acid positions selected from A17, P44, G45, I49, E54, G55, H56, F57, and P83, according to SEQ ID NO:296.

In some embodiments, an antibody of the present disclosure binds the extracellular domain (e.g., the D1 domain) of a human SIRP-α v1 polypeptide with a dissociation constant ($K_D$) of less than 100 nM, less than 50 nM, or less than 30 nM. In some embodiments, the antibody blocks binding between an extracellular domain (e.g., the D1 domain) of a human SIRP-α polypeptide and an IgSF domain of a human CD47 polypeptide, and the antibody binds the extracellular domain (e.g., the D1 domain) of a human SIRP-α v1 polypeptide with a dissociation constant ($K_D$) of less than 100 nM, less than 50 nM, or less than 30 nM. In some embodiments, the antibody binds the D1 domain of a human SIRP-α v1 polypeptide and the D1 domain of a human SIRP-α v2 polypeptide. In some embodiments, the antibody binds an extracellular domain (e.g., the D1 domain) of a cynomolgus SIRP-α polypeptide. In some embodiments, the antibody binds an extracellular domain (e.g., the D1 domain) of a human SIRP-β polypeptide. In some embodiments, the antibody binds an extracellular domain (e.g., the D1 domain) of a human SIRP-γ polypeptide. In some embodiments, the antibody binds an extracellular domain (e.g., the D1 domain) of a murine SIRP-α polypeptide.

In some embodiments, an antibody of the present disclosure binds the D1 domain of a human SIRP-α polypeptide and does not block binding between an extracellular domain (e.g., the D1 domain) of a human SIRP-α polypeptide and an IgSF domain of a human CD47 polypeptide. In some embodiments, the antibody binds the extracellular domain (e.g., the D1 domain) of a human SIRP-α v1 polypeptide with a dissociation constant ($K_D$) of less than 100 nM, less than 50 nM, or less than 30 nM. In some embodiments, the antibody binds the D1 domain of a human SIRP-α v1 polypeptide. In some embodiments, the antibody binds the D1 domain of a human SIRP-α v1 polypeptide and the D1 domain of a human SIRP-α v2 polypeptide. In some embodiments, the antibody binds an extracellular domain (e.g., the D1 domain) of a cynomolgus SIRP-α polypeptide. In some embodiments, the antibody binds an extracellular domain (e.g., the D1 domain) of a human SIRP-β polypeptide. In some embodiments, the antibody binds an extracellular domain (e.g., the D1 domain) of a murine SIRP-α polypeptide.

In some embodiments, an antibody of the present disclosure competes for binding the extracellular domain (e.g., the D1 domain) of the human SIRP-α polypeptide with a reference anti-SIRP-α antibody. Techniques for determining whether an antibody competes for binding the extracellular domain (e.g., the D1 domain) of the human SIRP-α polypeptide with a reference anti-SIRP-α antibody are known in the art; exemplary and non-limiting descriptions are provided in Example 5.

In some embodiments, an antibody of the present disclosure competes for binding the extracellular domain (e.g., the D1 domain) of the human SIRP-α polypeptide with one or more reference anti-SIRP-α antibodies selected from 119, 120, 121, 122, 21, 25, 27, 66, and 135. In some embodiments, an antibody of the present disclosure competes for binding the extracellular domain (e.g., the D1 domain) of the human SIRP-α polypeptide with one or more of the following reference anti-SIRP-α antibodies: (a) an antibody comprising a VH domain comprising the amino acid sequence of SEQ ID NO:120 and a VL domain comprising the amino acid sequence of SEQ ID NO:97, (b) an antibody comprising a VH domain comprising the amino acid sequence of SEQ ID NO:121 and a VL domain comprising the amino acid sequence of SEQ ID NO:98, (c) an antibody comprising a VH domain comprising the amino acid sequence of SEQ ID NO:130 and a VL domain comprising the amino acid sequence of SEQ ID NO:107, (d) an antibody comprising a VH domain comprising the amino acid sequence of SEQ ID NO:122 and a VL domain comprising the amino acid sequence of SEQ ID NO:99, (e) an antibody comprising a VH domain comprising the amino acid sequence of SEQ ID NO:135 and a VL domain comprising the amino acid sequence of SEQ ID NO:136, (f) an antibody comprising a VH domain comprising the amino acid sequence of SEQ ID NO:137 and a VL domain comprising the amino acid sequence of SEQ ID NO:138, (g) an antibody comprising a VH domain comprising the amino acid sequence of SEQ ID NO:139 and a VL domain comprising the amino acid sequence of SEQ ID NO:140, (h) an antibody comprising a VH domain comprising the amino acid sequence of SEQ ID NO:141 and a VL domain comprising the amino acid sequence of SEQ ID NO:142, and (i) an antibody comprising a VH domain comprising the amino acid sequence of SEQ ID NO:127 and a VL domain comprising the amino acid sequence of SEQ ID NO:104.

In some embodiments, an antibody of the present disclosure competes for binding the extracellular domain (e.g., the D1 domain) of the human SIRP-α polypeptide with one or more reference anti-SIRP-α antibodies selected from 136 and 137. In some embodiments, an antibody of the present disclosure competes for binding the extracellular domain (e.g., the D1 domain) of the human SIRP-α polypeptide with one or more of the following reference anti-SIRP-α antibodies: (a) an antibody comprising a VH domain comprising the amino acid sequence of SEQ ID NO:133 and a VL domain comprising the amino acid sequence of SEQ ID NO:134, and (b) an antibody comprising a VH domain comprising the amino acid sequence of SEQ ID NO:128 and a VL domain comprising the amino acid sequence of SEQ ID NO:105.

In some embodiments, an antibody of the present disclosure competes for binding the extracellular domain (e.g., the D1 domain) of the human SIRP-α polypeptide with one or more reference anti-SIRP-α antibodies selected from 3, 213, 173, and 209. In some embodiments, an antibody of the present disclosure competes for binding the extracellular domain (e.g., the D1 domain) of the human SIRP-α polypeptide with one or more of the following reference anti-SIRP-α antibodies: (a) an antibody comprising a VH domain comprising the amino acid sequence of SEQ ID NO:242 and a VL domain comprising the amino acid sequence of SEQ ID NO:243, (b) an antibody comprising a VH domain comprising the amino acid sequence of SEQ ID NO:275 and a VL domain comprising the amino acid sequence of SEQ ID NO:276, (c) an antibody comprising a VH domain comprising the amino acid sequence of SEQ ID NO:278 and a VL domain comprising the amino acid sequence of SEQ ID NO:279, and (d) an antibody comprising a VH domain comprising the amino acid sequence of SEQ ID NO:280 and a VL domain comprising the amino acid sequence of SEQ ID NO:281.

In some embodiments, an antibody of the present disclosure competes for binding the extracellular domain (e.g., the D1 domain) of the human SIRP-α polypeptide with one or more reference anti-SIRP-α antibodies selected from 115, 116, 117, 118, and 132. In some embodiments, an antibody of the present disclosure competes for binding the extracellular domain (e.g., the D1 domain) of the human SIRP-α polypeptide with one or more of the following reference anti-SIRP-α antibodies: (a) an antibody comprising a VH domain comprising the amino acid sequence of SEQ ID NO:116 and a VL domain comprising the amino acid sequence of SEQ ID NO:93, (b) an antibody comprising a VH domain comprising the amino acid sequence of SEQ ID NO:117 and a VL domain comprising the amino acid sequence of SEQ ID NO:94, (c) an antibody comprising a VH domain comprising the amino acid sequence of SEQ ID NO: 118 and a VL domain comprising the amino acid sequence of SEQ ID NO:95, (d) an antibody comprising a VH domain comprising the amino acid sequence of SEQ ID NO:119 and a VL domain comprising the amino acid sequence of SEQ ID NO:96, and (e) an antibody comprising a VH domain comprising the amino acid sequence of SEQ ID NO:282 and a VL domain comprising the amino acid sequence of SEQ ID NO:283.

In some embodiments, an antibody of the present disclosure competes for binding the extracellular domain (e.g., the D1 domain) of the human SIRP-α polypeptide with one or more reference anti-SIRP-α antibodies selected from 218, 123, 149, 161, 162, and 194. In some embodiments, an antibody of the present disclosure competes for binding the extracellular domain (e.g., the D1 domain) of the human SIRP-α polypeptide with one or more of the following reference anti-SIRP-α antibodies: (a) an antibody comprising a VH domain comprising the amino acid sequence of SEQ ID NO:284 and a VL domain comprising the amino acid sequence of SEQ ID NO:285, (b) an antibody comprising a VH domain comprising the amino acid sequence of SEQ ID NO:123 and a VL domain comprising the amino acid sequence of SEQ ID NO:100, (c) an antibody comprising a VH domain comprising the amino acid sequence of SEQ ID NO:286 and a VL domain comprising the amino acid sequence of SEQ ID NO:287, (d) an antibody comprising a VH domain comprising the amino acid sequence of SEQ ID NO:288 and a VL domain comprising the amino acid sequence of SEQ ID NO:289, (e) an antibody comprising a VH domain comprising the amino acid sequence of SEQ ID NO:290 and a VL domain comprising the amino acid sequence of SEQ ID NO:291, and (f) an antibody comprising a VH domain comprising the amino acid sequence of SEQ ID NO:292 and a VL domain comprising the amino acid sequence of SEQ ID NO:293.

In some embodiments, an antibody of the present disclosure competes for binding the extracellular domain (e.g., the D1 domain) of the human SIRP-α polypeptide with reference anti-SIRP-α antibody 45. In some embodiments, an antibody of the present disclosure competes for binding the extracellular domain (e.g., the D1 domain) of the human SIRP-α polypeptide with an antibody comprising a VH domain comprising the amino acid sequence of SEQ ID NO:244 and a VL domain comprising the amino acid sequence of SEQ ID NO:245.

The present disclosure provides multiple families of anti-SIRP-α antibodies, each family comprising multiple antibodies. As demonstrated herein, antibodies within a given family may share certain structural properties (e.g., similar or identical HVR or CDR sequences) as well as one or more functional properties, including but not limited to binding affinity to human, monkey, and/or mouse SIRP-α polypeptide(s), binding affinity to SIRP-0 polypeptides, binding affinity to SIRP-γ polypeptides, mode of binding to SIRP-α (e.g., CD47 blocking, CD47 non-blocking, or "kick off" binding), induction of phagocytosis (e.g., in an in vitro assay), activation of dendritic cells, anti-tumor efficacy, SIRP-α binding epitope residue(s) or "bin" (e.g., as determined by a binning assay), and the like (see, e.g., Tables P-T). Because of these shared properties, it is contemplated that HVR and/or VH or VL sequences of antibodies belonging to the same family can be interchanged or intermingled, such that an anti-SIRP-α antibody can comprise HVR and/or VH or VL derived from more than one specific an anti-SIRP-α antibody described herein. As discussed in greater detail herein, various methodologies for determining HVR or CDR sequences of an antibody variable domain are known in the art and can be used interchangeably herein, including without limitation the Kabat, Chothia, and IMGT definitions, as well as combinations thereof.

In some embodiments, an antibody of the present disclosure comprises an HVR-H1 from a VH domain sequence selected from the amino acid sequences of SEQ ID NOs: 120, 246, 258, 327, 121, 130, 122, 127, 247, 259, 335, and 328; an HVR-H2 from a VH domain sequence selected from the amino acid sequences of SEQ ID NOs:120, 246, 258, 327, 121, 130, 122, 127, 247, 259, 335, and 328; an HVR-H3 from a VH domain sequence selected from the amino acid sequences of SEQ ID NOs:120, 246, 258, 327, 121, 130, 122, 127, 247, 259, 335, and 328; an HVR-L1 from a VL domain sequence selected from the amino acid sequences of SEQ ID NOs:97, 98, 107, 99, 104, and 312; an HVR-L2 from a VL domain sequence selected from the amino acid sequences of SEQ ID NOs: 97, 98, 107, 99, 104, and 312; and/or an HVR-L3 from a VL domain sequence selected from the amino acid sequences of SEQ ID NOs: 97, 98, 107, 99, 104, and 312. In some embodiments, an antibody of the present disclosure comprises an HVR-H1 from a VH domain sequence selected from the amino acid sequences of SEQ ID NOs:120, 246, 258, 327, 121, 130, 122, 127, 247, 259, 335, and 328; an HVR-H2 from a VH domain sequence selected from the amino acid sequences of SEQ ID NOs: 120, 246, 258, 327, 121, 130, 122, 127, 247, 259, 335, and 328; and an HVR-H3 from a VH domain sequence selected from the amino acid sequences of SEQ ID NOs: 120, 246, 258, 327, 121, 130, 122, 127, 247, 259, 335, and 328. In some embodiments, an antibody of the present disclosure comprises an HVR-L1 from a VL domain sequence selected from the amino acid sequences of SEQ ID NOs: 97, 98, 107, 99, 104, and 312; an HVR-L2 from a VL domain sequence selected from the amino acid sequences of SEQ ID NOs: 97, 98, 107, 99, 104, and 312; and an HVR-L3 from a VL domain sequence selected from the amino acid sequences of SEQ ID NOs: 97, 98, 107, 99, 104, and 312. In some embodiments, an antibody of the present disclosure comprises an HVR-H1 from a VH domain sequence selected from the amino acid sequences of SEQ ID NOs:120, 246, 258, 327, 121, 130, 122, 127, 247, 259, 335, and 328; an HVR-H2 from a VH domain sequence selected from the amino acid sequences of SEQ ID NOs: 120, 246, 258, 327, 121, 130, 122, 127, 247, 259, 335, and 328; an HVR-H3 from a VH domain sequence selected from the amino acid sequences of SEQ ID NOs: 120, 246, 258, 327, 121, 130, 122, 127, 247, 259, 335, and 328; an HVR-L1 from a VL domain sequence selected from the amino acid sequences of SEQ ID NOs: 97, 98, 107, 99, 104, and 312; an HVR-L2 from a VL domain sequence selected from the amino acid sequences of SEQ ID NOs: 97, 98, 107, 99, 104, and 312; and an HVR-L3 from a VL domain sequence selected from the amino acid sequences of SEQ ID NOs: 97, 98, 107, 99, 104, and 312.

In some embodiments, an antibody of the present disclosure comprises an HVR-H1 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-H2 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-H3 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-L1 from a VL domain sequence selected from the amino acid sequences of SEQ ID NOs:136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; an HVR-L2 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; and/or an HVR-L3 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385. In some embodiments, an antibody of the present disclosure comprises an HVR-H1 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-H2 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; and an HVR-H3 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384. In some embodiments, an antibody of the present disclosure comprises an HVR-L1 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; an HVR-L2 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; and an HVR-L3 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385. In some embodiments, an antibody of the present disclosure comprises an HVR-H1 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-H2 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-H3 from a VH domain sequence selected from the amino acid sequences of SEQ ID NOs: 135, 137, 265, 266, 331, 139, 267, 332, 141, 263, 264, 268, 330, 294, 342, 344, 346, 348, 350, 352, 354, 356, 358, 360, 362, 364, 366, 368, 370, 372, 374, 376, 378, 380, 382, and 384; an HVR-L1 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; an HVR-L2 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385; and an HVR-L3 from a VL domain sequence selected from the amino acid sequences of SEQ ID NOs: 136, 138, 140, 142, 252, 254, 262, 416, 295, 343, 345, 347, 349, 351, 353, 355, 357, 359, 361, 363, 365, 367, 369, 371, 373, 375, 377, 379, 381, 383, and 385.

In some embodiments, an antibody of the present disclosure comprises an HVR-H1 from a VH domain sequence selected from the amino acid sequences of SEQ ID NOs: 133, 249, 260, 329, 128, 386, 388, 390, 392, 394, 396, 398, 400, and 402; an HVR-H2 from a VH domain sequence selected from the amino acid sequences of SEQ ID NOs: 133, 249, 260, 329, 128, 386, 388, 390, 392, 394, 396, 398, 400, and 402; an HVR-H3 from a VH domain sequence selected from the amino acid sequences of SEQ ID NOs: 133, 249, 260, 329, 128, 386, 388, 390, 392, 394, 396, 398, 400, and 402; an HVR-L1 from a VL domain sequence selected from the amino acid sequences of SEQ ID NOs: 134, 251, 105, 250, 417, 418, 419, 387, 389, 391, 393, 395, 397, 399, 401, and 403; an HVR-L2 from a VL domain sequence selected from the amino acid sequences of SEQ ID NOs: 134, 251, 105, 250, 417, 418, 419, 387, 389, 391, 393, 395, 397, 399, 401, and 403; and/or an HVR-L3 from a VL domain sequence selected from the amino acid sequences of SEQ ID NOs: 134, 251, 105, 250, 417, 418, 419, 387, 389, 391, 393, 395, 397, 399, 401, and 403. In some embodiments, an antibody of the present disclosure comprises an HVR-H1 from a VH domain sequence selected from the amino acid sequences of SEQ ID NOs: 133, 249, 260, 329, 128, 386, 388, 390, 392, 394, 396, 398, 400, and 402; an HVR-H2 from a VH domain sequence selected from the amino acid sequences of SEQ ID NOs: 133, 249, 260, 329, 128, 386, 388, 390, 392, 394, 396, 398, 400, and 402; and an HVR-H3 from a VH domain sequence selected from the amino acid sequences of SEQ ID NOs: 133, 249, 260, 329, 128, 386, 388, 390, 392, 394, 396, 398, 400, and 402. In some embodiments, an antibody of the present disclosure comprises an HVR-L1 from a VL domain sequence selected from the amino acid sequences of SEQ ID NOs: 134, 251, 105, 250, 417, 418, 419, 387, 389, 391, 393, 395, 397, 399, 401, and 403; an HVR-L2 from a VL domain sequence selected from the amino acid sequences of SEQ ID NOs: 134, 251, 105, 250, 417, 418, 419, 387, 389, 391, 393, 395, 397, 399, 401, and 403; and an HVR-L3 from a VL domain sequence selected from the amino acid sequences of SEQ ID NOs: 134, 251, 105, 250, 417, 418, 419, 387, 389, 391, 393, 395, 397, 399, 401, and 403. In some embodiments, an antibody of the present disclosure comprises an HVR-H1 from a VH domain sequence selected from the amino acid sequences of SEQ ID NOs: 133, 249, 260, 329, 128, 386, 388, 390, 392, 394, 396, 398, 400, and 402; an HVR-H2 from a VH domain sequence selected from the amino acid sequences of SEQ ID NOs: 133, 249, 260, 329, 128, 386, 388, 390, 392, 394, 396, 398, 400, and 402; an HVR-H3 from a VH domain sequence selected from the amino acid sequences of SEQ ID NOs: 133, 249, 260, 329, 128, 386, 388, 390, 392, 394, 396, 398, 400, and 402; an HVR-L1 from a VL domain sequence selected from the amino acid sequences of SEQ ID NOs: 134, 251, 105, 250, 417, 418, 419, 387, 389, 391, 393, 395, 397, 399, 401, and 403; an HVR-L2 from a VL domain sequence selected from the amino acid sequences of SEQ ID NOs: 134, 251, 105, 250, 417, 418, 419, 387, 389, 391, 393, 395, 397, 399, 401, and 403; and an HVR-L3 from a VL domain sequence selected from the amino acid sequences of SEQ ID NOs: 134, 251, 105, 250, 417, 418, 419, 387, 389, 391, 393, 395, 397, 399, 401, and 403.

In some embodiments, an antibody of the present disclosure comprises an HVR-H1 from a VH domain sequence selected from the amino acid sequences of SEQ ID NOs:116, 117, 118, 119, 282, 404, and 406; an HVR-H2 from a VH domain sequence selected from the amino acid sequences of SEQ ID NOs: 116, 117, 118, 119, 282, 404, and 406; an HVR-H3 from a VH domain sequence selected from the amino acid sequences of SEQ ID NOs: 116, 117, 118, 119, 282, 404, and 406; an HVR-L1 from a VL domain sequence selected from the amino acid sequences of SEQ ID NOs:93, 94, 95, 96, 283, 405, and 407; an HVR-L2 from a VL domain sequence selected from the amino acid sequences of SEQ ID NOs: 93, 94, 95, 96, 283, 405, and 407; and/or an HVR-L3 from a VL domain sequence selected from the amino acid sequences of SEQ ID NOs: 93, 94, 95, 96, 283, 405, and 407. In some embodiments, an antibody of the present disclosure comprises an HVR-H1 from a VH domain sequence selected from the amino acid sequences of SEQ ID NOs: 116, 117, 118, 119, 282, 404, and 406; an HVR-H2 from a VH domain sequence selected from the amino acid sequences of SEQ ID NOs: 116, 117, 118, 119, 282, 404, and 406; and an HVR-H3 from a VH domain sequence selected from the amino acid sequences of SEQ ID NOs: 116, 117, 118, 119, 282, 404, and 406. In some embodiments, an antibody of the present disclosure comprises an HVR-L1 from a VL domain sequence selected from the amino acid sequences of SEQ ID NOs: 93, 94, 95, 96, 283, 405, and 407; an HVR-L2 from a VL domain sequence selected from the amino acid sequences of SEQ ID NOs: 93, 94, 95, 96, 283, 405, and 407; and an HVR-L3 from a VL domain sequence selected from the amino acid sequences of SEQ ID NOs: 93, 94, 95, 96, 283, 405, and 407. In some embodiments, an antibody of the present disclosure comprises an HVR-H1 from a VH domain sequence selected from the amino acid sequences of SEQ ID NOs: 116, 117, 118, 119, 282, 404, and 406; an HVR-H2 from a VH domain sequence selected from the amino acid sequences of SEQ ID NOs: 116, 117, 118, 119, 282, 404, and 406; an HVR-H3 from a VH domain sequence selected from the amino acid sequences of SEQ ID NOs: 116, 117, 118, 119, 282, 404, and 406; an HVR-L1 from a VL domain sequence selected from the amino acid sequences of SEQ ID NOs: 93, 94, 95, 96, 283, 405, and 407; an HVR-L2 from a VL domain sequence selected from the amino acid sequences of SEQ ID NOs: 93, 94, 95, 96, 283, 405, and 407; and an HVR-L3 from a VL domain sequence selected from the amino acid sequences of SEQ ID NOs: 93, 94, 95, 96, 283, 405, and 407.

In some embodiments, an antibody of the present disclosure comprises an HVR-H1 from a VH domain sequence set forth in SEQ ID NO: 242; an HVR-H2 from a VH domain sequence set forth in SEQ ID NO: 242; an HVR-H3 from a VH domain sequence set forth in SEQ ID NO: 242; an HVR-L1 from a VL domain sequence set forth in SEQ ID NO: 243; an HVR-L2 from a VL domain sequence set forth in SEQ ID NO: 243; and/or an HVR-L3 from a VL domain sequence set forth in SEQ ID NO: 243. In some embodiments, an antibody of the present disclosure comprises an HVR-H1 from a VH domain sequence set forth in SEQ ID NO: 242; an HVR-H2 from a VH domain sequence set forth in SEQ ID NO: 242; and an HVR-H3 from a VH domain sequence set forth in SEQ ID NO: 242. In some embodiments, an antibody of the present disclosure comprises an HVR-L1 from a VL domain sequence set forth in SEQ ID NO: 243; an HVR-L2 from a VL domain sequence set forth in SEQ ID NO: 243; and an HVR-L3 from a VL domain sequence set forth in SEQ ID NO: 243. In some embodiments, an antibody of the present disclosure comprises an HVR-H1 from a VH domain sequence set forth in SEQ ID NO: 242; an HVR-H2 from a VH domain sequence set forth in SEQ ID NO: 242; an HVR-H3 from a VH domain sequence set forth in SEQ ID NO: 242; an HVR-L1 from a VL domain sequence set forth in SEQ ID NO: 243; an HVR-L2 from a VL domain sequence set forth in SEQ ID NO: 243; and an HVR-L3 from a VL domain sequence set forth in SEQ ID NO: 243.

In some embodiments, an antibody of the present disclosure comprises an HVR-H1 from a VH domain sequence selected from the amino acid sequences of SEQ ID NOs: 278 and 412; an HVR-H2 from a VH domain sequence selected from the amino acid sequences of SEQ ID NOs: 278 and 412; an HVR-H3 from a VH domain sequence selected from the amino acid sequences of SEQ ID NOs: 278 and 412; an HVR-L1 from a VL domain sequence selected from the amino acid sequences of SEQ ID NOs: 279 and 413; an HVR-L2 from a VL domain sequence selected from the amino acid sequences of SEQ ID NOs: 279 and 413; and/or an HVR-L3 from a VL domain sequence selected from the amino acid sequences of SEQ ID NOs: 279 and 413. In some embodiments, an antibody of the present disclosure comprises an HVR-H1 from a VH domain sequence selected from the amino acid sequences of SEQ ID NOs: 278 and 412; an HVR-H2 from a VH domain sequence selected from the amino acid sequences of SEQ ID NOs: 278 and 412; and an HVR-H3 from a VH domain sequence selected from the amino acid sequences of SEQ ID NOs: 278 and 412. In some embodiments, an antibody of the present disclosure comprises an HVR-L1 from a VL domain sequence selected from the amino acid sequences of SEQ ID NOs: 279 and 413; an HVR-L2 from a VL domain sequence selected from the amino acid sequences of SEQ ID NOs: 279 and 413; and an HVR-L3 from a VL domain sequence selected from the amino acid sequences of SEQ ID NOs: 279 and 413. In some embodiments, an antibody of the present disclosure comprises an HVR-H1 from a VH domain sequence selected from the amino acid sequences of SEQ ID NOs: 278 and 412; an HVR-H2 from a VH domain sequence selected from the amino acid sequences of SEQ ID NOs: 278 and 412; an HVR-H3 from a VH domain sequence selected from the amino acid sequences of SEQ ID NOs: 278 and 412; an HVR-L1 from a VL domain sequence selected from the amino acid sequences of SEQ ID NOs: 279 and 413; an HVR-L2 from a VL domain sequence selected from the amino acid sequences of SEQ ID NOs: 279 and 413; and an HVR-L3 from a VL domain sequence selected from the amino acid sequences of SEQ ID NOs: 279 and 413.

In some embodiments, an antibody of the present disclosure comprises an HVR-H1 from a VH domain sequence selected from the amino acid sequences of SEQ ID NOs: 275 and 414; an HVR-H2 from a VH domain sequence selected from the amino acid sequences of SEQ ID NOs: 275 and 414; an HVR-H3 from a VH domain sequence selected from the amino acid sequences of SEQ ID NOs: 275 and 414; an HVR-L1 from a VL domain sequence selected from the amino acid sequences of SEQ ID NOs: 276 and 415; an HVR-L2 from a VL domain sequence selected from the amino acid sequences of SEQ ID NOs: 276 and 415; and/or an HVR-L3 from a VL domain sequence selected from the amino acid sequences of SEQ ID NOs: 276 and 415. In some embodiments, an antibody of the present disclosure comprises an HVR-H1 from a VH domain sequence selected from the amino acid sequences of SEQ ID NOs: 275 and 414; an HVR-H2 from a VH domain sequence selected from the amino acid sequences of SEQ ID NOs: 275 and 414; and an HVR-H3 from a VH domain sequence selected from the amino acid sequences of SEQ ID NOs: 275 and 414. In some embodiments, an antibody of the present disclosure comprises an HVR-L1 from a VL domain sequence selected from the amino acid sequences of SEQ ID NOs: 276 and 415; an HVR-L2 from a VL domain sequence selected from the amino acid sequences of SEQ ID NOs: 276 and 415; and an HVR-L3 from a VL domain sequence selected from the amino acid sequences of SEQ ID NOs: 276 and 415. In some embodiments, an antibody of the present disclosure comprises an HVR-H1 from a VH domain sequence selected from the amino acid sequences of SEQ ID NOs: 275 and 414; an HVR-H2 from a VH domain sequence selected from the amino acid sequences of SEQ ID NOs: 275 and 414; an HVR-H3 from a VH domain sequence selected from the amino acid sequences of SEQ ID NOs: 275 and 414; an HVR-L1 from a VL domain sequence selected from the amino acid sequences of SEQ ID NOs: 276 and 415; an HVR-L2 from a VL domain sequence selected from the amino acid sequences of SEQ ID NOs: 276 and 415; and an HVR-L3 from a VL domain sequence selected from the amino acid sequences of SEQ ID NOs: 276 and 415.

In some embodiments, an antibody of the present disclosure comprises an HVR-H1 from a VH domain sequence set forth in SEQ ID NO: 280; an HVR-H2 from a VH domain sequence set forth in SEQ ID NO: 280; an HVR-H3 from a VH domain sequence set forth in SEQ ID NO: 280; an HVR-L1 from a VL domain sequence set forth in SEQ ID NO: 281; an HVR-L2 from a VL domain sequence set forth in SEQ ID NO: 281; and/or an HVR-L3 from a VL domain sequence set forth in SEQ ID NO: 281. In some embodiments, an antibody of the present disclosure comprises an HVR-H1 from a VH domain sequence set forth in SEQ ID NO: 280; an HVR-H2 from a VH domain sequence set forth in SEQ ID NO: 280; and an HVR-H3 from a VH domain sequence set forth in SEQ ID NO: 280. In some embodiments, an antibody of the present disclosure comprises an HVR-L1 from a VL domain sequence set forth in SEQ ID NO: 281; an HVR-L2 from a VL domain sequence set forth in SEQ ID NO: 281; and an HVR-L3 from a VL domain sequence set forth in SEQ ID NO: 281. In some embodiments, an antibody of the present disclosure comprises an HVR-H1 from a VH domain sequence set forth in SEQ ID NO: 280; an HVR-H2 from a VH domain sequence set forth in SEQ ID NO: 280; an HVR-H3 from a VH domain sequence set forth in SEQ ID NO: 280; an HVR-L1 from a VL domain sequence set forth in SEQ ID NO: 281; an HVR-L2 from a VL domain sequence set forth in SEQ ID NO: 281; and an HVR-L3 from a VL domain sequence set forth in SEQ ID NO: 281.

In some embodiments, an antibody of the present disclosure comprises an HVR-H1 from a VH domain sequence selected from the amino acid sequences of SEQ ID NOs: 123 and 292; an HVR-H2 from a VH domain sequence selected from the amino acid sequences of SEQ ID NOs: 123 and 292; an HVR-H3 from a VH domain sequence selected from the amino acid sequences of SEQ ID NOs: 123 and 292; an HVR-L1 from a VL domain sequence selected from the amino acid sequences of SEQ ID NOs: 100 and 293; an HVR-L2 from a VL domain sequence selected from the amino acid sequences of SEQ ID NOs: 100 and 293; and/or an HVR-L3 from a VL domain sequence selected from the amino acid sequences of SEQ ID NOs: 100 and 293. In some embodiments, an antibody of the present disclosure comprises an HVR-H1 from a VH domain sequence selected from the amino acid sequences of SEQ ID NOs: 123 and 292; an HVR-H2 from a VH domain sequence selected from the amino acid sequences of SEQ ID NOs: 123 and 292; and an HVR-H3 from a VH domain sequence selected from the amino acid sequences of SEQ ID NOs: 123 and 292. In some embodiments, an antibody of the present disclosure comprises an HVR-L1 from a VL domain sequence selected from the amino acid sequences of SEQ ID NOs: 100 and 293; an HVR-L2 from a VL domain sequence selected from the amino acid sequences of SEQ ID NOs: 100 and 293; and an HVR-L3 from a VL domain sequence selected from the amino acid sequences of SEQ ID NOs: 100 and 293. In some embodiments, an antibody of the present disclosure comprises an HVR-H1 from a VH domain sequence selected from the amino acid sequences of SEQ ID NOs: 123 and 292; an HVR-H2 from a VH domain sequence selected from the amino acid sequences of SEQ ID NOs: 123 and 292; an HVR-H3 from a VH domain sequence selected from the amino acid sequences of SEQ ID NOs: 123 and 292; an HVR-L1 from a VL domain sequence selected from the amino acid sequences of SEQ ID NOs: 100 and 293; an HVR-L2 from a VL domain sequence selected from the amino acid sequences of SEQ ID NOs: 100 and 293; and an HVR-L3 from a VL domain sequence selected from the amino acid sequences of SEQ ID NOs: 100 and 293.

In some embodiments, an antibody of the present disclosure comprises an HVR-H1 from a VH domain sequence selected from the amino acid sequences of SEQ ID NOs: 288, 290, 408, and 410; an HVR-H2 from a VH domain sequence selected from the amino acid sequences of SEQ ID NOs: 288, 290, 408, and 410; an HVR-H3 from a VH domain sequence selected from the amino acid sequences of SEQ ID NOs: 288, 290, 408, and 410; an HVR-L1 from a VL domain sequence selected from the amino acid sequences of SEQ ID NOs: 289, 291, 409, and 411; an HVR-L2 from a VL domain sequence selected from the amino acid sequences of SEQ ID NOs: 289, 291, 409, and 411; and/or an HVR-L3 from a VL domain sequence selected from the amino acid sequences of SEQ ID NOs: 289, 291, 409, and 411. In some embodiments, an antibody of the present disclosure comprises an HVR-H1 from a VH domain sequence selected from the amino acid sequences of SEQ ID NOs: 288, 290, 408, and 410; an HVR-H2 from a VH domain sequence selected from the amino acid sequences of SEQ ID NOs: 288, 290, 408, and 410; and an HVR-H3 from a VH domain sequence selected from the amino acid sequences of SEQ ID NOs: 288, 290, 408, and 410. In some embodiments, an antibody of the present disclosure comprises an HVR-L1 from a VL domain sequence selected from the amino acid sequences of SEQ ID NOs: 289, 291, 409, and 411; an HVR-L2 from a VL domain sequence selected from the amino acid sequences of SEQ ID NOs: 289, 291, 409, and 411; and an HVR-L3 from a VL domain sequence selected from the amino acid sequences of SEQ ID NOs: 289, 291, 409, and 411. In some embodiments, an antibody of the present disclosure comprises an HVR-H1 from a VH domain sequence selected from the amino acid sequences of SEQ ID NOs: 288, 290, 408, and 410; an HVR-H2 from a VH domain sequence selected from the amino acid sequences of SEQ ID NOs: 288, 290, 408, and 410; an HVR-H3 from a VH domain sequence selected from the amino acid sequences of SEQ ID NOs: 288, 290, 408, and 410; an HVR-L1 from a VL domain sequence selected from the amino acid sequences of SEQ ID NOs: 289, 291, 409, and 411; an HVR-L2 from a VL domain sequence selected from the amino acid sequences of SEQ ID NOs: 289, 291, 409, and 411; and an HVR-L3 from a VL domain sequence selected from the amino acid sequences of SEQ ID NOs: 289, 291, 409, and 411.

In some embodiments, an antibody of the present disclosure comprises an HVR-H1 from a VH domain sequence set forth in SEQ ID NO: 286; an HVR-H2 from a VH domain sequence set forth in SEQ ID NO: 286; an HVR-H3 from a VH domain sequence set forth in SEQ ID NO: 286; an HVR-L1 from a VL domain sequence set forth in SEQ ID NO: 287; an HVR-L2 from a VL domain sequence set forth in SEQ ID NO: 287; and/or an HVR-L3 from a VL domain sequence set forth in SEQ ID NO: 287. In some embodiments, an antibody of the present disclosure comprises an HVR-H1 from a VH domain sequence set forth in SEQ ID NO: 286; an HVR-H2 from a VH domain sequence set forth in SEQ ID NO: 286; and an HVR-H3 from a VH domain sequence set forth in SEQ ID NO: 286. In some embodiments, an antibody of the present disclosure comprises an HVR-L1 from a VL domain sequence set forth in SEQ ID NO: 287; an HVR-L2 from a VL domain sequence set forth in SEQ ID NO: 287; and an HVR-L3 from a VL domain sequence set forth in SEQ ID NO: 287. In some embodiments, an antibody of the present disclosure comprises an HVR-H1 from a VH domain sequence set forth in SEQ ID NO: 286; an HVR-H2 from a VH domain sequence set forth in SEQ ID NO: 286; an HVR-H3 from a VH domain sequence set forth in SEQ ID NO: 286; an HVR-L1 from a VL domain sequence set forth in SEQ ID NO: 287; an HVR-L2 from a VL domain sequence set forth in SEQ ID NO: 287; and an HVR-L3 from a VL domain sequence set forth in SEQ ID NO: 287.

In some embodiments, an antibody of the present disclosure comprises an HVR-H1 from a VH domain sequence set forth in SEQ ID NO: 284; an HVR-H2 from a VH domain sequence set forth in SEQ ID NO: 284; an HVR-H3 from a VH domain sequence set forth in SEQ ID NO: 284; an HVR-L1 from a VL domain sequence set forth in SEQ ID NO: 285; an HVR-L2 from a VL domain sequence set forth in SEQ ID NO: 285; and/or an HVR-L3 from a VL domain sequence set forth in SEQ ID NO: 285. In some embodiments, an antibody of the present disclosure comprises an HVR-H1 from a VH domain sequence set forth in SEQ ID NO: 284; an HVR-H2 from a VH domain sequence set forth in SEQ ID NO: 284; and an HVR-H3 from a VH domain sequence set forth in SEQ ID NO: 284. In some embodiments, an antibody of the present disclosure comprises an HVR-L1 from a VL domain sequence set forth in SEQ ID NO: 285; an HVR-L2 from a VL domain sequence set forth in SEQ ID NO: 285; and an HVR-L3 from a VL domain sequence set forth in SEQ ID NO: 285. In some embodiments, an antibody of the present disclosure comprises an HVR-H1 from a VH domain sequence set forth in SEQ ID NO: 284; an HVR-H2 from a VH domain sequence set forth in SEQ ID NO: 284; an HVR-H3 from a VH domain sequence set forth in SEQ ID NO: 284; an HVR-L1 from a VL domain sequence set forth in SEQ ID NO: 285; an HVR-L2 from a VL domain sequence set forth in SEQ ID NO: 285; and an HVR-L3 from a VL domain sequence set forth in SEQ ID NO: 285.

In some embodiments, an antibody of the present disclosure comprises an HVR-H1 from a VH domain sequence set forth in SEQ ID NO:244; an HVR-H2 from a VH domain sequence set forth in SEQ ID NO: 244; an HVR-H3 from a VH domain sequence set forth in SEQ ID NO: 244; an HVR-L1 from a VL domain sequence set forth in SEQ ID NO: 245; an HVR-L2 from a VL domain sequence set forth in SEQ ID NO: 245; and/or an HVR-L3 from a VL domain sequence s set forth in SEQ ID NO: 245. In some embodiments, an antibody of the present disclosure comprises an HVR-H1 from a VH domain sequence set forth in SEQ ID NO: 244; an HVR-H2 from a VH domain sequence set forth in SEQ ID NO: 244; and an HVR-H3 from a VH domain sequence set forth in SEQ ID NO: 244. In some embodiments, an antibody of the present disclosure comprises an HVR-L1 from a VL domain sequence s set forth in SEQ ID NO:245; an HVR-L2 from a VL domain sequence set forth in SEQ ID NO:245; and an HVR-L3 from a VL domain sequence selected set forth in SEQ ID NO:245. In some embodiments, an antibody of the present disclosure comprises an HVR-H1 from a VH domain sequence set forth in SEQ ID NO:244; an HVR-H2 from a VH domain sequence set forth in SEQ ID NO:244; an HVR-H3 from a VH domain sequence set forth in SEQ ID NO:244; an HVR-L1 from a VL domain sequence s set forth in SEQ ID NO:245; an HVR-L2 from a VL domain sequence set forth in SEQ ID NO: 245; and an HVR-L3 from a VL domain sequence set forth in SEQ ID NO: 245.

In some embodiments, an antibody of the present disclosure comprises one, two, or three heavy chain HVR sequences from a VH domain comprising the amino acid sequence of SEQ ID NO:242 and/or one, two, or three light chain HVR sequences from a VL domain comprising the amino acid sequence of SEQ ID NO:243. In some embodiments, an antibody of the present disclosure comprises a VH domain comprising the amino acid sequence of SEQ ID NO:242 and/or a VL domain comprising the amino acid sequence of SEQ ID NO:243. In some embodiments, an antibody of the present disclosure comprises one, two, or three heavy chain HVR sequences from a VH domain comprising the amino acid sequence of SEQ ID NO:244 and/or one, two, or three light chain HVR sequences from a VL domain comprising the amino acid sequence of SEQ ID NO:245. In some embodiments, an antibody of the present disclosure comprises a VH domain comprising the amino acid sequence of SEQ ID NO:244 and/or a VL domain comprising the amino acid sequence of SEQ ID NO:245. In some embodiments, an antibody of the present disclosure comprises one, two, or three heavy chain HVR sequences from a VH domain comprising the amino acid sequence of SEQ ID NO:275 and/or one, two, or three light chain HVR sequences from a VL domain comprising the amino acid sequence of SEQ ID NO:276. In some embodiments, an antibody of the present disclosure comprises a VH domain comprising the amino acid sequence of SEQ ID NO:275 and/or a VL domain comprising the amino acid sequence of SEQ ID NO:276. In some embodiments, an antibody of the present disclosure comprises one, two, or three heavy chain HVR sequences from a VH domain comprising the amino acid sequence of SEQ ID NO:278 and/or one, two, or three light chain HVR sequences from a VL domain comprising the amino acid sequence of SEQ ID NO:279. In some embodiments, an antibody of the present disclosure comprises a VH domain comprising the amino acid sequence of SEQ ID NO:278 and/or a VL domain comprising the amino acid sequence of SEQ ID NO:279. In some embodiments, an antibody of the present disclosure comprises one, two, or three heavy chain HVR sequences from a VH domain comprising the amino acid sequence of SEQ ID NO:280 and/or one, two, or three light chain HVR sequences from a VL domain comprising the amino acid sequence of SEQ ID NO:281. In some embodiments, an antibody of the present disclosure comprises a VH domain comprising the amino acid sequence of SEQ ID NO:280 and/or a VL domain comprising the amino acid sequence of SEQ ID NO:281. In some embodiments, an antibody of the present disclosure comprises one, two, or three heavy chain HVR sequences from a VH domain comprising the amino acid sequence of SEQ ID NO:282 and/or one, two, or three light chain HVR sequences from a VL domain comprising the amino acid sequence of SEQ ID NO:283. In some embodiments, an antibody of the present disclosure comprises a VH domain comprising the amino acid sequence of SEQ ID NO:282 and/or a VL domain comprising the amino acid sequence of SEQ ID NO:283. In some embodiments, an antibody of the present disclosure comprises one, two, or three heavy chain HVR sequences from a VH domain comprising the amino acid sequence of SEQ ID NO:284 and/or one, two, or three light chain HVR sequences from a VL domain comprising the amino acid sequence of SEQ ID NO:285. In some embodiments, an antibody of the present disclosure comprises a VH domain comprising the amino acid sequence of SEQ ID NO:284 and/or a VL domain comprising the amino acid sequence of SEQ ID NO:285. In some embodiments, an antibody of the present disclosure comprises one, two, or three heavy chain HVR sequences from a VH domain comprising the amino acid sequence of SEQ ID NO:286 and/or one, two, or three light chain HVR sequences from a VL domain comprising the amino acid sequence of SEQ ID NO:287. In some embodiments, an antibody of the present disclosure comprises a VH domain comprising the amino acid sequence of SEQ ID NO:286 and/or a VL domain comprising the amino acid sequence of SEQ ID NO:287. In some embodiments, an antibody of the present disclosure comprises one, two, or three heavy chain HVR sequences from a VH domain comprising the amino acid sequence of SEQ ID NO:288 and/or one, two, or three light chain HVR sequences from a VL domain comprising the amino acid sequence of SEQ ID NO:289. In some embodiments, an antibody of the present disclosure comprises a VH domain comprising the amino acid sequence of SEQ ID NO:288 and/or a VL domain comprising the amino acid sequence of SEQ ID NO:289. In some embodiments, an antibody of the present disclosure comprises one, two, or three heavy chain HVR sequences from a VH domain comprising the amino acid sequence of SEQ ID NO:290 and/or one, two, or three light chain HVR sequences from a VL domain comprising the amino acid sequence of SEQ ID NO:291. In some embodiments, an antibody of the present disclosure comprises a VH domain comprising the amino acid sequence of SEQ ID NO:290 and/or a VL domain comprising the amino acid sequence of SEQ ID NO:291. In some embodiments, an antibody of the present disclosure comprises one, two, or three heavy chain HVR sequences from a VH domain comprising the amino acid sequence of SEQ ID NO:292 and/or one, two, or three light chain HVR sequences from a VL domain comprising the amino acid sequence of SEQ ID NO:293. In some embodiments, an antibody of the present disclosure comprises a VH domain comprising the amino acid sequence of SEQ ID NO:292 and/or a VL domain comprising the amino acid sequence of SEQ ID NO:293.

In some embodiments, an antibody of the present disclosure comprises one, two, or three heavy chain HVR sequences from a VH domain comprising the amino acid sequence of SEQ ID NO:278 and/or one, two, or three light chain HVR sequences from a VL domain comprising the amino acid sequence of SEQ ID NO:279. In some embodiments, an antibody of the present disclosure comprises a VH domain comprising the amino acid sequence of SEQ ID NO:278 and/or a VL domain comprising the amino acid sequence of SEQ ID NO:279. In some embodiments, an antibody of the present disclosure comprises one, two, or three heavy chain HVR sequences from a VH domain comprising the amino acid sequence of SEQ ID NO:280 and/or one, two, or three light chain HVR sequences from a VL domain comprising the amino acid sequence of SEQ ID NO:281. In some embodiments, an antibody of the present disclosure comprises a VH domain comprising the amino acid sequence of SEQ ID NO:280 and/or a VL domain comprising the amino acid sequence of SEQ ID NO:281. In some embodiments, an antibody of the present disclosure comprises one, two, or three heavy chain HVR sequences from a VH domain comprising the amino acid sequence of SEQ ID NO:275 and/or one, two, or three light chain HVR sequences from a VL domain comprising the amino acid sequence of SEQ ID NO:276. In some embodiments, an antibody of the present disclosure comprises a VH domain comprising the amino acid sequence of SEQ ID NO:275 and/or a VL domain comprising the amino acid sequence of SEQ ID NO:276. In some embodiments, an antibody of the present disclosure comprises one, two, or three heavy chain HVR sequences from a VH domain comprising the amino acid sequence of SEQ ID NO:414 and/or one, two, or three light chain HVR sequences from a VL domain comprising the amino acid sequence of SEQ ID NO:415. In some embodiments, an antibody of the present disclosure comprises a VH domain comprising the amino acid sequence of SEQ ID NO:414 and/or a VL domain comprising the amino acid sequence of SEQ ID NO:415. In some embodiments, an antibody of the present disclosure comprises one, two, or three heavy chain HVR sequences from a VH domain comprising the amino acid sequence of SEQ ID NO:123 and/or one, two, or three light chain HVR sequences from a VL domain comprising the amino acid sequence of SEQ ID NO:100. In some embodiments, an antibody of the present disclosure comprises a VH domain comprising the amino acid sequence of SEQ ID NO:123 and/or a VL domain comprising the amino acid sequence of SEQ ID NO:100. In some embodiments, an antibody of the present disclosure comprises one, two, or three heavy chain HVR sequences from a VH domain comprising the amino acid sequence of SEQ ID NO:292 and/or one, two, or three light chain HVR sequences from a VL domain comprising the amino acid sequence of SEQ ID NO:293. In some embodiments, an antibody of the present disclosure comprises a VH domain comprising the amino acid sequence of SEQ ID NO:292 and/or a VL domain comprising the amino acid sequence of SEQ ID NO:293. In some embodiments, an antibody of the present disclosure comprises one, two, or three heavy chain HVR sequences from a VH domain comprising the amino acid sequence of SEQ ID NO:288 and/or one, two, or three light chain HVR sequences from a VL domain comprising the amino acid sequence of SEQ ID NO:289. In some embodiments, an antibody of the present disclosure comprises a VH domain comprising the amino acid sequence of SEQ ID NO:288 and/or a VL domain comprising the amino acid sequence of SEQ ID NO:289. In some embodiments, an antibody of the present disclosure comprises one, two, or three heavy chain HVR sequences from a VH domain comprising the amino acid sequence of SEQ ID NO:290 and/or one, two, or three light chain HVR sequences from a VL domain comprising the amino acid sequence of SEQ ID NO:291. In some embodiments, an antibody of the present disclosure comprises a VH domain comprising the amino acid sequence of SEQ ID NO:290 and/or a VL domain comprising the amino acid sequence of SEQ ID NO:291. In some embodiments, an antibody of the present disclosure comprises one, two, or three heavy chain HVR sequences from a VH domain comprising the amino acid sequence of SEQ ID NO:286 and/or one, two, or three light chain HVR sequences from a VL domain comprising the amino acid sequence of SEQ ID NO:287. In some embodiments, an antibody of the present disclosure comprises a VH domain comprising the amino acid sequence of SEQ ID NO:286 and/or a VL domain comprising the amino acid sequence of SEQ ID NO:287. In some embodiments, an antibody of the present disclosure comprises one, two, or three heavy chain HVR sequences from a VH domain comprising the amino acid sequence of SEQ ID NO:284 and/or one, two, or three light chain HVR sequences from a VL domain comprising the amino acid sequence of SEQ ID NOs:285, 333, or 334. In some embodiments, an antibody of the present disclosure comprises a VH domain comprising the amino acid sequence of SEQ ID NO:284 and/or a VL domain comprising the amino acid sequence of SEQ ID NOs: 285, 333, or 334.

In some embodiments, an antibody of the present disclosure comprises (a) a heavy chain variable (VH) domain comprising (i) an HVR-H1 sequence comprising the amino acid sequence of NFAMT (SEQ ID NO:175), NFAVT (SEQ ID NO:204), or NFALT (SEQ ID NO:305), (ii) an HVR-H2 sequence comprising the amino acid sequence of TIGSGDTYYADSVKG (SEQ ID NO:144), and (iii) an HVR-H3 sequence comprising the amino acid sequence of DSTVSWSGDFFDY (SEQ ID NO:145); and/or (b) a light chain variable (VL) domain comprising (i) an HVR-L1 sequence comprising the amino acid sequence of RASQNVKNDLA (SEQ ID NO:146), (ii) an HVR-L2 sequence comprising the amino acid sequence of AARIRET (SEQ ID NO:147), and (iii) an HVR-L3 sequence comprising the amino acid sequence of QQYYDWPPFT (SEQ ID NO:148). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:120, 246, 258, or 327; and/or the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:97 or 312. In some embodiments, the VH domain comprises the amino acid sequence of SEQ ID NO:246, and the VL domain comprises the amino acid sequence of SEQ ID NO:97; the VH domain comprises the amino acid sequence of SEQ ID NO:258, and the VL domain comprises the amino acid sequence of SEQ ID NO:97; the VH domain comprises the amino acid sequence of SEQ ID NO:120, and the VL domain comprises the amino acid sequence of SEQ ID NO:97; the VH domain comprises the amino acid sequence of SEQ ID NO:327, and the VL domain comprises the amino acid sequence of SEQ ID NO:97; the VH domain comprises the amino acid sequence of SEQ ID NO:246, and the VL domain comprises the amino acid sequence of SEQ ID NO:312; the VH domain comprises the amino acid sequence of SEQ ID NO:258, and the VL domain comprises the amino acid sequence of SEQ ID NO:312; the VH domain comprises the amino acid sequence of SEQ ID NO:120, and the VL domain comprises the amino acid sequence of SEQ ID NO:312; or the VH domain comprises the amino acid sequence of SEQ ID NO:327, and the VL domain comprises the amino acid sequence of SEQ ID NO:312.

In some embodiments, an antibody of the present disclosure comprises (a) a heavy chain variable (VH) domain comprising (i) an HVR-H1 sequence comprising the amino acid sequence of IYAMS (SEQ ID NO:269), IYAVS (SEQ ID NO:213), or IYALS (SEQ ID NO:306), (ii) an HVR-H2 sequence comprising the amino acid sequence of TIGADDTYYADSVKG (SEQ ID NO:150), and (iii) an HVR-H3 sequence comprising the amino acid sequence of DSTVGWSGDFFDY (SEQ ID NO:151); and/or (b) a light chain variable (VL) domain comprising (i) an HVR-L1 sequence comprising the amino acid sequence of RASQNVRSDIA (SEQ ID NO:152), (ii) an HVR-L2 sequence comprising the amino acid sequence of AASSRDT (SEQ ID NO:153), and (iii) an HVR-L3 sequence comprising the amino acid sequence of QQYYDWPPFT (SEQ ID NO:148). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:341, 127, 247, 259, or 328; and/or the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:104 or 248. In some embodiments, the VH domain comprises the amino acid sequence of SEQ ID NO:127, and the VL domain comprises the amino acid sequence of SEQ ID NO:104; the VH domain comprises the amino acid sequence of SEQ ID NO:341, and the VL domain comprises the amino acid sequence of SEQ ID NO:104; the VH domain comprises the amino acid sequence of SEQ ID NO:247, and the VL domain comprises the amino acid sequence of SEQ ID NO:104; the VH domain comprises the amino acid sequence of SEQ ID NO:259, and the VL domain comprises the amino acid sequence of SEQ ID NO:104; the VH domain comprises the amino acid sequence of SEQ ID NO:328, and the VL domain comprises the amino acid sequence of SEQ ID NO:104; the VH domain comprises the amino acid sequence of SEQ ID NO:127, and the VL domain comprises the amino acid sequence of SEQ ID NO:248; the VH domain comprises the amino acid sequence of SEQ ID NO:341, and the VL domain comprises the amino acid sequence of SEQ ID NO:248; the VH domain comprises the amino acid sequence of SEQ ID NO:247, and the VL domain comprises the amino acid sequence of SEQ ID NO:248; the VH domain comprises the amino acid sequence of SEQ ID NO:259, and the VL domain comprises the amino acid sequence of SEQ ID NO:248; or the VH domain comprises the amino acid sequence of SEQ ID NO:328, and the VL domain comprises the amino acid sequence of SEQ ID NO:248.

In some embodiments, an antibody of the present disclosure comprises (a) a heavy chain variable (VH) domain comprising: (i) an HVR-H1 sequence comprising the amino acid sequence of $X_1X_2DX_3N$, wherein $X_1$ is S or T; $X_2$ is Y or S; and $X_3$ is M, L, or V (SEQ ID NO:307); (ii) an HVR-H2 sequence comprising the amino acid sequence of LISGSGEIX$_1$YYADSVKG, wherein $X_1$ is I or T (SEQ ID NO:308); and (iii) an HVR-H3 sequence comprising the amino acid sequence of $EX_1X_2X_3YRFFDX_4$, wherein $X_1$ is N or D; $X_2$ is N or D; $X_3$ is R or M; and $X_4$ is D or Y (SEQ ID NO:309); and/or (b) a light chain variable (VL) domain comprising: (i) an HVR-L1 sequence comprising the amino acid sequence of RAX$_1$QSVYX$_2$YLA, wherein $X_1$ is S or D; and $X_2$ is T or S (SEQ ID NO:310); (ii) an HVR-L2 sequence comprising the amino acid sequence of $X_1AX_2X_3RAX_4$, wherein $X_1$ is G, A, or D; $X_2$ is S or R; $X_3$ is S, N, or T; and $X_4$ is T or A (SEQ ID NO:311); and (iii) an HVR-L3 sequence comprising the amino acid sequence of QQYYDRPPLT (SEQ ID NO:160). In some embodiments, an antibody of the present disclosure comprises (a) a heavy chain variable (VH) domain comprising (i) an HVR-H1 sequence comprising the amino acid sequence of SYDMN (SEQ ID NO:270), SYDVN (SEQ ID NO:221), or SYDLN (SEQ ID NO:313), (ii) an HVR-H2 sequence comprising the amino acid sequence of LISGSGEIIYY-ADSVKG (SEQ ID NO:156), and (iii) an HVR-H3 sequence comprising the amino acid sequence of ENN-RYRFFDD (SEQ ID NO:157); and/or (b) a light chain variable (VL) domain comprising (i) an HVR-L1 sequence comprising the amino acid sequence of RASQSVYTYLA (SEQ ID NO:158), (ii) an HVR-L2 sequence comprising the amino acid sequence of GASSRAT (SEQ ID NO:159), and (iii) an HVR-L3 sequence comprising the amino acid sequence of QQYYDRPPLT (SEQ ID NO:160). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:133, 260, 329, or 249; and/or the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:134, 250, 251, 417, 418, or 419. In some embodiments, the VH domain comprises the amino acid sequence of SEQ ID NO:133, and the VL domain comprises the amino acid sequence of SEQ ID NO:134; the VH domain comprises the amino acid sequence of SEQ ID NO:260, and the VL domain comprises the amino acid sequence of SEQ ID NO:134; the VH domain comprises the amino acid sequence of SEQ ID NO:329, and the VL domain comprises the amino acid sequence of SEQ ID NO:134; the VH domain comprises the amino acid sequence of SEQ ID NO:249, and the VL domain comprises the amino acid sequence of SEQ ID NO:134; the VH domain comprises the amino acid sequence of SEQ ID NO:133, and the VL domain comprises the amino acid sequence of SEQ ID NO:417; the VH domain comprises the amino acid sequence of SEQ ID NO:260, and the VL domain comprises the amino acid sequence of SEQ ID NO:417; the VH domain comprises the amino acid sequence of SEQ ID NO:329, and the VL domain comprises the amino acid sequence of SEQ ID NO:417; the VH domain comprises the amino acid sequence of SEQ ID NO:249, and the VL domain comprises the amino acid sequence of SEQ ID NO:417; the VH domain comprises the amino acid sequence of SEQ ID NO:133, and the VL domain comprises the amino acid sequence of SEQ ID NO:418; the VH domain comprises the amino acid sequence of SEQ ID NO:260, and the VL domain comprises the amino acid sequence of SEQ ID NO:418; the VH domain comprises the amino acid sequence of SEQ ID NO:329, and the VL domain comprises the amino acid sequence of SEQ ID NO:418; the VH domain comprises the amino acid sequence of SEQ ID NO:249, and the VL domain comprises the amino acid sequence of SEQ ID NO:418; the VH domain comprises the amino acid sequence of SEQ ID NO:133, and the VL domain comprises the amino acid sequence of SEQ ID NO:419; the VH domain comprises the amino acid sequence of SEQ ID NO:260, and the VL domain comprises the amino acid sequence of SEQ ID NO:419; the VH domain comprises the amino acid sequence of SEQ ID NO:329, and the VL domain comprises the amino acid sequence of SEQ ID NO:419; the VH domain comprises the amino acid sequence of SEQ ID NO:249, and the VL domain comprises the amino acid sequence of SEQ ID NO:419; the VH domain comprises the amino acid sequence of SEQ ID NO:133, and the VL domain comprises the amino acid sequence of SEQ ID NO:250; the VH domain comprises the amino acid sequence of SEQ ID NO:260, and the VL domain comprises the amino acid sequence of SEQ ID NO:250; the VH domain comprises the amino acid sequence of SEQ ID NO:329, and the VL domain comprises the amino acid sequence of SEQ ID NO:250; the VH domain comprises the amino acid sequence of SEQ ID NO:133, and the VL domain comprises the amino acid sequence of SEQ ID NO:251; the VH domain comprises the amino acid sequence of SEQ ID NO:260, and the VL domain comprises the amino acid sequence of SEQ ID NO:251; the VH domain comprises the amino acid sequence of SEQ ID NO:329, and the VL domain comprises the amino acid sequence of SEQ ID NO:251; the VH domain comprises the amino acid sequence of SEQ ID NO:249, and the VL domain comprises the amino acid sequence of SEQ ID NO:134; the VH domain comprises the amino acid sequence of SEQ ID NO:249, and the VL domain comprises the amino acid sequence of SEQ ID NO:250; or the VH domain comprises the amino acid sequence of SEQ ID NO:249, and the VL domain comprises the amino acid sequence of SEQ ID NO:251.

In some embodiments, an antibody of the present disclosure comprises (a) a heavy chain variable (VH) domain comprising: (i) an HVR-H1 sequence comprising the amino acid sequence of $X_1X_2AX_3S$, wherein $X_1$ is S or T; $X_2$ is N, Y, H, or D; and $X_3$ is M, L, or V (SEQ ID NO:297); (ii) an HVR-H2 sequence comprising the amino acid sequence of $GISX_1X_2X_3X_4X_5X_6YYX_7X_8SX_9KG$, wherein $X_1$ is A or S; $X_2$ is G, S, or absent; $X_3$ is S, D or G; $X_4$ is G or S; $X_5$ is D, S, or G; $X_6$ is T or A; $X_7$ is P, G, V, I, A, or S; $X_8$ is A, D, or G; and $X_9$ is V or M (SEQ ID NO:298); and (iii) an HVR-H3 sequence comprising the amino acid sequence of ETWNHLFDY (SEQ ID NO:193); and/or (b) a light chain variable (VL) domain comprising: (i) an HVR-L1 sequence comprising the amino acid sequence of $SGGX_1X_2X_3SX_4YYX_5$, wherein $X_1$ is D, G, S, I, or absent; $X_2$ is S, W, G, Y, D, or absent; $X_3$ is S, Y, T, or D; $X_4$ is H, T, S, or Y; and $X_5$ is G or A (SEQ ID NO:299); (ii) an HVR-L2 sequence comprising the amino acid sequence of $SDX_1X_2RPX_3$, wherein $X_1$ is D or N; $X_2$ is E, K, or Q; and $X_3$ is S or P (SEQ ID NO:300); and (iii) an HVR-L3 sequence comprising the amino acid sequence of $X_1X_2YDX_3X_4X_5YX_6NX_7$, wherein $X_1$ is G or A; $X_2$ is G or A; $X_3$ is G, Y, Q, S, or A; $X_4$ is S, R, or T; $X_5$ is T or S; $X_6$ is A, I, V, L, or T; and $X_7$ is T, A, D, or P (SEQ ID NO:301). In some embodiments, an antibody of the present disclosure comprises (a) a heavy chain variable (VH) domain comprising: (i) an HVR-H1 sequence comprising the amino acid sequence of $SX_1AX_2S$, wherein $X_1$ is N or Y; and wherein $X_2$ is M, L, or V (SEQ ID NO:302); (ii) an HVR-H2 sequence comprising the amino acid sequence of $GISX_1GX_2X_3DTYYX_4X_5SVKG$, wherein $X_1$ is A or S; $X_2$ is G or absent; $X_3$ is S or G; $X_4$ is P, G, or V; and $X_5$ is A or D (SEQ ID NO:303); and (iii) an HVR-H3 sequence comprising the amino acid sequence of ETWNHLFDY (SEQ ID NO:193); and/or (b) a light chain variable (VL) domain comprising: (i) an HVR-L1 sequence comprising the amino acid sequence of $SGGX_1YSSYYYA$, wherein $X_1$ is S or A (SEQ ID NO:304); (ii) an HVR-L2 sequence comprising the amino acid sequence of SDDKRPS (SEQ ID NO:336); and (iii) an HVR-L3 sequence comprising the amino acid sequence of GGYDQSSYTNP (SEQ ID NO:172). In some embodiments, the VH domain comprises (i) an HVR-H1 sequence comprising the amino acid sequence of SNAMS (SEQ ID NO:194), SNAVS (SEQ ID NO:271), or SNALS (SEQ ID NO:318), (ii) an HVR-H2 sequence comprising the amino acid sequence of GIS-AGGSDTYYPASVKG (SEQ ID NO:195), and (iii) an HVR-H3 sequence comprising the amino acid sequence of ETWNHLFDY (SEQ ID NO:193). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO: 135, 263, 264, or 330. In some embodiments, the VH domain comprises (i) an HVR-H1 sequence comprising the amino acid sequence of SNAMS (SEQ ID NO:194), SNAVS (SEQ ID NO:271), or SNALS (SEQ ID NO:318), (ii) an HVR-H2 sequence comprising the amino acid sequence of GISSGSDTYYGDSVKG (SEQ ID NO:197), and (iii) an HVR-H3 sequence comprising the amino acid sequence of ETWNHLFDY (SEQ ID NO:193). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO: 137, 265, 266, or 331. In some embodiments, the VH domain comprises (i) an HVR-H1 sequence comprising the amino acid sequence of SYAMS (SEQ ID NO:200), SYAVS (SEQ ID NO:272), or SYALS (SEQ ID NO:319), (ii) an HVR-H2 sequence comprising the amino acid sequence of GISSGGDTYYVDSVKG (SEQ ID NO:201), and (iii) an HVR-H3 sequence comprising the amino acid sequence of ETWNHLFDY (SEQ ID NO:193). In some embodiments, the VH domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO: 139, 267, 268, or 332. In some embodiments, the VL domain comprises one or more human IGLV3 framework sequences. In some embodiments, the VL domain comprises four human IGLV3 framework sequences. In some embodiments, the VL domain comprises the sequence FW1-HVR-L1-FW2-HVR-L2-FW3-HVR-L3-FW4 (N-terminus to C-terminus), wherein FW1 comprises the amino acid sequence SYELTQPPSVSVSPGQTARITC (SEQ ID NO:314), FW2 comprises the amino acid sequence WYQQKPGQAPVTLIY (SEQ ID NO:315), FW3 comprises the amino acid sequence NIPERFSGSSSGTTVTLTISGVQAEDEADYYC (SEQ ID NO:316), and FW4 comprises the amino acid sequence FGGGTKLTVL (SEQ ID NO:317). In some embodiments, the VL domain comprises (i) an HVR-L1 sequence comprising the amino acid sequence of SGGSYSSYYYA (SEQ ID NO:170), (ii) an HVR-L2 sequence comprising the amino acid sequence of SDDKRPS (SEQ ID NO:336), and (iii) an HVR-L3 sequence comprising the amino acid sequence of GGYDQSSYTNP (SEQ ID NO:172). In some embodiments, the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:252. In some embodiments, the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:254. In some embodiments, the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:416. In some embodiments, the VL domain comprises (i) an HVR-L1 sequence comprising the amino acid sequence of SGGAYSSYYYA (SEQ ID NO:261), (ii) an HVR-L2 sequence comprising the amino acid sequence of SDDKRPS (SEQ ID NO:336), and (iii) an HVR-L3 sequence comprising the amino acid sequence of GGYDQSSYTNP (SEQ ID NO:172). In some embodiments, the VL domain comprises an amino acid sequence that is at least 90%, at least 91%, at least 92%, at least 93%, at least 94%, at least 95%, at least 96%, at least 97%, at least 98%, at least 99%, or 100% identical to the amino acid sequence of SEQ ID NO:262. In some embodiments, the VH domain comprises the amino acid sequence of SEQ ID NO:263, and the VL domain comprises the amino acid sequence of SEQ ID NO:252; the VH domain comprises the amino acid sequence of SEQ ID NO:264, and the VL domain comprises the amino acid sequence of SEQ ID NO:252; the VH domain comprises the amino acid sequence of SEQ ID NO:330, and the VL domain comprises the amino acid sequence of SEQ ID NO:252; the VH domain comprises the amino acid sequence of SEQ ID NO:135, and the VL domain comprises the amino acid sequence of SEQ ID NO:252; the VH domain comprises the amino acid sequence of SEQ ID NO:137, and the VL domain comprises the amino acid sequence of SEQ ID NO:252; the VH domain comprises the amino acid sequence of SEQ ID NO:139, and the VL domain comprises the amino acid sequence of SEQ ID NO:252; the VH domain comprises the amino acid sequence of SEQ ID NO:265, and the VL domain comprises the amino acid sequence of SEQ ID NO:252; the VH domain comprises the amino acid sequence of SEQ ID NO:266, and the VL domain comprises the amino acid sequence of SEQ ID NO:252; the VH domain comprises the amino acid sequence of SEQ ID NO:331, and the VL domain comprises the amino acid sequence of SEQ ID NO:252; the VH domain comprises the amino acid sequence of SEQ ID NO:267, and the VL domain comprises the amino acid sequence of SEQ ID NO:252; the VH domain comprises the amino acid sequence of SEQ ID NO:268, and the VL domain comprises the amino acid sequence of SEQ ID NO:252; the VH domain comprises the amino acid sequence of SEQ ID NO:332, and the VL domain comprises the amino acid sequence of SEQ ID NO:252; the VH domain comprises the amino acid sequence of SEQ ID NO:263, and the VL domain comprises the amino acid sequence of SEQ ID NO:262; the VH domain comprises the amino acid sequence of SEQ ID NO:264, and the VL domain comprises the amino acid sequence of SEQ ID NO:262; the VH domain comprises the amino acid sequence of SEQ ID NO:330, and the VL domain comprises the amino acid sequence of SEQ ID NO:262; the VH domain comprises the amino acid sequence of SEQ ID NO:265, and the VL domain comprises the amino acid sequence of SEQ ID NO:262; the VH domain comprises the amino acid sequence of SEQ ID NO:266, and the VL domain comprises the amino acid sequence of SEQ ID NO:262; the VH domain comprises the amino acid sequence of SEQ ID NO:331, and the VL domain comprises the amino acid sequence of SEQ ID NO:262; the VH domain comprises the amino acid sequence of SEQ ID NO:267, and the VL domain comprises the amino acid sequence of SEQ ID NO:262; the VH domain comprises the amino acid sequence of SEQ ID NO:268, and the VL domain comprises the amino acid sequence of SEQ ID NO:262; the VH domain comprises the amino acid sequence of SEQ ID NO:332, and the VL domain comprises the amino acid sequence of SEQ ID NO:262; the VH domain comprises the amino acid sequence of SEQ ID NO:263, and the VL domain comprises the amino acid sequence of SEQ ID NO:254; the VH domain comprises the amino acid sequence of SEQ ID NO:264, and the VL domain comprises the amino acid sequence of SEQ ID NO: 254; the VH domain comprises the amino acid sequence of SEQ ID NO:330, and the VL domain comprises the amino acid sequence of SEQ ID NO: 254; the VH domain comprises the amino acid sequence of SEQ ID NO:265, and the VL domain comprises the amino acid sequence of SEQ ID NO: 254; the VH domain comprises the amino acid sequence of SEQ ID NO:266, and the VL domain comprises the amino acid sequence of SEQ ID NO: 254; the VH domain comprises the amino acid sequence of SEQ ID NO:331, and the VL domain comprises the amino acid sequence of SEQ ID NO: 254; the VH domain comprises the amino acid sequence of SEQ ID NO:267, and the VL domain comprises the amino acid sequence of SEQ ID NO: 254; the VH domain comprises the amino acid sequence of SEQ ID NO:268, and the VL domain comprises the amino acid sequence of SEQ ID NO: 254; the VH domain comprises the amino acid sequence of SEQ ID NO:332, and the VL domain comprises the amino acid sequence of SEQ ID NO: 254; the VH domain comprises the amino acid sequence of SEQ ID NO:263, and the VL domain comprises the amino acid sequence of SEQ ID NO: 416; the VH domain comprises the amino acid sequence of SEQ ID NO:264, and the VL domain comprises the amino acid sequence of SEQ ID NO: 416; the VH domain comprises the amino acid sequence of SEQ ID NO:330, and the VL domain comprises the amino acid sequence of SEQ ID NO: 416; the VH domain comprises the amino acid sequence of SEQ ID NO:265, and the VL domain comprises the amino acid sequence of SEQ ID NO: 416; the VH domain comprises the amino acid sequence of SEQ ID NO:266, and the VL domain comprises the amino acid sequence of SEQ ID NO: 416; the VH domain comprises the amino acid sequence of SEQ ID NO:331, and the VL domain comprises the amino acid sequence of SEQ ID NO: 416; the VH domain comprises the amino acid sequence of SEQ ID NO:267, and the VL domain comprises the amino acid sequence of SEQ ID NO: 416; the VH domain comprises the amino acid sequence of SEQ ID NO:268, and the VL domain comprises the amino acid sequence of SEQ ID NO: 416; the VH domain comprises the amino acid sequence of SEQ ID NO:332, and the VL domain comprises the amino acid sequence of SEQ ID NO: 416; the VH domain comprises the amino acid sequence of SEQ ID NO:135, and the VL domain comprises the amino acid sequence of SEQ ID NO:262; the VH domain comprises the amino acid sequence of SEQ ID NO:137, and the VL domain comprises the amino acid sequence of SEQ ID NO:262; the VH domain comprises the amino acid sequence of SEQ ID NO:135, and the VL domain comprises the amino acid sequence of SEQ ID NO:254; the VH domain comprises the amino acid sequence of SEQ ID NO:135, and the VL domain comprises the amino acid sequence of SEQ ID NO:416; the VH domain comprises the amino acid sequence of SEQ ID NO:137, and the VL domain comprises the amino acid sequence of SEQ ID NO:254; the VH domain comprises the amino acid sequence of SEQ ID NO:137, and the VL domain comprises the amino acid sequence of SEQ ID NO:416; the VH domain comprises the amino acid sequence of SEQ ID NO:139, and the VL domain comprises the amino acid sequence of SEQ ID NO:254; the VH domain comprises the amino acid sequence of SEQ ID NO:139, and the VL domain comprises the amino acid sequence of SEQ ID NO:416; or the VH domain comprises the amino acid sequence of SEQ ID NO:139, and the VL domain comprises the amino acid sequence of SEQ ID NO:262.

In some embodiments, an antibody of the present disclosure comprises a VH domain comprising the amino acid sequence of SEQ ID NO:120 and/or a VL domain comprising the amino acid sequence of SEQ ID NO:97. In some embodiments, an antibody of the present disclosure comprises a VH domain comprising the amino acid sequence of SEQ ID NO:127 and/or a VL domain comprising the amino acid sequence of SEQ ID NO:104. In some embodiments, an antibody of the present disclosure comprises a VH domain comprising the amino acid sequence of SEQ ID NO:133 and/or a VL domain comprising the amino acid sequence of SEQ ID NO:134. In some embodiments, an antibody of the present disclosure comprises a VH domain comprising the amino acid sequence of SEQ ID NO:135 and/or a VL domain comprising the amino acid sequence of SEQ ID NO:136. In some embodiments, an antibody of the present disclosure comprises a VH domain comprising the amino acid sequence of SEQ ID NO:137 and/or a VL domain comprising the amino acid sequence of SEQ ID NO:138. In some embodiments, an antibody of the present disclosure comprises a VH domain comprising the amino acid sequence of SEQ ID NO:139 and/or a VL domain comprising the amino acid sequence of SEQ ID NO:140. In some embodiments, an antibody of the present disclosure comprises a VH domain comprising the amino acid sequence of SEQ ID NO:141 and/or a VL domain comprising the amino acid sequence of SEQ ID NO:142.

In some embodiments, the antibody comprises (a) an HVR-H1 sequence comprising the amino acid sequence of GFSFSX$_1$X$_2$AMX$_3$, wherein X$_1$ is N or I; X$_2$ is F or Y; and X$_3$ is T or S (SEQ ID NO:185); (b) an HVR-H2 sequence comprising the amino acid sequence of TIGX$_4$X$_5$DTYYADSVKG, wherein X$_4$ is S or A and X$_5$ is G or D (SEQ ID NO:186); (c) an HVR-H3 sequence comprising the amino acid sequence of DSTVX$_6$WSGDFFDY, wherein X$_6$ is S or G (SEQ ID NO:187); (d) an HVR-L1 sequence comprising the amino acid sequence of RASQNVX$_7$X$_8$DX$_9$A, wherein X$_7$ is K or R; X$_8$ is N or S; and X$_9$ is L or I (SEQ ID NO:188); (e) an HVR-L2 sequence comprising the amino acid sequence of AAX$_{10}$X$_{11}$RX$_{12}$T, wherein X$_{10}$ is R or S; X$_{11}$ is I or S; and X$_{12}$ is E or D (SEQ ID NO:189); and (f) an HVR-L3 sequence comprising the amino acid sequence of QQYYDWPPFT (SEQ ID NO:148).

In some embodiments, an antibody of the present disclosure comprises one, two, three, four, five, or six HVR sequences having an amino acid sequence selected from SEQ ID NOs:143-148 (e.g., one, two, or three heavy chain HVR sequences selected from SEQ ID NOs:143-145 and/or one, two, or three light chain HVR sequences selected from SEQ ID NOs:146-148). In some embodiments, an antibody of the present disclosure comprises one, two, three, four, five, or six HVR sequences having an amino acid sequence selected from SEQ ID NOs:148-153 (e.g., one, two, or three heavy chain HVR sequences selected from SEQ ID NOs: 149-151 and/or one, two, or three light chain HVR sequences selected from SEQ ID NOs:152, 153, and 148). In some embodiments, an antibody of the present disclosure comprises one, two, three, four, five, or six HVR sequences having an amino acid sequence selected from SEQ ID NOs:155-160 (e.g., one, two, or three heavy chain HVR sequences selected from SEQ ID NOs:155-157 and/or one, two, or three light chain HVR sequences selected from SEQ ID NOs:158-160). In some embodiments, an antibody of the present disclosure comprises one, two, three, four, five, or six HVR sequences having an amino acid sequence selected from SEQ ID NOs:161-166 (e.g., one, two, or three heavy chain HVR sequences selected from SEQ ID NOs:161-163 and/or one, two, or three light chain HVR sequences selected from SEQ ID NOs:164-166). In some embodiments, an antibody of the present disclosure comprises one, two, three, four, five, or six HVR sequences having an amino acid sequence selected from SEQ ID NOs:161-166 (e.g., one, two, or three heavy chain HVR sequences selected from SEQ ID NOs:161-163 and/or one, two, or three light chain HVR sequences of a variable domain shown in Table 2). In some embodiments, an antibody of the present disclosure comprises one, two, three, four, five, or six HVR sequences having an amino acid sequence selected from SEQ ID NOs:161, 163, 168, and 170-172 (e.g., one, two, or three heavy chain HVR sequences selected from SEQ ID NOs: 161, 168, and 163 and/or one, two, or three light chain HVR sequences selected from SEQ ID NOs:170-172). In some embodiments, an antibody of the present disclosure comprises one, two, three, four, five, or six HVR sequences having an amino acid sequence selected from SEQ ID NOs: 161, 163, 168, and 170-172 (e.g., one, two, or three heavy chain HVR sequences selected from SEQ ID NOs: 161, 168, and 163 and/or one, two, or three light chain HVR sequences of a variable domain shown in Table 2). In some embodiments, an antibody of the present disclosure comprises one, two, three, four, five, or six HVR sequences having an amino acid sequence selected from SEQ ID NOs:163, 173, 174, and 176-178 (e.g., one, two, or three heavy chain HVR sequences selected from SEQ ID NOs:163, 173, and 174 and/or one, two, or three light chain HVR sequences selected from SEQ ID NOs:176-178). In some embodiments, an antibody of the present disclosure comprises one, two, three, four, five, or six HVR sequences having an amino acid sequence selected from SEQ ID NOs: 162, 163, 179, and 182-184 (e.g., one, two, or three heavy chain HVR sequences selected from SEQ ID NOs: 162, 163, and 179 and/or one, two, or three light chain HVR sequences selected from SEQ ID NOs:182-184). In some embodiments, an antibody of the present disclosure comprises one, two, three, four, five, or six HVR sequences having an amino acid sequence selected from SEQ ID NOs: 162, 163, 179, and 182-184 (e.g., one, two, or three heavy chain HVR sequences selected from SEQ ID NOs: 162, 163, and 179 and/or one, two, or three light chain HVR sequences of a variable domain shown in Table 2). In some embodiments, an antibody of the present disclosure comprises one, two, three, four, five, or six HVR sequences from the variable domain sequences of SEQ ID NOs:120 and 97 (e.g., one, two, or three heavy chain HVR sequences from the heavy chain variable domain sequence of SEQ ID NO:120 and/or one, two, or three light chain HVR sequences from the light chain variable domain sequence of SEQ ID NO:97). In some embodiments, an antibody of the present disclosure comprises one, two, three, four, five, or six HVR sequences from the variable domain sequences of SEQ ID NOs:127 and 104 (e.g., one, two, or three heavy chain HVR sequences from the heavy chain variable domain sequence of SEQ ID NO:127 and/or one, two, or three light chain HVR sequences from the light chain variable domain sequence of SEQ ID NO:104). In some embodiments, an antibody of the present disclosure comprises one, two, three, four, five, or six HVR sequences from the variable domain sequences of SEQ ID NOs:97, 104, 120, and 127 (e.g., one, two, or three heavy chain HVR sequences from the heavy chain variable domain sequence of SEQ ID NOs:120 and 127 and/or one, two, or three light chain HVR sequences from the light chain variable domain sequence of SEQ ID NOs:97 and 104).

In some embodiments, an antibody of the present disclosure comprises (a) a VH domain comprising an HVR-H1 comprising the amino acid sequence of SEQ ID NO:143, an HVR-H2 comprising the amino acid sequence of SEQ ID NO:144, and an HVR-H3 comprising the amino acid sequence of SEQ ID NO:145; and/or (b) a VL domain comprising an HVR-L1 comprising the amino acid sequence of SEQ ID NO:146, an HVR-L2 comprising the amino acid sequence of SEQ ID NO:147, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO:149, an HVR-H2 comprising the amino acid sequence of SEQ ID NO:150, and an HVR-H3 comprising the amino acid sequence of SEQ ID NO:151; and/or (b) a VL domain comprising an HVR-L1 comprising the amino acid sequence of SEQ ID NO:152, an HVR-L2 comprising the amino acid sequence of SEQ ID NO:153, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO:143 or 149, an HVR-H2 comprising the amino acid sequence of SEQ ID NO:144 or 150, and an HVR-H3 comprising the amino acid sequence of SEQ ID NO:145 or 151; and/or (b) a VL domain comprising an HVR-L1 comprising the amino acid sequence of SEQ ID NO:146 or 152, an HVR-L2 comprising the amino acid sequence of SEQ ID NO:147 or 153, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO:155, an HVR-H2 comprising the amino acid sequence of SEQ ID NO:156, and an HVR-H3 comprising the amino acid sequence of SEQ ID NO:157; and/or (b) a VL domain comprising an HVR-L1 comprising the amino acid sequence of SEQ ID NO:158, an HVR-L2 comprising the amino acid sequence of SEQ ID NO:159, and an HVR-L3 comprising the amino acid sequence of SEQ ID NO:160. In some embodiments, an antibody of the present disclosure comprises (a) a VH domain comprising an HVR-H1 comprising the amino acid sequence of SEQ ID NO:161, an HVR-H2 comprising the amino acid sequence of SEQ ID NO:162, and an HVR-H3 comprising the amino acid sequence of SEQ ID NO:163; and/or (b) a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO:166. In some embodiments, an antibody of the present disclosure comprises (a) a VH domain comprising an HVR-H1 comprising the amino acid sequence of SEQ ID NO:161, an HVR-H2 comprising the amino acid sequence of SEQ ID NO:168, and an HVR-H3 comprising the amino acid sequence of SEQ ID NO:163; and/or (b) a VL domain comprising an HVR-L1 comprising the amino acid sequence of SEQ ID NO:170, an HVR-L2 comprising the amino acid sequence of SEQ ID NO:171, and an HVR-L3 comprising the amino acid sequence of SEQ ID NO:172. In some embodiments, an antibody of the present disclosure comprises (a) a VH domain comprising an HVR-H1 comprising the amino acid sequence of SEQ ID NO:173, an HVR-H2 comprising the amino acid sequence of SEQ ID NO:174, and an HVR-H3 comprising the amino acid sequence of SEQ ID NO:163; and/or (b) a VL domain comprising an HVR-L1 comprising the amino acid sequence of SEQ ID NO:176, an HVR-L2 comprising the amino acid sequence of SEQ ID NO:177, and an HVR-L3 comprising the amino acid sequence of SEQ ID NO:178. In some embodiments, an antibody of the present disclosure comprises (a) a VH domain comprising an HVR-H1 comprising the amino acid sequence of SEQ ID NO:179, an HVR-H2 comprising the amino acid sequence of SEQ ID NO:162, and an HVR-H3 comprising the amino acid sequence of SEQ ID NO:163; and/or (b) a VL domain comprising an HVR-L1 comprising the amino acid sequence of SEQ ID NO:182, an HVR-L2 comprising the amino acid sequence of SEQ ID NO:183, and an HVR-L3 comprising the amino acid sequence of SEQ ID NO:184.

In some embodiments, an antibody of the present disclosure comprises a VH domain comprising the amino acid sequence of SEQ ID NO:135 and/or a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO:166. In some embodiments, an antibody of the present disclosure comprises a VH domain comprising the amino acid sequence of SEQ ID NO:137 and/or a VL domain comprising an HVR-L1 comprising the amino acid sequence of SEQ ID NO:170, an HVR-L2 comprising the amino acid sequence of SEQ ID NO:171, and an HVR-L3 comprising the amino acid sequence of SEQ ID NO:172. In some embodiments, an antibody of the present disclosure comprises a VH domain comprising the amino acid sequence of SEQ ID NO:139 and/or a VL domain comprising an HVR-L1 comprising the amino acid sequence of SEQ ID NO:176, an HVR-L2 comprising the amino acid sequence of SEQ ID NO:177, and an HVR-L3 comprising the amino acid sequence of SEQ ID NO:178. In some embodiments, an antibody of the present disclosure comprises a VH domain comprising the amino acid sequence of SEQ ID NO:141 and/or a VL domain comprising an HVR-L1 comprising the amino acid sequence of SEQ ID NO:182, an HVR-L2 comprising the amino acid sequence of SEQ ID NO:183, and an HVR-L3 comprising the amino acid sequence of SEQ ID NO:184.

In some embodiments, an antibody of the present disclosure comprises (a) a VH domain comprising an HVR-H1 comprising the amino acid sequence of SEQ ID NO:161, an HVR-H2 comprising the amino acid sequence of SEQ ID NO:162, and an HVR-H3 comprising the amino acid sequence of SEQ ID NO:163; and/or (b) a VL domain comprising an HVR-L1 comprising the amino acid sequence of SEQ ID NO:164, 170, 176, or 182, an HVR-L2 comprising the amino acid sequence of SEQ ID NO:165, 171, 177, or 183, and an HVR-L3 comprising the amino acid sequence of SEQ ID NO:166, 172, 178, or 184. In some embodiments, an antibody of the present disclosure comprises (a) a VH domain comprising an HVR-H1 comprising the amino acid sequence of SEQ ID NO:161, an HVR-H2 comprising the amino acid sequence of SEQ ID NO:168, and an HVR-H3 comprising the amino acid sequence of SEQ ID NO:163; and/or (b) a VL domain comprising an HVR-L1 comprising the amino acid sequence of SEQ ID NO:164, 170, 176, or 182, an HVR-L2 comprising the amino acid sequence of SEQ ID NO:165, 171, 177, or 183, and an HVR-L3 comprising the amino acid sequence of SEQ ID NO:166, 172, 178, or 184. In some embodiments, an antibody of the present disclosure comprises (a) a VH domain comprising an HVR-H1 comprising the amino acid sequence of SEQ ID NO:173, an HVR-H2 comprising the amino acid sequence of SEQ ID NO:174, and an HVR-H3 comprising the amino acid sequence of SEQ ID NO:163; and/or (b) a VL domain comprising an HVR-L1 comprising the amino acid sequence of SEQ ID NO:164, 170, 176, or 182, an HVR-L2 comprising the amino acid sequence of SEQ ID NO:165, 171, 177, or 183, and an HVR-L3 comprising the amino acid sequence of SEQ ID NO:166, 172, 178, or 184. In some embodiments, an antibody of the present disclosure comprises (a) a VH domain comprising an HVR-H1 comprising the amino acid sequence of SEQ ID NO:179, an HVR-H2 comprising the amino acid sequence of SEQ ID NO:162, and an HVR-H3 comprising the amino acid sequence of SEQ ID NO:163; and/or (b) a VL domain comprising an HVR-L1 comprising the amino acid sequence of SEQ ID NO:164, 170, 176, or 182, an HVR-L2 comprising the amino acid sequence of SEQ ID NO:165, 171, 177, or 183, and an HVR-L3 comprising the amino acid sequence of SEQ ID NO:166, 172, 178, or 184. In some embodiments, an antibody of the present disclosure comprises a VH domain comprising the amino acid sequence of SEQ ID NO:135 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, an antibody of the present disclosure comprises a VH domain comprising the amino acid sequence of SEQ ID NO:137 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, an antibody of the present disclosure comprises a VH domain comprising the amino acid sequence of SEQ ID NO:139 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184. In some embodiments, an antibody of the present disclosure comprises a VH domain comprising the amino acid sequence of SEQ ID NO:141 and/or a VL domain comprising an HVR-L1 comprising the amino acid sequence of SEQ ID NO:164, 170, 176, or 182; an HVR-L2 comprising the amino acid sequence of SEQ ID NO:165, 171, 177, or 183; and an HVR-L3 comprising the amino acid sequence of SEQ ID NO:166, 172, 178, or 184.

In some embodiments, an antibody of the present disclosure comprises (a) a VH domain comprising one, two, or three HVR sequences from SEQ ID NO:242; and/or (b) a VL domain comprising one, two, or three HVR sequences from SEQ ID NO:243. In some embodiments, an antibody of the present disclosure comprises (a) a VH domain comprising one, two, or three HVR sequences from SEQ ID NO:244; and/or (b) a VL domain comprising one, two, or three HVR sequences from SEQ ID NO:245.

As described supra, various techniques for delineating hypervariable regions (HVRs) or complementarity determining regions (CDRs) are known in the art and can be applied to the variable domain sequences described herein. In some embodiments, an antibody of the present disclosure comprises HVRs as defined by Chothia, Kabat, IMGT, or a combination thereof (e.g., one or more HVRs as defined by one delineation and one or more HVRs as defined by a different delineation). HVR sequences of antibodies of the present disclosure delineated using three known delineation (Chothia, Kabat, and IMGT) are provided in Table 5. As used herein, unless otherwise specified, the numbering of HVR residues is defined by Kabat numbering.

TABLE 5

HVR delineations.

| | | | |
|---|---|---|---|
| Hum 1 (Chothia) | HVR-L1 | 170 | SGGSYSSYYYA |
| | HVR-L2 | 336 | SDDKRPS |
| | HVR-L3 | 172 | GGYDQSSYTNP |
| Hum 1 (Kabat) | HVR-L1 | 170 | SGGSYSSYYYA |
| | HVR-L2 | 336 | SDDKRPS |
| | HVR-L3 | 172 | GGYDQSSYTNP |
| Hum 1 (IMGT) | HVR-L1 | 337 | GSYSS |
| | HVR-L2 | 338 | IYS |
| | HVR-L3 | 339 | GGYDQSSYT |
| Hum 7 (Chothia) | HVR-L1 | 164 | SGGDYYSYYYG |
| | HVR-L2 | 336 | SDDKRPS |
| | HVR-L3 | 166 | GGYDYSTYANA |

TABLE 5-continued

HVR delineations.

| | | | |
|---|---|---|---|
| Hum 7 (Kabat) | HVR-L1 | 164 | SGGDYYSYYYG |
| | HVR-L2 | 336 | SDDKRPS |
| | HVR-L3 | 166 | GGYDYSTYANA |
| Hum 7 (IMGT) | HVR-L1 | 340 | GDYYS |
| | HVR-L2 | 338 | IYS |
| | HVR-L3 | 190 | GGYDYSTYA |
| AB21 (Chothia) | HVR-H1 | 191 | GFTFSSN |
| | HVR-H2 | 192 | SAGGSD |
| | HVR-H3 | 193 | ETWNHLFDY |
| AB21 (Kabat) | HVR-H1 | 194 | SNAMS |
| | HVR-H2 | 195 | GISAGGSDTYYPASVKG |
| | HVR-H3 | 193 | ETWNHLFDY |
| AB21 (IMGT) | HVR-H1 | 161 | GFTFSSNA |
| | HVR-H2 | 162 | ISAGGSDT |
| | HVR-H3 | 163 | ARETWNHLFDY |
| AB25 (Chothia) | HVR-H1 | 191 | GFTFSSN |
| | HVR-H2 | 196 | SSGSD |
| | HVR-H3 | 193 | ETWNHLFDY |
| AB25 (Kabat) | HVR-H1 | 194 | SNAMS |
| | HVR-H2 | 197 | GISSGSDTYYGDSVKG |
| | HVR-H3 | 193 | ETWNHLFDY |
| AB25 (IMGT) | HVR-H1 | 161 | GFTFSSNA |
| | HVR-H2 | 168 | ISSGSDT |
| | HVR-H3 | 163 | ARETWNHLFDY |
| AB27 (Chothia) | HVR-H1 | 198 | GFRFSSY |
| | HVR-H2 | 199 | SSGGD |
| | HVR-H3 | 193 | ETWNHLFDY |
| AB27 (Kabat) | HVR-H1 | 200 | SYAMS |
| | HVR-H2 | 201 | GISSGGDTYYVDSVKG |
| | HVR-H3 | 193 | ETWNHLFDY |
| AB27 (IMGT) | HVR-H1 | 173 | GFRFSSYA |
| | HVR-H2 | 174 | ISSGGDT |
| | HVR-H3 | 163 | ARETWNHLFDY |
| AB119 (Chothia) | HVR-H1 | 202 | GFSFSNF |
| | HVR-H2 | 203 | GSGD |
| | HVR-H3 | 145 | DSTVSWSGDFFDY |
| AB119 (Kabat) | HVR-H1 | 204 | NFAVT |
| | HVR-H2 | 144 | TIGSGDTYYADSVKG |
| | HVR-H3 | 145 | DSTVSWSGDFFDY |
| AB119 (IMGT) | HVR-H1 | 205 | GFSFSNFA |
| | HVR-H2 | 206 | IGSGDT |
| | HVR-H3 | 207 | AKDSTVSWSGDFFDY |
| AB119 (Chothia) | HVR-L1 | 146 | RASQNVKNDLA |
| | HVR-L2 | 147 | AARIRET |
| | HVR-L3 | 148 | QQYYDWPPFT |
| AB119 (Kabat) | HVR-L1 | 146 | RASQNVKNDLA |
| | HVR-L2 | 147 | AARIRET |
| | HVR-L3 | 148 | QQYYDWPPFT |
| AB119 (IMGT) | HVR-L1 | 208 | QNVKND |
| | HVR-L2 | 209 | AAR |
| | HVR-L3 | 210 | QQYYDWP |
| AB135 (Chothia) | HVR-H1 | 211 | GFSFSIY |
| | HVR-H2 | 212 | GADD |
| | HVR-H3 | 151 | DSTVGWSGDFFDY |
| AB135 (Kabat) | HVR-H1 | 213 | IYAVS |
| | HVR-H2 | 150 | TIGADDTYYADSVKG |
| | HVR-H3 | 151 | DSTVGWSGDFFDY |
| AB135 (IMGT) | HVR-H1 | 214 | GFSFSIYA |
| | HVR-H2 | 215 | IGADDT |
| | HVR-H3 | 216 | AKDSTVGWSGDFFDY |
| AB135 (Chothia) | HVR-L1 | 152 | RASQNVRSDIA |
| | HVR-L2 | 153 | AASSRDT |
| | HVR-L3 | 148 | QQYYDWPPFT |
| AB135 (Kabat) | HVR-L1 | 152 | RASQNVRSDIA |
| | HVR-L2 | 153 | AASSRDT |
| | HVR-L3 | 148 | QQYYDWPPFT |
| AB135 (IMGT) | HVR-L1 | 217 | QNVRSD |
| | HVR-L2 | 218 | AAS |
| | HVR-L3 | 148 | QQYYDWPPFT |
| AB136 (Chothia) | HVR-H1 | 219 | GFTFSSY |
| | HVR-H2 | 220 | SGSGEI |
| | HVR-H3 | 157 | ENNRYRFFDD |
| AB136 (Kabat) | HVR-H1 | 221 | SYDVN |
| | HVR-H2 | 156 | LISGSGEIIYYADSVKG |
| | HVR-H3 | 157 | ENNRYRFFDD |
| AB136 (IMGT) | HVR-H1 | 222 | GFTFSSYD |
| | HVR-H2 | 223 | ISGSGEII |
| | HVR-H3 | 224 | AKENNRYRFFDD |
| AB136 (Chothia) | HVR-L1 | 158 | RASQSVYTYLA |
| | HVR-L2 | 159 | GASSRAT |
| | HVR-L3 | 160 | QQYYDRPPLT |
| AB136 (Kabat) | HVR-L1 | 158 | RASQSVYTYLA |
| | HVR-L2 | 159 | GASSRAT |
| | HVR-L3 | 160 | QQYYDRPPLT |
| AB136 (IMGT) | HVR-L1 | 225 | QSVYTY |
| | HVR-L2 | 226 | GAS |
| | HVR-L3 | 160 | QQYYDRPPLT |
| AB3 (Kabat) | HVR-H1 | 227 | DYGMN |
| | HVR-H2 | 228 | QITSGSRTYYGAAVKG |
| | HVR-H3 | 229 | DFGSGVGSIDA |
| AB3 (CHOTHIA) | HVR-H1 | 230 | GFIFSDY |
| | HVR-H2 | 231 | TSGSR |
| | HVR-H3 | 229 | DFGSGVGSIDA |
| AB3 (Chothia) | HVR-L1 | 232 | SGSRGRYG |
| | HVR-L2 | 233 | RDNQRPS |
| | HVR-L3 | 234 | GSYDGSIDI |
| AB3 (Kabat) | HVR-L1 | 232 | SGSRGRYG |
| | HVR-L2 | 233 | RDNQRPS |
| | HVR-L3 | 234 | GSYDGSIDI |
| AB45 (Kabat) | HVR-H1 | 235 | SYAMG |
| | HVR-H2 | 236 | GIDDDGSTANYGPAVKG |
| | HVR-H3 | 237 | ASVTGWSAHISGRLDT |
| AB45 (CHOTHIA) | HVR-H1 | 219 | GFTFSSY |
| | HVR-H2 | 238 | DDGST |
| | HVR-H3 | 237 | ASVTGWSAHISGRLDT |
| AB45 (Chothia) | HVR-L1 | 239 | SGGGIYYYG |
| | HVR-L2 | 240 | ENDKRPS |
| | HVR-L3 | 241 | GGYDSNTTSGI |
| AB45 (Kabat) | HVR-L1 | 239 | SGGGIYYYG |
| | HVR-L2 | 240 | ENDKRPS |
| | HVR-L3 | 241 | GGYDSNTTSGI |

In some embodiments, an antibody of the present disclosure comprises 1, 2, 3, 4, 5, or 6 HVRs listed in Table 5 (e.g., a VL domain comprising 1, 2, or 3 light chain HVRs listed in Table 5 and/or a VH domain comprising 1, 2, or 3 heavy chain HVRs listed in Table 5).

In some embodiments, an antibody of the present disclosure comprises a VH domain comprising an HVR-H1 comprising the amino acid sequence of SEQ ID NO:191, an HVR-H2 comprising the amino acid sequence of SEQ ID NO: 192, and an HVR-H3 comprising the amino acid sequence of SEQ ID NO: 193. In some embodiments, an antibody of the present disclosure comprises a VH domain comprising an HVR-H1 comprising the amino acid sequence of SEQ ID NO:191, an HVR-H2 comprising the amino acid sequence of SEQ ID NO: 196, and an HVR-H3 comprising the amino acid sequence of SEQ ID NO: 193. In some embodiments, an antibody of the present disclosure comprises a VH domain comprising an HVR-H1 comprising the amino acid sequence of SEQ ID NO: 198, an HVR-H2 comprising the amino acid sequence of SEQ ID NO: 199, and an HVR-H3 comprising the amino acid sequence of SEQ ID NO: 193. In some embodiments, an antibody of the present disclosure comprises a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO: 166 and/or a VH domain comprising an HVR-H1 comprising the amino acid sequence of SEQ ID NO:191 or 198, an HVR-H2 comprising the amino acid sequence of SEQ ID NO: 192, 196, or 199, and an HVR-H3 comprising the amino acid sequence of SEQ ID NO: 193. In some embodiments, an antibody of the present disclosure comprises a VL domain comprising an HVR-L1 comprising the amino acid sequence of SEQ ID NO:232, an HVR-L2 comprising the amino acid sequence of SEQ ID NO:233, and an HVR-L3 comprising the amino acid sequence of SEQ ID NO:234 and/or a VH domain comprising an HVR-H1 comprising the amino acid sequence of SEQ ID NO:230, an HVR-H2 comprising the amino acid sequence of SEQ ID NO:231, and an HVR-H3 comprising the amino acid sequence of SEQ ID NO:232. In some embodiments, an antibody of the present disclosure comprises a VL domain comprising an HVR-L1 comprising the amino acid sequence of SEQ ID NO:239, an HVR-L2 comprising the amino acid sequence of SEQ ID NO:240, and an HVR-L3 comprising the amino acid sequence of SEQ ID NO:241 and/or a VH domain comprising an HVR-H1 comprising the amino acid sequence of SEQ ID NO:219, an HVR-H2 comprising the amino acid sequence of SEQ ID NO:238, and an HVR-H3 comprising the amino acid sequence of SEQ ID NO:237.

In some embodiments, an antibody of the present disclosure comprises a VH domain comprising an HVR-H1 comprising the amino acid sequence of SEQ ID NO: 194, an HVR-H2 comprising the amino acid sequence of SEQ ID NO: 195, and an HVR-H3 comprising the amino acid sequence of SEQ ID NO: 193. In some embodiments, an antibody of the present disclosure comprises a VH domain comprising an HVR-H1 comprising the amino acid sequence of SEQ ID NO: 194, an HVR-H2 comprising the amino acid sequence of SEQ ID NO: 197, and an HVR-H3 comprising the amino acid sequence of SEQ ID NO: 193. In some embodiments, an antibody of the present disclosure comprises a VH domain comprising an HVR-H1 comprising the amino acid sequence of SEQ ID NO: 200, an HVR-H2 comprising the amino acid sequence of SEQ ID NO: 201, and an HVR-H3 comprising the amino acid sequence of SEQ ID NO: 193. In some embodiments, an antibody of the present disclosure comprises a VL domain comprising an HVR-L1 comprising the amino acid sequence of SEQ ID NO:164, an HVR-L2 comprising the amino acid sequence of SEQ ID NO:165, and an HVR-L3 comprising the amino acid sequence of SEQ ID NO: 166 and/or a VH domain comprising an HVR-H1 comprising the amino acid sequence of SEQ ID NO: 194, 198, or 200, an HVR-H2 comprising the amino acid sequence of SEQ ID NO: 195, 197, or 201, and an HVR-H3 comprising the amino acid sequence of SEQ ID NO: 193. In some embodiments, an antibody of the present disclosure comprises a VL domain comprising an HVR-L1 comprising the amino acid sequence of SEQ ID NO:232, an HVR-L2 comprising the amino acid sequence of SEQ ID NO:233, and an HVR-L3 comprising the amino acid sequence of SEQ ID NO:234 and/or a VH domain comprising an HVR-H1 comprising the amino acid sequence of SEQ ID NO:227, an HVR-H2 comprising the amino acid sequence of SEQ ID NO:228, and an HVR-H3 comprising the amino acid sequence of SEQ ID NO:230. In some embodiments, an antibody of the present disclosure comprises a VL domain comprising an HVR-L1 comprising the amino acid sequence of SEQ ID NO:239, an HVR-L2 comprising the amino acid sequence of SEQ ID NO:240, and an HVR-L3 comprising the amino acid sequence of SEQ ID NO:241 and/or a VH domain comprising an HVR-H1 comprising the amino acid sequence of SEQ ID NO:235, an HVR-H2 comprising the amino acid sequence of SEQ ID NO:236, and an HVR-H3 comprising the amino acid sequence of SEQ ID NO:237.

In some embodiments, an antibody of the present disclosure comprises a VH domain comprising an HVR-H1 comprising the amino acid sequence of SEQ ID NO:161, an HVR-H2 comprising the amino acid sequence of SEQ ID NO:162, and an HVR-H3 comprising the amino acid sequence of SEQ ID NO:163. In some embodiments, an antibody of the present disclosure comprises a VH domain comprising an HVR-H1 comprising the amino acid sequence of SEQ ID NO:161, an HVR-H2 comprising the amino acid sequence of SEQ ID NO:168, and an HVR-H3 comprising the amino acid sequence of SEQ ID NO:163. In some embodiments, an antibody of the present disclosure comprises a VH domain comprising an HVR-H1 comprising the amino acid sequence of SEQ ID NO:173, an HVR-H2 comprising the amino acid sequence of SEQ ID NO:174, and an HVR-H3 comprising the amino acid sequence of SEQ ID NO:163.

In some embodiments, an antibody of the present disclosure comprises (a) a VH domain comprising an HVR-H1 comprising the amino acid sequence of SEQ ID NO: 202, an HVR-H2 comprising the amino acid sequence of SEQ ID NO: 203, and an HVR-H3 comprising the amino acid sequence of SEQ ID NO:145; and/or (b) a VL domain comprising an HVR-L1 comprising the amino acid sequence of SEQ ID NO:146, an HVR-L2 comprising the amino acid sequence of SEQ ID NO:147, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO: 211, an HVR-H2 comprising the amino acid sequence of SEQ ID NO: 212, and an HVR-H3 comprising the amino acid sequence of SEQ ID NO:151; and/or (b) a VL domain comprising an HVR-L1 comprising the amino acid sequence of SEQ ID NO:152, an HVR-L2 comprising the amino acid sequence of SEQ ID NO:153, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO: 219, an HVR-H2 comprising the amino acid sequence of SEQ ID NO: 220, and an HVR-H3 comprising the amino acid sequence of SEQ ID NO:157;

and/or (b) a VL domain comprising an HVR-L1 comprising the amino acid sequence of SEQ ID NO:158, an HVR-L2 comprising the amino acid sequence of SEQ ID NO:159, and an HVR-L3 comprising the amino acid sequence of SEQ ID NO:160.

In some embodiments, an antibody of the present disclosure comprises (a) a VH domain comprising an HVR-H1 comprising the amino acid sequence of SEQ ID NO: 204, an HVR-H2 comprising the amino acid sequence of SEQ ID NO:144, and an HVR-H3 comprising the amino acid sequence of SEQ ID NO:145; and/or (b) a VL domain comprising an HVR-L1 comprising the amino acid sequence of SEQ ID NO:146, an HVR-L2 comprising the amino acid sequence of SEQ ID NO:147, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO: 213, an HVR-H2 comprising the amino acid sequence of SEQ ID NO:150, and an HVR-H3 comprising the amino acid sequence of SEQ ID NO:151; and/or (b) a VL domain comprising an HVR-L1 comprising the amino acid sequence of SEQ ID NO:152, an HVR-L2 comprising the amino acid sequence of SEQ ID NO:153, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO: 221, an HVR-H2 comprising the amino acid sequence of SEQ ID NO:156, and an HVR-H3 comprising the amino acid sequence of SEQ ID NO:157; and/or (b) a VL domain comprising an HVR-L1 comprising the amino acid sequence of SEQ ID NO:158, an HVR-L2 comprising the amino acid sequence of SEQ ID NO:159, and an HVR-L3 comprising the amino acid sequence of SEQ ID NO:160.

In some embodiments, an antibody of the present disclosure comprises (a) a VH domain comprising an HVR-H1 comprising the amino acid sequence of SEQ ID NO: 205, an HVR-H2 comprising the amino acid sequence of SEQ ID NO: 206, and an HVR-H3 comprising the amino acid sequence of SEQ ID NO: 207; and/or (b) a VL domain comprising an HVR-L1 comprising the amino acid sequence of SEQ ID NO: 208, an HVR-L2 comprising the amino acid sequence of SEQ ID NO: 209, and an HVR-L3 comprising the amino acid sequence of SEQ ID NO: 210. In some embodiments, an antibody of the present disclosure comprises (a) a VH domain comprising an HVR-H1 comprising the amino acid sequence of SEQ ID NO: 214, an HVR-H2 comprising the amino acid sequence of SEQ ID NO: 215, and an HVR-H3 comprising the amino acid sequence of SEQ ID NO: 216; and/or (b) a VL domain comprising an HVR-L1 comprising the amino acid sequence of SEQ ID NO: 217, an HVR-L2 comprising the amino acid sequence of SEQ ID NO: 218, and an HVR-L3 comprising the amino acid sequence of SEQ ID NO:148. In some embodiments, an antibody of the present disclosure comprises (a) a VH domain comprising an HVR-H1 comprising the amino acid sequence of SEQ ID NO: 222, an HVR-H2 comprising the amino acid sequence of SEQ ID NO: 223, and an HVR-H3 comprising the amino acid sequence of SEQ ID NO: 224; and/or (b) a VL domain comprising an HVR-L1 comprising the amino acid sequence of SEQ ID NO: 225, an HVR-L2 comprising the amino acid sequence of SEQ ID NO: 226, and an HVR-L3 comprising the amino acid sequence of SEQ ID NO:160.

In some embodiments of any of the above embodiments, the antibody enhances phagocytosis by a macrophage expressing a human SIRP-α polypeptide, enhances activation of a dendritic cell expressing a human SIRP-α polypeptide, inhibits in vivo growth of a tumor or tumor cell(s) that expresses CD47, and/or does not prevent interactions between a CD47-expressing cell and a T cell. Exemplary assays for measuring phagocytosis, dendritic cell activation, tumor growth inhibition, and interactions between CD47-expressing cells and T cells (e.g., adhesion assays) are described herein and known in the art.

Antibody Production and Other Antibody Properties

An antibody of the present disclosure may be produced by any means known in the art. Exemplary techniques for antibody production are described below; however these exemplary techniques are provided for illustrative purposes only and are not intended to be limiting. In addition, exemplary antibody properties contemplated for use with the antibodies described herein are further described.

In some embodiments, an antibody that "binds" an antigen has a dissociation constant ($K_D$) for the antigen that is less than or equal to 1 µM at 25° C. In some embodiments, an antibody of the present disclosure has a dissociation constant ($K_D$) for human v1 and/or v2 SIRP-α polypeptides that is less than or equal to 1 µM at 25° C., less than or equal to 500 nM at 25° C., less than or equal to 400 nM at 25° C., less than or equal to 300 nM at 25° C., less than or equal to 250 nM at 25° C., less than or equal to 200 nM at 25° C., less than or equal to 200 nM at 25° C., less than or equal to 100 nM at 25° C., or less than or equal to 50 nM at 25° C. In some embodiments, an antibody that binds a human SIRP-α polypeptide and one or more non-human SIRP-α polypeptides binds the human SIRP-α polypeptide at a higher affinity (e.g., 10-fold or 100-fold higher) than the non-human SIRP-α polypeptide, though it still considered to "bind" both polypeptides. In some embodiments, an antibody that binds a non-human SIRP-α polypeptide and one or more human SIRP-α polypeptides binds the non-human SIRP-α polypeptide at a higher affinity (e.g., 10-fold or 100-fold higher) than the human SIRP-α polypeptide, though it still considered to "bind" both polypeptides. Assays for determining binding affinity are known in the art and include without limitation surface plasmon resonance (SPR), e.g., as described herein; radiolabeled antigen binding assay (RIA), e.g., using a Fab version of an antibody and its antigen; and the like. Other exemplary binding assays are described herein.

To prepare an antigen, the antigen may be purified or otherwise obtained from a natural source, or it may be expressed using recombinant techniques. In some embodiments, the antigen may be used as a soluble protein. In some embodiments, the antigen may be conjugate to another polypeptide or other moiety, e.g., to increase its immunogenicity. For example, an antigen described herein may be coupled with an Fc region. In some embodiments, a cell expressing the antigen on its cell surface may be used as the antigen.

Polyclonal antibodies can be raised in an animal by multiple subcutaneous (sc) or intraperitoneal (ip) injections of the antigen and an adjuvant. For example, descriptions of chicken immunization are described herein. In some embodiments, the antigen is conjugated with an immunogenic protein, e.g., keyhole limpet hemocyanin, serum albumin, bovine thyroglobulin, or soybean trypsin inhibitor using a bifunctional or derivatizing agent. Exemplary methods for immunization of chickens are provided herein. Relevant methods suitable for a variety of other organisms, such as mammals, are well known in the art.

As described supra, monoclonal antibodies may be produced by a variety of methods. In some embodiments, a monoclonal antibody of the present disclosure is made using the hybridoma method first described by Kohler et al., *Nature,* 256:495 (1975), and further described in Hongo et al., *Hybridoma,* 14 (3): 253-260 (1995); Harlow et al., *Antibodies: A Laboratory Manual,* (Cold Spring Harbor Laboratory Press, 2nd ed. 1988); and Hammerling et al., in: *Monoclonal Antibodies and T-Cell Hybridomas* 563-681 (Elsevier, N.Y., 1981). Human hybridoma technology (Trioma technology) is described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005). A culture medium in which hybridoma cells are grown may be screened for the presence of an antibody of interest, e.g., by in vitro binding assay, immunoprecipitation, ELISA, RIA, etc.; and the binding affinity may be determined, e.g., by Scatchard analysis. A hybridoma that produces an antibody with desired binding properties can be subcloned and grown using known culture techniques, grown in vivo as ascites tumors in an animal, and the like.

In some embodiments, a monoclonal antibody is made using a library method, such as a phage display library. See, e.g., Hoogenboom et al. in *Methods in Molecular Biology* 178:1-37 (O'Brien et al., ed., Human Press, Totowa, NJ, 2001). In some embodiments, repertoires of VH and VL genes are cloned by polymerase chain reaction (PCR) and recombined randomly in phage libraries, which are then screened for antigen-binding phage, e.g., as described in Winter et al., *Ann. Rev. Immunol.,* 12: 433-455 (1994). Phage typically display antibody fragments, either as single-chain Fv (scFv) fragments or as Fab fragments. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992).

In some embodiments, an antibody of the present disclosure is a chicken antibody. Chicken antibodies can be produced using various techniques known in the art; see, e.g., U.S. Pat. Nos. 6,143,559; 8,592,644; and 9,380,769.

In some embodiments, an antibody of the present disclosure is a chimeric antibody. See, e.g., U.S. Pat. No. 4,816,567 and Morrison et al., *Proc. Natl. Acad. Sci. USA,* 81:6851-6855 (1984). In some embodiments, a chimeric antibody comprises a non-human variable region (e.g., a variable region derived from a chicken, mouse, rat, hamster, rabbit, or non-human primate, such as a monkey) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. A non-human antibody can be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody (e.g., a chicken antibody), and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in Almagro and Fransson, *Front. Biosci.* 13:1619-1633 (2008). Methods of humanizing a chicken antibody have also been described, e.g., in WO2005014653.

Human framework regions useful for humanization include but are not limited to: framework regions selected using the "best-fit" method; framework regions derived from the consensus sequence of human antibodies of a particular subgroup of light or heavy chain variable regions; human somatically mutated framework regions or human germline framework regions; and framework regions derived from screening FR libraries. See, e.g., Sims et al. *J. Immunol.* 151:2296 (1993); Carter et al. *Proc. Natl. Acad. Sci. USA,* 89:4285 (1992); Presta et al. *J. Immunol.,* 151:2623 (1993); Almagro and Fransson, *Front. Biosci.* 13:1619-1633 (2008); and Baca et al., *J. Biol. Chem.* 272:10678-10684 (1997).

In some embodiments, an antibody of the present disclosure is a human antibody. Human antibodies can be produced using various techniques known in the art. In some embodiments, the human antibody is produced by a non-human animal, such as the genetically engineered chickens (see, e.g., U.S. Pat. Nos. 8,592,644; and 9,380,769) and/or mice described herein. Human antibodies are described generally in Lonberg, *Curr. Opin. Immunol.* 20:450-459 (2008).

In some embodiments, an antibody of the present disclosure is generated by or derived from a chicken, e.g., using the methods described herein.

In some embodiments, an antibody of the present disclosure is an antibody fragment, including without limitation a Fab, F(ab')2, Fab'-SH, Fv, or scFv fragment, or a single domain, single heavy chain, or single light chain antibody. Antibody fragments can be generated, e.g., by enzymatic digestion or by recombinant techniques. In some embodiments, Proteolytic digestion of an intact antibody is used to generate an antibody fragment, e.g., as described in Morimoto et al., *Journal of Biochemical and Biophysical Methods* 24:107-117 (1992) and Brennan et al., *Science,* 229:81 (1985). In some embodiments, an antibody fragment is produced by a recombinant host cell. For example, Fab, Fv and ScFv antibody fragments are expressed by and secreted from *E. coli.* Antibody fragments can alternatively be isolated from an antibody phage library.

Fab'-SH fragments can be directly recovered from *E. coli* and chemically coupled to form F(ab')$_2$ fragments. See Carter et al., *Bio Technology* 10:163-167 (1992). F(ab')$_2$ fragments can also be isolated directly from a recombinant host cell culture. Fab and F(ab')$_2$ fragment with increased in vivo half-life comprising salvage receptor binding epitope residues are described in U.S. Pat. No. 5,869,046.

In some embodiments, an antibody is a single chain Fv fragment (scFv). See WO 93/16185 and U.S. Pat. Nos. 5,571,894 and 5,587,458. scFv fusion proteins can be constructed to produce a fusion of an effector protein at either the amino or the carboxy terminus of an scFv. The antibody fragment may also be a "linear antibody", e.g., as described in U.S. Pat. No. 5,641,870, for example. Such linear antibodies may be monospecific or bispecific.

In some embodiments, an antibody of the present disclosure is a multispecific antibody. Multispecific antibodies possess binding specificities against more than one antigen (e.g., having two, three, or more binding specificities). In some embodiments, the antibody is a bispecific antibody. In some embodiments, a bispecific antibody comprises two different binding specificities for the same antigen (e.g., having different binding affinity and/or specific epitope of the same antigen). In some embodiments, a bispecific antibody comprises binding specificities for two distinct antigens. In some embodiments, the bispecific antibody is a full-length or intact antibody. In some embodiments, the bispecific antibody is an antibody fragment of the present disclosure.

Bispecific or multispecific antibodies with a variety of combinations of binding specificities are contemplated herein. In some embodiments, the bispecific antibody has a first binding specificity for one or more SIRP-α polypeptides as described herein. In some embodiments, the bispecific antibody has a second binding specificity for an antigen expressed by a cancer cell, e.g., on the cell surface. Exemplary such antigens include without limitation CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, PD-L1, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. Without wishing to be bound to theory, it is thought that combining such a binding specificity with a binding specificity against a SIRP-α is particularly advantageous, e.g., to direct FcR-expressing leukocytes to target a tumor cell with the second binding specificity while also inhibiting the responsiveness of SIRP-α expressed by the leukocyte to any CD47 expressed by the tumor cell with the first binding specificity.

Various methods are known in the art for generating and purifying a bispecific antibody. Numerous approaches have been described. One approach is the "knobs-into-holes" or "protuberance-into-cavity" approach (see, e.g., U.S. Pat. No. 5,731,168). In some embodiments, heterodimerization of Fc domain monomers is promoted by introducing different, but compatible, substitutions in the two Fc domain monomers, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain monomer and involved in the dimerization of two Fc domain monomers. In some embodiments, a hole in one CH3 antibody constant domain is created to accommodate a knob in another CH3 antibody constant domain, such that the knob and hole amino acids act to promote or favor the heterodimerization of the two Fc domain monomers. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain monomer includes the knob mutation T366W and the other Fc domain monomer includes hole mutations T366S, L358A, and Y407V. In some embodiments, a polypeptide of the disclosure including a high affinity SIRP-α D1 variant is fused to an Fc domain monomer including the knob mutation T366W to limit unwanted knob-knob homodimer formation. Examples of knob-into-hole amino acid pairs are included, without limitation, in Table 3.

TABLE 3

| Knob-into-hole amino acid pairs. | | | | | | | | |
|---|---|---|---|---|---|---|---|---|
| Fc domain monomer 1 | Y407A | Y407A | F405A | T394S | T366S L358A Y407V | T394W Y407T | T394S Y407A | T366W T394S |
| Fc domain monomer 2 | T366Y | T366W | T394W | F405W | T366W | T366Y F405A | T366W F405W | F405W Y407A |

Another approach uses antibody variable domains with the desired binding specificities (antibody-antigen combining sites) fused to immunoglobulin constant domain sequences, e.g., with an immunoglobulin heavy chain constant domain, comprising at least part of the hinge, CH2, and CH3 regions. In some embodiments, the bispecific antibody has a hybrid immunoglobulin heavy chain with a first binding specificity in one arm and a hybrid immunoglobulin heavy chain-light chain pair (providing a second binding specificity) in the other arm. See WO 94/04690. Another approach uses cross-linking (see, e.g., U.S. Pat. No. 4,676, 980) to produce a heteroconjugate antibody. In some embodiments, bispecific antibodies can be prepared using chemical linkage (see, e.g., Brennan et al., *Science,* 229: 81 (1985)) to proteolytically cleave an intact antibody into F(ab')$_2$ fragments that are reduced in the presence of a dithiol complexing agent and converted to thionitrobenzoate (TNB) derivatives, one of which is reconverted to the Fab'-thiol by reduction and mixed with the other Fab'-TNB derivative to form the bispecific antibody. In some embodiments, Fab'-SH fragments are chemically coupled. In some embodiments, bispecific antibody fragments are produced in cell culture using leucine zippers, as in Kostelny et al., *J. Immunol.*, 148(5):1547-1553 (1992). For other bispecific antibody formats, see, e.g., Spiess, C. et al. (2015)*Mol. Immunol.* 67:95-106.

In some embodiments, an antibody of the present disclosure is a diabody. See, e.g., Hollinger et al., *Proc. Natl. Acad. Sci. USA*, 90:6444-6448 (1993). In a diabody, the VH and VL domains of one fragment pair with complementary VL and VH domains of another fragment, thus forming two antigen-binding sites. Another strategy for making bispecific antibody fragments by the use of single-chain Fv (sFv) dimers has also been reported. See Gruber et al, *J. Immunol*, 152:5368 (1994).

In some embodiments, an antibody of the present disclosure is a single-domain antibody. A single-domain antibody refers to a single polypeptide chain comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1). In one embodiment, a single-domain antibody includes all or a portion of the heavy chain variable domain of an antibody. Camelid antibodies are also known.

Antibodies can be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An antibody of the present disclosure can be produced recombinantly as a fusion polypeptide with a heterologous polypeptide, e.g., a signal sequence or other polypeptide having a specific cleavage site at the N-terminus of the mature protein or polypeptide. The heterologous signal sequence selected can be one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, etc. In mammalian cell expression, mammalian signal sequences as well as viral secretory leaders, for example, the herpes simplex gD signal, are available.

Both expression and cloning vectors contain a nucleic acid sequence that enables the vector to replicate in one or more selected host cells, e.g., to allow the vector to replicate independently of the host chromosomal DNA. This sequence can include origins of replication or autonomously replicating sequences. Such sequences are well known for a variety of bacteria, yeast, and viruses. Generally, the origin of replication component is not needed for mammalian expression vectors (the SV40 origin may be used because it contains the early promoter).

Expression and cloning vectors can contain a selection gene or selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media. Examples of dominant selection use the drugs neomycin, mycophenolic acid and hygromycin. Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, and the like. For example, a Chinese hamster ovary (CHO) cell line deficient in endogenous DHFR activity transformed with the DHFR gene is identified by culturing the transformants in a culture medium containing methotrexate (Mtx), a competitive antagonist of DHFR.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoter sequences are known for eukaryotes. Yeast promoters are well known in the art and can include inducible promoters/enhancers regulated by growth conditions. Virtually all eukaryotic genes have an AT-rich region located approximately 25 to 30 bases upstream from the site where transcription is initiated. Examples include without limitation the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Antibody transcription from vectors in mammalian host cells can be controlled, for example, by promoters obtained from the genomes of viruses. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Alternatively, the Rous Sarcoma Virus long terminal repeat can be used as the promoter.

Transcription of a DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus.

Expression vectors used in eukaryotic host cells (yeast, fungi, insect, plant, animal, human, or nucleated cells from other multicellular organisms) will also contain sequences necessary for the termination of transcription and for stabilizing the mRNA.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, etc. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006).

Plant cell cultures of cotton, corn, potato, soybean, petunia, tomato, duckweed (Leninaceae), alfalfa (*M. truncatula*), and tobacco can also be utilized as hosts.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified.

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J., 2003), pp. 255-268.

The host cells of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of skill in the art.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio Technology* 10:163-167 (1992) describe a procedure for isolating antibodies which are secreted to the periplasmic space of *E. coli*.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps.

In some embodiments, an antibody of the present disclosure comprises a kappa or lambda light chain constant region. In some embodiments, an antibody of the present disclosure comprises a light chain constant region comprising the amino acid sequence of SEQ ID NO:325, 326, or 426. Exemplary and non-limiting light chain constant region sequences are provided in Table 6. In some embodiments, an antibody of the present disclosure comprises an IGLC3 lambda light chain constant region or an IGLC7 constant region.

In some embodiments, an antibody of the present disclosure includes an Fc region. For example, in some embodiments, the Fc region is a human Fc region, e.g., IgG1, IgG2, or IgG4 and subtypes thereof. Exemplary and non-limiting Fc regions are provided within the amino acid sequences of SEQ ID NOs:320-324 shown in Table 6. In some embodiments, an Fc region within one or more of the amino acid sequences of SEQ ID NOs:320-324 comprises one or more of the mutations described herein, e.g., infra.

TABLE 6

Exemplary constant region sequences

| Name | SEQ ID NO | Sequence |
| --- | --- | --- |
| IgG1 wildtype | 320 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| IgG1_AAA_N297A | 321 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| IgG2 | 322 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| IgG2Da | 323 | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPSSIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK |
| IgG4_S228P | 324 | ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| Human Kappa | 325 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| Human Lambda IGLC1 | 326 | GQPKANPTVTLFPPSSEELQANKATLVCLISDFYPGAVTVAWKADGSPVKAGVETTKPSKQSNNKYAASSYLSLTPEQWKSHRSYSCQVTHEGSTVEKTVAPTECS |
| Human Lambda IGLC2 | 426 | GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |

In some embodiments, the Fc region includes one or more mutations that influence one or more antibody properties, such as stability, pattern of glycosylation or other modifications, effector cell function, pharmacokinetics, and so forth. In some embodiments, an antibody of the present disclosure has reduced or minimal glycosylation. In some embodiments, an antibody of the present disclosure has ablated or reduced effector function. Exemplary Fc mutations include without limitation (i) a human IgG1 Fc region mutations L234A, L235A, G237A, and N297A; (ii) a human IgG2 Fc region mutations A330S, P331S and N297A; and (iii) a human IgG4 Fc region mutations S228P, E233P, F234V, L235A, delG236, and N297A (EU numbering). In some embodiments, the human IgG2 Fc region comprises A330S and P331S mutations. In some embodiments, the human IgG4 Fc region comprises an S288P mutation. In some embodiments, the human IgG4 Fc region comprises S288P and L235E mutations.

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a Fc domain monomer refers to a polypeptide chain that includes second and third antibody constant domains (e.g., CH2 and CH3). In some embodiments, an Fc domain monomer also includes a hinge domain. In some embodiments, the Fc domain monomer is of any immunoglobulin antibody isotype, including IgG, IgE, IgM, IgA, and IgD. Additionally, in some embodiments, an Fc domain monomer is of any IgG subtype (e.g., IgG1, IgG2, IgG2a, IgG2b, IgG2c, IgG3, and IgG4). In some embodiments, Fc domain monomers include as many as ten changes from a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

In some embodiments, an Fc domain monomer of an immunoglobulin or a fragment of an Fc domain monomer is capable of forming an Fc domain with another Fc domain monomer. In some embodiments, an Fc domain monomer of an immunoglobulin or a fragment of an Fc domain monomer is not capable of forming an Fc domain with another Fc domain monomer. In some embodiments, an Fc domain monomer or a fragment of an Fc domain is fused to a polypeptide of the disclosure to increase serum half-life of the polypeptide. In some embodiments, an Fc domain monomer or a fragment of an Fc domain monomer fused to a polypeptide of the disclosure dimerizes with a second Fc domain monomer to form an Fc domain which binds an Fc receptor, or alternatively, an Fc domain monomer binds to an Fc receptor. In some embodiments, an Fc domain or a fragment of the Fc domain fused to a polypeptide to increase serum half-life of the polypeptide does not induce any immune system-related response. An Fc domain includes two Fc domain monomers that are dimerized by the interaction between the CH3 antibody constant domains.

A wild-type Fc domain forms the minimum structure that binds to an Fc receptor, e.g., FcγRI, FcγRIIa, FcγRIIb, FcγRIIIa, FcγRIIIb, and FcγRIV. In some embodiments, the Fc domain in an antibody of the present disclosure comprises one or more amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. For example, an antibody of the present disclosure can exhibit decreased binding (e.g., minimal binding or absence of binding) to a human Fc receptor and decreased binding (e.g., minimal binding or absence of binding) to complement protein C1q; decreased binding (e.g., minimal binding or absence of binding) to human FcγRI, FcγRIIA, FcγRIIB, FcγRIIIB, FcγRIIIB, or any combinations thereof, and C1q; altered or reduced antibody-dependent effector function, such as ADCC, CDC, ADCP, or any combinations thereof, and so forth. Exemplary mutations include without limitation one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda, MD (1991)).

In some embodiments, an antibody of the present disclosure has reduced or ablated binding to CD16a, CD32a, CD32b, CD32c, and CD64 Fcγ receptors. In some embodiments, an antibody with a non-native Fc region described herein exhibits at least a 5%, 10%, 15%, 20%, 30%, 40%, 50%, 60%, 70%, 80%, 90% or greater reduction in C1q binding compared to an antibody comprising a wild-type Fc region. In some embodiments, an antibody with a non-native Fc region as described herein exhibit at least a 5%, 10%, 15%, 20%, 30%, 40%, 50%, 60%, 70%, 80%, 90% or greater reduction in CDC compared to an antibody comprising a wild-type Fc region.

In some embodiments, the Fc variants herein are minimally glycosylated or have reduced glycosylation relative to a wild-type sequence. In some embodiments, deglycosylation is accomplished with a mutation of N297A, or by mutating N297 to any amino acid which is not N.

In some embodiments, variants of antibody IgG constant regions (e.g., Fc variants) possess a reduced capacity to specifically bind Fcγ receptors or have a reduced capacity to induce phagocytosis. In some embodiments, variants of antibody IgG constant regions (e.g., Fc variants) possess a reduced capacity to specifically bind Fcγ receptors and have a reduced capacity to induce phagocytosis. For example, in some embodiments, an Fc domain is mutated to lack effector functions, typical of a "dead" Fc domain. For example, in some embodiments, an Fc domain includes specific amino acid substitutions that are known to minimize the interaction between the Fc domain and an Fcγ receptor. In some embodiments, an Fc domain monomer is from an IgG1 antibody and includes one or more of amino acid substitutions L234A, L235A, G237A, and N297A (as designated according to the EU numbering system per Kabat et al., 1991). In some embodiments, one or more additional mutations are included in such IgG1 Fc variant. Non-limiting examples of such additional mutations for human IgG1 Fc variants include E318A and K322A. In some instances, a human IgG1 Fc variant has up to 12, 11, 10, 9, 8, 7, 6, 5 or 4 or fewer mutations in total as compared to wild-type human IgG1 sequence. In some embodiments, one or more additional deletions are included in such IgG1 Fc variant. For example, in some embodiments, the C-terminal lysine of the Fc IgG1 heavy chain constant region is deleted, for example to increase the homogeneity of the polypeptide when the polypeptide is produced in bacterial or mammalian cells. In some instances, a human IgG1 Fc variant has up to 12, 11, 10, 9, 8, 7, 6, 5 or 4 or fewer deletions in total as compared to wild-type human IgG1 sequence.

In some embodiments, an Fc domain monomer is from an IgG2 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc variant comprises a human IgG2 Fc sequence comprising one or more of A330S, P331S and N297A amino acid substitutions (as designated according to the EU numbering system per Kabat, et al. (1991). In some embodiments, one or more additional mutations are included in such IgG2 Fc variants. Non-limiting examples of such additional mutations for human IgG2 Fc variant include V234A, G237A, P238S, V309L and H268A (as designated according to the EU numbering system per Kabat et al. (1991)). In some instances, a human IgG2 Fc variant has up to 12, 11, 10, 9, 8, 7, 6, 5, 4, 3 or fewer mutations in total as compared to wild-type human IgG2 sequence. In some embodiments, one or more additional deletions are included in such IgG2 Fc variant.

When the Fc variant is an IgG4 Fc variant, in some embodiments, such Fc variant comprises a S228P, E233P, F234V, L235A, L235E, or delG236 mutation (as designated according to Kabat, et al. (1991)). In some instances, a human IgG4 Fc variant has up to 12, 11, 10, 9, 8, 7, 6, 5, 4, 3, 2 or 1 mutation(s) in total as compared to wild-type human IgG4 sequence.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc variant as described herein exhibit reduced ADCC or ADCP as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in ADCC or ADCP compared to a polypeptide construct comprising a wild-type Fc region. In some embodiments, antibodies comprising an Fc variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc. In some embodiments, polypeptide constructs comprising an Fc variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc variant as described herein exhibit reduced CDC as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, antibodies comprising an Fc variant as described herein exhibit negligible CDC as compared to a polypeptide construct comprising a wild-type Fc region.

Fc variants herein include those that exhibit reduced binding to an Fcγ receptor compared to the wild-type human IgG Fc region. For example, in some embodiments, an Fc variant exhibits binding to an Fcγ receptor that is less than the binding exhibited by a wild-type human IgG Fc region to an Fcγ receptor. In some instances, an Fc variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptors, e.g., CD16a, CD32a, CD32b, CD32c, or CD64.

In some instances, the Fc variants disclosed herein exhibit a reduction of phagocytosis compared to its wild-type human IgG Fc region. Such Fc variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc variant exhibits ablated phagocytosis compared to its wild-type human IgG Fc region.

In some embodiments, the Fc variants disclosed herein are coupled to one or more fusion partners. In some cases the fusion partner is a therapeutic moiety, such as a cytotoxic agent of the present disclosure. In some cases, the fusion partner is selected to enable targeting of an expressed protein, purification, screening, display, and the like. In some embodiments, the fusion partner also affects the degree of binding to Fc receptors or the degree of phagocytosis reduction.

In some embodiments, fusion partners are linked to the Fc variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 and His10) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc variant is purified using a His-tag by immobilizing it to a Ni+2 affinity column, and then after purification the same His-tag is used to immobilize the antibody to a Ni+2 coated plate to perform an ELISA or other binding assay.

Various fusion partners that enable a variety of selection methods are available. For example, by fusing the members of an Fc variant library to the gene III protein, phage display can be employed. In some embodiments, fusion partners enable Fc variants to be labeled. Alternatively, in some embodiments, a fusion partner binds to a specific sequence on the expression vector, enabling the fusion partner and associated Fc variant to be linked covalently or noncovalently with the nucleic acid that encodes them.

In some embodiments, when a fusion partner is a therapeutic moiety, the therapeutic moiety is, e.g., a cytotoxic agent, a peptide, a protein, an antibody, a siRNA, or a small molecule.

In some embodiments, an antibody of the present disclosure is bound to various carriers or labels and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble. Various different labels and methods of labeling are known. Examples of labels include enzymes, radioisotopes, fluorescent compounds, colloidal metals, chemiluminescent compounds, and bio-luminescent compounds. Various techniques for binding labels to antibodies disclosed herein are available. In some embodiments, the antibodies are coupled to low molecular weight haptens. These haptens are then specifically detected by means of a second reaction. For example, in some embodiments, the hapten biotin is used with avidin or the haptens dinitrophenol, pyridoxal, or fluorescein are detected with specific anti-hapten antibodies (e.g., anti-dinitrophenol antibodies, anti-pyridoxal antibodies, and anti-fluorescein antibodies respectively). In some embodiments, the antibodies described herein are utilized in vitro for binding assays, such as immune assays. For example, in some embodiments, the antibodies are utilized in liquid phase or bound to a solid phase carrier. In some embodiments, antibodies utilized for immunoassays are detectably labeled in various ways.

Methods of Identifying and/or Generating Antibodies

Certain aspects of the present disclosure relate to methods of identifying an antigen binding domain that binds an extracellular domain (e.g., the D1 domain) of a human SIRP-α polypeptide. Advantageously, the methods described herein can be used to identify antigen binding domains that block binding between human CD47 and a human SIRP-α polypeptide, do not block binding between human CD47 and a human SIRP-α polypeptide, or reduce affinity of a human SIRP-α polypeptide for human CD47.

In some embodiments, the methods include providing an antigen binding domain that binds the extracellular domain (e.g., the D1 domain) of a human SIRP-α polypeptide. Exemplary antigen binding domains and antibodies that bind the extracellular domain (e.g., the D1 domain) of a human SIRP-α polypeptide, and/or other SIRP polypeptides, are described herein, as are exemplary methods for identifying such antigen binding domains/antibodies. Exemplary methods are described in greater detail in the Examples infra.

In some embodiments, the methods include assembling a complex comprising a SIRP-α D1 variant bound to a polypeptide comprising an IgSF domain of CD47. In some embodiments, "assembling" the complex includes providing a solution containing both a SIRP-α D1 variant and a polypeptide comprising an IgSF domain of CD47. In some embodiments, the SIRP-α D1 variant is a non-naturally occurring variant, e.g., that binds to human CD47 with an affinity that is at least 10-fold, at least 100-fold, or at least 100-fold greater than the affinity of a naturally occurring SIRP-α D1 domain binding to human CD47. Advantageously, this facilitates antibody screening, as a natural SIRP-α:CD47 interaction may be too weak for use in binding and screening assays. Exemplary variants are described in greater detail infra.

In some embodiments, the methods include contacting the antigen binding domain with the assembled complex. In some embodiments, binding, or a lack or deficiency thereof, of the antigen binding domain to the complex is detected. Various detection techniques are described herein. In some embodiments, SPR or ELISA is used. Detectable binding of the antigen binding domain to the complex indicates that the antigen binding domain does not block binding between human CD47 and the human SIRP-α polypeptide. A lack of binding of the antigen binding domain to the complex indicates that the antigen binding domain blocks binding between human CD47 and the human SIRP-α polypeptide. In addition, SPR is used to distinguish blocking, non-blocking and kick-off antibodies. For example, in some embodiments, a non-blocking antibody increases RUs when injected on top of pre-formed SIRPα:CD47 complex, a kick-off antibody increases $K_{off}$ of a pre-formed SIRPα:CD47 complex, and blocking antibody does not change the RUs or $K_{off}$ of a pre-formed SIRPα:CD47 complex.

In some embodiments, the IgSF domain of CD47 is a human IgSF domain. In some embodiments, the polypeptide comprising the IgSF domain of CD47 comprises a human CD47 extracellular domain. In some embodiments, the IgSF domain of CD47 comprises the amino acid sequence of QLLFNKTKSVEFTFSNDTVVIPCFVTNMEAQNTTE-VYVKWKFKGRDIYTFDGALNKSTV PTDFSSAKI-EVSQLLKGDASLKMDKSDAVSHTGNYTCEVTEL-TREGETIIELKYRVVS (SEQ ID NO:16). In some embodiments, the polypeptide comprising the IgSF domain of CD47 is conjugated to another polypeptide or other moiety, e.g., an Ig Fc region.

High Affinity SIRP-α D1 Domain Variants

A variety of high affinity SIRP-α D1 variants are contemplated for use herein. For example, in certain embodiments, the SIRP-α D1 variant comprises an amino acid sequence selected from the group consisting of SEQ ID NOs: 17-52 (see Table 4). Further descriptions of SIRP-α D1 variants follow.

TABLE 4

Exemplary SIRP-α D1 variant amino acid sequences.

| SEQ ID NO | Sequence |
|---|---|
| 17 | EEELQIIQPDKSVLVAAGETATLRCTITSLFPVGPIQWFRGAGPGRELIYNQREG PFPRVTTVSDTTKRNNMDFSIRIGAITPADAGTYYCVKFRKGSPDDVEFKSGAG TELSVRAKPS |
| 18 | EEELQIIQPDKSVSVAAGESAILHCTITSLFPVGPIQWFRGAGPARVLIYNQRQG PFPRVTTVSETTKRENMDFSISISNITPADAGTYYCIKFRKGSPDTEFKSGAGTE LSVRAKPS |
| 19 | EEELQVIQPDKSVSVAAGESAILHCTVTSLFPVGPIQWFRGAGPARELIYNQRQ GPFPRVTTVSESTKRENMDFSISISNITPADAGTYYCVKFRKGSPDTEFKSGAGT ELSVRAKPS |
| 20 | EEELQVIQPDKSVSVAAGESAILHCTITSLFPVGPIQWFRGAGPARVLIYNQRQG PFPRVTTVSETTKRENMDFSISISNITPADAGTYYCIKFRKGSPDTEFKSGAGTE LSVRAKPS |
| 21 | EEELQIIQPDKSVSVAAGESAILHCTVTSLFPVGPIQWFRGAGPARVLIYNQRQG PFPRVTTVSETTKRENMDFSISISNITPADAGTYYCIKFRKGSPDTEFKSGAGTE LSVRAKPS |
| 22 | EEELQIIQPDKSVSVAAGESAILHCTITSLIPVGPIQWFRGAGPARVLIYNQRQGP FPPRVTTVSETTKRENMDFSISISNITPADAGTYYCIKFRKGSPDTEFKSGAGTEL SVRAKPS |
| 23 | EEELQIIQPDKSVSVAAGESAILHCTITSLFPVGPIQWFRGAGPARELIYNQRQG PFPRVTTVSETTKRENMDFSISISNITPADAGTYYCIKFRKGSPDTEFKSGAGTE LSVRAKPS |
| 24 | EEELQIIQPDKSVSVAAGESAILHCTITSLFPVGPIQWFRGAGPARVLIYNQKQG PFPRVTTVSETTKRENMDFSISISNITPADAGTYYCIKFRKGSPDTEFKSGAGTE LSVRAKPS |
| 25 | EEELQIIQPDKSVSVAAGESAILHCTITSLFPVGPIQWFRGAGPARVLIYNQREG PFPRVTTVSETTKRENMDFSISISNITPADAGTYYCIKFRKGSPDTEFKSGAGTE LSVRAKPS |
| 26 | EEELQIIQPDKSVSVAAGESAILHCTITSLFPVGPIQWFRGAGPARVLIYNQRQG HFPRVTTVSETTKRENMDFSISISNITPADAGTYYCIKFRKGSPDTEFKSGAGTE LSVRAKPS |
| 27 | EEELQIIQPDKSVSVAAGESAILHCTITSLFPVGPIQWFRGAGPARVLIYNQRQG PFPRVTTVSESTKRENMDFSISISNITPADAGTYYCIKFRKGSPDTEFKSGAGTEL SVRAKPS |
| 28 | EEELQIIQPDKSVSVAAGESAILHCTITSLFPVGPIQWFRGAGPARVLIYNQRQG PFPRVTTVSETTKRENMDFSISISNITPADAGTYYCVKFRKGSPDTEFKSGAGTE LSVRAKPS |
| 29 | EEELQVIQPDKSVSVAAGESAILHCTVTSLIPVGPIQWFRGAGPARELIYNQREG PFPRVTTVSESTKRENMDFSISISNITPADAGTYYCVKFRKGSPDTEFKSGAGTE LSVRAKPS |
| 30 | EEELQVIQPDKSVSVAAGESAILHCTVTSLFPVGPIQWFRGAGPARELIYNQRE GPFPRVTTVSESTKRENMDFSISISNITPADAGTYYCVKFRKGSPDTEFKSGAGT ELSVRAKPS |
| 31 | EEELQVIQPDKSVSVAAGESAILHCTVTSLFPVGPIQWFRGAGPARELIYNQREG PFPRVTTVSESTKRENMDFSISISNITPADAGTYYCVKFRKGSPDTEFKSGAGTE LSVRAKPS |
| 32 | EEELQVIQPDKSVSVAAGESAILHCTVTSLFPVGPIQWFRGAGPARELIYNQREG PFPRVTTVSETTKRENMDFSISISNITPADAGTYYCVKFRKGSPDTEFKSGAGTE LSVRAKPS |
| 33 | EEELQIIQPDKSVSVAAGESAILHCTITSLFPVGPIQWFRGAGPARELIYNQREGP FPRVTTVSESTKRENMDFSISISNITPADAGTYYCVKFRKGSPDTEFKSGAGTEL SVRAKPS |
| 34 | EEELQVIQPDKSVSVAAGESAILHCTITSLIPVGPIQWFRGAGPARELIYNQREG PFPRVTTVSESTKRENMDFSISISNITPADAGTYYCVKFRKGSPDTEFKSGAGTE LSVRAKPS |
| 35 | EEELQIIQPDKSVSVAAGESAILHCTITSLFPVGPIQWFRGAGPARELIYNQREGP FPRVTTVSETTKRENMDFSISISNITPADAGTYYCVKFRKGSPDTEFKSGAGTEL SVRAKPS |

TABLE 4-continued

Exemplary SIRP-α D1 variant amino acid sequences.

| SEQ ID NO | Sequence |
|---|---|
| 36 | EEELQVIQPDKSVLVAAGETATLRCTATSLFPVGPIQWFRGAGPGRELIYNQRQ GPFPRVTTVSDLTKRNNMDFSIRIGNITPADAGTYYCVKFRKGSPDDVEFKSGA GTELSVRAKPS |
| 37 | EEELQIIQPDKSVLVAAGETATLRCTITSLFPVGPIQWFRGAGPGRELIYNQREG PFPRVTTVSDLTKRNNMDFSIRIGNITPADAGTYYCVKFRKGSPDDVEFKSGAG TELSVRAKPS |
| 38 | EEELQVIQPDKSVLVAAGETATLRCTITSLFPVGPIQWFRGAGPGRELIYNQRE GPFPRVTTVSDTTKRNNMDFSIRIGNITPADAGTYYCVKFRKGSPDDVEFKSGA GTELSVRAKPS |
| 39 | EEELQIIQPDKSVLVAAGETATLRCTITSLFPVGPIQWFRGAGPGRELIYNQREG PFPRVTTVSDTTKRNNMDFSIRIGNITPADAGTYYCVKFRKGSPDDVEFKSGAG TELSVRAKPS |
| 40 | EEELQVIQPDKSVLVAAGETATLRCTITSLFPVGPIQWFRGAGPGRELIYNQRE GPFPRVTTVSDLTKRNNMDFSIRIGNITPADAGTYYCVKFRKGSPDDVEFKSGA GTELSVRAKPS |
| 41 | EEELQVIQPDKSVLVAAGETATLRCTATSLFPVGPIQWFRGAGPGRELIYNQRE GPFPRVTTVSDLTKRNNMDFSIRIGNITPADAGTYYCVKFRKGSPDDVEFKSGA GTELSVRAKPS |
| 42 | EEELQIIQPDKSVLVAAGETATLRCTITSLFPVGPIQWFRGAGPGRVLIYNQRQG PFPRVTTVSDTTKRNNMDFSIRIGNITPADAGTYYCIKFRKGSPDDVEFKSGAG TELSVRAKPS |
| 43 | EEELQIIQPDKSVLVAAGETATLRCTITSLFPVGPIQWFRGAGPGRVLIYNQRQG PFPRVTTVSDTTKRNNMDFSIRIGAITPADAGTYYCIKFRKGSPDDVEFKSGAG TELSVRAKPS |
| 44 | EEELQVIQPDKSVLVAAGETATLRCTATSLFPVGPIQWFRGAGPGRELIYNQRQ GPFPRVTTVSDLTKRNNMDFSIRIGAITPADAGTYYCVKFRKGSPDDVEFKSGA GTELSVRAKPS |
| 45 | EEELQIIQPDKSVLVAAGETATLRCTITSLFPVGPIQWFRGAGPGRVLIYNQREG PFPRVTTVSDTTKRNNMDFSIRIGAITPADAGTYYCIKFRKGSPDDVEFKSGAG TELSVRAKPS |
| 46 | EEELQVIQPDKSVLVAAGETATLRCTATSLFPVGPIQWFRGAGPGRELIYNQRE GPFPRVTTVSDLTKRNNMDFSIRIGAITPADAGTYYCVKFRKGSPDDVEFKSGA GTELSVRAKPS |
| 47 | EEELQVIQPDKSVLVAAGETATLRCTITSLFPVGPIQWFRGAGPGRELIYNQRE GPFPRVTTVSDLTKRNNMDFSIRIGAITPADAGTYYCVKFRKGSPDDVEFKSGA GTELSVRAKPS |
| 48 | EEELQIIQPDKSVLVAAGETATLRCTITSLFPVGPIQWFRGAGPGRELIYNQREG PFPRVTTVSDLTKRNNMDFSIRIGAITPADAGTYYCVKFRKGSPDDVEFKSGAG TELSVRAKPS |
| 49 | EEELQVIQPDKSVLVAAGETATLRCTITSLFPVGPIQWFRGAGPGRELIYNQRE GPFPRVTTVSDTTKRNNMDFSIRIGAITPADAGTYYCVKFRKGSPDDVEFKSGA GTELSVRAKPS |
| 50 | EEELQVIQPDKSVLVAAGETATLRCTATSLIPVGPIQWFRGAGPGRELIYNQKE GHFPRVTTVSDLTKRNNMDFSIRIGNITPADAGTYYCVKFRKGSPDDVEFKSG AGTELSVRAKPS |
| 51 | EEELQIIQPDKSVLVAAGETATLRCTITSLFPVGPIQWFRGAGPGRELIYNQREG PFPRVTTVSDTTKRNNMDFSIRIGAITPADAGTYYCVKFRKGSPDDVEFKSGAG TELSVRAKPS |
| 52 | EEELQVIQPDKSVLVAAGETATLRCTATSLFPVGPIQWFRGAGPGRELIYNQR QGPFPRVTTVSDLTKRNNMDFSIRIGNITVADAGTYYCVKFRKGSPDDVEFK SGAGTELSVRAKPS |

In some embodiments, a SIRP-α D1 variant polypeptide or fragment thereof binds to CD47 with a $K_D$ less than $1\times10^{-8}$ M, less than $5\times10^{-9}$ M, less than $1\times10^{-9}$ M, less $5\times10^{-10}$ M, less than $1\times10^{-10}$ M or less than $1\times10^{-11}$ M. In some embodiments, a SIRP-α D1 variant polypeptide or fragment thereof binds to CD47 with a $K_D$ between about 500 nM and 100 nM, between about 100 nM and 50 nM, between about 50 nM and 10 nM, between about 10 nM and 5 nM, between about 5 nM and 1 nM, between about 1 nM and 500 pM, between about 500 pM and 100 pM, between about 100 pM and 50 pM, or between about 50 pM and 10 pM.

In some embodiments, fragments include polypeptides of less than 10 amino acids in length, about 10 amino acids in length, about 20 amino acids in length, about 30 amino acids in length, about 40 amino acids in length, about 50 amino acids in length, about 60 amino acids in length, about 70 amino acids in length, about 80 amino acids in length, about 90 amino acids in length, about 100 amino acids in length, or more than about 100 amino acids in length. Fragments retain the ability to bind to CD47. Preferably, SIRP-α D1 variant polypeptides and fragments thereof bind to CD47 with a higher affinity than a SIRP-α polypeptide binds to CD47.

In some embodiments, the above-mentioned SIRP-α D1 variant polypeptides are attached or fused to a second polypeptide. In some embodiments, the second polypeptide includes, without limitation, an Fc polypeptide, an Fc variant, an HSA polypeptide, an albumin peptide, a PEG polymer or a fragment of the foregoing.

In some embodiments, the polypeptide includes a high affinity SIRP-α D1 domain that has at least 85% sequence identity (e.g., at least 86%, 87%, 88%, 89%, 90%, 91%, 92%, 93%, 94%, 95%, 96%, 97%, 98%, 99%, or 100% sequence identity) to any variant provided in Table 4.

Antibody Generation in Chicken

Certain aspects of the present disclosure relate to methods of producing an anti-SIRP-α antibody that binds the extracellular domains (e.g., the D1 domains) of two or more different human SIRP-α variant polypeptides. Without wishing to be bound to theory, it is thought that the use of chicken is particularly advantageous because of the greater diversity between chicken SIRP-α and mammalian (e.g., human, monkey, mouse, etc.) SIRP-α. Further, the phylogenetic distance between chickens and mammals allows for the identification of antibodies that cross-react against, e.g., human and mouse SIRP-α polypeptides, which can be difficult to achieve by producing antibodies in mouse due to self-tolerance.

In some embodiments, the methods include immunizing a chicken with a peptide comprising at least a portion of a human SIRP-α extracellular domain (e.g., the D1 domain). An exemplary immunization schedule is described infra. Methods for chicken immunization are described, e.g., in Mettler Izquierdo, S. et al. (2016) *Microscopy (Oxf)* 1-16. In some embodiments, the methods include obtaining an antibody from an antibody-producing cell from the immunized chicken.

In some embodiments, the methods include detecting binding between the antibody obtained from the cell and the extracellular domains (e.g., the D1 domains) of two or more different human SIRP-α variant polypeptides. For example, in some embodiments, human SIRP-α v1 and v2, e.g., as described herein, are used. Exemplary detection techniques are described herein and include without limitation the GEM assay (see. e.g., WO2009111014 and Mettler Izquierdo, S. et al. (2016) *Microscopy (Oxf)* 1-16), SPR, and ELISA.

Methods of Treatment

Certain aspects of the present disclosure relate to treating a disease or disorder using an antibody described herein. In some embodiments, the disease is cancer. In some embodiments, the disease is an autoimmune or inflammatory disease.

For example, provided herein are methods of treating or delaying progression of cancer in an individual by administering an effective amount of an antibody of the present disclosure. Without wishing to be bound to theory, it is thought that the antibodies described herein may be useful in the treatment of cancer, e.g., by abrogating the cancer's ability to inhibit phagocytosis and immune surveillance through the CD47: SIRP-α signaling axis, or by otherwise enhancing activation of the immune system (such as by activation of dendritic cells).

In some embodiments, an antibody of the present disclosure is administered in combination with a chemotherapeutic agent.

In some embodiments, an antibody of the present disclosure is administered in combination with a second antibody, e.g., an antibody that binds an antigen expressed by the cancer. Exemplary antigens expressed by cancers are known in the art and include without limitation CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, PD-L1, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. For example, in some embodiments, an antibody of the present disclosure is administered in combination with a monoclonal antibody that binds CD123 (also known as IL-3 receptor alpha), such as talacotuzumab (also known as CSL362 and JNJ-56022473). In some embodiments, an antibody of the present disclosure is administered in combination with a monoclonal antibody that binds EGFR (such as cetuximab). In some embodiments, the second antibody includes one or more effector functions, e.g., effector functions that are associated with Fc receptor (FcR) engagement on immune cells including without limitation ADCC or ADCP, and/or complement-dependent cytotoxicity (CDC). Without wishing to be bound to theory, it is thought that combining such an antibody with an antibody of the present disclosure is particularly advantageous, e.g., to direct FcR-expressing leukocytes to target a tumor cell to which the second antibody is bound while also inhibiting the responsiveness of SIRP-α expressed by the leukocyte to any CD47 expressed by the tumor cell with the SIRP-α antibody.

In some embodiments, an antibody of the present disclosure is administered in combination with an immunotherapeutic agent. An immunotherapeutic agent may refer to any therapeutic that targets the immune system and promotes a therapeutic redirection of the immune system, such as a modulator of a costimulatory pathway, cancer vaccine, recombinantly modified immune cell, etc. In some embodiments, the immunotherapeutic agent comprises an antibody. Exemplary antigens of immunotherapeutic antibodies are known in the art and include without limitation PD-1, PD-L1, OX40, CTLA-4, CD137/4-1BB, B7-H3, FZD7, CD27, TNFR2, CCR4, CSF1R, CSF, TIM-3, LAG-3, VISTA, ICOS, CCR2, IDO, A2R, CD39, CD73, TIGIT, CD80, CD47, arginase, TDO, and PVRIG. Immunotherapeutic agents that are approved or in late-stage clinical testing include, without limitation, ipilimumab, pembrolizumab, nivolumab, atezolizumab, avelumab, durvalumab, and the like. Without wishing to be bound to theory, it is thought that the antibodies of the present disclosure are suitable for use with immunotherapeutic agents due to complementary mechanisms of action, e.g., in activating both macrophages and $T_{effector}$ cells to target tumor cells. In certain embodiments, an antibody of the present disclosure is administered in combination with an inhibitor of the PD-L1/PD-1 pathway, e.g., an anti-PD-L1 or anti-PD-1 antibody. As demonstrated herein, combined administration of an anti-SIRP-α antibody of the present disclosure and an inhibitor of the PD-L1/PD-1 pathway can result in synergistic anti-tumor activity. For example, in some embodiments, a blocking anti-SIRP-α antibody of the present disclosure is administered in combination with an anti-PD-1 antibody. In some embodiments, a non-blocking anti-SIRP-α antibody of the present disclosure is administered in combination with an anti-PD-1 antibody. In some embodiments, a blocking anti-SIRP-α antibody of the present disclosure is administered in combination with an anti-PD-L1 antibody. In some embodiments, a non-blocking anti-SIRP-α antibody of the present disclosure is administered in combination with an anti-PD-L1 antibody.

Any cancer type known in the art may be included, such as but not limited to carcinoma, sarcoma, lymphoma, leukemia, lymphoma, and blastoma. More particular examples of such cancers include, but are not limited to, lung cancer, squamous cell cancer, brain tumors, glioblastoma, head and neck cancer, hepatocellular cancer, colorectal cancer (e.g., colon or rectal cancers), liver cancer, bladder cancer, gastric or stomach cancer, pancreatic cancer, cervical cancer, ovarian cancer, cancer of the urinary tract, breast cancer, peritoneal cancer, uterine cancer, salivary gland cancer, kidney or renal cancer, prostate cancer, vulval cancer, thyroid cancer, anal carcinoma, penile carcinoma, melanoma, multiple myeloma and B-cell lymphoma (including non-Hodgkin's lymphomas (NHL)); acute lymphoblastic leukemia (ALL); chronic lymphocytic leukemia (CLL); acute myeloid leukemia (AML); Merkel cell carcinoma; hairy cell leukemia; chronic myeloblastic leukemia (CML); and associated metastases.

In addition to cancer therapies, the antibodies provided herein are useful in therapies in which monoclonal antibodies are administered for the purpose of depleting cells, e.g., in the treatment of inflammatory diseases by depletion immune cells. For such purposes the an antibody provided herein is administered in combination with a second therapeutic antibody, e.g. with rituximab for depletion of B cells in inflammatory diseases and autoimmune conditions; alemtuzumab for multiple sclerosis; OKT3 for immunosuppression; others for bone marrow transplant conditioning; and the like.

Further provided herein are methods of treating or delaying progression of an autoimmune disease or an inflammatory disease in an individual by administering an effective amount of an antibody of the present disclosure. Autoimmune diseases and inflammatory diseases amenable to treatment according to the disclosure include, but are not limited to, multiple sclerosis, rheumatoid arthritis, a spondyloarthropathy, systemic lupus erythematosus, an antibody-mediated inflammatory or autoimmune disease, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, asthma, acute respiratory distress syndrome (ARDS), vasculitis, and inflammatory autoimmune myositis. In some embodiments, an antibody of the present disclosure is administered in combination with a therapeutic agent, such as an immunosuppressive, anti-inflammatory, or immunomodulatory agent. In some embodiments, an antibody provided herein is used in the treatment of an autoimmune disease or an inflammatory disease, e.g., multiple sclerosis, rheumatoid arthritis, a spondyloarthropathy, systemic lupus erythematosus, an antibody-mediated inflammatory or autoimmune disease, graft versus host disease, sepsis, diabetes, psoriasis, psoriatic arthritis, atherosclerosis, Sjogren's syndrome, progressive systemic sclerosis, scleroderma, acute coronary syndrome, ischemic reperfusion, Crohn's Disease, ulcerative colitis, endometriosis, glomerulonephritis, IgA nephropathy, polycystic kidney disease, myasthenia gravis, idiopathic pulmonary fibrosis, asthma, atopic dermatitis, acute respiratory distress syndrome (ARDS), vasculitis, or inflammatory autoimmune myositis.

In some embodiments, an antibody of the present disclosure is part of a pharmaceutical formulation, e.g., including the antibody and one or more pharmaceutically acceptable carriers. Pharmaceutical compositions and formulations as described herein can be prepared by mixing the active ingredients (such as an antibody or a polypeptide) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). In some embodiments, an antibody of the present disclosure is lyophilized.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Identification of Antibodies with Novel Binding Specificities to SIRP-α Proteins Methods Antibody Production The following proteins were used for immunization. Each includes a human or mouse SIRP-α peptide fused to a modified Fc region (either an S228P human IgG4 Fc or an L234A/L235A/G237A/N297A human IgG1 Fc designated as IgG1_AAA_N297A) for increased immunogenicity.

TABLE A

Immunogen sequences.

| Description | SEQ ID NO | Sequence |
|---|---|---|
| Human sirpa v1 (Fusion with Fc of IgG4_S228P) | 1 | EEELQVIQPDKSVLVAAGETATLRCTATSLIPV GPIQWFRGAGPGRELIYNQKEGHFPRVTTVSD LTKRNNMDFSIRIGNITPADAGTYYCVKFRKG SPDDVEFKSGAGTELSVRAKPSESKYGPPCPP CPAPEFLGGPSVFLFPPKPKDTLMISRTPEVTC VVVDVSQEDPEVQFNWYVDGVEVHNAKTKP REEQFNSTYRVVSVLTVLHQDWLNGKEYKCK VSNKGLPSSIEKTISKAKGQPREPQVYTLPPSQ EEMTKNQVSLTCLVKGFYPSDIAVEWESNGQ PENNYKTTPPVLDSDGSFFLYSRLTVDKSRWQ EGNVFSCSVMHEALHNHYTQKSLSLSLGK |
| Human sirpa v2 (Fusion with Fc of IgG4_S228P) | 2 | EEELQVIQPDKSVSVAAGESAILHCTVTSLIPV GPIQWFRGAGPARELIYNQKEGHFPRVTTVSE STKRENMDFSISISNITPADAGTYYCVKFRKGS PDTEFKSGAGTELSVRAKPSESKYGPPCPPCPA PEFLGGPSVFLPPPKPKDTLMISRTPEVTCVVV DVSQEDPEVQFNWYVDGVEVHNAKTKPREE QFNSTYRVVSVLTVLHQDWLNGKEYKCKVS NKGLPSSIEKTISKAKGQPREPQVYTLPPSQEE MTKNQVSLTCLVKGFYPSDIAVEWESNGQPE NNYKTTPPVLDSDGSFFLYSRLTVDKSRWQE GNVFSCSVMHEALHNHYTQKSLSLSLGK |
| Mouse 129 sirpa (Fusion with Fc of IgG1_AAA_N297A) | 3 | KELKVTQPEKSVSVAAGDSTVLNCTLTSLLPV GPIKWYRGVGQSRLLIYSFTGEHFPRVTNVSD ATKRNNMDFSIRISNVTPEDAGTYYCVKFQKG PSEPDTEIQSGGGTEVYVLAKPSDKTHTCPPCP APEAAGAPSVFLFPPKPKDTLMISRTPEVTCVV VDVSHEDPEVKFNWYVDGVEVHNAKTKPRE EQYASTYRVVSVLTVLHQDWLNGKEYKCKV SNKALPAPIEKTISKAKGQPREPQVYTLPPSRE EMTKNQVSLTCLVKGFYPSDIAVEWESNGQP ENNYKTTPPVLDSDGSFFLYSKLTVDKSRWQ QGNVFSCSVMHEALHNHYTQKSLSLSPGK |
| Mouse NOD sirpa (Fusion with Fc of IgG1_AAA_N297A) | 4 | TEVKVIQPEKSVSVAAGDSTVLNCTLTSLLPV GPIRWYRGVGQSRQUYSFTTEHFPRVTNVSD ATKRSNLDFSIRISNVTPEDAGTYYCVKFQRG SPDTEIQSGGGTEVYVLAKDKTHTCPPCPAPE AAGAPSVFLFPPKPKDTLMISRTPEVTCVVVD VSHEDPEVKFNWYVDGVEVHNAKTKPREEQ YASTYRVVSVLTVLHQDWLNGKEYKCKVSN KALPAPIEKTISKAKGQPREPQVYTLPPSREEM TKNQVSLTCLVKGFYPSDIAVEWESNGQPEN NYKTTPPVLDSDGSFFLYSKLTVDKSRWQQG NVFSCSVMHEALHNHYTQKSLSLSPGK |

The above proteins were used to immunize wild-type chickens, SynVH chickens which are transgenic chickens containing VH from human and VL from chicken, or chickens with fully human "HuMAB" immunoglobulin loci (Crystal Bioscience; see, e.g., WO2012162422, WO2011019844, and WO2013059159). Chickens were immunized with varied schedules having alternating doses of antigen. An exemplary immunization schedule is as follows: initial immunization with 100 μg dose of antigen having the sequence of SEQ ID NO:1 at week 1, boost of 100 μg of antigen having the sequence of SEQ ID NO: 2 at week 3, draw at week 4, boost with 50 μg dose of antigen having the sequence of SEQ ID NO:1 at week 5, draw at week 6, boost with 50 μg of antigen having the sequence of SEQ ID NO: 2 at week 7, and draw at week 8. Additional descriptions of chicken immunization may be found, e.g., in Mettler Izquierdo, S. et al. (2016) *Microscopy (Oxf)* 1-16.

Screening and Expression of Antibody Clones

Clones were generated and screened according to the GEM assay (see Mettler Izquierdo, S. et al. (2016) *Microscopy (Oxf)* 1-16). Clones were tested in a scFv-Fc format in which the light chain is fused via linker with the heavy chain. The scFv was fused to the N-terminus of human Fc-IgG1. Clones were expressed in FreeStyle™ 293-FS cells (Thermo Fisher) and secreted media was used for ELISA and SPR binding characterization.

SPR

Binding of the antibody clones to various SIRP proteins was determined using surface plasmon resonance (SPR) detection on a ProteOn XPR36 instrument (Bio-Rad, Hercules, CA) using phosphate buffered saline (PBS, pH 7.4) supplemented with 0.01% Tween-20 (PBST) as running buffer. The pre-filtered media containing the secreted antibodies was used directly for the assay. First, anti-Human IgG Fc (BR-1008-39, GE Healthcare) was amine-coupled onto a GLC sensor chip to generate the capture surfaces for the antibodies. About 4000 RU per flow cell of immobilized anti-human IgG Fc is achieved. Each clone is screened using the same method as follows. The SIRP analytes used for the screen are listed in Table C.

(1) ~5-10 uL of pre-filtered media in 10 mM sodium acetate buffer (pH4.5) was injected for 2 mins at 30 ul/min;
(2) buffer flow for 1 min at 100 uL/min;

(3) SIRP analyte (100 nM) injected for 1 min at 100 uL/min, followed by a dissociation cycle of 10 mins;
(4) regeneration of chip surface by flowing 3M Magnesium Chloride for 1 min at 25 uL/min in both orientation; and
(5) buffer flow for 1 min at 100 uL/min.

Biosensor data were double-referenced by subtracting the interspot data (containing no immobilized anti-human IgG Fc) from the reaction spot data (immobilized anti-human IgG Fc) and then subtracting the response of a buffer "blank" analyte injection from that of an analyte injection. Binding was fitted using a 1:1 Langmuir and $K_{off}$ (1/S) values calculated. All SPR assays were performed at 25° C.

ELISA

ELISA assays were carried out to screen binding of antibody clones to SIRP analytes and SIRP-α:CD47 complex. Briefly, 96-well flat-bottom, high binding plates (Greiner Bio-One #655061) were coated with the following proteins in separate ELISA experiments: Avidin (Sigma A9275) (2 ug/ml) followed by biotinylated human SIRPα V1 (0.5 ug/ml), Avidin (2 ug/ml) followed by human SIRPα V2 biotin (0.5 ug/ml), mouse NOD SIRPα (2 ug/ml), human SIRPγ (2 ug/ml), CD47 (2 ug/ml) followed by high affinity human SIRPα V1 and V2 (at 2 ug/ml each) or anti-hFc (2 ug/ml Rockland 609-4103). Plates were blocked with PBSTM (Phosphate Buffered Saline pH 7.4, 0.05% Tween®20 polysorbate, 3% milk), 50 ul of supernatant containing the secreted scFv-Fc are added for 1 hr at room temp. Plates were washed with PBST. 50 ul of anti-hFc-HRP (1:5000 Rockland 609-4303) added for 1 hr at room temp. Plates were washed with PBST. TMB was developed for 5 min and stopped with 1N HCl. ELISA results were read using BioTek Synergy H1 Hybrid Reader. The corresponding proteins used for the assay and described here are: human SIRPα V1 (SEQ ID NO: 5); human SIRPα V2 (SEQ ID NO:6); cynomolgus SIRPα (SEQ ID NO:11); mouse NOD SIRPα (SEQ ID NO: 8); human SIRPγ (SEQ ID NO: 15); CD47 (SEQ ID NO: 16); high affinity SIRPα V1 (SEQ ID NO: 42); high affinity SIRPα V2 (SEQ ID NO:17).

Results

SIRP-α is a highly polymorphic protein in humans, monkeys, and mice. For example, 20 amino acid differences have been identified between SIRP-α proteins in the NOD and C57BL/6 mouse strains, and these polymorphisms lead to functional consequences related to CD47 binding and engraftment of human hematopoietic stem cells in these mouse strains. In humans, at least 10 distinct alleles of SIRPA have been identified, and amino acid variations that distinguish the alleles are found in predicted CD47-binding residues (Takenaka, K. et al. (2007) Nat. Immunol. 8:1313-23). An alignment of 10 human variant SIRP-α protein sequences is provided in FIG. 1A. The identification of antibodies having different binding specificities with intra- and/or inter-species cross-reactivity is of great interest for development of clinical candidates that are effective across human populations and the characterization of these candidates in various animal models.

The D1 domains of SIRP-α proteins from human (v1 and v2 variants), cynomologus monkey, and mouse 129 were aligned to identify conserved amino acids (FIG. 1B). While the cynomolgus monkey and mouse 129 sequences are much more divergent from human v1 and v2 than human variants v3-v10 as shown in FIG. 1A, these alignments demonstrate some degree of conservation among all four proteins, suggesting that cross-reactive antibodies could perhaps be identified. However, each protein also shows unique polymorphisms, suggesting that specific antibodies were also possible.

As shown in FIG. 1C, SIRP-α protein sequences representing multiple human variants and mouse strains (e.g., 129, NOD, C57BL/6, and BALB/c) were also aligned. R1, R2, R3 delineate residues located around binding sites of SIRPα to CD47. These alignments demonstrated that the R2 and R3 are considerably more divergent among and between human and mouse sequences than the R1. Without wishing to be bound to theory, it is thought that anti-SIRP-α antibodies that bind to specific murine SIRP-α proteins may be useful, e.g., for pharmacokinetic studies (such as those using CD-1 mice), development of transgenic mice (such as those in a C57BL/6 background), and/or characterization in SCID (e.g., in a NOD background) or syngeneic (e.g., in a BALB/c or C57BL/6 background) mouse models.

Mammalian SIRP-α D1 domains described above were also aligned with the D1 domain of chicken SIRP-α comprising the sequence DFKLQQPQSSVVVIKGDTLTLNC-TASGSGPIGAVKWVKGWGSDNQTVYEHKGSFPRVM RAVPDPTNDFTIRISNVSLEDAGTYYCVKLRK-GIVDDVVFTRGGGTEVSVHA (SEQ ID NO:84) (FIG. 2). Compared with the mammalian SIRP-α sequences, the sequence of chicken SIPRα was found to be significantly more divergent. Pairwise comparisons of the percentage of sequence identity between various SIRP-α proteins is shown in Table B.

TABLE B

| Pairwise sequence identities (%) between SIRP-α proteins. | | | | | |
|---|---|---|---|---|---|
| | Human v1 (SEQ ID NO: 5) | Human v2 (SEQ ID NO: 6) | Mouse (SEQ ID NO: 7) | Cyno (SEQ ID NO: 11) | Chicken (SEQ ID NO: 84) |
| Human v1 (SEQ ID NO: 5) | — | 89 | 66 | 91 | 46 |
| Human v2 (SEQ ID NO: 6) | 89 | — | 68 | 88 | 41 |
| Mouse (SEQ ID NO: 7) | 66 | 68 | — | 72 | 47 |
| Cyno (SEQ ID NO: 11) | 91 | 88 | 72 | — | 47 |
| Chicken SEQ ID NO: 84) | 46 | 41 | 47 | 47 | — |

Without wishing to be bound to theory, it was thought that this divergence would provide unique opportunities to generate antibodies that cross-react across multiple mammalian SIRP-α proteins. For example, it may be difficult to generate anti-SIRP-α antibodies that cross-react with the murine sequence from a mouse host due to immune tolerance. Moreover, the greater divergence between the chicken and mammalian immune systems may lead to a greater diversity in antibody production.

In order to identify antibodies with novel binding specificities to SIRP-α proteins, antibody clones were characterized in the scFv-Fc format as described above. Each antibody clone was tested at concentrations between 0.008 and 1.0 µg/mL for binding using ELISA to the following targets: the D1 domain of human SIRP-α v1 (sequence according to SEQ ID NO:5), the D1 domain of human SIRP-α v2 (sequence according to SEQ ID NO:6), the D1 domain of a cynomolgus SIRP-α variant (sequence according to SEQ ID NO:11), the D1 domain of mouse 129 SIRP-α (sequence according to SEQ ID NO:7), and a human SIRPγ isoform (sequence according to SEQ ID NO:15). As used hereinafter, antibody clones are referred to by clone ID number. In addition, the notation "S[clone number]" refers to an sc-Fv-Fc format; the notation "AB[clone number]" refers to a full IgG antibody format; the notation "AB[clone number]a" refers to a human IgG1 with L234A, L235A, G237A, and N297A mutations; "AB[clone number]b" refers to a mouse IgG1 N297A format; "AB[clone number]c" refers to a mouse IgG2a format; and "[clone number] Fab" refers to a Fab fragment format.

In addition, the binding of each antibody clone to a pre-complex prepared using a 1:1 mix of two high affinity SIRP-α variants (SEQ ID NO:42 and SEQ ID NO:18) bound with the IgSF domain of CD47 (sequence according to SEQ ID NO:16) was characterized. Advantageously, since the affinity between the wild-type SIRP-α D1 domain and the IgSF domain of CD47 is relatively low, the use of a complex comprising a high affinity SIRP-α variant allows the identification of antibodies that bind to SIRP-α while it is complexed with CD47 (e.g., a non-blocking antibody). It also allows the identification of antibodies that are unable to bind SIRP-α while it is complexed with CD47, suggesting that the antibody and CD47 compete for the same binding interface on SIRP-α (e.g., a blocking antibody). The two SIRPα variants used (SEQ ID NO:17 and SEQ ID NO:19) correspond to high affinity SIRPα D1 domain engineered using human SIRPα polypeptide variant 1 and variant 2, respectively.

FIG. 3A shows the ELISA binding curve for clone S130 (SEQ ID NO:71). This clone demonstrated cross-reactivity across mammalian SIRP-α proteins, with binding to multiple human variants as well as cynomolgus and murine proteins (FIG. 3B). However, its binding was also isoform-specific, since no binding was observed with human SIRPγ. This clone was also identified as a blocker of the interaction between SIRP-α and CD47, as no binding to a pre-formed complex containing CD47 bound to a high-affinity SIRP-α variant was detected.

FIG. 4A shows the ELISA binding curve for clone S121 (SEQ ID NO:75). This clone also demonstrated cross-reactivity across mammalian SIRP-α proteins, but it also bound to human SIRPγ, indicating pan-isoformic binding (FIG. 4B). This clone was also identified as a blocker of the interaction between SIRP-α and CD47.

FIG. 5A shows the ELISA binding curve for clone S137 (SEQ ID NO:73). Like the clone shown in FIGS. 3A & 3B, this clone demonstrated cross-reactivity across mammalian SIRP-α proteins with isoform-specific binding, as it did not bind to human SIRPγ (FIG. 5B). However, this clone was identified as a non-blocker of the interaction between SIRP-α and CD47, since it bound to the pre-formed complex.

FIG. 6A shows the ELISA binding curve for clone S128 (SEQ ID NO:70). This clone demonstrated isoform-specific cross-reactivity across primate SIRP-α proteins, but it did not bind to the murine protein (FIG. 6B). This clone was also identified as a blocker of the interaction between SIRP-α and CD47.

FIG. 7A shows the ELISA binding curve for clone S135 (SEQ ID NO:72). Similar to the clone shown in FIGS. 6A & 6B, this blocking clone demonstrated cross-reactivity across primate SIRP-α proteins, but it did not bind to the murine protein (FIG. 7B). Unlike clone S128, this clone was found to cross-react with human SIRPγ.

FIG. 8A shows the ELISA binding curve for clone S126 (SEQ ID NO:69). This clone was found to be human-specific, binding to both human SIRP-α variants but none of the other peptides (FIG. 8B). This clone was identified as a blocker of the interaction between SIRP-α and CD47.

Figure 9A:
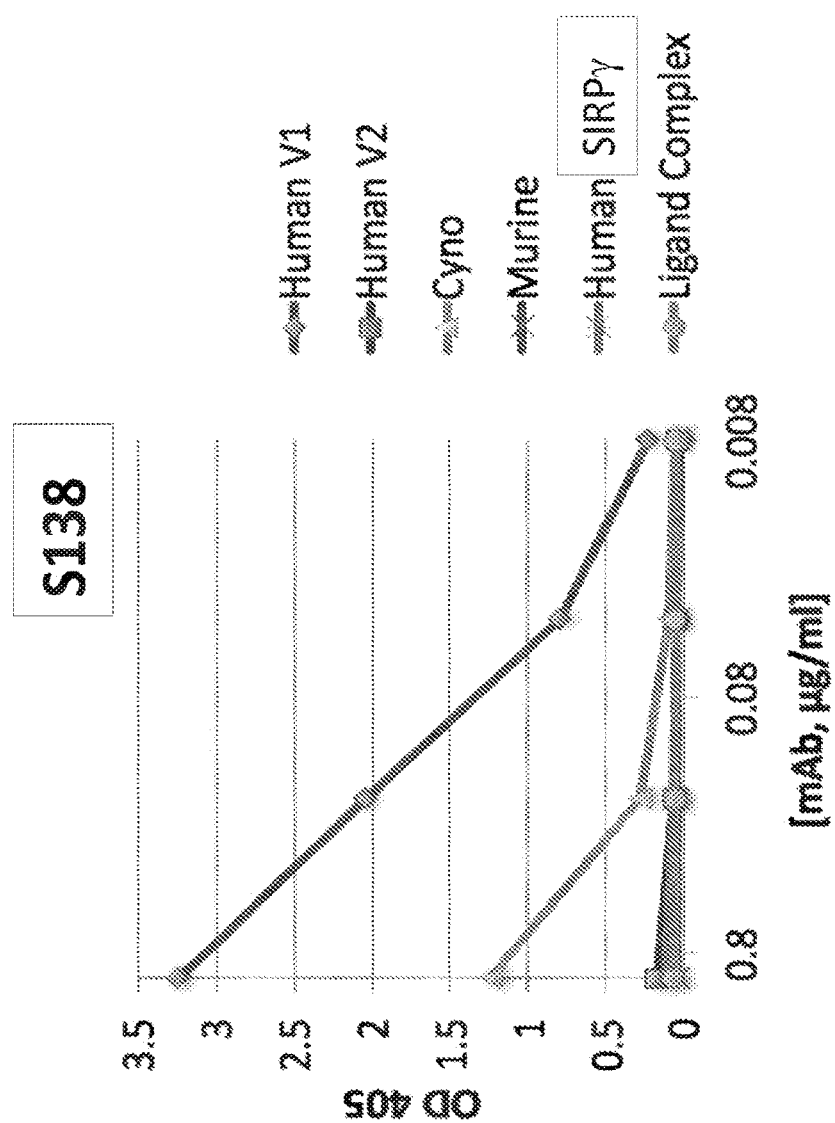
Figure 9B:
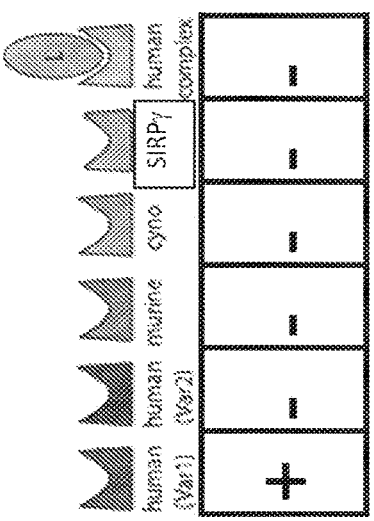

FIG. 9A shows the ELISA binding curve for clone S138 (SEQ ID NO:74). This clone only bound human SIRP-α variant 1, demonstrating a high degree of intra- and inter-species binding specificity (FIG. 9B). This clone was identified as a blocker of the interaction between SIRP-α and CD47.

Figure 10E:
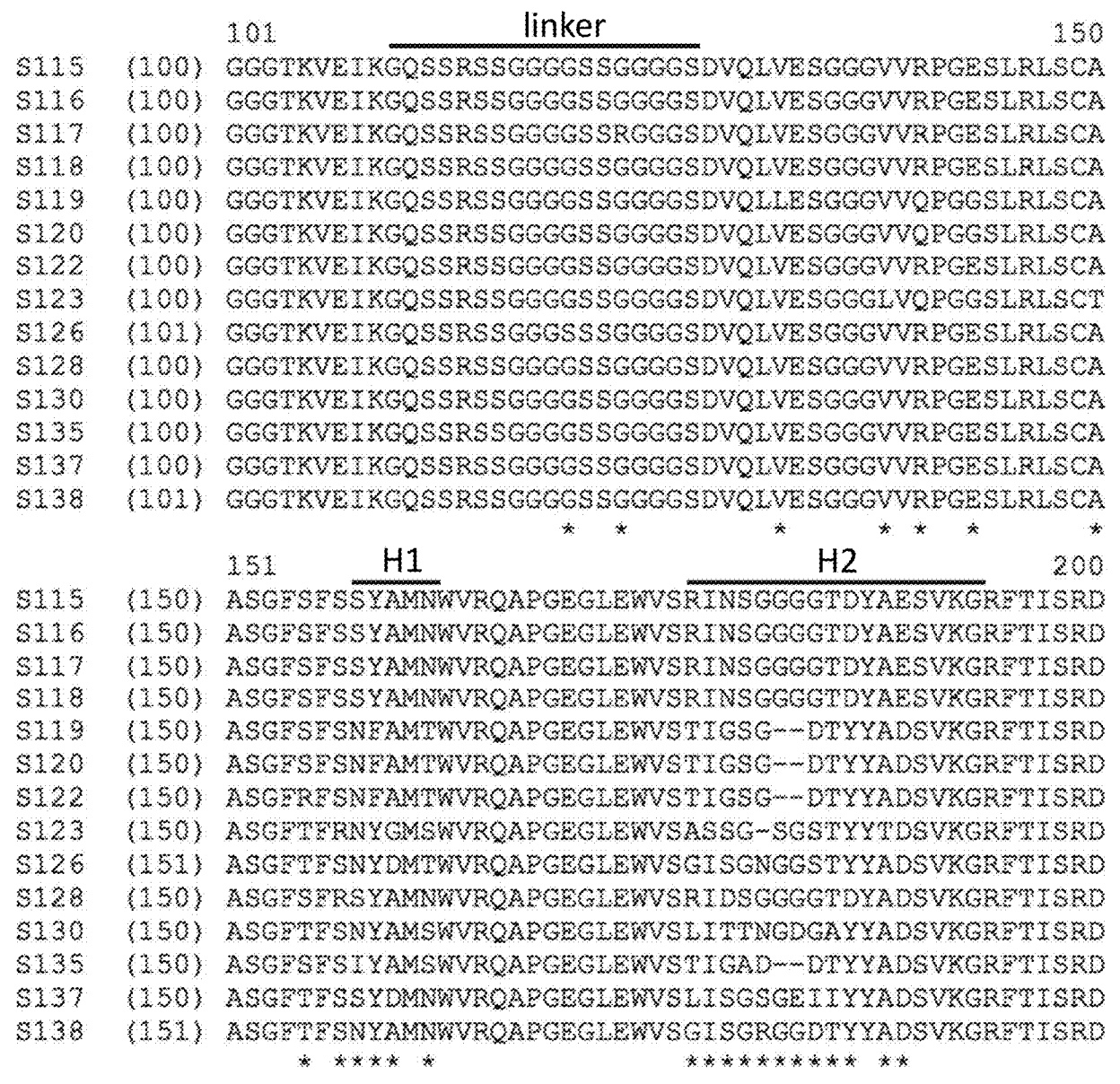

In conclusion, novel antibodies with a number of unique binding specificities to SIRP-α proteins were characterized. FIGS. 10A-10C provide an alignment showing scFv-Fc variable domain sequences obtained from a chicken that produces chicken antibodies (CDRs are indicated). FIGS. 10D-10F provide an alignment showing scFv-Fc variable domain sequences obtained from a chicken that produces human antibodies (CDRs are indicated). These studies highlight the utility of the chicken as a source of antibody diversity for the identification of anti-SIRP-α antibodies.

To assess if antibodies can block binding of SIRPα to CD47, an SPR screen was also carried out, in addition to screening by ELISA. Antibody capture was carried out using an anti-human IgG-Fc immobilized GLC surface prepared as described above. A SIRPα variant (SEQ ID NO:17) engineered to bind CD47 (SEQ ID NO:16) with high nM affinity was used for the screen rather than a wildtype SIRP-α. This is because the wildtype SIRP-α variant has low uM binding affinity to CD47, which does not allow stable complex interaction to assess sandwich formation. Phosphate buffered saline (PBS, pH 7.4) supplemented with 0.01% Tween-20 (PBST) as running buffer.

First, approximately 5-10 uL of pre-filtered media containing the antibodies in 10 mM sodium acetate buffer (pH4.5) was injected for 2 mins at 30 ul/min and captured over the anti-human IgG-Fc immobilized GLC surface followed by a brief buffer flow of 1 min at 100 uL/min. Next, 100 nM of a high affinity SIRP-α variant (SEQ ID NO:17) pre-mixed with CD47 (SEQ ID NO:16) at different concentrations of 0, 20, 55, 500, or 1500 nM was injected separately for a minute at 100 uL/min with a dissociation time for 10 mins. For the description below, SIRP-α refers to SEQ ID NO:17.

Figure 12A:
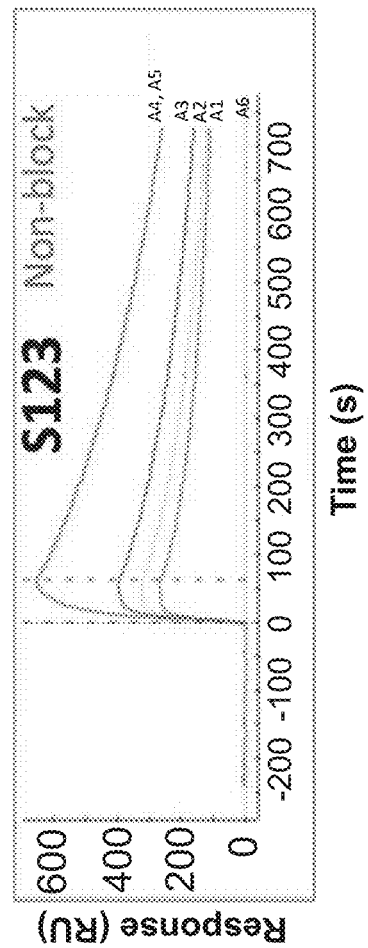

For an antibody that does not block binding of SIRP-α to CD47, it would be expected to bind to SIRP-α/CD47 complex and form a sandwich. Therefore, at increasing concentration of CD47, the resonance increased accordingly due to increased sandwich formation. Antibody clone S123 was found to match this profile. An example of the profile for S123 is shown in FIG. 12A.

Figure 12B:
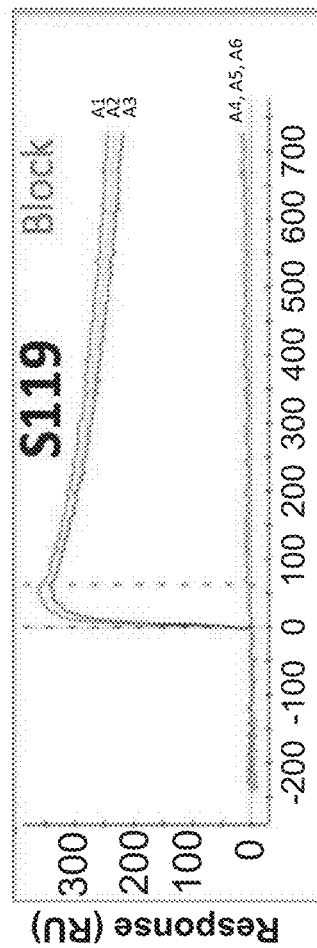

For an antibody that blocks binding of SIRP-α to CD47, the profile will be different than a non-blocking antibody. At increasing concentration of CD47, one would expect fewer molecules of SIRP-α to be available to bind to the antibody since the antibody competes for the same binding site as CD47 and most/all SIRP-α is complexed with CD47. Therefore, one would expect the resonance (RU) to decrease with increasing concentration of CD47 in the mixture. Antibody clone S119 was found to match this profile. An example of the profile for S119 is shown in FIG. 12B.

Figure 12C:
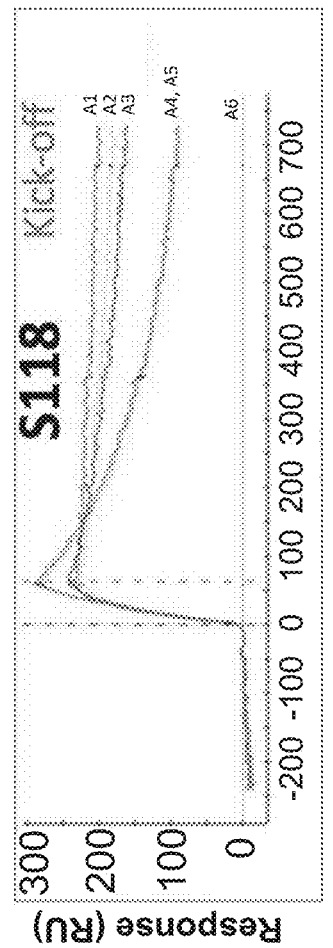

In addition to blockers and non-blockers, a third category of antibodies was isolated that have a "kick off" profile. Antibody clone S118 was found to match this profile. An example of the profile for S118 is shown in FIG. 12C. At higher concentration of CD47 (e.g 500 nM and 1500 nM CD47), a transient sandwich was formed between the antibody, SIRP-α and CD47 as indicated by the higher resonance of 300 RU which then decayed over time. This decay of resonance units indicates that the antibody was able to bind to SIRP-α in the complex and "kick SIRP-α off" from binding to CD47.

The $k_{off}$ rates of binding of each clone to each SIRP analyte were determined using SPR (Table C). The SPR screening conditions have been described herein, and the Koff values were determined using Langmuir kinetic fittings. The CD47 blocking properties (block, non-block, kick-off) are described in the last column of the Table C. Each antibody is identified according to its corresponding SEQ ID NO. SIRP analyte sequences are as follows: CV1-3, SEQ ID NO:18; v1, SEQ ID NO:5; v2, SEQ ID NO:6; cyno1, SEQ ID NO:11; cyno2, SEQ ID NO:12; m129, SEQ ID NO:7; NOD, SEQ ID NO:8; BL6, SEQ ID NO: 9; sirpb1, SEQ ID NO:13; sirpg, SEQ ID NO:15.

TABLE C

Langmuir kinetic fittings ($k_{off}$ 1/s)

| Clone | SEQ ID NO | CV1-3 | v1 | v2 | cyno1 | cyno2 | m129 | NOD | BL6 | sirpb1 | sirpg | cd47 blocking |
|---|---|---|---|---|---|---|---|---|---|---|---|---|
| S1 | 53 | 2.19E-03 | 2.33E-03 | NB | 3.48E-02 | 4.06E-03 | 2.12E-03 | 7.89E-03 | 1.70E-03 | NB | 2.19E-03 | Block |
| S2 | 54 | 1.49E-01 | 2.52E-03 | NB | LB | 5.59E-03 | 1.42E-02 | NB | 8.85E-03 | — | — | Block |
| S8 | 55 | LB | 1.14E-04 | 1.42E-04 | 4.15E-03 | 6.12E-04 | 1.29E-02 | 1.79E-03 | 6.96E-03 | 9.30E-04 | 3.23E-04 | Block |
| S9 | 56 | 1.68E-04 | 1.29E-04 | 1.40E-04 | 3.38E-04 | 2.70E-04 | NB | 1.81E-02 | NB | 1.03E-04 | 7.10E-03 | Block |
| S11 | 57 | 2.69E-03 | 3.35E-05 | 1.86E-04 | 1.11E-03 | 3.92E-03 | NB | LB | LB | 1.59E-04 | 3.86E-04 | Block |
| S12 | 58 | 5.15E-02 | 1.01E-04 | 1.68E-04 | 1.17E-03 | 5.24E-04 | NB | 2.60E-02 | 1.98E-03 | 1.73E-04 | 3.07E-04 | Block |
| S13 | 59 | LB | 2.07E-04 | 2.91E-04 | 1.84E-03 | 5.01E-04 | 4.93E-02 | 3.83E-03 | 1.03E-02 | 1.35E-04 | 4.02E-04 | Block |
| S14 | 60 | 3.33E-03 | 5.42E-05 | 7.64E-05 | 6.49E-04 | 4.52E-04 | 3.73E-02 | 4.98E-03 | 1.81E-02 | 6.01E-05 | 1.26E-04 | Block |
| S115 | 61 | 4.84E-04 | 7.86E-06 | 1.95E-05 | 2.22E-05 | 6.91E-05 | NB | NB | NB | — | 3.34E-05 | Kick off |
| S116 | 62 | 4.80E-04 | 2.84E-05 | 5.07E-05 | 7.01E-05 | 1.20E-04 | NB | NB | NB | — | 8.25E-05 | Kick off |
| S117 | 63 | 2.75E-04 | 1.20E-05 | 3.40E-05 | 1.83E-05 | 5.92E-05 | NB | NB | NB | — | 4.30E-06 | Kick off |
| S118 | 64 | 2.47E-04 | 9.17E-06 | 4.12E-05 | 6.97E-05 | 8.06E-05 | NB | NB | NB | 1.31E-05 | 1.13E-05 | Kick off |
| S119 | 65 | 5.65E-04 | 4.15E-04 | 1.48E-04 | 2.34E-04 | 3.10E-04 | NB | LB | NB | 4.28E-04 | 3.95E-04 | Block |
| S120 | 66 | 6.26E-04 | 4.04E-04 | 1.49E-04 | 2.36E-04 | 3.14E-04 | NB | LB | NB | 4.25E-04 | 3.93E-04 | Block |
| S122 | 67 | 6.63E-04 | 4.98E-04 | 2.26E-04 | 2.66E-04 | 3.27E-04 | NB | LB | NB | 3.52E-04 | 3.61E-04 | Block |
| S123 | 68 | 1.31E-03 | 1.55E-03 | NB | 1.57E-03 | 1.54E-03 | NB | NB | NB | NB/LB | 1.43E-03 | Non-block |
| S126 | 69 | NB | NB | NB | NB | NB | NB | NB | NB | NB | NB | — |
| S128 | 70 | NB | 4.59E-03 | 2.11E-03 | 1.52E-02 | 1.47E-02 | NB | NB | NB | 4.21E-03 | NB | — |
| S130 | 71 | 3.73E-03 | 2.82E-03 | 2.08E-02 | LB | LB | LB | NB | NB | LB | 5.06E-03 | Block |
| S135 | 72 | 3.63E-03 | 6.58E-04 | 8.78E-05 | 4.73E-04 | 3.88E-04 | NB | NB | NB | 5.21E-04 | 1.46E-03 | Block |
| S137 | 73 | 1.37E-03 | 1.65E-03 | 1.88E-03 | 2.04E-03 | 1.79E-03 | 5.15E-04 | 4.43E-04 | 4.63E-03 | 3.76E-03 | 1.48E-02 | Non-block |
| S138 | 74 | LB | NB | NB | NB | NB | NB | NB | NB | NB | NB | — |

NB = No binding
LB = very low binding ($K_{off}$ cannot be calculated by Langmuir fittings)
— = not screened These data indicate that antibody clones with a variety of binding specificities for SIRP-α proteins across different species and intra-species variants were identified. The binding specificities for selected antibodies were further characterized using ELISA as described above by generating binding curves against the human v1 (SEQ ID NO: 5), human v2 (SEQ ID NO: 6), NOD mouse (SEQ ID NO:8), and cynomolgus SIRP-α D1 domains (SEQ ID NO:11), as well as human SIRPγ (SEQ ID NO: 15) and a pre-formed complex of a 1:1 mixture of two high-affinity SIRP-α variants (SEQ ID NOs:17 and 19) bound to the IgSF domain of CD47 (SEQ ID NO: 16).

Sequences of scFv-Fc clones tested are provided in Table D.

TABLE D scFv-Fc sequences.

| Clone | Framework/CDR | SEQ ID NO | Sequence |
|---|---|---|---|
| S1 | Chicken | 53 | ALTQPASVSANPGETVEITCSGGGSNNAYGWFQQKSPGSAPLTVIYDNGKRPSDIPSRFSGSKSDSTGTLTITRVQAEDEAVYYCGSADNSGAGVFGAGTTLTVLGQSSRSSGGGGSSGGGGSMAAVTLDESGGGLQTPGGALSLVCKGSGFTFSSHAMNWVRQAPGKGLEWVAGISSDGRFTYYGAAVQGRATISRDNGQSTVRLQLNNLRAEDTATYYCTKNGGCGSGGDLDCIDAWGHGTEVIVSSSLDPKSSDKTHTCPPCPAPELLGGPSVFLFPPKPKDTLMISRTPEVTCVVVDVSHEDPEVKFNWYVDGVEVHNAKTKPREEQYNSTYRVVSVLTV |

TABLE D-continued scFv-Fc sequences.

| Clone | Framework/ CDR | SEQ ID NO | Sequence |
|---|---|---|---|
| | | | LHQDWLNGKEYKCKVSNKALPAPIEKTISKAKGQ<br>PREPQVYTLPPSRDELTKNQVSLTCLVKGFYPSDIA<br>VEWESNGQPENNYKTTPPVLDSDGSFFLYSKLTVD<br>KSRWQQGNVFSCSVMHEALHNHYTQKSLSLSPGK<br>V |
| S2 | Chicken | 54 | AVTQPASVSANPGETVRITCSGDSSSYYSWHQQKS<br>PGSAPVSVIYSNTDRPSDIPSRFSGSASGSTATLTIT<br>GVQAEDEAVYFCGAYDSSSDSDIFGAGTTLTVLGQ<br>SSRSSGGGGSSGGGGSMAAVTLDESGGGLQTPGG<br>GLSLVCKASGFDFSNFNMAWVRQGPGKGLEYVA<br>EISDTGSTPYYGSAVQGRATISRDNGQSTVRLQLN<br>NLRAEDTGTYFCTRNFGSSVSSIDAWGHGTEVIVS<br>SSLDPKSSDKTHTCPPCPAPELLGGPSVFLFPPKPK<br>DTLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQVYT<br>LPPSRDELTKNQVSLTCLVKGFYPSDIAVEWESNG<br>QPENNYKTTPPVLDSDGSFFLYSKLTVDKSRWQQ<br>GNVFSCSVMHEALHNHYTQKSLSLSPGKV |
| S8 | Chicken | 55 | AVTQPSSVSANPGETVEITCSGSSTYYGWYQQKSP<br>GSAPVTVIYDNDKRPSDIPSRFSGSKSGSTHTLIITG<br>VQVEDEAVYFCGNEDNNYVAIFGAGTTLTVLGQS<br>SRSSGGGGSSGGGGSMAAVTLDESGGGLQTPGGA<br>LSLVCKASGFTFSSYNMGWVRQAPGKGLEFVAGI<br>YASGSSTDTDTTYGPAVAGRATISRDNGQSTVRLQ<br>LNNLRAEDTGTYYCAKAAGGCSTHTCTAYIADSID<br>AWGHGTEVIVSSSLDPKSSDKTHTCPPCPAPELLG<br>GPSVFLFPPKPKDTLMISRTPEVTCVVVDVSHEDPE<br>VKFNWYVDGVEVHNAKTKPREEQYNSTYRVVSV<br>LTVLHQDWLNGKEYKCKVSNKALPAPIEKTISKA<br>KGQPREPQVYTLPPSRDELTKNQVSLTCLVKGFYP<br>SDIAVEWESNGQPENNYKTTPPVLDSDGSFFLYSK<br>LTVDKSRWQQGNVFSCSVMHEALHNHYTQKSLSL<br>SPGKV |
| S9 | Chicken | 56 | ALTQPSSVSANPGETVKITCSGDNSAHYYYGWYQ<br>QKSPGSAPVTVIYYNDKRPSGIPSRFSGSASGSTAT<br>LIITGVQVEDEAVYFCGSADSSNPAIFGAGTTLTVL<br>GQSSRSSGGGGSSGGGGSMAAVTLDESGGGLQTP<br>GRALSLVCRGSGFSISSYNMGWVRQAPGKGLEFIA<br>SIGSDGSSTHYAPAVKGRATITRDVGQSTVRLQLN<br>NLRAEDTGTYFCAKDAYQCSYATCNDYLDTIDAW<br>GHGTEVIVSSSLDPKSSDKTHTCPPCPAPELLGGPS<br>VFLFPPKPKDTLMISRTPEVTCVVVDVSHEDPEVK<br>FNWYVDGVEVHNAKTKPREEQYNSTYRVVSVLT<br>VLHQDWLNGKEYKCKVSNKALPAPIEKTISKAKG<br>QPREPQVYTLPPSRDELTKNQVSLTCLVKGFYPSDI<br>AVEWESNGQPENNYKTTPPVLDSDGSFFLYSKLTV<br>DKSRWQQGNVFSCSVMHEALHNHYTQKSLSLSPG<br>KV |
| S11 | Chicken | 57 | AVTQPASVSANPGETVKITCSGSSSGSYGWYQQKS<br>PGSAPVTLIYETNKRPSNIPSRFSGSKSGSTATLTIT<br>GVQADDEAVYYCGSEDSSTYLSIFGAGTTLTVLGQ<br>SSRSSGGGGSSGGGGSMAAVTLDESGGGLQTPGG<br>ALSLVCKASGFTFSSFNMGWVRQAPGKGLEFVAA<br>IYSGNSAEYGAAVQGRATISRDNGQSTVRLQLNNL<br>RAEDTGIYFCAKDAGSGCYSGVCAGTSSIDAWGH<br>GTEVIVSSSLDPKSSDKTHTCPPCPAPELLGGPSVFL<br>FPPKPKDTLMISRTPEVTCVVVDVSHEDPEVKFNW<br>YVDGVEVHNAKTKPREEQYNSTYRVVSVLTVLHQ<br>DWLNGEEYKCKVSNKALPAPIEKTISKAKGQPREP<br>QVYTLPPSRDELTKNQVSLTCLVKGFYPSDIAVEW<br>ESNGQPENNYKTTPPVLDSDGSFFLYSKLTVDKSR<br>WQQGNVFSCSVMHEALHNHYTQKSLSLSPGKV |
| S12 | Chicken | 58 | AVTQPASVSANPGETVKITCSGDSSYYGWYQQKS<br>PGSAPVTVIYDDNKRPSNIPSRFSGSKSGSTGTLTIT<br>GVQADDEAVYFCGNEDNSYVAIFGAGTTLTVLGQ<br>SSRSSGGGGSSGGGGSMAAVTLDESGGGLQTPGG<br>ALSLVCKASGFTFSSYNMGWVRQAPGKGLEFVAG<br>IYIASGDLGTTYGAAVQGRATISRDDGQSTVRLQL<br>NNLRAEDTGTYFCAKSAGGCSAHSCDTYIADSIDA |

TABLE D-continued scFv-Fc sequences.

| Clone | Framework/ CDR | SEQ ID NO | Sequence |
|---|---|---|---|
| | | | WGHGTEVIVSSSLDPKSSDKTHTCPPCPAPELLGGP SVFLFPPKPKDTLMISRTPEVTCVVVDVSHEDPEV KFNWYVDGVEVHNAKTKPREEQYNSTYRVVSVL TVLHQDWLNGKEYKCKVSNKALPAPIEKTISKAK GQPREPQVYTLPPSRDELTKNQVSLTCLVKGFYPS DIAVEWESNGQPENNYKTTPPVLDSDGSFFLYSKL TVDKSRWQQGNVFSCSVMHEALHNHYTQKSLSLS PGKV |
| S13 | Chicken | 59 | AVTQPASVSANPGETVKITCSGSSSYYGWYRQKSP GSAPVTLIYDNDKRPSGIPSRFSGSKSGSTNTLTITG VQADDEAVYYCGNEDNSYVGIFGAGTTLTVLGQS SRSSGGGGSSGGGGSMAAVTLDESGGGLQTPGGA LSLVCKASGFTFSSYNMGWVRQAPDKGLEFVAGI YTGSDAGLSTTYGAAVQGRATISRDNGQSTVRLQ LNNLGAEDTGIYFCTKSAGGCSDYNCDAYIADSID AWGHGTEVIVSSSLDPKSSDKTHTCPPCPAPELLG GPSVFLFPPKPKDTLMISRTPEVTCVVVDVSHEDPE VKFNWYVDGVEVHNAKTKPREEQYNSTYRVVSV LTVLHQDWLNGKEYKCKVSNKALPAPIEKTISKA KGQPREPQVYTLPPSRDELTKNQVSLTCLVKGFYP SDIAVEWESNGQPENNYKTTPPVLDSDGSFFLYSK LTVDKSRWQQGNVFSCSVMHEALHNHYTQKSLSL SPGKV |
| S14 | Chicken | 60 | AVTQPASVSANLGETVKITCSGDSSYYGWYQQKA PGSAPVTLIYDNDKRPSNIPSRFSGSKSGSTATLTIT GVQADDEAVYYCGNEDMNYVGIFGAGTTLTVLG QSSRSSGGGGSSGGGGSMAAVTLDESGGGLQTPG GALSLVCKASGFTFNSYNMGWVRQAPGKGLEFV AGIYSAGGDTSTTYGAAVNGRATISRDNGQSTVRL QLNNLRAEDTGIYFCAKAAGGCTAHNCDAYIADSI DAWGHGTEVIVSSSLDPKSSDKTHTCPPCPAPELL GGPSVFLFPPKPKDTLMISRTPEVTCVVVDVSHEDP EVKFNWYVDGVEVHNAKTKPREEQYNSTYRVVS VLTVLHQDWLNGKEYKCKVSNKALPAPIEKTISK AKGQPREPQVYTLPPSRDELTKNQVSLTCLVKGFY PSDIAVEWESNGQPENNYKTTPPVLDSDGSFFLYS KLTVDKSRWQQGNVFSCSVMHEALHNHYTQKSL SLSPGKV |
| S115 | Human | 61 | ETVLTQSPATLSVSPGERATLSCRASQTVGSKLAW HQQKPGQAPRLLIYDATNRATGISDRFSGSGSGTD FTLTISSLQTEDSAVYYCQQYYYWPPYRFGGGTKV EIKGQSSRSSGGGGSSGGGGSDVQLVESGGGVVRP GESLRLSCAASGFSFSSYAMNWVRQAPGEGLEWV SRINSGGGGTDYAESVKGRFTISRDNSENTLYLQM NSLRAEDTAVYYCAKQYDWNSFFDYWGLGALVT VSSSLDPKSSDKTHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S116 | Human | 62 | ETVLTQSPATLSVSPGERATLSCRASQTVGSKLAW HQQKPGQAPRLLIYDATNRATGISDRFSGSRSGTD FTLTISSLQTEDSAVYYCQQYYYWPPYRFGGGTKV EIKGQSSRSSGGGGSSGGGGSDVQLVESGGGVVRP GESLRLSCAASGFSFSSYAMNWVRQAPGEGLEWV SRINSGGGGTDYAESVKGRFTISRDNSENTLYLQM NSLRAEDTAVYYCAKQYDWNSFFDYWGLGALVT VSSSLDPKSSDKTHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S117 | Human | 63 | ETVLTQSPATLSVSPGERATLSCRASQTVGSKLAW HQQKPGQAPRLLIYDATNRATGIPDRFSGSGSGTD FTLTISSLQTEDSAVYYCQQYYYWPPYRFGGGTKV EIKGQSSRSSGGGGSSRGGGSDVQLVESGGGVVRP |

TABLE D-continued scFv-Fc sequences.

| Clone | Framework/CDR | SEQ ID NO | Sequence |
|---|---|---|---|
| | | | GESLRLSCAASGFSFSSYAMNWVRQAPGEGLEWV SRINSGGGGTDYAESVKGRFTISRDNSENTLYLQM NSLRAEDTAVYYCAKQYDWNGFFDYWGLGALVT VSSSLDPKSSDKTHTCPPCPVPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S118 | Human | 64 | ETVLTQSPATLSVSPGERATLSCRASQTVGSKLAW HQQKPGQAPRLLIYDASRRATGIPDRFSGSGSTDF TLTISSLQTEDSAVYYCQQYYYWPPYRFGGGTKV EIKGQSSRSSGGGGSSGGGGSDVQLVESGGGVVRP GESLRLSCAASGFSFSSYAMNWVRQAPGEGLEWV SRINSGGGGTDYAESVKGRFTISRDNSENTLYLQM NSLRAEDTAVYYCAKQYDWNGFFDYWGLGALVT VSSSLDPKSSDKTHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S119 | Human | 65 | EIVLTQSPATLSVSPGERATFSCRASQNVKNDLAW YQQRPGQAPRLLIYAARIRETGIPERFSGSGSGTEFT LTITSLQSEDFAVYYCQQYYDWPPFTFGGGTKVEI KGQSSRSSGGGGSSGGGGSDVQLLESGGGVVQPG GSLRLSCAASGFSFSNFAMTWVRQAPGEGLEWVS TIGSGDTYYADSVKGRFTISRDNSKNTLYLQMNSL RAEDTAVYYCAKDSTVSWSGDFFDYWGLGTLVT VSSSLDPKSSDKPHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S120 | Human | 66 | EIVLTQSPATLSVSPGERATFSCRASQNVKNDLAW YQQRPGQAPRLLIYAARIRETGIPERFSGSGSGTEFT LTITSLQSEDFAVYYCQQYYDWPPFTFGGGTKVEI KGQSSRSSGGGGSSGGGGSDVQLVESGGGVVQPG GSLRLSCAASGFSFSNFAMTWVRQAPGEGLEWVS TIGSGDTYYADSVKGRFTISRDNSKNTLYLQMNSL RAEDTAVYYCAKDSTVSWSGDFFDYWGLGTRVT VSSSLDPKSSDKTHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S122 | Human | 67 | EIVLTQSPATLSVSPGERATFSCRASQNVKNDLAW YQQRPGQAPRLLIYAARIRETGIPERFSGSGSGTEFT LTITSLQSEDFAVYYCQQYYDWPPFTFGGGTKVEI KGQSSRSSGGGGSSGGGGSDVQLVESGGGVVRPG ESLRLSCAASGFRFSNFAMTWVRQAPGEGLEWVS TIGSGDTYYADSVKGRFTISRDNSKNTLYLQMNSL RAEDTAVYYCAKDSTVSWSGDFFDYWGLGTLVT VSSSLDPKSSDKTHTCPPCPAPELLGGPSVFLFPPKP KDTLMISRTPEVTCVVVDVSHEDPEVKFNWYVDG VEVHNAKTKPREEQYNSTYRVVSVLTVLHQDWL NGKEYKCKVSNKALPAPIEKTISKAKGQPREPQVY TLPPSRDELTKNQVSLTCLVKGFYPSDIAVEWESN GQPENNYKTTPPVLDSDGSFFLYSKLTVDKSRWQ QGNVFSCSVMHEALHNHYTQKSLSLSPGKV |
| S123 | Human | 68 | EIVLTQSPGTLSVSPGERVTLTCRASQGIAGKIAWY QQKPGQAPRLLIYDASSRATGIPGRFSGSGSGTEFT LTITSLQSEDFAVYYCQQHYDWSPLTFGGGTKVEI KGQSSRSSGGGGSSGGGGSDVQLVESGGGLVQPG |

TABLE D-continued scFv-Fc sequences.

| Clone | Framework/CDR | SEQ ID NO | Sequence |
|---|---|---|---|
| | | | GSLRLSCTASGFTFRNYGMSWVRQAPGEGLEWVS<br>ASSGSGSTYYTDSVKGRFTISRDNSKNTLYLQMNS<br>LRAEDTAIYYCAKVTWNNFFDYWGLGTLVTVSSS<br>LDPKSSDKTHTCPPCPAPELLGGPSVFLFPPKPKDT<br>LMISRTPEVTCVVVDVSHEDPEVKFNWYVDGVEV<br>HNAKTKPREEQYNSTYRVVSVLTVLHQDWLNGK<br>EYKCKVSNKALPAPIEKTISKAKGQPREPQVYTLPP<br>SRDELTKNQVSLTCLVKGFYPSDIAVEWESNGQPE<br>NNYKTTPPVLDSDGSFFLYSKLTVDKSRWQQGNV<br>FSCSVMHEALHNHYTQKSLSLSPGKV |
| S126 | Human | 69 | EIVLTQSPGTLTLSPGERATLSCRASQSIGSSYLAW<br>YQQKPGQAPRLLIYDATNRATGIPDRFSGSGSGTD<br>FTLTISSLQTEDSAVYYCQQYYWPPYRFGGGTKV<br>EIKGQSSRSSGGGSSSGGGGSDVQLVESGGGVVRP<br>GESLRLSCAASGFTFSNYDMTWVRQAPGEGLEWV<br>SGISGNGGSTYYADSVKGRFTISRDNSKNTLYLQM<br>NSLRAEDTAVYYCAMNRWWFDYWGLGTLVTVSS<br>SLDPKSSDKTHTCPPCPAPELLGGPSVFLFPPKPKD<br>TLMISRTPEVTCVVVDVSHEDPEVKFNWYVDGVE<br>VHNAKTKPREEQYNSTYRVVSVLTVLHQDWLNG<br>KEYKCKVSNKALPAPIEKTISKAKGQPREPQVYTL<br>PPSRDELTKNQVSLTCLVKGFYPSDIAVEWESNGQ<br>PENNYKTTPPVLDSDGSFFLYSKLTVDKSRWQQG<br>NVFSCSVMHEALHNHYTQKSLSLSPGKV |
| S128 | Human | 70 | ETVLTQSPATLSVSPGERATLSCRASQTVGSKLAW<br>HQQKPGQAPRLLIYDASNRATGIPDRFSGSGSGTD<br>FTLTISSLQTEDSAVYYCQQYYYWPPYRFGGGTKV<br>EIKGQSSRSSGGGGSSGGGGSDVQLVESGGGVVRP<br>GESLRLSCAASGFSFRSYAMNWVRQAPGEGLEWV<br>SRIDSGGGTDYADSVKGRFTISRDNSKNTLYLQM<br>NSLRAEDTAVYYCAKQYDWNSFFDYWGLGAPVT<br>VSSSLDPKSSDKTHTCPPCPAPELLGGPSVFLFPPKP<br>KDTLMISRTPEVTCVVVDVSHEDPEVKFNWYVDG<br>VEVHNAKTKPREEQYNSTYRVVSVLTVLHQDWL<br>NGKEYKCKVSNKALPAPIEKTISKAKGQPREPQVY<br>TLPPSRDELTKNQVSLTCLVKGFYPSDIAVEWESN<br>GQPENNYKTTPPVLDSDGSFFLYSKLTVDKSRWQ<br>QGNVFSCSVMHEALHNHYTQKSLSLSPGKV |
| S130 | Human | 71 | EIVLTQSPGTLSVSPGERATLSCRASQNVRSDLAW<br>YQQKLGQAPRLLIYDANTRATDIPDRFSGSGSGTE<br>FTLTISSLQSEDFAVYYCQHYYDWPPVTFGGGTKV<br>EIKGQSSRSSGGGGSSGGGGSDVQLVESGGGVVRP<br>GESLRLSCAASGFTFSNYAMSWVRQAPGEGLEWV<br>SLITTNGDGAYYADSVKGRFTISRDNSKNTLYLQM<br>NSLRAEDTAIYYCAKDGAAHYYDIFFDYWGLGTP<br>VTVSSSLDPKSSDKTHTCPPCPAPELLGGPSVFLFPP<br>KPKDTLMISRTPEVTCVVVDVSHEDPEVKFNWYV<br>DGVEVHNAKTKPREEQYNSTYRVVSVLTVLHQD<br>WLNGKEYKCKVSNKALPAPIEKTISKAKGQPREPQ<br>VYTLPPSRDELTKNQVSLTCLVKGFYPSDIAVEWE<br>SNGQPENNYKTTPPVLDSDGSFFLYSKLTVDKSRW<br>QQGNVFSCSVMHEALHNHYTQKSLSLSPGKV |
| S135 | Human | 72 | EIVLTQSPATLSVSPGERVTFSCRASQNVRSDIAWY<br>QQKPGQAPRLLIYAASSRDTGIPDRFSGSGSGTDFT<br>LTISSLQSEDFGVYYCQQYYDWPPFTFGGGTKVEI<br>KGQSSRSSGGGGSSGGGGSDVQLVESGGGVVRPG<br>ESLRLSCAASGFSFSIYAMSWVRQAPGEGLEWVST<br>IGADDTYYADSVKGRFTISRDNSKNTLYLQMNSLR<br>AEDTAVYYCAKDSTVGWSGDFFDYWGLGTLVTV<br>SSSLDPKSSDKTHTCPPCPAPELLGGPSVFLFPPKPK<br>DTLMISRTPEVTCVVVDVSHEDPEVKFNWYVDGV<br>EVHNAKTKPREEQYNSTYRVVSVLTVLHQDWLN<br>GKEYKCKVSNKALPAPIEKTISKAKGQPREPQVYT<br>LPPSRDELTKNQVSLTCLVKGFYPSDIAVEWESNG<br>QPENNYKTTPPVLDSDGSFFLYSKLTVDKSRWQQ<br>GNVFSCSVMHEALHNHYTQKSLSLSPGKV |
| S137 | Human | 73 | ETVLTQSPGTLTLSPGERATLTCRASQSVYTYLAW<br>YQEKPGQAPRLLIYGASSRATGIPDRFSGSGSGTVF<br>TLTISSLQSEDFAVYYCQQYYDRPPLTFGGGTKVEI<br>KGQSSRSSGGGGSSGGGGSDVQLVESGGGVVRPG |

TABLE D-continued scFv-Fc sequences.

| Clone | Framework/CDR | SEQ ID NO | Sequence |
|---|---|---|---|
| | | | ESLRLSCAASGFTFSSYDMNWVRQAPGEGLEWVS<br>LISGSGEIIYYADSVKGRFTISRDNSKNTLYLQMNS<br>LRAEDTAVYYCAKENNRYRFFDDWGLGTLVTVSS<br>SLDPKSSDKTHTCPPCPAPELLGGPSVFLFPPKPKD<br>TLMISRTPEVTCVVVDVSHEDPEVKFNWYVDGVE<br>VHNAKTKPREEQYNSTYRVVSVLTVLHQDWLNG<br>KEYKCKVSNKALPAPIEKTISKAKGQPREPQVYTL<br>PPSRDELTKNQVSLTCLVKGFYPSDIAVEWESNGQ<br>PENNYKTTPPVLDSDGSFFLYSKLTVDKSRWQQG<br>NVFSCSVMHEALHNHYTQKSLSLSPGKV |
| S138 | Human | 74 | EIVLTQSPGTLSVSPGERVILTCRASQSVDTYNLAW<br>YQQKPGQAPRLLIYDLSTRATGIPDRFSGSGSGTEF<br>TLTINSLEPEDFAVYYCHQYYDWPPYTFGGGTKVE<br>IKGQSSRSSGGGGSSGGGGSDVQLVESGGGVVRPG<br>ESLRLSCAASGFTFSNYAMNWVRQAPGEGLEWVS<br>GISGRGGDTYYADSVKGRFTISRDNSKNTLYLQM<br>NSLRAEDTAIYYCAKGTWNYGSFDYWGLGTLVT<br>VSSSLDPKSSDKTDTCPPCPAPELLGGPSVFLFPPKP<br>KDTLMISRTPEVTCVVVDVSHEDPEVKFNWYVDG<br>V |
| S121 | Human | 75 | EIVLTQSPATLSVSPGERATFSCRASQNVKNDLAW<br>YQQRPGQAPRLLIYAARIRETGIPERFSGSGSGTEFT<br>LTITSLQSEDFAVYYCQQYYDWPPFTFGGGTKVEI<br>KGQSSRSSGGGGSSGGGGSDVQLVESGGGVVQPG<br>GSLRLSCAASGFSFSNFAMTWVRQAPGEGLEWVS<br>TIGSGDTYYADSVKGRFTISRDNSKNTLYLQMNSL<br>RAEDTAVYYCAKDSTVSWSGDFFDYWGLGTLVT<br>VSSSLDPKSSDKTHTCPPCPAPELLGGPSVFLFPPKP<br>KDTLMISRTPEVTCVVVDVSHEDPEVKFNWYVDG<br>VEVHNAKTKPREEQYNSTYRVVSVLTVLHQDWL<br>NGKEYKCKVSNKALPAPIEKTISKAKGQPREPQVY<br>TLPPSRDELTKNQVSLTCLVKGFYPSDIAVEWESN<br>GQPENNYKTTPPVLDSDGSFFLYSKLTVDKSRWQ<br>QGNVFSCSVMHEALHNHYTQKSLSLSPGKV |

Without wishing to be bound to theory, it is thought that antibodies with cross-reactive binding among human, cynomologus, and/or murine proteins may allow for characterization of antibodies in both animal models and clinical testing. Antibodies with isoform- and/or variant-specific binding may be useful for personalized medicine approaches to specific human populations and/or studies on specific variants of interest. In addition to profiling intra- and inter-species binding specificities, the methods described herein also allow for identification of antibodies that block or do not block binding between SIRP-α and CD47, as well as antibodies that "kick SIRPα-off" from binding to CD47.

Example 2: Identification of Additional Antibodies with Novel Binding Specificities to SIRP-α Proteins Methods
Determination of $K_D$ The interactions of anti-SIRPα antibodies with SIPRα from various species (human v1, human v2, cynomolgus, mouse 129, BL6, BALBc, NOD), SIRPβ and SIRPγ were analyzed using two methods, direct immobilization of the antibodies (via GLC chip) or capture via biotinylated Protein A (via NLC chip), according to the following protocols. All experiments were performed at 25° C. using a SPR-based ProteOn XPR36 biosensor (BioRad, Inc, Hercules, CA) equipped with GLC or NLC sensor chips. Antibodies were expressed using FreeStyle™ 293-FS cells (Thermo Fisher) as described in Example 1. Purification was carried out by standard Protein A affinity column chromatography and eluted antibodies were stored in PBS buffer.

The running buffer was PBS pH 7.4 with 0.01% Tween-20 (PBST+). All analytes were used at their nominal concentrations as determined by A280 Absorbance and using their molar calculated extinction coefficient. Analytes were injected in a "one-shot" kinetic mode as described elsewhere (see, e.g., Bravman, T. et al. (2006) Anal. Biochem. 358: 281-288).

For the method using GLC chip, the analytes were injected and flowed over anti-SIRPα antibodies immobilized (~1000 RUs) on GLC chips using Proteon™ Amine Coupling Kit. For the immobilization step, GLC chip was activated with EDAC/Sulpho-NHS 1:1 (Biorad) diluted 1/100 for 300 s at 25 µL/min. Anti-SIRPα antibodies were diluted to 80 nM concentration in 10 mM sodium acetate buffer pH 4.5 and immobilized to the chip at 30 µL/min for 50 s. Chip was inactivated with ethanolamine for 300 s at 25 µL/min. The analytes (e.g., SIRP-α from different species, SIRP-β, SIRP-γ) were injected in a "one-shot" kinetic mode at nominal concentrations of 100, 33, 11, 3.7, 1.2 and 0 nM. Association times were monitored for 90 s at 100 µL/min, and dissociation times were monitored for 1200 s. The surfaces were regenerated with a 2:1 v/v blend of Pierce IgG elution buffer/4M NaCl.

Alternatively, $K_D$ determination was performed using antibody capture via an NLC chip. In this case, 15 ug/mL biotinylated protein A (Thermofisher) was injected at 30 uL/min for 120 s over the NLC chip to obtain an immobilization response of ~1000-1200RUs. Next, anti-SIRPα antibodies (~160 nM) were injected for 80 s at 30 uL/min. The analytes (SIRPα from different species, SIRP-β and SIPR-γ) were subsequently injected in a "one-shot" kinetic mode at nominal concentrations of 100, 33, 11, 3.7, 1.2 and 0 nM. Association times were monitored for 60 s at 25 μL/min, and dissociation times were monitored for 120 s. The surfaces were regenerated with a 2:1 v/v blend of Pierce IgG elution buffer/4M NaCl.

Biosensor data were double-referenced by subtracting the interspot data (containing no immobilized protein) from the reaction spot data (immobilized protein) and then subtracting the response of a buffer "blank" analyte injection from that of an analyte injection. Double-referenced data were fit globally to a simple Langmuir model and the $K_D$ value was calculated from the ratio of the apparent kinetic rate constants ($K_D = k_d/k_a$).

Results

Three representative antibodies (a blocking, non-blocking, and "kick off" antibody) were further characterized for binding to various SIRP-α, -β, -γ proteins as described above. The three antibodies contain human sequences and were derived from the HuMab chicken immunization experiments. These antibodies were tested as full-length human IgG1 antibodies with L234A, L235A, G237A, and N297A mutations. SIRP-α proteins examined in these experiments corresponded to human SIRP-α v1 (SEQ ID NO:5), human SIRP-α v2 (SEQ ID NO:6), cynomolgus SIRP-α (SEQ ID NO:11), human SIRPβ isoform 1 (SEQ ID NO:13), human SIRPβ isoform 2 (SEQ ID NO:14), and human SIRPγ isoform 1 (SEQ ID NO:15). Human SIRPβ isoform 1 (SEQ ID NO:13) is also known in the art as SIRPβ1 isoform 1.

$K_D$ values obtained for the three antibodies are shown in Table E below.

TABLE E

Summary of $K_D$ values (M)

| | | v1 | v2 | cyno | beta isoform 1 | beta isoform 2 | gamma isoform 1 |
|---|---|---|---|---|---|---|---|
| Kick-off | AB132a | $4.26 \times 10^{-10}$ | $1.86 \times 10^{-9}$ | $2.41 \times 10^{-9}$ | $1.31 \times 10^{-10}$ | $1.64 \times 10^{-10}$ | $5.19 \times 10^{-10}$ |
| Blocker | AB119a | $1.98 \times 10^{-10}$ | $7.99 \times 10^{-11}$ | $1.45 \times 10^{-10}$ | $3.42 \times 10^{-10}$ | $3.76 \times 10^{-10}$ | $8.86 \times 10^{-10}$ |
| Non-blocker | AB136a | $6.88 \times 10^{-10}$ | $3.22 \times 10^{-9}$ | $2.65 \times 10^{-9}$ | $4.35 \times 10^{-9}$ | $2.27 \times 10^{-9}$ | $1.20 \times 10^{-7}$ |

Next, the binding kinetics of various antibody clones to selected mouse SIRP-α proteins were determined as described above. Mouse proteins that were tested include BALBc (SEQ ID NO:10), BL6 (SEQ ID NO:9), NOD (SEQ ID NO:8), and m129 (SEQ ID NO:7) SIRP-α proteins. The results are summarized in Tables F-I below. Antibody clones labeled as "c" were tested as full-length mouse IgG2a antibodies; antibody clones labeled as "a" were tested as full-length human IgG1 antibodies with L234A, L235A, G237A, and N297A mutations.

TABLE F

Summary of kinetics for binding of selected antibodies to BALBc mouse SIRP-α protein (SEQ ID NO: 10)

| Antibody | $K_{on}$ (1/Ms) | $K_{off}$ (1/s) | $K_D$ (M) |
|---|---|---|---|
| AB136a | $8.27 \times 10^5$ | $2.73 \times 10^{-4}$ | $3.31 \times 10^{-10}$ |
| AB3c | $7.76 \times 10^5$ | $4.12 \times 10^{-3}$ | $5.31 \times 10^{-9}$ |
| AB21c | $4.62 \times 10^5$ | $6.18 \times 10^{-4}$ | $1.34 \times 10^{-9}$ |
| AB25c | $3.03 \times 10^5$ | $2.92 \times 10^{-3}$ | $9.64 \times 10^{-9}$ |

TABLE F-continued

Summary of kinetics for binding of selected antibodies to BALBc mouse SIRP-α protein (SEQ ID NO: 10)

| Antibody | $K_{on}$ (1/Ms) | $K_{off}$ (1/s) | $K_D$ (M) |
|---|---|---|---|
| AB27c | $1.50 \times 10^5$ | $2.26 \times 10^{-3}$ | $1.50 \times 10^{-8}$ |
| AB66c | $2.24 \times 10^5$ | $7.62 \times 10^{-4}$ | $3.41 \times 10^{-9}$ |

TABLE G

Summary of kinetics for binding of selected antibodies to BL6 mouse SIRP-α protein (SEQ ID NO: 9)

| Antibody | $K_{on}$ (1/Ms) | $K_{off}$ (1/s) | $K_D$ (M) |
|---|---|---|---|
| AB136a | $6.24 \times 10^5$ | $5.85 \times 10^{-3}$ | $9.37 \times 10^{-9}$ |
| AB3c | $4.12 \times 10^5$ | $6.19 \times 10^{-3}$ | $1.50 \times 10^{-8}$ |
| AB21c | $2.76 \times 10^5$ | $2.41 \times 10^{-4}$ | $8.76 \times 10^{-10}$ |
| AB25c | $1.42 \times 10^5$ | $3.99 \times 10^{-4}$ | $2.81 \times 10^{-9}$ |
| AB27c | $1.47 \times 10^5$ | $1.40 \times 10^{-3}$ | $9.49 \times 10^{-9}$ |
| AB66c | $1.07 \times 10^5$ | $6.19 \times 10^{-4}$ | $5.80 \times 10^{-9}$ |

TABLE H

Summary of kinetics for binding of selected antibodies to NOD mouse SIRP-α protein (SEQ ID NO: 8)

| Antibody | $K_{on}$ (1/Ms) | $K_{off}$ (1/s) | $K_D$ (M) |
|---|---|---|---|
| AB136a | $8.41 \times 10^5$ | $4.48 \times 10^{-4}$ | $5.33 \times 10^{-10}$ |
| AB3c | $9.99 \times 10^5$ | $1.43 \times 10^{-3}$ | $1.43 \times 10^{-9}$ |
| AB21c | $7.49 \times 10^5$ | $4.79 \times 10^{-4}$ | $6.40 \times 10^{-10}$ |
| AB25c | $3.66 \times 10^5$ | $1.43 \times 10^{-3}$ | $3.90 \times 10^{-9}$ |

TABLE H-continued

Summary of kinetics for binding of selected antibodies to NOD mouse SIRP-α protein (SEQ ID NO: 8)

| Antibody | $K_{on}$ (1/Ms) | $K_{off}$ (1/s) | $K_D$ (M) |
|---|---|---|---|
| AB27c | $2.96 \times 10^5$ | $1.01 \times 10^{-3}$ | $3.42 \times 10^{-9}$ |
| AB66c | $4.12 \times 10^5$ | $2.32 \times 10^{-4}$ | $5.64 \times 10^{-10}$ |

TABLE I

Summary of kinetics for binding of selected antibodies to m129 mouse SIRP-α protein (SEQ ID NO: 7)

| Antibody | $K_{on}$ (1/Ms) | $K_{off}$ (1/s) | $K_D$ (M) |
|---|---|---|---|
| AB136a | $6.88 \times 10^5$ | $5.97 \times 10^{-4}$ | $8.67 \times 10^{-10}$ |
| AB3c | $5.34 \times 10^5$ | $1.18 \times 10^{-2}$ | $2.20 \times 10^{-8}$ |
| AB21c | $5.63 \times 10^5$ | $3.31 \times 10^{-5}$ | $5.88 \times 10^{-11}$ |
| AB25c | $3.52 \times 10^5$ | $2.07 \times 10^{-5}$ | $5.87 \times 10^{-11}$ |

TABLE I-continued

Summary of kinetics for binding of selected antibodies to m129 mouse SIRP-α protein (SEQ ID NO: 7)

| Antibody | $K_{on}$ (1/Ms) | $K_{off}$ (1/s) | $K_D$ (M) |
|---|---|---|---|
| AB27c | $2.07 \times 10^5$ | $1.01 \times 10^{-4}$ | $4.87 \times 10^{-10}$ |
| AB66c | $2.07 \times 10^5$ | $1.98 \times 10^{-5}$ | $9.55 \times 10^{-11}$ |

For the above antibodies, VH and VL domain sequences (respectively) were as follows: AB136a: SEQ ID NO: 133 and 134; AB3c: SEQ ID NO: 242 and 243; AB21c: SEQ ID NO: 135 and 136; AB25c: SEQ ID NO: 137 and 138; AB27c: SEQ ID NO: 139 and 140; AB66c: SEQ ID NO: 141 and 142.

These results demonstrate that multiple antibody clones bound to all four mouse SIRP-α proteins, making these antibodies suitable for characterization in in vivo mouse models.

Example 3: Functional Properties of Anti-SIRP-α Antibodies

The previous Examples describe the identification and characterization of anti-SIRP-α antibodies with a diverse array of properties, such as binding specificity for various human, cynomolgus, and/or murine SIRP-α, SIRP-β, and SIRP-γ proteins, and whether or not the antibodies block binding between SIRP-α and CD47. Antibodies representing particular categories of interest were next examined in a variety of in vitro and in vivo functional assays aimed at characterizing their effects on SIRP-α's biological functions. In particular, "blocking" (i.e., antibodies that block binding between SIRP-α and CD47) and "non-blocking" (i.e., antibodies that do not block binding between SIRP-α and CD47) were characterized for activities in various in vitro and in vivo assays.

As noted above, antibody clones labeled as "a" were tested as full-length human IgG1 antibodies with L234A, L235A, G237A, and N297A mutations. Antibody clones labeled as "b" were tested as full-length mouse IgG1 antibodies with an N297A mutation. Antibody clones labeled as "c" were tested as full-length mouse IgG2a antibodies.

Methods

Tumor Cell Line Culturing

DLD-1 (human colorectal adenocarcinoma) and OE19 (human esophageal carcinoma) cells were maintained in growth medium comprised of RPMI (Gibco) supplemented with 10 percent heat-inactivated Fetal Bovine Serum (Gibco), one percent penicillin/streptomycin (Gibco), and one percent Glutamax™ glutamine supplement (Gibco).

Derivation and Culture of Human Monocyte-Derived Macrophages

Trima residuals were received from Blood Centers of the Pacific and diluted 1:4 with Phosphate Buffered Saline (PBS, Gibco). Diluted blood was split into four tubes and underlayed with 20 ml Ficoll-Paque® Plus (GE Healthcare) lymphocyte medium. Tubes were centrifuged for 30 minutes at 400×g. PBMCs were collected from the interface and resuspended in FACS buffer (PBS with 0.5 percent Bovine Serum Albumin (Gibco)). CD14+ monocytes were purified by negative selection using the Monocyte Isolation Kit II (Miltenyi Biotec) and LS columns (Miltenyi Biotec) according to the manufacturer's protocol.

For nonpolarized macrophages, CD14+ monocytes were seeded into 15 cm tissue culture plates (Corning) at 10 million cells per dish in 25 ml IMDM (Gibco) supplemented with 10 percent human AB serum (Corning), one percent penicillin/streptomycin, and one percent Glutamax™ glutamine supplement. Cells were cultured for seven to ten days.

For M2 polarized macrophages, CD14+ monocytes were seeded into 15 cm tissue culture plates (Corning) at 6 million cells per dish in 25 ml RPMI (Gibco) supplemented with 10 fetal bovine serum (Thermo Fisher), one percent penicillin/streptomycin, and one percent Glutamax, and 50 ng/ml M-CSF (Miltenyi). Cells were cultured for seven to ten days.

In Vitro Phagocytosis Assays

DLD-1 and OE19 cells were detached from culture plates by washing twice with 20 ml PBS and incubation in 10 ml TrypLE™ Select (Gibco) adherent cell dissociation enzyme for 10 minutes at 37° C. Cells were centrifuged, washed in PBS, and resuspended in medium. Cells were labeled with the Celltrace™ CFSE Cell Proliferation kit (Thermo Fisher) according to the manufacturer's instructions and resuspended in IMDM. Macrophages were detached from culture plates by washing twice with 20 ml PBS and incubation in 10 ml TrypLE™ Select adherent cell dissociation enzyme for 20 minutes at 37° C. Cells were removed with a cell scraper (Corning), washed in PBS, and resuspended in IMDM.

Phagocytosis assays were assembled in ultra-low attachment U-bottom 96 well plates (Corning) containing 100,000 DLD-1 or OE19 cells, 50,000 macrophages, five-fold serial dilutions of anti-SIRP-α antibody from 100 nM to 6.4 pM and cetuximab (Absolute Antibody) at 1 or 0.01 ug/ml, trastuzumab at 0.01 ug/ml, or control antibody of the same isotype (Southern Biotech). All anti-SIRP-α antibodies tested had a human IgG1 with L234A, L235A, G237A, and N297A mutations except AB136c, which had a mouse IgG2a. Plates were incubated two hours at 37° C. in a humidified incubator with 5 percent carbon dioxide. Cells were pelleted by centrifugation for five minutes at 400×g and washed in 250 μl FACS buffer. Macrophages were stained on ice for 15 minutes in 50 μl FACS buffer containing 10 μl human FcR Blocking Reagent (Miltenyi Biotec), 0.5 μl anti-CD33 BV421 (Biolegend), and 0.5 μl anti-CD206 APC-Cy7 (Biolegend). Cells were washed in 200 μl FACS buffer, washed in 250 μl PBS, and stained on ice for 30 minutes in 50 μl Fixable Viability Dye eFluor™ 506 (ebioscience) dye diluted 1:1000 in PBS. Cells were washed twice in 250 μl FACS buffer and fixed for 30 minutes on ice in 75 μl Cytofix™ (BD Biosciences) fixation solution. Cells were washed in 175 μl FACS buffer and resuspended in 75 μl FACS buffer. Cells were analyzed on a FACS Canto™ II (BD Biosciences) flow cytometer, with subsequent data analysis by Flowjo 10.7 (Treestar). Dead cells were excluded by gating on the e506-negative population. Macrophages that had phagocytosed tumor cells were identified as cells positive for CD33, CD206, and CFSE.

In Vivo Dendritic Cell Activation

Balb/c mice (n=3/group) were intravenously injected with a control rat anti-mouse anti-SIRP-α antagonistic antibody (clone p84), rat IgG control, AB136b (AB136 with a mouse IgG1 Fc region bearing an N297A mutation), mouse IgG control, or vehicle (PBS) at 10 mg/kg. Five hours post injection, spleens were harvested and processed into single cell suspension by mechanical dissociation through a 70 μM cell strainer. Cells were washed two with PBS and red blood cell lysis was performed. Subsequently, cells were washed for an additional two times with PBS/10% FBS and prepared for cell staining. Cells were stained with fluorochrome conjugated MHC-II, CD8, 33D1, CD4, CD11c, CD86, CCR7 and viability dye at 4 degrees for one hour. Cells were washed two times and analyzed using a BD Canto™ II flow cytometer and data were processed using Flowjo.

In Vivo Anti-Tumor Activity

For the CT26 syngeneic mouse colon carcinoma model, CT26 cells were implanted subcutaneously in BALB/c mice and randomized into groups (8-9 mice/group). Treatment groups included vehicle (PBS) and AB136b. AB136 anti-SIRP-α had a mouse IgG1 Fc region bearing an N297A mutation. Treatment was initiated when tumors were an average of 75-80 mm³, day 7 or 8 post implant. Mice were dosed intraperitoneally (IP) at 3 mg/kg twice a week for three weeks with AB136b. Animals were sacrificed when tumors reached a volume of ~2000 mm³.

For the MC38 syngeneic mouse colon carcinoma model, MC38 cells were implanted subcutaneously in C57BL/6 mice and randomized into groups (8-10 mice/group). Treatment groups included vehicle (PBS), AB25b, AB25c, AB27b, AB3b, and AB136b. All anti-SIRPα antibodies had a mouse IgG1 Fc region bearing an N297A mutation except for AB25c, which had a mouse IgG2a. Treatment was initiated when tumors were an average of 60-65 mm³, day 7 post implant. Mice were dosed intraperitoneally (IP) at 10 mg/kg twice a week for three weeks for anti-SIRPα. Animals were sacrificed when tumors reached a volume of ~2000 mm³.

Results

Various anti-SIRP-α antibodies were examined for induction of phagocytosis in in vitro phagocytosis assays using polarized and non-polarized macrophages.

Additional anti-SIRP-α antibodies AB3 and AB45 were tested in the experiments described below. Both are non-blocking antibodies. The $k_{off}$ rates of binding of each clone (in scFv-Fc format) to each SIRP analyte were determined using SPR (Table J1). The SPR screening conditions have been described herein, and the Koff values were determined using Langmuir kinetic fittings. SIRP analyte sequences are as follows: CV1-3, SEQ ID NO:18; v1, SEQ ID NO:5; v2, SEQ ID NO:6; cyno1, SEQ ID NO: 11; cyno2, SEQ ID NO:12; m129, SEQ ID NO:7; NOD, SEQ ID NO:8; BL6, SEQ ID NO:9; sirpb1, SEQ ID NO: 13; sirpg, SEQ ID NO:15.

to induce phagocytosis of OE19 tumor cells when co-administered with trastuzumab (anti-HER2 antibody). Non-blocking anti-SIRP-α antibody AB136c was also found to induce phagocytosis of DLD-1 tumor cells (FIG. 13G).

Figure 14:
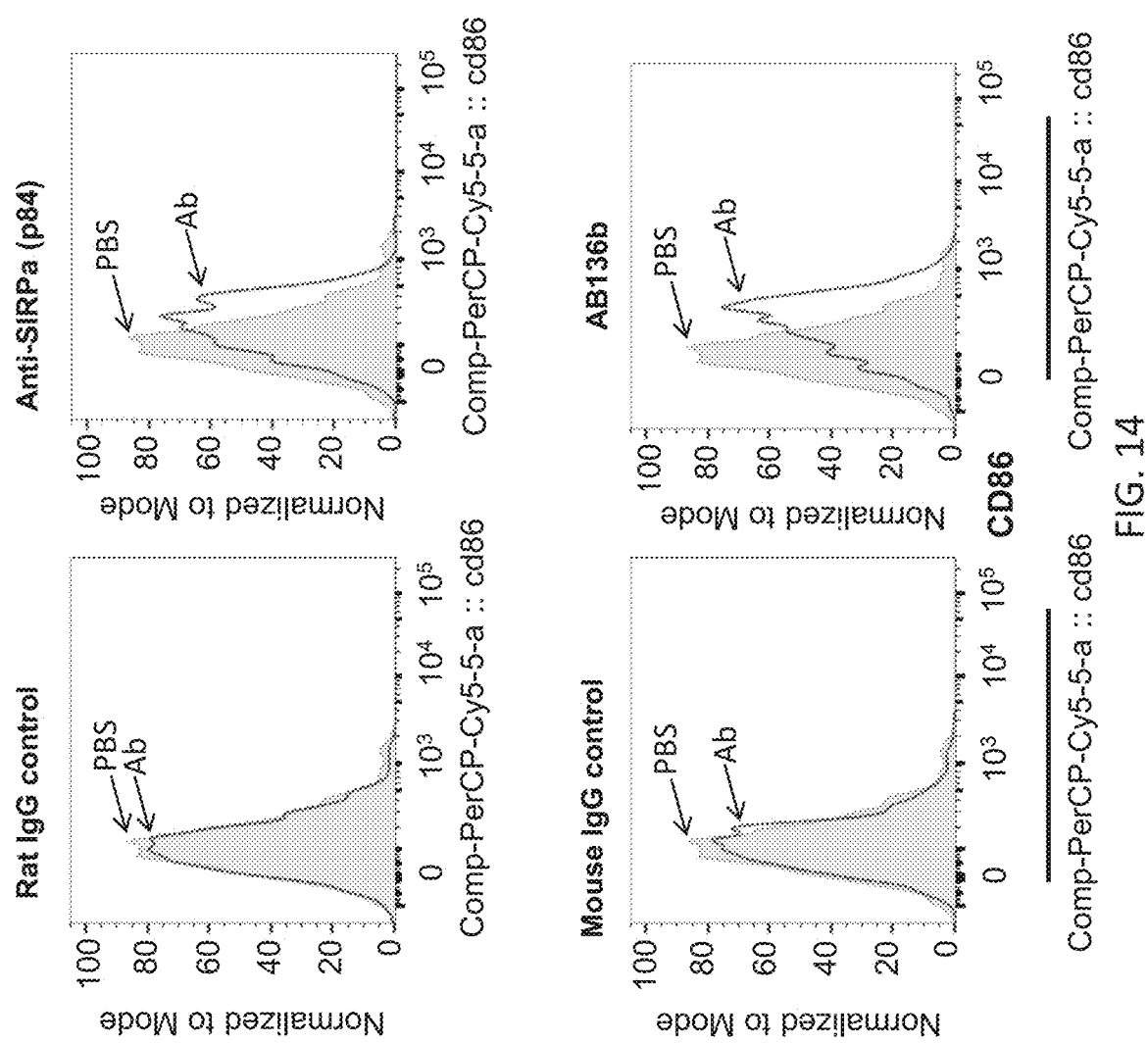

A dendritic cell activation assay was used to characterize the in vivo effects of non-blocking anti-SIRP-α antibody AB136b (SEQ ID NOs:133 and 134 for VH and VL domain sequences, respectively). Failure to engage mouse SIRP-α receptor on splenic dendritic cells via CD47 binding leads to splenic dendritic cell activation. Control anti-SIRP-α antagonist antibody p84 activated splenic dendritic cells when injected intravenously into mice (FIG. 14). Non-blocking anti-SIRP-α antibody AB136b was tested in vivo to determine if it leads to dendritic cell activation. Interestingly, AB136b treatment led to activation of splenic dendritic cells at a similar level as p84 (FIG. 14).

Figure 15:
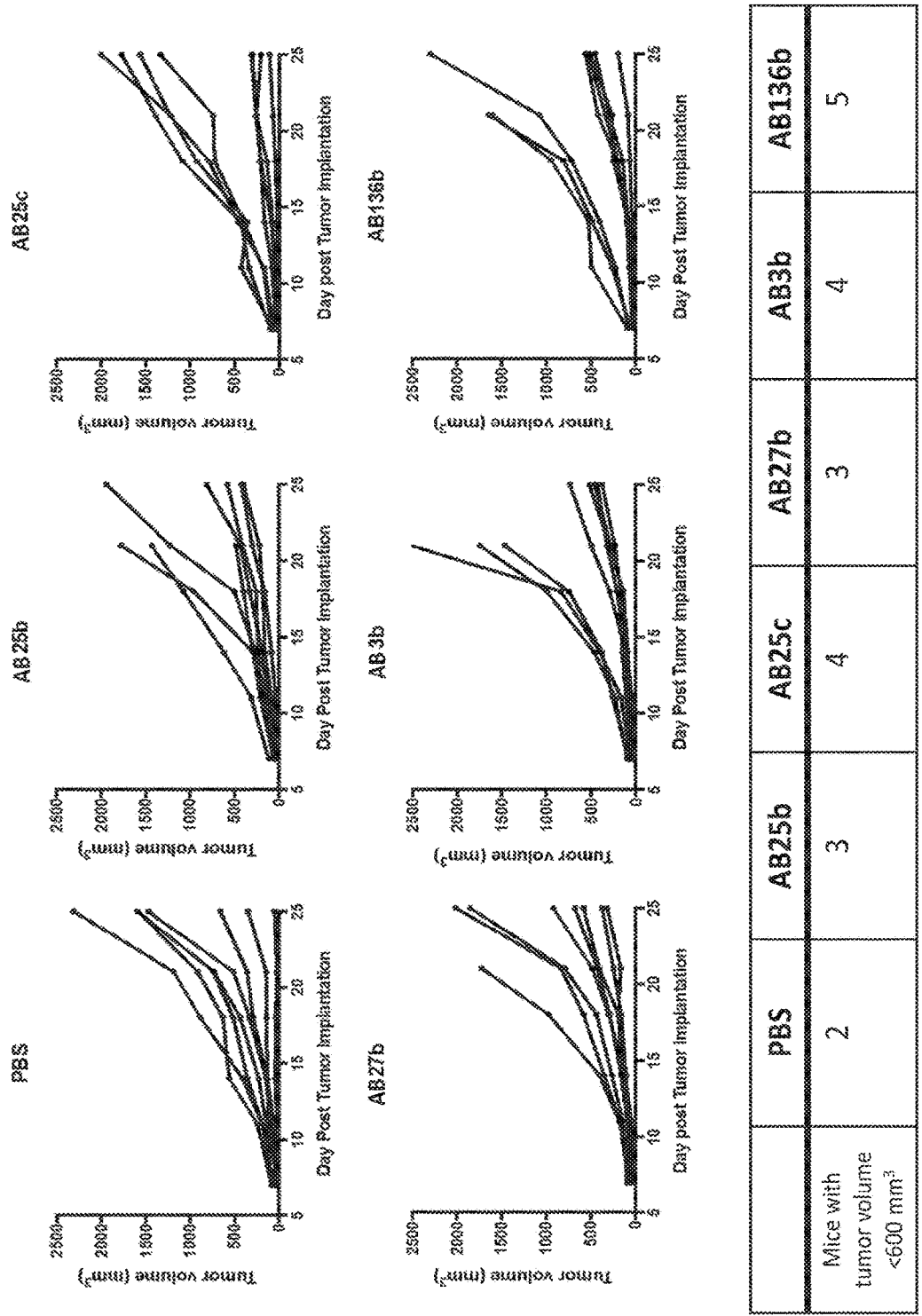

Next, the in vivo anti-tumor effects of various anti-SIRP-α antibodies were assayed in two syngeneic mouse colon carcinoma models. The anti-tumor activities of blocking anti-SIRP-α antibodies AB25b, AB25c and AB27b and non-blocking anti-SIRP-α antibodies AB3b and AB136b were examined in an MC38 syngeneic mouse colon carcinoma model to assess their single agent activities. Both blocking (AB25b, AB25c and AB27b) and non-blocking (AB3b and AB136b) anti-SIRP-α antibodies delayed tumor formation at 10 mg/kg as compared to vehicle alone (FIG. 15) in the MC38 syngeneic mouse model. On day 25, groups treated with anti-SIRPα antibodies had three mice below 600 mm³ for AB25b and AB27b, four mice below 600 mm³ for AB25c and AB3b and five mice below 600 mm³ for AB136b, while the vehicle-treated group had only two mice below 600 mm³.

Figure 16:
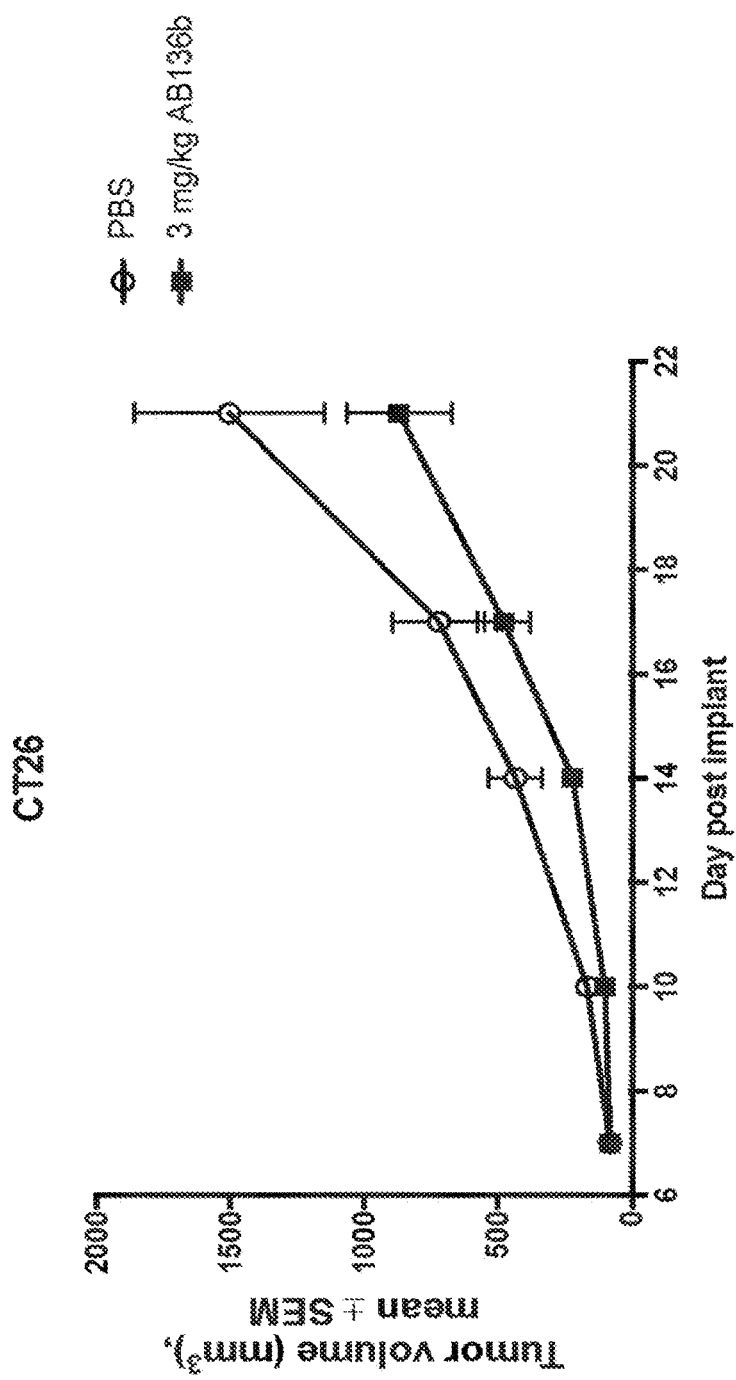

The anti-tumor activity of non-blocking AB136b was next evaluated in a CT26 syngeneic mouse colon carcinoma model to assess single agent activity. These results confirmed that AB136b treatment delayed tumor formation at 3 mg/kg as compared to vehicle alone in the CT26 syngeneic mouse model (FIG. 16).

Taken together, these results demonstrate the efficacy of anti-SIRP-α antibody treatment in inducing tumor cell

TABLE J1

Langmuir kinetic fittings $K_D$ (M) for AB3 and AB45

| | SEQ ID NO: | | | | | | | | | |
|---|---|---|---|---|---|---|---|---|---|---|
| | 5<br>V1 | 6<br>v2 | 11<br>cyno1 | 12<br>Cyno2 | 8<br>NOD | 9<br>BL6 | 10<br>BALBc | 15<br>sirp-g | 13<br>Sirpb1 | 14<br>Sirpb2 |
| AB3* | 1.62E−10 | 7.67E−11 | 2.29E−09 | 2.85E−09 | 1.63E−09 | 3.65E−09 | 1.16E−09 | 8.36E−08 | 1.63E−09 | 6.78E−11 |
| AB45** | 6.63E−11 | 1.34E−10 | NB | NB | NB | NB | NB | 2.71E−08 | 1.06E−08 | 2.53E−11 |

NB—No binding.
*See SEQ ID NOs: 242 and 243 for VH and VL domains, respectively.
**See SEQ ID NOs: 244 and 245 for VH and VL domains, respectively.

Figures 13A, 13B:
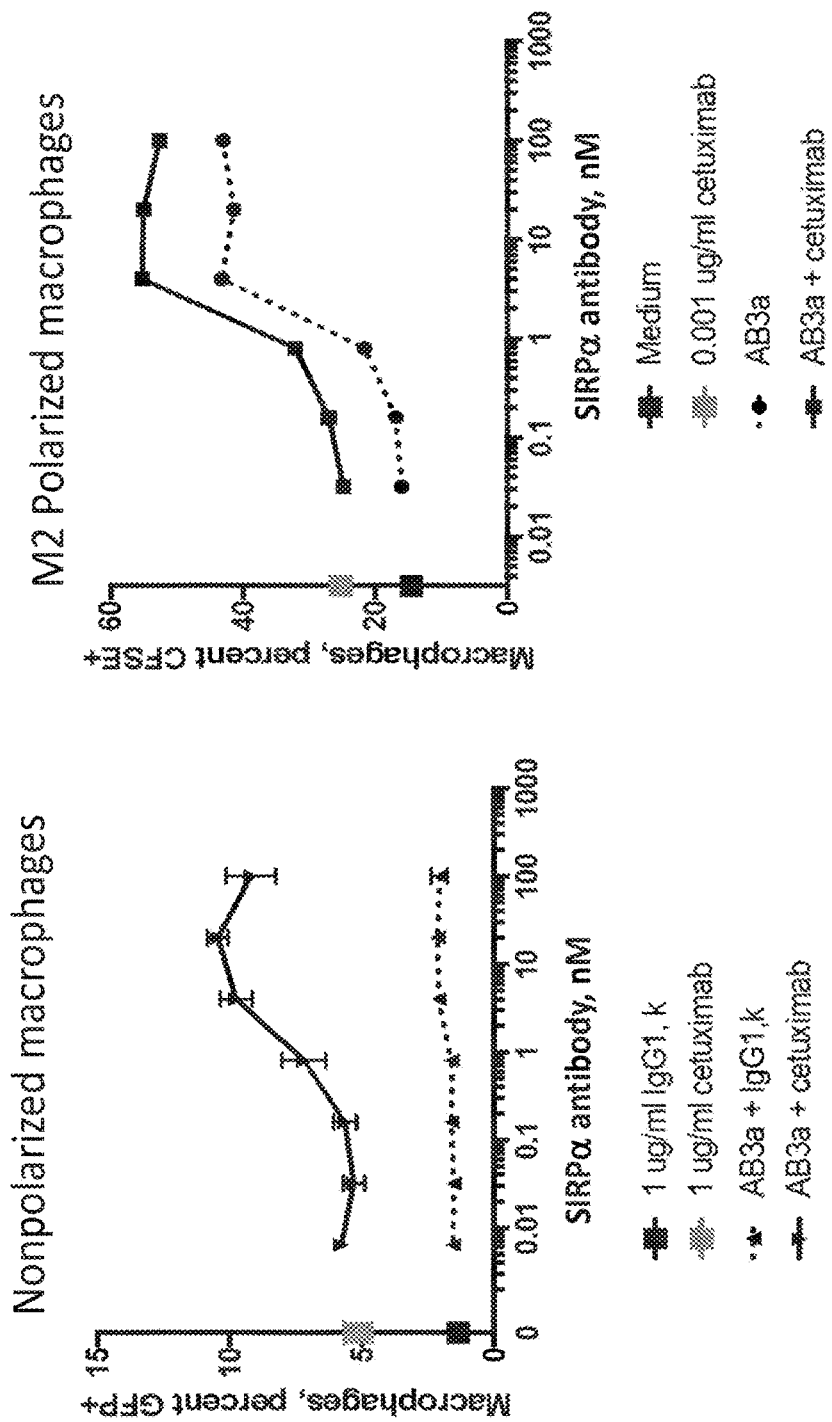
Figures 13C, 13D:
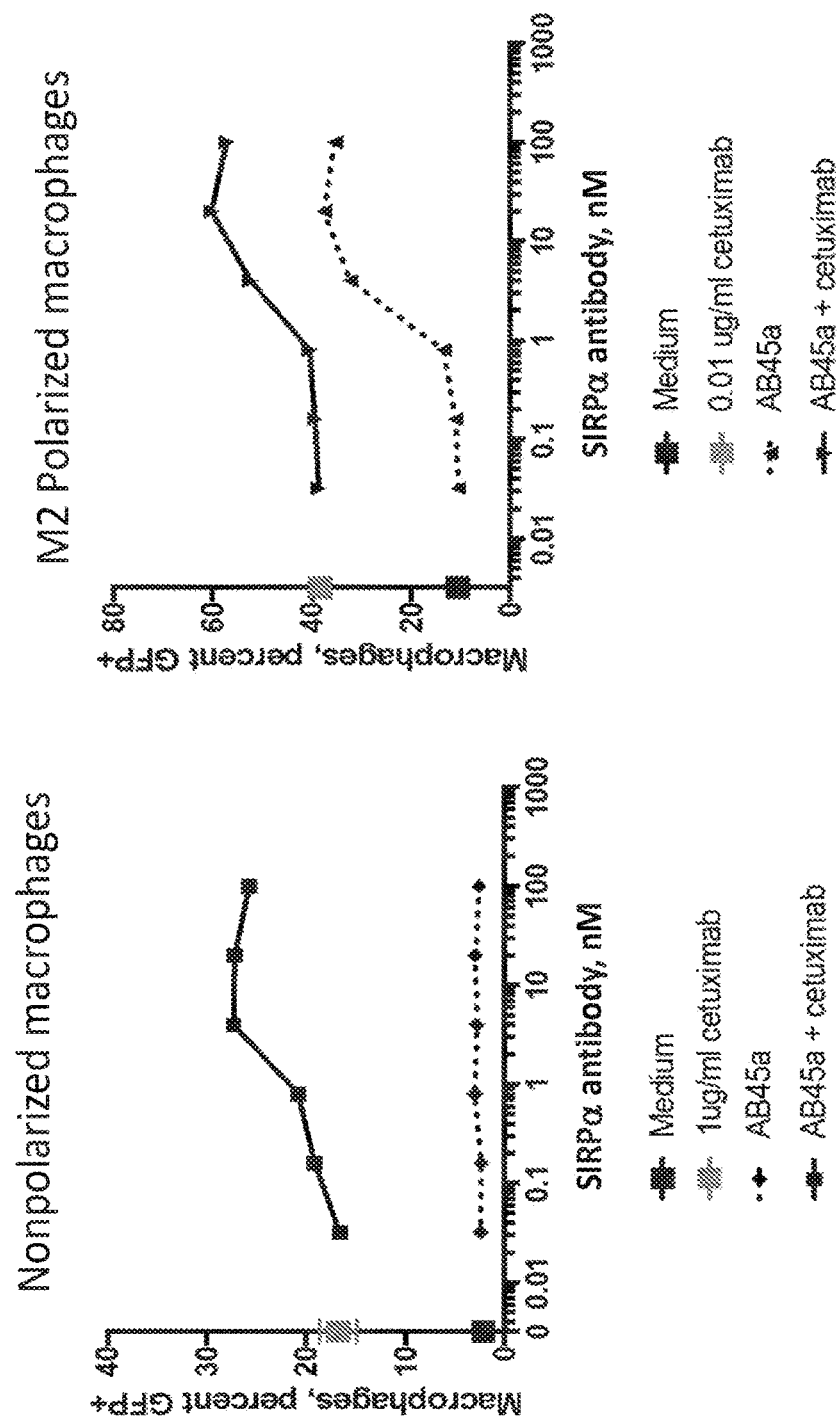
Figures 13E, 13F, 13G:
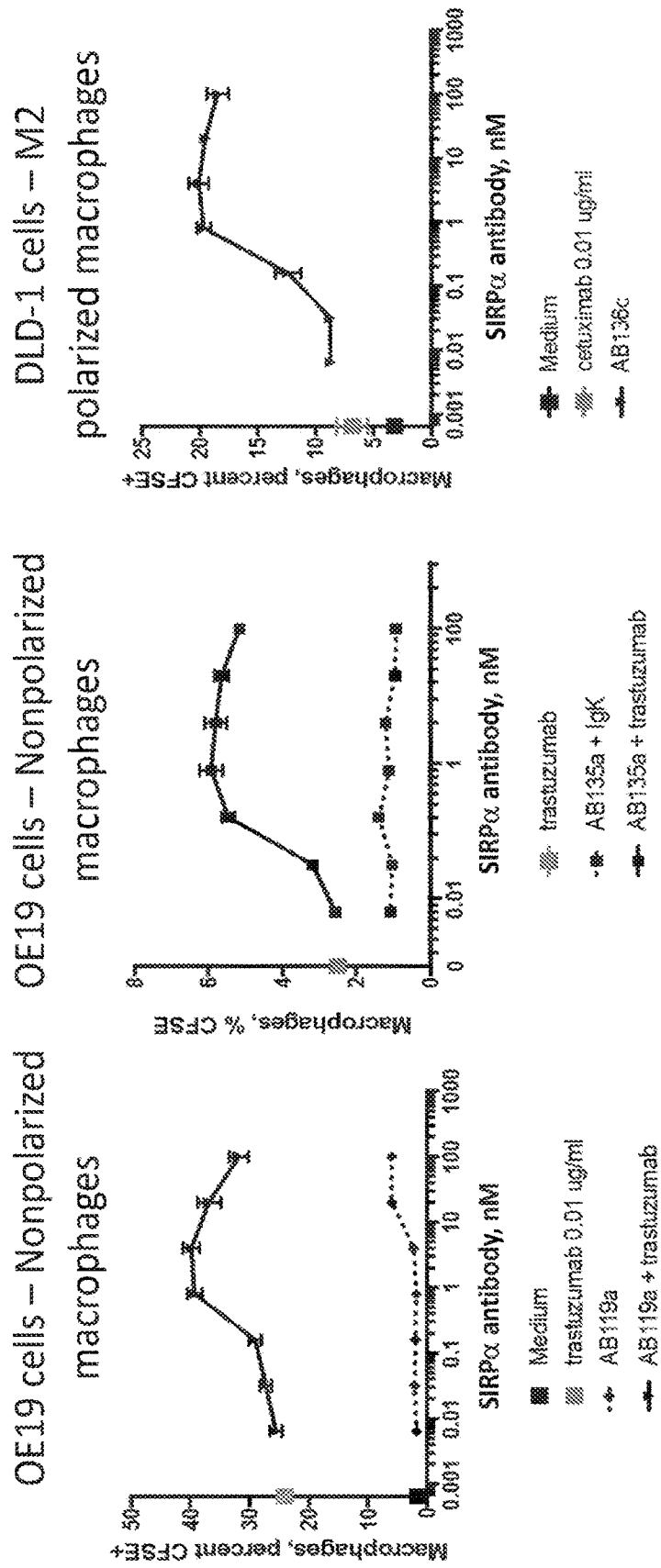

As shown in FIGS. 13A & 13B, non-blocking anti-SIRP-α antibody AB3a was found to induce phagocytosis of DLD-1 tumor cells in M2 polarized macrophages. In particular, treatment of macrophages with cetuximab (anti-EGFR antibody) and AB3a led to robust induction of tumor cell phagocytosis. Similarly, non-blocking anti-SIRP-α antibody AB45a was found to induce phagocytosis of DLD-1 tumor cells M2 polarized macrophages, and treatment of macrophages with cetuximab (anti-EGFR antibody) and AB45a led to robust induction of tumor cell phagocytosis (FIGS. 13C & 13D). Blocking anti-SIRP-α antibodies AB119a (FIG. 13E) and AB135a (FIG. 13F) were also found phagocytosis by macrophages, activating dendritic cells, and inhibiting tumor growth in vivo. Multiple blocking anti-SIRP-α antibodies were found to promote tumor cell phagocytosis, activate dendritic cells and block in vivo tumor growth. Surprisingly, however, treatment with non-blocking anti-SIRP-α antibody was also found to activate splenic dendritic cells and inhibit tumor growth in vivo in two different syngeneic mouse tumor models. The finding that non-blocking anti-SIRP-α antibodies were able to increase phagocytosis and block in vivo tumor growth was both surprising and unexpected. Previous work has suggested that only blocking anti-SIRP-α antibodies would be able to inhibit in vivo tumor growth (see Yanagita, T. et al. (2017) *JCI Insight* 2:e89140).

Example 4: Structural Analysis of Anti-SIRP-α Antibody Epitopes on SIRP-α

As described in Examples 1-3 above, anti-SIRP-α antibodies have been generated with a variety of specificities and modes of binding to SIRP-α, e.g., antibodies that block CD47 binding to SIRP-α, antibodies that do not block CD47 binding to SIRP-α, and antibodies that bind to SIRP-α and reduce its affinity for binding CD47 ("kick off" antibodies). Structural analyses were undertaken in order to understand how these types of antibodies bind to the D1 domain of SIRP-α as compared to CD47 and characterize the epitopes of selected anti-SIRP-α antibodies.

Methods
Crystallography and Structural Analysis

Expression of the Fabs and SIRPα was similar to previously established protocols and involved traditional methods of affinity chromatography and size exclusion for protein purification. A human SIRP-α v1 mutant bearing an N80A mutation as compared to SEQ ID NO:5 was used for ease of protein production in Expi293 (SEQ ID NO:296). The goal of using an N80A SIRPα was to produce a homogenous, non-glycosylated form of SIRPα that would be most amenable for crystallization. The final purification buffer is minimal with only 10 mM Tris pH 7.5 and 50 mM NaCl. The purified complex sample is stable at 4° C. and was concentrated to 10-12 mg/mL in preparation for crystallization experiments and eventual structure determination.

The methods for the Fab:SIRPα complex project followed well established principles or crystallography starting with the sparse matrix technique, which led to custom optimized conditions, establishing a routine protocol. Crystallization was carried out utilizing the sitting drop vapor diffusion technique. For the initial sparse matrix screening, condition kits commercially available through Qiagen® were utilized (Table J2). These crystallization experiments were set in drops with varying ratios of protein to crystallant condition. The ratios set were in the range of 1:1, 2:1, and 3:1 protein to condition in total volume of 1 µL in the subwells of the 96 well (8×12) tray. 100 uL of crystallization condition was place in the well reservoir. These drops were set by utilizing the Mosquito drop setting robot and the completed plates were sealed and stored in a 12° C. incubator. The experiment was monitored by viewing the plates/drops under the microscope to see developments that included drop precipitation, aggregation, phase separation, amorphous formation, as well as initial protein crystals.

TABLE J2

Kits used for initial sparse matrix screening.

| Kit | Cat. No./ID |
| --- | --- |
| Classics Suite | 130901 |
| Classics II Suite | 130923 |
| Classics L Suite | 130902 |
| PEGs Suite | 130904 |
| PEGs II Suite | 130916 |
| PACT Suite | 130918 |
| ProComplex Suite | 130915 |
| AmSO₄ Suite | 130905 |

Crystallization Summary and Crystal Harvesting

Crystallization of the 4 complexes was achieved with derivatives of two main conditions as shown in Table J3). Crystal harvesting was done on optimal crystal forms so that manipulation and cryo-freezing in liquid nitrogen would not jeopardize the integrity of the crystal prior to X-ray diffraction screening and possible data collection. To prevent icing, a cryo-protectant was implemented during freezing. The typical cryo-protectant included an addition of 20% glycerol to the crystallization condition that formed the crystal. When crystals formed in conditions with 30% PEG 4000 or above, the addition of glycerol was not necessary. The high percentage of PEG 4000 behaved as a viable cryo-protectant. Crystals of complexes were manipulated with cryo loops that are either nylon or Mitigen® crystal mount style. Single crystals were isolated and excised out of the drop in which they formed and transferred into cryo-protectant for a short period before plunging into liquid nitrogen to flash freeze.

TABLE J3

Crystallization conditions for forming Fab:SIRP-α complex crystals.

| Fab Antibody | Buffer | Salt | Precipitant |
| --- | --- | --- | --- |
| 119 | 0.1M Tris-HCl pH 8.5 | 0.2M MgCl2 | 15% (w/v) PEG 4000 |
| 136 | 0.1M Tris-HCl pH 8.5 | 0.2M MgCl2 | 30% (w/v) PEG 4000 |
| 3 | 0.1M Sodium Acetate pH 4.6 | 0.45M Ammonium Sulfate | 35% (w/v) PEG 4000 |
| 115 | 0.1M Tris pH 7.2 | 0.2M MgCl2 | 18% (w/v) PEG 4000 |

Data Collection and Processing

Data were collected on crystals flash frozen in liquid nitrogen as described above. These samples remained in the cryo stream when screened for protein lattice diffraction prior to subsequent dataset collection via the oscillation method. Collection occurred at either the Advanced Photon Source or Diamond Light Source. Datasets were reduced using the xia2 suite. xia2 is a wrapper script that allows for automated reduction of macromolecular crystallographic data. The program is able to utilize multiple data reducing programs such as XDS, DIALS, Mosfim, and Aimless. These programs allow for the diffraction data to be indexed into the appropriate space group and unit cell, integration of intensities, and scaling to produce an estimate of intensity of each unique reflection. For the initial Complex 1 dataset, phases were calculated via molecular replacement (MR) using Phaser MR of the CCP4 Suite utilizing homolog models of SIRPα, as well as Fab (see PDB CODE: 2UV3 and PDB CODE: 4NM4 respectively). For subsequent datasets of Complex 2, 3, and 4, the completed structure model coordinates of Complex 1 was used as the search model for the phase calculation and the initial model build.

Structure Building and Refinement

Model building utilized the Coot program. As an example, Complex 1 was calculated to have 4 molecules in the ASU, therefore, 4 pairs of AB119f complexed with SIRPα are to be built to complete the structure model. The strategy of structure building was to build amino acid residues into electron density following the known sequence of the target proteins. Quality of data directly correlates to the fit of the structure model into the observed crystal dataset. Therefore, building the tertiary structure of the Complex followed established protocol. Initially, the peptide bone of the residue was built. This was followed by the placement of the correct residue side chain if the electron density map permits. In the instance an original amino acid in the protein sequence was not modeled, it was due to lack of density for the respective side chain, thus only the peptide backbone of the amino acid can be modeled and an alanine residue side chain is built in place. Stretches of the sequence may be a disordered region and cannot be built due to lack of density even for placement of the amino acid backbone. The builds were followed by subsequent rounds of refinement through the Refmac program, a part of the CCP4 Suite. The refinement program is utilized to minimize coordinate parameters through the Maximum Likelihood residual. Refinement was completed when the model parameters fell into favorable statistical tolerances for parameters including: the Rvalue, bond length and angles, and Ramachandran fit. In addition, to check physical tolerances of the model, Molprobity was also utilized to ensure complete and proper structure determination.

Epitope Mapping and Superimposition Analysis

Buried surface area of the antigen for the epitope was calculated as the difference between the solvent-accessible surface area of the antigen alone and antigen in complex with Fab fragment of the antibody. Conversely, buried surface area of the antibody heavy and light chains for the paratope was calculated as the difference between the solvent-accessible surface area of the fab fragment alone and in complex with its antigen. The surface accessible area was calculated by the rolling ball method with probe radius of 1.4 Å. Buried surface area is reported in $Å^2$. All antibody: SIRPα complexes were superimposed by selecting SIRPα from each structure and superimposing its carbon atoms. CD47: SIRPα, complex (V1 variant) structure used for the analysis is PDB:4CMM. The superimposition and the RMSD calculation was performed using PYMOL.

Results

Figure 17A:
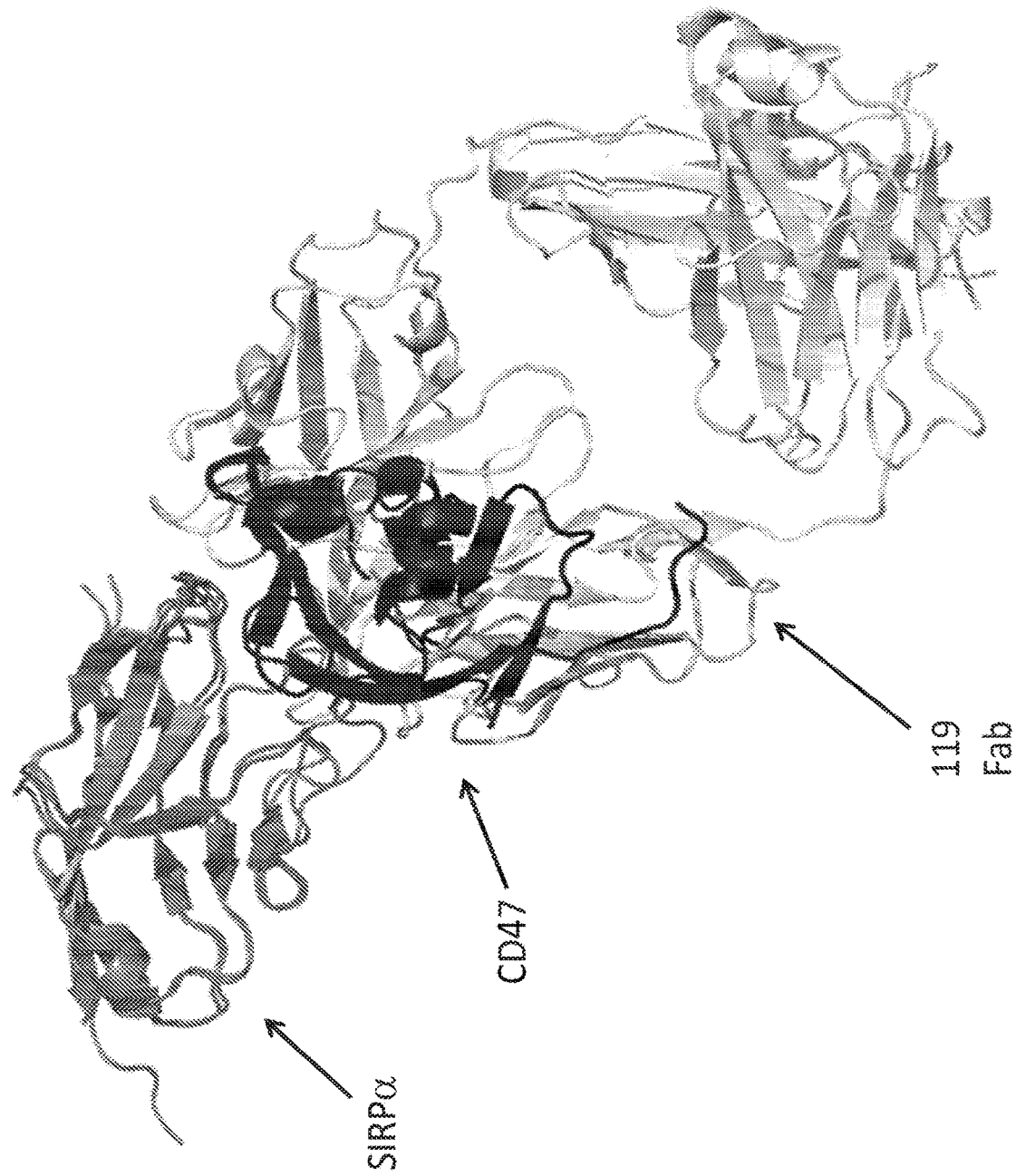
Figure 17B:
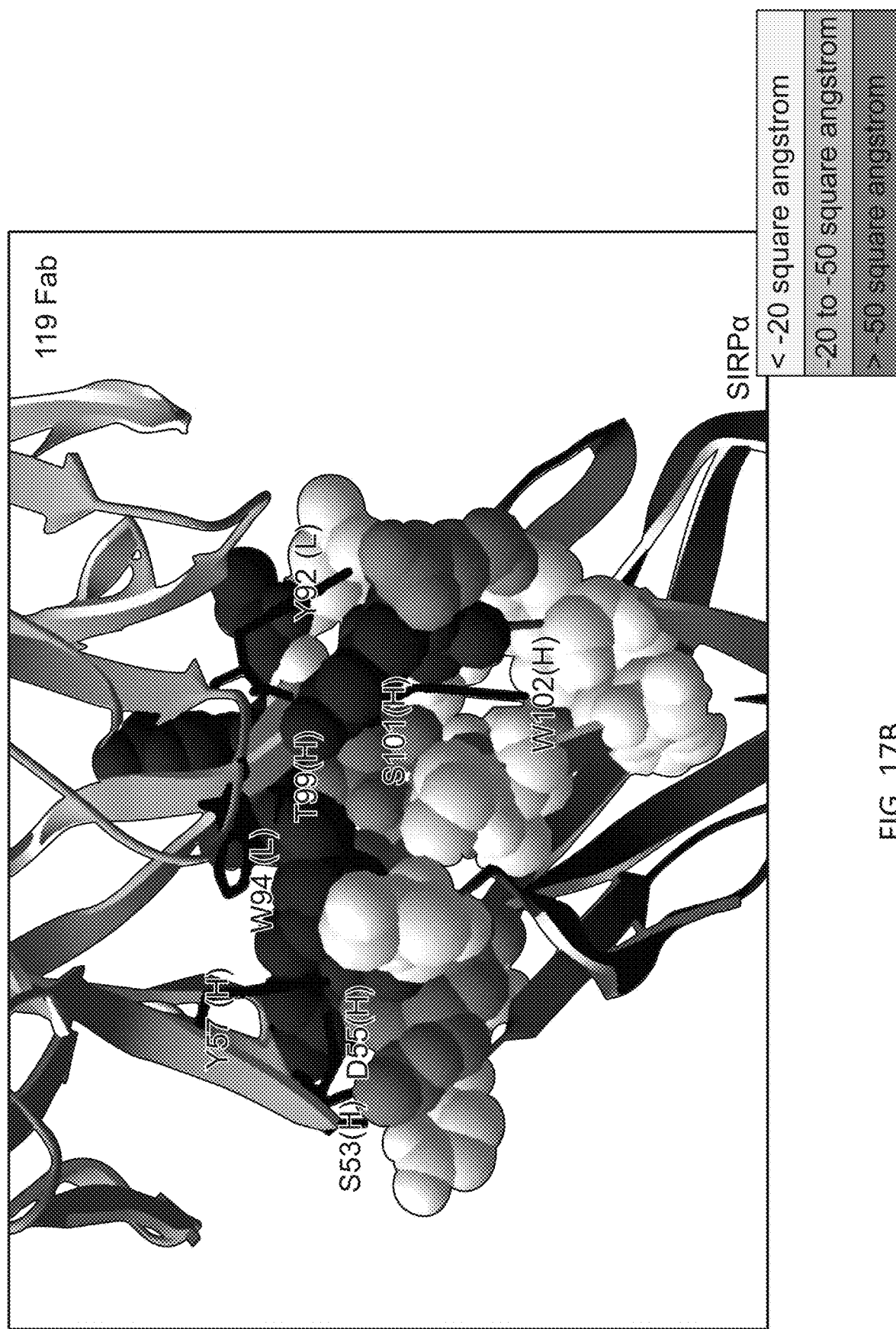

First, the structure of blocking antibody 119 Fab bound to SIRP-α was determined and compared to CD47 binding to SIRP-α. As shown in FIG. 17A, antibody 119 and CD47 bound to a similar epitope of the SIRP-α D1 domain. 56% of the SIRP-α residues in the antibody 119 epitope were also found in the CD47 epitope, while 75% of the SIRP-α residues in the CD47 epitope were also found in the antibody 119 epitope. The SIRP-α residues participating in the interaction with antibody 119 (as determined by buried surface area changes, described supra) are shaded and shown as space-filled models in FIG. 17B. Key residues from the antibody 119 Fab paratope are also shown (black sticks), including heavy chain residues N31, S53, D55, Y57, T99, S101, and W102 (N31 is not visible in the structure orientation shown in FIG. 17B) and light chain residues Y92 and W94 (based on the heavy and light chain variable domain sequences according to SEQ ID NOs:335 and 97, respectively).

Figure 18A:
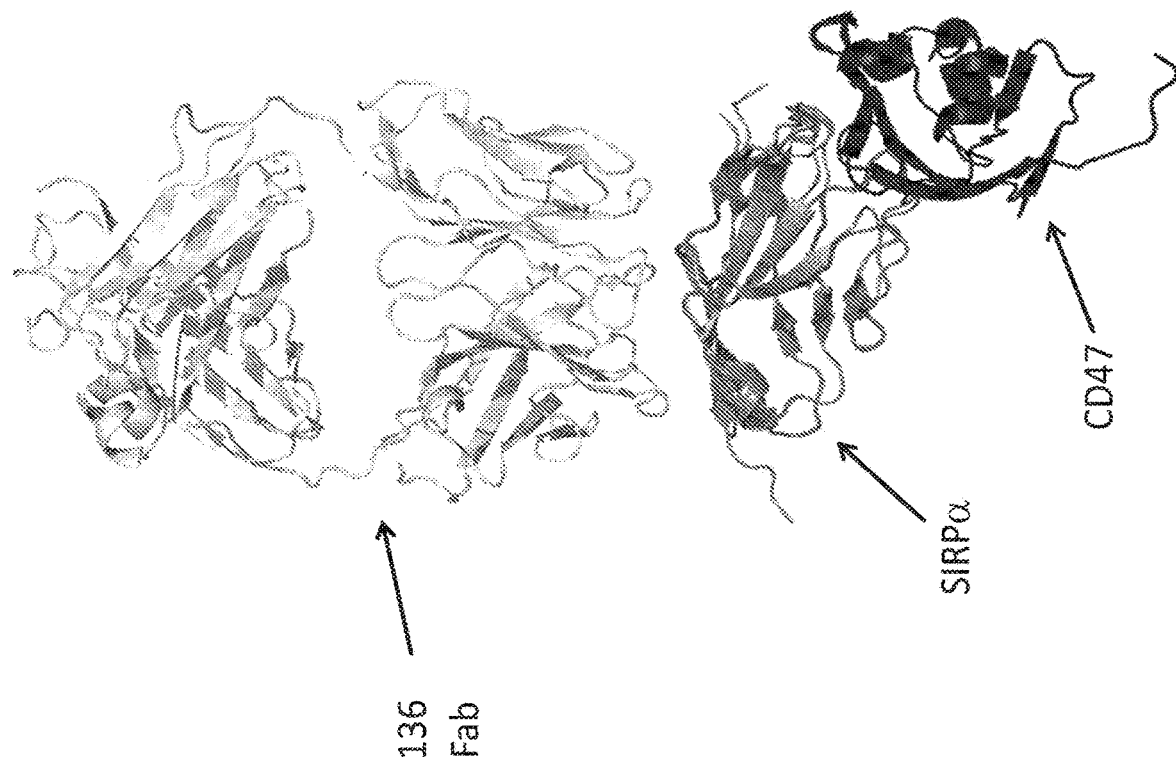
Figure 18B:
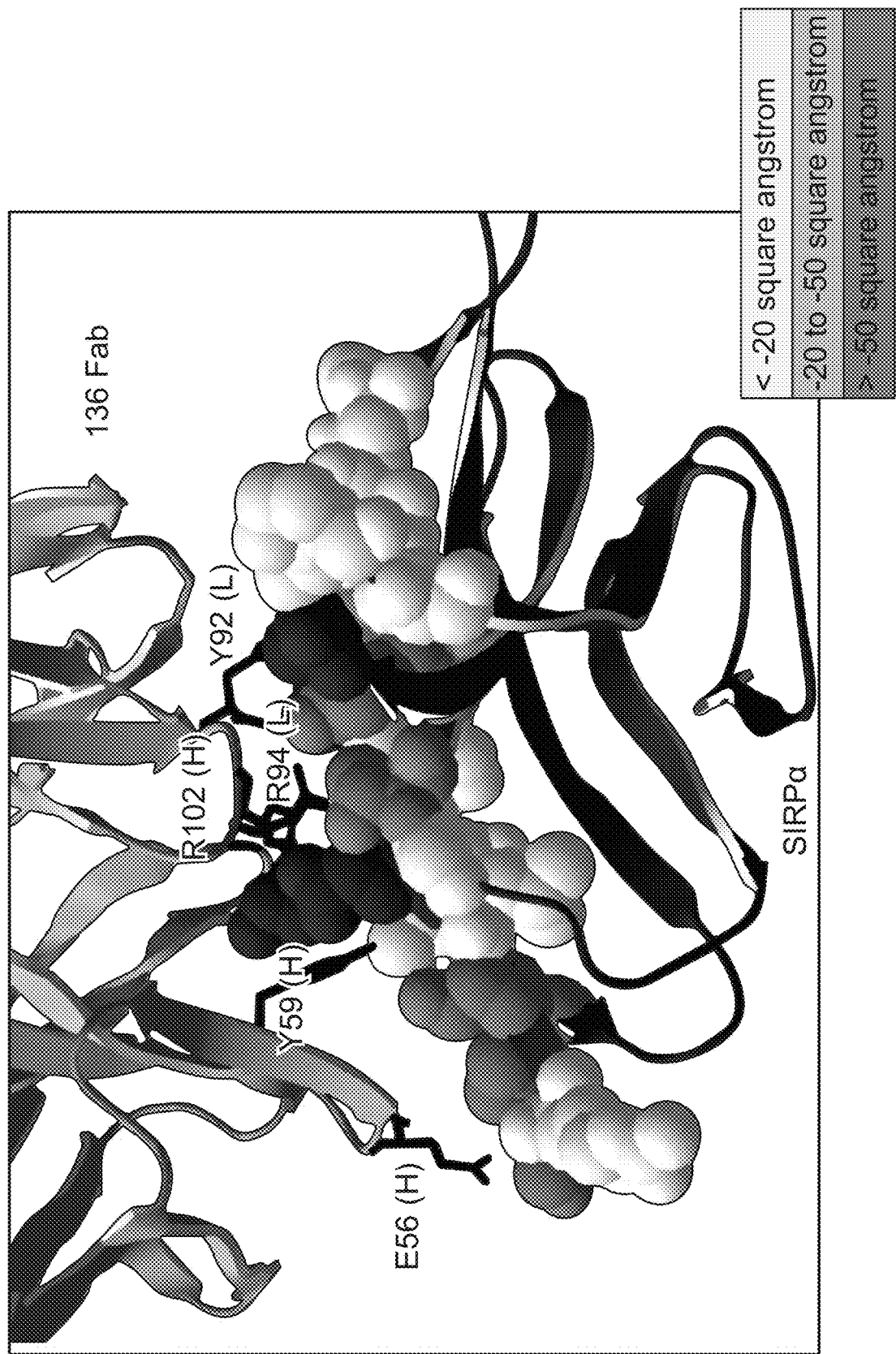

FIG. 18A shows a comparison between CD47 binding to the SIRP-α D1 domain and non-blocking antibody 136 Fab binding to the SIRP-α D1 domain. The SIRP-α binding epitopes of antibody 136 and CD47 were found to be completely non-overlapping. The SIRP-α residues participating in the interaction with antibody 136 are shaded and shown as space-filled models in FIG. 18B. Key residues from the antibody 136 Fab paratope are also shown (black sticks), including heavy chain residues E56, Y59, and R102, and light chain residues Y92 and R94 (based on the heavy and light chain variable domain sequences according to SEQ ID NOs:133 and 134, respectively).

Figure 19A:
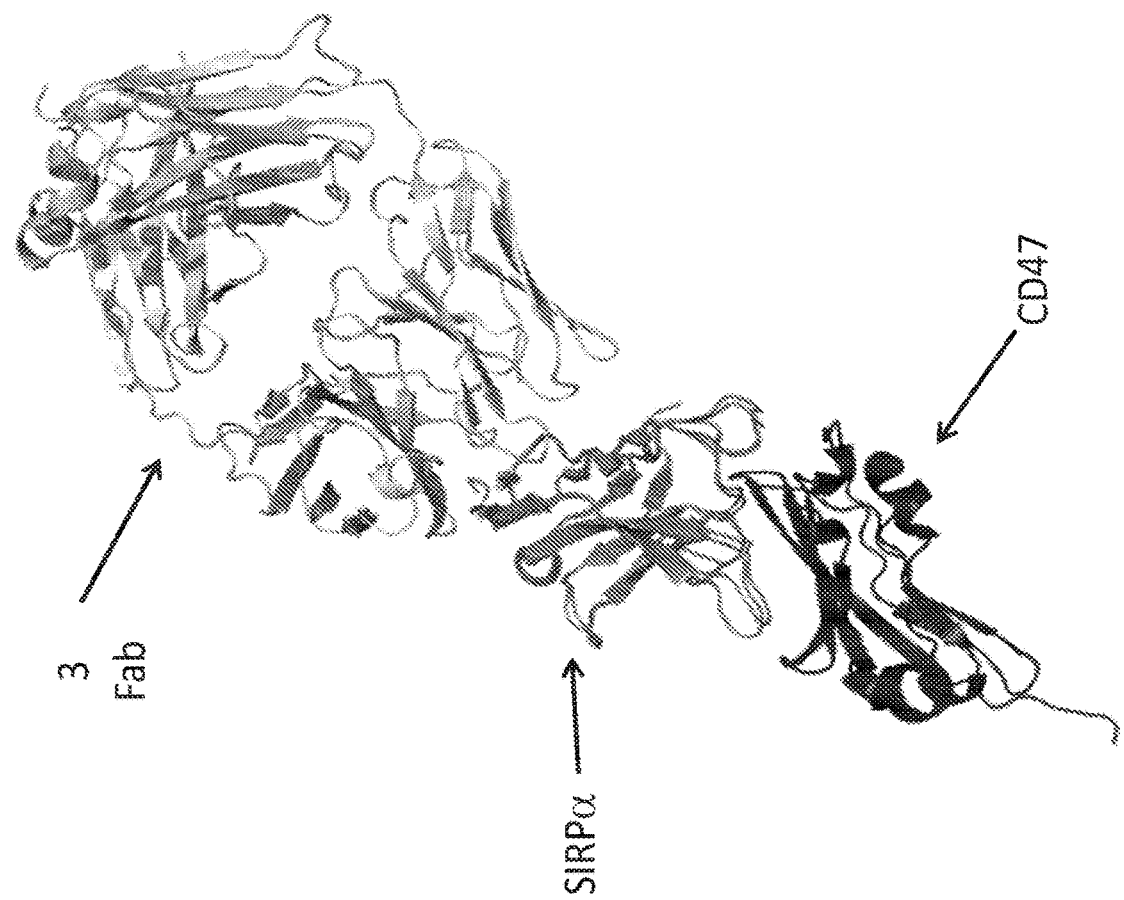
Figure 19B:
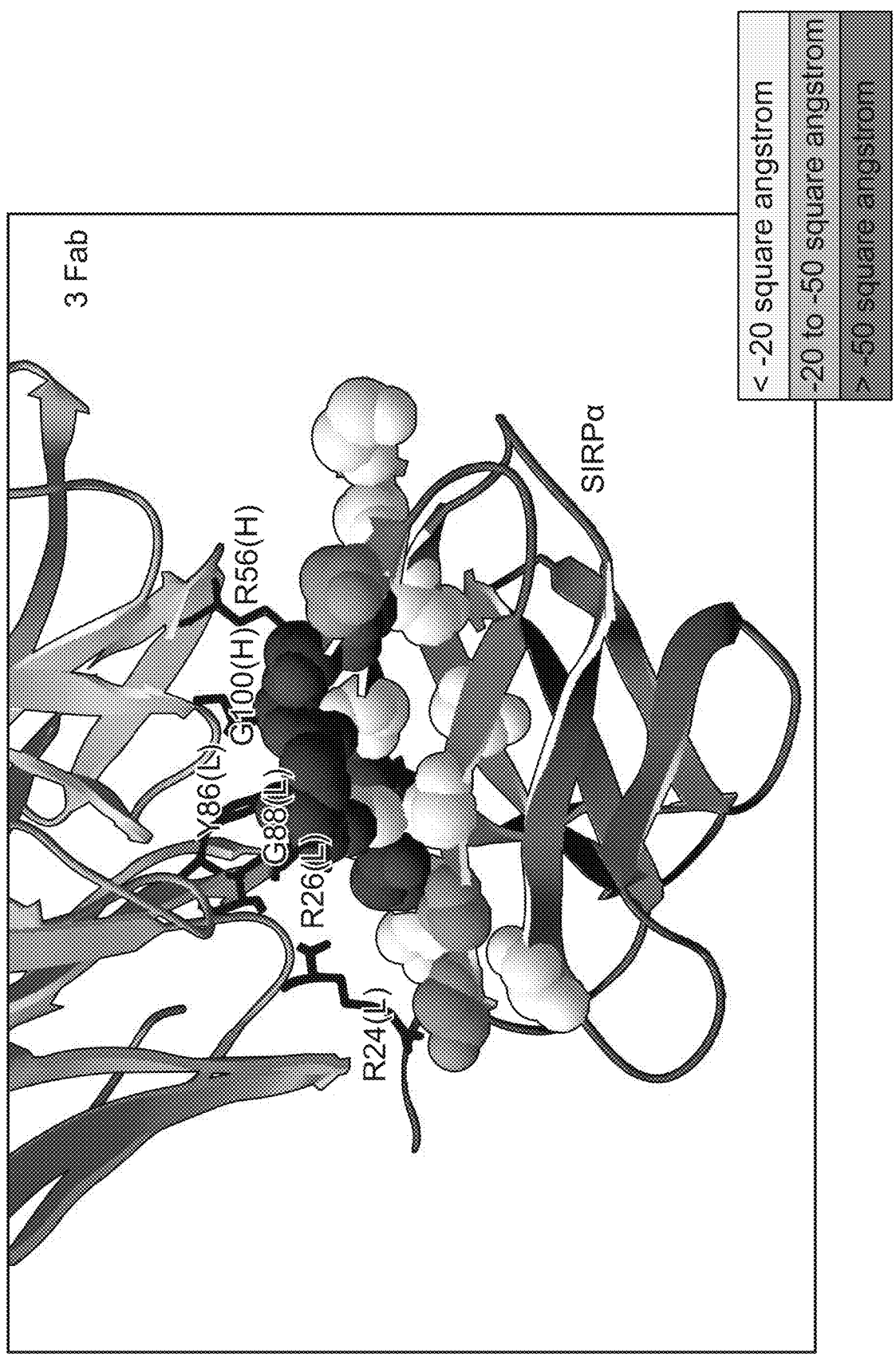

FIG. 19A shows a comparison between CD47 binding to the SIRP-α D1 domain and non-blocking antibody 3 Fab binding to the SIRP-α D1 domain. The SIRP-α binding epitopes of antibody 3 and CD47 were also found to be completely non-overlapping. The SIRP-α residues participating in the interaction with antibody 3 are shaded and shown as space-filled models in FIG. 19B. Key residues from the antibody 3 Fab paratope are also shown (black sticks), including heavy chain residues R56 and G100 and light chain residues R24, R26, Y86, and G88 (based on the heavy and light chain variable domain sequences according to SEQ ID NOs:242 and 243, respectively).

Figure 19C:
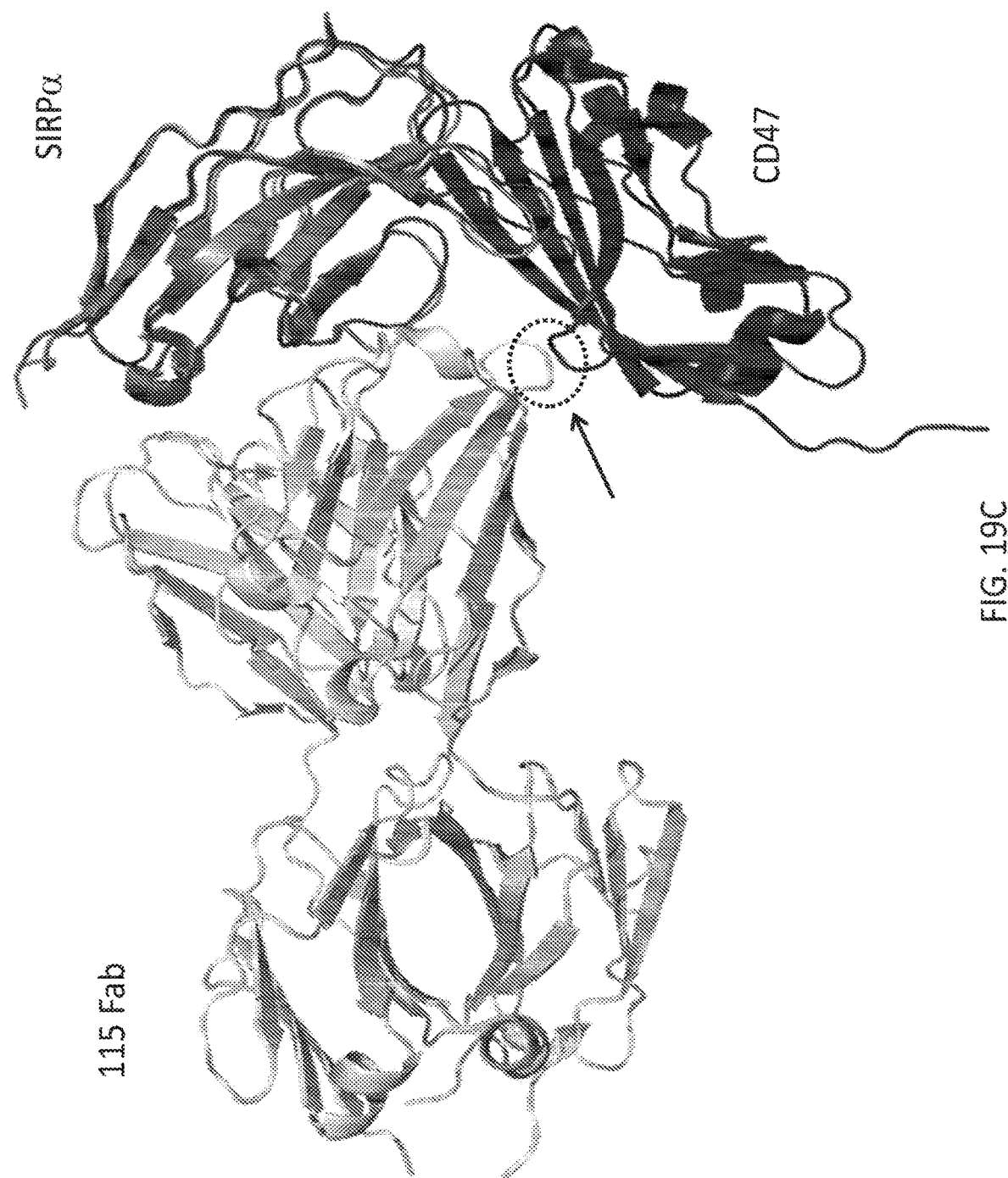
Figure 19D:
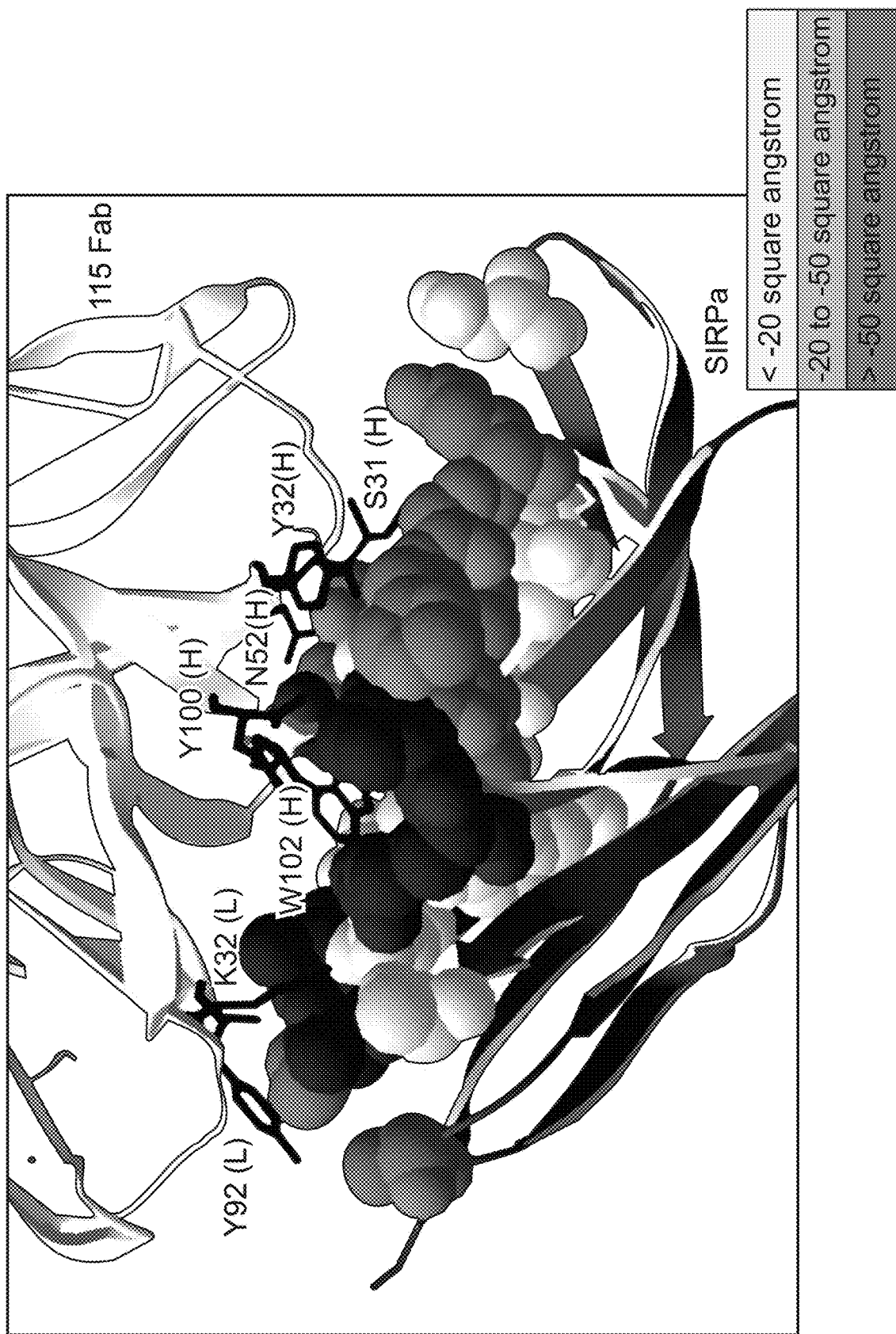

FIG. 19C shows a comparison between CD47 binding to the SIRP-α D1 domain and "kick off" antibody 115 Fab binding to the SIRP-α D1 domain. The SIRP-α binding epitope of antibody 115 was found to be adjacent to the epitope of CD47. While mAb 115 was found to bind an epitope of the SIRP-α D1 domain adjacent to that of CD47, parts of the 115 epitope likely overlap with CD47 itself. Comparing both epitopes, there are 2 identical residues, suggesting that the interactions from the non-overlapping portions of each epitope allow the 115 Fab and CD47 to bind SIRP-α simultaneously. Kinetic analyses described herein demonstrate that antibody 115 forms a transient complex with SIRP-α and CD47 but reduces the affinity of CD47 for the SIRP-α D1 domain. The SIRP-α residues participating in the interaction with antibody 115 are shaded in FIG. 19D. Key residues from the antibody 115 Fab paratope are also shown, including heavy chain residues S31, Y32, N52, Y100, and W102 and light chain residues K32 and Y92 (based on the heavy and light chain variable domain sequences according to SEQ ID NOs:273 and 274, respectively).

Figure 20A:
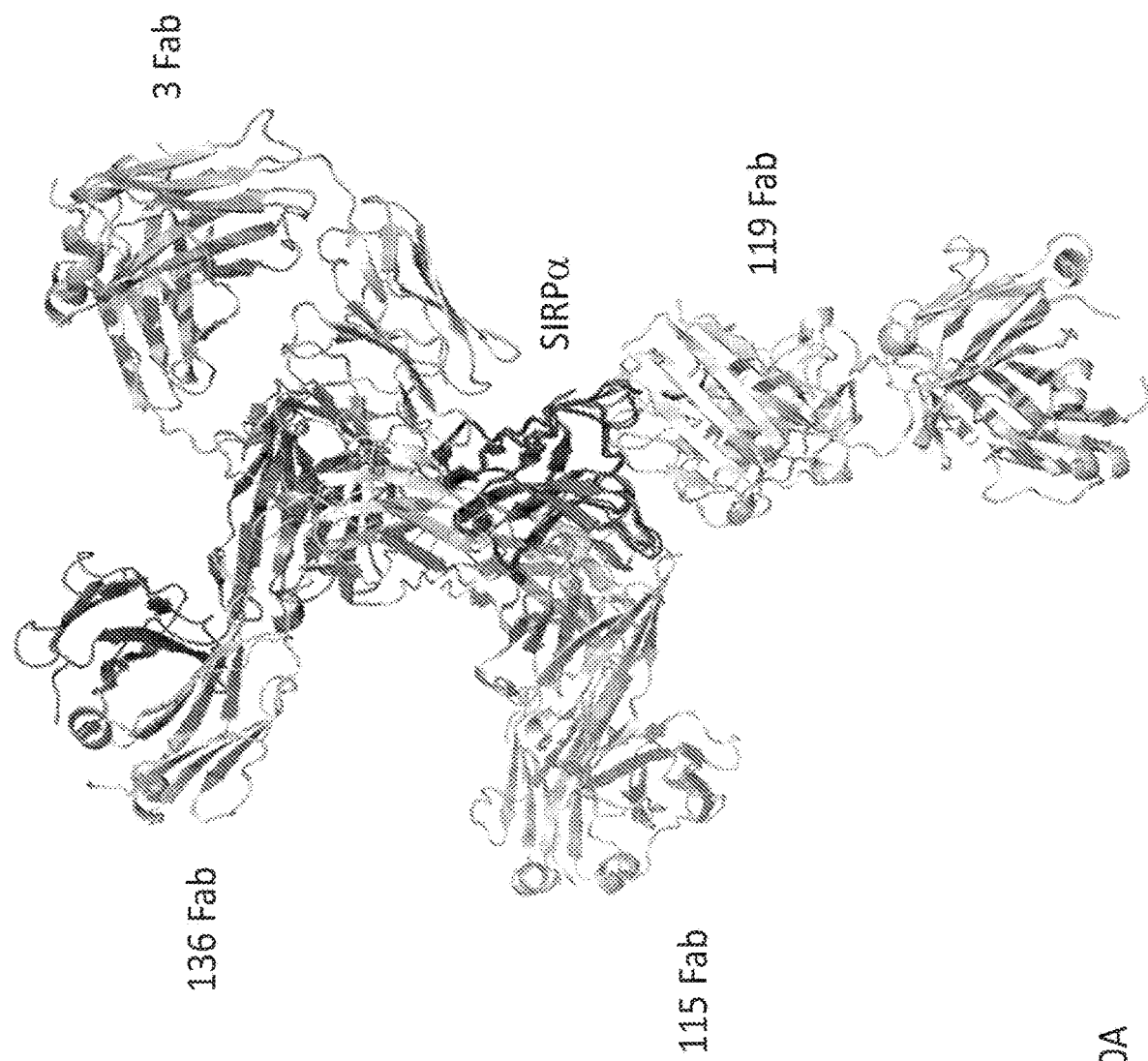
Figure 20B:
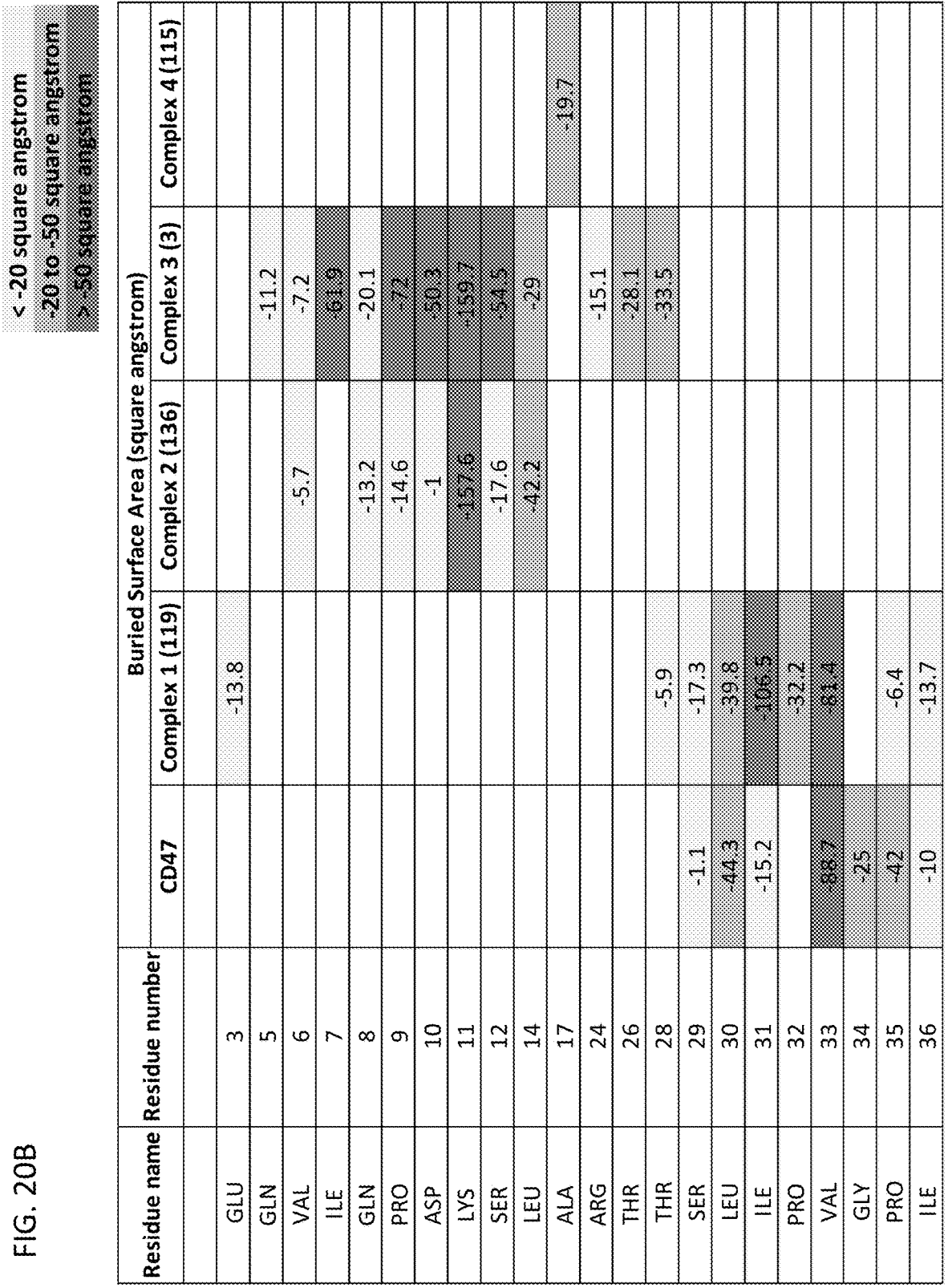
Figure 20C:
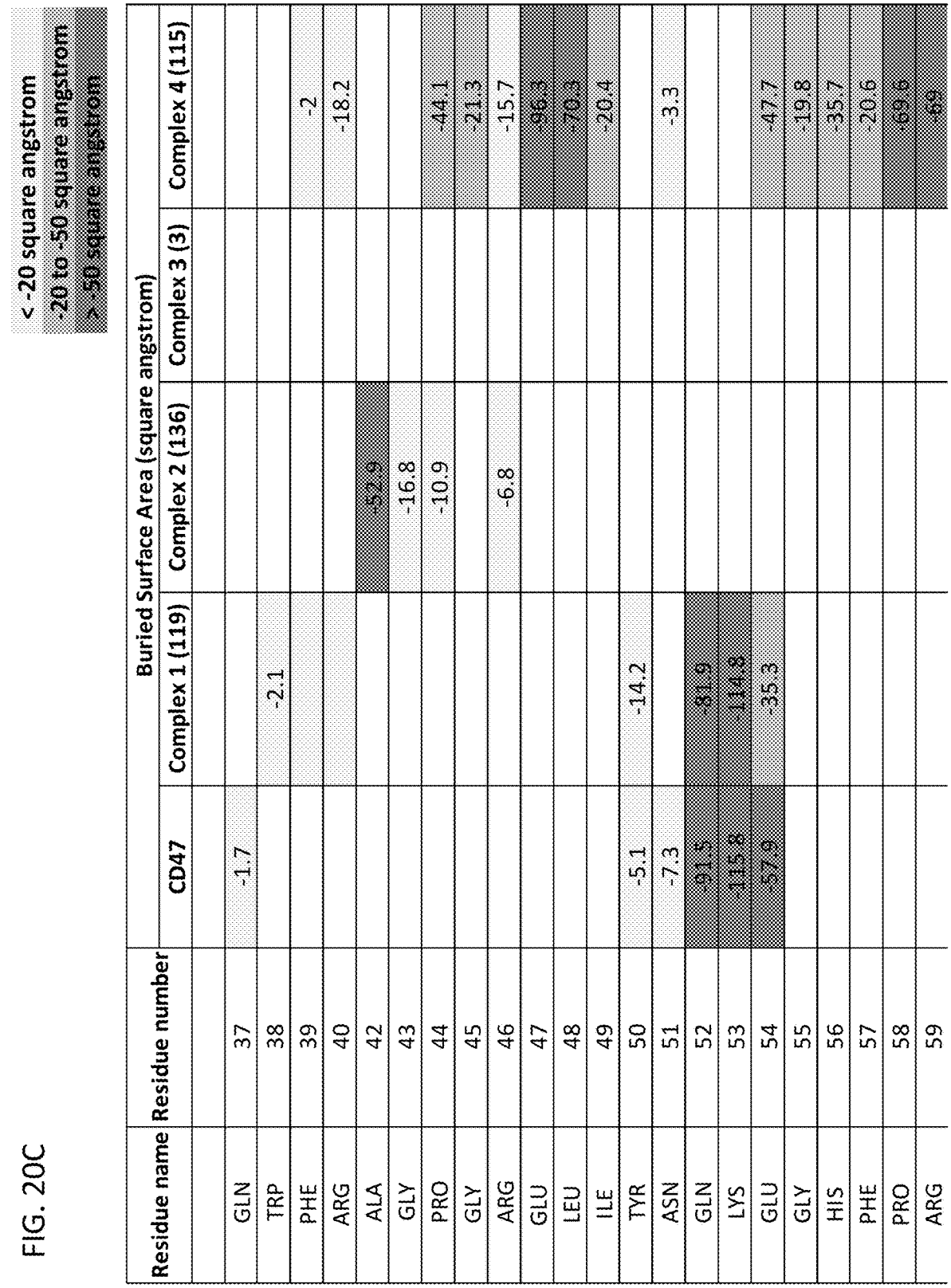
Figure 20D:
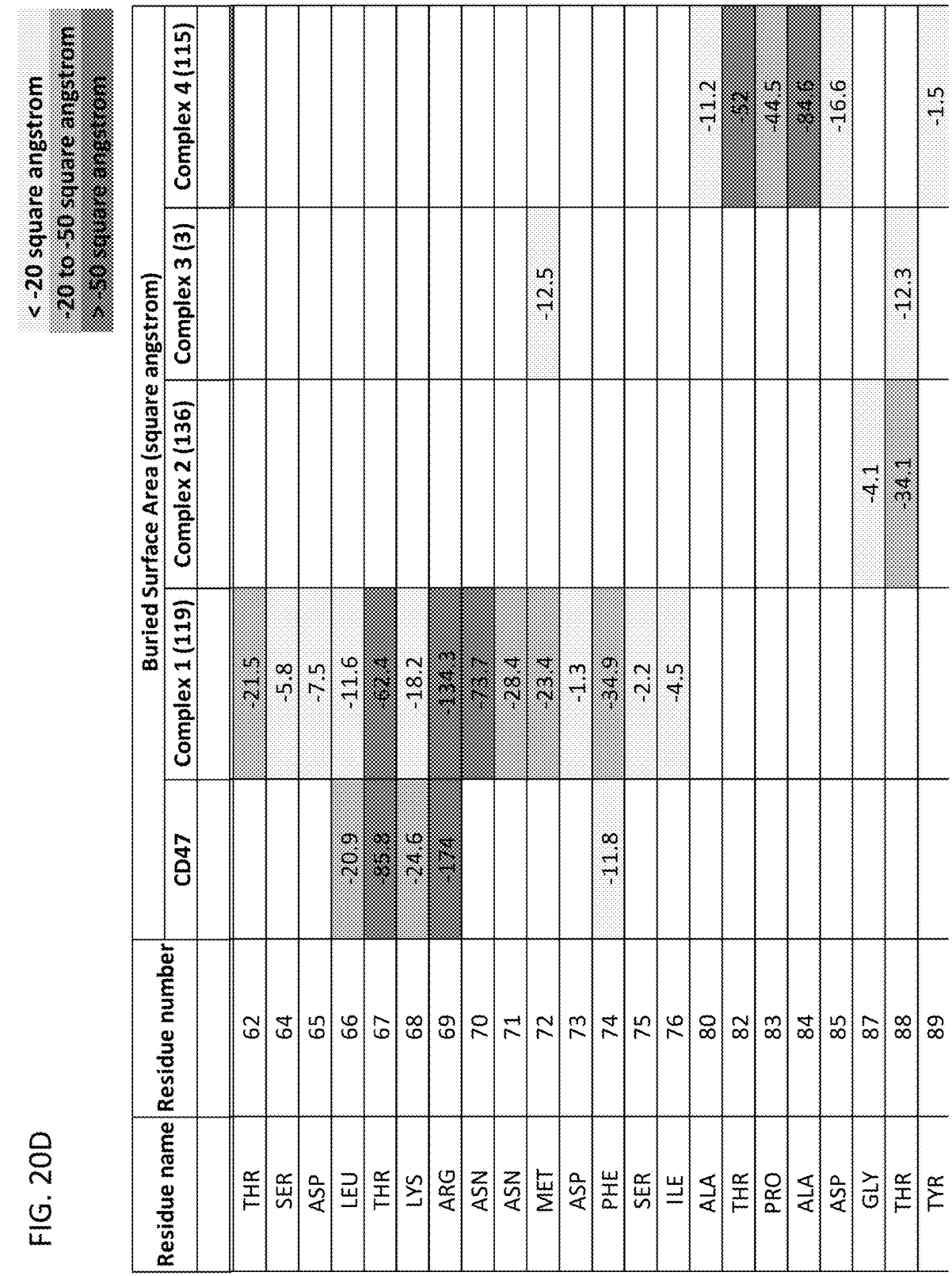

FIG. 20A illustrates the binding of antibodies 119, 136, 3, and 115 to SIRP-α, as compared to CD47 binding to SIRP-α. Blocking antibody 119 was found to bind a completely non-overlapping SIRP-α epitope, as compared with the SIRP-α epitopes of both non-blocking antibodies 136 and 3. SIRP-α and antibody residues that participate in these interactions are summarized in Table K1. SIRP-α residues determined to interact with CD47 were determined as follows: 29, 30, 31, 33, 34, 35, 36, 37, 50, 51, 52, 53, 54, 66, 67, 68, 69, 74, 93, 96, 97, 98, 99, and 101 (according to SEQ ID NO:5). FIGS. 20B-20E summarize the epitopes for CD47 and anti-SIRP-α Fabs 119, 136, 3, and 115 binding to SIRP-α (residues according to SEQ ID NO:296) and lists buried surface area changes. As described herein, the numbering of amino acid residues of an antibody used to indicate the paratope is based on numbering according to the amino acid sequence of the heavy or light chain, and not, e.g., the Kabat or Chothia numbering of antibody residues.

TABLE K1

SIRP-α epitopes and antibody paratopes for selected anti-SIRP-α antibodies.

| Antibody clone | SIRP-α epitope residues | Heavy chain antibody paratope residues | Light chain antibody paratope residues |
|---|---|---|---|
| 119 | 3, 28, 29, 30, 31, 32, 33, 35, 36, 38, 50, 52, 53, 54, 62, 64, 65, 66, | 30, 31, 32, 33, 50, 52, 53, 54, 55, 56, 57, 96, 98, 99, | 27, 29, 30, 32, 49, 53, 55, 56, 91, 92, 94, and 95 |

TABLE K1-continued

SIRP-α epitopes and antibody paratopes for selected anti-SIRP-α antibodies.

| Antibody clone | SIRP-α epitope residues | Heavy chain antibody paratope residues | Light chain antibody paratope residues |
|---|---|---|---|
|  | 67, 68, 69, 70, 71, 72, 73, 74, 75, 76, 95, 96, 97, and 98 (SEQ ID NO: 296) | 100, 101, 102, 103, 104, 105, 106, and 108 (SEQ ID NO: 335) | (SEQ ID NO: 97) |
| 136 | 6, 8, 9, 10, 11, 12, 14, 42, 43, 44, 46, 87, 88, 90, 103, 104, 105, 106, 107, 108, 109, 111, 112, 113, 115, and 116 (SEQ ID NO: 296) | 33, 52, 54, 56, 57, 59, 99, 100, 101, 102, 103, and 104 (SEQ ID NO: 133) | 27, 30, 32, 92, 93, 94, and 95 (SEQ ID NO: 134) |
| 3 | 5, 6, 7, 8, 9, 10, 11, 12, 14, 24, 26, 28, 72, 88, 90, 108, 109, 111, 113, and 115 (SEQ ID NO: 296) | 31, 50, 52, 53, 54, 56, 58, 99, 100, 101, and 102 (SEQ ID NO: 242) | 24, 25, 26, 45, 86, 87, 88, and 89 (SEQ ID NO: 243) |
| 115 | 17, 39, 40, 44, 45, 46, 47, 48, 49, 51, 54, 55, 56, 57, 58, 59, 80, 82, 83, 84, 85, 89, 100 (SEQ ID NO: 296) | 28, 30, 31, 32, 33, 50, 52, 53, 54, 56, 57, 75, 100, 101, 102 (SEQ ID NO: 273) | 32, 91, 92, 93, and 94 (SEQ ID NO: 274) |

TABLE K2

Anti-SIRP-α antibody paratopes and buried surface area calculations.

| Residue name | Residue number | Change in buried area (Å²) |
|---|---|---|
| 119 Heavy Chain |  |  |
| TRP | 102 | −228 |
| SER | 101 | −97.2 |
| THR | 99 | −70.4 |
| SER | 53 | −60.9 |
| ASP | 55 | −59.2 |
| ASN | 31 | −58.2 |
| TYR | 57 | −53.5 |
| PHE | 32 | −43.1 |
| SER | 103 | −30.7 |
| SER | 98 | −24.7 |
| SER | 30 | −19.3 |
| GLY | 52 | −18.4 |
| VAL | 100 | −18.4 |
| ASP | 105 | −17.2 |
| ALA | 33 | −16.3 |
| GLY | 54 | −7.8 |
| ASP | 108 | −6.2 |
| PHE | 106 | −5.7 |
| GLY | 104 | −5.6 |
| LYS | 96 | −5.3 |
| THR | 56 | −2.9 |
| THR | 50 | −1.7 |
| 119 Light Chain |  |  |
| TYR | 92 | −78 |
| TRP | 94 | −57.5 |
| ILE | 53 | −31.5 |
| TYR | 49 | −30.2 |
| PRO | 95 | −20.4 |
| GLU | 55 | −16.6 |
| VAL | 29 | −12.3 |
| ALA | 30 | −8.8 |
| ASP | 32 | −8 |
| TYR | 91 | −3.5 |
| THR | 56 | −1.5 |
| GLN | 27 | −3.4 |
| 136 Heavy Chain |  |  |
| ARG | 102 | −114.9 |
| GLU | 56 | −67.6 |
| TYR | 59 | −57.3 |
| ARG | 104 | −46.7 |
| ILE | 57 | −30.8 |
| ASN | 101 | −12.6 |
| ASP | 33 | −12 |
| TYR | 103 | −10.9 |
| SER | 52 | −5.1 |
| SER | 54 | −4 |
| GLU | 99 | −3.3 |
| ASN | 100 | −1.1 |
| 136 Light Chain |  |  |
| ARG | 94 | −97.6 |
| TYR | 92 | −95.2 |
| TYR | 30 | −89 |
| GLN | 27 | −46.6 |
| TYR | 32 | −46.5 |
| ASP | 93 | −19.1 |
| PRO | 95 | −7.3 |
| 3 Heavy Chain |  |  |
| ARG | 56 | −107.9 |
| GLY | 100 | −62 |
| ASP | 31 | −34.9 |
| SER | 53 | −27.1 |
| THR | 52 | −25.2 |
| SER | 101 | −22.7 |
| GLY | 54 | −15.1 |
| TYR | 58 | −12.2 |
| GLN | 50 | −7.3 |
| GLY | 102 | −5.1 |
| PHE | 99 | −4.5 |
| 3 Light Chain |  |  |
| ARG | 24 | −123.6 |
| TYR | 86 | −62.5 |
| ARG | 26 | −56.4 |
| GLY | 88 | −49.1 |
| ASP | 87 | −22.1 |
| GLY | 25 | −13.1 |
| ARG | 45 | −4.8 |
| SER | 89 | −1.7 |
| 115 Light Chain |  |  |
| LYS | 32 | −70.2 |
| TYR | 91 | −2.9 |
| TYR | 92 | −85 |
| TYR | 93 | −22.3 |
| TRP | 94 | −21.4 |
| 115 Heavy Chain |  |  |
| SER | 28 | −35.3 |
| SER | 30 | −17.2 |
| SER | 31 | −70.6 |

TABLE K2-continued

Anti-SIRP-α antibody paratopes and buried surface area calculations.

| Residue name | Residue number | Change in buried area (Å$^2$) |
|---|---|---|
| TYR | 32 | −50.2 |
| ALA | 33 | −1.3 |
| ARG | 50 | −9.5 |
| ASN | 52 | −54.4 |
| SER | 53 | −39.8 |
| GLY | 54 | −1.4 |
| GLY | 56 | −34 |
| GLY | 57 | −11.2 |
| SER | 75 | −13.3 |
| TYR | 100 | −53.6 |
| ASP | 101 | −45.8 |
| TRP | 102 | −136.4 |

These results elucidate the binding interfaces between the SIRP-α D1 domain and various anti-SIRP-α antibodies, as well as the binding interface between CD47 and SIRP-α. They also provide a structural basis for the observations that antibody 119 blocks binding between CD47 and SIRP-α (since they share overlapping SIRP-α epitopes), that antibodies 136 and 3 do not block binding (as their epitopes do not overlap with that of CD47), and that antibody 115 "kicks CD47 off" from binding SIRP-α (since they share only slightly overlapping SIRP-α epitopes). These studies further highlight specific antibody and SIRP-α residues that participate in each interaction.

With the SIRPα binding epitopes of non-blockers (3, 136), blockers (119) and kick-off (115) antibodies defined by crystallography, the binding locations for additional anti-SIRPα antibodies can be characterized by carrying out epitope binning described in Example 5. For instance, for any anti-SIRPα antibodies that compete with non-blocker 136 for binding to SIRPα, we can predict that these antibodies would share similar binding epitopes as 136 as defined by crystallography.

Example 5: Epitope Binning of Anti-SIRP-α Antibodies

Figure 21A:
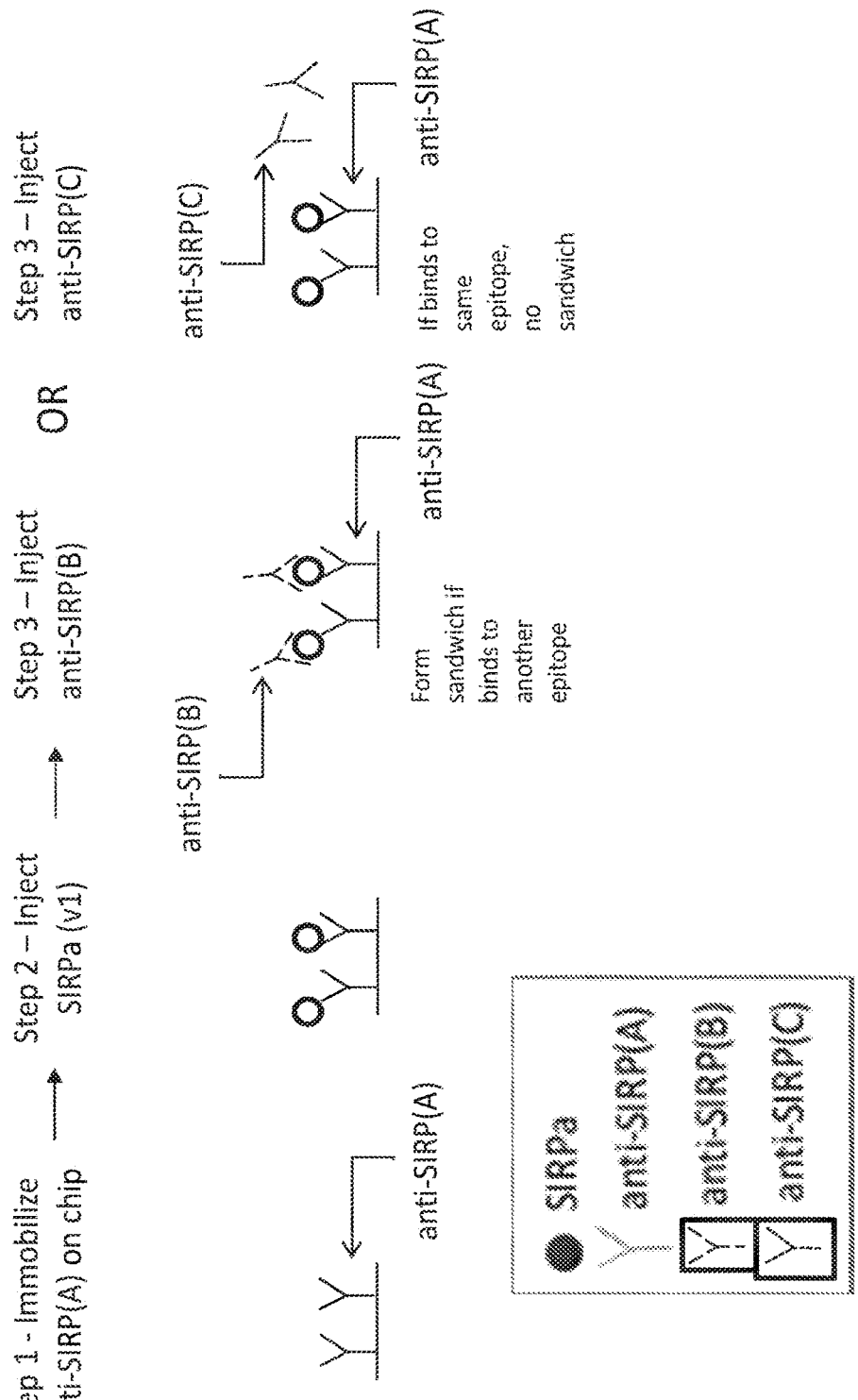
FIG. 21A shows a flowchart for epitope binning of anti-SIRP-α antibodies.

Anti-SIRP-α antibodies described above were next assayed in epitope binning experiments with SIRP-α in order to categorize antibodies having shared and distinct epitopes.
Methods
Epitope Binning Briefly, epitope binning was conducted as shown in FIG. 21A. A first anti-SIRP-α antibody was immobilized on a chip, then human SIRP-α v1 (SEQ ID NO:5) was injected. A second anti-SIRP-α antibody was then injected. If the second antibody was able to bind the complex formed between the first anti-SIRP-α antibody and SIRP-α, the first and second antibodies were determined to bind different epitopes. If the second antibody was not able to bind, the first and second antibodies were determined to share an epitope.

Figure 21B:
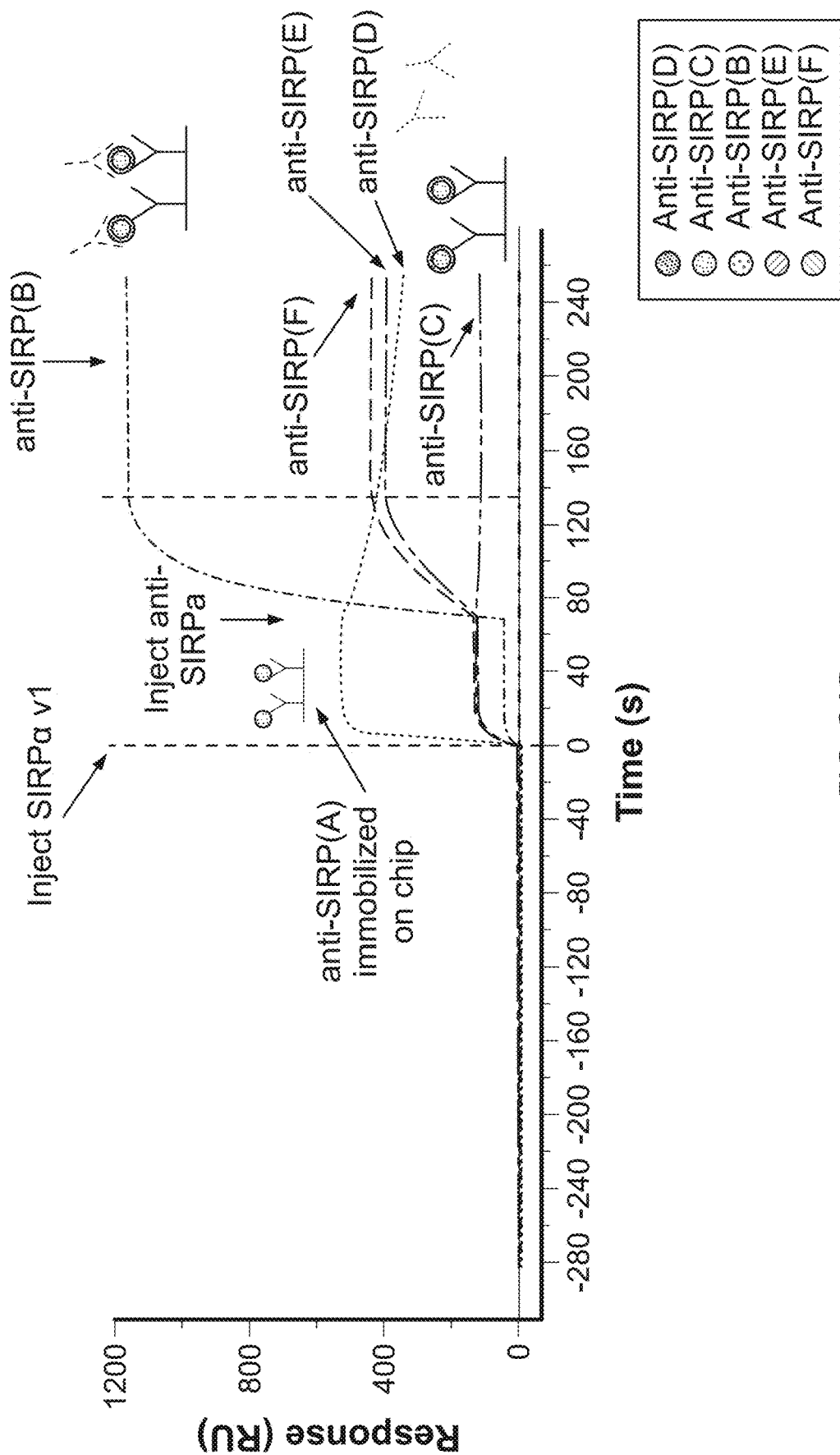
FIG. 21B shows results of an exemplary assay for epitope binning of anti-SIRP-α antibodies A, B, C, D, E, and F.

Exemplary results of a binning assay using anti-SIRP-α antibody (A) immobilized to the chip and injecting anti-SIRP-α antibodies (B-F) are shown in FIG. 21B. Anti-SIRPα antibody (B), (E) and (F) form sandwiches with the complex, and this is indicated by the increasing RU at time 60 s (upon injection of respective anti-SIRPα antibodies). As such, they are determined to bind different epitopes than anti-SIRPα (A) and are indicated by white boxes in the binning plot (FIGS. 22A & 22B). For anti-SIRPα antibody (C) and (D), they did not form a sandwich, and this is indicated by a steady RU after injection of respective anti-SIRPα antibodies. As such, they are determined to bind the same epitope as anti-SIRPα (A) and are shaded gray in the binning plot (FIGS. 22A & 22B). The clone number for the ligand (anti-SIRPα) bound to the chip is indicated as rows, and the clone number for the analytes (anti-SIRPα) injected over the chip is indicated as columns in FIGS. 22A & 22B. "X" indicates scenarios where the data from one orientation disagreed with the other.

First, anti-SIRPα antibodies were immobilized on GLC chips using Proteon™ Amine Coupling Kit as described before. Briefly, for the immobilization step, GLC chip was activated with EDAC/Sulpho-NHS 1:1 (Biorad) diluted 1/80 for 300 s at 25 μL/min. Anti-SIRPα antibodies were diluted to 80 nM concentration in 10 mM sodium acetate buffer pH 4.5 and immobilized to the chip at 30 μL/min for 50 s. Chip was inactivated with ethanolamine for 300 s at 25 μL/min. Afterwhich, SIRP-α v1 (SEQ ID NO:5) (100 nM) was first injected at 100 uL/min for 60 s followed by injecting the anti-SIRPα antibodies in testing (100-150 nM) at 100 uL/min for 60 s. The surfaces were regenerated with a 2:1 v/v blend of Pierce IgG elution buffer/4M NaCl. The resultant sensograms were used to score and group the antibodies into different bins according to their binding profiles.
Results The following anti-SIRP-α antibody clones were binned: 3, 21, 25, 27, 45, 66, 115, 116, 117, 118, 119, 120, 121, 122, 123, 132, 135, 136, 137, 149, 161, 162, 173, 194, 209, 213, and 218. As shown in FIGS. 22A & 22B, the results demonstrated that each mode (B:blocking, NB:non-blocking, and KO: "kick off") of anti-SIRP-α antibody binding to human SIRP-α v1 binned separately. For the non-blockers, the anti-SIRPα antibodies could be further separated into 4 bins based on their binding profiles. For instance, anti-SIRPα antibodies 123, 149, 161, 162, 194 and 218 were grouped as Bin5. Anti-SIRPα antibodies 3, 173, 209 and 213 were grouped as Bin 4. Anti-SIRPα antibodies 136 and 137 were grouped as Bin 2. Anti-SIRPα antibody 45 has a unique binding profile and is grouped as Bin 6.

Combined with the structural analyses described in Example 4, these results led to the model of antibody and CD47 binding to the SIRP-α D1 domain shown in FIG. 23. For instance, various anti-SIRPα antibodies in Bins 1, 2, 3 and 4 are postulated to share similar binding epitopes with anti-SIRPα 119, 136, 115 and 3 which were categorized in the respective bins. The binding epitopes for anti-SIRPα 119, 136, 115 and 3 have been obtained from crystal solutions as described in Example 4.

In addition, anti-SIRPα antibodies in Bin 5 are postulated to bind adjacent to anti-SIRPα 136 (Bin 2) and 115 (Bin 3) respectively and share overlapping epitopes. This is based on binning data showing anti-SIRPα antibodies in Bin 5 competed with antibodies in Bins 2 and 3 for binding to SIRPα V1, and they did not compete with antibodies in Bins 1, 4 and 6 (FIG. 22B).

Anti-SIRPα antibody 45 (Bin 6) is postulated to bind adjacent to anti-SIRPα 3 (Bin 4) and 136 (Bin 2) respectively and share overlapping epitopes. This is based on binning data showing anti-SIRPα 45 competed with antibodies in Bins 2 and 4 for binding to SIRPα V1, and anti-SIRPα 45 did not compete with antibodies in Bins 1, 3 and 5 (FIG. 22B).

The model in FIG. 23 illustrates the epitope of each antibody bin based on structural and binning analyses, and demonstrates the overlap between various antibody bins using exemplary antibody clones. Additional anti-SIRP-α antibodies isolated herein are grouped into families and bins based on their epitope mapping profiles, homologies in their VH/VL domain sequences, binding specificities to SIRP proteins and the sources of the antibodies. For instance, anti-SIRP-α antibodies in family 1/Bin 1 are CD47 blockers that share high sequence homologies in their VH and VL domains (Table P and FIGS. 11O & 11P). The VH and VL are fully human sequences. Anti-SIRP-α antibodies in family2/Bin 1 are also CD47 blockers. Their VH and VL share high homologies and are from human and chicken sources respectively (Table P, FIGS. 11A-11D). The anti-SIRP-α antibodies in Family 3/Bin 2 include CD47 non-blockers, and their highly homologous VH/VL are fully human sequences (Table P, FIGS. 11E-11F). The anti-SIRP-α antibodies in Family 4/Bin3 include kick-off antibodies, and their highly homologous VH/VL are fully human sequences (Table P, FIGS. 11G & 11H). Family 5 includes CD47 non-blockers that are separately mapped into Bins 4, 5, and 6. The sequence alignments of these antibodies and their binding profiles are shown in FIGS. 11I-11N and Table P, respectively. The $K_{off}$ binding values to various SIRP-α, SIRP-β, and SIRP-γ polypeptides of the corresponding anti-SIRPα antibodies in Families 1-5 are presented in Table T.

Example 6: Germline and Liability Mutation Variants of Anti-SIRP-α Antibodies

Some anti-SIRP-α antibodies described above are fully human antibodies generated in a chicken (e.g., antibodies 119, 135, and 136). As such, some of these antibodies may contain mutations in the variable domain framework sequences, as compared to wild-type human germline sequence, by virtue of generating these antibodies in chicken B cells. Therefore, it is desirable to "back-mutate" these respective residues to match that of human germline sequence with the goal of limiting immunogenicity when these anti-SIRPα antibodies are tested in humans as potential therapeutics. In addition to germline back-mutations, the CDRs and framework region of antibodies 119, 135 and 136 were analyzed for liability hot spots. These analyses identified sites where engineering may be desired to limit risk due to modifications that may occur during manufacturing, storage and/or drug development of anti-SIRPα antibodies.

Methods

Germline/Liability Mutations

The $K_D$ for respective germline and liability mutants binding to SIRP were determined using direct immobilization using GLC chip as described supra.

The wildtype and mutant antibodies were expressed in Expi293 and purified by Protein A affinity column chromatography as described earlier. All antibodies were expressed as human L234A/L235A/G237A/N297A IgG1 Fc antibodies. Mutagenesis was carried out using QuikChange Lightning Site Directed Mutagenesis kit according to manufacturer's instructions (Agilent Catalog #210518).

Results

Antibodies 119, 135, and 136 were examined. Selected antibody sequences were aligned with available human germline sequences using IgBlast (NCBI). For instance, a total of 7 sites on the heavy and light chains of 119 were identified. As shown in FIG. 24A, residues that were not commonly occurring in human germline sequence of 119 VH (e.g., D1, E43, and L112) were back-mutated to match human germline sequence (e.g., D1E, E43K, and L112Q) while keeping CDR sequences intact. As for 119 VL (FIG. 24B), residues that were not commonly occurring in human germline sequence of 119 VL (e.g. F21, R39, E60, and T76) were back-mutated to match human germline sequence (e.g. F21L, R39K, E60A, and T76S) while keeping CDR sequences intact. As used herein, the terms "all mut" and "mut" refer to variable domains containing all of the germline mutations described herein for a particular antibody variable domain. The amino acid numberings used to describe the germline and liability mutations are based on sequential numbering accordingly to respective SEQ IDs.

In addition, antibody sequences were also analyzed for "liability" hot spots, including residues that may be susceptible to oxidation, deamidation, isomerization, hydrolysis, and N-linked glycosylation. Potential hot spots are shown in Table L. In particular, M34V and M34L variants of HVR-H1 were generated for the VH domain of multiple antibodies.

TABLE L

| Potential and known hot spots | |
|---|---|
| Oxidation | M |
| Deamidation | NG |
| | NS |
| | NT |
| Isomerization | DG |
| | DS |
| | DT |
| Hydrolysis | DP |
| N-linked glycosylation site(s) | NXS/T |

Variants of antibody 119 were generated using heavy and/or light chain variable domains bearing germline and liability back-mutations. A 119 mutant ("mut") VH domain was generated with the germline back mutations D1E, E43K, and L112Q, as well as the M34V mutations in CDR-H1 that remove a methionine residue that could potentially be oxidized (see SEQ ID NOs:246 for VH sequences). Another variant was generated with the germline back mutations D1E, E43K, and L112Q (see SEQ ID NO:258 for VH sequence). Alignments between the parental and variant sequences are shown in FIG. 24A. A 119 mutant ("mut") light chain was also generated with the germline back mutations F21L, R39K, E60A, and T76S; an alignment between the parental and variant sequence is shown in FIG. 24B.

Antibody 119 variants with the mutant heavy and/or light chain were compared with the parental 119 antibody with an IgG1 Fc region bearing L234A, L235A, G237A, and N297A mutations (EU numbering), and a parental 119 antibody with an IgG4 Fc region bearing an S228P mutation (EU numbering), for binding affinity to human SIRP-α v1 (SEQ ID NO:5), human SIRP-α v2 (SEQ ID NO:6), and cynomolgus SIRP-α (SEQ ID NO:11). The 119 mutant heavy and light chains were both found to cause slight reductions in binding affinity to all three SIRP-α proteins. However, the 119 antibody variant with mutated heavy and light chains still displayed strong binding to both human SIRP-α proteins, with a $K_D$ of approximately 30 nM (Table M). Compared with the parental antibody, yield of the 119 antibody variant with mutated heavy and light chains also decreased by approximately 4.5-fold (Table M).

To investigate effect of methionine in HVR-H1 on 119 SIRPα binding, M34V and M34L single mutations were generated in the 119 VH wildtype background and combined with 119 wildtype light chain. Both 119 wt/wt_M34V and 119 wt/wt_M34L had comparable affinities ($K_D$, M) to human SIRPα v1 and v2 as compared with 119 wt/wt. This indicates that residue M34 is not critical for SIRP-α binding and can be substituted with M34L or M34V mutations. The corresponding VH sequences for M34V and M34L single mutations generated in the 119 VH wildtype background are SEQ ID NO: 421 and 420, respectively.

TABLE M

Binding affinities ($K_D$, M) of 119 variant antibodies to human and cyno SIRP-α proteins

| Antibody | VL/VH | $K_D$ for human v1 | $K_D$ for human v2 | $K_D$ for cyno | Yield (mg/ml) |
| --- | --- | --- | --- | --- | --- |
| 119 | Mut/mut | 3.17E−10 | 8.75E−11 | 1.95E−10 | 1.575 |
| 119 | wt/mut | 2.54E−10 | 6.94E−11 | 1.55E−10 | 5.377 |
| 119 | mut/wt | 2.14E−10 | 8.64E−11 | 1.38E−10 | 3.527 |
| 119 | wt/wt | 1.83E−10 | 6.82E−11 | 1.12E−10 | 7.192 |
| 119 | Mut/mut_V34M | 2.15E−10 | 6.88E−11 | 1.18E−10 | NT |
| AB119 | Wt/wt with hIgG4 | 1.74E−10 | 5.98E−11 | 1.16E−10 | 0.659 |

NT = not tested

Next, similar variants of antibody 135 were generated. A 135 mutant (mut) heavy chain was generated with the germline back mutations D1E, R13Q, E16G, E43K, and L12Q, as well as the M34V mutation in CDR-H1 that removes a methionine residue that could potentially be oxidized (see SEQ ID NO:247 for VH sequence). A similar variant was constructed without the M34V mutation in CDR-H1 (see SEQ ID NO:259 for VH sequence). A 135 mutant (mut) light chain was generated with the germline back mutations F21L and D60A (see SEQ ID NO:248 for VL sequence). Alignments between the parental and variant sequences are shown in FIGS. 25A & 25B.

Antibody 135 variants with the mutant heavy and/or light chain were compared with the parental 135 antibody for binding affinity to human SIRP-α v1 (SEQ ID NO:5), human SIRP-α v2 (SEQ ID NO:6), cynomolgus SIRP-α (SEQ ID NO:11), and human SIRP-γ v1 (SEQ ID NO:15). The 135 mutant heavy and light chains had comparable binding affinity to all four SIRP-α proteins, as well as comparable yields (Table N1).

To investigate the effect of methionine in HVR-H1 of 135 on SIRP-α binding, M34V and M34L single mutations were generated in the 135 VH wildtype background and combined with a 135 wildtype light chain. Both 135 wt/wt_M34V and 135 wt/wt_M34L had comparable affinities ($K_D$, M) to human SIRPα v1 and v2 as compared with 135 wt/wt. This indicates that residue M34 is not critical for SIRP-α binding and can be substituted with an M34L or M34V mutation. The corresponding VH sequences for M34V and M34L single mutations generated in the 135 VH wildtype background are SEQ ID NO: 423 and 422, respectively.

TABLE N1

Binding affinities ($K_D$, M) of 135 variant antibodies to human and cyno SIRP-α proteins and human SIRP-γ protein

| Antibody | VL/VH | $K_D$ for human α v1 | $K_D$ for human α v2 | $K_D$ for cyno | $K_D$ for human γ v1 | Yield (mg/mL) |
| --- | --- | --- | --- | --- | --- | --- |
| 135 | mut/mut | 1.92E−10 | 1.75E−11 | 1.27E−10 | 7.33E−10 | 3.189 |
| 135 | wt/mut | 1.84E−10 | 1.97E−11 | 1.25E−10 | 7.79E−10 | 2.885 |
| 135 | mut/wt | 1.49E−10 | 2.66E−11 | 1.02E−10 | 5.22E−10 | 2.689 |
| 135 | wt/wt | 1.51E−10 | 2.90E−11 | 9.69E−11 | 5.39E−10 | 3.264 |
| 135 | wt/mut V34M | 1.50E−10 | 1.61E−11 | 7.94E−11 | NT | NT |

NT = not tested

Similar variants of antibody 136 were generated. A 136 mutant (mut) heavy chain was generated with the germline back mutations D1E, R13Q, E16R, E43K, and L111Q, as well as the M34V mutation in CDR-H1 that removes a methionine residue that could potentially be oxidized (see SEQ ID NO:249 for VH sequence). A similar variant was constructed without the M34V mutation in CDR-H1 (see SEQ ID NO:260 for VH sequence). A 136 mutant (mut) light chain was generated with the germline back mutations T2I, T12S, T22S, and E38Q (see SEQ ID NO:250 for VL). Alignments between the parental and variant sequences are shown in FIGS. 26A & 26B.

As shown in FIG. 27A, antibody 136 variants with the mutant heavy and/or light chain were compared with the parental ("wt") 136 antibody as IgG1_AAA_N297A for binding affinity to human SIRP-α v1 (SEQ ID NO:5), human SIRP-α v2 (SEQ ID NO:6), cynomolgus SIRP-α (SEQ ID NO:11), NOD mouse SIRP-α (SEQ ID NO:8), BL/6 mouse SIRP-α (SEQ ID NO:9), and BALB/c mouse SIRP-α (SEQ ID NO:10). In FIG. 27A, the Y-axis shows the ratio of $K_D$ mut/$K_D$ wt binding to various SIRP. If ratio=1 indicated no change in $K_D$ compare to parental antibody binding. Ratio=>1 and <1 indicated decrease and increase affinity binding to SIRPα(s) compare to parental antibody. While the 136 wt (VL)/mut (VH) antibody behaved similar to wt (VL)/wt(VH), both variants with the mutated light chain had poorer binding affinities, indicating that some VL mutations were not tolerated.

In order to analyze the effect of each light chain back mutation on binding affinity, additional antibody 136 variants were constructed and characterized for binding affinity to BL/6 mouse SIRP-α (SEQ ID NO:9), NOD mouse SIRP-α (SEQ ID NO:8), BALB/c mouse SIRP-α (SEQ ID NO:10), human SIRP-α v1 (SEQ ID NO:5), human SIRP-α v2 (SEQ ID NO:6), cynomolgus SIRP-α (SEQ ID NO:11), and human SIRP-γ v1 (SEQ ID NO:15). Starting with the "all mutant" background, each individual mutation was reversed. I2T, S12T, S22T, and Q38E mutations were individually tested in otherwise "all mutant" light chains, as shown in FIG. 27B. The I2T mutation in an otherwise all mut background showed consistently similar binding affinity, as compared with the parental wt/wt antibody (see SEQ ID NO:251 for I2T in all mut background and FIG. 27A for alignment with parental and mutant 136 antibodies). However, the other three reverse mutations (S12T, S22T, and Q38E) consistently showed binding affinities more similar to 136 mut/mut, indicating that the T2I mutation is responsible for reduced binding affinity to various SIRP proteins. Additional data from these experiments are provided in Table Q infra.

TABLE N2

Binding affinities ($K_D$, M) of 136 variant antibodies to human, mouse, and cyno SIRP-α proteins and human SIRP-γ protein

| | Light chain/ Heavy chain | V1 SEQ ID NO: 5 | V2 SEQ ID NO: 6 | NOD SEQ ID NO: 8 | BL6 SEQ ID NO: 9 | BALBc SEQ ID NO: 10 | Cyno SEQ ID NO: 11 | Sirpg SEQ ID NO: 15 |
|---|---|---|---|---|---|---|---|---|
| 136 | MutRv_I2T/mut | 7.17E-10 | 1.86E-09 | 6.80E-10 | 1.53E-08 | 4.22E-10 | 2.33E-09 | 4.00E-08 |
| 136 | MutRv_S12T/mt | 4.88E-09 | 1.05E-08 | 2.85E-09 | 1.63E-08 | 2.09E-09 | 7.99E-09 | 6.67E-08 |
| 136 | MutRv_S22T/mut | 4.99E-09 | 8.28E-09 | 2.44E-09 | 1.33E-08 | 1.64E-09 | 6.84E-09 | 6.17E-08 |
| 136 | MutRv_Q38E/mut | 6.18E-09 | 1.25E-08 | 5.98E-09 | 3.31E-08 | 2.98E-09 | 1.04E-08 | 1.93E-08 |
| 136 | MutRv_I2T/mut_V34M | 5.51E-10 | 1.74E-09 | 5.96E-10 | 1.38E-08 | 3.61E-10 | 2.11E-09 | 3.35E-08 |
| 136 | Mut/mut | 7.32E-09 | 1.27E-08 | 5.42E-09 | 2.16E-08 | 2.67E-09 | 9.48E-09 | 2.88E-08 |
| 136 | Wt/wt | 9.72E-10 | 2.54E-09 | 8.21E-10 | 1.64E-08 | 4.58E-10 | 2.83E-09 | 3.36E-08 |

Example 7: Humanization of Anti-SIRP-α Antibodies

The Examples above describe the generation of anti-SIRP-α antibodies having a fully human heavy chain and a chicken light chain. In order to humanize the chicken-derived light chains, chicken HVRs of these antibodies were grafted onto various human lambda light chain frameworks.

Methods

Humanization

Antibodies were humanized using standard techniques. For measuring production yield, equal volume of Expi293 cultures expressing anti-SIRPα antibodies were purified by Protein A affinity chromatography. After buffer exchange into PBS, the protein concentration was determined by A280 and expressed in mg/mL.

Results

In order to design humanized light chains, each chicken light chain sequence was aligned to the closest human germline framework by IgBLAST (NCBI). Using this analysis, the closest match to the chicken lambda light chain framework is human IGLV3 (see SEQ ID NOs:314-317).

In another approach, a literature search was undertaken to determine the optimal human lambda light chain framework sequences to pair with a human VH3 sequences (the human heavy chain used for these antibodies). Based on these analyses, it was thought that human VH3 would pair well with human IGLV1 and IGLV2. See Glanville, J. et al. (2009) *Proc. Natl. Acad. Sci.* 106:20216-20221; Lloyd, C. et al. (2009) *Protein Eng. Des. Sel.* 22:159-168; and Jayaram, N. et al. (2012) *Protein Eng. Des. Sel.* 25:523-529.

Therefore, six humanized light chains were created: Hum1 (AB25 HVRs+human IGLV3 framework), Hum2 (AB25 HVRs+human IGLV1 framework), Hum3 (AB66 HVRs+human IGLV3 framework), Hum4 (AB66 HVRs+human IGLV1 framework), Hum5 (AB25 HVRs+human IGLV2 framework), and Hum6 (AB21 HVRs+human IGLV1 framework). Sequences of the resulting light chain variable domains are provided in Table O1.

TABLE O1

Sequences of humanized variable light chain domains tested. HVR sequences are bolded and underlined.

| Name | LC HVRs | Human LC framework | Sequence |
|---|---|---|---|
| Hum1 | AB25 | IGLV3 | SYELTQPPSVSVSPGQTARITCSGGSYSSYYYAWYQQKPGQAPVTLIYSDDKRPSNIPERFSGSSSGTTVTLTISGVQAEDEADYYCGGYDQSSYTNPFGGGTKLTVL (SEQ ID NO: 252) |
| Hum2 | AB25 | IGLV1 | QSVLTQPPSVSAAPGQKVTISCSGGSYSSYYYAWYQQLPGTAPKTLIYSDDKRPSNIPDRFSGSKSGTSATLGITGLQTGDEADYYCGGYDQSSYTNPFGTGTKVTVL (SEQ ID NO: 253) |
| Hum3 | AB66 | IGLV3 | SYELTQPPSVSVSPGQTARITCSGGDYYSTYYAWYQQKPGQAPVTVIHSDDKRPSDIPERFSGSSSGTTVTLTISGVQAEDEADYYCGGYDGRTYINTFGGGTKLTVL (SEQ ID NO: 254) |
| Hum4 | AB66 | IGLV1 | QSVLTQPPSVSAAPGQKVTISCSGGDYYSTYYAWYQQLPGTAPKTVIHSDDKRPSDIPDRFSGSKSGTSATLGITGLQTGDEADYYCGGYDGRTYINTFGTGTKVTVL (SEQ ID NO: 255) |
| Hum5 | AB25 | IGLV2 | QSALTQPASVSGSPGQSITISCTGTSSDVGSYSSYYYAWYQQHPGKAPKTLIYSDDKRPSNVSNRFSGSKSGNTASLTISGLQAEDEADYYCGGYDQSSYTNPFGGGTKLTVL (SEQ ID NO: 256) |
| Hum6 | AB21 | IGLV1 | QSVLTQPPSVSAAPGQKVTISCSGGDYYSYYYGWYQQLPGTAPKTVIYSDDKRPSDIPDRFSGSKSGTSATLGITGLQTGDEADYYCGGYDYSTYANAFGTGTKVTVL (SEQ ID NO: 257) |

Each of the 6 humanized light chains was paired with each of four heavy chains (derived from A1B21, A1B25, AB327, and AB366), generating 24 unique antibodies. Antibodies were expressed as described above. Surprisingly, human IGLV1 framework sequences resulted in decreased antibody expression regardless of the heavy chain. This refers to all the heavy chain pairings with Hum2, Hum4 and Hum6 (except when pairing was carried out with heavy chain from AB366). The results are summarized in FIG. 28 as "protein yield" (row 1). In contrast, antibodies with light chains including human IGLV2 and IGLV3 frameworks (Hum 1, Hum3, Hum5) showed higher levels of expression regardless of the heavy chain.

Selected antibodies were next characterized for binding to a variety of SIRP proteins (e.g., to human SIRP-α v1, human SIRP-α v2, cynomolgus SIRP-α, mouse BALB/c SIRP-α, and human SIRP-7). These data are also summarized in FIG. 28. Selected humanized light chains caused a decrease in binding to one or more antigens. For instance, the human IGLV3 framework (represented by Hum1 and Hum3) was found to allow for superior levels of antibody production without perturbing binding affinity. For example, light chain variable domains with the IGLV3 frameworks and either the antibody 25 or antibody 66 HVR sequences (represented by Hum1 and Hum 3 respectively) combined well with a variety of heavy chains (e.g., heavy variable domains from antibodies 21, 25, 27, and 66) and showed similar binding to different SIRP-α and SIRP-γ proteins. In contrast, IGLV1 and IGLV2 frameworks (represented by Hum2, Hum4, Hum5 and Hum6) were found to either lower expression and/or decrease binding to SIRP when paired with heavy chains from antibodies 21, 25, and 27 and 66. Additional binding data from these experiments are provided in Table R infra. The human IGLV3 framework was selected for further testing.

Another goal for humanization of these antibodies was antibody sequences having greater than or equal to 85% identity to human germline light chain/heavy chain sequences. Additional VL domain Hum9 and Hum8 was generated based on the Hum1 VL domain. Compared to Hum1, Hum9 contains 4 amino acid substitutions near or in HVR-L1 and -L2 that increase the humanness of the light chain to greater than or equal to 85% identity to human light chain sequence (FIG. 29). Compared to Hum1, Hum8 contains 5 amino acid substitutions respectively near or in HVR-L1 and -L2 that increase the humanness of the light chain to greater than or equal to 85% identity to human light chain sequence (FIG. 29). Hum1, Hum8 and Hum9 VLs when paired with heavy chain all_mut_AB21 (carrying germline mutations) produced anti-SIRPα antibodies that bind to human v1 with affinity equal or better than 10 pM (Table S). Similarly, when Hum1, Hum8 and Hum9 VLs were paired with heavy chain all_mut_AB25 (carrying germline mutations), the anti-SIRPα antibodies bind to human v1 with affinity equal or better than 10 pM Additional binding data from these experiments are provided in Table S infra. These light chains can be combined interchangeably with antibody VH domains 21, 25, and 27 (as well as variants thereof, which were modified as described supra for antibodies 119, 135, and 136; FIG. 30). Without wishing to be bound to theory, it is thought that the humanization process described above can be applied to the light chain of any antibody of family 2 (bin 1).

Example 8: Induction of Phagocytosis and Dendritic Cell Activation by Anti-SIRP-α Antibodies Various anti-SIRP-α antibodies representing different modes of binding to SIRP-α (e.g., blocking, non-blocking, and "kick off" antibodies) were next examined in phagocytosis assays.

CD47-Fc Binding Assays

CD47-Fc was conjugated with Alexa Fluor 647 (AF647) using the Alexa Fluor 647 Microscale Protein Labeling Kit (Thermo Fisher Scientific). In 96 well polypropylene plates (Corning), 100,000 PBMCs were suspended in 100 µl 0.25 µM AF647-labeled CD47-Fc and 1 µl anti-CD14 PE antibody (Biolegend) in FACS buffer. Cells were incubated on ice for 30 minutes, washed in FACS buffer, and incubated in 10-fold serial dilutions of anti-SIRP-α antibody from 1.25 µM to 25 pM. Cells were incubated on ice for 30 minutes, washed in FACS buffer, and fixed in 75 µl of 0.5 percent formaldehyde. Cells were analyzed on a FACS Canto™ II (BD Biosciences) flow cytometer, with subsequent data analysis by Flowjo 10.7 (Treestar). Geometric mean fluorescence intensity of the CD47-Fc signal was determined in the CD14-positive monocyte population.

Dendritic Cell Activation Assays

The dendritic cell activation assays were performed as described elsewhere herein. Briefly, Balb/c mice (n=3/group) were intravenously injected with a control rat anti-mouse anti-SIRP-α antagonistic antibody (clone p84), human IgG1 control, various anti-SIRP-α antibodies, mouse IgG control, or vehicle (PBS) at 10 mg/kg. Five hours post injection, spleens were harvested and processed into single cell suspension by mechanical dissociation. Activation marker CD86, MHCII and CCR7 level on CD4+ splenic dendritic cells was measured by flow cytometry.

Cell Adhesion Assays

The adhesion assay was performed using isogenic cells lacking or expressing human CD47. Hamster CD47 knock-out CHO cells ($CHO^{CD47\ KO}$) were generated using CRISPR technology. Isogenic cells expressing human CD47 were generated by transiently transfecting human CD47 into $CHO^{CD47\ KO}$ 24 hours post transfection, human CD47 transfected $CHO^{CD47\ KO}$ cells ($4 \times 10^5$) were re-plated onto 24 well tissue culture treated plates and allowed to reattach and reach confluency overnight at 37° C.

Human peripheral blood mononuclear cells (PBMCs) were separated from peripheral blood of healthy donors by Ficoll gradient centrifugation. CD3+ and CD14+ cells were isolated from PBMCs by negative selection using magnetic beads. Isolated CD3+ and CD14+ cells ($5 \times 10^6$) were pre-incubated with Hum1/AB21mutall, Hum9/AB21mutall or 136 wt/mut antibodies containing mutated human IgG1 (L234A L235A G237A, and N297A) (20 ug/mL) at 37° C. for 20 minutes, before plating onto $CHO^{CD47\ KO}$ and $CHO^{hCD47+}$ cells and allowed to adhere for 1 hour at 37° C. Non-adherent cells were removed by five gentle washes with PBS. Adherent cells were detached with trypsin and neutralized with 10% FBS. Cells were transferred to 96 well plate and washed 2 times with PBS+0.5% BSA followed by cell surface labeling with fluorochrome conjugated human CD3, CD4, CD8 and CD14 antibodies. Counting beads were added and cell adhesion was quantified using a BD Canto™ II flow cytometer. Analysis of flow cytometry data was done using Flowjo.

Results

Five antibodies that "kick off" CD47 from binding SIRP-α were examined for their effects on phagocytosis of HER2(+) OE19 cells by M2 macrophages in combination with the anti-HER2 antibody trastuzumab (FIG. 31). All 5 "kick off" antibodies were found to enhance trastuzumab-induced phagocytosis.

Five antibodies that do not block CD47 from binding SIRP-α were next examined for their effects on phagocytosis of EGFR(+) DLD-1 cells by M2 macrophages in combination with the anti-EGFR antibody cetuximab (FIG. 32). All non-blocking antibodies were found to enhance cetuzimab-induced phagocytosis.

Next, humanized antibodies described above were tested for their effects on phagocytosis of EGFR(+) DLD-1 cells by M2 macrophages in combination with the anti-EGFR antibody cetuximab (FIG. 33A). All humanized antibodies were found to enhance cetuzimab-induced phagocytosis. Additional variants of antibody 136 (described supra) were tested for their effects on phagocytosis of EGFR(+) DLD-1 cells by M2 macrophages in combination with the anti-EGFR antibody cetuximab (FIG. 33B). All variants of antibody 136 enhanced cetuximab-induced phagocytosis, but to varying degrees. Additional humanized antibodies described above (antibody 25 and 27 heavy chain variants combined with Hum1 or Hum9 light chain) were tested for their effects on phagocytosis of EGFR(+) DLD-1 cells by M2 macrophages in combination with the anti-EGFR antibody cetuximab (FIG. 33C). All humanized antibodies were found to enhance cetuximab-induced phagocytosis.

To investigate the effect of anti-SIRP-α antibody Fc regions on phagocytosis, two non-blocking antibodies were tested either as full-length antibodies or F(ab)₂ fragments for their effects on phagocytosis of EGFR(+) DLD-1 cells by M2 macrophages in combination with the anti-EGFR antibody cetuximab (FIG. 34). These results indicated that non-blocking antibodies lose the ability to induce phagocytosis as F(ab)₂ fragments, suggesting that the Fc region of this class of antibody is required for induction of phagocytosis.

Three variants of blocking antibody 119 (described supra) were tested for their effects on phagocytosis of EGFR(+) DLD-1 cells by M2 macrophages in combination with the anti-EGFR antibody cetuximab (FIG. 35). The results demonstrated that all three variants enhanced cetuximab-induced phagocytosis.

Two variants of blocking antibody 135 (described supra) were tested for their effects on phagocytosis of EGFR(+) DLD-1 cells by M2 macrophages in combination with the anti-EGFR antibody cetuximab (FIG. 36). The results demonstrated that both variants enhanced cetuximab-induced phagocytosis.

Additional non-blocking antibodies (described supra) were tested for their effects on phagocytosis of EGFR(+) DLD-1 cells by M2 macrophages in combination with the anti-EGFR antibody cetuximab (FIG. 37). All non-blocking antibodies were found to enhance cetuximab-induced phagocytosis.

Next, various anti-SIRP-α antibodies were examined for their effects on in vivo dendritic cell activation (FIGS. 38A-38B), including known anti-SIRP-α antibody p84 (see, e.g., Tangsheng, Y. et al (2015) *Immunity* 433:1-12). Failure to engage mouse SIRP-α receptor on splenic dendritic cells via CD47 binding leads to splenic dendritic cell activation. Control anti-SIRP-α antagonist antibody p84 activated splenic dendritic cells when injected intravenously into mice. Non-blocking anti-SIRP-α antibodies (AB136b, AB3b and AB136 wt/mut) and blocking anti-SIRP-α antibodies (Hum1/AB21mutall, Hum8/AB21mutall, and Hum9/AB21mutall) were tested in vivo to determine if it leads to dendritic cell activation. As determined by CD86 and MHCII expression, both SIRP-α blockers and non-blockers induce activation of dendritic cells. These results suggest that blocking and non-blocking anti-SIRP-α antibodies induce activation of dendritic cells.

Two variants of antibody 218, 218-Hum13/VH_wt and 218-Hum14/VH_wt, were generated by expressing humanized light chains (Hum13 and Hum14 respectively) with the wild-type heavy chain of antibody 218. Hum13 used the human IGLV2 framework, whereas Hum14 used the human IGLV3 framework (see SEQ ID NOs:333 and 334 for VL sequences of Hum13 and Hum14, respectively). Both clones showed lower affinity binding to v1 and v2 ($K_D$ is ~29.3 to 53.1 nM), as shown in Table O2.

TABLE O2

Binding affinity ($K_D$, M) of antibody 218 and 218 variants for human SIRP-α v1 and v2.

| $K_D$ (M) | v1 ALX135 | v2 ALX269 |
| --- | --- | --- |
| AB218a | 1.60E−10 | 3.23E−10 |
| 218-Hum13/VH_wt | 2.93E−08 | 3.38E−08 |
| 218-Hum14/VH_wt | 3.45E−08 | 5.31E−08 |

Both antibodies were tested in a phagocytosis assay in combination with cetuximab in DLD-1 cells. Interestingly, neither humanized variant was able to enhance phagocytosis over the parental AB218a antibody (FIG. 39A). Without wishing to be bound to theory, these results suggest that antibodies with $K_D$ at or below an approximate range of 30-50 nM may be more effective in inducing phagocytosis than antibodies that bind with weaker affinity.

Exemplary blocking, non-blocking, and kick off anti-SIRP-α antibodies were next tested for induction of phagocytosis as single agents. First, three antibodies that block CD47 from binding SIRP-α, AB119a, AB120a, and AB122a, were examined for their effects as single agents on phagocytosis of EGFR(+) DLD-1 cells by M2 macrophages (as described above). All blocking antibodies were found to induce phagocytosis as single agents (FIG. 39B). Next, two antibodies that do not block CD47 from binding SIRP-α, AB136a and AB137a, were examined for their effects as single agents on phagocytosis of EGFR(+) DLD-1 cells by M2 macrophages. All non-blocking antibodies were found to induce phagocytosis as single agents (FIG. 39C). Finally, five "kick-off" anti-SIRP-α antibodies, AB115a, AB116a, AB117a, AB118a, and AB132a, were examined for their effects as single agents on phagocytosis of EGFR(+) DLD-1 cells by M2 macrophages. All "kick-off" antibodies were found to induce phagocytosis as single agents (FIG. 39D).

Example 9: Synergistic Anti-Tumor Effects of Combining Blocking or Non-Blocking Anti-SIRP-α Antibodies with Inhibition of the PD-L1/PD-1 Pathway Methods
In Vivo Anti-Tumor Activity For the CT26 syngeneic mouse colon carcinoma model, CT26 cells were implanted subcutaneously in BALB/c mice and randomized into groups (8-9 mice/group). Treatment groups included vehicle (PBS), AB25b, anti-PD-L1, and AB25b/anti-PD-L1. Anti-PD-L1 is generated by fusing the VH and VL domain of Atezolizumab with mouse IgG1 Fc region bearing an N297A mutation. All anti-SIRP-α antibodies also have a mouse IgG1 Fc region bearing an N297A mutation. Treatment was initiated when tumors were an average of 75-80 mm³, day 7 or 8 post implant. Mice were dosed intraperitoneally (IP) at 3 mg/kg or 10 mg/kg twice a week for three weeks for anti-SIRPα antibodies and three doses at 3 mg/kg, five days apart for anti-PD-L1. Animals were sacrificed when tumors reached a volume of ~2000 mm³.

For the MC38 syngeneic mouse colon carcinoma model, MC38 cells were implanted subcutaneously in C57BL/6 mice and randomized into groups (8-10 mice/group). Treatment groups included vehicle (PBS), AB25b, AB136b, anti-PD1 (clone RMP1-14, BioXCell), AB136b/anti-PD1, and AB25b/anti-PD1. All anti-SIRPα antibodies had a murine IgG1 Fc region bearing an N297A mutation except for AB25c. Treatment was initiated when tumors were an average of 60-65 mm³, day 7 post implant. Mice were dosed intraperitoneally (IP) at 10 mg/kg twice a week for three weeks for anti-SIRPα and three doses at 2 mg/kg for anti-PD1. Animals were sacrificed when tumors reached a volume of ~2000 mm³.

Results

Anti-tumor activity of the blocking AB25b anti-SIRP-α antibody was tested alone and in combination with an anti-PD-L1 antibody in the CT26 syngeneic mouse colon carcinoma model. As shown in FIG. 40, administration of AB25b at 10 mg/kg in combination with anti-PD-L1 at 3 mg/kg delayed tumor formation when compared to treatment with each single agent or vehicle control. On day 27 of the study, the combination treatment group had six mice with tumors below 600 mm³ in size, as compared to two, two, and two mice with tumors below 600 mm³ in size in the vehicle, anti-PD-L1 single agent, and anti-SIRP-α single agent treatment groups, respectively.

Next, the anti-tumor activities of the blocking AB25b anti-SIRP-α antibody and non-blocking AB136b anti-SIRP-α antibody were tested alone and in combination with an anti-PD-1 antibody in the MC38 syngeneic mouse colon carcinoma model. As shown in FIG. 41, combining either AB25b or AB136b (at 10 mg/kg) with anti-PD-1 at 5 mg/kg delayed tumor formation when compared to treatment with each single agent or vehicle control. On day 27 of the study, the AB25b/PD-1 combination treatment group had seven mice with tumors below 600 mm³ in size, and the AB136b/PD-1 combination treatment group had six mice with tumors below 600 mm³ in size, as compared to one, five, two, and one mice with tumors below 600 mm³ in size in the vehicle, anti-PD-1 single agent, AB25b single agent, and AB136b single agent treatment groups, respectively.

A summary of antibodies described herein and their properties is provided in Table P. Additional binding data are provided in Table T.

Although the foregoing disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

TABLE P

Anti-SIRP-α antibody summary.

| Antibody | Type of Binding (NB/B/KO) | Bin No. | In vitro phago (+/−) | In vivo mouse (+/−) | Species Binding (+/−) (Koff) Human v1 (SEQ ID NO: 5) | Cyno (SEQ ID NO: 1) | Mouse 129 (SEQ ID NO: 7) | Human Isoforms (+/−) (Koff) Beta (SEQ ID NO: 13) | Gamma (SEQ ID NO: 15) | $K_D$ Human V1 (SEQ ID NO: 5) | $K_D$ Human V2 (SEQ ID NO: 6) | Heavy chain (Human/Chicken) | Light Chain (Human/Chicken) |
|---|---|---|---|---|---|---|---|---|---|---|---|---|---|
| Family 1 | | | | | | | | | | | | | |
| 119 | B | 1 | + | N.A. | + | + | − | + | + | 1.83E−10 | 7.99E−11 | Human | Human |
| 120 | B | 1 | + | N.A. | + | + | − | + | + | 2.14E−10 | 8.56E−11 | Human | Human |
| 121 | B | 1 | + | N.A. | + | + | − | + | + | 1.57E−10 | 5.01E−11 | Human | Human |
| 122 | B | 1 | | N.A. | + | + | − | + | + | 2.14E−10 | 7.78E−11 | Human | Human |
| 135 | b | 1 | + | N.A. | + | + | − | + | + | 1.51E−10 | 2.90E−11 | Human | Human |
| Family 2 | | | | | | | | | | | | | |
| 16 | B | 1 | + | | + | + | + | + | + | <1.0E−12 | <1.0E−12 | Human | Chicken |
| 17 | B | 1 | + | | + | + | + | + | + | | | Human | Chicken |
| 21 | B | 1 | + | + | + | + | + | + | + | <1.0E−12 | <1.0E−12 | Human | Chicken |
| 22 | B | 1 | | | + | + | + | + | + | | | Human | Chicken |
| 23 | B | 1 | | | + | + | + | + | + | | | Human | Chicken |
| 24 | B | 1 | | | + | + | + | + | + | | | Human | Chicken |
| 25 | B | 1 | + | + | + | + | + | + | + | <1.0E−12 | <1.0E−12 | Human | Chicken |
| 26 | B | 1 | + | NT | + | + | + | + | + | | | Human | Chicken |
| 27 | B | 1 | + | + | + | + | + | + | + | 2.15E−11 | | Human | Chicken |
| 28 | B | 1 | NT | NT | + | + | + | + | + | | | Human | Chicken |
| 29 | B | 1 | NT | NT | + | + | + | + | + | | | Human | Chicken |
| 30 | B | 1 | + | NT | + | + | + | + | + | | | Human | Chicken |
| 55 | B | 1 | NT | NT | + | + | + | + | + | | | Human | Chicken |
| 56 | B | 1 | NT | NT | + | + | + | + | + | | | Human | Chicken |
| 59 | B | 1 | NT | NT | + | + | + | + | + | | | Human | Chicken |
| 60 | B | 1 | NT | NT | + | + | + | + | + | | | Human | Chicken |
| 65 | B | 1 | NT | NT | + | + | + | + | + | | | Human | Chicken |
| 66 | B | 1 | NT | + | + | + | + | + | + | <1.0E−12 | | Human | Chicken |
| 69 | B | 1 | NT | NT | + | + | + | + | + | | | Human | Chicken |
| 70 | B | 1 | NT | NT | + | + | + | + | + | | | Human | Chicken |
| 71 | B | 1 | NT | NT | + | + | + | + | + | | | Human | Chicken |
| 73 | B | 1 | NT | NT | + | + | + | + | + | <1.0E−12 | <1.0E−12 | Human | Chicken |
| 74 | B | 1 | NT | NT | + | + | + | + | + | | | Human | Chicken |
| 76 | B | 1 | NT | NT | + | + | + | + | + | | | Human | Chicken |

TABLE P-continued

Anti-SIRP-α antibody summary.

| Antibody | Type of Binding (NB/B/KO) | Bin No. | In vitro phago (+/−) | In vivo mouse (+/−) | Species Binding (+/−) (Koff) Human v1 (SEQ ID NO: 5) | Cyno (SEQ ID NO: 1) | Mouse 129 (SEQ ID NO: 7) | Human Isoforms (+/−) (Koff) Beta (SEQ ID NO: 13) | Gamma (SEQ ID NO: 15) | $K_D$ Human V1 (SEQ ID NO: 5) | $K_D$ Human V2 (SEQ ID NO: 6) | Heavy chain (Human/Chicken) | Light Chain (Human/Chicken) |
|---|---|---|---|---|---|---|---|---|---|---|---|---|---|
| 201 | B | 1 | + | NT | + | + | + | + | + | <1.0E−12 | 4.87E−12 | Human | Chicken |
| 202 | B | 1 | + | NT | + | + | + | + | + | <1.0E−12 | <1.0E−12 | Human | Chicken |
| 206 | B | 1 | NT | NT | + | + | + | + | + |  |  | Human | Chicken |
| Family 3 |  |  |  |  |  |  |  |  |  |  |  |  |  |
| 136 | NB | 2 | + | + | + | + | + | + | − | 4.58E−10 | 3.22E−09 | Human | Human |
| 137 | NB | 2 | + | NT | + | + | + | + | − | 7.74E−10 | 3.14E−09 | Human | Human |
| 175 | NB | 2 | + | NT | + | + | + | + | NT | 1.37E−10 | 6.62E−10 | Human | Human |
| 177 | NB | 2 | NT | NT | + | + | + | + | NT |  |  | Human | Human |
| 178 | NB | 2 | NT | NT | + | + | + | + | NT |  |  | Human | Human |
| 180 | NB | 2 | NT | NT | + | + | + | + | NT |  |  | Human | Human |
| 184 | NB | 2 | NT | NT | + | + | + | + | NT |  |  | Human | Human |
| 185 | NB | 2 | NT | NT | + | + | + | + | NT |  |  | Human | Human |
| 189 | NB | 2 | + | NT | + | + | + | + | NT | 3.10E−10 | 1.90E−09 | Human | Human |
| 190 | NB | 2 | NT | NT | + | + | + | + | NT |  |  | Human | Human |
| 193 | NB | 2 | + | NT | + | + | + | + | NT | 7.79E−10 | 5.23E−09 | Human | Human |
| Family 4 |  |  |  |  |  |  |  |  |  |  |  |  |  |
| 115 | KO | 3 | + | N.A. | + | + | − | + | + | 1.77E−11 | 1.50E−11 | Human | Human |
| 116 | KO | 3 | + | N.A. | + | + | − | + | + | 1.10E−10 | 2.99E−10 | Human | Human |
| 117 | KO | 3 | + | N.A. | + | + | − | + | + | 3.12E−11 |  | Human | Human |
| 118 | KO | 3 | + | N.A. | + | + | − | + | + | 4.03E−11 |  | Human | Human |
| 132 | KO | 3 | + | N.A. | + | + | − | + | + | 4.26E−10 | 1.86E−09 | Human | Human |
| 191 | KO | 3 | NT | N.A. | + | + | − | + | NT |  |  | Human | Human |
| 198 | KO | 3 | NT | N.A. | + | + | − | + | NT |  |  | Human | Human |
| Family 5 (additional non-blockers) |  |  |  |  |  |  |  |  |  |  |  |  |  |
| 3 | NB | 4 | + | + | + | + | + | + | + | 1.62E−10 | 7.67E−11 | Chicken | Chicken |
| 173 | NB | 4 | + | NT | + | − | − | − | − | 9.37E−10 | 9.28E−09 | Human | Human |
| 174 | NB | 4 | NT | NT | + | − | − | − | − |  |  | Human | Human |
| 209 | NB | 4 | + | NT | + | − | − | + | − | 1.71E−10 | 5.01E−10 | Human | Chicken |
| 213 | NB | 4 | + | NT | − | + | − | − | NT | 6.05E−09 | 1.69E−09 | Human | Chicken |
| 214 | NB | 4 | NT | NT | − | + | − | − | NT |  |  | Human | Chicken |
| 123 | NB | 5 | + | NT | + | + | − | − | + | 6.05E−10 | NLB | Human | Human |
| 149 | NB | 5 | + | NT | + | + | − | + | − | 8.73E−10 | 2.38E−10 | Human | Human |
| 161 | NB | 5 | + | NT | + | + | − | + | − | 1.03E−9 | 1.27E−10 | Human | Human |
| 162 | NB | 5 | + | NT | + | + | − | + | + | 4.50E−10 | 1.57E−08 | Human | Human |
| 163 | NB | 5 | NT | NT | + | + | − | + | + |  |  | Human | Human |
| 164 | NB | 5 | NT | NT | + | + | − | + | + |  |  | Human | Human |
| 194 | NB | 5 | + | NT | + | + | − | − | NT | 4.97E−10 | NLB | Human | Human |
| 218 | NB | 5 | + | NT | + | + | − | NT | + | 1.23E−10 | 2.76E−10 | Chicken | Human |
| S45 | NB | 6 | + | NT | + | − | − | − | − | 6.63E−11 | 1.34E−10 | Chicken | Chicken |

B = blocker; NB = non-blocker; KO = kick off.
NT or blank = not tested; NA = not applicable (anitbodies do not cross-react).
NLB = no binding

TABLE Q

Anti-SIRP-α antibody germline/liability mutation summary.

| Antibody | Human Light Chain | Human Heavy Chain | Type of Binding (NB/B/KO) | Bin No. | $K_D$ (M) SEQ ID NO: 5 Human v1 | SEQ ID NO: 6 Human v2 | SEQ ID NO: 11 Cyno | SEQ ID NO: 8 NOD | SEQ ID NO: 9 BL6 | SEQ ID NO: 10 BALBc | SEQ ID NO: 13 Human SIRPb | SEQ ID NO: 15 Human SIRPg | In vitro phago (+/−) | In vivo mouse (+/−) |
|---|---|---|---|---|---|---|---|---|---|---|---|---|---|---|
| 119 | wt | wt | B | 1 | 1.83E−10 | 6.82E−11 | 1.12E−10 | NLB | NLB | NLB | 3.42E−10 | 2.67E−10 | + | N.A. |
| 119 | Mut | wt | B | 1 | 2.14E−10 | 8.64E−11 | 1.38E−10 | NLB | NLB | NLB | NT | 2.33E−10 | NT | N.A. |
| 119 | wt | Mut | B | 1 | 2.54E−10 | 6.94E−11 | 1.55E−10 | NLB | NLB | NLB | NT | NT | + | N.A. |
| 119 | Mut | Mut | B | 1 | 3.17E−10 | 8.75E−11 | 1.95E−10 | NLB | NLB | NLB | 4.60E−10 | 3.36E−10 | + | N.A. |
| 119 | Mut | Mut_V34M | B | 1 | 2.15E−10 | 6.88E−11 | 1.18E−10 | NLB | NLB | NLB | 3.37E−10 | 2.63E−10 | NT | N.A. |

TABLE Q-continued

Anti-SIRP-α antibody germline/liability mutation summary.

| Antibody | Human Light Chain | Human Heavy Chain | Type of Binding (NB/B/KO) | Bin No. | $K_D$ (M) SEQ ID NO: 5 Human v1 | SEQ ID NO: 6 Human v2 | SEQ ID NO: 11 Cyno | SEQ ID NO: 8 NOD | SEQ ID NO: 9 BL6 | SEQ ID NO: 10 BALBc | SEQ ID NO: 13 Human SIRPb | SEQ ID NO: 15 Human SIRPg | In vitro phago (+/−) | In vivo mouse (+/−) |
|---|---|---|---|---|---|---|---|---|---|---|---|---|---|---|
| 135 | wt | wt | B | 1 | 1.51E−10 | 2.90E−11 | 9.69E−11 | NLB | NLB | NLB | | 5.39E−10 | + | N.A. |
| 135 | Mut | wt | B | 1 | 1.49E−10 | 2.66E−11 | 1.02E−10 | NLB | NLB | NLB | | 5.22E−10 | NT | N.A. |
| 135 | Wt | Mut | B | 1 | 1.84E−10 | 1.97E−11 | 1.25E−10 | NLB | NLB | NLB | 7.79E−10 | 7.33E−10 | NT | N.A. |
| 135 | Mut | Mut | B | 1 | 1.92E−10 | 1.75E−11 | 1.27E−10 | NLB | NLB | NLB | 1.88E−10 | 7.33E−10 | + | N.A |
| 135 | wt | Mut_V34M | B | 1 | 1.50E−10 | 1.61E−11 | 7.94E−11 | NLB | NLB | NLB | 1.60E−10 | 5.33E−10 | NT | N.A. |
| 136 | wt | wt | NB | 2 | 4.58E−10 | 1.63E−09 | 2.15E−09 | 5.54E−10 | 1.27E−08 | 3.50E−10 | 4.35E−9 | 2.39E−08 | + | + |
| 136 | Mut | wt | NB | 2 | 7.28E−09 | 1.74E−08 | 1.13E−08 | 4.12E−09 | 3.26E−08 | 2.80E−09 | | 1.96E−08 | − | |
| 136 | wt | Mut | NB | 2 | 5.58E−10 | 1.74E−09 | 2.26E−09 | 6.78E−10 | 2.31E−08 | 4.16E−10 | 3.54E−09 | 1.65E−08 | NT | |
| 136 | Mut | Mut | NB | 2 | 7.29E−09 | 1.95E−08 | 1.30E−08 | 5.21E−09 | 3.17E−08 | 3.14E−09 | | 1.68E−09 | − | |
| 136 | Mut_I2T | Mut | NB | 2 | 7.17E−10 | 1.86E−09 | 2.33E−09 | 6.80E−10 | 1.53E−08 | 4.22E−10 | 3.16E−09 | 4.00E−08 | + | |
| 136 | Mut_S12T | Mut | NB | 2 | 4.88E−09 | 1.05E−08 | 7.99E−09 | 2.85E−09 | 1.63E−08 | 2.09E−09 | | 6.67E−08 | NT | |
| 136 | Mut_S22T | Mut | NB | 2 | 4.99E−09 | 8.28E−09 | 6.84E−09 | 2.44E−09 | 1.33E−08 | 1.64E−09 | | 6.17E−08 | NT | |
| 136 | Mut_Q38E | Mut | NB | 2 | 6.18E−09 | 1.25E−08 | 1.04E−08 | 5.98E−09 | 3.31E−08 | 2.98E−09 | | 1.93E−08 | NT | |
| 136 | Mut_I2T | Mut_V34M | NB | 2 | 5.51E−10 | 1.74E−09 | 2.11E−09 | 5.96E−10 | 1.38E−08 | 3.61E−10 | 2.22E−09 | 3.35E−08 | NT | |

B = blocker; NB = non-blocker.
NT or blank = not tested; NA = not applicable (antibodies do not cross-react); NLB = no binding
119 heavy chain mut = D1E, E43K, L112Q, M34V
119 light chain mut = F21L, R39K, E60A, T76S
135 heavy chain mut = D1E, R13Q, E16G, M34V, E43K, L112Q

TABLE R

Anti-SIRP-α antibody humanization summary (round 1).

| Antibody Designation | VL | VH | Koff (1/s) SEQ ID NO: 5 Human V1 | SEQ ID NO: 6 Human V2 | SEQ ID NO: 11 Cyno | SEQ ID NO: 10 BALBc | SEQ ID NO: 15 SIRPg | In vitro phago (+/−) | In vivo mouse (+/−) |
|---|---|---|---|---|---|---|---|---|---|
| Parental Antibodies | | | | | | | | | |
| AB21 | Chicken (AB21_LC_wt) SEQ ID NO: 136 | Human (AB21_HC_wt) SEQ ID NO: 135) | 7.07E−04 | 1.92E−03 | 2.29E−03 | 2.41E−03 | 9.02E−04 | NT | + |
| AB25 | Chicken (AB25_LC_wt) SEQ ID NO: 138 | Human (AB25_HC_wt) SEQ ID NO: 137 | 1.63E−04 | 3.53E−04 | 3.94E−04 | 1.78E−03 | 2.03E−04 | + | + |
| AB27 | Chicken (AB27_LC_wt) SEQ ID NO: 140 | Human (AB27_HC_wt) SEQ ID NO: 139 | 3.15E−04 | 5.79E−04 | 6.83E−04 | 5.00E−03 | 4.07E−04 | + | + |
| AB66 | Chicken (AB66_LC_wt) SEQ ID NO: 142 | Human (AB66_HC_wt) SEQ ID NO: 141 | 9.49E−04 | 2.81E−03 | 2.69E−03 | 3.46E−03 | 9.97E−04 | NT | + |
| Humanization of chicken light chain of AB25, AB66 - replaced with human IGLV3 framework | | | | | | | | | |
| Hum1/AB21_HC_wt | Hum1_Humanized (AB25_IGLV3) SEQ ID NO: 252 | Human (AB21_HC_wt) SEQ ID NO: 135 | 1.93E−04 | 3.03E−04 | 3.95E−04 | 2.91E−03 | 1.88E−04 | + | |
| Hum1/AB25_HC_wt | Hum1_Humanized (AB25_IGLV3) SEQ ID NO: 252 | Human (AB25_HC_wt) SEQ ID NO: 137 | 1.33E−04 | 2.67E−04 | 3.30E−04 | 3.74E−03 | 2.03E−04 | + | |
| Hum1/AB27_HC_wt | Hum1_Humanized (AB25_IGLV3) SEQ ID NO: 252 | Human (AB27_HC_wt) SEQ ID NO: 139 | 1.92E−04 | 2.92E−04 | 3.79E−04 | 3.70E−03 | 1.78E−04 | + | |
| Hum1/AB66_HC_wt | Hum1_Humanized (AB25_IGLV3) SEQ ID NO: 252 | Human (AB66_HC_wt) SEQ ID NO: 141 | 1.24E−04 | 2.39E−04 | 3.03E−04 | 2.46E−03 | 1.36E−04 | NT | |
| Hum3/ | Hum3_Humanized | Human | 1.37E−04 | 4.38E−04 | 4.32E−04 | 2.31E−03 | 2.10E−04 | NT | |

TABLE R-continued

Anti-SIRP-α antibody humanization summary (round 1).

| Antibody Designation | VL | VH | Koff (1/s) | | | | | In vitro phago (+/−) | In vivo mouse (+/−) |
|---|---|---|---|---|---|---|---|---|---|
| | | | SEQ ID NO: 5 Human V1 | SEQ ID NO: 6 Human V2 | SEQ ID NO: 11 Cyno | SEQ ID NO: 10 BALBc | SEQ ID NO: 15 SIRPg | | |
| AB21_HC_wt Hum3/ AB25_HC_wt | (AB66_IGLV3) SEQ ID NO: 254 Hum3_Humanized (AB66_IGLV3) SEQ ID NO: 254 | (AB21_HC_wt) SEQ ID NO: 135 Human (AB25_HC_wt) SEQ ID NO: 137 | 5.94E−05 | 3.53E−04 | 3.75E−04 | 2.27E−04 | 1.69E−04 | NT | |
| Hum3/ AB27_HC_wt | Hum3_Humanized (AB66_IGLV3) SEQ ID NO: 254 | Human (AB27_HC_wt) SEQ ID NO: 139 | 2.16E−04 | 3.96E−04 | 4.64E−04 | 2.02E−04 | 2.07E−04 | NT | |
| Hum3/ AB66 HC wt | Hum3_Humanized (AB66_IGLV3) SEQ ID NO: 254 | Human (AB66_HC_wt) SEQ ID NO: 141 | 1.24E−04 | 2.87E−04 | 3.06E−04 | 2.05E−03 | 1.35E−04 | NT | |

NT or blank = not tested.

TABLE S

Anti-SIRP-α antibody humanization summary (round 2).

| Antibody Designation | VL | VH | KD (M) | | | | | | | | In vitro phago (+/−) |
|---|---|---|---|---|---|---|---|---|---|---|---|
| | | | SEQ ID NO: 5 Human v1 | SEQ ID NO: 6 Human V2 | SEQ ID NO: 11 Cyno | SEQ ID NO: 8 NOD | SEQ ID NO: 9 BL6 | SEQ ID NO: 10 BALBc | SEQ ID NO: 13 SIRPb | SEQ ID NO: 15 SIRPg | |
| Pairing of humanized light chain with heavy chain (Germline mut) | | | | | | | | | | | |
| Hum1/ AB21_HC_ Mutall | Hum1_ Humanized (AB25_IGL V3) SEQ ID NO: 252 | Human (AB21_HC_ Mutall) SEQ ID NO: 263 | 5.32E−12 | 4.60E−12 | 2.91E−11 | 3.70E−09 | 9.50E−09 | 7.91E−09 | 6.7E−12 | >1.0E−12 | + |
| Hum1/ AB25_HC_ Mutall | Hum1_ Humanized (AB25_IGL V3) SEQ ID NO: 252 | Human (AB25_HC_ Mutall) SEQ ID NO: 265 | 5.19E−12 | | | 4.83E−09 | 1.03E−08 | 7.25E−09 | | | + |
| Hum1/ AB27_HC_ Mutall | Hum1_ Humanized (AB25_IGL V3) SEQ ID NO: 252 | Human (AB27_HC_ MutAll) SEQ ID NO: 267 | 4.37E−12 | | | 2.92E−09 | 9.03E−09 | 5.77E−09 | | | + |
| Mutation of humanized light chain to increase % humaness | | | | | | | | | | | |
| Hum8/ AB21_HC_ Mutall | Hum8_ Humanized (AB25_IGL V3) + 5aa in CDR SEQ ID NO: 416 | Human (AB21_HC_ Mutall) SEQ ID NO: 263 | 2.01E−11 | | | 2.78E−08 | 4.15E−04 | 7.12E−08 | | | + |
| Hum8/ AB25_HC_ Mutall | Hum8_ Humanized (AB25_IGL V3) + 5aa in CDR SEQ ID NO: 416 | Human (AB25_HC_ Mutall) SEQ ID NO: 265 | 2.62E−11 | | | 2.05E−08 | 4.97E−04 | 5.99E−08 | | | NT |
| Hum9/ AB21_HC_ Mutall | Hum9_ Humanized (AB25_IGL V3) + 4aa in CDR SEQ ID NO: 262 | Human (AB21_HC_ Mutall) SEQ ID NO: 263 | 1.19E−11 | 1.19E−10 | 2.22E−10 | 2.41E−08 | 5.33E−04 | 1.36E−07 | 5.69E−11 | 3.45E−11 | + |
| Hum9/ AB25_HC_ Mutall | Hum9_ Humanized (AB25_IGL V3) + 4aa in SEQ ID | Human (AB25_HC_ | 1.29E−11 | | | 6.12E−08 | 1.15E−08 | 3.83E−08 | | | + |

TABLE S-continued

Anti-SIRP-α antibody humanization summary (round 2).

| | | | KD (M) | | | | | | | | |
|---|---|---|---|---|---|---|---|---|---|---|---|
| Antibody Designation | VL | VH | SEQ ID NO: 5 Human v1 | SEQ ID NO: 6 Human V2 | SEQ ID NO: 11 Cyno | SEQ ID NO: 8 NOD | SEQ ID NO: 9 BL6 | SEQ ID NO: 10 BALBc | SEQ ID NO: 13 SIRPb | SEQ ID NO: 15 SIRPg | In vitro phago (+/−) |
| | CDR SEQ ID NO: 262 | NO: 265 | | | | | | | | | |

NT or blank = not tested.

TABLE T

Anti-SIRP-α antibody binding data summary. Values indicated are tested by SPR ($K_{off}$, 1/s).

| Antibody | CV1-3 SEQ ID NO: 18 | v1 SEQ ID NO: 5 | v2 SEQ ID NO: 6 | cyno1 SEQ ID NO: 11 | cyno2 SEQ ID NO: 12 | m129 SEQ ID NO: 7 | NOD SEQ ID NO: 8 | BL6 SEQ ID NO: 9 | SIRPb SEQ ID NO: 13 | SIRPg SEQ ID NO: 15 | CD47 blocking |
|---|---|---|---|---|---|---|---|---|---|---|---|
| Family 1 | | | | | | | | | | | |
| S119 | 5.65E−04 | 4.15E−04 | 1.48E−04 | 2.34E−04 | 3.10E−04 | NLB | NLB | NLB | 4.28E−04 | 3.95E−04 | block |
| S120 | 6.26E−04 | 4.04E−04 | 1.49E−04 | 2.36E−04 | 3.14E−04 | NLB | NLB | NLB | 4.25E−04 | 3.93E−04 | block |
| S121 | NT | 4.79E−04 | 1.12E−04 | 3.02E−04 | 3.19E−04 | NLB | NLB | NLB | 5.64E−04 | 4.82E−04 | block |
| S122 | 6.63E−04 | 4.98E−04 | 2.26E−04 | 2.66E−04 | 3.27E−04 | NLB | NLB | NLB | 3.52E−04 | 3.61E−04 | block |
| S135 | 3.63E−03 | 6.58E−04 | 8.78E−05 | 4.73E−04 | 3.88E−04 | NLB | NLB | NLB | 5.21E−04 | 1.46E−03 | block |
| Family 2 | | | | | | | | | | | |
| S16 | 1.00E−04 | 6.22E−05 | 1.11E−04 | 1.32E−04 | 1.38E−04 | 1.76E−04 | 1.28E−03 | 2.35E−03 | 1.13E−04 | 8.17E−05 | block |
| S17 | 1.54E−04 | 1.24E−04 | 1.97E−04 | 1.93E−04 | 2.07E−04 | 2.34E−04 | 6.12E−04 | 1.13E−03 | 1.25E−04 | 1.02E−04 | block |
| S21 | 1.95E−04 | 1.80E−04 | 2.07E−04 | 2.33E−04 | 2.52E−04 | 2.81E−04 | 2.64E−03 | 8.06E−04 | 1.90E−04 | 1.84E−04 | block |
| S22 | 1.35E−04 | 1.21E−04 | 1.46E−04 | 1.77E−04 | 1.77E−04 | 1.53E−04 | 5.83E−04 | 7.36E−04 | 1.38E−04 | 1.08E−04 | block |
| S23 | 1.06E−04 | 8.35E−05 | 1.35E−04 | 1.60E−04 | 1.83E−04 | 1.34E−04 | 8.23E−04 | 1.32E−03 | 1.14E−04 | 1.04E−04 | block |
| S24 | 2.16E−04 | 2.57E−04 | 3.17E−04 | 3.82E−04 | 3.34E−04 | 4.02E−04 | 3.86E−03 | 1.26E−03 | 1.94E−04 | 1.97E−04 | block |
| S25 | 1.40E−04 | 1.12E−04 | 2.09E−04 | 2.19E−04 | 2.12E−04 | 1.33E−04 | 7.79E−04 | 2.90E−04 | 1.71E−04 | 1.41E−04 | block |
| S26 | 4.74E−05 | 5.81E−05 | 1.11E−04 | 9.67E−04 | 7.43E−04 | 1.08E−03 | 7.64E−04 | NLB | 1.29E−04 | 8.35E−05 | block |
| S27 | 8.94E−05 | 5.81E−05 | 9.97E−05 | 1.38E−04 | 1.61E−04 | 1.36E−04 | 1.30E−03 | 1.84E−03 | 8.97E−05 | 9.46E−05 | block |
| S28 | 6.59E−05 | 2.11E−05 | 1.47E−05 | 1.15E−04 | 1.32E−04 | 3.06E−04 | 6.16E−04 | 1.86E−03 | 6.29E−05 | 3.27E−05 | block |
| S29 | 3.43E−04 | 9.61E−05 | 1.78E−04 | 3.87E−04 | 3.69E−04 | 1.14E−03 | NLB | 1.86E−03 | 2.79E−04 | 2.16E−04 | block |
| S30 | 1.42E−04 | 1.32E−04 | 1.88E−04 | 3.35E−04 | 3.66E−04 | 4.76E−04 | NLB | 2.44E−03 | 2.37E−04 | 1.93E−04 | block |
| S55 | 6.00E−04 | 4.18E−05 | 7.16E−05 | 9.63E−05 | 1.16E−04 | 1.43E−04 | 1.19E−03 | 1.97E−03 | 6.48E−05 | 4.69E−05 | block |
| S56 | 2.03E−04 | 2.28E−04 | 2.86E−04 | 2.95E−04 | 2.80E−04 | 4.06E−04 | 1.06E−03 | 4.29E−03 | 3.62E−04 | 2.15E−04 | block |
| S59 | 8.19E−05 | 4.98E−05 | 8.63E−05 | 1.06E−04 | 1.13E−04 | 2.09E−04 | 1.35E−03 | 2.39E−03 | 1.07E−04 | 4.28E−05 | block |
| S60 | 1.45E−04 | 1.40E−04 | 1.86E−04 | 1.92E−04 | 1.75E−04 | 2.21E−04 | 7.26E−04 | 1.50E−03 | 1.53E−04 | 1.00E−04 | block |
| S65 | 1.47E−04 | 1.45E−04 | 1.72E−04 | 1.88E−04 | 1.90E−04 | 1.59E−04 | 6.07E−04 | 7.86E−04 | 1.54E−04 | 1.34E−04 | block |
| S66 | 1.10E−04 | 1.18E−04 | 2.06E−04 | 2.50E−04 | 2.55E−04 | 1.27E−04 | 4.90E−04 | 1.02E−03 | 1.38E−04 | 1.26E−04 | block |
| S69 | 2.33E−04 | 2.05E−04 | 2.67E−04 | 2.55E−04 | 2.16E−04 | 2.46E−04 | 7.09E−04 | 7.65E−04 | 2.29E−04 | 1.99E−04 | block |
| S70 | 2.60E−04 | 2.25E−04 | 2.90E−04 | 2.96E−04 | 2.45E−04 | 2.70E−04 | 6.72E−04 | 9.87E−04 | 2.25E−04 | 2.22E−04 | block |
| S71 | 3.79E−04 | 3.35E−04 | 4.03E−04 | 3.64E−04 | 3.13E−04 | 4.17E−04 | 1.12E−03 | 3.41E−03 | 3.88E−04 | 3.16E−04 | block |
| S73 | 5.28E−05 | 1.90E−05 | 7.49E−05 | 1.27E−04 | 1.19E−04 | 1.64E−04 | 1.48E−03 | 3.73E−04 | 1.08E−04 | 7.30E−05 | block |
| S74 | 1.66E−04 | 1.61E−04 | 2.78E−04 | 3.37E−04 | 3.20E−04 | 4.12E−04 | NLB | 1.37E−03 | 2.66E−04 | 2.25E−04 | block |
| S76 | 1.55E−04 | 1.40E−04 | 2.09E−04 | 2.77E−04 | 2.69E−04 | 1.79E−04 | 5.76E−04 | 9.98E−04 | 1.87E−04 | 1.77E−04 | block |
| S201 | 8.32E−05 | 3.46E−05 | 4.27E−05 | 6.36E−04 | 5.22E−04 | 8.18E−04 | 2.15E−03 | 1.11E−03 | 4.10E−03 | 1.85E−04 | block |
| S202 | 6.86E−05 | 3.75E−05 | 5.40E−05 | 1.13E−04 | 1.20E−04 | 4.58E−05 | 5.09E−04 | 6.30E−04 | 2.05E−03 | 4.44E−05 | block |
| S206 | 8.22E−05 | 3.50E−05 | 3.60E−05 | 6.24E−04 | 5.18E−04 | 9.01E−04 | 2.23E−03 | 1.57E−03 | 4.37E−03 | 1.92E−04 | block |
| Family 3 | | | | | | | | | | | |
| S136 | 1.59E−03 | 8.45E−04 | 1.61E−03 | 1.79E−03 | 1.32E−03 | 4.59E−04 | 3.86E−04 | 4.78E−03 | 3.60E−03 | NLB | Non-block |
| S137 | 1.37E−03 | 1.65E−03 | 1.88E−03 | 2.04E−03 | 1.79E−03 | 5.15E−04 | 4.43E−04 | 4.63E−03 | 3.76E−03 | NLB | Non-block |
| S175 | 1.65E−03 | 8.39E−04 | 1.83E−03 | 1.77E−03 | 1.07E−03 | 6.05E−04 | 4.17E−04 | 3.20E−03 | 2.99E−03 | NT | Non-block |
| S177 | NLB | 3.32E−03 | 5.37E−03 | 4.47E−03 | 2.69E−03 | 1.04E−03 | 7.36E−04 | NLB | NLB | NT | Non-block |
| S178 | 4.26E−03 | 2.23E−03 | 3.17E−03 | 3.44E−03 | 1.77E−03 | 1.12E−03 | 7.62E−04 | NLB | 4.73E−03 | NT | Non-block |
| S180 | 3.07E−03 | 1.60E−03 | 2.27E−03 | 2.50E−03 | 1.38E−03 | 8.06E−04 | 5.76E−04 | 4.66E−03 | 3.75E−03 | NT | Non-block |
| S184 | 5.14E−03 | 2.53E−03 | 3.91E−03 | 3.90E−03 | 2.21E−03 | 8.21E−03 | 6.38E−04 | 4.22E−03 | NLB | NT | Non-block |
| S185 | 2.39E−03 | 1.22E−03 | 2.05E−03 | 1.78E−03 | 1.03E−03 | 7.17E−04 | 5.73E−04 | 5.14E−03 | 3.85E−03 | NT | Non-block |
| S189 | 2.28E−03 | 1.06E−03 | 2.81E−03 | 3.31E−03 | 1.87E−03 | 8.37E−04 | 5.04E−04 | 3.90E−03 | 2.78E−03 | NT | Non-block |
| S190 | 3.08E−03 | 1.56E−03 | 1.99E−03 | 2.17E−03 | 1.24E−03 | 7.73E−04 | 5.63E−04 | NLB | 2.56E−03 | NT | Non-block |
| S193 | NLB | 3.08E−03 | 5.17E−03 | NLB | 4.28E−03 | 2.09E−03 | 1.57E−03 | 3.89E−03 | NLB | NT | Non-block |
| Family 4 | | | | | | | | | | | |
| S115 | 4.84E−04 | 7.86E−06 | 1.95E−05 | 2.22E−05 | 6.91E−05 | NLB | NLB | NLB | 3.69E−05 | 3.34E−05 | Kick-off |
| S116 | 4.80E−04 | 2.84E−05 | 5.07E−05 | 7.01E−05 | 1.20E−04 | NLB | NLB | NLB | 3.09E−05 | 8.25E−05 | Kick-off |
| S117 | 2.75E−04 | 1.20E−05 | 3.40E−05 | 1.83E−05 | 5.92E−05 | NLB | NLB | NLB | 3.54E−05 | 4.30E−06 | kick-off |
| S118 | 2.47E−04 | 9.17E−06 | 4.12E−05 | 6.97E−05 | 8.06E−05 | NLB | NLB | NLB | 1.31E−05 | 1.13E−05 | Kick-off |
| S132 | 7.95E−05 | 3.34E−05 | 2.06E−05 | 4.28E−05 | 7.12E−05 | NLB | NLB | NLB | 1.01E−05 | 1.05E−05 | Kick-off |
| S191 | 2.95E−04 | 6.67E−05 | 3.53E−05 | 5.54E−05 | 1.38E−05 | NLB | NLB | NLB | 1.01E−05 | NT | Kick-off |

TABLE T-continued

Anti-SIRP-α antibody binding data summary. Values indicated are tested by SPR ($K_{off}$, 1/s).

| Antibody | CV1-3 SEQ ID NO: 18 | v1 SEQ ID NO: 5 | v2 SEQ ID NO: 6 | cyno1 SEQ ID NO: 11 | cyno2 SEQ ID NO: 12 | m129 SEQ ID NO: 7 | NOD SEQ ID NO: 8 | BL6 SEQ ID NO: 9 | SIRPb SEQ ID NO: 13 | SIRPg SEQ ID NO: 15 | CD47 blocking |
|---|---|---|---|---|---|---|---|---|---|---|---|
| S198 | 7.87E−04 | 3.67E−05 | 4.95E−05 | 8.34E−05 | 7.73E−05 | NLB | NLB | NLB | 4.72E−05 | NT | kick-off |
| Family 5 | | | | | | | | | | | |
| S3 | 3.94E−04 | 4.10E−04 | 2.76E−04 | 2.18E−03 | 1.74E−03 | 6.55E−04 | 1.19E−03 | 1.97E−03 | 1.92E−03 | 1.62E−04 | Non-block |
| S45 | 4.76E−05 | 7.24E−05 | 1.44E−05 | NLB | NLB | NLB | NLB | NLB | NLB | NLB | Non-block |
| S123 | 1.31E−03 | 1.55E−03 | NLB | 1.57E−03 | 1.54E−03 | NLB | NLB | NLB | NLB | 1.43E−03 | Non-block |
| S149 | NLB | 4.15E−03 | 5.44E−04 | NLB | 2.58E−03 | NLB | NLB | NLB | 3.31E−04 | NLB | Non-block |
| S161 | NLB | 3.37E−03 | 3.84E−04 | NLB | 2.15E−03 | NLB | NLB | NLB | 3.21E−03 | NLB | Non-block |
| S162 | 1.52E−03 | 6.84E−04 | NLB | NLB | 3.18E−04 | NLB | NLB | NLB | 1.98E−03 | 4.66E−03 | Non-block |
| S163 | 1.74E−03 | 5.35E−04 | 6.64E−03 | NLB | 2.42E−04 | NLB | NLB | NLB | 1.70E−03 | 3.15E−03 | Non-block |
| S164 | 1.34E−03 | 5.95E−04 | 9.89E−03 | NLB | 4.08E−04 | NLB | NLB | NLB | 1.67E−03 | 4.26E−03 | Non-block |
| S173 | 1.37E−03 | 1.12E−03 | 5.04E−03 | NLB | NLB | NLB | NLB | NLB | NLB | NLB | Non-block |
| S174 | 1.89E−03 | 1.43E−03 | 3.99E−03 | NLB | NLB | NLB | NLB | NLB | NLB | NLB | Non-block |
| S194 | 1.11E−03 | 1.17E−03 | NLB | 1.31E−03 | 1.11E−03 | NT | NLB | NLB | NLB | NT | Non-block |
| S209 | 2.45E−03 | 6.59E−04 | 4.01E−03 | NLB | NLB | NT | NLB | NLB | 6.54E−05 | NLB | Non-block |
| S213 | 4.82E−03 | NLB | 6.85E−04 | 2.60E−04 | 3.13E−03 | NT | NLB | NLB | NLB | NT | Non-block |
| S214 | 4.53E−03 | NLB | 6.77E−04 | 3.51E−03 | 2.71E−03 | NT | NLB | NLB | NLB | NT | Non-block |
| S218 | NT | 7.06E−05 | 5.47E−05 | 2.49E−05 | NT | NT | NLB | NLB | NT | 2.12E−05 | Non-block |

NLB = $K_{off}$ > 5 × 10³ and no binding; NT = not tested.

What is claimed is:

1. An isolated antibody that binds an extracellular domain of a human SIRP-α polypeptide, wherein the antibody comprises:
   (a) a heavy chain variable (VH) domain comprising:
      (i) an HVR-H1 sequence comprising the amino acid sequence of SYDMN (SEQ ID NO: 270), SYDVN (SEQ ID NO:221), or SYDLN (SEQ ID NO:313);
      (ii) an HVR-H2 sequence comprising the amino acid sequence of LISGSGEIIYYADSVKG (SEQ ID NO: 156); and
      (iii) an HVR-H3 sequence comprising the amino acid sequence of ENNRYRFFDD (SEQ ID NO: 157); and
   (b) a light chain variable (VL) domain comprising:
      (i) an HVR-L1 sequence comprising the amino acid sequence of RASQSVYTYLA (SEQ ID NO:158);
      (ii) an HVR-L2 sequence comprising the amino acid sequence of GASSRAT (SEQ ID NO:159); and
      (iii) an HVR-L3 sequence comprising the amino acid sequence of QQYYDRPPLT (SEQ ID NO:160).

2. The antibody of claim 1, wherein the VH domain comprises an amino acid sequence that is at least 90% identical to the amino acid sequence of SEQ ID NO: 249, 133, 260, or 329; and the VL domain comprises an amino acid sequence that is at least 90% identical to the amino acid sequence of SEQ ID NO: 134, 250, or 251.

3. The antibody of claim 1, wherein:
   (a) the VH domain comprises the amino acid sequence of SEQ ID NO: 133, and the VL domain comprises the amino acid sequence of SEQ ID NO:134;
   (b) the VH domain comprises the amino acid sequence of SEQ ID NO:260, and the VL domain comprises the amino acid sequence of SEQ ID NO:134;
   (c) the VH domain comprises the amino acid sequence of SEQ ID NO:329, and the VL domain comprises the amino acid sequence of SEQ ID NO:134;
   (d) the VH domain comprises the amino acid sequence of SEQ ID NO: 133, and the VL domain comprises the amino acid sequence of SEQ ID NO:250;
   (e) the VH domain comprises the amino acid sequence of SEQ ID NO:260, and the VL domain comprises the amino acid sequence of SEQ ID NO:250;
   (f) the VH domain comprises the amino acid sequence of SEQ ID NO:329, and the VL domain comprises the amino acid sequence of SEQ ID NO:250;
   (g) the VH domain comprises the amino acid sequence of SEQ ID NO: 133, and the VL domain comprises the amino acid sequence of SEQ ID NO:251;
   (h) the VH domain comprises the amino acid sequence of SEQ ID NO:260, and the VL domain comprises the amino acid sequence of SEQ ID NO:251;
   (i) the VH domain comprises the amino acid sequence of SEQ ID NO:329, and the VL domain comprises the amino acid sequence of SEQ ID NO:251;
   (j) the VH domain comprises the amino acid sequence of SEQ ID NO:249, and the VL domain comprises the amino acid sequence of SEQ ID NO:134;
   (k) the VH domain comprises the amino acid sequence of SEQ ID NO:249, and the VL domain comprises the amino acid sequence of SEQ ID NO:250; or
   (l) the VH domain comprises the amino acid sequence of SEQ ID NO:249, and the VL domain comprises the amino acid sequence of SEQ ID NO:251.

4. The antibody of claim 1, wherein the antibody enhances phagocytosis by a macrophage expressing a human SIRP-α polypeptide.

5. The antibody of claim 1, wherein the antibody enhances activation of a dendritic cell expressing a human SIRP-α polypeptide.

6. The antibody of claim 1, wherein the antibody inhibits in vivo growth of a tumor that expresses CD47.

7. The antibody of claim 1, wherein the antibody does not prevent interactions between a CD47-expressing cell and a T cell.

8. The antibody of claim 1, wherein the antibody is a monoclonal antibody.

9. The antibody of claim 1, wherein the antibody is a scFv-Fc antibody.

10. The antibody of claim 1, wherein the antibody comprises a light chain constant region comprising the amino acid sequence of SEQ ID NO:325, 326, or 426.

11. The antibody of claim 1, wherein the antibody comprises an Fc region.

12. The antibody of claim 11, wherein the antibody comprises an antibody heavy chain polypeptide that comprises the VH domain and a constant region comprising an amino acid sequence selected from the group consisting of SEQ ID NOs: 320-324.

13. The antibody of claim 11, wherein the Fc region is a human Fc region selected from the group consisting of an IgG1 Fc region, an IgG2 Fc region, and an IgG4 Fc region.

14. The antibody of claim 11, wherein the Fc region comprises a human IgG1 Fc region comprising one or more mutations selected from the group consisting of L234A, L235A, G237A, and N297A, according to EU numbering.

15. The antibody of claim 11, wherein the Fc region comprises a human IgG2 Fc region comprising one or more mutations selected from the group consisting of A330S, P331S and N297A, according to EU numbering.

16. The antibody of claim 11, wherein the Fc region comprises a human IgG4 Fc region comprising one or more mutations selected from the group consisting of S228P, E233P, F234V, L235A, L235E, delG236, and N297A, according to EU numbering.

17. The antibody of claim 1, wherein the antibody is an antibody fragment selected from the group consisting of a Fab, F(ab')2, Fab'-SH, Fv, and scFv fragment.

18. The antibody of claim 1, wherein the antibody is conjugated to a cytotoxic agent or label.

19. The antibody of claim 1, wherein the antibody is a bispecific antibody.

20. The antibody of claim 19, wherein the antibody comprises a first antigen binding domain comprising the VH and VL domain that bind an extracellular domain of a human SIRP-α polypeptide and a second antigen binding domain comprising a second VH domain and second VL domain that bind an antigen expressed by a cancer cell.

21. The antibody of claim 20, wherein the antigen expressed by the cancer cell is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PD-L1, PTK7, STEAP1, Endothelin B Receptor, mesothelin, EGFRVIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING- 4, EpCAM, MUC1, PRAME, survivin, BRCA1, BRCA2, CDK4, CML66, MART-2, p53, Ras, β-catenin, TGF-βRII, HPV E6, or HPV E7.

22. The antibody of claim 1, wherein the antibody is a human antibody.

23. A polynucleotide encoding the antibody of claim 1.

24. A vector comprising the polynucleotide of claim 23.

25. A host cell comprising the polynucleotide of claim 23.

26. A method of producing an antibody, the method comprising culturing the host cell of claim 25 such that the antibody that binds the extracellular domain of a human SIRP-α polypeptide is produced.

27. The method of claim 26, further comprising recovering the antibody from the host cell.

28. The antibody of claim 1, wherein the antibody binds an extracellular domain of a human SIRP-α v1 polypeptide comprising the amino acid sequence of

```
                                          (SEQ ID NO: 5)
EEELQVIQPDKSVLVAAGETATLRCTATSLIPVGPIQWFRGAGPGRELIY

NQKEGHFPRVTTVSDLTKRNNMDFSIRIGNITPADAGTYYCVKFRKGSPD

DVEFKSGAGTELSVRAKPS.
```

29. The antibody of claim 1, wherein the antibody binds an extracellular domain of a human SIRP-α v2 polypeptide comprising the amino acid sequence of

```
                                          (SEQ ID NO: 6)
EEELQVIQPDKSVSVAAGESAILHCTVTSLIPVGPIQWFRGAGPARELI

YNQKEGHFPRVTTVSESTKRENMDFSISISNITPADAGTYYCVKFRKGS

PDTEFKSGAGTELSVRAKPS.
```

30. The antibody of claim 1, wherein the antibody is capable of binding an extracellular domain of a human SIRP-α v1 polypeptide comprising the amino acid sequence of EEELQVIQPDKSVLVAAGETATLRCTATSLIPVG-PIQWFRGAGPGRELIYNQKEGHFPRV TTVSDLTKRNNMDFSIRIGNIT-PADAGTYYCVKFRKGSPDDVEFKSGAG-TELSVRAKPS (SEQ ID NO:5) and is capable of binding an extracellular domain of a human SIRP-α v2 polypeptide comprising the amino acid sequence of

```
                                          (SEQ ID NO: 6)
EEELQVIQPDKSVSVAAGESAILHCTVTSLIPVGPIQWFRGAGPARELIY

NQKEGHFPRVTTVSESTKRENMDFSISISNITPADAGTYYCVKFRKGSPD

TEFKSGAGTELSVRAKPS.
```

31. The antibody of claim 1, wherein the antibody binds an extracellular domain of a cynomolgus SIRP-α polypeptide comprising the amino acid sequence of SEQ ID NO:11.

32. The antibody of claim 1, wherein the antibody binds an extracellular domain of a murine SIRP-α polypeptide comprising the amino acid sequence of SEQ ID NO:7.

33. The antibody of claim 1, wherein the antibody binds the extracellular domain of a human SIRP-β polypeptide comprising the amino acid sequence of SEQ ID NO:13.

34. The antibody of claim 1, wherein the antibody does not block binding between an extracellular domain of a human SIRP-α polypeptide and an IgSF domain of a human CD47 polypeptide.

35. A host cell comprising the vector of claim 24.

36. A method of producing an antibody, the method comprising culturing the host cell of claim 35 such that the antibody that binds the extracellular domain of a human SIRP-α polypeptide is produced.

37. The method of claim 36, further comprising recovering the antibody from the host cell.

* * * * *